United States Patent
Qi et al.

(10) Patent No.: US 11,571,420 B2
(45) Date of Patent: *Feb. 7, 2023

(54) PYRAZINE COMPOUNDS AND USES THEREOF

(71) Applicant: Dizal (Jiangsu) Pharmaceutical Co., Ltd., Shanghai (CN)

(72) Inventors: Changhe Qi, Shanghai (CN); Honchung Tsui, Shanghai (CN); Qingbei Zeng, Shanghai (CN); Zhenfan Yang, Shanghai (CN); Xiaolin Zhang, Shanghai (CN)

(73) Assignee: DIZAL (JIANGSU) PHARMACEUTICAL CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/029,013

(22) Filed: Sep. 22, 2020

(65) Prior Publication Data
US 2021/0251989 A1 Aug. 19, 2021

Related U.S. Application Data

(63) Continuation of application No. 16/910,308, filed on Jun. 24, 2020, now Pat. No. 10,898,481, which is a continuation of application No. PCT/CN2019/100996, filed on Aug. 16, 2019.

(30) Foreign Application Priority Data

Aug. 17, 2018 (WO) ................ PCT/CN2018/101006

(51) Int. Cl.
| | |
|---|---|
| C07D 403/14 | (2006.01) |
| A61K 31/497 | (2006.01) |
| A61K 33/243 | (2019.01) |
| A61K 31/136 | (2006.01) |
| A61K 31/337 | (2006.01) |
| A61K 31/501 | (2006.01) |
| A61K 31/704 | (2006.01) |
| A61K 31/7048 | (2006.01) |
| A61K 39/395 | (2006.01) |
| C07D 401/04 | (2006.01) |
| C07D 401/14 | (2006.01) |
| C07D 405/04 | (2006.01) |
| C07D 405/14 | (2006.01) |
| C07D 413/14 | (2006.01) |
| C07D 417/14 | (2006.01) |
| C07D 471/04 | (2006.01) |

(52) U.S. Cl.
CPC .......... *A61K 31/497* (2013.01); *A61K 31/136* (2013.01); *A61K 31/337* (2013.01); *A61K 31/501* (2013.01); *A61K 31/704* (2013.01); *A61K 31/7048* (2013.01); *A61K 33/243* (2019.01); *A61K 39/3955* (2013.01); *C07D 401/04* (2013.01); *C07D 401/14* (2013.01); *C07D 405/04* (2013.01); *C07D 405/14* (2013.01); *C07D 413/14* (2013.01); *C07D 417/14* (2013.01); *C07D 471/04* (2013.01)

(58) Field of Classification Search
CPC .. C07D 401/14; C07D 401/04; C07D 403/14; A61K 31/497; A61K 31/5377
USPC ................. 544/120, 405; 514/235.8, 255.05
See application file for complete search history.

(56) References Cited

U.S. PATENT DOCUMENTS 10,898,481 B2 * 1/2021 Changehe et al. ... C07D 471/04
544/405

FOREIGN PATENT DOCUMENTS

| CN | 1871231 A | | 11/2006 | |
|---|---|---|---|---|
| CN | 1938296 A | | 3/2007 | |
| JP | WO 2005/040151 | * | 5/2005 | ........... C07D 401/04 |
| WO | WO 2019/018584 | * | 1/2019 | ........... C07D 241/10 |

OTHER PUBLICATIONS

Carmen Ochoa et al., "Anthelmintic activity of 6,7-Diaryl-pteridines", Arzneimittel-Forschung,vol. 46, No. 6, Dec. 30, 1996 (Dec. 30, 1996), pp. 643-648.
International Search Report of PCT Application No. PCT/CN2019/100996, dated Nov. 20, 2019.
Written Opinion of the International Searching Authority of PCT Application No. PCT/CN2019/100996, dated Nov. 20, 2019.

* cited by examiner

*Primary Examiner* — Jeffrey H Murray
(74) *Attorney, Agent, or Firm* — Jun He Law Offices P.C.; Zhaohui Wang

(57) ABSTRACT

The present disclosure novel pyrazine compounds targeting adenosine receptors (especially A1 and A2, particularly A2a). The present disclosure also relates to pharmaceutical compositions comprising one or more of the compounds as an active ingredient, and use of the compounds in the treatment of adenosine receptor (AR) associated diseases, for example cancer such as NSCLC, RCC, prostate cancer, and breast cancer.

22 Claims, No Drawings

PYRAZINE COMPOUNDS AND USES THEREOF

CROSS-REFERENCE TO RELATED APPLICATIONS

This application is a continuation of U.S. Ser. No. 16/910,308, filed on Jun. 24, 2020, which is a continuation of PCT Patent Application No. PCT/CN2019/100996, filed on Aug. 16, 2019, which claims foreign priority of PCT Patent Application No. PCT/2018/101006, filed on Aug. 17, 2018, now abandoned. Each of these applications is hereby incorporated by reference herein in its entirety.

FIELD OF THE DISCLOSURE

The present disclosure relates to novel pyrazine compounds targeting adenosine receptors (especially A1 and A2, particularly A2a). The present disclosure also relates to pharmaceutical compositions comprising one or more of the compounds as an active ingredient, and use of the compounds in the treatment of adenosine receptor (AR) associated diseases, for example cancer such as non-small cell lung cancer (NSCLC), renal cell carcinoma (RCC), prostate cancer, and breast cancer.

BACKGROUND

Adenosine is a naturally occurring nucleoside, which elicits a variety of physiological responses by interacting with a family of adenosine receptors. Four subtypes of adenosine receptors (A1, A2a, A2b, and A3) in humans have been differentiated based on their biochemical and pharmacological properties such as ligand binding characteristics, glycosylations, and functions.

The inflammatory response helps eliminate harmful agents from the body, but inflammation is also a non-specific response that can harm healthy tissue. There is a wide range of pathogenic insults that can initiate an inflammatory response including infection, allergens, autoimmune stimuli, immune response to transplanted tissue, noxious chemicals, and toxins, ischemia/reperfusion, hypoxia, mechanical and thermal trauma, as well as growth of tumors.

It is reported that adenosine receptors play a non-redundant role in down-regulation of inflammation in vivo by acting as a physiological "STOP" (a termination mechanism) that can limit the immune response and thereby protect normal tissues form excessive immune damage during pathogenesis of different diseases. Adenosine receptors, such as A2a, A2b, and A3, are shown to down-regulate the immune response during inflammation and protect tissues from immune damage. Inhibition of signaling through the adenosine receptor can be used to intensify and prolong the immune response. Adenosine suppresses prolonged inflammation acting through the A2a adenosine receptor (Ohta et al., Nature 2001; 414:916-920). A2b adenosine receptor has been implicated in regulation of cell growth (See Adenosine A2b Receptors as Therapeutic Targets, Drug Dev Res 45:198; Feoktistov et al., Trends Pharmacol Sci 19:148-153).

Therefore, compounds that targeting adenosine receptors are needed as pharmacological tools and are of considerable interest as drugs for treating Adenosine receptor-associated diseases such as cancer (e.g., NSCLC, RCC, prostate cancer, or breast cancer), Parkinson disease, epilepsy, cerebral ischemia and stroke, depression, cognitive impairment, HIV, ADA-SCID, AHF and chronic heart failure, chronic obstructive pulmonary disease (COPD), or asthma.

SUMMARY

In one aspect, the present disclosure provides a compound represented by Formula (I):

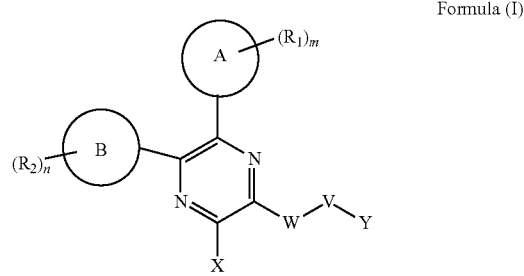

Formula (I)

or a pharmaceutically acceptable salt thereof, wherein X, ring A, ring B, W, V, Y, $R_1$, $R_2$, m and n are as herein defined.

In one aspect, the present disclosure provides a compound represented by Formula (Ia):

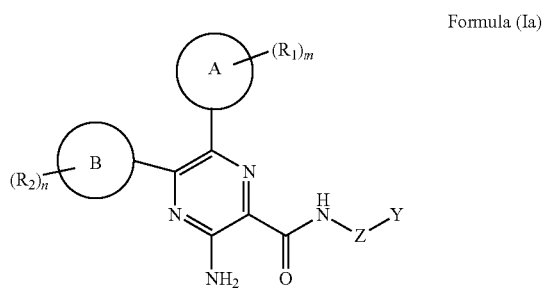

Formula (Ia)

or a pharmaceutically acceptable salt thereof, wherein ring A, ring B, Z, Y, $R_1$, $R_2$, m and n are as herein defined.

In one aspect, the present disclosure provides a compound represented by Formula (Ia-i):

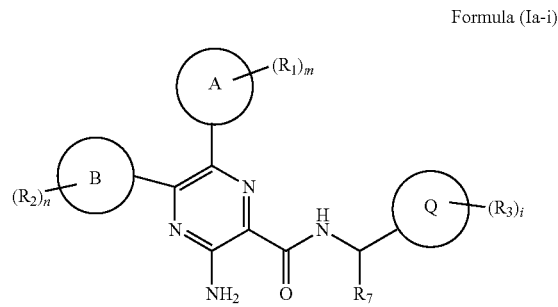

Formula (Ia-i)

or a pharmaceutically acceptable salt thereof, wherein ring A, ring B, ring Q, $R_1$, $R_2$, $R_3$, $R_7$, m, n and i are as herein defined.

In one aspect, the present disclosure provides a compound represented by Formula (Ia-ii):

Formula (Ia-ii)

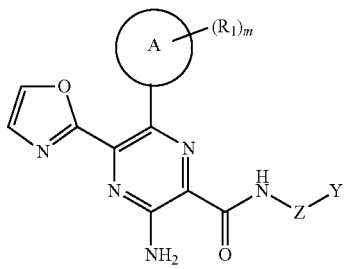

or a pharmaceutically acceptable salt thereof, wherein ring A, Z, Y, $R_1$, and m are as herein defined.

In one aspect, the present disclosure provides a compound represented by Formula (Ib):

Formula (Ib)

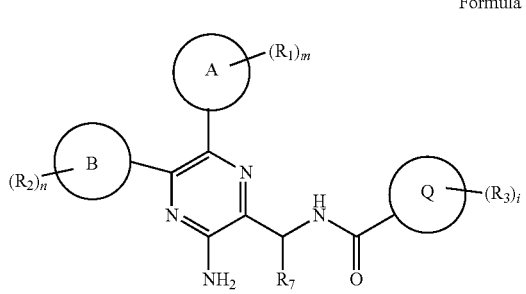

or a pharmaceutically acceptable salt thereof, wherein ring A, ring B, ring Q, $R_1$, $R_2$, $R_3$, $R_7$, m, n and i are as herein defined.

In another aspect, the present disclosure also relates to pharmaceutical compositions comprising one or more of the compounds, or a pharmaceutically acceptable salt thereof, as an active ingredient, and use of the compounds, or a pharmaceutically acceptable salt thereof, in the treatment of adenosine receptors (AR) associated diseases, for example cancer, such as NSCLC, RCC, prostate cancer, or breast cancer.

DETAILED DESCRIPTION

In one aspect, the present disclosure provides compounds of Formula (I):

Formula (I)

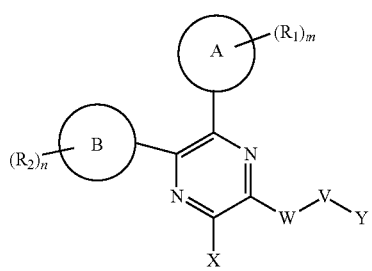

or a pharmaceutically acceptable salt thereof, wherein,

X is selected from amino, halogen, hydroxyl, cyano, $C_{1-12}$ alkoxyl, N—($C_{1-12}$ alkyl)amino, N,N—($C_{1-12}$ alkyl)$_2$amino, $C_{1-12}$ alkanoylamino;

ring A is 3-12 membered saturated or unsaturated mono- or poly-cyclic heterocyclyl; ring B is selected from 3-12 membered saturated or unsaturated carbocyclyl, or 3-12 membered saturated or unsaturated mono- or poly-cyclic heterocyclyl;

W is —$C_{1-12}$ alkylene- or —C(O)—, which can be mono or independently multi-substituted by hydroxyl, $C_{1-12}$ alkyl, $C_{1-12}$ alkoxyl, or $C_{1-12}$ alkyl-OH;

V is —NH—, —NH—$C_{1-12}$ alkylene-, —NH—C(O)—, or N-linked pyrrolidinyl, which can be mono or independently multi-substituted by hydroxyl, $C_{1-12}$ alkyl, $C_{1-12}$ alkoxyl, N—($C_{1-12}$ alkyl)amino, N,N—($C_{1-12}$ alkyl)$_2$amino or $C_{1-12}$ alkyl-OH;

Y is hydrogen, halogen, hydroxyl, cyano, amino, carbamoyl, urea, carbonyl, carbamate, sulphonyl, $C_{1-12}$ alkyl, $C_{1-12}$ alkoxyl, $C_{1-12}$ alkanoyl, $C_{1-12}$ alkyl-OH, $C_{1-12}$ alkyl-cyano, $C_{1-12}$ haloalkyl, $C_{1-12}$ haloalkoxyl, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkylsulphonyl, $C_{1-12}$ alkanoylamino, 3-12 membered saturated or unsaturated carbocyclyl, or 3-12 membered saturated or unsaturated heterocyclyl, which can be optionally mono- or independently multi-substituted by $R_3$;

each $R_1$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$ amino, N—($C_{1-12}$ alkyl)carbamoyl, N,N—($C_{1-12}$ alkyl)$_2$carbamoyl, $C_{1-12}$ alkanoylamino, a 3-10 membered saturated or unsaturated carbocyclyl, or a 3-10 membered saturated or unsaturated heterocyclyl, wherein each $R_1$ can be optionally further mono- or independently multi-substituted by $R_4$;

each $R_2$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$ amino, N—($C_{1-12}$ alkyl)carbamoyl, N,N—($C_{1-12}$ alkyl)$_2$carbamoyl, $C_{1-12}$ alkanoylamino, a 3-10 membered saturated or unsaturated carbocyclyl, or a 3-10 membered saturated or unsaturated heterocyclyl, wherein each $R_2$ can be optionally further mono- or independently multi-substituted by $R_5$;

each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$ amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_6$;

wherein each $R_4$, $R_5$ or $R_6$ is independently selected from halogen, hydroxyl, cyano, amino, carbamoyl, sulphonyl, phosphinyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, ($C_{1-12}$ alkyl) sulphonyl, ($C_{1-12}$ alkyl)phosphinyl, ($C_{1-12}$ alkyl)$_2$phosphinyl, $C_{1-12}$ alkanoylamino, $C_{1-12}$ alkylsulphonyl, and $C_{1-12}$ haloalkoxyl;

m is 0, 1, 2, 3 or 4; and n is 0, 1, 2, 3, or 4.

In some embodiments, X is selected from amino, N—(C$_{1-12}$ alkyl)amino, N,N—(C$_{1-12}$ alkyl)$_2$amino, or C$_{1-12}$ alkanoylamino.

In some embodiments, X is amino.

In some embodiments, ring A is 3-12 membered saturated or unsaturated mono- or poly-cyclic heterocyclyl having 1, 2, or 3 heteroatoms selected from N, O, or S.

In some embodiments, ring A is 6-10 membered unsaturated mono- or poly-cyclic heterocyclyl.

In some embodiments, ring A is selected from

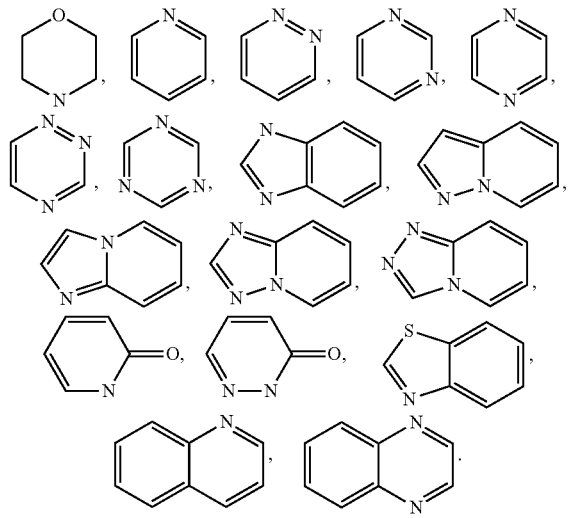

In some embodiments, ring A is selected from

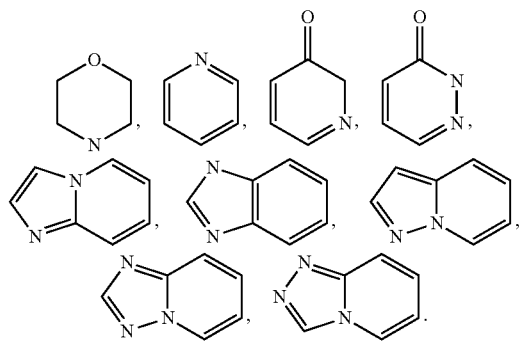

In some embodiments, each R$_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino or ethylamino, hydroxymethyl, hydroxyethyl, cyclopropyl, oxacyclopentanyl, oxetanyl, or 1,1-dioxothietanyl, which can be optionally further mono- or independently multi-substituted by R$_4$, wherein each R$_4$ is independently selected from halogen, hydroxyl, cyano, amino, C$_{1-12}$ alkyl, C$_{1-12}$ haloalkyl, C$_{1-12}$ alkoxyl, or C$_{1-12}$ haloalkoxyl.

In some embodiments, each R$_1$ is independently selected from amino, chloro, methyl, difluoromethyl, trifluoromethyl, aminomethyl, ethyl, hydroxyethyl, isopropyl, hydroxypropyl, methoxyethyl, 2-hydroxyl-n-propyl, cyclopropyl, and oxetanyl. In some embodiments, m is 0.

In some embodiments, m is 1.
In some embodiments, m is 2.
In some embodiments, m is 3.
In some embodiments, m is 4.
In some embodiments, m is 0, 1 or 2.

In some embodiments, ring B is 3-12 membered saturated or unsaturated mono- or poly-cyclic heterocyclyl having 1, 2, or 3 heteroatoms selected from N, O, or S.

In some embodiments, ring B is selected from:

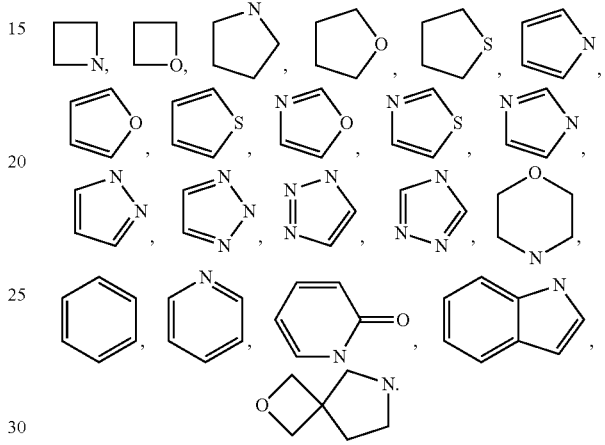

In some embodiments, ring B is selected from:

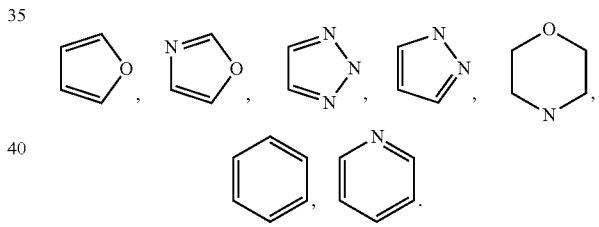

In some embodiments, each R$_2$ is independently selected from halogen, hydroxyl, amino, C$_{1-12}$ alkyl, or C$_{1-12}$ haloalkyl, wherein each R$_2$ can be optionally further mono- or independently multi-substituted by R$_5$ selected from halogen, hydroxyl, cyano, C$_{1-12}$ alkyl, C$_{1-12}$ haloalkyl, C$_{1-12}$ alkoxyl, or C$_{1-12}$ haloalkoxyl.

In some embodiments, each R$_2$ is independently selected from cyano, fluoro, chloro, bromo, methyl, ethyl, n-propyl, isopropyl, fluoromethyl, difluoromethyl, trifluoromethyl, fluoroethyl, difluoroethyl, trifluoroethyl, ethoxyl, methoxyl, difluoromethoxy, trifluoromethoxy, methylamino, dimethylamino, ethylamino, isopropanylamino, hydroxymethyl, or hydroxyethyl.

In some embodiments, each R$_2$ is independently fluoro or methyl.

In some embodiments, n is 0.
In some embodiments, n is 1.
In some embodiments, n is 2.
In some embodiments, n is 3.
In some embodiments, n is 4.
In some embodiments, n is 0, 1 or 2.
In some embodiments, W is methylene or —C(O)—.

In some embodiments, when W is methylene, V is —NH—C(O)—; when W is —C(O)—, V is —NH—, —NH—C$_{1-12}$ alkylene-, or N-linked pyrrolidinyl, which can be mono or independently multi-substituted by hydroxyl, C$_{1-12}$ alkyl, C$_{1-12}$ alkoxyl, or C$_{1-12}$ alkyl-OH.

In some embodiments, Y is hydrogen, hydroxyl, amino, cyano, carbonyl, carbamoyl, C$_{1-12}$ alkyl, C$_{1-12}$ alkyl-OH, C$_{1-12}$ alkoxyl, sulphonyl, (C$_{1-12}$ alkyl)sulphonyl, N—(C$_{12}$ alkyl)amino, N,N—(C$_{1-12}$ alkyl)$_2$amino, N—(C$_{1-12}$ alkyl)carbamoyl, N,N—(C$_{1-12}$ alkyl)$_2$carbamoyl, 3-12 membered saturated or unsaturated carbocyclyl or 3-12 membered saturated or unsaturated heterocyclyl, which can be optionally mono- or independently multi-substituted by R$_3$.

In some embodiments, Y is 3-12 membered saturated or unsaturated carbocyclyl or 3-12 membered saturated or unsaturated heterocyclyl selected from:

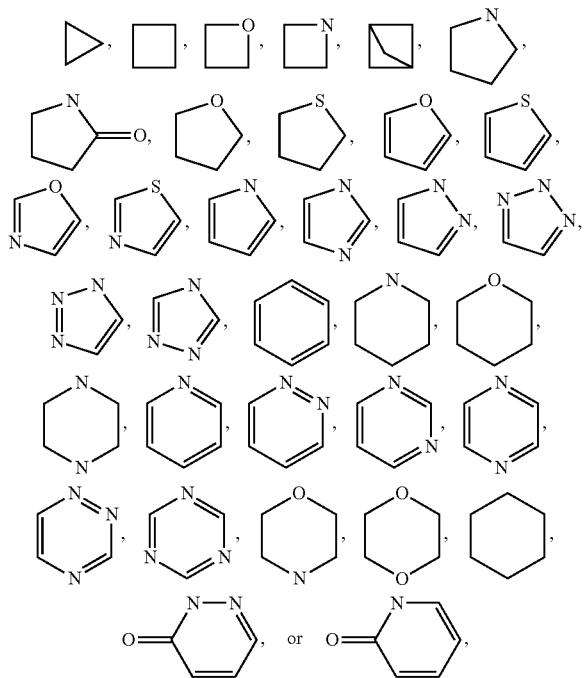

which can be optionally mono- or independently multi-substituted by R$_3$.

In some embodiments, Y is selected from:

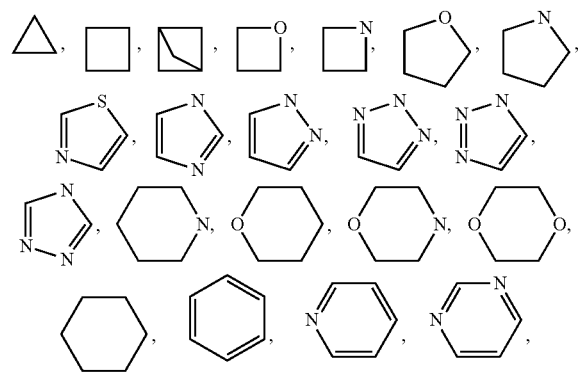

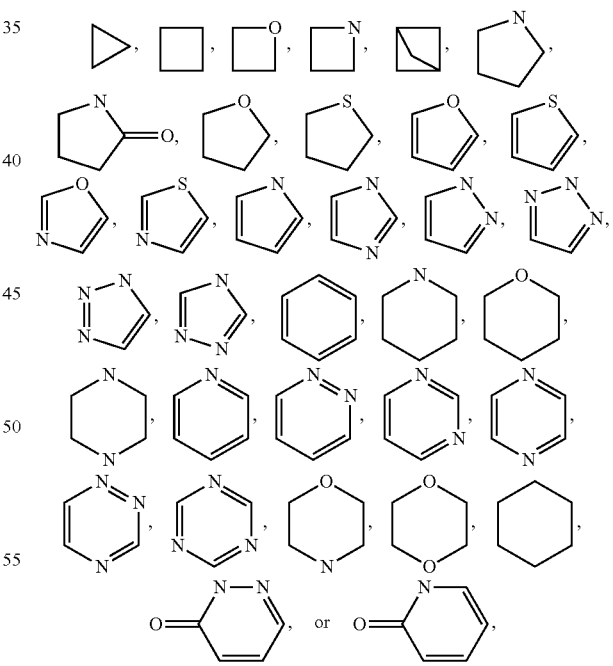

which can be optionally mono- or independently multi-substituted by R$_3$.

In some embodiments, Y is hydrogen, halogen, hydroxyl, cyano, amino, carbamoyl, urea, carbamate, sulphonyl, C$_{1-12}$ alkyl, C$_{1-12}$ alkoxyl, C$_{1-12}$ alkanoyl, C$_{1-12}$ alkyl-OH, C$_{1-12}$ alkyl-cyano, C$_{1-12}$ haloalkyl, C$_{1-12}$ haloalkoxyl, N—(C$_{1-12}$ alkyl)amino, N,N—(C$_{1-12}$ alkyl)$_2$amino, N—(C$_{1-12}$ alkyl)carbamoyl, N,N—(C$_{1-12}$ alkyl)$_2$carbamoyl, C$_{1-12}$ alkylsulphonyl, which can be optionally mono- or independently multi-substituted by R$_3$.

In some embodiments, each R$_3$ is independently selected from halogen, hydroxyl, cyano, amino, carbamoyl, urea, carbamate, sulphonyl, phosphate, phosphoryl, phosphinyl, C$_{1-12}$ alkyl, C$_{1-12}$ haloalkyl, C$_{1-12}$ alkoxyl, C$_{1-12}$ haloalkoxyl, C$_{1-12}$ alkyl-OH, N—(C$_{1-12}$ alkyl)amino, N,N—(C$_{1-12}$ alkyl)$_2$amino, N—(C$_{3-12}$ cycloalkyl)amino, N—(C$_{1-12}$ alkyl)carbamoyl, N,N—(C$_{1-12}$ alkyl)$_2$carbamoyl, (C$_{1-12}$ alkyl)sulphonyl, (C$_{1-12}$ alkyl)phosphinyl, (C$_{1-12}$ alkyl)$_2$phosphinyl, (C$_{1-12}$ alkyl)phosphoryl, (C$_{1-12}$ alkyl)$_2$phosphoryl, C$_{1-12}$ alkanoylamino, N—(C$_{1-12}$ alkyl-OH)amino, C$_{1-12}$ haloalkoxyl, a 3-10 membered saturated or unsaturated carbocyclyl, or a 3-10 membered saturated or unsaturated heterocyclyl, wherein each R$_3$ can be optionally further mono- or independently multi-substituted by R$_5$. In some embodiments, each R$_3$ is independently selected from which can be optionally further mono- or independently multi-substituted by R$_6$.

In some embodiments, each R$_6$ is independently selected from halogen, hydroxyl, cyano, amino, carbamoyl, sulphonyl, urea, carbamate, C$_{1-12}$ alkyl, C$_{1-12}$ haloalkyl, C$_{1-12}$ alkoxyl, C$_{1-12}$ haloalkoxyl, C$_{1-12}$ alkyl-OH, N—(C$_{1-12}$ alkyl)amino, N,N—(C$_{1-12}$ alkyl)$_2$amino, N—(C$_{1-12}$ alkyl)carbamoyl, N,N—($C_{1-12}$ alkyl)$_2$carbamoyl, $C_{1-12}$ alkanoylamino, $C_{1-12}$ alkylsulphonyl, $C_{1-12}$ haloalkoxyl or $C_{1-12}$ alkyl substituted cycloalkyl.

In some embodiments, each $R_3$ is independently selected from: hydroxyl, amino, cyano, carbamoyl, sulphonyl, phosphoryl, phosphinyl, fluoro, chloro, bromo, methyl, ethyl, n-propyl, isopropyl, methoxyl, ethoxyl, ethylamino, hydroxyethyl, hydroxymethyl, hydroxyethoxyl, sulphonylmethyl, aminomethyl, cyclopropyl, cyclopropylcarbonyl, cyclobutylamino, cyclopropyl, cyclobutanyl, cyclohexyl, pyranyl, furanyl, phenyl, pyridinyl, pyrazinyl, piperazinyl, morpholinyl, azetidinyl, pyrrolidinyl, piperidinyl, 1,4-oxanyl, bicycle[1.1.1]petanyl, 1,6-diazaspiro[3.3]heptanyl, 2,6-diazaspiro[3.3]heptanyl, 2,6-diazaspiro[3.4]octanyl, 3,6-diazabicyclo[3.1.1]heptanyl, 2,5-diazabicyclo[2.2.1]heptanyl, and 3,8-diazabicyclo[3.2.1]octanyl, which can be optionally further mono- or independently multi-substituted by fluoro, hydroxyl, methoxyl, ethyoxyl, amino, methylamino, dimethylamino, sulphonyl, methylsulphonyl, carbamoyl, N-methylcarbamoyl, N,N-dimethylcarbamoyl, hydroxymethyl, hydroxyethyl, cyclopropyl, cyclopropanecarbonyl.

In some embodiments, each $R_3$ is independently selected from: hydroxyl, cyano, fluoro, chloro, bromo, methyl, fluoromethyl, difluoromethyl, trifluoromethyl, methoxyl, difluoromethoxyl, trifluoromethoxyl, amino, methylamino, dimethylamino, hydroxyethoxy, methylaminoethoxyl, dimethylaminoethoxyl, hydroxyethylamino, aminocarbonylmethoxyl, 2-hydroxyl-ethyl, methyoxymethyl, methylsulphonyl, methylsulphonylmethyl, N-methylcarbamoyl, N,N-dimethylcarbamoyl, dimethylaminomethyl, hydroxymethyl, dimethylphosphoryl, methylaminocarbonyl, methylaminocarbonylmethyl, dimethylaminocarbonyl, dimethylaminocarbonylmethyl, 2-methoxyl-ethyl, hydroxylethoxy, methylaminoethoxyl, cyclopropyl, cyclopropylcarbonyl, 3-(dimethylamino)cyclobutylamino, phenyl, pyridin-2-yl, azetidin-1-yl, pyrrolidin-1-yl, N-morpholinyl, 3-(dimethylamino)azetidin-1-yl, 4-methylpiperazin-1-yl, 1,6-diazaspiro[3.3]heptan-6-yl, 3-methyl-1,6-diazaspiro[3.3]heptan-6-yl, 3,8-diazabicyclo[3.2.1]octan-8-yl, 8-methyl-3,8-diazabicyclo[3.2.1]octan-8-yl, 3,8-diazabicyclo[3.2.1]octan-3-yl, 8-methyl-3,8-diazabicyclo[3.2.1]octan-3-yl, 3,6-diazabicyclo[3.1.1]heptan-6-yl, 3-methyl-3,6-diazabicyclo[3.1.1]heptan-6-yl, 2,6-diazaspiro[3.4]octan-2-yl, 6-methyl-2,6-diazaspiro[3.4]octan-2-yl, piperidinyl, piperazin-1-yl, 1-methylpiperidin-4-yl, 3-(dimethylamino)pyrrolidin, 3-(dimethylaminomethyl)azetidin-1-yl, 2,5-diazabicyclo[2.2.1]heptan-2-yl, 5-methyl-2,5-diazabicyclo[2.2.1]heptan-2-yl, 2,6-diazaspiro[3.3]heptan-2-yl, or 3,4-dimethylpiperazin-1-yl.

In some embodiments, Y is hydrogen, hydroxyl, amino, cyano, carbonyl, carbamoyl, methyl, ethyl, propyl, isopropyl, hydroxymethyl, hydroxyethyl, hydroxypropyl, methoxyl, ethoxyl, sulphonyl, methylamino, dimethylamino, methylcarbamoyl, dimethylcarbamoyl, 3-12 membered saturated or unsaturated carbocyclyl or 3-12 membered saturated or unsaturated heterocyclyl, which can be optionally mono- or independently multi-substituted by $R_3$, wherein each $R_3$ is independently selected from hydroxyl, methyl, fluoro, cyano, dimethylamino, dimethylcarbamoyl, hydroxyethyl, hydroxymethyl, methoxyl, trifluoromethyl, trifluoromethoxyl, methylsulphonyl, dimethylamino, methoxymethyl, methylcarbamoyl, phenyl, pyridinyl, cyclopropyl.

In some embodiments, Y is hydrogen, hydroxyl, cyano, carbamoyl, methyl, methoxyl, methoxymethyl, 1-methoxyethyl, 2-methoxy-ethyl, trifluoromethoxyl, trifluoromethoxymethyl, trifluoromethoxyethyl, 1-hydroxyl-ethyl, 2-hydroxyl-ethyl, methoxymethyl, methoxyethyl, methylamino, dimethylamino, methylsulphonyl, methylsulphonylmethyl, methylsulphonylethyl, methylcarbamoyl, dimethylcarbamoyl, dimethylaminomethyl, or piperidin-1-ylcarbonyl.

In another aspect, the present disclosure provides compounds of Formula (Ia):

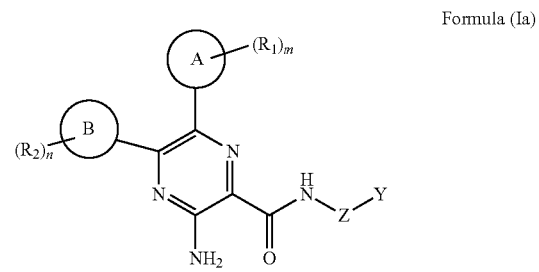

Formula (Ia)

or a pharmaceutically acceptable salt thereof,
wherein,
ring A is 6-10 membered saturated or unsaturated mono- or poly-cyclic heterocyclyl having 1, 2, or 3 heteroatoms selected from N, O, or S;
ring B is 5-6 membered saturated or unsaturated carbocyclyl, or 5-6 membered saturated or unsaturated heterocyclyl;
Z is —$C_{1-12}$ alkylene- or bond;
Y is hydrogen, amino, carbamoyl, carbonyl, sulphonyl, $C_{1-12}$ alkyl, $C_{1-12}$ alkoxyl, $C_{1-12}$ alkyl-OH, $C_{1-12}$ alkylcyano, $C_{1-12}$ haloalkyl, $C_{1-12}$ haloalkoxyl, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkylsulphonyl, $C_{1-12}$ alkanoylamino, 3-6 membered saturated or unsaturated carbocyclyl, or 3-6 membered saturated or unsaturated heterocyclyl, which can be optionally mono- or independently multi-substituted by $R_3$;
each $R_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino or ethylamino, hydroxymethyl, hydroxyethyl, cyclopropyl, oxacyclopentanyl, oxetanyl, or 1,1-dioxothietanyl, which can be optionally further mono- or independently multi-substituted by $R_4$;
each $R_2$ is independently halogen, hydroxyl, amino, $C_{1-12}$ alkyl, or $C_{1-12}$ haloalkyl, wherein each $R_2$ can be optionally further mono- or independently multi-substituted by $R_5$;
each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_6$;

each $R_4$ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl;

each $R_5$ is independently selected from halogen, hydroxyl, cyano, $C_{1-12}$ alkyl, $C_{1-12}$ haloalkyl, $C_{1-12}$ alkoxyl, or $C_{1-12}$ haloalkoxyl;

each $R_6$ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, $C_{1-12}$ alkylsulphonyl, $C_{1-12}$ haloalkoxyl or $C_{1-12}$ alkyl substituted cycloalkyl;

m is 0, 1, 2, 3 or 4; and n is 0, 1, 2, 3 or 4.

In some embodiments, Z is bond, Y is cyclobutyl mono-substituted by $C_{1-12}$ alkoxyl, optionally by methoxyl.

In some embodiments, Z is ethylene, Y is methoxyl.

In another aspect, the present disclosure provides compounds of formula (Ia-i):

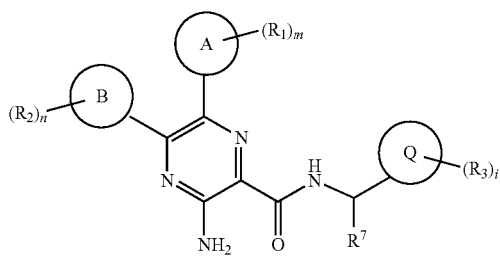

Formula (Ia-i)

or a pharmaceutically acceptable salt thereof,
wherein, ring A is 6-10 membered saturated or unsaturated mono- or poly-cyclic heterocyclyl having 1, 2, or 3 heteroatoms selected from N, O, or S;

ring B is 5-6 membered saturated or unsaturated carbocyclyl, or 5-6 membered saturated or unsaturated heterocyclyl;

ring Q is 3-6 membered saturated or unsaturated carbocyclyl, or 3-6 membered saturated or unsaturated heterocyclyl;

each $R_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino or ethylamino, hydroxymethyl, hydroxyethyl, cyclopropyl, oxacyclopentanyl, oxetanyl, or 1,1-dioxothietanyl, which can be optionally further mono- or independently multi-substituted by $R_4$;

each $R_2$ is independently halogen, hydroxyl, amino, $C_{1-12}$ alkyl, or $C_{1-12}$ haloalkyl, wherein each $R_2$ can be optionally further mono- or independently multi-substituted by $R_5$;

each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_6$;

each $R_4$ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl;

each $R_5$ is independently selected from halogen, hydroxyl, cyano, $C_{1-12}$ alkyl, $C_{1-12}$ haloalkyl, $C_{1-12}$ alkoxyl, or $C_{1-12}$ haloalkoxyl;

each $R_6$ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, $C_{1-12}$ alkylsulphonyl, $C_{1-12}$ haloalkoxyl or $C_{1-12}$ alkyl substituted cycloalkyl;

$R_7$ is hydrogen, $C_{1-12}$ alkyl, $C_{1-12}$ alkoxyl, or $C_{1-12}$ alkyl-OH;

m is 0, 1, 2, 3 or 4;

n is 0, 1, 2, 3 or 4; and i is 0, 1, 2, 3 or 4.

In some embodiments, $R_7$ is hydrogen, methyl, or ethyl.

In some embodiments, ring Q is selected from:

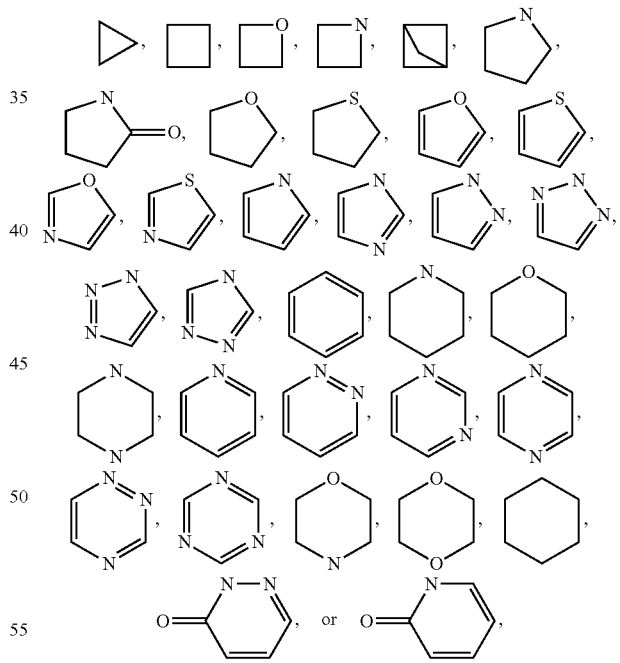

In some embodiments, i is 0.

In some embodiments, i is 1.

In some embodiments, i is 2.

In some embodiments, i is 3.

In some embodiments, i is 4.

In some embodiments, i is 0, 1, 2 or 3.

In yet another aspect, the present disclosure provides compounds of formula (Ia-ii):

Formula (Ia-ii)

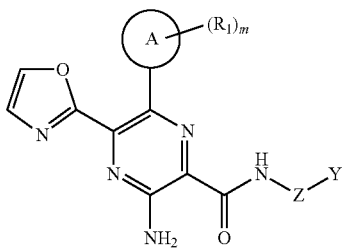

or a pharmaceutically acceptable salt thereof,
wherein,
ring A is 6-10 membered saturated or unsaturated mono- or poly-cyclic heterocyclyl having 1, 2, or 3 heteroatoms selected from N, O, or S;
Z is —$C_{1-12}$ alkylene- or bond;
Y is hydrogen, $C_{1-12}$ alkyl, $C_{1-12}$ alkoxyl, $C_{1-12}$ alkyl-OH, 3-6 membered saturated or unsaturated carbocyclyl, or 3-6 membered saturated or unsaturated heterocyclyl, which can be optionally mono- or independently multi-substituted by $R_3$;
each $R_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino or ethylamino, hydroxymethyl, hydroxyethyl, cyclopropyl, oxacyclopentanyl, oxetanyl, or 1,1-dioxothietanyl, which can be optionally further mono- or independently multi-substituted by $R_4$;
each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_6$;
each $R_4$ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl;
each $R_6$ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, $C_{1-12}$ alkylsulphonyl, $C_{1-12}$ haloalkoxyl or $C_{1-12}$ alkyl substituted cycloalkyl; and
m is 0, 1, 2, 3 or 4.
In some embodiments, ring A is pyridonyl or azaindolizinyl.
In some embodiments, m is 1 and R is $C_{1-12}$ alkyl, optionally $C_{1-3}$ alkyl, optionally methyl.
In some embodiments, Z is bond, Y is cyclobutyl mono-substituted by methoxyl.
In some embodiments, Z is ethylene, Y is methoxyl.

In some embodiments, Z is methylene, Y is phenyl, pyrrolidyl, or tetrahydrofuryl, which can be optionally mono- or independently multi-substituted by $R_3$.
In some embodiments, $R_3$ is halogen or $C_{1-12}$ alkyl.
In some embodiments, $R_3$ is fluoro or methyl.
In another aspect, the present disclosure provides compounds of formula (Ib):

Formula (Ib)

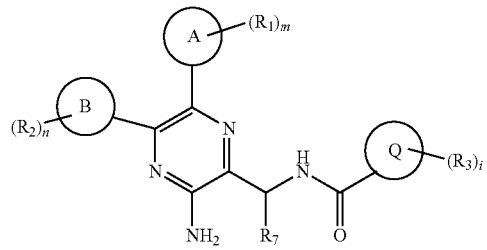

or a pharmaceutically acceptable salt thereof,
wherein,
ring A is 6-10 membered saturated or unsaturated mono- or poly-cyclic heterocyclyl having 1, 2, or 3 heteroatoms selected from N, O, or S;
ring B is 5-6 membered saturated or unsaturated carbocyclyl, or 5-6 membered saturated or unsaturated heterocyclyl;
ring Q is 3-6 membered saturated or unsaturated carbocyclyl, or 3-6 membered saturated or unsaturated heterocyclyl;
$R_7$ is hydrogen, $C_{1-12}$ alkyl, $C_{1-12}$ alkoxyl, or $C_{1-12}$ alkyl-OH;
each $R_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino or ethylamino, hydroxymethyl, hydroxyethyl, cyclopropyl, oxacyclopentanyl, oxetanyl, or 1,1-dioxothietanyl, which can be optionally further mono- or independently multi-substituted by $R_4$;
each $R_2$ is independently halogen, hydroxyl, amino, $C_{1-12}$ alkyl, or $C_{1-12}$ haloalkyl, wherein each $R_2$ can be optionally further mono- or independently multi-substituted by $R_5$;
each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_5$;
each $R_4$ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl;
each $R_5$ is independently selected from halogen, hydroxyl, cyano, $C_{1-12}$ alkyl, $C_{1-12}$ haloalkyl, $C_{1-12}$ alkoxyl, or $C_{1-12}$ haloalkoxyl;

each $R_6$ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, $C_{1-12}$ alkylsulphonyl, $C_{1-12}$ haloalkoxyl or $C_{1-12}$ alkyl substituted cycloalkyl;

m is 0, 1, 2, 3 or 4;

n is 0, 1, 2, 3 or 4; and i is 0, 1, 2, 3 or 4.

In some embodiments, ring A is selected from

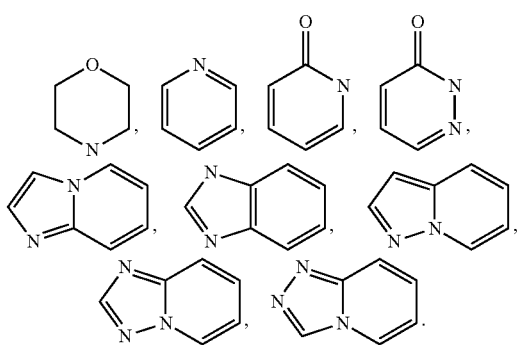

In some embodiments, each $R_1$ is independently selected from fluoro, chloro, amino, methyl, ethyl, isopropyl, fluoromethyl, difluoromethyl, trifluoromethyl, hydroxyethyl, hydroxypropyl, methoxyethyl, 2-hydroxypropyl, cyclopropyl, or oxetanyl.

In some embodiments, m=0, 1 or 2.

In some embodiments, ring B is selected from:

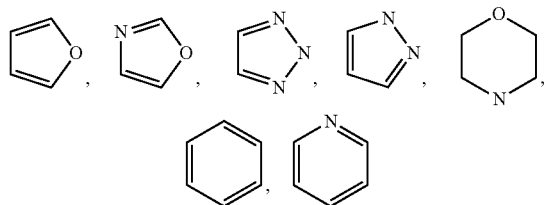

In some embodiments, $R_2$ is methyl or fluoro.

In some embodiments, n=0 or 1.

In some embodiments, ring Q is selected from:

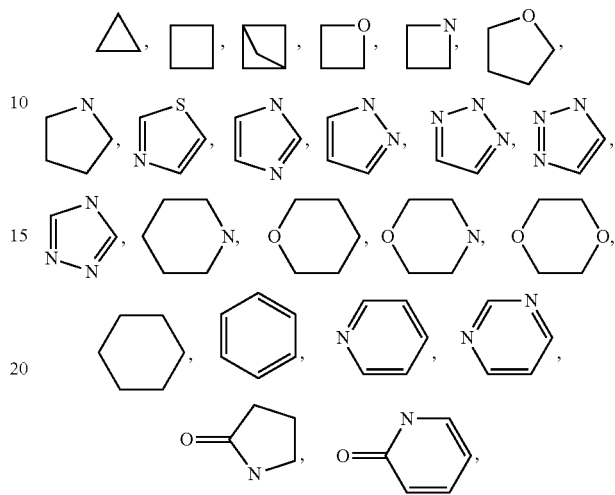

In some embodiments, each $R_3$ is independently selected from fluoro, chloro, bromo, cyano, methyl, ethyl, fluoromethyl, difluoromethyl, trifluoromethyl, methoxyl, ethoxyl, difluoromethoxyl, trifluoromethoxyl, trifluoroethoxyl, hydroxymethyl, hydroxyethyl, hydroxyethyloxyl, methoxyethyloxyl, amino, methylamino, dimethylamino, ethylamino, isopropylamino, hydroxyethylamino, methylaminoethyloxyl, dimethylaminoethyloxyl, dimethylphosphinylmethyl, carbamoyl, carbamoylmethoxyl, azetidinyl, pyrrolidyl, morpholinyl, pyrazinyl, dimethylaminoazetidinyl, 1-methyl-pyrazin-4-yl, 3-methyl-3,8-diaza-bicyclo[3.2.1]octan-8-yl, 3-Methyl-3,6-diaza-bicyclo[3.1.1]heptanyl, 8-methyl-3,8-diaza-bicyclo[3.2.1]octan-3-yl, 6-methyl-2,6-diaza-spiro[3.4]octan-2-yl, or 5-methyl-2,5-diaza-spiro[3.3]-heptan-2-yl.

In some embodiments, i=0, 1, 2 or 3.

In one aspect, the present disclosure provides a compound of Formula (I) selected from exemplary compounds 1-306 in Table 1 below.

TABLE 1

| Compound number | Compound structure | Compound name |
|---|---|---|
| 1 | 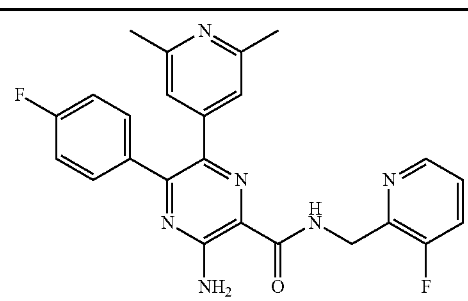 | 3-amino-6-(2,6-dimethylpyridin-4-yl)-5-(4-fluorophenyl)-N-((3-fluoropyridin-2-yl)methyl)pyrazine-2-carboxamide |

TABLE 1-continued

Exemplary Compound 1-306

| Compound number | Compound structure | Compound name |
|---|---|---|
| 2 | 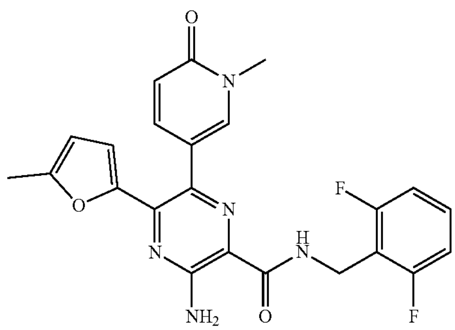 [SMILES: Cc1ccc(-c2nc(N)c(C(=O)NCc3c(F)cccc3F)nc2-c2ccc(=O)n(C)c2)o1] | 3-amino-N-(2,6-difluorobenzyl)-6-(1-methyl-6-oxo-1,6-dihydropyridin-3-yl)-5-(5-methylfuran-2-yl)pyrazine-2-carboxamide |
| 3 | 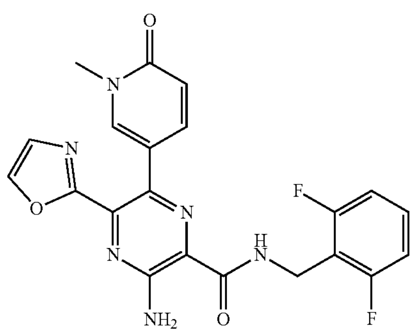 [SMILES: Cn1cc(-c2nc(C(=O)NCc3c(F)cccc3F)c(N)nc2-c2ncco2)ccc1=O] | 3-amino-N-(2,6-difluorobenzyl)-6-(1-methyl-6-oxo-1,6-dihydropyridin-3-yl)-5-(oxazol-2-yl)pyrazine-2-carboxamide |
| 4 | 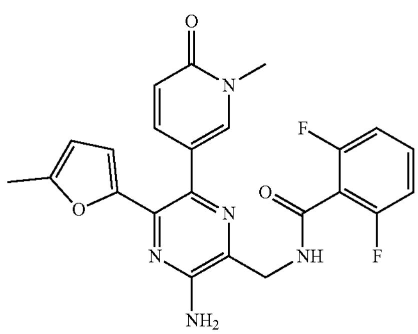 [SMILES: Cc1ccc(-c2nc(N)c(CNC(=O)c3c(F)cccc3F)nc2-c2ccc(=O)n(C)c2)o1] | N-((3-amino-6-(1-methyl-6-oxo-1,6-dihydropyridin-3-yl)-5-(5-methylfuran-2-yl)pyrazin-2-yl)methyl)-2,6-difluorobenzamide |
| 5 | 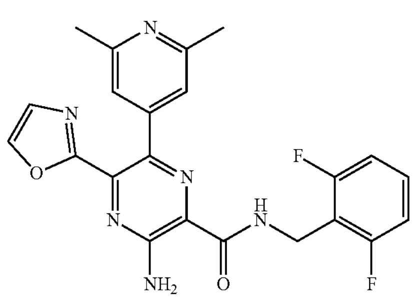 [SMILES: Cc1cc(-c2nc(C(=O)NCc3c(F)cccc3F)c(N)nc2-c2ncco2)cc(C)n1] | 3-amino-N-(2,6-difluorobenzyl)-6-(2,6-dimethylpyridin-4-yl)-5-(oxazol-2-yl)pyrazine-2-carboxamide |

TABLE 1-continued

Exemplary Compound 1-306

| Compound number | Compound structure | Compound name |
|---|---|---|
| 6 | 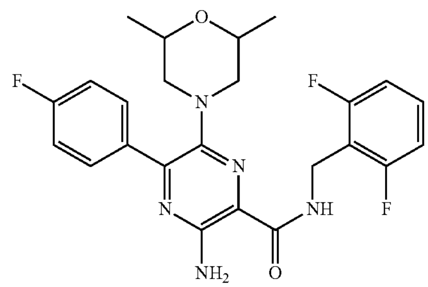 [SMILES: CC1CN(c2nc(C(=O)NCc3c(F)cccc3F)c(N)nc2-c2ccc(F)cc2)CC(C)O1] | 3-amino-N-(2,6-difluorobenzyl)-6-(2,6-dimethylmorpholino)-5-(4-fluorophenyl)pyrazine-2-carboxamide |
| 7 | 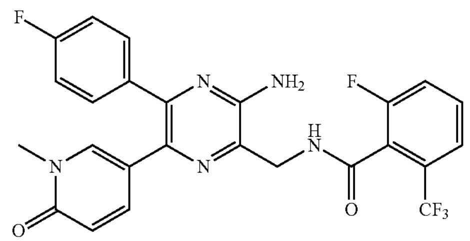 [SMILES: Cn1cc(-c2nc(CNC(=O)c3c(F)cccc3C(F)(F)F)c(N)nc2-c2ccc(F)cc2)ccc1=O] | N-((3-amino-5-(4-fluorophenyl)-6-(1-methyl-6-oxo-1,6-dihydropyridin-3-yl)pyrazin-2-yl)methyl)-2-fluoro-6-(trifluoromethyl)benzamide |
| 8 | 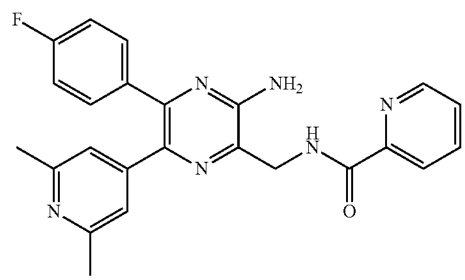 [SMILES: Cc1cc(-c2nc(CNC(=O)c3ccccn3)c(N)nc2-c2ccc(F)cc2)cc(C)n1] | N-((3-amino-6-(2,6-dimethylpyridin-4-yl)-5-(4-fluorophenyl)pyrazin-2-yl)methyl)picolinamide |
| 9 | 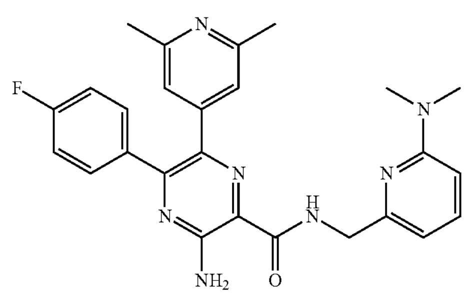 [SMILES: Cc1cc(-c2nc(C(=O)NCc3cccc(N(C)C)n3)c(N)nc2-c2ccc(F)cc2)cc(C)n1] | 3-amino-N-((6-(dimethylamino)pyridin-2-yl)methyl)-6-(2,6-dimethylpyridin-4-yl)-5-(4-fluorophenyl)pyrazine-2-carboxamide |
| 10 | 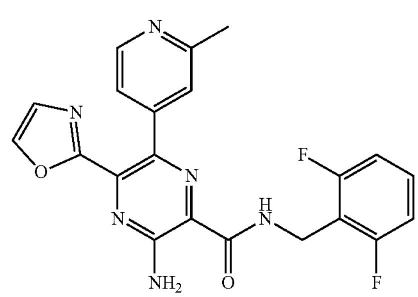 [SMILES: Cc1cc(-c2nc(C(=O)NCc3c(F)cccc3F)c(N)nc2-c2ncco2)ccn1] | 3-amino-N-(2,6-difluorobenzyl)-6-(2-methylpyridin-4-yl)-5-(oxazol-2-yl)pyrazine-2-carboxamide |

TABLE 1-continued

Exemplary Compound 1-306

| Compound number | Compound structure | Compound name |
|---|---|---|
| 11 | 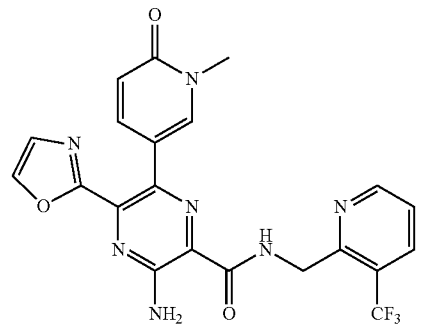 [SMILES: Cn1cc(-c2nc(C(=O)NCc3ncccc3C(F)(F)F)c(N)nc2-c2ncco2)ccc1=O] | 3-amino-6-(1-methyl-6-oxo-1,6-dihydropyridin-3-yl)-5-(oxazol-2-yl)-N-((3-(trifluoromethyl)pyridin-2-yl)methyl) pyrazine-2-carboxamide |
| 12 | 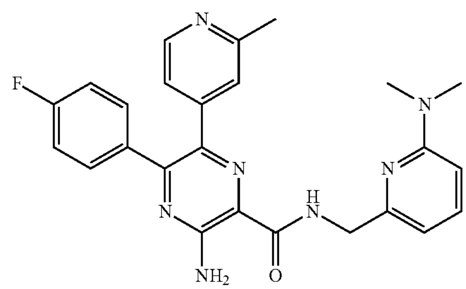 [SMILES: Cc1cc(-c2nc(C(=O)NCc3cccc(N(C)C)n3)c(N)nc2-c2ccc(F)cc2)ccn1] | 3-amino-N-((6-(dimethylamino) pyridin-2-yl)methyl)-5-(4-fluorophenyl)-6-(2-methylpyridin-4-yl)pyrazine-2-carboxamide |
| 13 | 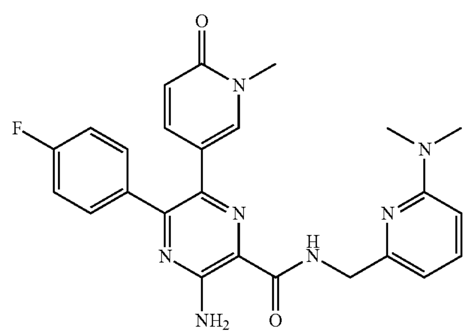 [SMILES: CN(C)c1cccc(CNC(=O)c2nc(-c3ccc(=O)n(C)c3)c(-c3ccc(F)cc3)nc2N)n1] | 3-amino-N-((6-(dimethylamino)pyridin-2-yl)methyl)-5-(4-fluorophenyl)-6-(1-methyl-6-oxo-1,6-dihydropyridin-3-yl) pyrazine-2-carboxamide |
| 14 | 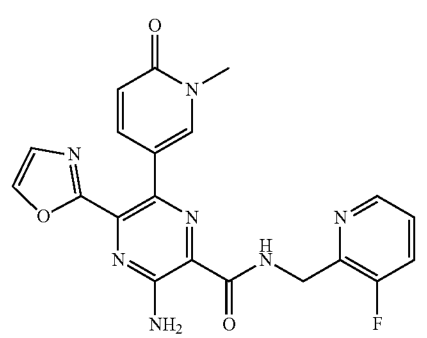 [SMILES: Cn1cc(-c2nc(C(=O)NCc3ncccc3F)c(N)nc2-c2ncco2)ccc1=O] | 3-amino-N-((3-fluoropyridin-2-yl) methyl)-6-(1-methyl-6-oxo-1,6-dihydropyridin-3-yl)-5-(oxazol-2-yl) pyrazine-2-carboxamide |

TABLE 1-continued

Exemplary Compound 1-306

| Compound number | Compound structure | Compound name |
|---|---|---|
| 15 | 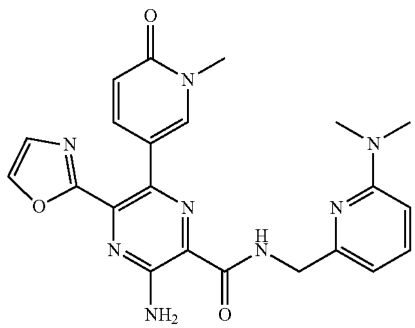 [SMILES: CN(C)c1cccc(CNC(=O)c2nc(-c3ccc(=O)n(C)c3)c(-c3ncco3)nc2N)n1] | 3-amino-N-((6-(dimethylamino)pyridin-2-yl)methyl)-6-(1-methyl-6-oxo-1,6-dihydropyridin-3-yl)-5-(oxazol-2-yl)pyrazine-2-carboxamide |
| 16 | 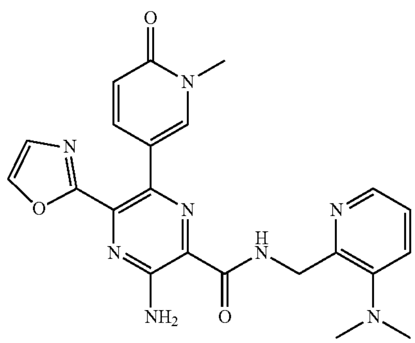 [SMILES: CN(C)c1cccnc1CNC(=O)c1nc(-c2ccc(=O)n(C)c2)c(-c2ncco2)nc1N] | 3-amino-N-((6-(dimethylamino)pyridin-2-yl)methyl)-6-(1-methyl-6-oxo-1,6-dihydropyridin-3-yl)-5-(oxazol-2-yl)pyrazine-2-carboxamide |
| 17 | 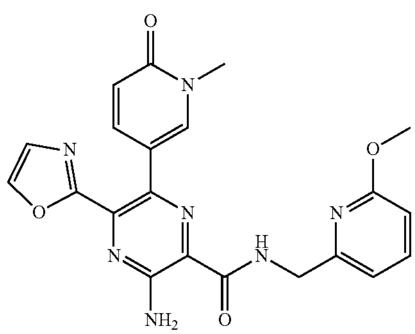 [SMILES: COc1cccc(CNC(=O)c2nc(-c3ccc(=O)n(C)c3)c(-c3ncco3)nc2N)n1] | 3-amino-N-((6-methoxypyridin-2-yl)methyl)-6-(1-methyl-6-oxo-1,6-dihydropyridin-3-yl)-5-(oxazol-2-yl)pyrazine-2-carboxamide |
| 18 | 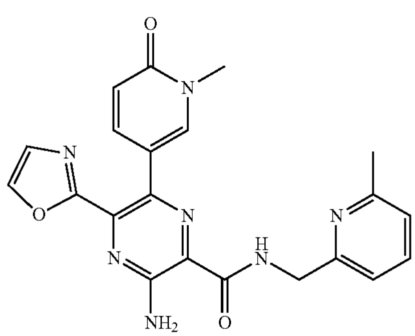 [SMILES: Cc1cccc(CNC(=O)c2nc(-c3ccc(=O)n(C)c3)c(-c3ncco3)nc2N)n1] | 3-amino-6-(1-methyl-6-oxo-1,6-dihydropyridin-3-yl)-N-((6-methylpyridin-2-yl)methyl)-5-(oxazol-2-yl)pyrazine-2-carboxamide |

TABLE 1-continued

Exemplary Compound 1-306

| Compound number | Compound structure | Compound name |
|---|---|---|
| 19 | 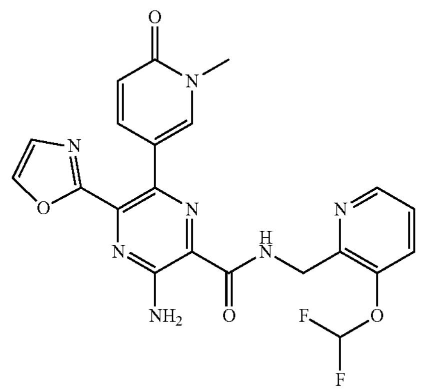 [SMILES: Cn1cc(-c2nc(C(=O)NCc3ncccc3OC(F)F)c(N)nc2-c2ncco2)ccc1=O] | 3-amino-N-((3-(difluoromethoxy)pyridin-2-yl)methyl)-6-(1-methyl-6-oxo-1,6-dihydropyridin-3-yl)-5-(oxazol-2-yl)pyrazine-2-carboxamide |
| 20 | 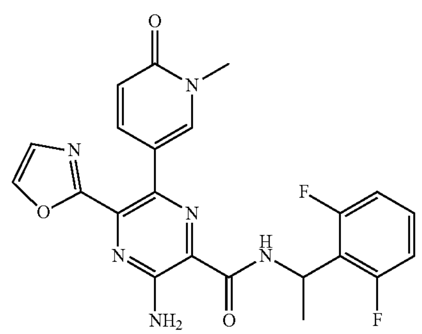 [SMILES: CC(NC(=O)c1nc(-c2ccc(=O)n(C)c2)c(-c2ncco2)nc1N)c1c(F)cccc1F] | 3-amino-N-(1-(2,6-difluorophenyl)ethyl)-6-(1-methyl-6-oxo-1,6-dihydropyridin-3-yl)-5-(oxazol-2-yl)pyrazine-2-carboxamide |
| 21 | 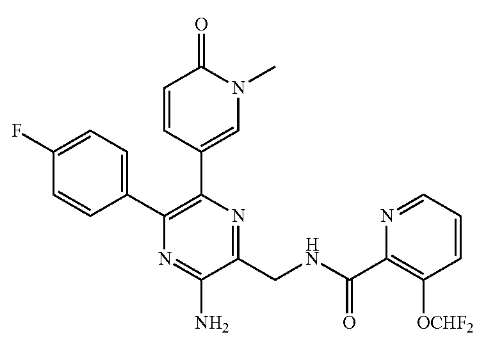 [SMILES: Cn1cc(-c2nc(CNC(=O)c3ncccc3OC(F)F)c(N)nc2-c2ccc(F)cc2)ccc1=O] | N-((3-amino-5-(4-fluorophenyl)-6-(1-methyl-6-oxo-1,6-dihydropyridin-3-yl)pyrazin-2-yl)methyl)-3-(difluoromethoxy)picolinamide |
| 22 | 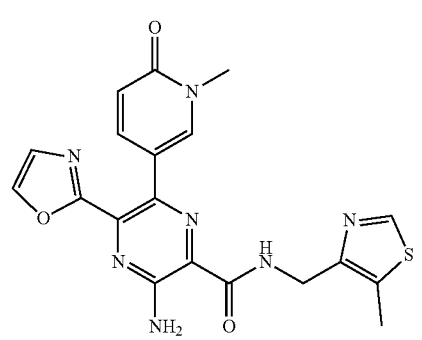 [SMILES: Cc1scnc1CNC(=O)c1nc(-c2ccc(=O)n(C)c2)c(-c2ncco2)nc1N] | 3-amino-6-(1-methyl-6-oxo-1,6-dihydropyridin-3-yl)-N-((5-methylthiazol-4-yl)methyl)-5-(oxazol-2-yl)pyrazine-2-carboxamide |

TABLE 1-continued

Exemplary Compound 1-306

| Compound number | Compound structure | Compound name |
|---|---|---|
| 23 | 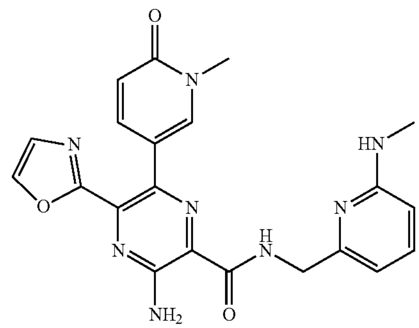 [SMILES: CNc1cccc(CNC(=O)c2nc(-c3ccc(=O)n(C)c3)c(-c3ncco3)nc2N)n1] | 3-amino-6-(1-methyl-6-oxo-1,6-dihydropyridin-3-yl)-N-((6-(methylamino)pyridin-2-yl)methyl)-5-(oxazol-2-yl)pyrazine-2-carboxamide |
| 24 | 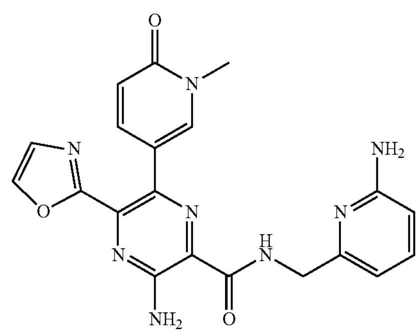 [SMILES: Cn1cc(-c2nc(C(=O)NCc3cccc(N)n3)c(N)nc2-c2ncco2)ccc1=O] | 3-amino-N-((6-aminopyridin-2-yl)methyl)-6-(1-methyl-6-oxo-1,6-dihydropyridin-3-yl)-5-(oxazol-2-yl)pyrazine-2-carboxamide |
| 25 | 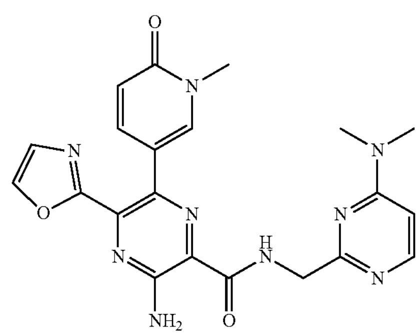 | 3-amino-N-((4-(dimethylamino)pyrimidin-2-yl)methyl)-6-(1-methyl-6-oxo-1,6-dihydropyridin-3-yl)-5-(oxazol-2-yl)pyrazine-2-carboxamide |
| 26 | 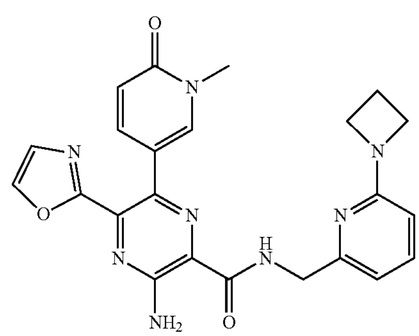 [SMILES: Cn1cc(-c2nc(C(=O)NCc3cccc(N4CCC4)n3)c(N)nc2-c2ncco2)ccc1=O] | 3-amino-N-((6-(azetidin-1-yl)pyridin-2-yl)methyl)-6-(1-methyl-6-oxo-1,6-dihydropyridin-3-yl)-5-(oxazol-2-yl)pyrazine-2-carboxamide |

TABLE 1-continued

Exemplary Compound 1-306

| Compound number | Compound structure | Compound name |
|---|---|---|
| 27 | 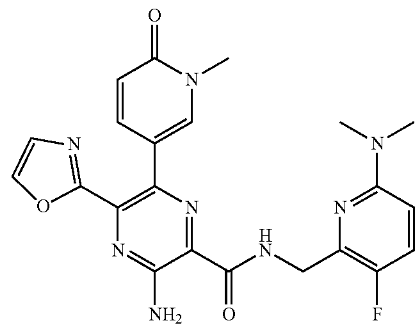 [SMILES: CN(C)c1ccc(F)c(CNC(=O)c2nc(-c3ccc(=O)n(C)c3)c(-c3ncco3)nc2N)n1] | 3-amino-N-(5-(dimethylamino)-2-fluorobenzyl)-6-(1-methyl-6-oxo-1,6-dihydropyridin-3-yl)-5-(oxazol-2-yl)pyrazine-2-carboxamide |
| 28 | 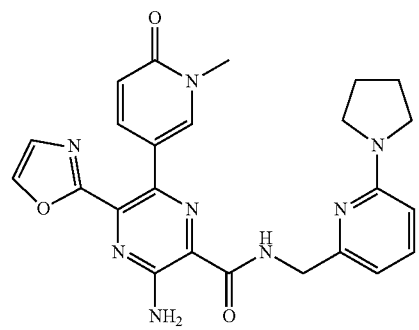 [SMILES: Cn1cc(-c2nc(C(=O)NCc3cccc(N4CCCC4)n3)c(N)nc2-c2ncco2)ccc1=O] | 3-amino-6-(1-methyl-6-oxo-1,6-dihydropyridin-3-yl)-5-(oxazol-2-yl)-N-((6-(pyrrolidin-1-yl)pyridin-2-yl)methyl)pyrazine-2-carboxamide |
| 29 | 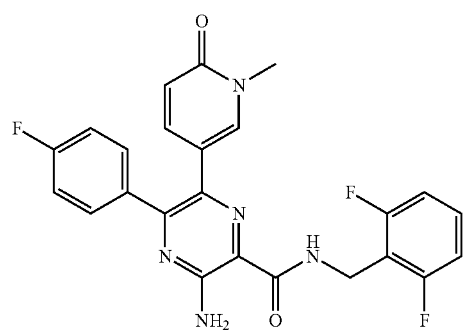 [SMILES: Cn1cc(-c2nc(C(=O)NCc3c(F)cccc3F)c(N)nc2-c2ccc(F)cc2)ccc1=O] | 3-amino-N-(2,6-difluorobenzyl)-5-(4-fluorophenyl)-6-(1-methyl-6-oxo-1,6-dihydropyridin-3-yl)pyrazine-2-carboxamide |
| 30 | 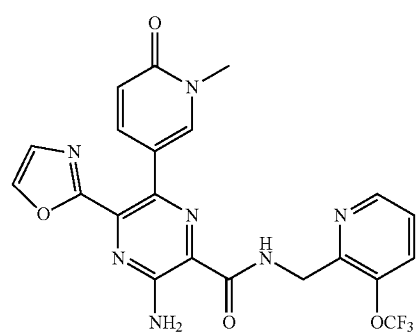 [SMILES: Cn1cc(-c2nc(C(=O)NCc3ncccc3OC(F)(F)F)c(N)nc2-c2ncco2)ccc1=O] | 3-amino-6-(1-methyl-6-oxo-1,6-dihydropyridin-3-yl)-5-(oxazol-2-yl)-N-((3-(trifluoromethoxy)pyridin-2-yl)methyl)pyrazine-2-carboxamide |

TABLE 1-continued

Exemplary Compound 1-306

| Compound number | Compound structure | Compound name |
|---|---|---|
| 31 | 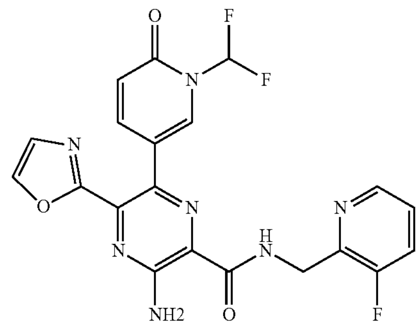 [SMILES: Nc1nc(-c2ncco2)c(-c2ccc(=O)n(C(F)F)c2)nc1C(=O)NCc1ncccc1F] | 3-amino-6-(1-(difluoromethyl)-6-oxo-1,6-dihydropyridin-3-yl)-N-((3-fluoropyridin-2-yl)methyl)-5-(oxazol-2-yl)pyrazine-2-carboxamide |
| 32 | 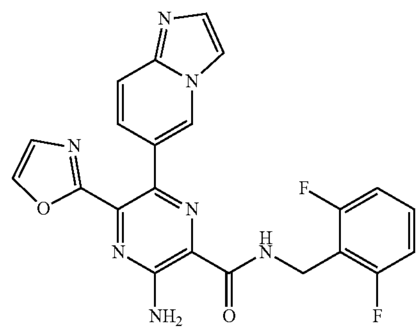 [SMILES: Nc1nc(-c2ncco2)c(-c2ccc3nccn3c2)nc1C(=O)NCc1c(F)cccc1F] | 3-amino-N-(2,6-difluorobenzyl)-6-(imidazo[1,2-a]pyridin-6-yl)-5-(oxazol-2-yl)pyrazine-2-carboxamide |
| 33 | 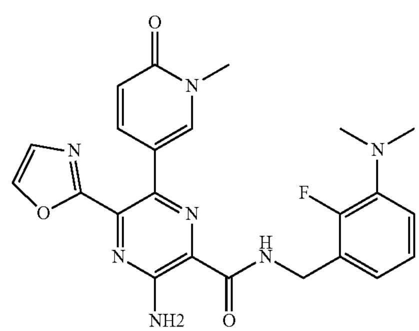 [SMILES: CN(C)c1cccc(CNC(=O)c2nc(-c3ccc(=O)n(C)c3)c(-c3ncco3)nc2N)c1F] | 3-amino-N-(3-(dimethylamino)-2-fluorobenzyl)-6-(1-methyl-6-oxo-1,6-dihydropyridin-3-yl)-5-(oxazol-2-yl)pyrazine-2-carboxamide |
| 34 | 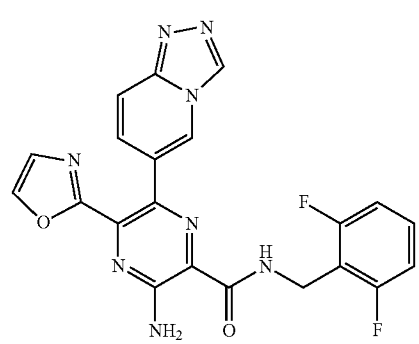 [SMILES: Nc1nc(-c2ncco2)c(-c2ccc3nncn3c2)nc1C(=O)NCc1c(F)cccc1F] | 6-([1,2,4]triazolo[4,3-a]pyridin-6-yl)-3-amino-N-(2,6-difluorobenzyl)-5-(oxazol-2-yl)pyrazine-2-carboxamide |

TABLE 1-continued

Exemplary Compound 1-306

| Compound number | Compound structure | Compound name |
|---|---|---|
| 35 | 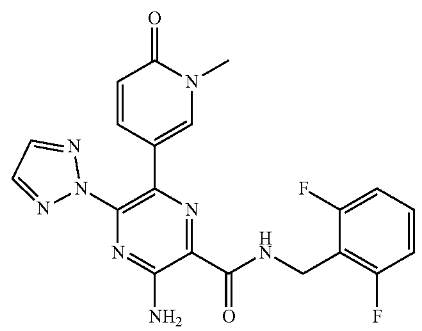 [SMILES: Cn1cc(-c2nc(C(=O)NCc3c(F)cccc3F)c(N)nc2-n2nccn2)ccc1=O] | 3-amino-N-(2,6-difluorobenzyl)-6-(1-methyl-6-oxo-1,6-dihydropyridin-3-yl)-5-(2H-1,2,3-triazol-2-yl)pyrazine-2-carboxamide |
| 36 | 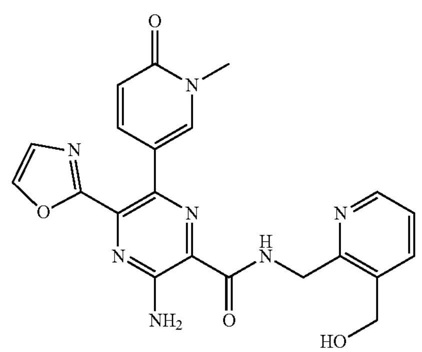 [SMILES: Cn1cc(-c2nc(C(=O)NCc3ncccc3CO)c(N)nc2-c2ncco2)ccc1=O] | 3-amino-N-((3-(hydroxymethyl)pyridin-2-yl)methyl)-6-(1-methyl-6-oxo-1,6-dihydropyridin-3-yl)-5-(oxazol-2-yl)pyrazine-2-carboxamide |
| 37 | 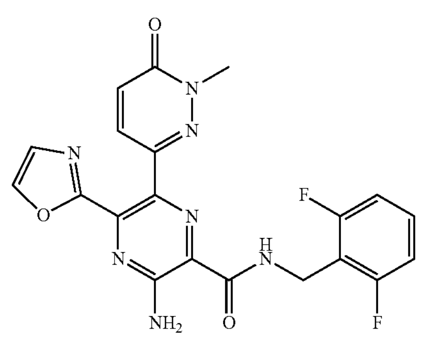 | 3-amino-N-(2,6-difluorobenzyl)-6-(1-methyl-6-oxo-1,6-dihydropyridazin-3-yl)-5-(oxazol-2-yl)pyrazine-2-carboxamide |
| 38 | 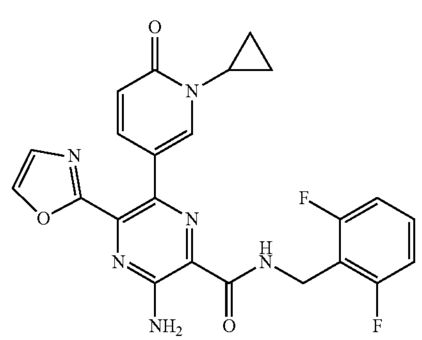 [SMILES: Nc1nc(-c2ncco2)c(-c2ccc(=O)n(C3CC3)c2)nc1C(=O)NCc1c(F)cccc1F] | 3-amino-6-(1-cyclopropyl-6-oxo-1,6-dihydropyridin-3-yl)-N-(2,6-difluorobenzyl)-5-(oxazol-2-yl)pyrazine-2-carboxamide |

TABLE 1-continued

Exemplary Compound 1-306

| Compound number | Compound structure | Compound name |
|---|---|---|
| 39 | 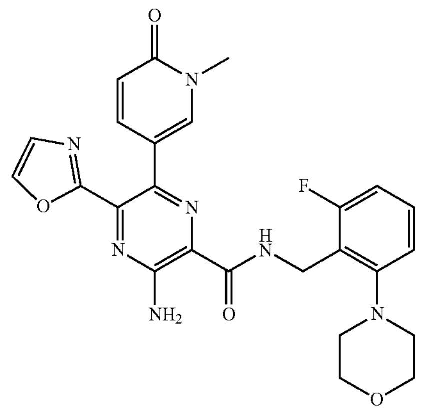 [SMILES: Cn1cc(-c2nc(C(=O)NCc3c(F)cccc3N3CCOCC3)c(N)nc2-c2ncco2)ccc1=O] | 3-amino-N-(2-fluoro-6-morpholinobenzyl)-6-(1-methyl-6-oxo-1,6-dihydropyridin-3-yl)-5-(oxazol-2-yl)pyrazine-2-carboxamide |
| 40-1/40-2 | 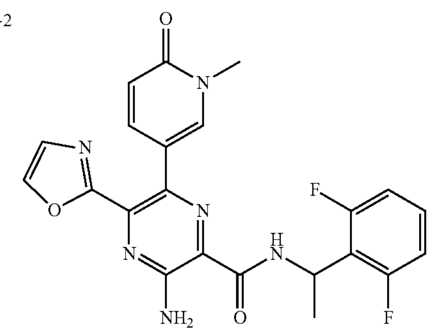 | 3-amino-N-(1-(2,6-difluorophenyl)ethyl)-6-(1-methyl-6-oxo-1,6-dihydropyridin-3-yl)-5-(oxazol-2-yl)pyrazine-2-carboxamide(isomer 1/(isomer 2) |
| 41 | 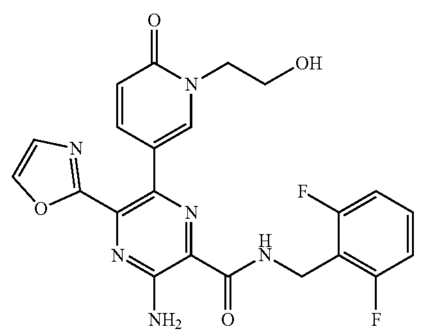 [SMILES: Nc1nc(-c2ncco2)c(-c2ccc(=O)n(CCO)c2)nc1C(=O)NCc1c(F)cccc1F] | 3-amino-N-(2,6-difluorobenzyl)-6-(1-(2-hydroxyethyl)-6-oxo-1,6-dihydropyridin-3-yl)-5-(oxazol-2-yl)pyrazine-2-carboxamide |
| 42 | 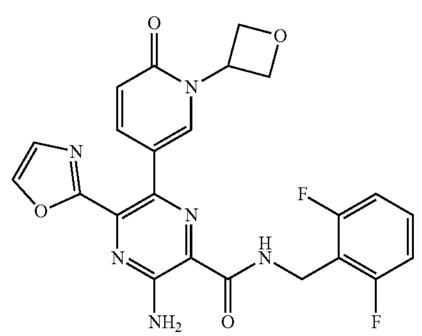 [SMILES: Nc1nc(-c2ncco2)c(-c2ccc(=O)n(C3COC3)c2)nc1C(=O)NCc1c(F)cccc1F] | 3-amino-N-(2,6-difluorobenzyl)-5-(oxazol-2-yl)-6-(1-(oxetan-3-yl)-6-oxo-1,6-dihydropyridin-3-yl)pyrazine-2-carboxamide |

TABLE 1-continued

Exemplary Compound 1-306

| Compound number | Compound structure | Compound name |
|---|---|---|
| 43 | 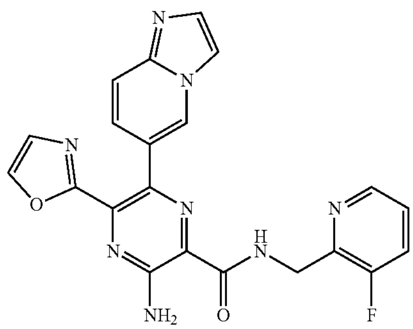 [SMILES: Nc1nc(-c2ncco2)c(-c2ccc3nccn3c2)nc1C(=O)NCc1ncccc1F] | 3-amino-N-((3-fluoropyridin-2-yl)methyl)-6-(imidazo[1,2-a]pyridin-6-yl)-5-(oxazol-2-yl)pyrazine-2-carboxamide |
| 44 | 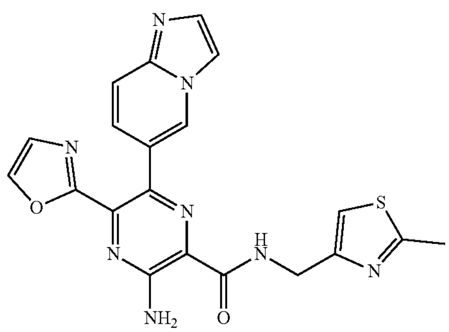 [SMILES: Cc1nc(CNC(=O)c2nc(-c3ccc4nccn4c3)c(-c3ncco3)nc2N)cs1] | 3-amino-6-(imidazo[1,2-a]pyridin-6-yl)-N-((2-methylthiazol-4-yl)methyl)-5-(oxazol-2-yl)pyrazine-2-carboxamide |
| 45 | 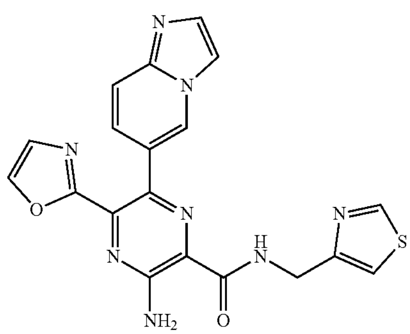 [SMILES: Nc1nc(-c2ncco2)c(-c2ccc3nccn3c2)nc1C(=O)NCc1cscn1] | 3-amino-6-(imidazo[1,2-a]pyridin-6-yl)-5-(oxazol-2-yl)-N-(thiazol-4-ylmethyl)pyrazine-2-carboxamide |
| 46 | 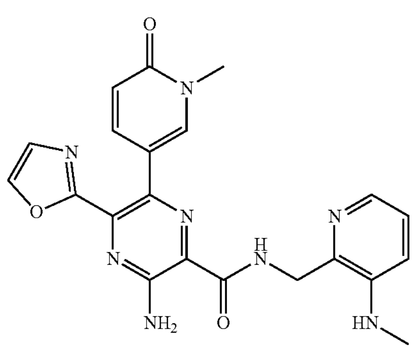 [SMILES: CNc1cccnc1CNC(=O)c1nc(-c2ccc(=O)n(C)c2)c(-c2ncco2)nc1N] | 3-amino-6-(1-methyl-6-oxo-1,6-dihydropyridin-3-yl)-N-((3-(methylamino)pyridin-2-yl)methyl)-5-(oxazol-2-yl)pyrazine-2-carboxamide |

TABLE 1-continued

Exemplary Compound 1-306

| Compound number | Compound structure | Compound name |
|---|---|---|
| 47 | 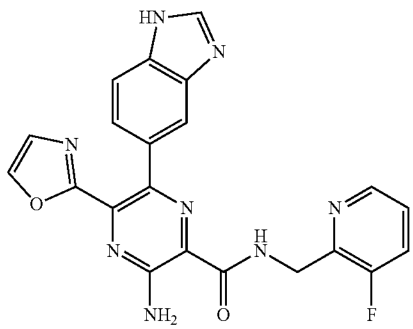 [SMILES: Nc1nc(-c2ncco2)c(-c2ccc3[nH]cnc3c2)nc1C(=O)NCc1ncccc1F] | 3-amino-6-(1H-benzo[d]imidazol-5-yl)-N-((3-fluoropyridin-2-yl)methyl)-5-(oxazol-2-yl)pyrazine-2-carboxamide |
| 48 | 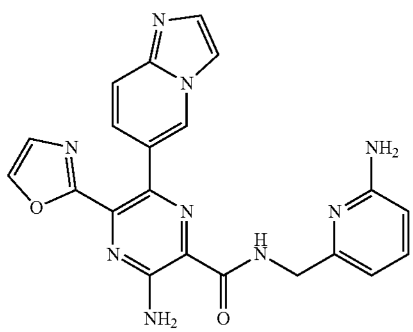 [SMILES: Nc1cccc(CNC(=O)c2nc(-c3ccc4nccn4c3)c(-c3ncco3)nc2N)n1] | 3-amino-N-((6-aminopyridin-2-yl)methyl)-6-(imidazo[1,2-a]pyridin-6-yl)-5-(oxazol-2-yl)pyrazine-2-carboxamide |
| 49 | 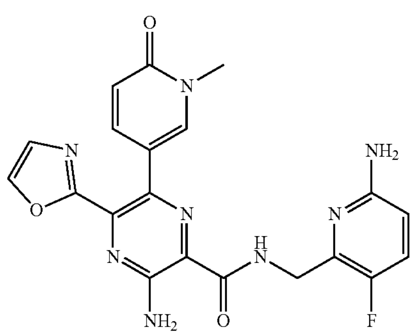 [SMILES: Cn1cc(-c2nc(C(=O)NCc3nc(N)ccc3F)c(N)nc2-c2ncco2)ccc1=O] | 3-amino-N-((6-amino-3-fluoropyridin-2-yl)methyl)-6-(1-methyl-6-oxo-1,6-dihydropyridin-3-yl)-5-(oxazol-2-yl)pyrazine-2-carboxamide |
| 50 | 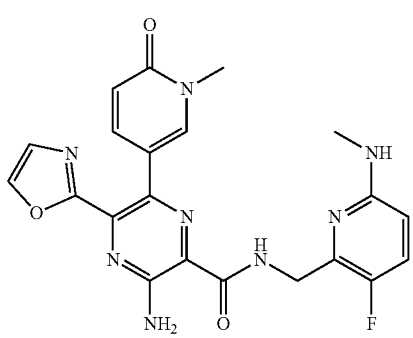 [SMILES: CNc1ccc(F)c(CNC(=O)c2nc(-c3ccc(=O)n(C)c3)c(-c3ncco3)nc2N)n1] | 3-amino-N-((3-fluoro-6-(methylamino)pyridin-2-yl)methyl)-6-(1-methyl-6-oxo-1,6-dihydropyridin-3-yl)-5-(oxazol-2-yl)pyrazine-2-carboxamide |

TABLE 1-continued

Exemplary Compound 1-306

| Compound number | Compound structure | Compound name |
|---|---|---|
| 51 | 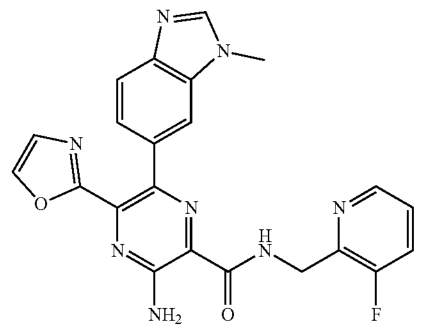 [SMILES: Cn1cnc2ccc(-c3nc(C(=O)NCc4ncccc4F)c(N)nc3-c3ncco3)cc21] | 3-amino-N-((3-fluoropyridin-2-yl)methyl)-6-(3-methyl-3H-benzo[d]imidazol-5-yl)-5-(oxazol-2-yl)pyrazine-2-carboxamide |
| 52 | 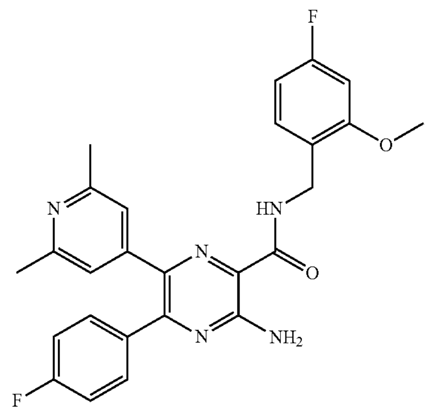 | 3-amino-6-(2,6-dimethylpyridin-4-yl)-N-(4-fluoro-2-methoxybenzyl)-5-(4-fluorophenyl)pyrazine-2-carboxamide |
| 53 | 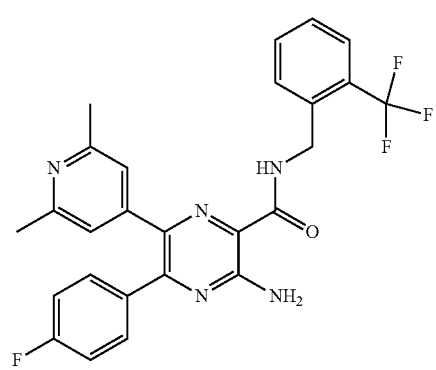 [SMILES: Cc1cc(-c2nc(C(=O)NCc3ccccc3C(F)(F)F)c(N)nc2-c2ccc(F)cc2)cc(C)n1] | 3-amino-6-(2,6-dimethylpyridin-4-yl)-5-(4-fluorophenyl)-N-(2-(trifluoromethyl)benzyl)pyrazine-2-carboxamide |
| 54 | 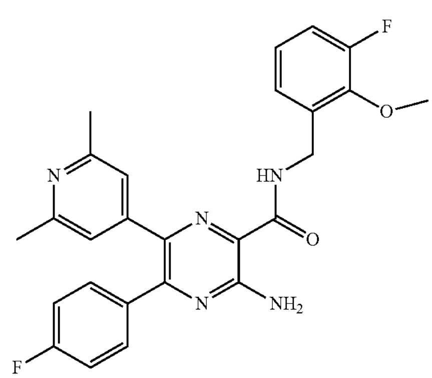 | 3-amino-6-(2,6-dimethylpyridin-4-yl)-N-(3-fluoro-2-methoxybenzyl)-5-(4-fluorophenyl)pyrazine-2-carboxamide |

TABLE 1-continued

Exemplary Compound 1-306

| Compound number | Compound structure | Compound name |
|---|---|---|
| 55 | 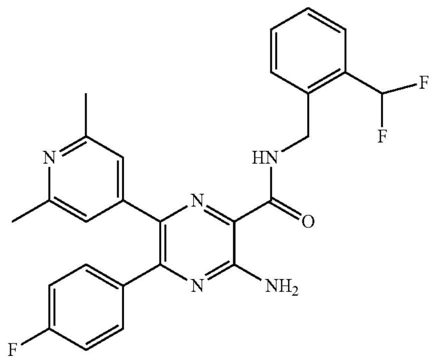 [SMILES: Cc1cc(-c2nc(C(=O)NCc3ccccc3C(F)F)c(N)nc2-c2ccc(F)cc2)cc(C)n1] | 3-amino-N-(2-(difluoromethyl)benzyl)-6-(2,6-dimethylpyridin-4-yl)-5-(4-fluorophenyl)pyrazine-2-carboxamide |
| 56 | 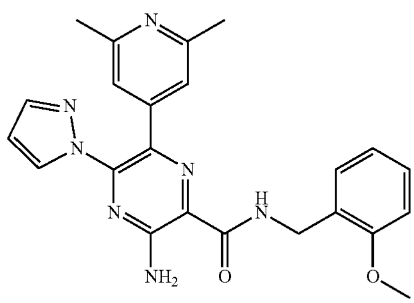 [SMILES: COc1ccccc1CNC(=O)c1nc(-c2cc(C)nc(C)c2)c(-n2cccn2)nc1N] | 3-amino-6-(2,6-dimethylpyridin-4-yl)-N-(2-methoxybenzyl)-5-(1H-pyrazol-1-yl)pyrazine-2-carboxamide |
| 57 | 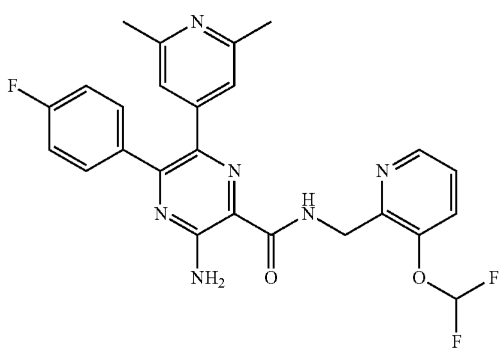 [SMILES: Cc1cc(-c2nc(C(=O)NCc3ncccc3OC(F)F)c(N)nc2-c2ccc(F)cc2)cc(C)n1] | 3-amino-N-((3-(difluoromethoxy)pyridin-2-yl)methyl)-6-(2,6-dimethylpyridin-4-yl)-5-(4-fluorophenyl)pyrazine-2-carboxamide |
| 58 | 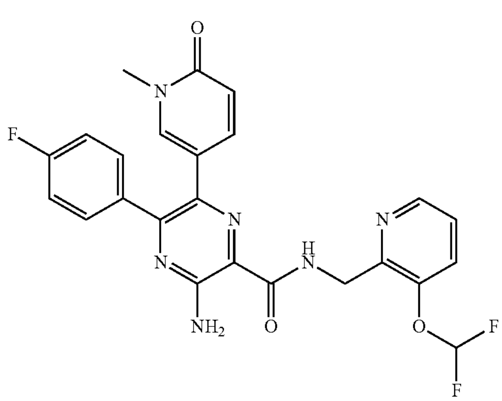 [SMILES: Cn1cc(-c2nc(C(=O)NCc3ncccc3OC(F)F)c(N)nc2-c2ccc(F)cc2)ccc1=O] | 3-amino-N-((3-(difluoromethoxy)pyridin-2-yl)methyl)-5-(4-fluorophenyl)-6-(1-methyl-6-oxo-1,6-dihydropyridin-3-yl)pyrazine-2-carboxamide |

TABLE 1-continued

Exemplary Compound 1-306

| Compound number | Compound structure | Compound name |
|---|---|---|
| 59 | 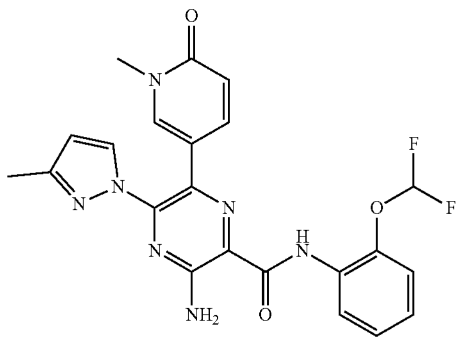 [SMILES: Cc1ccn(-c2nc(N)c(C(=O)Nc3ccccc3OC(F)F)nc2-c2ccc(=O)n(C)c2)n1] | 3-amino-N-(2-(difluoromethoxy)phenyl)-5-(3-methyl-1H-pyrazol-1-yl)-6-(1-methyl-6-oxo-1,6-dihydropyridin-3-yl)pyrazine-2-carboxamide |
| 60 | 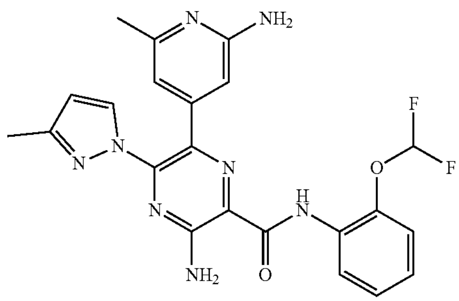 [SMILES: Cc1cc(-c2nc(C(=O)Nc3ccccc3OC(F)F)c(N)nc2-n2ccc(C)n2)cc(N)n1] | 3-amino-6-(2-amino-6-methylpyridin-4-yl)-N-(2-(difluoromethoxy)phenyl)-5-(3-methyl-1H-pyrazol-1-yl)pyrazine-2-carboxamide |
| 61 | 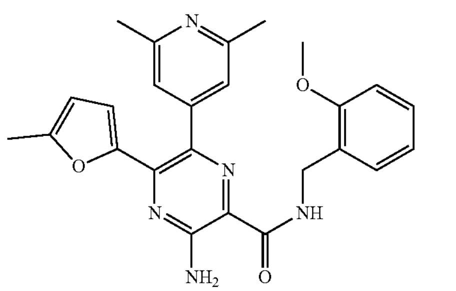 [SMILES: COc1ccccc1CNC(=O)c1nc(-c2cc(C)nc(C)c2)c(-c2ccc(C)o2)nc1N] | 3-amino-6-(2,6-dimethylpyridin-4-yl)-N-(2-methoxybenzyl)-5-(5-methylfuran-2-yl)pyrazine-2-carboxamide |
| 62 | 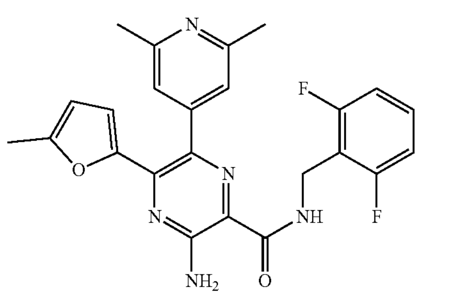 [SMILES: Cc1cc(-c2nc(C(=O)NCc3c(F)cccc3F)c(N)nc2-c2ccc(C)o2)cc(C)n1] | 3-amino-N-(2,6-difluorobenzyl)-6-(2,6-dimethylpyridin-4-yl)-5-(5-methylfuran-2-yl)pyrazine-2-carboxamide |
| 63 | 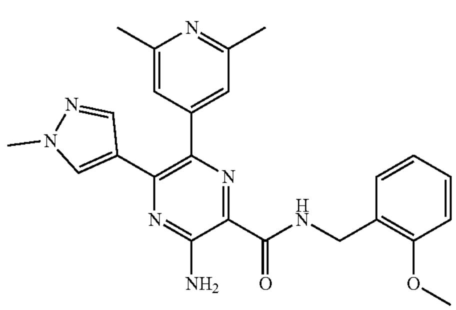 | 3-amino-6-(2,6-dimethylpyridin-4-yl)-N-(2-methoxybenzyl)-5-(1-methyl-1H-pyrazol-4-yl)pyrazine-2-carboxamide |

TABLE 1-continued

Exemplary Compound 1-306

| Compound number | Compound structure | Compound name |
|---|---|---|
| 64 | 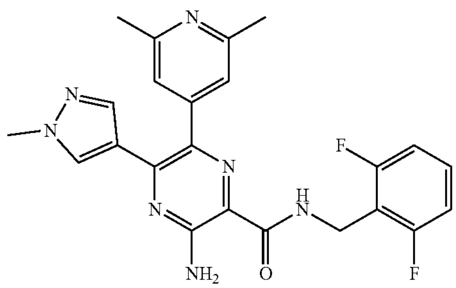 [SMILES: Cc1cc(-c2nc(C(=O)NCc3c(F)cccc3F)c(N)nc2-c2cnn(C)c2)cc(C)n1] | 3-amino-N-(2,6-difluorobenzyl)-6-(2,6-dimethylpyridin-4-yl)-5-(1-methyl-1H-pyrazol-4-yl)pyrazine-2-carboxamide |
| 65 | 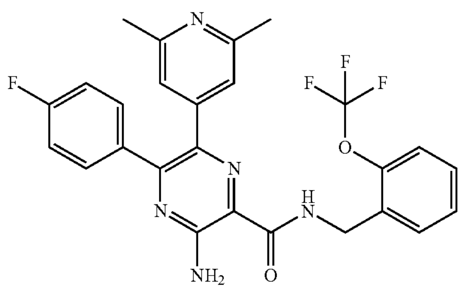 [SMILES: Cc1cc(-c2nc(C(=O)NCc3ccccc3OC(F)(F)F)c(N)nc2-c2ccc(F)cc2)cc(C)n1] | 3-amino-6-(2,6-dimethylpyridin-4-yl)-5-(4-fluorophenyl)-N-(2-(trifluoromethoxy)benzyl)pyrazine-2-carboxamide |
| 66 | 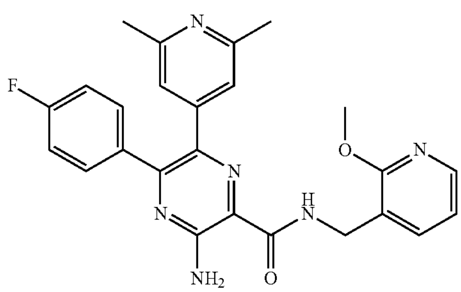 [SMILES: COc1ncccc1CNC(=O)c1nc(-c2cc(C)nc(C)c2)c(-c2ccc(F)cc2)nc1N] | 3-amino-6-(2,6-dimethylpyridin-4-yl)-5-(4-fluorophenyl)-N-((2-methoxypyridin-3-yl)methyl)pyrazine-2-carboxamide |
| 67 | 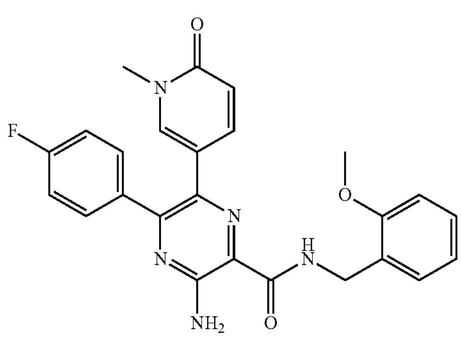 [SMILES: COc1ccccc1CNC(=O)c1nc(-c2ccc(=O)n(C)c2)c(-c2ccc(F)cc2)nc1N] | 3-amino-5-(4-fluorophenyl)-N-(2-methoxybenzyl)-6-(1-methyl-6-oxo-1,6-dihydropyridin-3-yl)pyrazine-2-carboxamide |
| 68 | 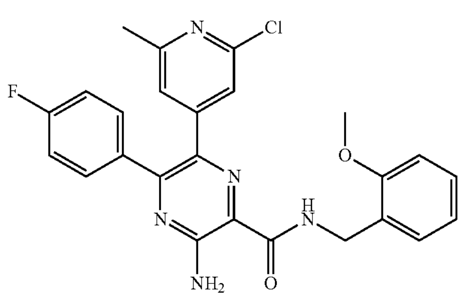 [SMILES: COc1ccccc1CNC(=O)c1nc(-c2cc(C)nc(Cl)c2)c(-c2ccc(F)cc2)nc1N] | 3-amino-6-(2-chloro-6-methylpyridin-4-yl)-5-(4-fluorophenyl)-N-(2-methoxybenzyl)pyrazine-2-carboxamide |

TABLE 1-continued

Exemplary Compound 1-306

| Compound number | Compound structure | Compound name |
|---|---|---|
| 69 | 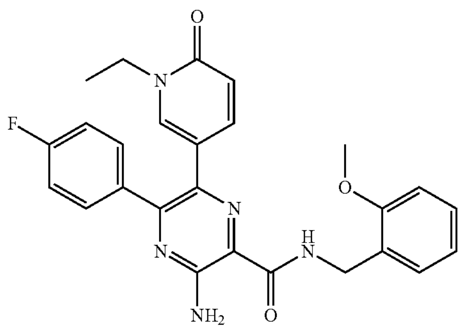 [SMILES: CCn1cc(-c2nc(C(=O)NCc3ccccc3OC)c(N)nc2-c2ccc(F)cc2)ccc1=O] | 3-amino-6-(1-ethyl-6-oxo-1,6-dihydro-pyridin-3-yl)-5-(4-fluorophenyl)-N-(2-methoxybenzyl)pyrazine-2-carboxamide |
| 70 | 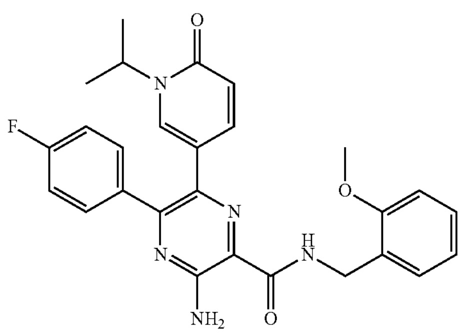 [SMILES: COc1ccccc1CNC(=O)c1nc(-c2ccc(=O)n(C(C)C)c2)c(-c2ccc(F)cc2)nc1N] | 3-amino-5-(4-fluorophenyl)-6-(1-isopropyl-6-oxo-1,6-dihydropyridin-3-yl)-N-(2-methoxybenzyl)pyrazine-2-carboxamide |
| 71 | 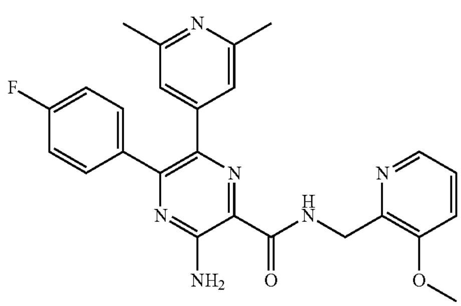 [SMILES: COc1cccnc1CNC(=O)c1nc(-c2cc(C)nc(C)c2)c(-c2ccc(F)cc2)nc1N] | 3-amino-6-(2,6-dimethylpyridin-4-yl)-5-(4-fluorophenyl)-N-((3-methoxypyridin-2-yl)methyl)pyrazine-2-carboxamide |
| 72 | 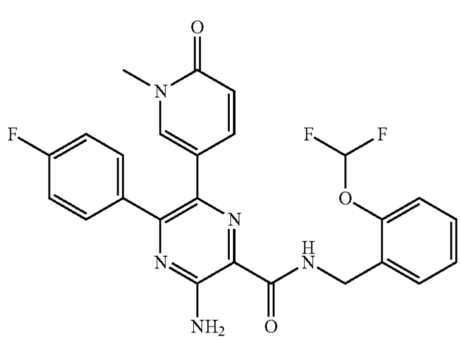 [SMILES: Cn1cc(-c2nc(C(=O)NCc3ccccc3OC(F)F)c(N)nc2-c2ccc(F)cc2)ccc1=O] | 3-amino-N-(2-(difluoromethoxy)benzyl)-5-(4-fluorophenyl)-6-(1-methyl-6-oxo-1,6-dihydropyridin-3-yl)pyrazine-2-carboxamide |

TABLE 1-continued

Exemplary Compound 1-306

| Compound number | Compound structure | Compound name |
|---|---|---|
| 73 | 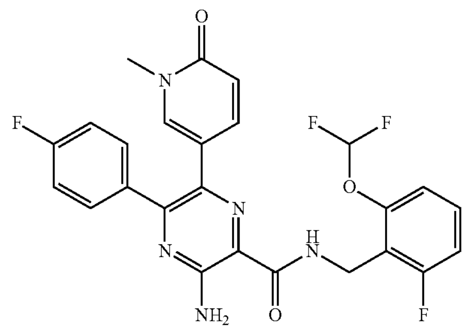 [SMILES: Cn1cc(-c2nc(C(=O)NCc3c(F)cccc3OC(F)F)c(N)nc2-c2ccc(F)cc2)ccc1=O] | 3-amino-N-(2-(difluoromethoxy)-6-fluorobenzyl)-5-(4-fluorophenyl)-6-(1-methyl-6-oxo-1,6-dihydropyridin-3-yl)pyrazine-2-carboxamide |
| 74 | 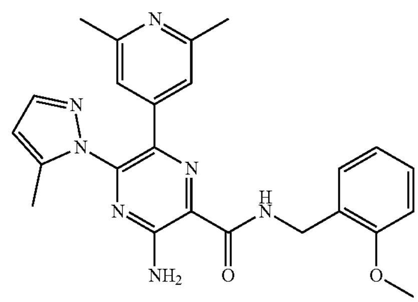 [SMILES: COc1ccccc1CNC(=O)c1nc(-c2cc(C)nc(C)c2)c(-n2nccc2C)nc1N] | 3-amino-6-(2,6-dimethylpyridin-4-yl)-N-(2-methoxybenzyl)-5-(5-methyl-1H-pyrazol-1-yl)pyrazine-2-carboxamide |
| 75 | 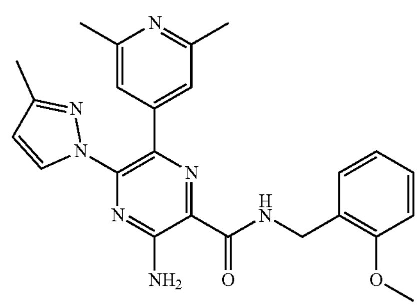 [SMILES: COc1ccccc1CNC(=O)c1nc(-c2cc(C)nc(C)c2)c(-n2ccc(C)n2)nc1N] | 3-amino-6-(2,6-dimethylpyridin-4-yl)-N-(2-methoxybenzyl)-5-(3-methyl-1H-pyrazol-1-yl)pyrazine-2-carboxamide |
| 76 | 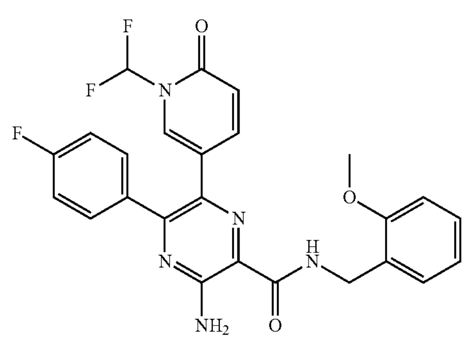 | 3-amino-6-(1-(difluoromethyl)-6-oxo-1,6-dihydropyridin-3-yl)-5-(4-fluorophenyl)-N-(2-methoxybenzyl)pyrazine-2-carboxamide |

TABLE 1-continued

Exemplary Compound 1-306

| Compound number | Compound structure | Compound name |
|---|---|---|
| 77 | 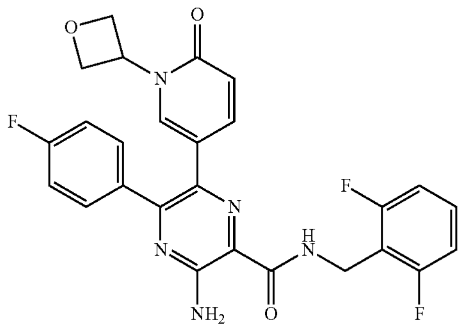 [SMILES: Nc1nc(-c2ccc(F)cc2)c(-c2ccc(=O)n(C3COC3)c2)nc1C(=O)NCc1c(F)cccc1F] | 3-amino-N-(2,6-difluorobenzyl)-5-(4-fluorophenyl)-6-(1-(oxetan-3-yl)-6-oxo-1,6-dihydropyridin-3-yl)pyrazine-2-carboxamide |
| 78 | 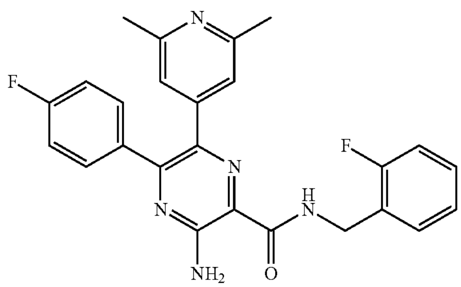 | 3-amino-6-(2,6-dimethylpyridin-4-yl)-N-(2-fluorobenzyl)-5-(4-fluorophenyl)pyrazine-2-carboxamide |
| 79 | 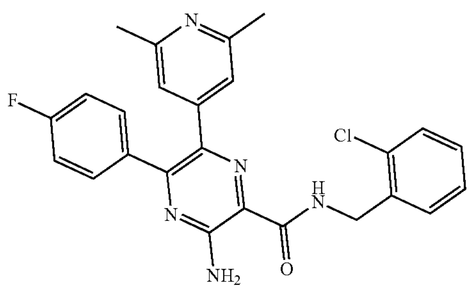 | 3-amino-N-(2-chlorobenzyl)-6-(2,6-dimethylpyridin-4-yl)-5-(4-fluorophenyl)pyrazine-2-carboxamide |
| 80 | 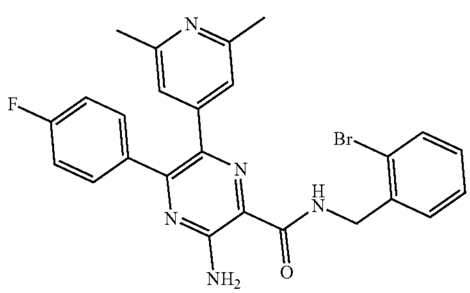 [SMILES: Cc1cc(-c2nc(C(=O)NCc3ccccc3Cl)c(N)nc2-c2ccc(F)cc2)cc(C)n1] | 3-amino-N-(2-bromobenzyl)-6-(2,6-dimethylpyridin-4-yl)-5-(4-fluorophenyl)pyrazine-2-carboxamide |
| 81 | 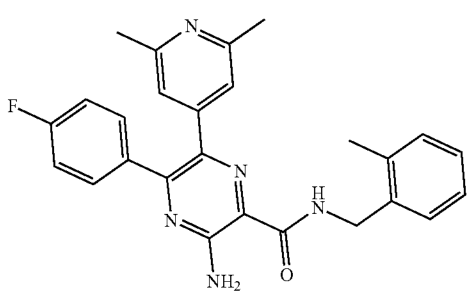 | 3-amino-6-(2,6-dimethylpyridin-4-yl)-5-(4-fluorophenyl)-N-(2-methylbenzyl)pyrazine-2-carboxamide |

TABLE 1-continued

Exemplary Compound 1-306

| Compound number | Compound structure | Compound name |
| --- | --- | --- |
| 82 | 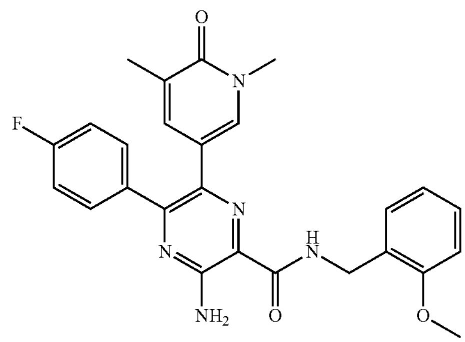 [SMILES: COc1ccccc1CNC(=O)c1nc(-c2cc(C)c(=O)n(C)c2)c(-c2ccc(F)cc2)nc1N] | 3-amino-6-(1,5-dimethyl-6-oxo-1,6-dihydropyridin-3-yl)-5-(4-fluorophenyl)-N-(2-methoxybenzyl)pyrazine-2-carboxamide |
| 83 | 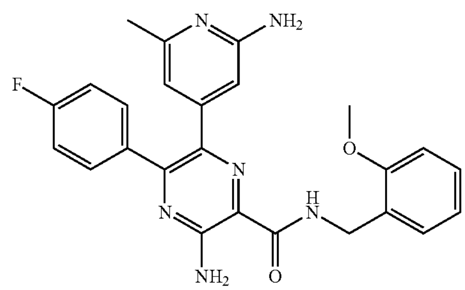 | 3-amino-6-(2-amino-6-methylpyridin-4-yl)-5-(4-fluorophenyl)-N-(2-methoxybenzyl)pyrazine-2-carboxamide |
| 84 | 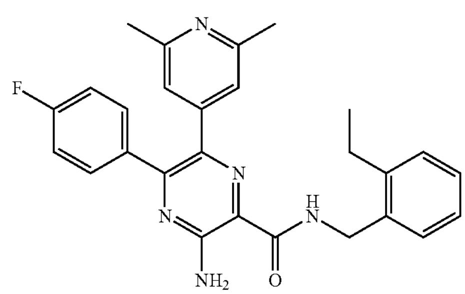 [SMILES: CCc1ccccc1CNC(=O)c1nc(-c2cc(C)nc(C)c2)c(-c2ccc(F)cc2)nc1N] | 3-amino-6-(2,6-dimethylpyridin-4-yl)-N-(2-ethylbenzyl)-5-(4-fluorophenyl)pyrazine-2-carboxamide |
| 85 | 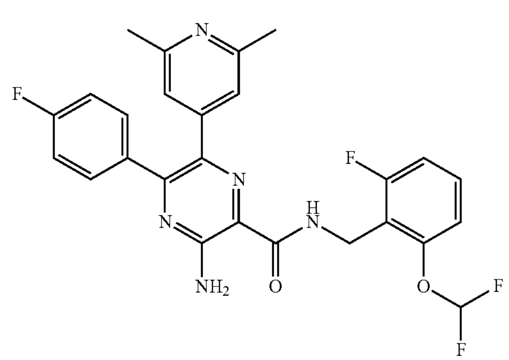 [SMILES: Cc1cc(-c2nc(C(=O)NCc3c(F)cccc3OC(F)F)c(N)nc2-c2ccc(F)cc2)cc(C)n1] | 3-amino-N-(2-(difluoromethoxy)-6-fluorobenzyl)-6-(2,6-dimethylpyridin-4-yl)-5-(4-fluorophenyl)pyrazine-2-carboxamide |

TABLE 1-continued

Exemplary Compound 1-306

| Compound number | Compound structure | Compound name |
|---|---|---|
| 86 | 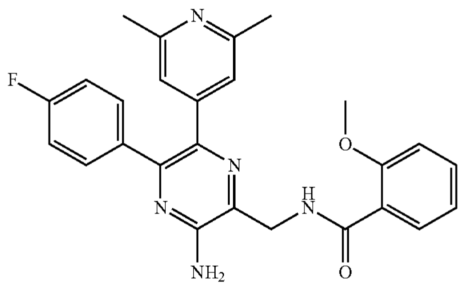 [SMILES: COc1ccccc1C(=O)NCc1nc(-c2cc(C)nc(C)c2)c(-c2ccc(F)cc2)nc1N] | N-((3-amino-6-(2,6-dimethylpyridin-4-yl)-5-(4-fluorophenyl)pyrazin-2-yl)methyl)-2-methoxybenzamide |
| 87 | 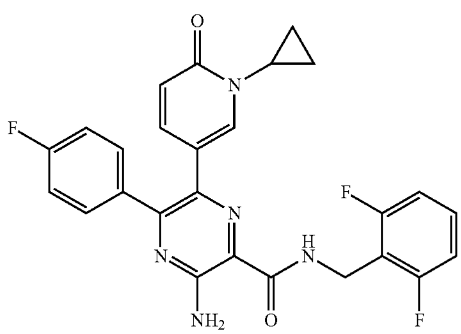 [SMILES: Nc1nc(-c2ccc(F)cc2)c(-c2ccc(=O)n(C3CC3)c2)nc1C(=O)NCc1c(F)cccc1F] | 3-amino-6-(1-cyclopropyl-6-oxo-1,6-dihydropyridin-3-yl)-N-(2,6-difluorobenzyl)-5-(4-fluorophenyl)pyrazine-2-carboxamide |
| 88 | 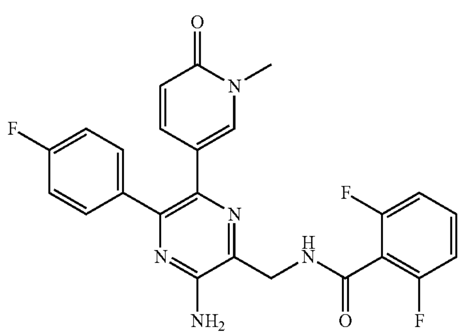 [SMILES: Cn1cc(-c2nc(CNC(=O)c3c(F)cccc3F)c(N)nc2-c2ccc(F)cc2)ccc1=O] | N-((3-amino-5-(4-fluorophenyl)-6-(1-methyl-6-oxo-1,6-dihydropyridin-3-yl)pyrazin-2-yl)methyl)-2,6-difluorobenzamide |
| 89 | 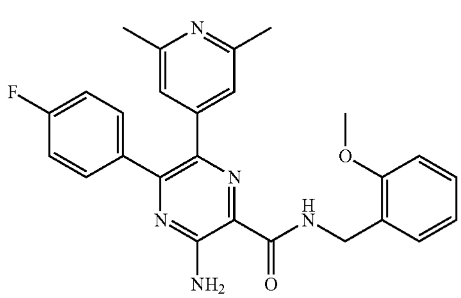 | 3-amino-6-(2,6-dimethylpyridin-4-yl)-5-(4-fluorophenyl)-N-(2-methoxybenzyl)pyrazine-2-carboxamide |

TABLE 1-continued

Exemplary Compound 1-306

| Compound number | Compound structure | Compound name |
|---|---|---|
| 90 | 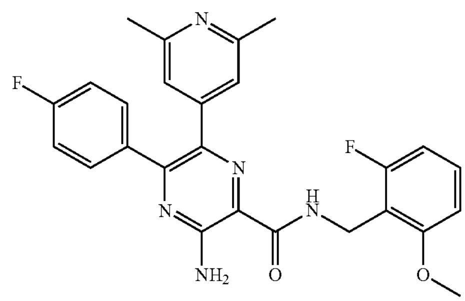 [SMILES: COc1cccc(F)c1CNC(=O)c1nc(-c2cc(C)nc(C)c2)c(-c2ccc(F)cc2)nc1N] | 3-amino-6-(2,6-dimethylpyridin-4-yl)-N-(2-fluoro-6-methoxybenzyl)-5-(4-fluorophenyl)pyrazine-2-carboxamide |
| 91 | 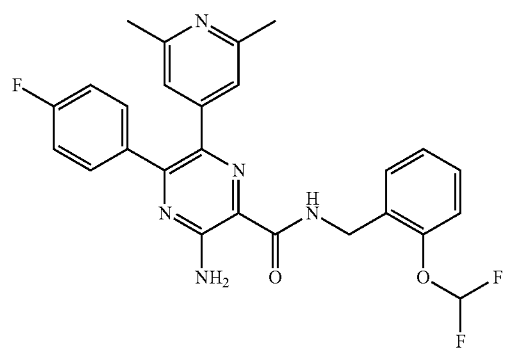 [SMILES: Cc1cc(-c2nc(C(=O)NCc3ccccc3OC(F)F)c(N)nc2-c2ccc(F)cc2)cc(C)n1] | 3-amino-N-(2-(difluoromethoxy)benzyl)-6-(2,6-dimethylpyridin-4-yl)-5-(4-fluorophenyl)pyrazine-2-carboxamide |
| 92 | 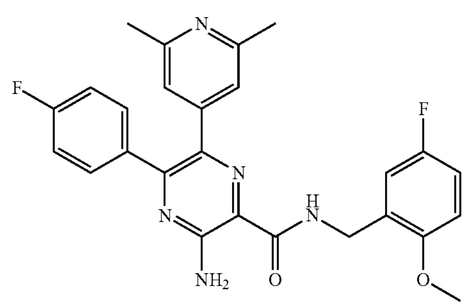 [SMILES: COc1ccc(F)cc1CNC(=O)c1nc(-c2cc(C)nc(C)c2)c(-c2ccc(F)cc2)nc1N] | 3-amino-6-(2,6-dimethylpyridin-4-yl)-N-(5-fluoro-2-methoxybenzyl)-5-(4-fluorophenyl)pyrazine-2-carboxamide |
| 93 | 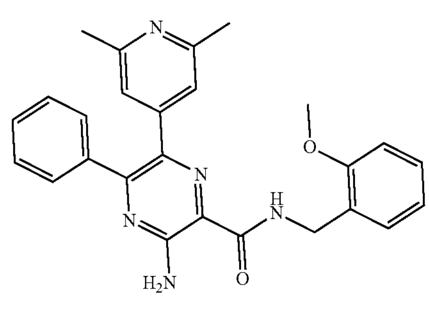 [SMILES: COc1ccccc1CNC(=O)c1nc(-c2cc(C)nc(C)c2)c(-c2ccccc2)nc1N] | 3-amino-6-(2,6-dimethylpyridin-4-yl)-N-(2-methoxybenzyl)-5-phenylpyrazine-2-carboxamide |

TABLE 1-continued

Exemplary Compound 1-306

| Compound number | Compound structure | Compound name |
|---|---|---|
| 94 | 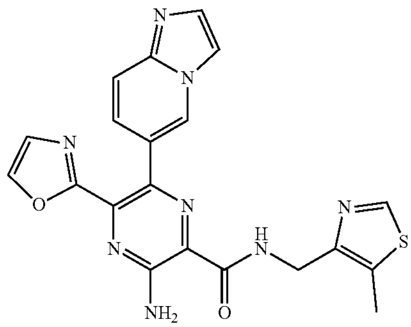 [SMILES: Cc1scnc1CNC(=O)c1nc(-c2ccc3nccn3c2)c(-c2ncco2)nc1N] | 3-amino-6-(imidazo[1,2-a]pyridin-6-yl)-N-((5-methylthiazol-4-yl)methyl)-5-(oxazol-2-yl)pyrazine-2-carboxamide |
| 95 | 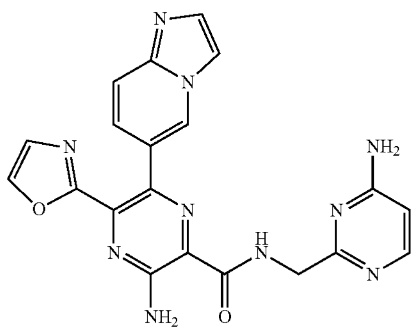 [SMILES: Nc1ccnc(CNC(=O)c2nc(-c3ccc4nccn4c3)c(-c3ncco3)nc2N)n1] | 3-amino-N-((4-aminopyrimidin-2-yl)methyl)-6-(imidazo[1,2-a]pyridin-6-yl)-5-(oxazol-2-yl)pyrazine-2-carboxamide |
| 96 | 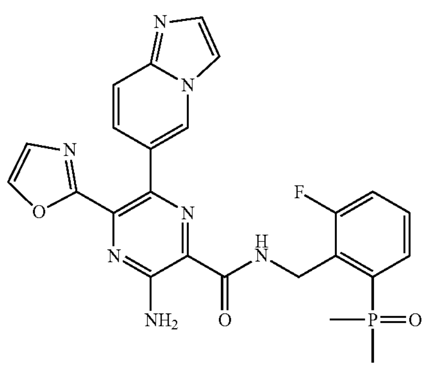 [SMILES: CP(C)(=O)c1cccc(F)c1CNC(=O)c1nc(-c2ccc3nccn3c2)c(-c2ncco2)nc1N] | 3-amino-N-(2-(dimethylphosphoryl)-6-fluorobenzyl)-6-(imidazo[1,2-a]pyridin-6-yl)-5-(oxazol-2-yl)pyrazine-2-carboxamide |
| 97 | 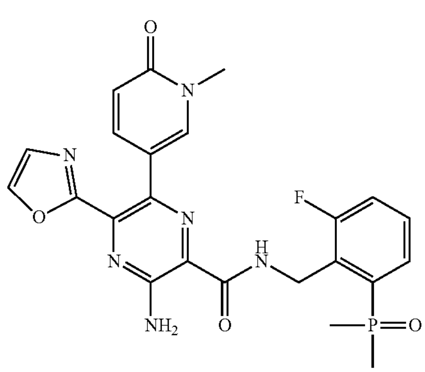 [SMILES: Cn1cc(-c2nc(C(=O)NCc3c(F)cccc3P(C)(C)=O)c(N)nc2-c2ncco2)ccc1=O] | 3-amino-N-(2-(dimethylphosphoryl)-6-fluorobenzyl)-6-(1-methyl-6-oxo-1,6-dihydropyridin-3-yl)-5-(oxazol-2-yl)pyrazine-2-carboxamide |

TABLE 1-continued

Exemplary Compound 1-306

| Compound number | Compound structure | Compound name |
|---|---|---|
| 98 | 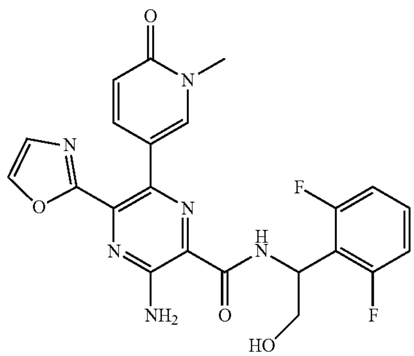 [SMILES: Cn1cc(-c2nc(C(=O)NC(CO)c3c(F)cccc3F)c(N)nc2-c2ncco2)ccc1=O] | 3-amino-N-(1-(2,6-difluorophenyl)-2-hydroxyethyl)-6-(1-methyl-6-oxo-1,6-dihydropyridin-3-yl)-5-(oxazol-2-yl)pyrazine-2-carboxamide |
| 99 | 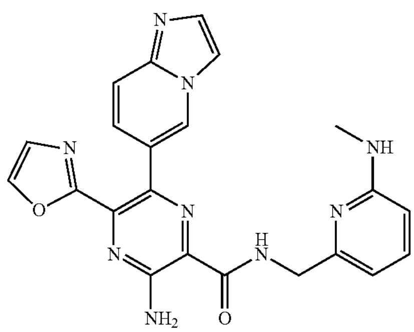 [SMILES: CNc1cccc(CNC(=O)c2nc(-c3ccc4nccn4c3)c(-c3ncco3)nc2N)n1] | 3-amino-6-(imidazo[1,2-a]pyridin-6-yl)-N-((6-(methylamino)pyridin-2-yl)methyl)-5-(oxazol-2-yl)pyrazine-2-carboxamide |
| 100 | 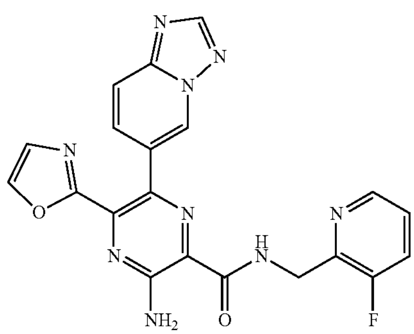 [SMILES: Nc1nc(-c2ncco2)c(-c2ccc3ncnn3c2)nc1C(=O)NCc1ncccc1F] | 6-([1,2,4]triazolo[1,5-a]pyridin-6-yl)-3-amino-N-((3-fluoropyridin-2-yl)methyl)-5-(oxazol-2-yl)pyrazine-2-carboxamide |
| 101 | 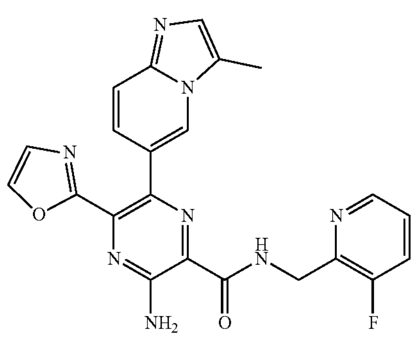 [SMILES: Cc1cnc2ccc(-c3nc(C(=O)NCc4ncccc4F)c(N)nc3-c3ncco3)cn12] | 3-amino-N-((3-fluoropyridin-2-yl)methyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 102 | 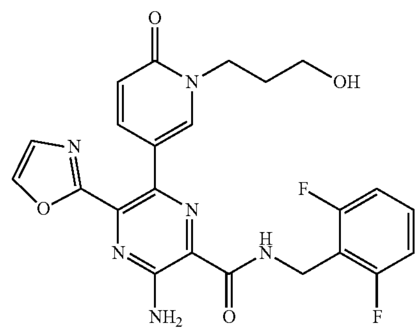 [SMILES: Nc1nc(-c2ncco2)c(-c2ccc(=O)n(CCCO)c2)nc1C(=O)NCc1c(F)cccc1F] | 3-amino-N-(2,6-difluorobenzyl)-6-(1-(3-hydroxypropyl)-6-oxo-1,6-dihydropyridin-3-yl)-5-(oxazol-2-yl)pyrazine-2-carboxamide |
| 103 | 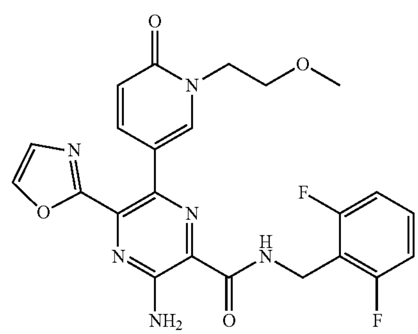 [SMILES: COCCn1cc(-c2nc(C(=O)NCc3c(F)cccc3F)c(N)nc2-c2ncco2)ccc1=O] | 3-amino-N-(2,6-difluorobenzyl)-6-(1-(2-methoxyethyl)-6-oxo-1,6-dihydropyridin-3-yl)-5-(oxazol-2-yl)pyrazine-2-carboxamide |
| 104 | 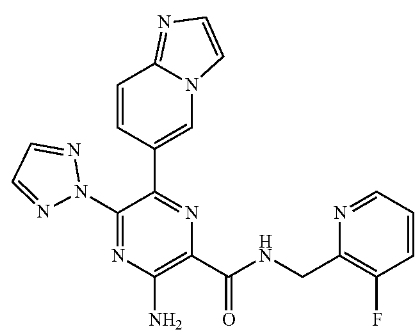 [SMILES: Nc1nc(-n2nccn2)c(-c2ccc3nccn3c2)nc1C(=O)NCc1ncccc1F] | 3-amino-N-((3-fluoropyridin-2-yl)methyl)-6-(imidazo[1,2-a]pyridin-6-yl)-5-(2H-1,2,3-triazol-2-yl)pyrazine-2-carboxamide |
| 105 | 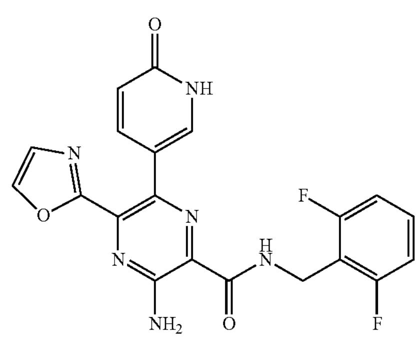 [SMILES: Nc1nc(-c2ncco2)c(-c2ccc(=O)[nH]c2)nc1C(=O)NCc1c(F)cccc1F] | 3-amino-N-(2,6-difluorobenzyl)-5-(oxazol-2-yl)-6-(6-oxo-1,6-dihydropyridin-3-yl)pyrazine-2-carboxamide |

TABLE 1-continued

Exemplary Compound 1-306

| Compound number | Compound structure | Compound name |
|---|---|---|
| 107 | 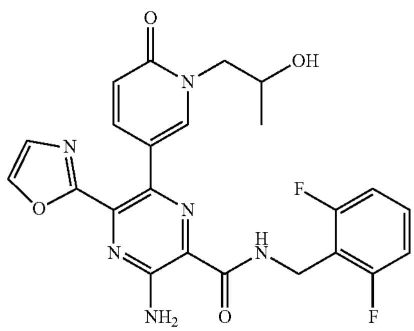 [SMILES: CC(O)Cn1cc(-c2nc(C(=O)NCc3c(F)cccc3F)c(N)nc2-c2ncco2)ccc1=O] | 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide(isomer 1) |
| 108 | 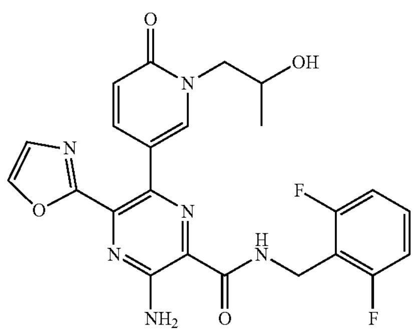 [SMILES: CC(O)Cn1cc(-c2nc(C(=O)NCc3c(F)cccc3F)c(N)nc2-c2ncco2)ccc1=O] | 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide(isomer 2) |
| 109 | 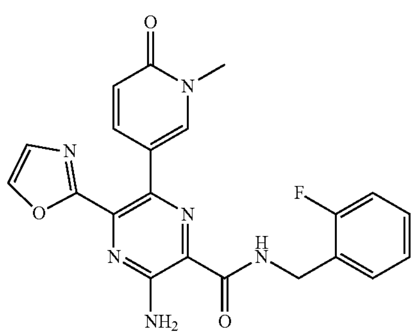 [SMILES: Cn1cc(-c2nc(C(=O)NCc3ccccc3F)c(N)nc2-c2ncco2)ccc1=O] | 3-amino-N-(2-fluorobenzyl)-6-(1-methyl-6-oxo-1,6-dihydropyridin-3-yl)-5-(oxazol-2-yl)pyrazine-2-carboxamide |
| 110 | 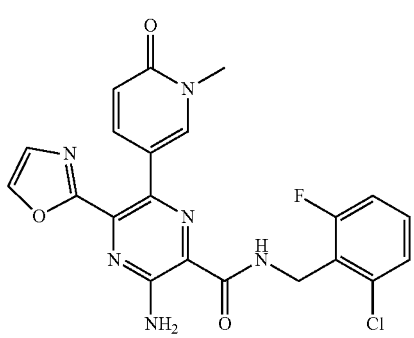 [SMILES: Cn1cc(-c2nc(C(=O)NCc3c(F)cccc3Cl)c(N)nc2-c2ncco2)ccc1=O] | 3-amino-N-(2-chloro-6-fluorobenzyl)-6-(1-methyl-6-oxo-1,6-dihydropyridin-3-yl)-5-(oxazol-2-yl)pyrazine-2-carboxamide |

TABLE 1-continued

Exemplary Compound 1-306

| Compound number | Compound structure | Compound name |
|---|---|---|
| 111 | 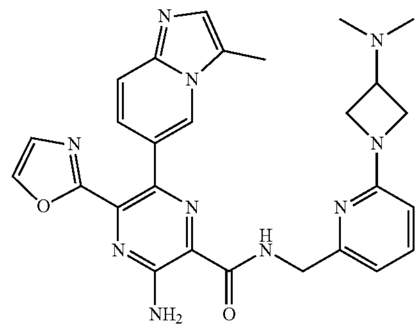 [SMILES: Cc1cnc2ccc(-c3nc(C(=O)NCc4cccc(N5CC(N(C)C)C5)n4)c(N)nc3-c3ncco3)cn12] | 3-amino-N-((6-(3-(dimethylamino)azetidin-1-yl)pyridin-2-yl)methyl)-6-(3-methylimidazo[1,2-a]pyridin-6-yl)-5-(oxazol-2-yl)pyrazine-2-carboxamide |
| 112 | 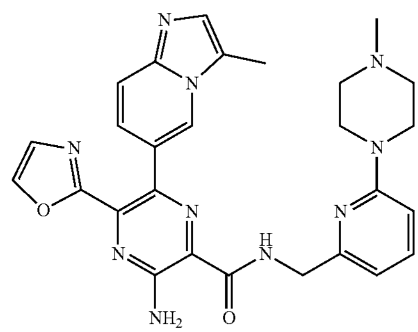 [SMILES: Cc1cnc2ccc(-c3nc(C(=O)NCc4cccc(N5CCN(C)CC5)n4)c(N)nc3-c3ncco3)cn12] | 3-amino-6-(3-methylimidazo[1,2-a]pyridin-6-yl)-N-((6-(4-methylpiperazin-1-yl)pyridin-2-yl)methyl)-5-(oxazol-2-yl)pyrazine-2-carboxamide |
| 113 | 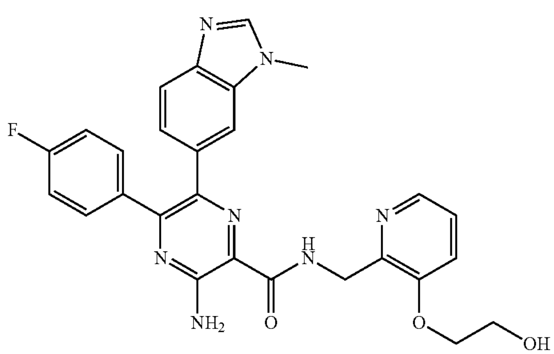 [SMILES: Cn1cnc2ccc(-c3nc(C(=O)NCc4ncccc4OCCO)c(N)nc3-c3ccc(F)cc3)cc21] | 3-amino-5-(4-fluorophenyl)-N-((3-(2-hydroxyethoxy)pyridin-2-yl)methyl)-6-(3-methyl-3H-benzo[d]imidazol-5-yl)pyrazine-2-carboxamide |
| 114 | 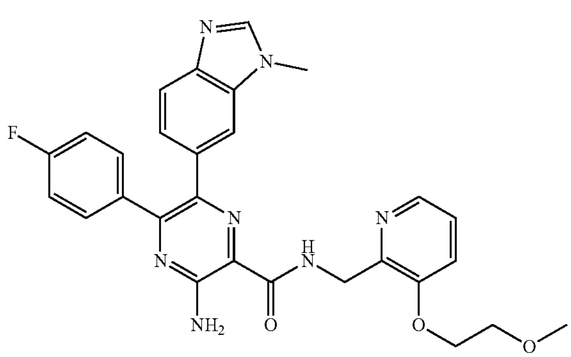 [SMILES: COCCOc1cccnc1CNC(=O)c1nc(-c2ccc3ncn(C)c3c2)c(-c2ccc(F)cc2)nc1N] | 3-amino-5-(4-fluorophenyl)-N-((3-(2-methoxyethoxy)pyridin-2-yl)methyl)-6-(3-methyl-3H-benzo[d]imidazol-5-yl)pyrazine-2-carboxamide |

TABLE 1-continued

Exemplary Compound 1-306

| Compound number | Compound structure | Compound name |
|---|---|---|
| 115 | 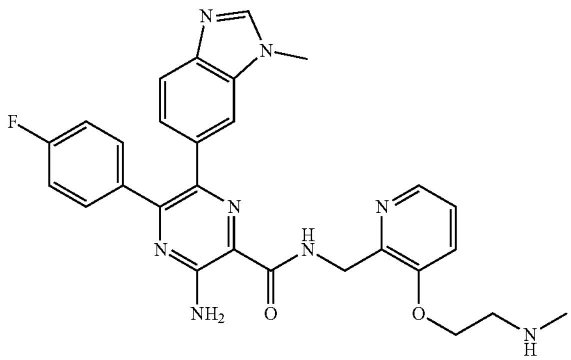 [SMILES: CNCCOc1cccnc1CNC(=O)c1nc(-c2ccc3ncn(C)c3c2)c(-c2ccc(F)cc2)nc1N] | 3-amino-5-(4-fluorophenyl)-6-(3-methyl-3H-benzo[d]imidazol-5-yl)-N-((3-(2-(methylamino)ethoxy)pyridin-2-yl)methyl)pyrazine-2-carboxamide |
| 116 | 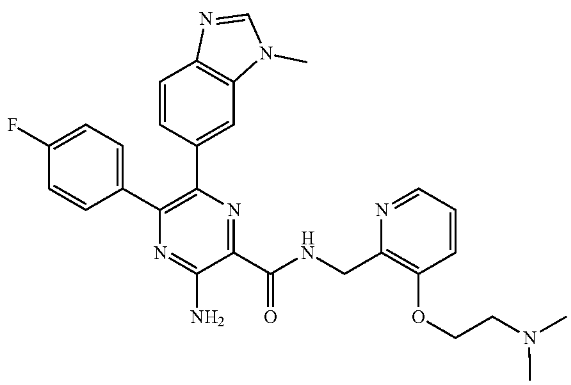 [SMILES: CN(C)CCOc1cccnc1CNC(=O)c1nc(-c2ccc3ncn(C)c3c2)c(-c2ccc(F)cc2)nc1N] | 3-amino-N-((3-(2-(dimethylamino)ethoxy)pyridin-2-yl)methyl)-5-(4-fluorophenyl)-6-(3-methyl-3H-benzo[d]imidazol-5-yl)pyrazine-2-carboxamide |
| 117 | 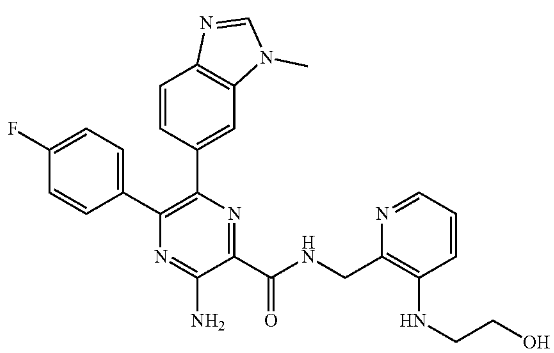 [SMILES: Cn1cnc2ccc(-c3nc(C(=O)NCc4ncccc4NCCO)c(N)nc3-c3ccc(F)cc3)cc21] | 3-amino-5-(4-fluorophenyl)-N-((3-(2-hydroxyethylamino)pyridin-2-yl)methyl)-6-(3-methyl-3H-benzo[d]imidazol-5-yl)pyrazine-2-carboxamide |
| 118 | 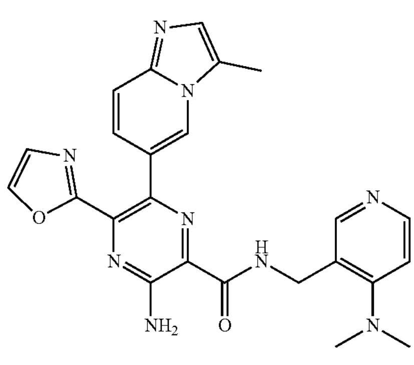 [SMILES: Cc1cnc2ccc(-c3nc(C(=O)NCc4cnccc4N(C)C)c(N)nc3-c3ncco3)cn12] | 3-amino-N-((4-(dimethylamino)pyridin-3-yl)methyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 119 | 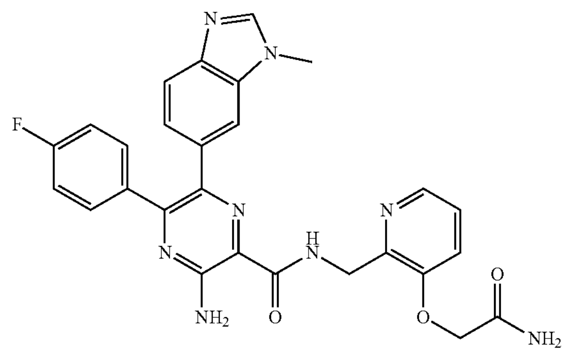 [SMILES: Cn1cnc2ccc(-c3nc(C(=O)NCc4ncccc4OCC(N)=O)c(N)nc3-c3ccc(F)cc3)cc21] | 3-amino-N-((3-(2-amino-2-oxoethoxy)pyridin-2-yl)methyl)-5-(4-fluorophenyl)-6-(3-methyl-3H-benzo[d]imidazol-5-yl)pyrazine-2-carboxamide |
| 120 | 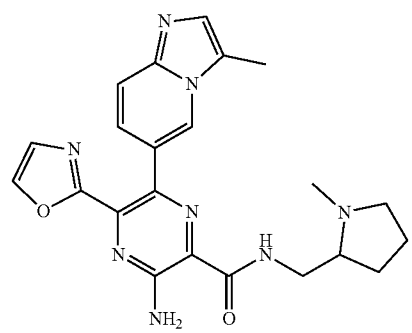 [SMILES: Cc1cnc2ccc(-c3nc(C(=O)NCC4CCCN4C)c(N)nc3-c3ncco3)cn12] | 3-amino-6-(3-methylimidazo[1,2-a]pyridin-6-yl)-N-((1-methylpyrrolidin-2-yl)methyl)-5-(oxazol-2-yl)pyrazine-2-carboxamide (isomer 1) |
| 121 | 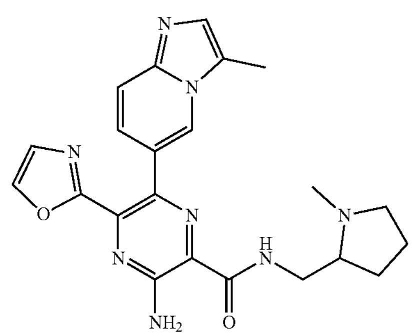 [SMILES: Cc1cnc2ccc(-c3nc(C(=O)NCC4CCCN4C)c(N)nc3-c3ncco3)cn12] | 3-amino-6-(3-methylimidazo[1,2-a]pyridin-6-yl)-N-((1-methylpyrrolidin-2-yl)methyl)-5-(oxazol-2-yl)pyrazine-2-carboxamide (isomer 2) |
| 122 | 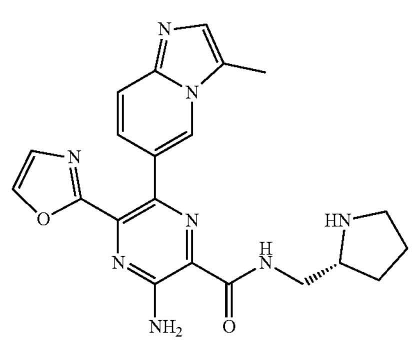 | (R)-3-amino-6-(3-methylimidazo[1,2-a]pyridin-6-yl)-5-(oxazol-2-yl)-N-(pyrrolidin-2-ylmethyl)pyrazine-2-carboxamide |

TABLE 1-continued

Exemplary Compound 1-306

| Compound number | Compound structure | Compound name |
|---|---|---|
| 123 | 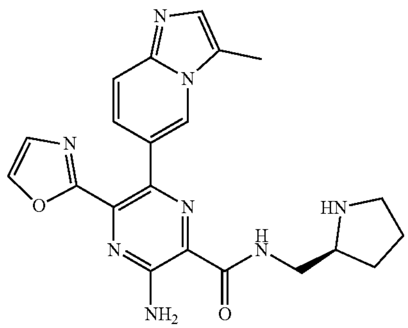 [SMILES: Cc1cnc2ccc(-c3nc(C(=O)NC[C@@H]4CCCN4)c(N)nc3-c3ncco3)cn12] | (S)-3-amino-6-(3-methylimidazo[1,2-a]pyridin-6-yl)-5-(oxazol-2-yl)-N-(pyrrolidin-2-ylmethyl)pyrazine-2-carboxamide |
| 124 | 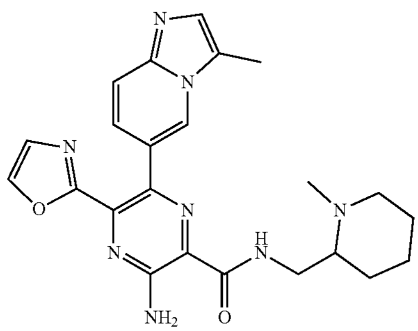 [SMILES: Cc1cnc2ccc(-c3nc(C(=O)NCC4CCCCN4C)c(N)nc3-c3ncco3)cn12] | 3-amino-6-(3-methylimidazo[1,2-a]pyridin-6-yl)-N-((1-methylpiperidin-2-yl)methyl)-5-(oxazol-2-yl)pyrazine-2-carboxamide (isomer 1) |
| 125 | 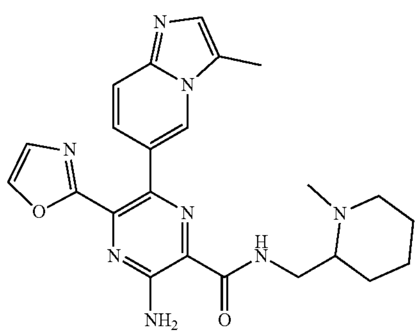 [SMILES: Cc1cnc2ccc(-c3nc(C(=O)NCC4CCCCN4C)c(N)nc3-c3ncco3)cn12] | 3-amino-6-(3-methylimidazo[1,2-a]pyridin-6-yl)-N-((1-methylpiperidin-2-yl)methyl)-5-(oxazol-2-yl)pyrazine-2-carboxamide (isomer 2) |
| 126 | 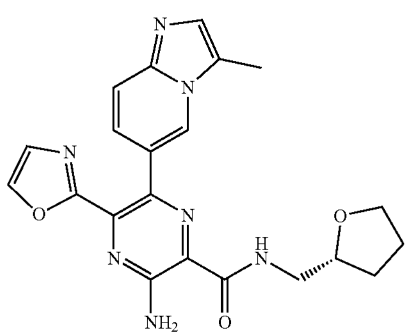 | (R)-3-amino-6-(3-methylimidazo[1,2-a]pyridin-6-yl)-5-(oxazol-2-yl)-N-((tetrahydrofuran-2-yl)methyl)pyrazine-2-carboxamide |

TABLE 1-continued

Exemplary Compound 1-306

| Compound number | Compound structure | Compound name |
|---|---|---|
| 127 | 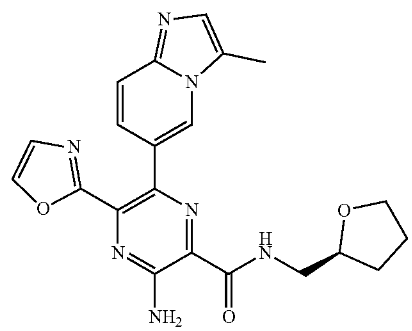 [SMILES: Cc1cnc2ccc(-c3nc(C(=O)NC[C@@H]4CCCO4)c(N)nc3-c3ncco3)cn12] | (S)-3-amino-6-(3-methylimidazo[1,2-a]pyridin-6-yl)-5-(oxazol-2-yl)-N-((tetrahydrofuran-2-yl)methyl)pyrazine-2-carboxamide |
| 128 | 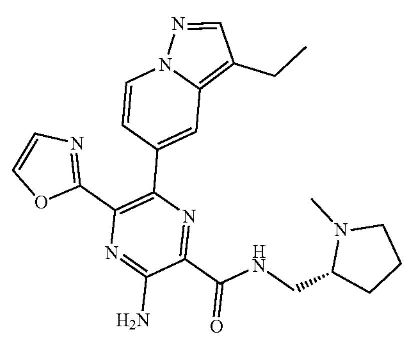 [SMILES: CCc1cnn2ccc(-c3nc(C(=O)NC[C@H]4CCCN4C)c(N)nc3-c3ncco3)cc12] | (R)-3-amino-6-(3-ethylpyrazolo[1,5-a]pyridin-5-yl)-N-((1-methylpyrrolidin-2-yl)methyl)-5-(oxazol-2-yl)pyrazine-2-carboxamide |
| 129 | 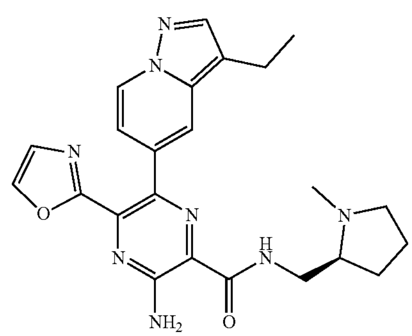 [SMILES: CCc1cnn2ccc(-c3nc(C(=O)NC[C@@H]4CCCN4C)c(N)nc3-c3ncco3)cc12] | (S)-3-amino-6-(3-ethylpyrazolo[1,5-a]pyridin-5-yl)-N-((1-methylpyrrolidin-2-yl)methyl)-5-(oxazol-2-yl)pyrazine-2-carboxamide |
| 130 | 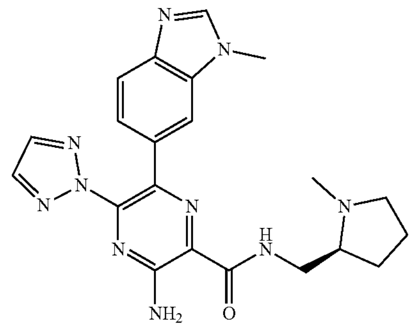 [SMILES: CN1CCC[C@H]1CNC(=O)c1nc(-c2ccc3ncn(C)c3c2)c(-n2nccn2)nc1N] | (S)-3-amino-6-(3-methyl-3H-benzo[d]imidazol-5-yl)-N-((1-methylpyrrolidin-2-yl)methyl)-5-(2H-1,2,3-triazol-2-yl)pyrazine-2-carboxamide |

TABLE 1-continued

Exemplary Compound 1-306

| Compound number | Compound structure | Compound name |
|---|---|---|
| 131 | 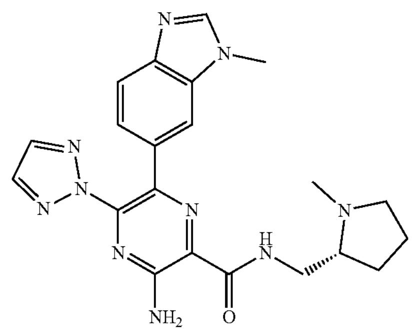 [SMILES: CN1CCC[C@@H]1CNC(=O)c1nc(-c2ccc3ncn(C)c3c2)c(-n2nccn2)nc1N] | (R)-3-amino-6-(3-methyl-3H-benzo[d]imidazol-5-yl)-N-((1-methylpyrrolidin-2-yl)methyl)-5-(2H-1,2,3-triazol-2-yl)pyrazine-2-carboxamide |
| 132 | 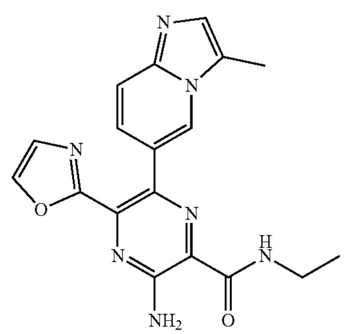 [SMILES: CCNC(=O)c1nc(-c2ccc3ncc(C)n3c2)c(-c2ncco2)nc1N] | 3-amino-N-ethyl-6-(3-methylimidazo[1,2-a]pyridin-6-yl)-5-(oxazol-2-yl)pyrazine-2-carboxamide |
| 133 | 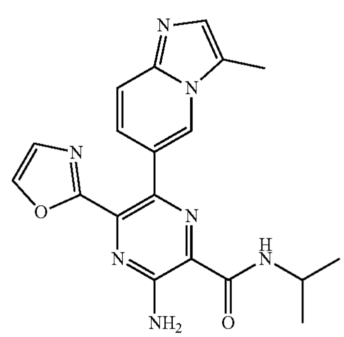 | 3-amino-N-isopropyl-6-(3-methyl-imidazo[1,2-a]pyridin-6-yl)-5-(oxazol-2-yl)pyrazine-2-carboxamide |
| 134 | 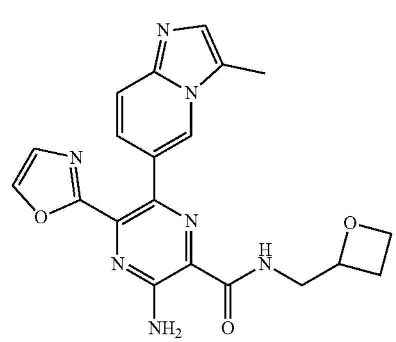 [SMILES: Cc1cnc2ccc(-c3nc(C(=O)NCC4CCO4)c(N)nc3-c3ncco3)cn12] | 3-amino-6-(3-methylimidazo[1,2-a]pyridin-6-yl)-5-(oxazol-2-yl)-N-(oxetan-2-ylmethyl)pyrazine-2-carboxamide (isomer 1) |

TABLE 1-continued

Exemplary Compound 1-306

| Compound number | Compound structure | Compound name |
|---|---|---|
| 135 | 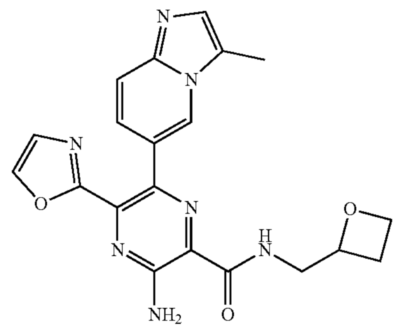 [SMILES: Cc1cnc2ccc(-c3nc(C(=O)NCC4CCO4)c(N)nc3-c3ncco3)cn12] | 3-amino-6-(3-methylimidazo[1,2-a]pyridin-6-yl)-5-(oxazol-2-yl)-N-(oxetan-2-ylmethyl)pyrazine-2-carboxamide (isomer 2) |
| 136 | 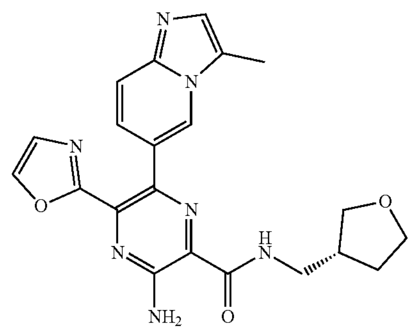 [SMILES: Cc1cnc2ccc(-c3nc(C(=O)NC[C@H]4CCOC4)c(N)nc3-c3ncco3)cn12] | (R)-3-amino-6-(3-methylimidazo[1,2-a]pyridin-6-yl)-5-(oxazol-2-yl)-N-((tetrahydrofuran-3-yl)methyl)pyrazine-2-carboxamide |
| 137 | 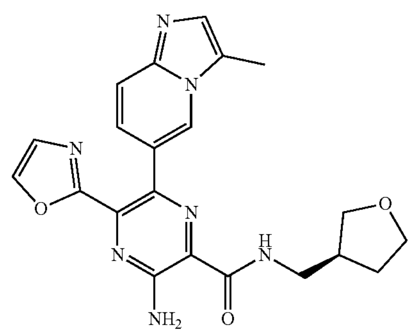 [SMILES: Cc1cnc2ccc(-c3nc(C(=O)NC[C@@H]4CCOC4)c(N)nc3-c3ncco3)cn12] | (S)-3-amino-6-(3-methylimidazo[1,2-a]pyridin-6-yl)-5-(oxazol-2-yl)-N-((tetrahydrofuran-3-yl)methyl)pyrazine-2-carboxamide |
| 138 | 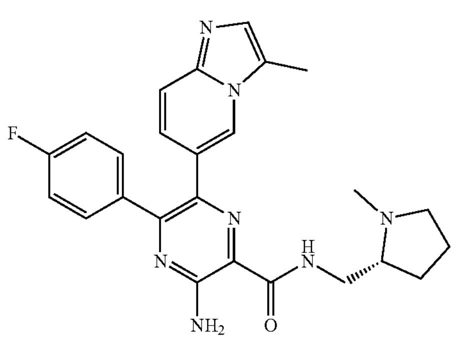 | (R)-3-amino-5-(4-fluorophenyl)-6-(3-methylimidazo[1,2-a]pyridin-6-yl)-N-((1-methylpyrrolidin-2-yl)methyl)pyrazine-2-carboxamide |

TABLE 1-continued

Exemplary Compound 1-306

| Compound number | Compound structure | Compound name |
|---|---|---|
| 139 | 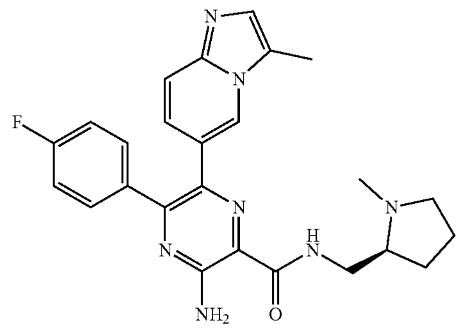 [SMILES: Cc1cnc2ccc(-c3nc(C(=O)NC[C@@H]4CCCN4C)c(N)nc3-c3ccc(F)cc3)cn12] | (S)-3-amino-5-(4-fluorophenyl)-6-(3-methylimidazo[1,2-a]pyridin-6-yl)-N-((1-methylpyrrolidin-2-yl)methyl)pyrazine-2-carboxamide |
| 142 | 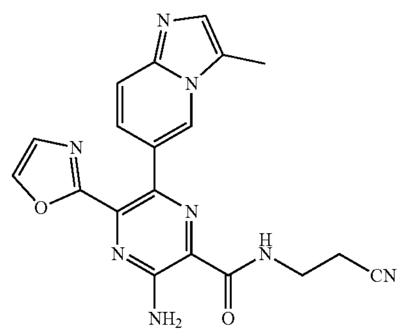 [SMILES: Cc1cnc2ccc(-c3nc(C(=O)NCCC#N)c(N)nc3-c3ncco3)cn12] | 3-amino-N-(2-cyanoethyl)-6-(3-methyl-imidazo[1,2-a]pyridin-6-yl)-5-(oxazol-2-yl)pyrazine-2-carboxamide |
| 143 | 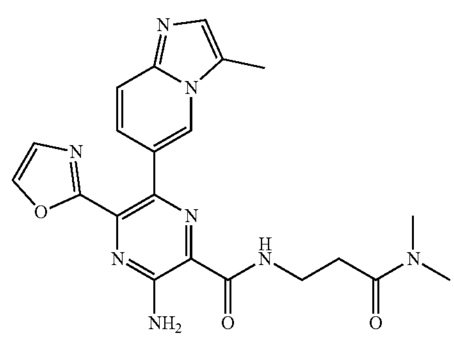 [SMILES: Cc1cnc2ccc(-c3nc(C(=O)NCCC(=O)N(C)C)c(N)nc3-c3ncco3)cn12] | 3-amino-N-(3-(dimethylamino)-3-oxopropyl)-6-(3-methylimidazo[1,2-a]pyridin-6-yl)-5-(oxazol-2-yl)pyrazine-2-carboxamide |
| 144 | 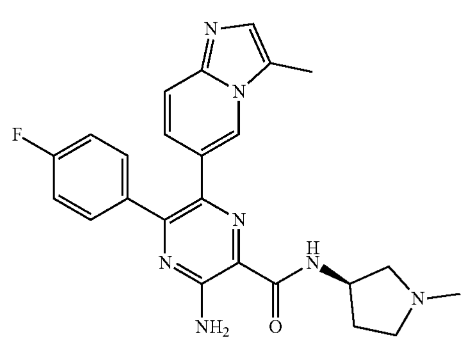 | (R)-3-amino-5-(4-fluorophenyl)-6-(3-methylimidazo[1,2-a]pyridin-6-yl)-N-(1-methylpyrrolidin-3-yl)pyrazine-2-carboxamide |

TABLE 1-continued

Exemplary Compound 1-306

| Compound number | Compound structure | Compound name |
|---|---|---|
| 145 | 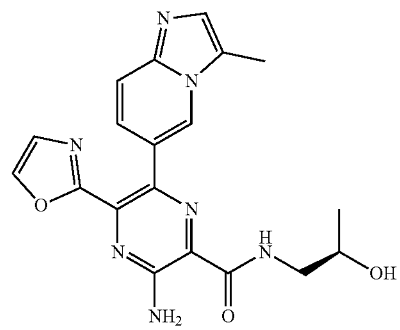 [SMILES: Cc1cnc2ccc(-c3nc(C(=O)NC[C@@H](C)O)c(N)nc3-c3ncco3)cn12] | (R)-3-amino-N-(2-hydroxypropyl)-6-(3-methylimidazo[1,2-a]pyridin-6-yl)-5-(oxazol-2-yl)pyrazine-2-carboxamide |
| 146 | 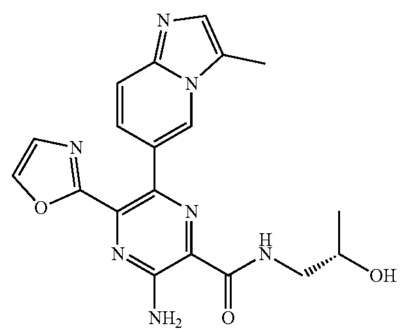 | (S)-3-amino-N-(2-hydroxypropyl)-6-(3-methylimidazo[1,2-a]pyridin-6-yl)-5-(oxazol-2-yl)pyrazine-2-carboxamide |
| 147 | 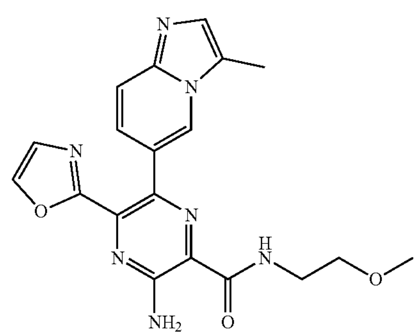 [SMILES: COCCNC(=O)c1nc(-c2ccc3ncc(C)n3c2)c(-c2ncco2)nc1N] | 3-amino-N-(2-methoxyethyl)-6-(3-methylimidazo[1,2-a]pyridin-6-yl)-5-(oxazol-2-yl)pyrazine-2-carboxamide |
| 148 | 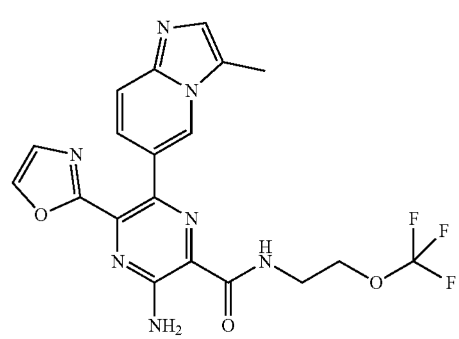 [SMILES: Cc1cnc2ccc(-c3nc(C(=O)NCCOC(F)(F)F)c(N)nc3-c3ncco3)cn12] | 3-amino-6-(3-methylimidazo[1,2-a]pyridin-6-yl)-5-(oxazol-2-yl)-N-(2-(trifluoromethoxy)ethyl)pyrazine-2-carboxamide |

TABLE 1-continued

Exemplary Compound 1-306

| Compound number | Compound structure | Compound name |
|---|---|---|
| 149 | 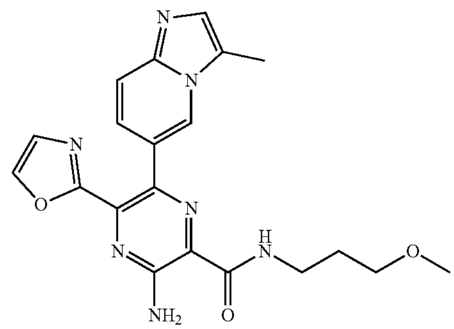 [SMILES: COCCCNC(=O)c1nc(-c2ccc3ncc(C)n3c2)c(-c2ncco2)nc1N] | 3-amino-N-(3-methoxypropyl)-6-(3-methylimidazo[1,2-a]pyridin-6-yl)-5-(oxazol-2-yl)pyrazine-2-carboxamide |
| 150 | 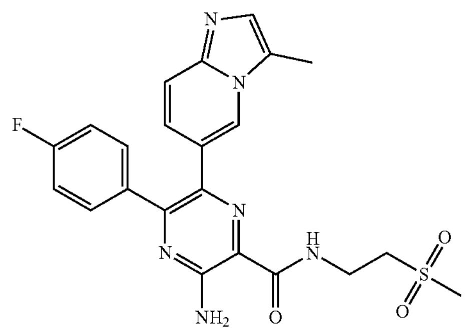 [SMILES: Cc1cnc2ccc(-c3nc(C(=O)NCCS(C)(=O)=O)c(N)nc3-c3ccc(F)cc3)cn12] | 3-amino-5-(4-fluorophenyl)-6-(3-methylimidazo[1,2-a]pyridin-6-yl)-N-(2-(methylsulfonyl)ethyl)pyrazine-2-carboxamide |
| 151 | 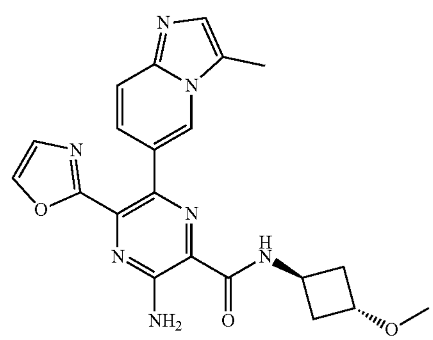 [SMILES: CO[C@H]1C[C@H](NC(=O)c2nc(-c3ccc4ncc(C)n4c3)c(-c3ncco3)nc2N)C1] | 3-amino-N-((1r,3r)-3-methoxycyclobutyl)-6-(3-methylimidazo[1,2-a]pyridin-6-yl)-5-(oxazol-2-yl)pyrazine-2-carboxamide |
| 152 | 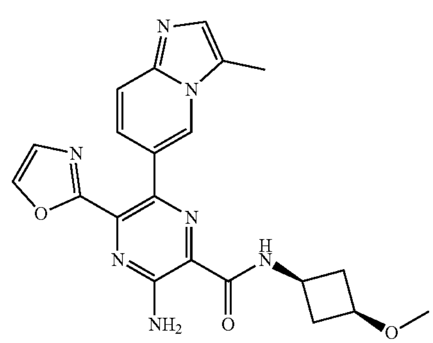 [SMILES: CO[C@H]1C[C@@H](NC(=O)c2nc(-c3ccc4ncc(C)n4c3)c(-c3ncco3)nc2N)C1] | 3-amino-N-((1s,3s)-3-methoxycyclobutyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 153 | 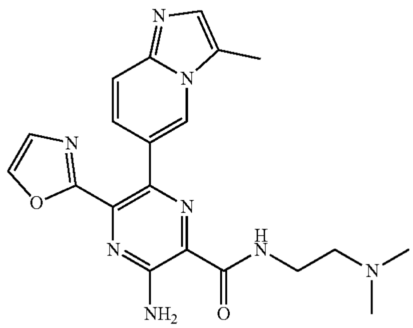 [SMILES: Cc1cnc2ccc(-c3nc(C(=O)NCCN(C)C)c(N)nc3-c3ncco3)cn12] | 3-amino-N-(2-(dimethylamino)ethyl)-6-(3-methylimidazo[1,2-a]pyridin-6-yl)-5-(oxazol-2-yl)pyrazine-2-carboxamide |
| 154 | 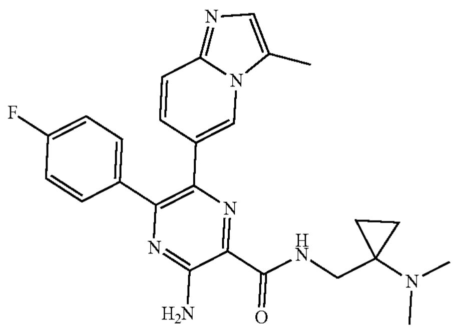 [SMILES: Cc1cnc2ccc(-c3nc(C(=O)NCC4(N(C)C)CC4)c(N)nc3-c3ccc(F)cc3)cn12] | 3-amino-N-((1-(dimethylamino)cyclopropyl)methyl)-5-(4-fluorophenyl)-6-(3-methylimidazo[1,2-a]pyridin-6-yl)pyrazine-2-carboxamide |
| 155 | 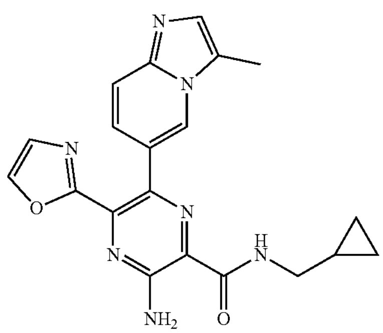 [SMILES: Cc1cnc2ccc(-c3nc(C(=O)NCC4CC4)c(N)nc3-c3ncco3)cn12] | 3-amino-N-(cyclopropylmethyl)-6-(3-methylimidazo[1,2-a]pyridin-6-yl)-5-(oxazol-2-yl)pyrazine-2-carboxamide |
| 156 | 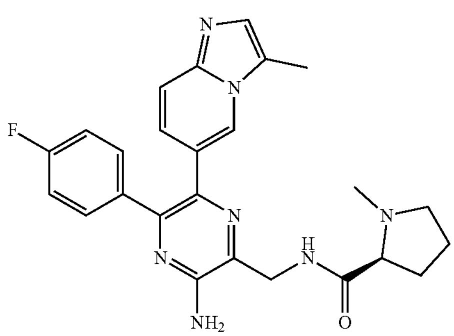 [SMILES: Cc1cnc2ccc(-c3nc(CNC(=O)[C@@H]4CCCN4C)c(N)nc3-c3ccc(F)cc3)cn12] | (S)-N-((3-amino-5-(4-fluorophenyl)-6-(3-methylimidazo[1,2-a]pyridin-6-yl)pyrazin-2-yl)methyl)-1-methylpyrrolidine-2-carboxamide |

TABLE 1-continued

Exemplary Compound 1-306

| Compound number | Compound structure | Compound name |
|---|---|---|
| 157 | 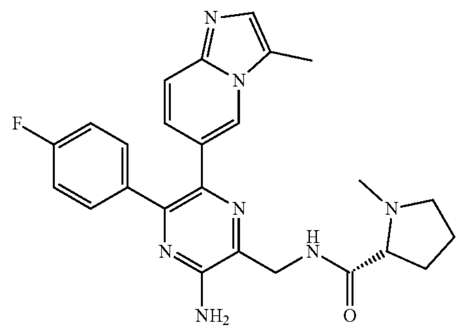 | (R)-N-((3-amino-5-(4-fluorophenyl)-6-(3-methylimidazo[1,2-a]pyridin-6-yl)pyrazin-2-yl)methyl)-1-methylpyrrolidine-2-carboxamide |
| 158 | 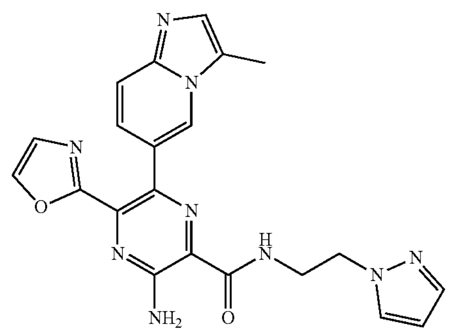 [SMILES: Cc1cnc2ccc(-c3nc(C(=O)NCCn4cccn4)c(N)nc3-c3ncco3)cn12] | N-(2-(1H-pyrazol-1-yl)ethyl)-3-amino-6-(3-methylimidazo[1,2-a]pyridin-6-yl)-5-(oxazol-2-yl)pyrazine-2-carboxamide |
| 159 | 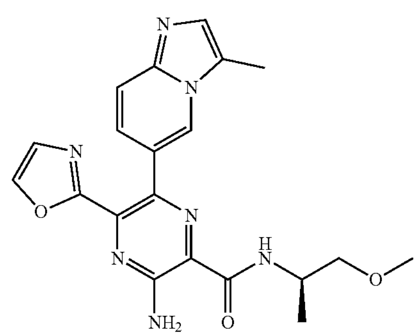 [SMILES: COC[C@@H](C)NC(=O)c1nc(-c2ccc3ncc(C)n3c2)c(-c2ncco2)nc1N] | (R)-3-amino-N-(1-methoxypropan-2-yl)-6-(3-methylimidazo[1,2-a]pyridin-6-yl)-5-(oxazol-2-yl)pyrazine-2-carboxamide |
| 160 | 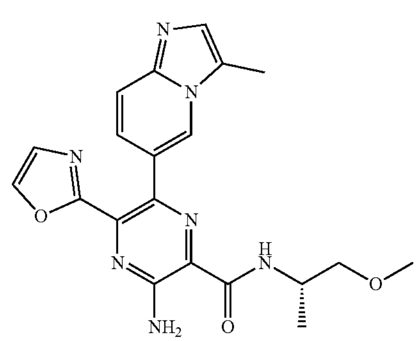 [SMILES: COC[C@H](C)NC(=O)c1nc(-c2ccc3ncc(C)n3c2)c(-c2ncco2)nc1N] | (S)-3-amino-N-(1-methoxypropan-2-yl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 161 | 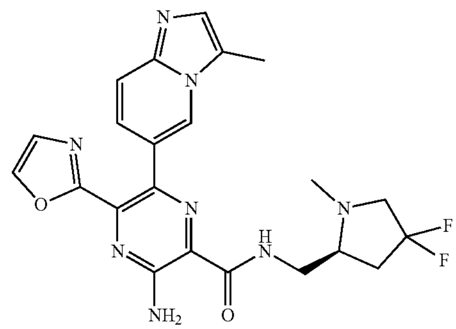 [SMILES: Cc1cnc2ccc(-c3nc(C(=O)NC[C@@H]4CC(F)(F)CN4C)c(N)nc3-c3ncco3)cn12] | (S)-3-amino-N-((4,4-difluoro-1-methyl pyrrolidin-2-yl)methyl)-6-(3-methylimidazo[1,2-a]pyridin-6-yl)-5-(oxazol-2-yl)pyrazine-2-carboxamide |
| 162 | 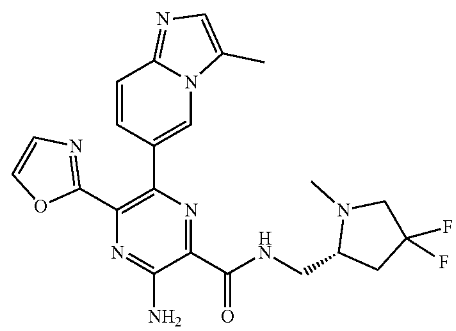 [SMILES: Cc1cnc2ccc(-c3nc(C(=O)NC[C@H]4CC(F)(F)CN4C)c(N)nc3-c3ncco3)cn12] | (R)-3-amino-N-((4,4-difluoro-1-methyl pyrrolidin-2-yl)methyl)-6-(3-methylimidazo[1,2-a]pyridin-6-yl)-5-(oxazol-2-yl)pyrazine-2-carboxamide |
| 163 | 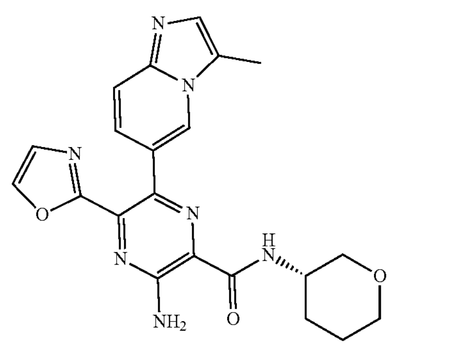 [SMILES: Cc1cnc2ccc(-c3nc(C(=O)N[C@H]4CCCOC4)c(N)nc3-c3ncco3)cn12] | 3-amino-6-(3-methylimidazo[1,2-a]pyridin-6-yl)-5-(oxazol-2-yl)-N-(tetrahydro-2H-pyran-3-yl)pyrazine-2-carboxamide (isomer 1) |
| 164 | 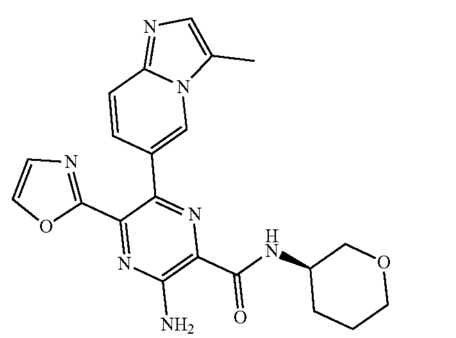 [SMILES: Cc1cnc2ccc(-c3nc(C(=O)N[C@@H]4CCCOC4)c(N)nc3-c3ncco3)cn12] | 3-amino-6-(3-methylimidazo[1,2-a]pyridin-6-yl)-5-(oxazol-2-yl)-N-(tetrahydro-2H-pyran-3-yl)pyrazine-2-carboxamide (isomer 2) |

TABLE 1-continued

Exemplary Compound 1-306

| Compound number | Compound structure | Compound name |
|---|---|---|
| 165 | 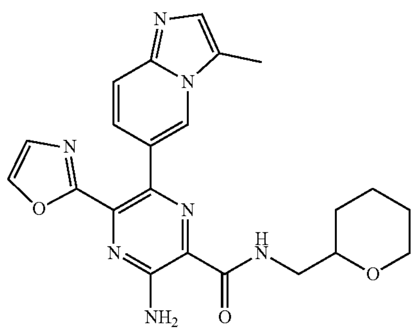 [SMILES: Cc1cnc2ccc(-c3nc(C(=O)NCC4CCCCO4)c(N)nc3-c3ncco3)cn12] | 3-amino-6-(3-methylimidazo[1,2-a]pyridin-6-yl)-5-(oxazol-2-yl)-N-((tetrahydro-2H-pyran-2-yl)methyl)pyrazine-2-carboxamide (isomer 1) |
| 166 | 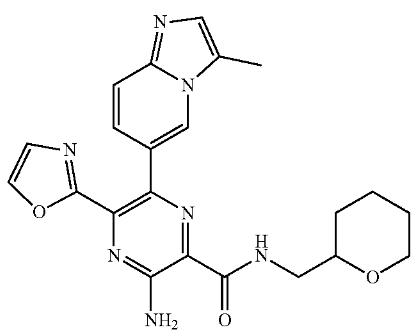 [SMILES: Cc1cnc2ccc(-c3nc(C(=O)NCC4CCCCO4)c(N)nc3-c3ncco3)cn12] | 3-amino-6-(3-methylimidazo[1,2-a]pyridin-6-yl)-5-(oxazol-2-yl)-N-((tetrahydro-2H-pyran-2-yl)methyl)pyrazine-2-carboxamide (isomer 2) |
| 167 | 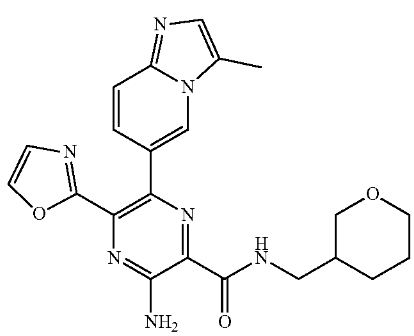 [SMILES: Cc1cnc2ccc(-c3nc(C(=O)NCC4CCCOC4)c(N)nc3-c3ncco3)cn12] | 3-amino-6-(3-methylimidazo[1,2-a]pyridin-6-yl)-5-(oxazol-2-yl)-N-((tetrahydro-2H-pyran-3-yl)methyl)pyrazine-2-carboxamide (isomer 1) |
| 168 | 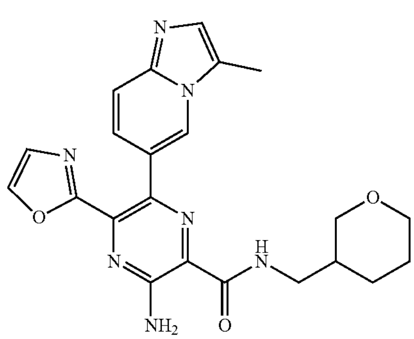 [SMILES: Cc1cnc2ccc(-c3nc(C(=O)NCC4CCCOC4)c(N)nc3-c3ncco3)cn12] | 3-amino-6-(3-methylimidazo[1,2-a]pyridin-6-yl)-5-(oxazol-2-yl)-N-((tetrahydro-2H-pyran-3-yl)methyl)pyrazine-2-carboxamide (isomer 2) |

TABLE 1-continued

Exemplary Compound 1-306

| Compound number | Compound structure | Compound name |
|---|---|---|
| 169 | 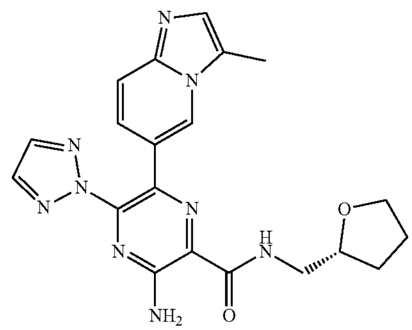 [SMILES: Cc1cnc2ccc(-c3nc(C(=O)NC[C@H]4CCCO4)c(N)nc3-n3nccn3)cn12] | (R)-3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide |
| 170 | 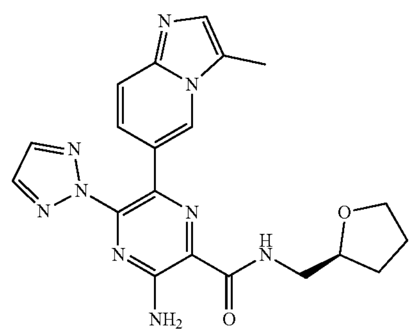 [SMILES: Cc1cnc2ccc(-c3nc(C(=O)NC[C@@H]4CCCO4)c(N)nc3-n3nccn3)cn12] | (S)-3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide |
| 171 | 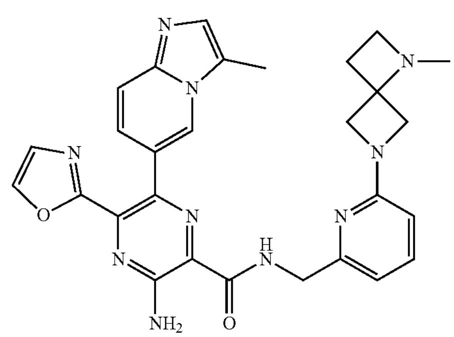 [SMILES: Cc1cnc2ccc(-c3nc(C(=O)NCc4cccc(N5CC6(CCN6C)C5)n4)c(N)nc3-c3ncco3)cn12] | 3-amino-N-((6-(1-methyl-1,6-diazaspiro[3.3]heptan-6-yl)pyridin-2-yl)methyl)-6-(3-methylimidazo[1,2-a]pyridin-6-yl)-5-(oxazol-2-yl)pyrazine-2-carboxamide |
| 172 | 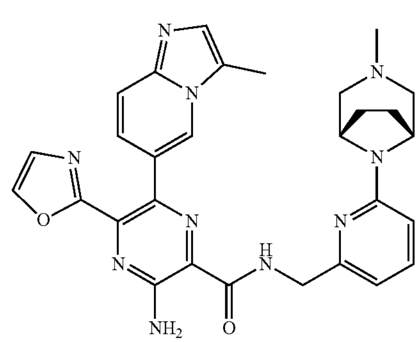 [SMILES: Cc1cnc2ccc(-c3nc(C(=O)NCc4cccc(N5[C@@H]6CC[C@H]5CN(C)C6)n4)c(N)nc3-c3ncco3)cn12] | 3-amino-N-((6-(((1R,5S)-3-methyl-3,8-diazabicyclo[3.2.1]octan-8-yl)pyridin-2-yl)methyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 173 | 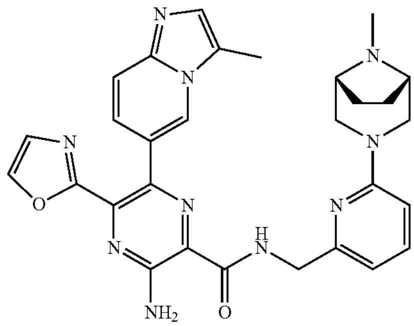 [SMILES: Cc1cnc2ccc(-c3nc(C(=O)NCc4cccc(N5C[C@H]6CC[C@@H](C5)N6C)n4)c(N)nc3-c3ncco3)cn12] | 3-amino-N-((6-((1R,5S)-8-methyl-3,8-diazabicyclo[3.2.1]octan-3-yl)pyridin-2-yl)methyl)-6-(3-methylimidazo[1,2-a]pyridin-6-yl)-5-(oxazol-2-yl)pyrazine-2-carboxamide |
| 174 | 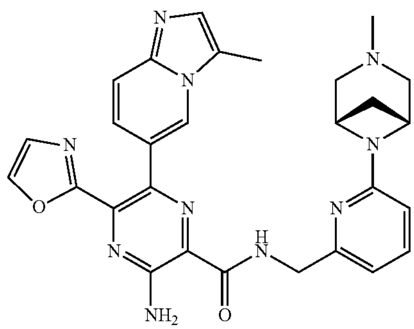 [SMILES: Cc1cnc2ccc(-c3nc(C(=O)NCc4cccc(N5[C@@H]6C[C@H]5CN(C)C6)n4)c(N)nc3-c3ncco3)cn12] | 3-amino-N-((6-(3-methyl-3,6-diazabicyclo[3.1.1]heptan-6-yl)pyridin-2-yl)methyl)-6-(3-methylimidazo[1,2-a]pyridin-6-yl)-5-(oxazol-2-yl)pyrazine-2-carboxamide |
| 175 | 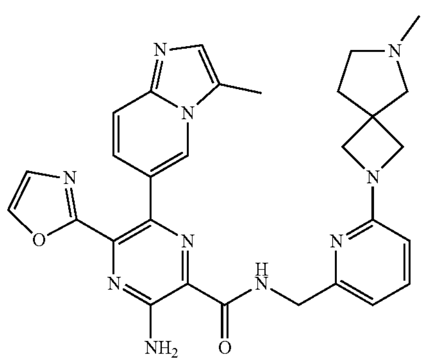 [SMILES: Cc1cnc2ccc(-c3nc(C(=O)NCc4cccc(N5CC6(CCN(C)C6)C5)n4)c(N)nc3-c3ncco3)cn12] | 3-amino-N-((6-(6-methyl-2,6-diazaspiro[3.4]octan-2-yl)pyridin-2-yl)methyl)-6-(3-methylimidazo[1,2-a]pyridin-6-yl)-5-(oxazol-2-yl)pyrazine-2-carboxamide |
| 176 | 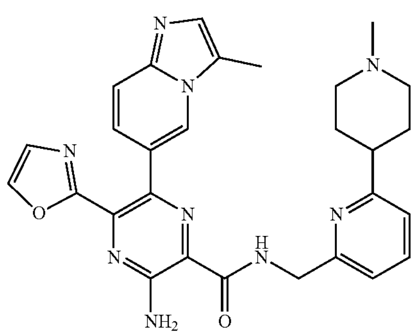 | 3-amino-6-(3-methylimidazo[1,2-a]pyridin-6-yl)-N-((6-(1-methylpiperidin-4-yl)pyridin-2-yl)methyl)-5-(oxazol-2-yl)pyrazine-2-carboxamide |

TABLE 1-continued

Exemplary Compound 1-306

| Compound number | Compound structure | Compound name |
|---|---|---|
| 177 | 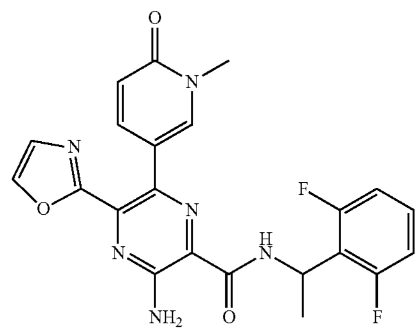 [SMILES: CC(NC(=O)c1nc(-c2ccc(=O)n(C)c2)c(-c2ncco2)nc1N)c1c(F)cccc1F] | 3-amino-N-(1-(2,6-difluorophenyl)ethyl)-6-(1-methyl-6-oxo-1,6-dihydropyridin-3-yl)-5-(oxazol-2-yl)pyrazine-2-carboxamide |
| 178 | 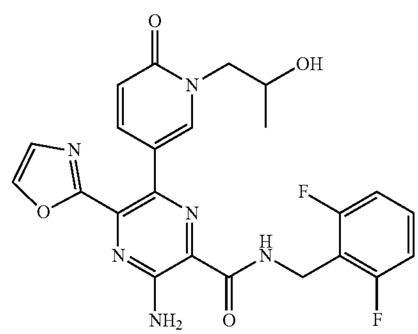 [SMILES: CC(O)Cn1cc(-c2nc(C(=O)NCc3c(F)cccc3F)c(N)nc2-c2ncco2)ccc1=O] | 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide |
| 179 | 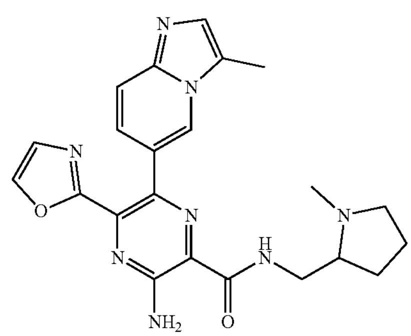 [SMILES: Cc1cnc2ccc(-c3nc(C(=O)NCC4CCCN4C)c(N)nc3-c3ncco3)cn12] | 3-amino-6-(3-methylimidazo[1,2-a]pyridin-6-yl)-N-((1-methylpyrrolidin-2-yl)methyl)-5-(oxazol-2-yl)pyrazine-2-carboxamide |
| 180 | 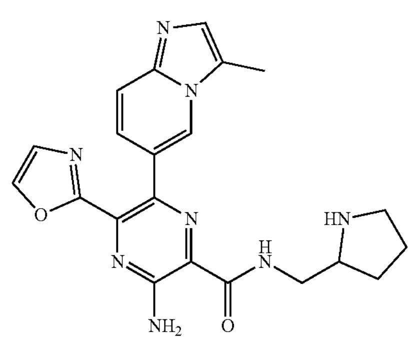 [SMILES: Cc1cnc2ccc(-c3nc(C(=O)NCC4CCCN4)c(N)nc3-c3ncco3)cn12] | 3-amino-6-(3-methylimidazo[1,2-a]pyridin-6-yl)-5-(oxazol-2-yl)-N-(pyrrolidin-2-ylmethyl)pyrazine-2-carboxamide |

TABLE 1-continued

Exemplary Compound 1-306

| Compound number | Compound structure | Compound name |
|---|---|---|
| 181 | 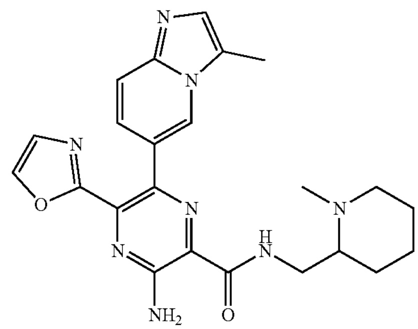 [SMILES: Cc1cnc2ccc(-c3nc(C(=O)NCC4CCCCN4C)c(N)nc3-c3ncco3)cn12] | 3-amino-6-(3-methylimidazo[1,2-a]pyridin-6-yl)-N-((1-methylpiperidin-2-yl)methyl)-5-(oxazol-2-yl)pyrazine-2-carboxamide |
| 182 | 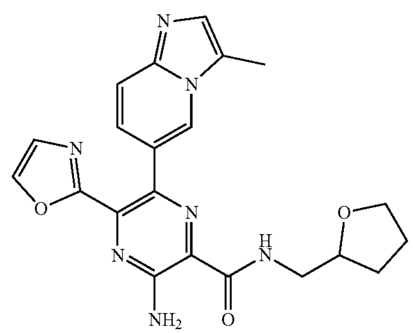 | 3-amino-6-(3-methylimidazo[1,2-a]pyridin-6-yl)-5-(oxazol-2-yl)-N-((tetrahydrofuran-2-yl)methyl)pyrazine-2-carboxamide |
| 183 | 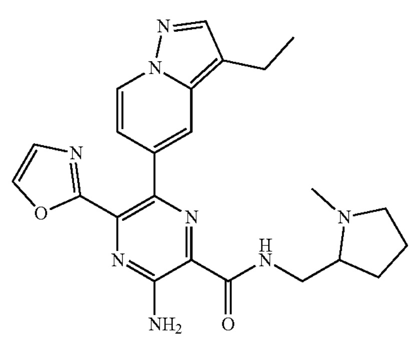 [SMILES: CCc1cnn2ccc(-c3nc(C(=O)NCC4CCCN4C)c(N)nc3-c3ncco3)cc12] | 3-amino-6-(3-ethylpyrazolo[1,5-a]pyridin-5-yl)-N-((1-methylpyrrolidin-2-yl)methyl)-5-(oxazol-2-yl)pyrazine-2-carboxamide |
| 184 | 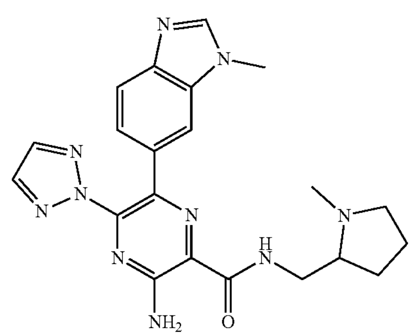 [SMILES: CN1CCCC1CNC(=O)c1nc(-c2ccc3ncn(C)c3c2)c(-n2nccn2)nc1N] | 3-amino-6-(3-methyl-3H-benzo[d]imidazol-5-yl)-N-((1-methylpyrrolidin-2-yl)methyl)-5-(2H-1,2,3-triazol-2-yl)pyrazine-2-carboxamide |

TABLE 1-continued

Exemplary Compound 1-306

| Compound number | Compound structure | Compound name |
|---|---|---|
| 185 | 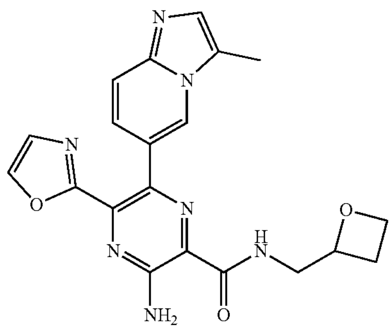 [SMILES: Cc1cnc2ccc(-c3nc(C(=O)NCC4CCO4)c(N)nc3-c3ncco3)cn12] | 3-amino-6-(3-methylimidazo[1,2-a]pyridin-6-yl)-5-(oxazol-2-yl)-N-(oxetan-2-ylmethyl)pyrazine-2-carboxamide |
| 186 | 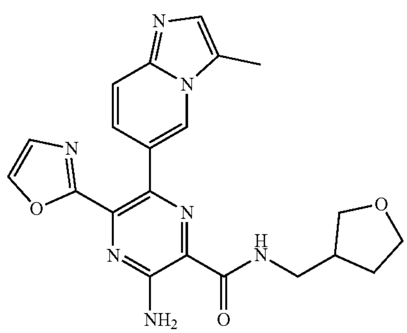 | 3-amino-6-(3-methylimidazo[1,2-a]pyridin-6-yl)-5-(oxazol-2-yl)-N-((tetrahydrofuran-3-yl)methyl)pyrazine-2-carboxamide |
| 187 | 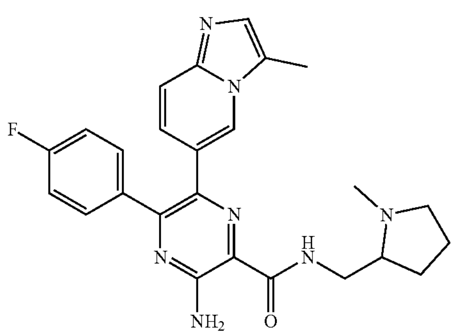 [SMILES: Cc1cnc2ccc(-c3nc(C(=O)NCC4CCCN4C)c(N)nc3-c3ccc(F)cc3)cn12] | 3-amino-5-(4-fluorophenyl)-6-(3-methylimidazo[1,2-a]pyridin-6-yl)-N-((1-methylpyrrolidin-2-yl)methyl)pyrazine-2-carboxamide |
| 188 | 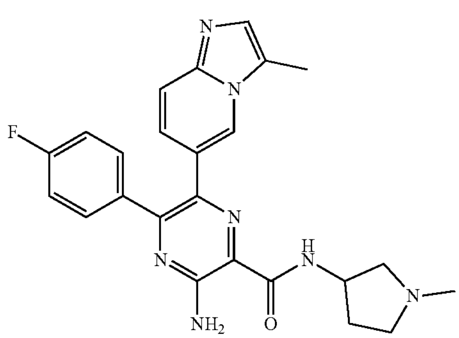 | 3-amino-5-(4-fluorophenyl)-6-(3-methylimidazo[1,2-a]pyridin-6-yl)-N-(1-methylpyrrolidin-3-yl)pyrazine-2-carboxamide |

TABLE 1-continued

Exemplary Compound 1-306

| Compound number | Compound structure | Compound name |
|---|---|---|
| 189 | 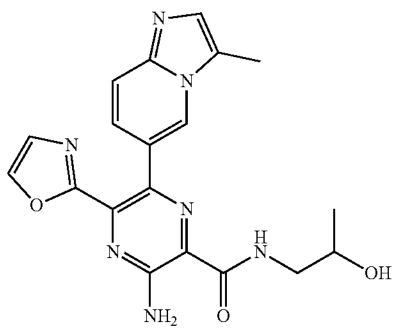 [SMILES: Cc1cnc2ccc(-c3nc(C(=O)NCC(C)O)c(N)nc3-c3ncco3)cn12] | 3-amino-N-(2-hydroxypropyl)-6-(3-methylimidazo[1,2-a]pyridin-6-yl)-5-(oxazol-2-yl)pyrazine-2-carboxamide |
| 190 | 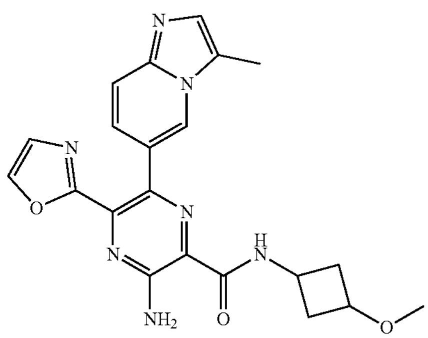 [SMILES: COC1CC(NC(=O)c2nc(-c3ccc4ncc(C)n4c3)c(-c3ncco3)nc2N)C1] | 3-amino-N-((1r,3r)-3-methoxycyclobutyl)-6-(3-methylimidazo[1,2-a]pyridin-6-yl)-5-(oxazol-2-yl)pyrazine-2-carboxamide |
| 191 | 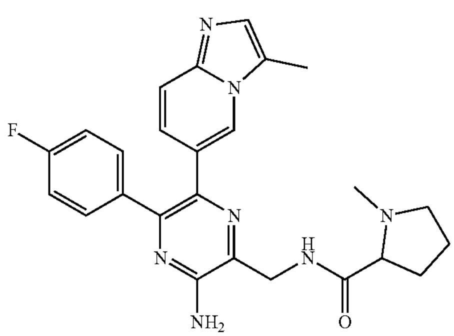 | N-((3-amino-5-(4-fluorophenyl)-6-(3-methylimidazo[1,2-a]pyridin-6-yl)pyrazin-2-yl)methyl)-1-methylpyrrolidine-2-carboxamide |
| 192 | 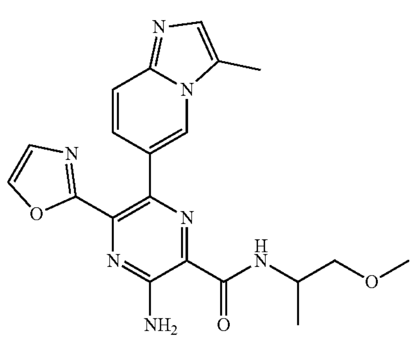 [SMILES: COCC(C)NC(=O)c1nc(-c2ccc3ncc(C)n3c2)c(-c2ncco2)nc1N] | 3-amino-N-(1-methoxypropan-2-yl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 193 | 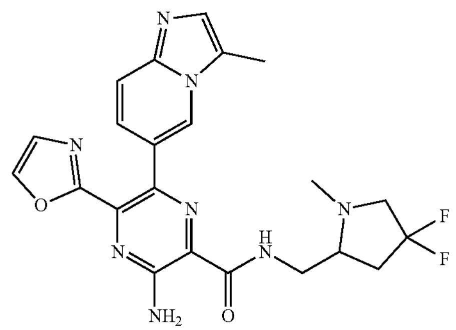 [SMILES: Cc1cnc2ccc(-c3nc(C(=O)NCC4CC(F)(F)CN4C)c(N)nc3-c3ncco3)cn12] | 3-amino-N-((4,4-difluoro-1-methylpyrrolidin-2-yl)methyl)-6-(3-methylimidazo[1,2-a]pyridin-6-yl)-5-(oxazol-2-yl)pyrazine-2-carboxamide |
| 194 | 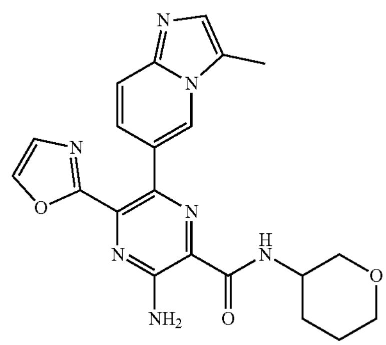 [SMILES: Cc1cnc2ccc(-c3nc(C(=O)NC4CCCOC4)c(N)nc3-c3ncco3)cn12] | 3-amino-6-(3-methylimidazo[1,2-a]pyridin-6-yl)-5-(oxazol-2-yl)-N-(tetrahydro-2H-pyran-3-yl)pyrazine-2-carboxamide |
| 195 | 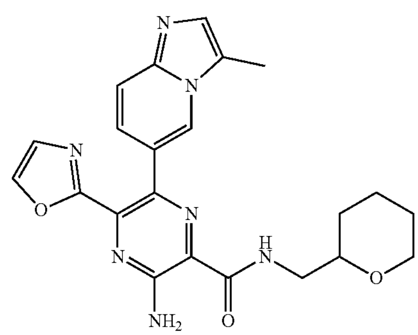 | 3-amino-6-(3-methylimidazo[1,2-a]pyridin-6-yl)-5-(oxazol-2-yl)-N-((tetrahydro-2H-pyran-2-yl)methyl)pyrazine-2-carboxamide |
| 196 | 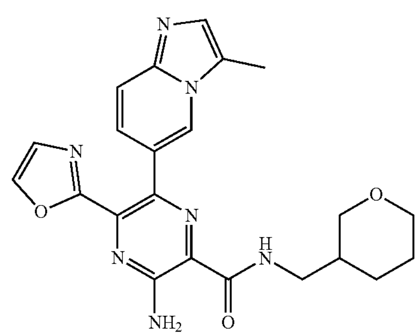 | 3-amino-6-(3-methylimidazo[1,2-a]pyridin-6-yl)-5-(oxazol-2-yl)-N-((tetrahydro-2H-pyran-3-yl)methyl)pyrazine-2-carboxamide |

TABLE 1-continued

Exemplary Compound 1-306

| Compound number | Compound structure | Compound name |
|---|---|---|
| 197 | 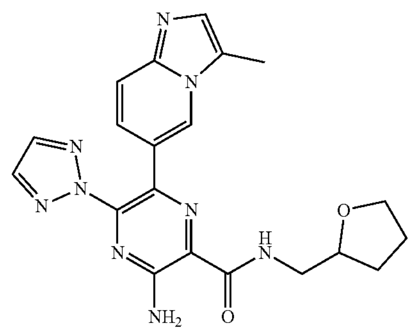 [SMILES: Cc1cnc2ccc(-c3nc(C(=O)NCC4CCCO4)c(N)nc3-n3nccn3)cn12] | 3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide |
| 198 | 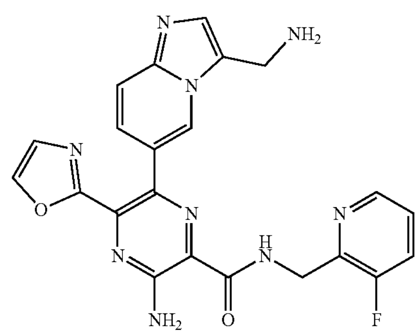 [SMILES: NCc1cnc2ccc(-c3nc(C(=O)NCc4ncccc4F)c(N)nc3-c3ncco3)cn12] | 3-amino-6-(3-(aminomethyl)imidazo[1,2-a]pyridin-6-yl)-N-((3-fluoropyridin-2-yl)methyl)-5-(oxazol-2-yl)pyrazine-2-carboxamide |
| 199 | 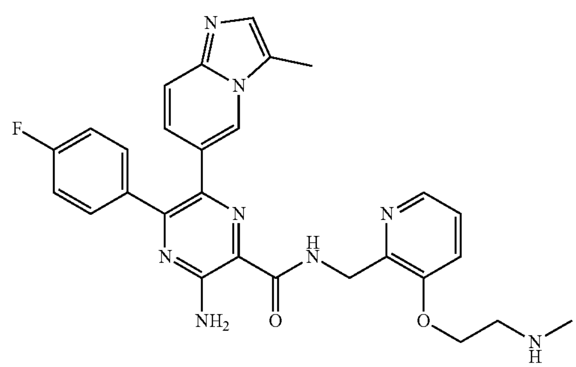 [SMILES: CNCCOc1cccnc1CNC(=O)c1nc(-c2ccc3ncc(C)n3c2)c(-c2ccc(F)cc2)nc1N] | 3-amino-5-(4-fluorophenyl)-N-((3-(2-(methylamino)ethoxy)pyridin-2-yl)methyl)-6-(3-methylimidazo[1,2-a]pyridin-6-yl)pyrazine-2-carboxamide 2,2,2-trifluoroacetate |
| 200-1 | 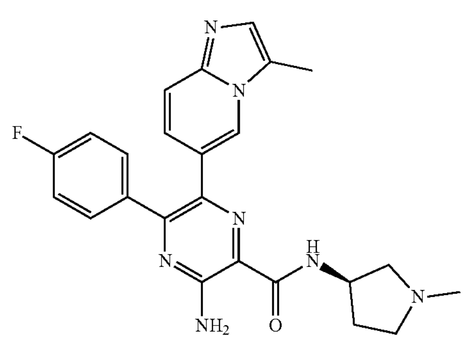 | (R)-3-amino-5-(4-fluorophenyl)-6-(3-methylimidazo[1,2-a]pyridin-6-yl)-N-(1-methylpyrrolidin-3-yl)pyrazine-2-carboxamide |

TABLE 1-continued

Exemplary Compound 1-306

| Compound number | Compound structure | Compound name |
|---|---|---|
| 200-2 | 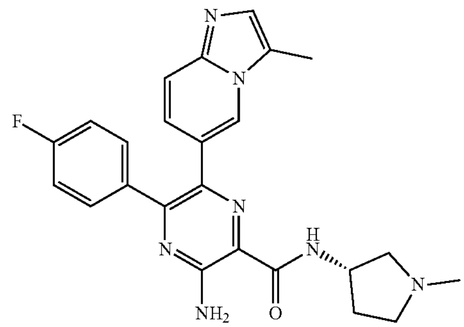 [SMILES: Cc1cnc2ccc(-c3nc(C(=O)N[C@H]4CCN(C)C4)c(N)nc3-c3ccc(F)cc3)cn12] | (S)-3-amino-5-(4-fluorophenyl)-6-(3-methylimidazo[1,2-a]pyridin-6-yl)-N-(1-methylpyrrolidin-3-yl)pyrazine-2-carboxamide |
| 201-1 | 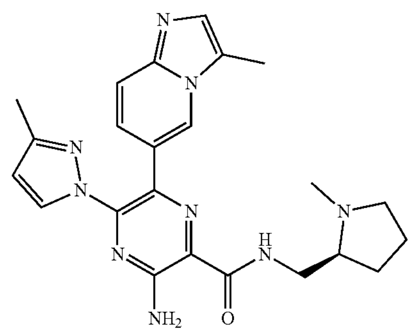 | (S)-3-amino-5-(3-methyl-1H-pyrazol-1-yl)-6-(3-methylimidazo[1,2-a]pyridin-6-yl)-N-((1-methylpyrrolidin-2-yl)methyl)pyrazine-2-carboxamide |
| 201-2 | 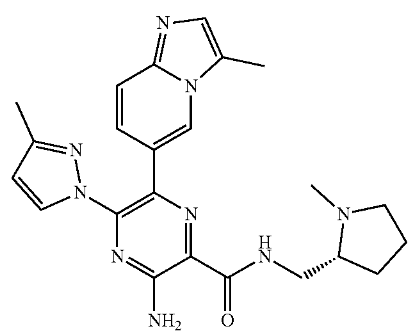 [SMILES: Cc1ccn(-c2nc(N)c(C(=O)NC[C@H]3CCCN3C)nc2-c2ccc3ncc(C)n3c2)n1] | (R)-3-amino-5-(3-methyl-1H-pyrazol-1-yl)-6-(3-methylimidazo[1,2-a]pyridin-6-yl)-N-((1-methylpyrrolidin-2-yl)methyl)pyrazine-2-carboxamide |
| 202 | 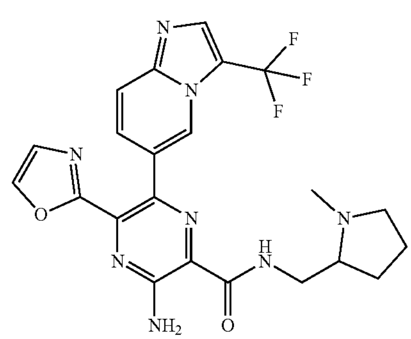 [SMILES: CN1CCCC1CNC(=O)c1nc(-c2ccc3ncc(C(F)(F)F)n3c2)c(-c2ncco2)nc1N] | 3-amino-N-((1-methylpyrrolidin-2-yl)methyl)-5-(oxazol-2-yl)-6-(3-(trifluoromethyl)imidazo[1,2-a]pyridin-6-yl)pyrazine-2-carboxamide (isomer 1) |

TABLE 1-continued

Exemplary Compound 1-306

| Compound number | Compound structure | Compound name |
|---|---|---|
| 203-1 | 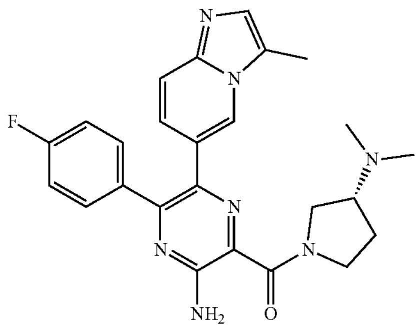 [SMILES: Cc1cnc2ccc(-c3nc(C(=O)N4CC[C@@H](N(C)C)C4)c(N)nc3-c3ccc(F)cc3)cn12] | (R)-(3-amino-5-(4-fluorophenyl)-6-(3-methylimidazo[1,2-a]pyridin-6-yl)pyrazin-2-yl)(3-(dimethylamino)pyrrolidin-1-yl)methanone |
| 203-2 | 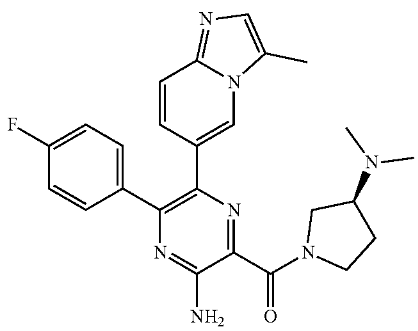 [SMILES: Cc1cnc2ccc(-c3nc(C(=O)N4CC[C@H](N(C)C)C4)c(N)nc3-c3ccc(F)cc3)cn12] | (S)-(3-amino-5-(4-fluorophenyl)-6-(3-methylimidazo[1,2-a]pyridin-6-yl)pyrazin-2-yl)(3-(dimethylamino)pyrrolidin-1-yl)methanone |
| 204-1 | 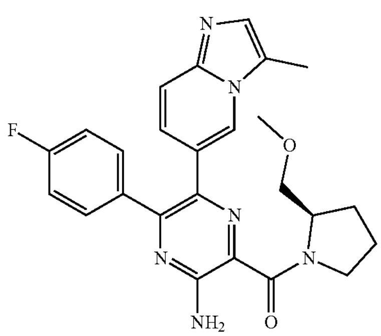 [SMILES: COC[C@H]1CCCN1C(=O)c1nc(-c2ccc3ncc(C)n3c2)c(-c2ccc(F)cc2)nc1N] | (R)-(3-amino-5-(4-fluorophenyl)-6-(3-methylimidazo[1,2-a]pyridin-6-yl)pyrazin-2-yl)(2-(methoxymethyl)pyrrolidin-1-yl)methanone |
| 204-2 | 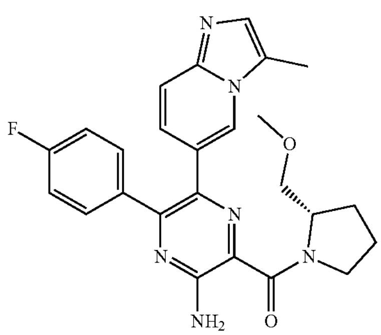 [SMILES: COC[C@@H]1CCCN1C(=O)c1nc(-c2ccc3ncc(C)n3c2)c(-c2ccc(F)cc2)nc1N] | (S)-(3-amino-5-(4-fluorophenyl)-6-(3-methylimidazo[1,2-a]pyridin-6-yl)pyrazin-2-yl)(2-(methoxymethyl)pyrrolidin-1-yl)methanone |

TABLE 1-continued

Exemplary Compound 1-306

| Compound number | Compound structure | Compound name |
|---|---|---|
| 205 | 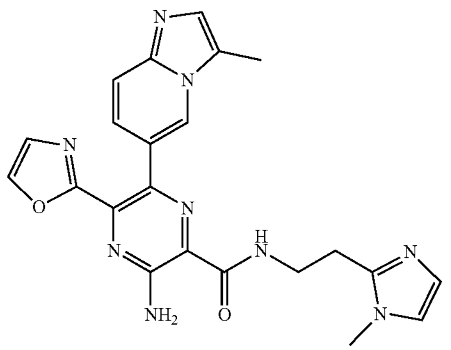 [SMILES: Cc1cnc2ccc(-c3nc(C(=O)NCCc4nccn4C)c(N)nc3-c3ncco3)cn12] | 3-amino-N-(2-(1-methyl-1H-imidazol-2-yl)ethyl)-6-(3-methylimidazo[1,2-a]pyridin-6-yl)-5-(oxazol-2-yl)pyrazine-2-carboxamide |
| 206 | 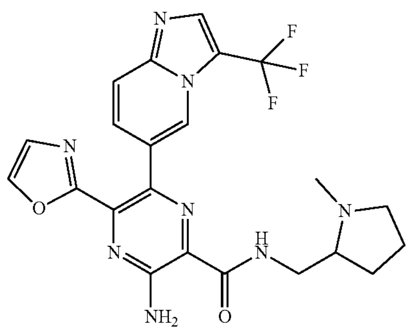 [SMILES: CN1CCCC1CNC(=O)c1nc(-c2ccc3ncc(C(F)(F)F)n3c2)c(-c2ncco2)nc1N] | 3-amino-N-((1-methylpyrrolidin-2-yl)methyl)-5-(oxazol-2-yl)-6-(3-(trifluoromethyl)imidazo[1,2-a]pyridin-6-yl)pyrazine-2-carboxamide (isomer 2) |
| 207 | 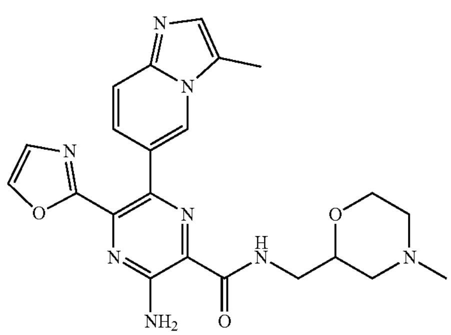 [SMILES: Cc1cnc2ccc(-c3nc(C(=O)NCC4CN(C)CCO4)c(N)nc3-c3ncco3)cn12] | rac-3-amino-6-(3-methylimidazo[1,2-a]pyridin-6-yl)-N-((4-methylmorpholin-2-yl)methyl)-5-(oxazol-2-yl)pyrazine-2-carboxamide |
| 208 | 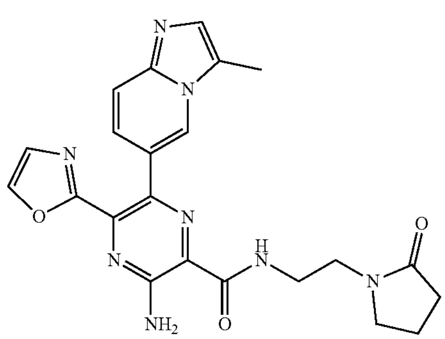 [SMILES: Cc1cnc2ccc(-c3nc(C(=O)NCCN4CCCC4=O)c(N)nc3-c3ncco3)cn12] | 3-amino-6-(3-methylimidazo[1,2-a]pyridin-6-yl)-5-(oxazol-2-yl)-N-(2-(2-oxopyrrolidin-1-yl)ethyl)pyrazine-2-carboxamide |

TABLE 1-continued

Exemplary Compound 1-306

| Compound number | Compound structure | Compound name |
|---|---|---|
| 209 | 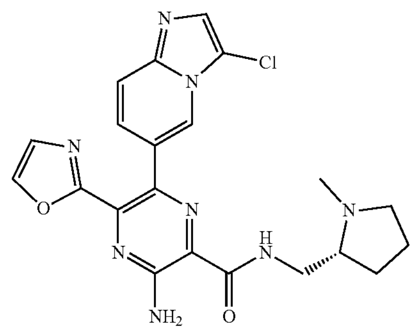 [SMILES: CN1CCC[C@@H]1CNC(=O)c1nc(-c2ccc3ncc(Cl)n3c2)c(-c2ncco2)nc1N] | (R)-3-amino-6-(3-chloroimidazo[1,2-a]pyridin-6-yl)-N-((1-methylpyrrolidin-2-yl)methyl)-5-(oxazol-2-yl)pyrazine-2-carboxamide |
| 210 | 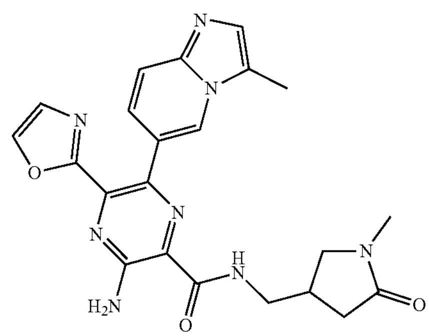 [SMILES: Cc1cnc2ccc(-c3nc(C(=O)NCC4CC(=O)N(C)C4)c(N)nc3-c3ncco3)cn12] | 3-amino-N-((1-methyl-5-oxopyrrolidin-3-yl)methyl)-6-(3-methylimidazo[1,2-a]pyridin-6-yl)-5-(oxazol-2-yl)pyrazine-2-carboxamide (isomer 2) |
| 211 | 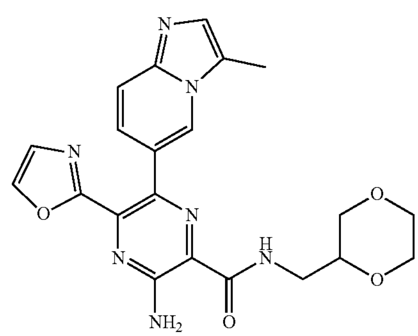 [SMILES: Cc1cnc2ccc(-c3nc(C(=O)NCC4COCCO4)c(N)nc3-c3ncco3)cn12] | rac-N-((1,4-dioxan-2-yl)methyl)-3-amino-6-(3-methylimidazo[1,2-a]pyridin-6-yl)-5-(oxazol-2-yl)pyrazine-2-carboxamide |
| 212 | 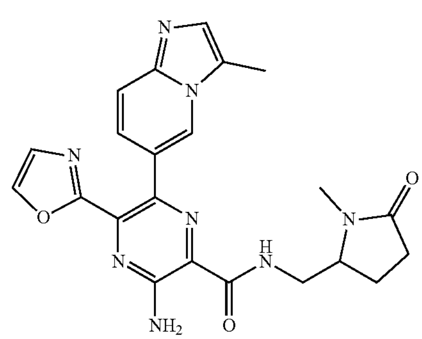 [SMILES: Cc1cnc2ccc(-c3nc(C(=O)NCC4CCC(=O)N4C)c(N)nc3-c3ncco3)cn12] | rac-3-amino-N-((1-methyl-5-oxopyrrolidin-2-yl)methyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 213 | 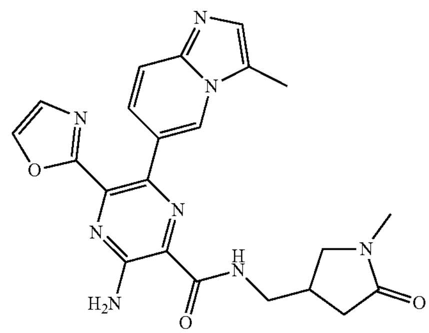 [SMILES: Cc1cnc2ccc(-c3nc(C(=O)NCC4CC(=O)N(C)C4)c(N)nc3-c3ncco3)cn12] | 3-amino-N-((1-methyl-5-oxopyrrolidin-3-yl)methyl)-6-(3-methylimidazo[1,2-a]pyridin-6-yl)-5-(oxazol-2-yl)pyrazine-2-carboxamide (isomer 1) |
| 214 | 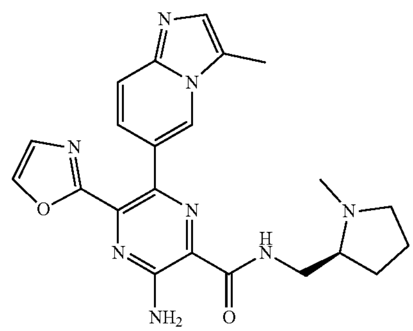 [SMILES: Cc1cnc2ccc(-c3nc(C(=O)NC[C@@H]4CCCN4C)c(N)nc3-c3ncco3)cn12] | (S)-3-amino-6-(3-chloroimidazo[1,2-a]pyridin-6-yl)-N-((1-methylpyrrolidin-2-yl)methyl)-5-(oxazol-2-yl)pyrazine-2-carboxamide |
| 215 | 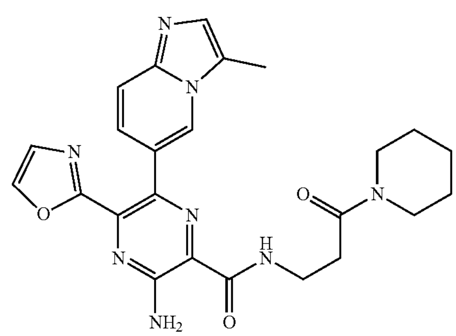 [SMILES: Cc1cnc2ccc(-c3nc(C(=O)NCCC(=O)N4CCCCC4)c(N)nc3-c3ncco3)cn12] | 3-amino-6-(3-methylimidazo[1,2-a]pyridin-6-yl)-5-(oxazol-2-yl)-N-(3-oxo-3-(piperidin-1-yl)propyl)pyrazine-2-carboxamide |
| 216 | 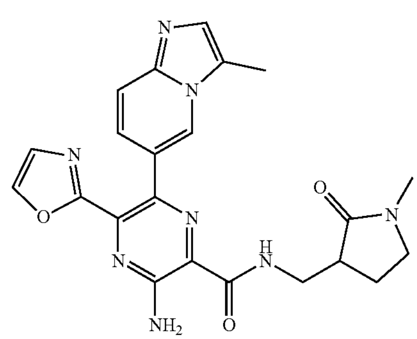 [SMILES: Cc1cnc2ccc(-c3nc(C(=O)NCC4CCN(C)C4=O)c(N)nc3-c3ncco3)cn12] | 3-amino-N-((1-methyl-2-oxopyrrolidin-3-yl)methyl)-6-(3-methylimidazo[1,2-a]pyridin-6-yl)-5-(oxazol-2-yl)pyrazine-2-carboxamide (isomer 1) |

TABLE 1-continued

Exemplary Compound 1-306

| Compound number | Compound structure | Compound name |
|---|---|---|
| 217 | 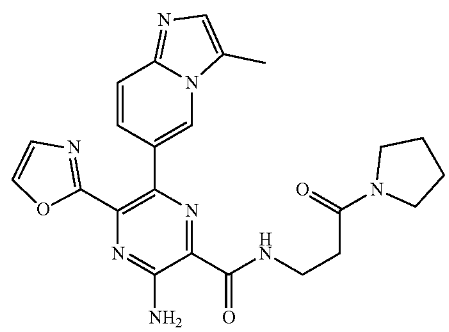 [SMILES: Cc1cnc2ccc(-c3nc(C(=O)NCCC(=O)N4CCCC4)c(N)nc3-c3ncco3)cn12] | 3-amino-6-(3-methylimidazo[1,2-a]pyridin-6-yl)-5-(oxazol-2-yl)-N-(3-oxo-3-(pyrrolidin-1-yl)propyl)pyrazine-2-carboxamide |
| 218 | 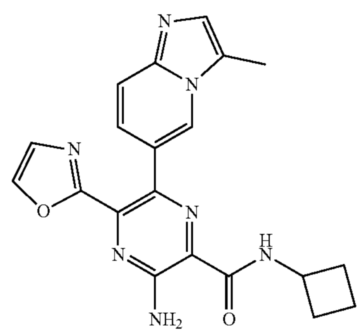 [SMILES: Cc1cnc2ccc(-c3nc(C(=O)NC4CCC4)c(N)nc3-c3ncco3)cn12] | 3-amino-N-cyclobutyl-6-(3-methylimidazo[1,2-a]pyridin-6-yl)-5-(oxazol-2-yl)pyrazine-2-carboxamide |
| 219 | 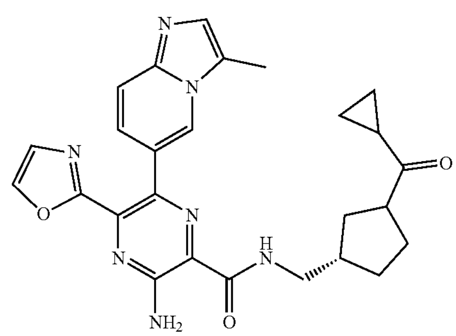 [SMILES: Cc1cnc2ccc(-c3nc(C(=O)NC[C@H]4CCC(C(=O)C5CC5)C4)c(N)nc3-c3ncco3)cn12] | (R)-3-amino-N-((1-(cyclopropanecarbonyl)pyrrolidin-3-yl)methyl)-6-(3-methylimidazo[1,2-a]pyridin-6-yl)-5-(oxazol-2-yl)pyrazine-2-carboxamide |
| 220 | 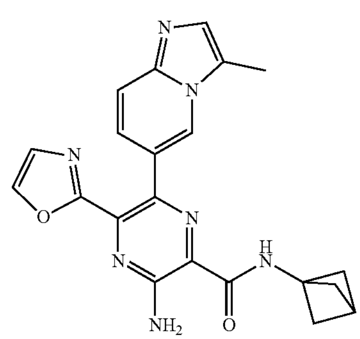 [SMILES: Cc1cnc2ccc(-c3nc(C(=O)NC45CC(C4)C5)c(N)nc3-c3ncco3)cn12] | 3-amino-N-(bicyclo[1.1.1]pentan-1-yl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 221 | 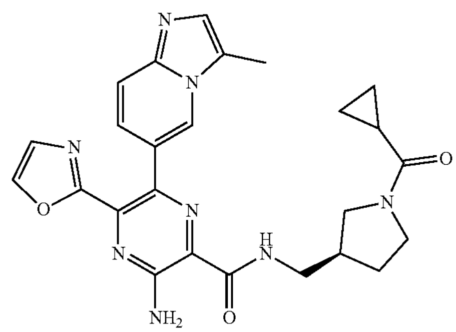 [SMILES: Cc1cnc2ccc(-c3nc(C(=O)NC[C@@H]4CCN(C(=O)C5CC5)C4)c(N)nc3-c3ncco3)cn12] | (S)-3-amino-N-((1-(cyclo-propanecarbonyl)pyrrolidin-3-yl)methyl)-6-(3-methylimidazo[1,2-a]pyridin-6-yl)-5-(oxazol-2-yl)pyrazine-2-carboxamide |
| 222 | 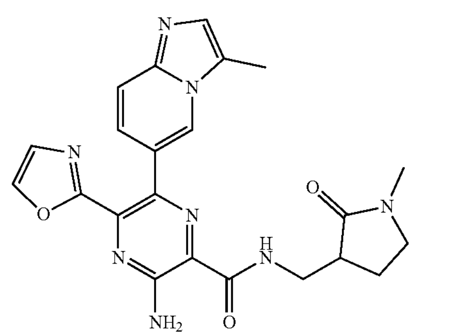 [SMILES: Cc1cnc2ccc(-c3nc(C(=O)NCC4CCN(C)C4=O)c(N)nc3-c3ncco3)cn12] | 3-amino-N-((1-methyl-2-oxopyrrolidin-3-yl)methyl)-6-(3-methylimidazo[1,2-a]pyridin-6-yl)-5-(oxazol-2-yl)pyrazine-2-carboxamide (isomer 2) |
| 223 | 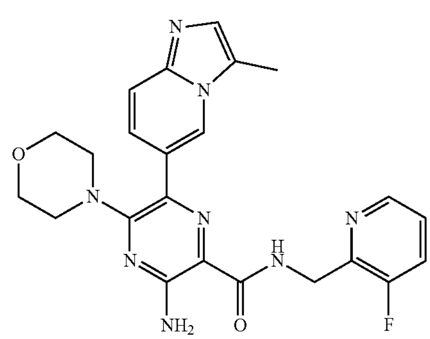 [SMILES: Cc1cnc2ccc(-c3nc(C(=O)NCc4ncccc4F)c(N)nc3N3CCOCC3)cn12] | 3-amino-N-((3-fluoropyridin-2-yl)methyl)-6-(3-methylimidazo[1,2-a]pyridin-6-yl)-5-morpholinopyrazine-2-carboxamide |
| 224 | 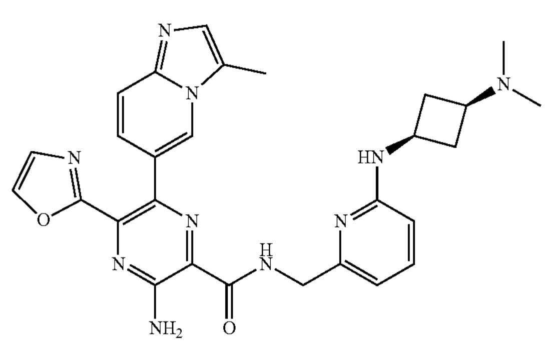 [SMILES: Cc1cnc2ccc(-c3nc(C(=O)NCc4cccc(N[C@H]5C[C@@H](N(C)C)C5)n4)c(N)nc3-c3ncco3)cn12] | Cis-3-amino-N-((6-(3-(dimethylamino)cyclobutylamino)pyridin-2-yl)methyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 225 | 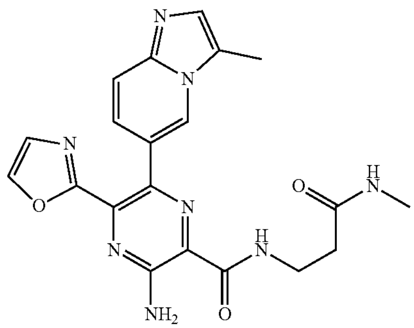 [SMILES: CNC(=O)CCNC(=O)c1nc(-c2ccc3ncc(C)n3c2)c(-c2ncco2)nc1N] | 3-amino-N-(3-(methylamino)-3-oxopropyl)-6-(3-methylimidazo[1,2-a]pyridin-6-yl)-5-(oxazol-2-yl)pyrazine-2-carboxamide |
| 226 | 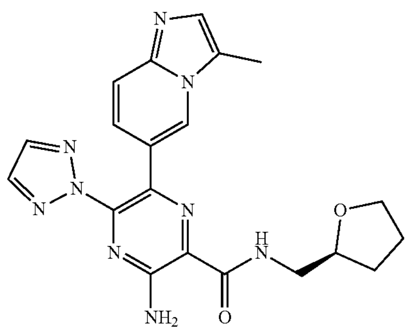 [SMILES: Cc1cnc2ccc(-c3nc(C(=O)NC[C@@H]4CCCO4)c(N)nc3-n3nccn3)cn12] | (S)-3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide |
| 227 | 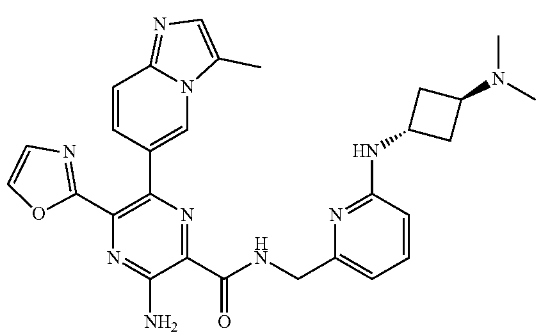 [SMILES: Cc1cnc2ccc(-c3nc(C(=O)NCc4cccc(N[C@H]5C[C@H](N(C)C)C5)n4)c(N)nc3-c3ncco3)cn12] | Trans-3-amino-N-((6-(3-(dimethylamino)cyclobutylamino)pyridin-2-yl)methyl)-6-(3-methylimidazo[1,2-a]pyridin-6-yl)-5-(oxazol-2-yl)pyrazine-2-carboxamide |
| 228 | 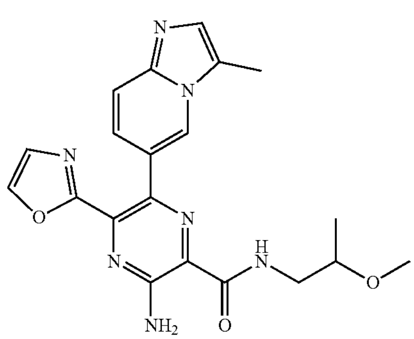 [SMILES: COC(C)CNC(=O)c1nc(-c2ccc3ncc(C)n3c2)c(-c2ncco2)nc1N] | rac-3-amino-N-(2-methoxypropyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 229 | 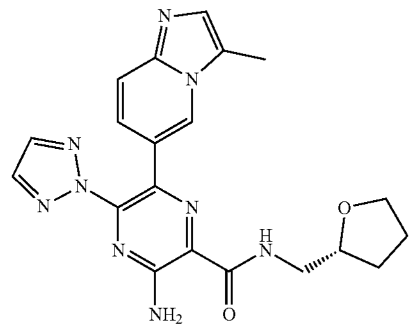 | (R)-3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide |
| 230 | 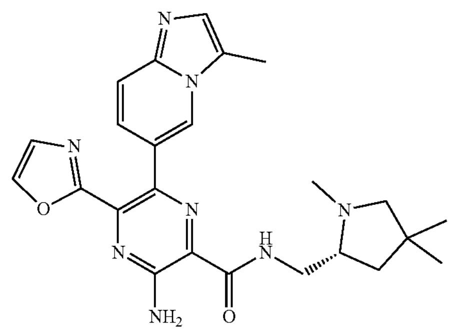 [SMILES: Cc1cnc2ccc(-c3nc(C(=O)NC[C@H]4CC(C)(C)CN4C)c(N)nc3-c3ncco3)cn12] | 3-amino-6-(3-methylimidazo[1,2-a]pyridin-6-yl)-5-(oxazol-2-yl)-N-((1,4,4-trimethylpyrrolidin-2-yl)methyl)pyrazine-2-carboxamide (isomer 2) |
| 231 | 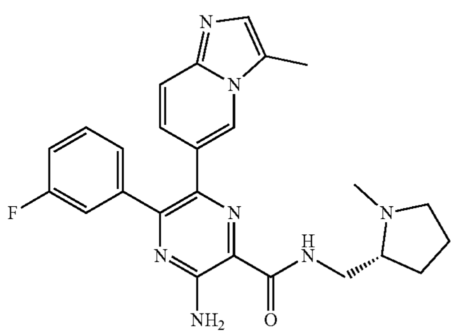 [SMILES: Cc1cnc2ccc(-c3nc(C(=O)NC[C@H]4CCCN4C)c(N)nc3-c3cccc(F)c3)cn12] | (R)-3-amino-5-(3-fluorophenyl)-6-(3-methylimidazo[1,2-a]pyridin-6-yl)-N-((1-methylpyrrolidin-2-yl)methyl)pyrazine-2-carboxamide |
| 232 | 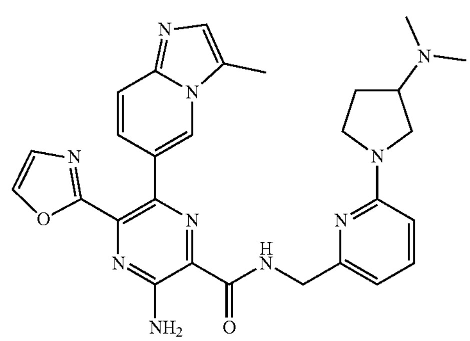 [SMILES: Cc1cnc2ccc(-c3nc(C(=O)NCc4cccc(N5CCC(N(C)C)C5)n4)c(N)nc3-c3ncco3)cn12] | 3-amino-N-((6-(3-(dimethylamino)pyrrolidin-1-yl)pyridin-2-yl)methyl)-6-(3-methylimidazo[1,2-a]pyridin-6-yl)-5-(oxazol-2-yl)pyrazine-2-carboxamide (isomer 2) |

TABLE 1-continued

Exemplary Compound 1-306

| Compound number | Compound structure | Compound name |
|---|---|---|
| 233 | 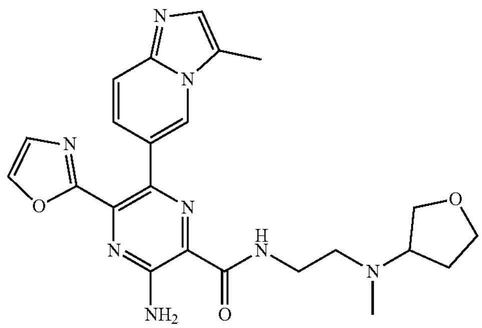 [SMILES: Cc1cnc2ccc(-c3nc(C(=O)NCCN(C)C4CCOC4)c(N)nc3-c3ncco3)cn12] | rac-3-amino-N-(2-(methyl(tetrahydrofuran-3-yl)amino)ethyl)-6-(3-methylimidazo[1,2-a]pyridin-6-yl)-5-(oxazol-2-yl)pyrazine-2-carboxamide |
| 234 | 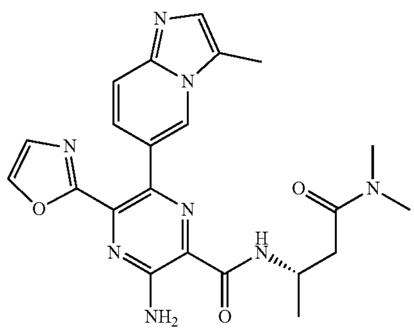 [SMILES: Cc1cnc2ccc(-c3nc(C(=O)N[C@@H](C)CC(=O)N(C)C)c(N)nc3-c3ncco3)cn12] | (S)-3-amino-N-(4-(dimethylamino)-4-oxobutan-2-yl)-6-(3-methylimidazo[1,2-a]pyridin-6-yl)-5-(oxazol-2-yl)pyrazine-2-carboxamide |
| 235 | 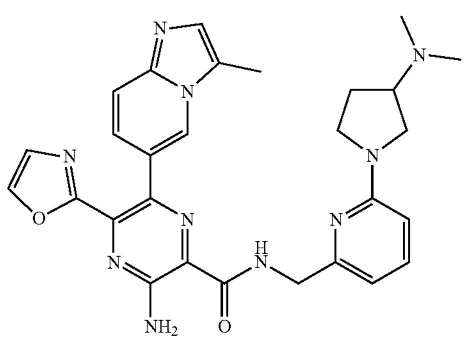 [SMILES: Cc1cnc2ccc(-c3nc(C(=O)NCc4cccc(N5CCC(N(C)C)C5)n4)c(N)nc3-c3ncco3)cn12] | 3-amino-N-((6-(3-(dimethylamino)pyrrolidin-1-yl)pyridin-2-yl)methyl)-6-(3-methylimidazo[1,2-a]pyridin-6-yl)-5-(oxazol-2-yl)pyrazine-2-carboxamide (isomer 1) |
| 236 | 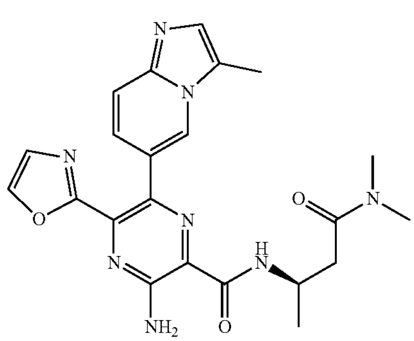 [SMILES: Cc1cnc2ccc(-c3nc(C(=O)N[C@H](C)CC(=O)N(C)C)c(N)nc3-c3ncco3)cn12] | (R)-3-amino-N-(4-(dimethylamino)-4-oxobutan-2-yl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 237 | 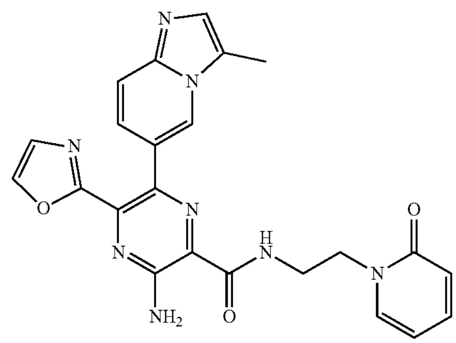 [SMILES: Cc1cnc2ccc(-c3nc(C(=O)NCCn4ccccc4=O)c(N)nc3-c3ncco3)cn12] | 3-amino-6-(3-methylimidazo[1,2-a]pyridin-6-yl)-5-(oxazol-2-yl)-N-(2-(2-oxopyridin-1(2H)-yl)ethyl)pyrazine-2-carboxamide |
| 238 | 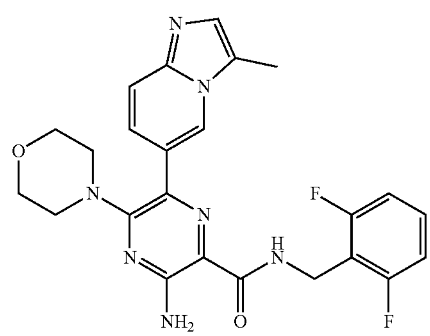 [SMILES: Cc1cnc2ccc(-c3nc(C(=O)NCc4c(F)cccc4F)c(N)nc3N3CCOCC3)cn12] | 3-amino-N-(2,6-difluorobenzyl)-6-(3-methylimidazo[1,2-a]pyridin-6-yl)-5-morpholinopyrazine-2-carboxamide |
| 239 | 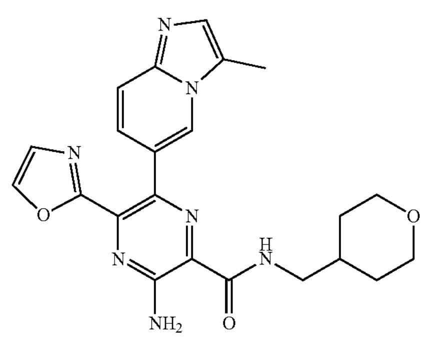 [SMILES: Cc1cnc2ccc(-c3nc(C(=O)NCC4CCOCC4)c(N)nc3-c3ncco3)cn12] | 3-amino-6-(3-methylimidazo[1,2-a]pyridin-6-yl)-5-(oxazol-2-yl)-N-((tetrahydro-2H-pyran-4-yl)methyl)pyrazine-2-carboxamide |
| 240 | 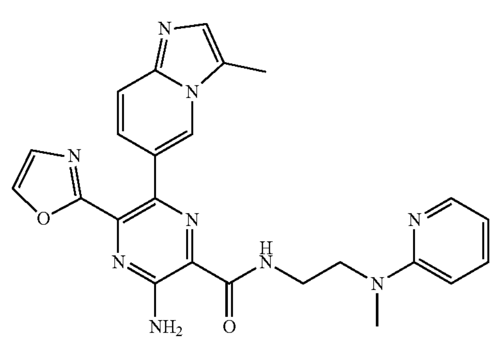 [SMILES: Cc1cnc2ccc(-c3nc(C(=O)NCCN(C)c4ccccn4)c(N)nc3-c3ncco3)cn12] | 3-amino-N-(2-(methyl(pyridin-2-yl)amino)ethyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 241 | 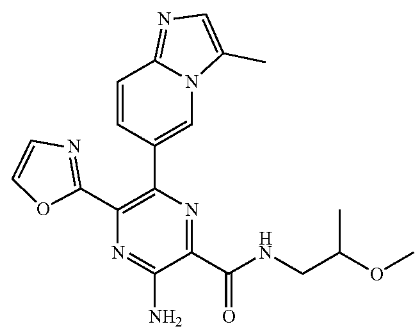 [SMILES: COC(C)CNC(=O)c1nc(-c2ccc3ncc(C)n3c2)c(-c2ncco2)nc1N] | 3-amino-N-(2-methoxypropyl)-6-(3-methylimidazo[1,2-a]pyridin-6-yl)-5-(oxazol-2-yl)pyrazine-2-carboxamide (isomer 2) |
| 242 | 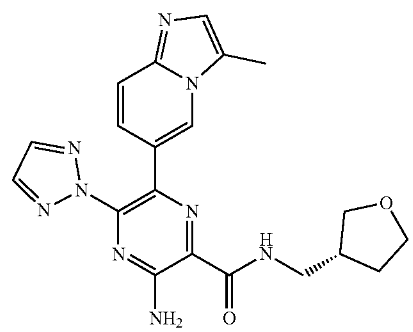 [SMILES: Cc1cnc2ccc(-c3nc(C(=O)NC[C@H]4CCOC4)c(N)nc3-n3nccn3)cn12] | (R)-3-amino-6-(3-methylimidazo[1,2-a]pyridin-6-yl)-N-((tetrahydrofuran-3-yl)methyl)-5-(2H-1,2,3-triazol-2-yl)pyrazine-2-carboxamide |
| 243 | 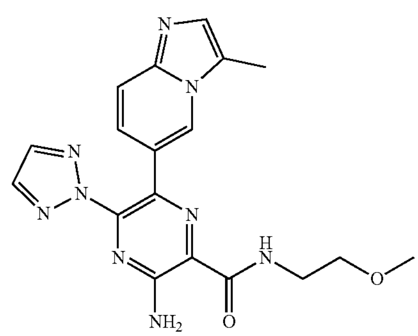 [SMILES: COCCNC(=O)c1nc(-c2ccc3ncc(C)n3c2)c(-n2nccn2)nc1N] | 3-amino-N-(2-methoxyethyl)-6-(3-methylimidazo[1,2-a]pyridin-6-yl)-5-(2H-1,2,3-triazol-2-yl)pyrazine-2-carboxamide |
| 244 | 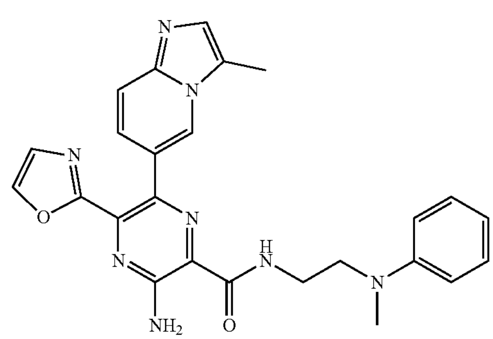 [SMILES: Cc1cnc2ccc(-c3nc(C(=O)NCCN(C)c4ccccc4)c(N)nc3-c3ncco3)cn12] | 3-amino-N-(2-(methyl(phenyl)amino)ethyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 245 | 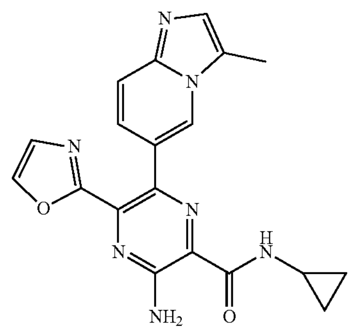 [SMILES: Cc1cnc2ccc(-c3nc(C(=O)NC4CC4)c(N)nc3-c3ncco3)cn12] | 3-amino-N-cyclopropyl-6-(3-methylimidazo[1,2-a]pyridin-6-yl)-5-(oxazol-2-yl)pyrazine-2-carboxamide |
| 246 | 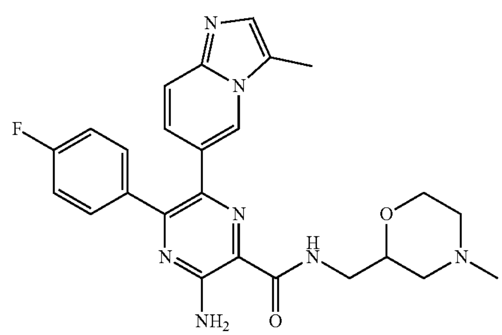 [SMILES: Cc1cnc2ccc(-c3nc(C(=O)NCC4CN(C)CCO4)c(N)nc3-c3ccc(F)cc3)cn12] | 3-amino-5-(4-fluorophenyl)-6-(3-methylimidazo[1,2-a]pyridin-6-yl)-N-((4-methylmorpholin-2-yl)methyl)pyrazine-2-carboxamide (isomer 1) |
| 247 | 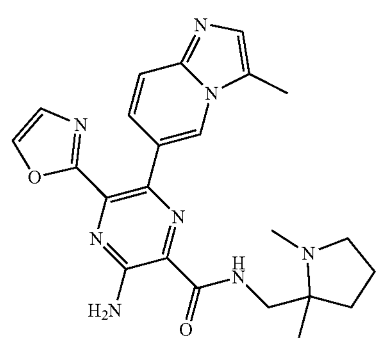 [SMILES: Cc1cnc2ccc(-c3nc(C(=O)NCC4(C)CCCN4C)c(N)nc3-c3ncco3)cn12] | 3-amino-N-((1,2-dimethylpyrrolidin-2-yl)methyl)-6-(3-methylimidazo[1,2-a]pyridin-6-yl)-5-(oxazol-2-yl)pyrazine-2-carboxamide (isomer 2) |
| 248 | 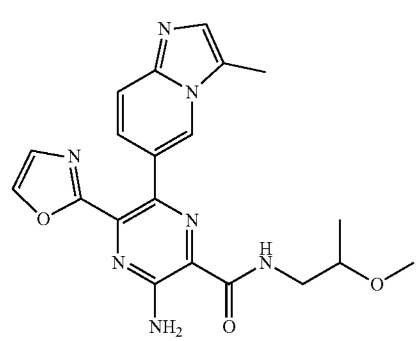 [SMILES: COC(C)CNC(=O)c1nc(-c2ccc3ncc(C)n3c2)c(-c2ncco2)nc1N] | 3-amino-N-(2-methoxypropyl)-6-(3-methylimidazo[1,2-a]pyridin-6-yl)-5-(oxazol-2-yl)pyrazine-2-carboxamide (isomer 1) |

TABLE 1-continued

Exemplary Compound 1-306

| Compound number | Compound structure | Compound name |
|---|---|---|
| 249 | 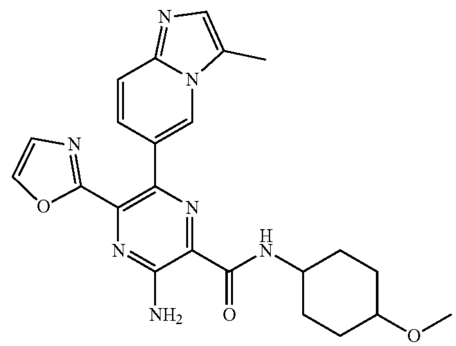 [SMILES: COC1CCC(NC(=O)c2nc(-c3ccc4ncc(C)n4c3)c(-c3ncco3)nc2N)CC1] | 3-amino-N-(4-methoxycyclohexyl)-6-(3-methylimidazo[1,2-a]pyridin-6-yl)-5-(oxazol-2-yl)pyrazine-2-carboxamide |
| 250 | 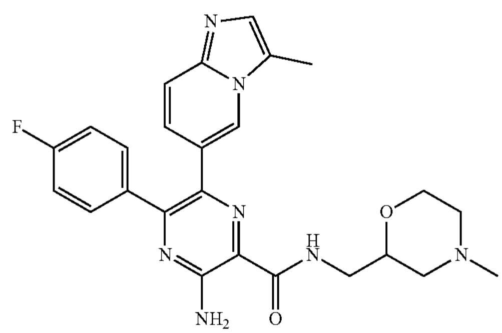 [SMILES: Cc1cnc2ccc(-c3nc(C(=O)NCC4CN(C)CCO4)c(N)nc3-c3ccc(F)cc3)cn12] | 3-amino-5-(4-fluorophenyl)-6-(3-methylimidazo[1,2-a]pyridin-6-yl)-N-((4-methylmorpholin-2-yl)methyl)pyrazine-2-carboxamide (isomer 2) |
| 251 | 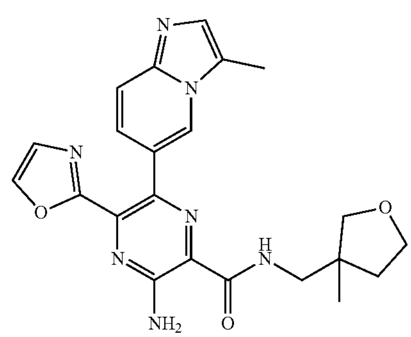 [SMILES: Cc1cnc2ccc(-c3nc(C(=O)NCC4(C)CCOC4)c(N)nc3-c3ncco3)cn12] | 3-amino-6-(3-methylimidazo[1,2-a]pyridin-6-yl)-N-((3-methyltetrahydrofuran-3-yl)methyl)-5-(oxazol-2-yl)pyrazine-2-carboxamide (isomer 1) |
| 252 | 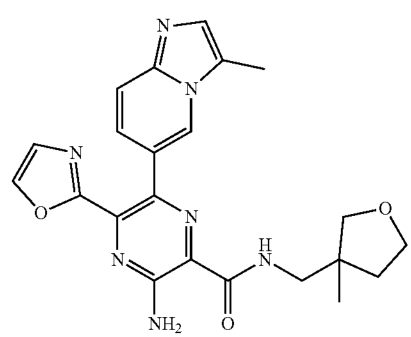 [SMILES: Cc1cnc2ccc(-c3nc(C(=O)NCC4(C)CCOC4)c(N)nc3-c3ncco3)cn12] | 3-amino-6-(3-methylimidazo[1,2-a]pyridin-6-yl)-N-((3-methyltetrahydrofuran-3-yl)methyl)-5-(oxazol-2-yl)pyrazine-2-carboxamide (isomer 2) |

TABLE 1-continued

Exemplary Compound 1-306

| Compound number | Compound structure | Compound name |
|---|---|---|
| 253 | 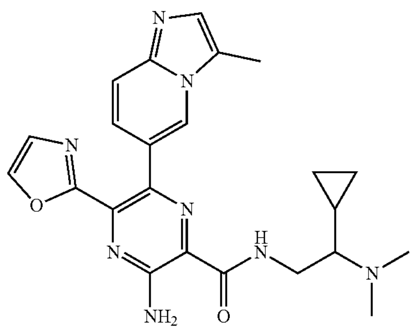 [SMILES: Cc1cnc2ccc(-c3nc(C(=O)NCC(C4CC4)N(C)C)c(N)nc3-c3ncco3)cn12] | 3-amino-N-(2-cyclopropyl-2-(dimethylamino)ethyl)-6-(3-methylimidazo[1,2-a]pyridin-6-yl)-5-(oxazol-2-yl)pyrazine-2-carboxamide (isomer 1) |
| 254 | 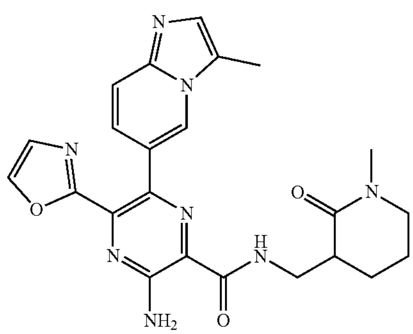 [SMILES: Cc1cnc2ccc(-c3nc(C(=O)NCC4CCCN(C)C4=O)c(N)nc3-c3ncco3)cn12] | 3-amino-N-((1-methyl-2-oxopiperidin-3-yl)methyl)-6-(3-methylimidazo[1,2-a]pyridin-6-yl)-5-(oxazol-2-yl)pyrazine-2-carboxamide (isomer 2) |
| 255 | 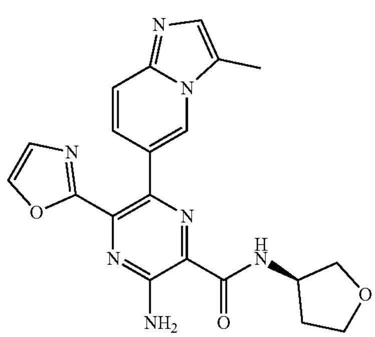 [SMILES: Cc1cnc2ccc(-c3nc(C(=O)N[C@@H]4CCOC4)c(N)nc3-c3ncco3)cn12] | (R)-3-amino-6-(3-methylimidazo[1,2-a]pyridin-6-yl)-5-(oxazol-2-yl)-N-(tetrahydrofuran-3-yl)pyrazine-2-carboxamide |
| 256 | 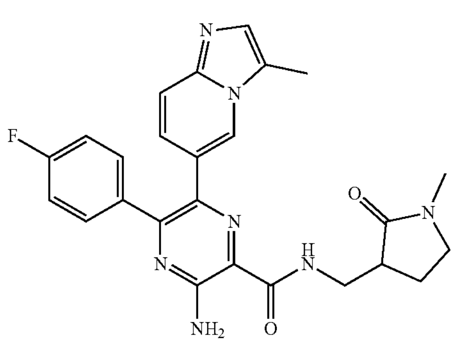 [SMILES: Cc1cnc2ccc(-c3nc(C(=O)NCC4CCN(C)C4=O)c(N)nc3-c3ccc(F)cc3)cn12] | 3-amino-5-(4-fluorophenyl)-N-((1-methyl-2-oxopyrrolidin-3-yl)methyl)-6-(3-methylimidazo[1,2-a]pyridin-6-yl)pyrazine-2-carboxamide (isomer 2) |

TABLE 1-continued

Exemplary Compound 1-306

| Compound number | Compound structure | Compound name |
|---|---|---|
| 257 | 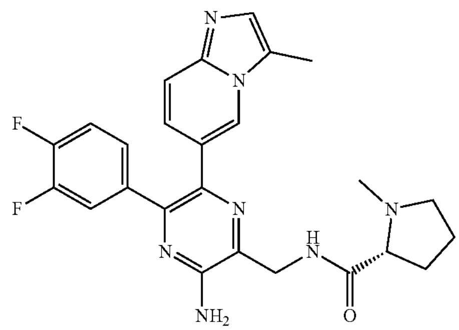 [SMILES: Cc1cnc2ccc(-c3nc(CNC(=O)[C@H]4CCCN4C)c(N)nc3-c3ccc(F)c(F)c3)cn12] | (R)-N-((3-amino-5-(3,4-difluorophenyl)-6-(3-methylimidazo[1,2-a]pyridin-6-yl)pyrazin-2-yl)methyl)-1-methylpyrrolidine-2-carboxamide |
| 258 | 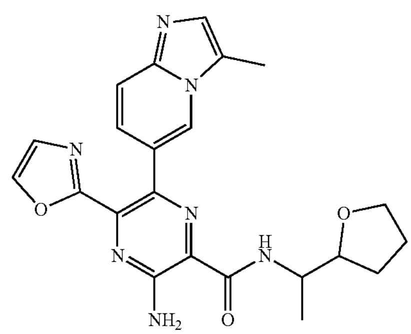 [SMILES: Cc1cnc2ccc(-c3nc(C(=O)NC(C)C4CCCO4)c(N)nc3-c3ncco3)cn12] | 3-amino-6-(3-methylimidazo[1,2-a]pyridin-6-yl)-5-(oxazol-2-yl)-N-(1-(tetrahydrofuran-2-yl)ethyl)pyrazine-2-carboxamide (isomer 4) |
| 259 | 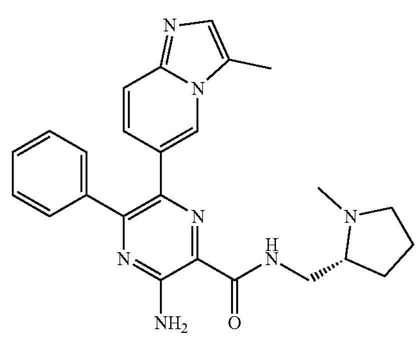 [SMILES: Cc1cnc2ccc(-c3nc(C(=O)NC[C@H]4CCCN4C)c(N)nc3-c3ccccc3)cn12] | (R)-3-amino-6-(3-methylimidazo[1,2-a]pyridin-6-yl)-N-((1-methylpyrrolidin-2-yl)methyl)-5-phenylpyrazine-2-carboxamide |
| 260 | 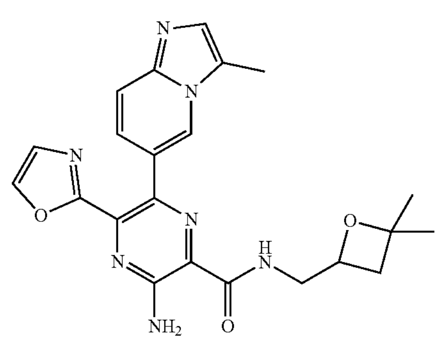 [SMILES: Cc1cnc2ccc(-c3nc(C(=O)NCC4CC(C)(C)O4)c(N)nc3-c3ncco3)cn12] | 3-amino-N-((4,4-dimethyloxetan-2-yl)methyl)-6-(3-methylimidazo[1,2-a]pyridin-6-yl)-5-(oxazol-2-yl)pyrazine-2-carboxamide (isomer 1) |

TABLE 1-continued

Exemplary Compound 1-306

| Compound number | Compound structure | Compound name |
|---|---|---|
| 261 | 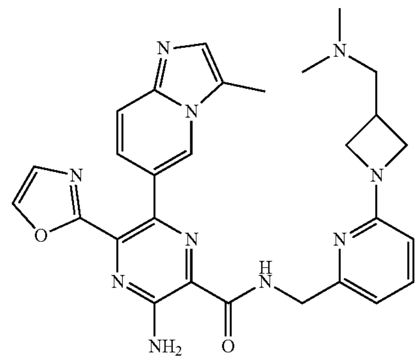 [SMILES: Cc1cnc2ccc(-c3nc(C(=O)NCc4cccc(N5CC(CN(C)C)C5)n4)c(N)nc3-c3ncco3)cn12] | 3-amino-N-((6-(3-((dimethylamino)methyl)azetidin-1-yl)pyridin-2-yl)methyl)-6-(3-methylimidazo[1,2-a]pyridin-6-yl)-5-(oxazol-2-yl)pyrazine-2-carboxamide |
| 262 | 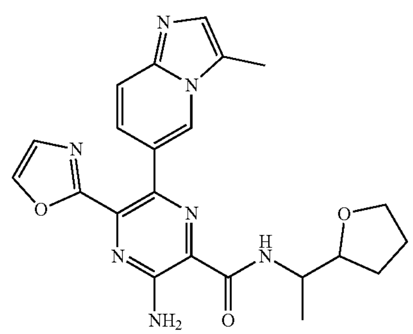 [SMILES: Cc1cnc2ccc(-c3nc(C(=O)NC(C)C4CCCO4)c(N)nc3-c3ncco3)cn12] | 3-amino-6-(3-methylimidazo[1,2-a]pyridin-6-yl)-5-(oxazol-2-yl)-N-(1-(tetrahydrofuran-2-yl)ethyl)pyrazine-2-carboxamide (isomer 2) |
| 263 | 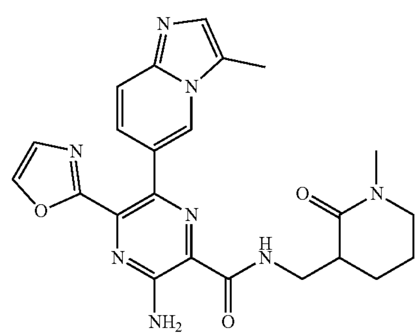 [SMILES: Cc1cnc2ccc(-c3nc(C(=O)NCC4CCCN(C)C4=O)c(N)nc3-c3ncco3)cn12] | 3-amino-N-((1-methyl-2-oxopiperidin-3-yl)methyl)-6-(3-methylimidazo[1,2-a]pyridin-6-yl)-5-(oxazol-2-yl)pyrazine-2-carboxamide (isomer 1) |
| 264 | 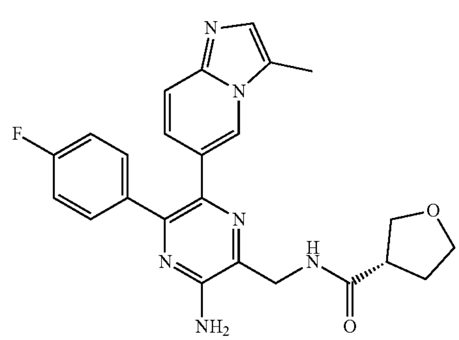 | (S)-N-((3-amino-5-(4-fluorophenyl)-6-(3-methylimidazo[1,2-a]pyridin-6-yl)pyrazin-2-yl)methyl)tetrahydrofuran-3-carboxamide |

TABLE 1-continued

Exemplary Compound 1-306

| Compound number | Compound structure | Compound name |
|---|---|---|
| 265 | 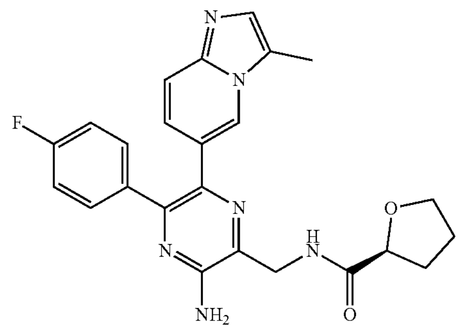 | (S)-N-((3-amino-5-(4-fluorophenyl)-6-(3-methylimidazo[1,2-a]pyridin-6-yl)pyrazin-2-yl)methyl)tetrahydrofuran-2-carboxamide |
| 266 | 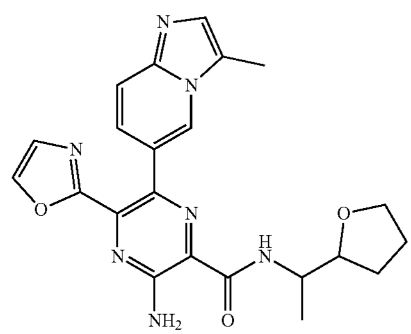 [SMILES: Cc1cnc2ccc(-c3nc(C(=O)NC(C)C4CCCO4)c(N)nc3-c3ncco3)cn12] | 3-amino-6-(3-methylimidazo[1,2-a]pyridin-6-yl)-5-(oxazol-2-yl)-N-(1-(tetrahydrofuran-2-yl)ethyl)pyrazine-2-carboxamide (isomer 1) |
| 267 | 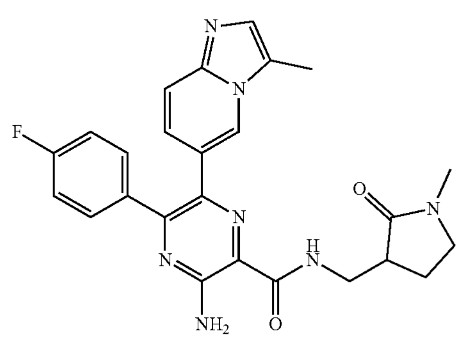 [SMILES: Cc1cnc2ccc(-c3nc(C(=O)NCC4CCN(C)C4=O)c(N)nc3-c3ccc(F)cc3)cn12] | 3-amino-5-(4-fluorophenyl)-N-((1-methyl-2-oxopyrrolidin-3-yl)methyl)-6-(3-methylimidazo[1,2-a]pyridin-6-yl)pyrazine-2-carboxamide (isomer 1) |
| 268 | 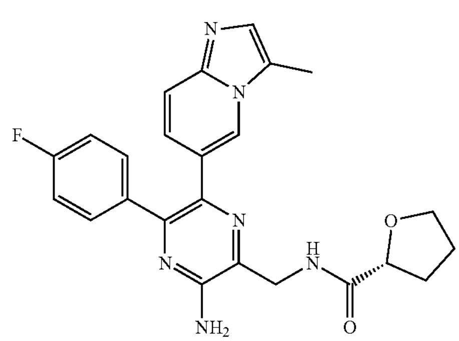 | (R)-N-((3-amino-5-(4-fluorophenyl)-6-(3-methylimidazo[1,2-a]pyridin-6-yl)pyrazin-2-yl)methyl)tetrahydrofuran-2-carboxamide |

TABLE 1-continued

Exemplary Compound 1-306

| Compound number | Compound structure | Compound name |
|---|---|---|
| 269 | 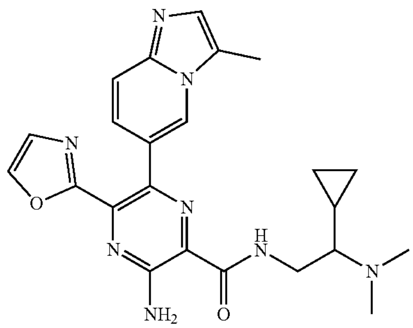 [SMILES: Cc1cnc2ccc(-c3nc(C(=O)NCC(C4CC4)N(C)C)c(N)nc3-c3ncco3)cn12] | 3-amino-N-(2-cyclopropyl-2-(dimethylamino)ethyl)-6-(3-methylimidazo[1,2-a]pyridin-6-yl)-5-(oxazol-2-yl)pyrazine-2-carboxamide (isomer 2) |
| 270 | 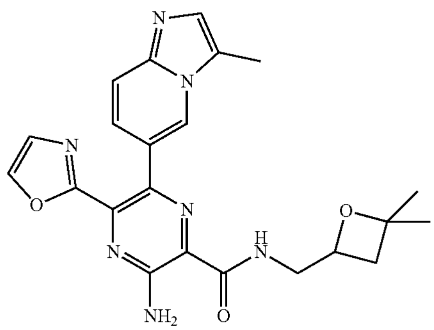 [SMILES: Cc1cnc2ccc(-c3nc(C(=O)NCC4CC(C)(C)O4)c(N)nc3-c3ncco3)cn12] | 3-amino-N-((4,4-dimethyloxetan-2-yl)methyl)-6-(3-methylimidazo[1,2-a]pyridin-6-yl)-5-(oxazol-2-yl)pyrazine-2-carboxamide (isomer 2) |
| 271-1 | 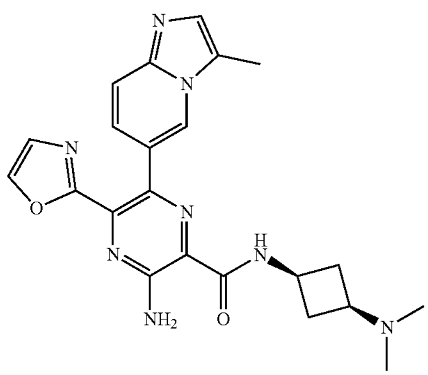 [SMILES: Cc1cnc2ccc(-c3nc(C(=O)N[C@H]4C[C@@H](N(C)C)C4)c(N)nc3-c3ncco3)cn12] | cis-3-amino-N-(3-(dimethylamino)cyclobutyl)-6-(3-methylimidazo[1,2-a]pyridin-6-yl)-5-(oxazol-2-yl)pyrazine-2-carboxamide |
| 271-2 | 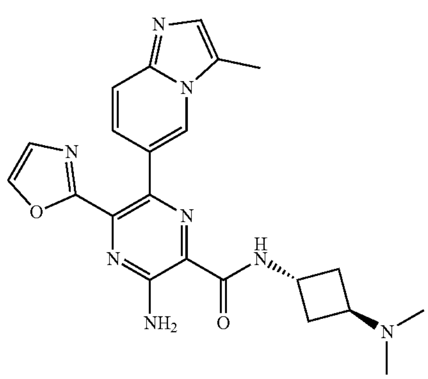 [SMILES: Cc1cnc2ccc(-c3nc(C(=O)N[C@H]4C[C@H](N(C)C)C4)c(N)nc3-c3ncco3)cn12] | Trans-3-amino-N-(3-(dimethylamino)cyclobutyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 272 | 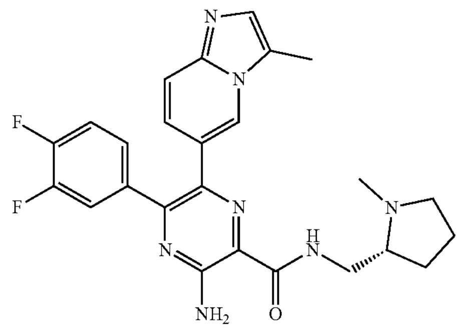 [SMILES: Cc1cnc2ccc(-c3nc(C(=O)NC[C@H]4CCCN4C)c(N)nc3-c3ccc(F)c(F)c3)cn12] | (R)-3-amino-5-(3,4-difluorophenyl)-6-(3-methylimidazo[1,2-a]pyridin-6-yl)-N-((1-methylpyrrolidin-2-yl)methyl)pyrazine-2-carboxamide |
| 273 | 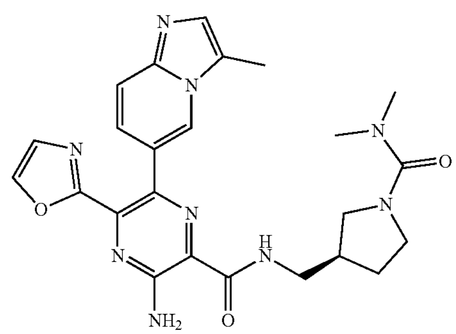 [SMILES: Cc1cnc2ccc(-c3nc(C(=O)NC[C@@H]4CCN(C(=O)N(C)C)C4)c(N)nc3-c3ncco3)cn12] | (S)-3-amino-N-((1-(dimethylcarbamoyl)pyrrolidin-3-yl)methyl)-6-(3-methylimidazo[1,2-a]pyridin-6-yl)-5-(oxazol-2-yl)pyrazine-2-carboxamide |
| 274 | 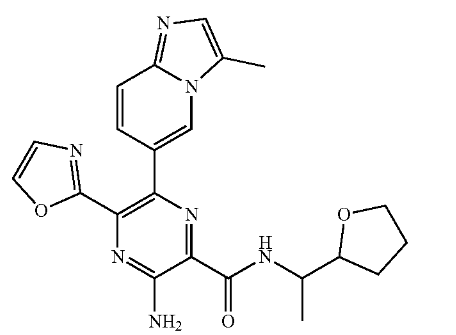 [SMILES: Cc1cnc2ccc(-c3nc(C(=O)NC(C)C4CCCO4)c(N)nc3-c3ncco3)cn12] | 3-amino-6-(3-methylimidazo[1,2-a]pyridin-6-yl)-5-(oxazol-2-yl)-N-(1-(tetrahydrofuran-2-yl)ethyl)pyrazine-2-carboxamide (isomer 3) |
| 275 | 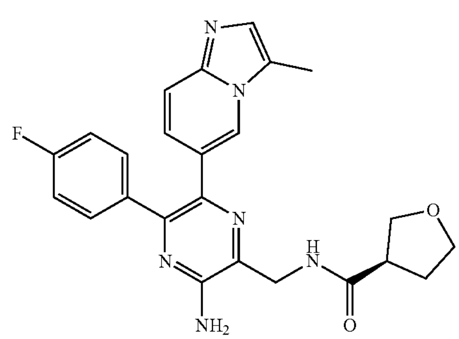 | (R)-N-((3-amino-5-(4-fluorophenyl)-6-(3-methylimidazo[1,2-a]pyridin-6-yl)pyrazin-2-yl)methyl)tetrahydrofuran-3-carboxamide |

TABLE 1-continued

Exemplary Compound 1-306

| Compound number | Compound structure | Compound name |
|---|---|---|
| 276 | 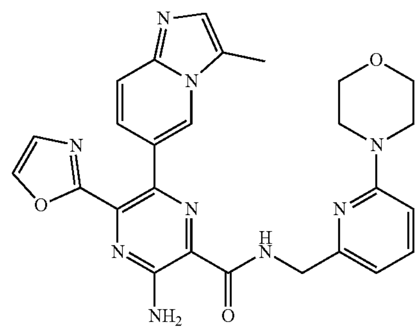 | 3-amino-6-(3-methylimidazo[1,2-a]pyridin-6-yl)-N-((6-morpholinopyridin-2-yl)methyl)-5-(oxazol-2-yl)pyrazine-2-carboxamide |
| 277 | 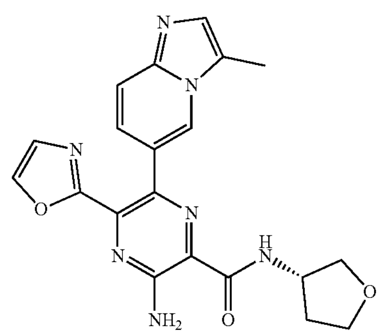 [SMILES: Cc1cnc2ccc(-c3nc(C(=O)N[C@H]4CCOC4)c(N)nc3-c3ncco3)cn12] | (S)-3-amino-6-(3-methylimidazo[1,2-a]pyridin-6-yl)-5-(oxazol-2-yl)-N-(tetrahydrofuran-3-yl)pyrazine-2-carboxamide |
| 278 | 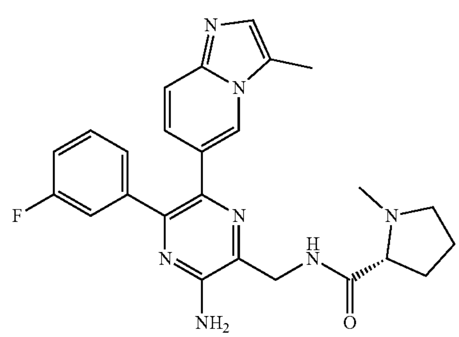 [SMILES: Cc1cnc2ccc(-c3nc(CNC(=O)[C@H]4CCCN4C)c(N)nc3-c3cccc(F)c3)cn12] | (R)-N-((3-amino-5-(3-fluorophenyl)-6-(3-methylimidazo[1,2-a]pyridin-6-yl)pyrazin-2-yl)methyl)-1-methylpyrrolidine-2-carboxamide |
| 279 | 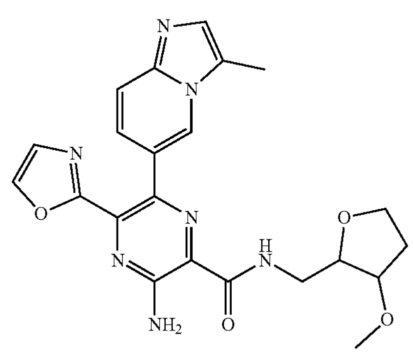 [SMILES: COC1CCOC1CNC(=O)c1nc(-c2ccc3ncc(C)n3c2)c(-c2ncco2)nc1N] | 3-amino-N-((-3-methoxytetrahydrofuran-2-yl)methyl)-6-(3-methylimidazo[1,2-a]pyridin-6-yl)-5-(oxazol-2-yl)pyrazine-2-carboxamide (isomer 1) |

TABLE 1-continued

Exemplary Compound 1-306

| Compound number | Compound structure | Compound name |
|---|---|---|
| 280 | 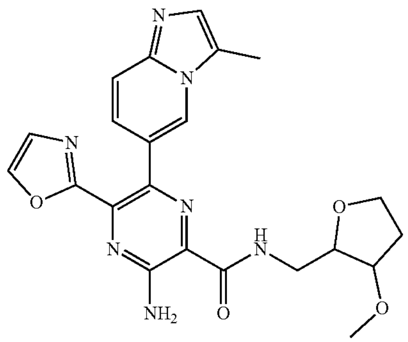 [SMILES: COC1CCOC1CNC(=O)c1nc(-c2ccc3ncc(C)n3c2)c(-c2ncco2)nc1N] | 3-amino-N-((-3-methoxytetrahydrofuran-2-yl)methyl)-6-(3-methylimidazo[1,2-a]pyridin-6-yl)-5-(oxazol-2-yl)pyrazine-2-carboxamide (isomer 2) |
| 281 | 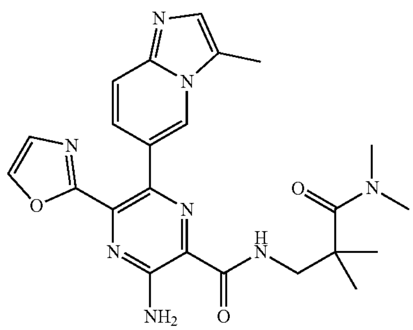 [SMILES: Cc1cnc2ccc(-c3nc(C(=O)NCC(C)(C)C(=O)N(C)C)c(N)nc3-c3ncco3)cn12] | 3-amino-N-(3-(dimethylamino)-2,2-dimethyl-3-oxopropyl)-6-(3-methylimidazo[1,2-a]pyridin-6-yl)-5-(oxazol-2-yl)pyrazine-2-carboxamide |
| 282 | 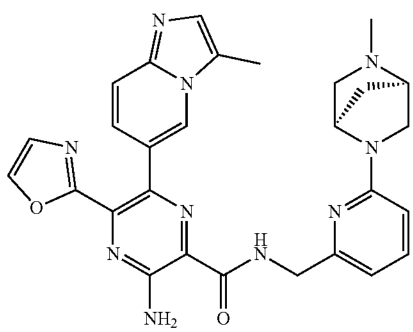 [SMILES: Cc1cnc2ccc(-c3nc(C(=O)NCc4cccc(N5C[C@H]6C[C@@H]5CN6C)n4)c(N)nc3-c3ncco3)cn12] | 3-amino-N-((6-((1R,4R)-5-methyl-2,5-diazabicyclo[2.2.1]heptan-2-yl)pyridin-2-yl)methyl)-6-(3-methylimidazo[1,2-a]pyridin-6-yl)-5-(oxazol-2-yl)pyrazine-2-carboxamide |
| 283 | 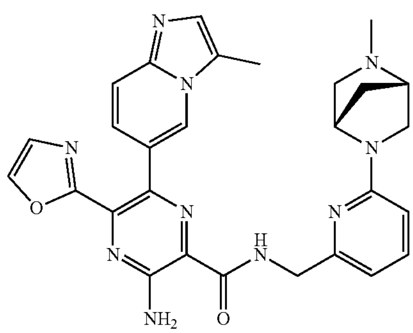 [SMILES: Cc1cnc2ccc(-c3nc(C(=O)NCc4cccc(N5C[C@@H]6C[C@H]5CN6C)n4)c(N)nc3-c3ncco3)cn12] | 3-amino-N-((6-((1S,4S)-5-methyl-2,5-diazabicyclo[2.2.1]heptan-2-yl)pyridin-2-yl)methyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 284 | 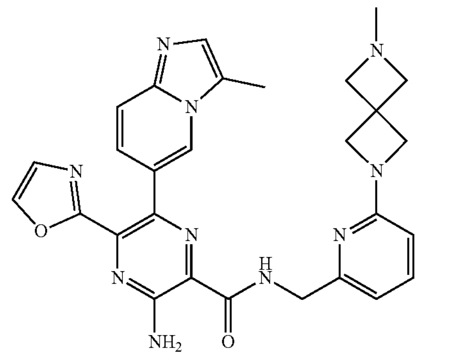 [SMILES: Cc1cnc2ccc(-c3nc(C(=O)NCc4cccc(N5CC6(CN(C)C6)C5)n4)c(N)nc3-c3ncco3)cn12] | 3-amino-N-((6-(6-methyl-2,6-diazaspiro[3.3]heptan-2-yl)pyridin-2-yl)methyl)-6-(3-methylimidazo[1,2-a]pyridin-6-yl)-5-(oxazol-2-yl)pyrazine-2-carboxamide |
| 285 | 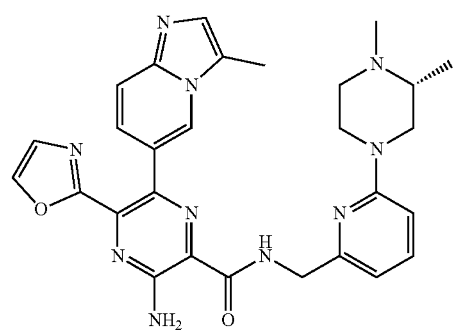 [SMILES: Cc1cnc2ccc(-c3nc(C(=O)NCc4cccc(N5CCN(C)[C@H](C)C5)n4)c(N)nc3-c3ncco3)cn12] | (R)-3-amino-N-((6-(3,4-dimethylpiperazin-1-yl)pyridin-2-yl)methyl)-6-(3-methylimidazo[1,2-a]pyridin-6-yl)-5-(oxazol-2-yl)pyrazine-2-carboxamide |
| 286 | 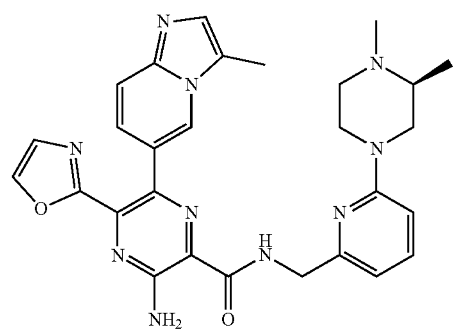 [SMILES: Cc1cnc2ccc(-c3nc(C(=O)NCc4cccc(N5CCN(C)[C@@H](C)C5)n4)c(N)nc3-c3ncco3)cn12] | (S)-3-amino-N-((6-(3,4-dimethylpiperazin-1-yl)pyridin-2-yl)methyl)-6-(3-methylimidazo[1,2-a]pyridin-6-yl)-5-(oxazol-2-yl)pyrazine-2-carboxamide |
| 287-1 | 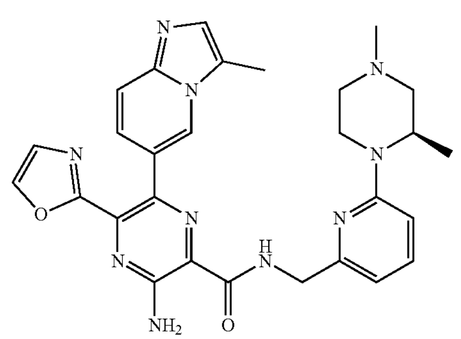 [SMILES: Cc1cnc2ccc(-c3nc(C(=O)NCc4cccc(N5CCN(C)C[C@H]5C)n4)c(N)nc3-c3ncco3)cn12] | (R)-3-amino-N-((6-(2,4-dimethylpiperazin-1-yl)pyridin-2-yl)methyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 287-2 | 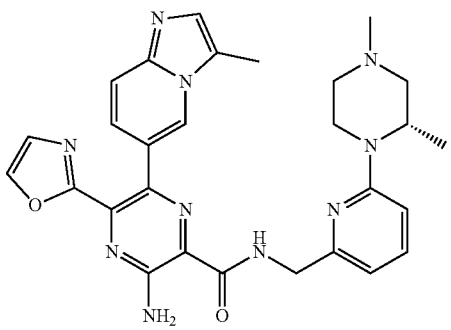 [SMILES: Cc1cnc2ccc(-c3nc(C(=O)NCc4cccc(N5CCN(C)C[C@@H]5C)n4)c(N)nc3-c3ncco3)cn12] | (S)-3-amino-N-((6-(2,4-dimethylpiperazin-1-yl)pyridin-2-yl)methyl)-6-(3-methylimidazo[1,2-a]pyridin-6-yl)-5-(oxazol-2-yl)pyrazine-2-carboxamide |
| 288 | 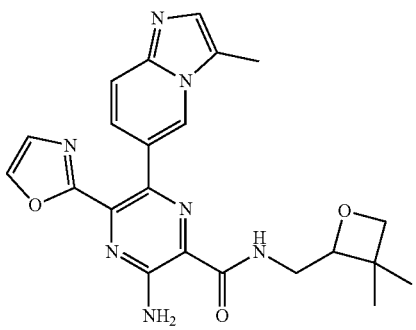 [SMILES: Cc1cnc2ccc(-c3nc(C(=O)NCC4OCC4(C)C)c(N)nc3-c3ncco3)cn12] | 3-amino-N-((3,3-dimethyloxetan-2-yl)methyl)-6-(3-methylimidazo[1,2-a]pyridin-6-yl)-5-(oxazol-2-yl)pyrazine-2-carboxamide (isomer 1) |
| 289 | 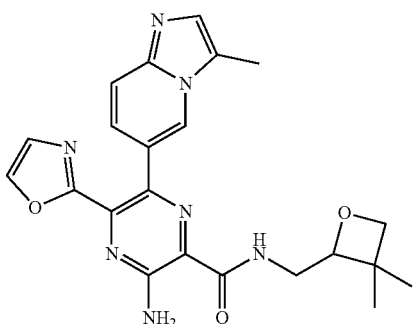 | 3-amino-N-((3,3-dimethyloxetan-2-yl)methyl)-6-(3-methylimidazo[1,2-a]pyridin-6-yl)-5-(oxazol-2-yl)pyrazine-2-carboxamide (isomer 2) |
| 290 | 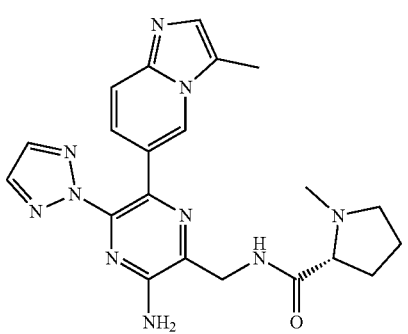 [SMILES: Cc1cnc2ccc(-c3nc(CNC(=O)[C@H]4CCCN4C)c(N)nc3-n3nccn3)cn12] | (R)-N-((3-amino-6-(3-methylimidazo[1,2-a]pyridin-6-yl)-5-(2H-1,2,3-triazol-2-yl)pyrazin-2-yl)methyl)-1-methylpyrrolidine-2-carboxamide |

TABLE 1-continued

Exemplary Compound 1-306

| Compound number | Compound structure | Compound name |
|---|---|---|
| 291 | 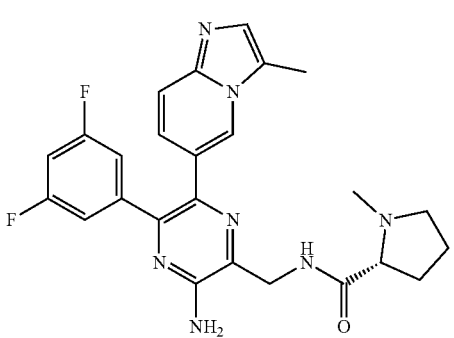 [SMILES: Cc1cnc2ccc(-c3nc(CNC(=O)[C@H]4CCCN4C)c(N)nc3-c3cc(F)cc(F)c3)cn12] | (R)-N-((3-amino-5-(3,5-difluorophenyl)-6-(3-methylimidazo[1,2-a]pyridin-6-yl)pyrazin-2-yl)methyl)-1-methylpyrrolidine-2-carboxamide |
| 292 | 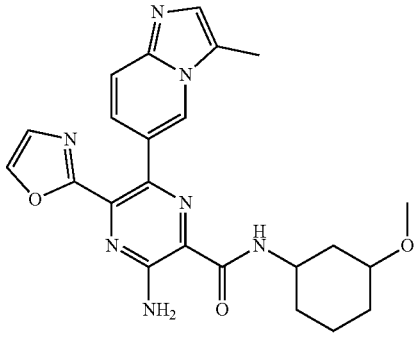 [SMILES: COC1CCCC(NC(=O)c2nc(-c3ccc4ncc(C)n4c3)c(-c3ncco3)nc2N)C1] | 3-amino-N-(3-methoxycyclohexyl)-6-(3-methylimidazo[1,2-a]pyridin-6-yl)-5-(oxazol-2-yl)pyrazine-2-carboxamide (isomer 1) |
| 293 | 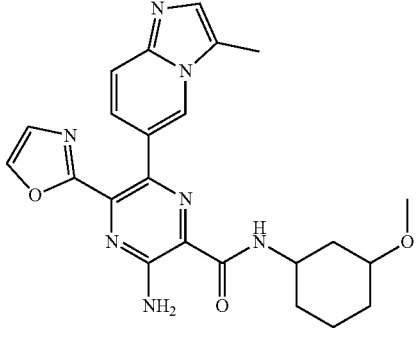 [SMILES: COC1CCCC(NC(=O)c2nc(-c3ccc4ncc(C)n4c3)c(-c3ncco3)nc2N)C1] | 3-amino-N-(3-methoxycyclohexyl)-6-(3-methylimidazo[1,2-a]pyridin-6-yl)-5-(oxazol-2-yl)pyrazine-2-carboxamide (isomer 2) |
| 294 | 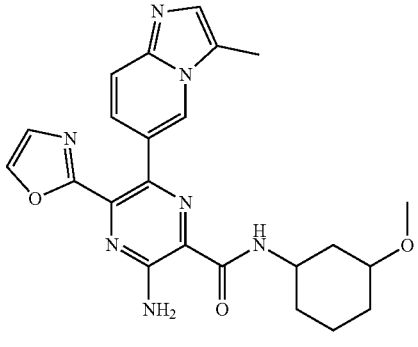 [SMILES: COC1CCCC(NC(=O)c2nc(-c3ccc4ncc(C)n4c3)c(-c3ncco3)nc2N)C1] | 3-amino-N-(3-methoxycyclohexyl)-6-(3-methylimidazo[1,2-a]pyridin-6-yl)-5-(oxazol-2-yl)pyrazine-2-carboxamide (isomer 3) |

TABLE 1-continued

Exemplary Compound 1-306

| Compound number | Compound structure | Compound name |
|---|---|---|
| 295 | 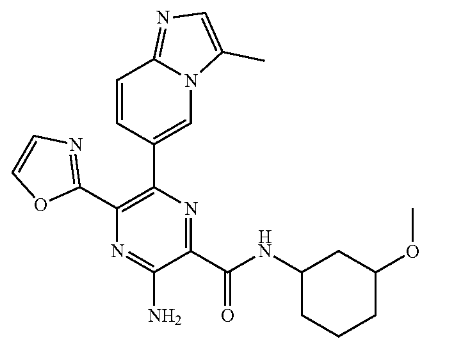 [SMILES: COC1CCCC(NC(=O)c2nc(-c3ccc4ncc(C)n4c3)c(-c3ncco3)nc2N)C1] | 3-amino-N-(3-methoxycyclohexyl)-6-(3-methylimidazo[1,2-a]pyridin-6-yl)-5-(oxazol-2-yl) pyrazine-2-carboxamide (isomer4) |
| 296 | 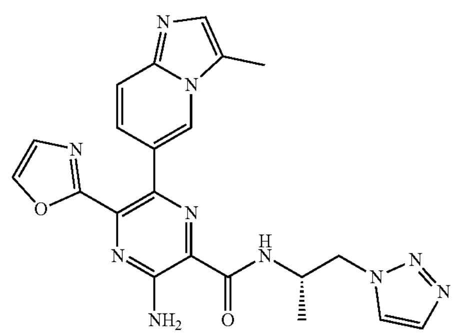 [SMILES: Cc1cnc2ccc(-c3nc(C(=O)N[C@@H](C)Cn4ccnn4)c(N)nc3-c3ncco3)cn12] | (S)-N-(1-(1H-1,2,3-triazol-1-yl) propan-2-yl)-3-amino-6-(3-methylimidazo[1,2-a]pyridin-6-yl)-5-(oxazol-2-yl) pyrazine-2-carboxamide |
| 296-2 | 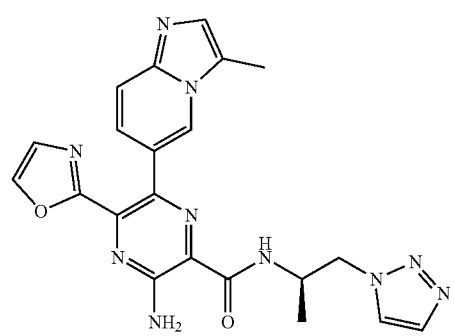 [SMILES: Cc1cnc2ccc(-c3nc(C(=O)N[C@H](C)Cn4ccnn4)c(N)nc3-c3ncco3)cn12] | 3-amino-6-[3-methylimidazo[1,2-a] pyridin-6-yl]-5-(1,3-oxazol-2-yl)-N-[(2R)-1-(2H-1,2,3-triazol-2-yl)propan-2-yl] pyrazine-2-carboxamide |
| 297 | 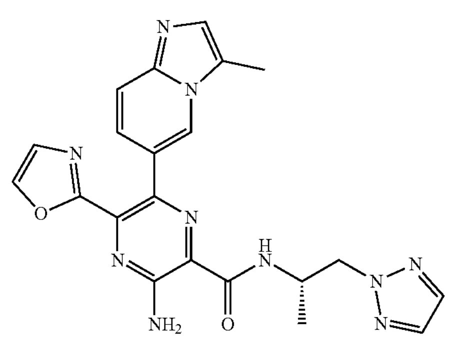 [SMILES: Cc1cnc2ccc(-c3nc(C(=O)N[C@@H](C)Cn4nccn4)c(N)nc3-c3ncco3)cn12] | (S)-N-(1-(2H-1,2,3-triazol-2-yl) propan-2-yl)-3-amino-6-(3-methylimidazo [1,2-a]pyridin-6-yl)-5-(oxazol-2-yl) pyrazine-2-carboxamide |

TABLE 1-continued

Exemplary Compound 1-306

| Compound number | Compound structure | Compound name |
|---|---|---|
| 298 | 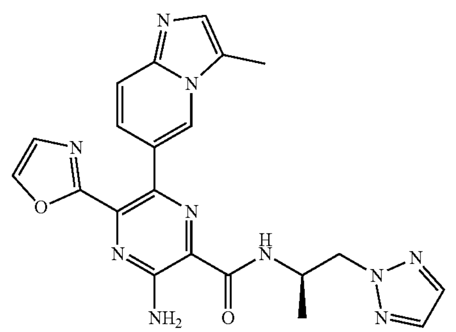 [SMILES: Cc1cnc2ccc(-c3nc(C(=O)N[C@H](C)Cn4nccn4)c(N)nc3-c3ncco3)cn12] | (R)-N-(1-(2H-1,2,3-triazol-2-yl)propan-2-yl)-3-amino-6-(3-methylimidazo[1,2-a]pyridin-6-yl)-5-(oxazol-2-yl)pyrazine-2-carboxamide |
| 299 | 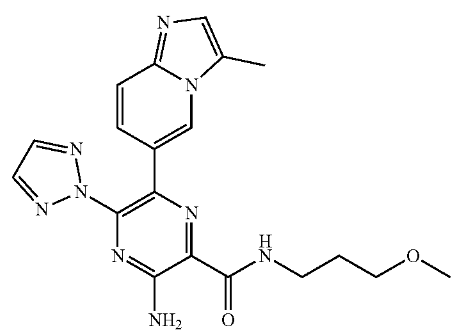 [SMILES: COCCCNC(=O)c1nc(-c2ccc3ncc(C)n3c2)c(-n2nccn2)nc1N] | 3-amino-N-(3-methoxypropyl)-6-(3-methylimidazo[1,2-a]pyridin-6-yl)-5-(2H-1,2,3-triazol-2-yl)pyrazine-2-carboxamide |
| 300 | 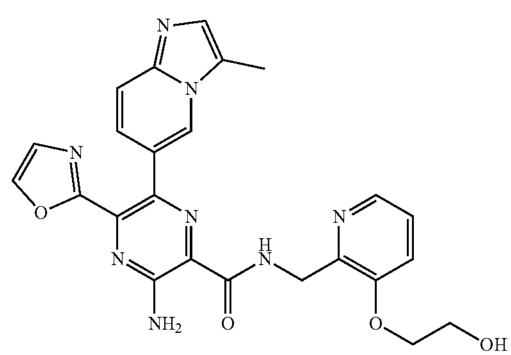 [SMILES: Cc1cnc2ccc(-c3nc(C(=O)NCc4ncccc4OCCO)c(N)nc3-c3ncco3)cn12] | 3-amino-N-((3-(2-hydroxyethoxy)pyridin-2-yl)methyl)-6-(3-methylimidazo[1,2-a]pyridin-6-yl)-5-(oxazol-2-yl)pyrazine-2-carboxamide |
| 301 | 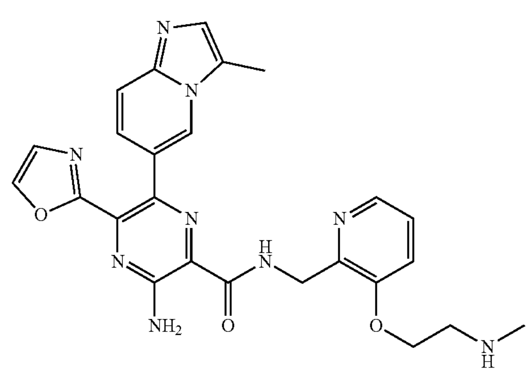 [SMILES: CNCCOc1cccnc1CNC(=O)c1nc(-c2ccc3ncc(C)n3c2)c(-c2ncco2)nc1N] | 3-amino-N-((3-(2-(methylamino)ethoxy)pyridin-2-yl)methyl)-6-(3-methylimidazo[1,2-a]pyridin-6-yl)-5-(oxazol-2-yl)pyrazine-2-carboxamide |

TABLE 1-continued

Exemplary Compound 1-306

| Compound number | Compound structure | Compound name |
|---|---|---|
| 302 | 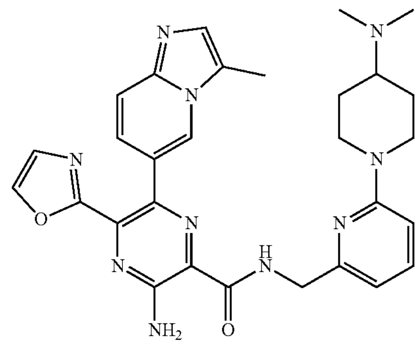 [SMILES: Cc1cnc2ccc(-c3nc(C(=O)NCc4cccc(N5CCC(N(C)C)CC5)n4)c(N)nc3-c3ncco3)cn12] | 3-amino-N-((6-(4-(dimethylamino)piperidin-1-yl)pyridin-2-yl)methyl)-6-(3-methylimidazo[1,2-a]pyridin-6-yl)-5-(oxazol-2-yl)pyrazine-2-carboxamide |
| 303 | 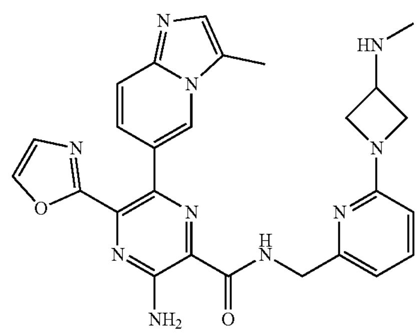 [SMILES: CNC1CN(c2cccc(CNC(=O)c3nc(-c4ccc5ncc(C)n5c4)c(-c4ncco4)nc3N)n2)C1] | 3-amino-N-((6-(3-(methylamino)azetidin-1-yl)pyridin-2-yl)methyl)-6-(3-methylimidazo[1,2-a]pyridin-6-yl)-5-(oxazol-2-yl)pyrazine-2-carboxamide |
| 304 | 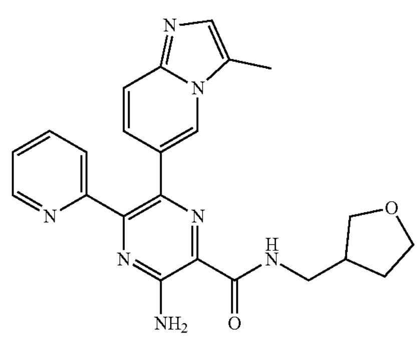 [SMILES: Cc1cnc2ccc(-c3nc(C(=O)NCC4CCOC4)c(N)nc3-c3ccccn3)cn12] | 3-amino-6-(3-methylimidazo[1,2-a]pyridin-6-yl)-5-(pyridin-2-yl)-N-((tetrahydrofuran-3-yl)methyl)pyrazine-2-carboxamide (isomer 1) |
| 305 | 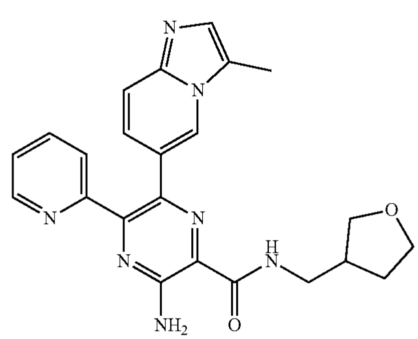 [SMILES: Cc1cnc2ccc(-c3nc(C(=O)NCC4CCOC4)c(N)nc3-c3ccccn3)cn12] | 3-amino-6-(3-methylimidazo[1,2-a]pyridin-6-yl)-5-(pyridin-2-yl)-N-((tetrahydrofuran-3-yl)methyl)pyrazine-2-carboxamide (isomer 2) |

TABLE 1-continued

Exemplary Compound 1-306

| Compound number | Compound structure | Compound name |
|---|---|---|
| 306 | 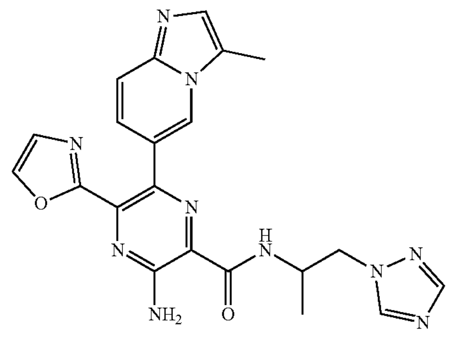 [SMILES: Cc1cnc2ccc(-c3nc(C(=O)NC(C)Cn4cncn4)c(N)nc3-c3ncco3)cn12] | rac-N-(1-(1H-1,2,4-triazol-1-yl)propan-2-yl)-3-amino-6-(3-methylimidazo[1,2-a]pyridin-6-yl)-5-(oxazol-2-yl)pyrazine-2-carboxamide |

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub combination.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate, fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{1-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, including 1 to 10, 1 to 8, 1 to 6, 1 to 5, 1 to 4, 1 to 3 or 1 to 2 carbon atoms.

As used herein, the term "alkyl", whether as part of another term or used independently, refers to a saturated or unsaturated hydrocarbon chain, while the latter may be further subdivided into hydrocarbon chain having at least one double or triple bonds (alkenyl or alkynyl). In some embodiments, alkyl refers to a saturated hydrocarbon chain. The hydrocarbon chain mentioned above may be straight-chain or branched-chain. The term "$C_{1-j}$ alkyl" refers to an alkyl having i to j carbon atoms. Examples of saturated alkyl group include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. Examples of unsaturated alkyl groups include, but are not limited to, ethenyl, n-propenyl, isopropenyl, n-butenyl, sec-butenyl, ethynyl, propyn-1-yl, propyn-2-yl, and the like. Examples of "$C_{1-12}$ alkyl" are methyl, ethyl, propyl, isopropyl and butyl. Examples of "$C_{1-3}$ alkyl" are methyl, ethyl, propyl and isopropyl.

As used herein, the term "alkylene", whether as part of another term or used independently, refers to a divalent alkyl. Examples of alkylene groups include, but are not limited to, methylene, 1,1-ethylene, 1,2-ethylene, 1,1-propylene, 1,2-propylene, 1,3-propylene, 2,2-propylene, and the like.

As used herein the terms "halo" and "halogen" refer to an atom selected from fluorine, chlorine, bromine or iodine.

As used herein, the term "alkoxyl", whether as part of another term or used independently, refers to a group of formula —O-alkyl. The term "$C_{1-j}$ alkoxyl" means that the alkyl moiety of the alkoxy group has i to j carbon atoms. Examples of alkoxy groups include, but are not limited to, methoxyl, ethoxyl, propoxyl (e.g. n-propoxy and isopropoxy), t-butoxy, and the like. Examples of "$C_{1-12}$ alkoxyl" are methoxyl, ethoxyl and propoxyl.

As used herein, the term "$C_{1-j}$ alkyl-OH", refers to a group of formula "—$C_{1-j}$ alkyl-OH", wherein the alkyl moiety of the group has i to j carbon atoms, and one or more hydroxyl groups may be linked to any carbon atoms in the alkyl moiety. In some embodiments, "C j alkyl-OH" has one hydroxyl group. Examples of "$C_{1-12}$ alkyl-OH" are hydroxymethyl, 1-hydroxyethyl, 2-hydroxyethyl and 1-hydroxyisopropyl.

As used herein, the term "$C_{1-j}$ haloalkyl", refers to a halogen substituted (mono- or multi-substituted) $C_{1-j}$ alkyl group. Examples of "$C_{1-12}$ haloalkyl" are fluoromethyl, difluoromethyl, trifluoromethyl, fluoroethyl, difluoroethyl, trifluoroethyl, chloroethyl and bromoisopropyl. Examples of "difluoroethyl" are 1,1-difluoroethyl. Examples of "trifluoroethyl" are 2,2,2-trifluoroethyl and 1,2,2-trifluoroethyl.

As used herein, the term "$C_{1-j}$ haloalkoxyl", refers to a halogen substituted (mono- or multi-substituted) $C_{1-j}$ alkoxyl group. Examples of "$C_{1-j}$ haloalkoxyl" are fluoromethoxyl, difluoromethoxyl, or trifluoromethoxyl. Examples of "trifluoroethoxy" are 2,2,2-trifluoroethoxy and 1,2,2-trifluoroethoxy.

Examples of "N—($C_{1-12}$ alkyl)amino" are methylamino and ethylamino.

Examples of "N—($C_{1-12}$ haloalkyl)amino" are fluoromethylamino, difluoromethylamino, trifluoromethylamino, 2-chloroethylamino and 1-bromoisopropylamino.

Examples of "N,N—($C_{1-12}$ alkyl)$_2$amino" are di-(N-methyl)amino, di-(N-ethyl)amino and N-ethyl-N-methylamino.

As used herein, the term "$C_{1-j}$ alkanoyl" refers to $C_{1-j}$ alkylcarbonyl. Examples of "$C_{1-12}$ alkanoyl" are propionyl and acetyl.

Examples of "$C_{1-12}$ alkanoylamino" are formamido, acetamido and propionylamino.

Examples of "$C_{1-12}$ alkanoyloxy" are acetoxy.

Examples of "$C_{1-12}$ alkoxycarbonyl" are methoxycarbonyl, ethoxycarbonyl, n- and t-butoxycarbonyl As used herein, the term "carbamoyl" refers to aminocarbonyl group. Examples of "N—($C_{1-12}$ alkyl)carbamoyl" are methylaminocarbonyl and ethylaminocarbonyl. Examples of "N,N—($C_{1-12}$ alkyl)$_2$carbamoyl" are dimethylaminocarbonyl and methylethylaminocarbonyl.

As used herein, the term "carbocyclyl", whether as part of another term or used independently, refers to any ring, including mono- or poly-cyclic ring(s) (e.g. having 2 or 3 fused, bridged or spiro rings), in which all the ring atoms are carbon and which contains at least three ring forming carbon atoms. In some embodiments, the carbocyclyl may contain 3 to 12 ring forming carbon atoms (i.e. 3-12 membered carbon atoms), 3 to 10 ring forming carbon atoms, 3 to 9 ring forming carbon atoms or 4 to 8 ring forming carbon atoms.

Carbocyclyl groups may be saturated, partially unsaturated or fully unsaturated. In some embodiments, the carbocyclyl group may be a saturated cyclic alkyl group. In some embodiments, the carbocyclyl group may be an unsaturated cyclic alkyl group that contains at least one double bond in its ring system. In some embodiments, an unsaturated carbocyclyl group may contains one or more aromatic rings. In some embodiments, one or more ring forming —$CH_2$— group of the saturated or unsaturated carbocyclyl may be replaced by a —C(O)— group.

In some embodiments, the carbocyclyl group is a monocyclic alkyl group. In some embodiments, the carbocyclyl group is a saturated monocyclic alkyl group. Examples of monocyclic saturated or unsaturated carbocyclyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, and the like.

As used herein, the term "spiro" rings refers to ring systems having two rings connected through one single common atom; the term "fused" rings refers to ring systems having two rings sharing two adjacent atoms; and the term "bridged" rings refers to ring systems with two rings sharing three or more atoms.

A 3-12, 3-10 or 5-6 "membered saturated or unsaturated carbocyclyl" is a saturated, partially unsaturated or fully unsaturated mono- or poly-cyclic ring system having 3 to 12, 3 to 10, or 5 to 6 ring forming carbon atoms respectively, wherein one or more ring forming —$CH_2$— group can optionally be replaced by a —C(O)— group.

Examples of "3-12 membered saturated or unsaturated carbocyclyl" are $C_{3-4}$ cycloalkyl, cyclohexyl, cyclohexenyl, cyclopentyl, phenyl, naphthyl and bicyclo[1.1.1]pentan-1-yl.

Examples of "$C_{3-4}$ cycloalkyl" are cyclopropyl and cyclobutyl. Examples of "5-6 membered saturated or unsaturated carbocyclyl" are cyclopentyl and phenyl.

As used herein, the term "heterocyclyl" refers to a carbocyclyl group, wherein one or more (e.g. 1, 2 or 3) ring atoms are replaced by heteroatoms, which include, but are not limited to, O, S, N, P, and the like. In some embodiments, the heterocyclyl is a saturated heterocyclyl. In some embodiments, the heterocyclyl is an unsaturated heterocyclyl having one or more double bonds in its ring system. In some embodiments, the heterocyclyl is a partially unsaturated heterocyclyl. In some embodiments, the heterocyclyl is a fully unsaturated heterocyclyl. In some embodiments, an unsaturated heterocyclyl group may contain one or more aromatic rings. In some embodiments, one or more ring forming —$CH_2$— group of the heterocyclyl can optionally be replaced by a —C(O)—, a —S—, a —S(O)—, or a —S(O)$_2$— group. In some embodiments, where the heterocyclyl contains a sulphur in its ring system, said ring forming sulphur atom may be optionally oxidised to form the S-oxides. In some embodiments the heterocyclyl is linked to the other portion of a compound through its ring forming carbon. In some embodiments the heterocyclyl is linked to the other portion of a compound through its ring forming nitrogen.

In some embodiments, 3-12 membered saturated or unsaturated mono- or poly-cyclic heterocyclyl having 1, 2, or 3 heteroatoms selected from N, O, or S.

A "3-12, 3-10 or 5-6 membered saturated or unsaturated heterocyclyl" is a saturated, partially unsaturated or fully unsaturated mono- or poly-cyclic ring(s) (e.g. having 2 or 3 fused, bridged or spiro rings) system having 3 to 12, 3 to 10, or 5 to 6 ring forming atoms respectively, of which at least one ring forming atom is chosen from nitrogen, sulphur or oxygen, which may, unless otherwise specified, linked to the other portion of a compound through its ring forming carbon or nitrogen, wherein one or more ring forming —$CH_2$— group of the saturated or unsaturated heterocyclyl may be replaced by a —C(O)—, a —S—, a —S(O)—, or a —S(O)$_2$-group, and wherein when the heterocyclyl contains a sulphur in its ring system, said ring sulphur atom may be optionally oxidised to form the S-oxides.

Exemplary monocyclic heterocyclyl groups include, but are not limited to oxetanyl, 1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperidyl, piperazinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, triazinonyl, and the like.

Examples of spiro heterocyclyl include, but are not limited to, spiropyranyl, spirooxazinyl, and the like. Examples of fused heterocyclyl include, but are not limited to, phenyl fused ring or pyridinyl fused ring, such as quinolinyl, isoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of bridged heterocyclyl include, but are not limited to, morphanyl, hexamethylenetetraminyl, 8-aza-bicyclo[3.2.1]octane, 1-aza-bicyclo[2.2.2]octane, 1,4-diazabicyclo[2.2.2]octane (DABCO), and the like.

The "compound" of present disclosure is intended to encompass all stereoisomers, geometric isomers, and tautomers of the structures depicted unless otherwise specified.

The term "stereoisomer" refers to any of the various stereoisomeric configurations (e.g. enantiomers, diastereomers and racemates) of an asymmetric compound (e.g. those having one or more asymmetrically substituted carbon atoms or "asymmetric centers"). Compounds of the present disclosure that contain asymmetric centers can be isolated in optically active (enantiomers or diastereomers) or optically inactive (racemic) forms. The term "enantiomer" includes pairs of stereoisomers that are non-superimposable mirror images of each other. A 1:1 mixture of a pair of enantiomers is a "racemic mixture". The terms "diastereomers" or "diastereoisomers" include stereoisomers that have at least two asymmetric atoms, but which are not mirror images of each other. Certain compounds containing one or more asymmetric centers may give rise to enantiomers, diastereomers or other stereoisomeric forms that may be defined, in terms of absolute configuration, as (R)- or (S)- at each asymmetric center according to the Cahn-Ingold-Prelog R-S system. Resolved compounds whose absolute configuration is unknown can be designated using the term "or" at the asymmetric center. Methods on how to prepare optically active forms from racemic mixtures are known in the art, such as resolution by HPLC or stereoselective synthesis.

The terms "geometric isomers" or "cis and trans isomers" refer to compounds with same formula but their functional groups are rotated into a different orientation in three-dimensional space.

The term "tautomers" include prototropic tautomers that are isomeric protonation states of compounds having the same formula and total charge. Examples of prototropic tautomers include, but are not limited to, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomers can be in equilibrium or sterically locked into one form by appropriate substitution. Compounds of the present disclosure identified by name or structure as one particular tautomeric form are intended to include other tautomeric forms unless otherwise specified.

The "compound" of the present disclosure is also intended to encompass all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the "compound" of present disclosure are meant to also include their isotopes such as but are not limited to $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$, $^{127}I$ and $^{131}I$. In some embodiments, hydrogen includes protium, deuterium and tritium. In some embodiments, the term "substituted by deuterium" or "deuterium substituted" to replace the other isoform of hydrogen (e.g. protium) in the chemical group with deuterium. In some embodiments, carbon includes $^{12}C$ and $^{13}C$. In some embodiments, "compound" of the present disclosure only encompasses the isotopes of hydrogen in the compound. In some embodiments, "compound" of the present disclosure only encompasses the isotopes of atoms in natural abundance.

It is also to be understood that the "compound" of present disclosure can exist in solvated as well as unsolvated forms, such as, for example, hydrated forms, solid forms, and the present disclosure is intended to encompass all such solvated and unsolvated forms.

It is further to be understood that the "compound" of present disclosure can exist in forms of pharmaceutically acceptable salts.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

As used herein, "pharmaceutically acceptable salts" refers to derivatives of the compounds of present disclosure wherein the parent compound is modified by converting an existing acidic moiety (e.g. carboxyl and the like) or base moiety (e.g. amine, alkali and the like) to its salt form. In many cases, compounds of present disclosure are capable of forming acid and/or base salts by virtue of the presence of amino and/or carboxyl groups or groups similar thereto. The pharmaceutically acceptable salts are acid and/or base salts that retain biological effectiveness and properties of the parent compound, which typically are not biologically or otherwise undesirable. Suitable pharmaceutically acceptable salts of a compound of the present disclosure includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenylacetic, benzoic, mandelic, methanesulfonic, napadisylic, ethanesulfonic, toluenesulfonic, trifluoroacetic, salicylic, sulfosalicylic acids and the like). In some embodiments, the pharmaceutically acceptable salt of the compound of the present disclosure is a formic acid salt. In some embodiments, the pharmaceutically acceptable salt of the compound of the present disclosure is a TFA salt.

Suitable pharmaceutically acceptable salts of a compound of the present disclosure also include, for example, an base-addition salt, which can be derived from for example an inorganic bases (for example, sodium, potassium, ammonium salts and hydroxide, carbonate, bicarbonate salts of metals from columns I to XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine and tromethamine. Those skilled in the art would appreciate that adding acids or bases for forming acid/base-addition salts other than those shown in the examples may also be possible. Lists of additional suitable salts can be found, e.g. in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002). In some embodiments, Suitable pharmaceutically acceptable salts of a compound of the present disclosure is inorganic bases salt.

The present disclosure also includes active intermediates, active metabolites and prodrugs of the compounds of present disclosure. As used herein, an "active intermediate" refer to intermediate compound in the synthetic process, which exhibits the same or essentially the same biological activity as the final synthesized compound.

As used herein, an "active metabolite" refers to a breakdown or end product of a compound of the present disclosure or its salt or prodrug produced through metabolism or biotransformation in the animal or human body, which exhibits the same or essentially the same biological activity as the specified compound. Such metabolites may result from, for example, oxidation, reduction, hydrolysis, amidation, deamidation, esterification, deesterification, enzymatic cleavage, and the like, of the administered compound or salt or prodrug.

As used herein, "prodrugs" refer to any compounds or conjugates which release the active parent drug when administered to an animal or human subject. Prodrugs can be prepared by modifying functional groups present in the compounds in such a way that the modifications are cleavable, either in routine manipulation or in vivo, from the parent compounds. Prodrugs include compounds wherein hydroxyl, amino, sulfhydryl, or carboxyl group is bonded to any group that, when administered to a mammalian subject, is cleavable to form a free hydroxyl, amino, sulfhydryl, or carboxyl group respectively. Examples of prodrugs include, but are not limited to, acetate, formate and benzoate derivatives of alcohol and amine functional groups in the compounds of the present disclosure. Preparation and use of prodrugs is discussed in T. Higuchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Synthetic Method

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^1$H or $^{13}$C), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The structures of the compounds in the examples are characterized by nuclear magnetic resonance (NMR) or/and liquid chromatography-mass spectrometry (LC-MS). NMR chemical shift (δ) is given in the unit of $10^{-6}$ (ppm). $^1$H-NMR spectra is recorded in dimethyl sulfoxide-$d_6$ (DMSO-$d_6$) or CDCl$_3$ or CD$_3$OD or D$_2$O or Acetone-$d_6$ or CD$_3$CN (from Innochem or Sigma-Aldrich or Cambridge Isotope Lab., Inc.) on Bruker AVANCE NMR (300 MHz or 400 MHz) spectrometers using ICON-NMR (under TopSpin program control) with tetramethylsilane as an internal standard.

MS measurement is carried out using Shimadzu 2020 Mass Spectrometer with an electrospray source at positive and negative ion mode.

High Performance Liquid Chromatography (HPLC) measurement is carried out on Shimadzu LC-20AD systems or Shimadzu LC-20ADXR systems or Shimadzu LC-30AD systems using Shim-pack XR-ODS C18 column (3.0*50 mm, 2.2 um), or Ascentis Express C18 column (2.1*50 mm, 2.7 um), or Agilent Poroshell HPH-C18 column (3.0*50 mm, 2.7 um).

Thin layer chromatography is carried out using Sinopharm Chemical Reagent Beijing Co., Ltd. and Xinnuo Chemical silica gel plates. The silica gel plates used for thin layer chromatography (TLC) are 175-225 μm. The silica gel plates used for separating and purifying products by TLC are 1.0 mm.

Purified chromatographic column uses the silica gel as the carrier (100-200, 200-300 or 300400 mesh, produced by Rushanshi Shangbang Xincailiao Co., Ltd. or Rushan Taiyang Desiccant Co., Ltd. etc.), or flash column (reversed phase C18 column 20-45 um, produced by Agela Technologies) in Agela Technologies flash system. The size of columns are adjusted according to the amount of compounds.

The known starting materials of the present disclosure can be synthesized by using or according to the known methods in the art, or can be purchased from Alfa Aesar, TCI, Sigma-Aldrich, Bepharm, Bide pharmatech, PharmaBlock, Enamine, Innochem and JW&Y PharmLab etc.

Unless otherwise specified, the reactions are all carried out under argon or nitrogen atmosphere. Argon or nitrogen atmosphere refers to that the reaction flask is connected to an argon or nitrogen balloon with a volume of about 1 L. Hydrogenation is usually carried out under pressure. Unless otherwise specified, the reaction temperature in the examples is ambient temperature, which is 10° C.~30° C.

The reaction progress are monitored by TLC or/and LC-MS. The eluent systems used for the reactions include dichloromethane-methanol system and petroleum ether-ethyl acetate system. The volume ratios of the solvents are adjusted according to the different polarities of compounds.

The elution system of column chromatography used for purifying compounds and eluent system of TLC include dichloromethane-methanol system and petroleum ether-ethyl acetate system. The volume ratios of the solvents are adjusted according to the different polarities of compounds. A small amount of alkaline or acidic agents (0.1%~1%) such as formic acid, or acetic acid, or TFA, or ammonia can be added for adjustment.

Abbreviations for chemicals used in the synthesis of the compounds provided herein are listed below:

| | |
|---|---|
| AcOH | Acetic acid |
| AcOK | Potassium acetate |
| BnSH | Benzyl mercaptan |
| $Br_2$ | Bromine |
| BSA | N,O-Bis(trimethylsilyl)acetamide |
| $CH_3CN$ | Acetonitrile |
| $ClCH_2CH_2Cl$ | 1,2-Dichloroethane |
| $Cs_2CO_3$ | Caesium carbonate |
| $Cu(OAc)_2$ | Cupric Acetate |
| DCM | Dichloromethane |
| DIEA | N,N-Diisopropylethylamine |
| DMF | N,N-Dimethylformamide |
| DMSO | Dimethyl sulfoxide |
| dtbpf | 1,1'-Bis(di-t-butylphosphino)ferrocene |
| EtOAc | Ethyl acetate |
| EtOH | Ethanol |
| HATU | 1-[Bis(dimethylamino)methylene]-1H-1,2,3-triazolo[4,5-b]pyridinium 3-oxid hexafluorophosphate |
| ICl | Iodine monochloride |
| $K_2CO_3$ | Potassium carbonate |
| $K_3PO_4$ | Tripotassium phosphate |
| KF | Potassium fluoride |
| LiCl | Lithium chloride |
| LiOH | Lithium hydroxide |
| MeOH | Methanol |
| MTBE | Methyl tert-butyl ether |
| $Na_2CO_3$ | Sodium Carbonate |
| NaCl | Sodium chloride |
| NaOH | Sodium hydroxide |
| NBS | N-Bromosuccinimide |
| n-BuOH | Butyl alcohol |
| NMP | N-Methyl pyrrolidone |
| $Pd(amphos)Cl_2$ | Bis(di-tert-butyl(4-dimethylamino-phenyl)phosphine)dichloropalladium(II) |
| $Pd(dppf)Cl_2$ | [1,1'-Bis(diphenylphosphino)ferrocene]dichloropalladium(II) |
| $Pd(PPh_3)_4$ | Tetrakis(triphenylphosphine)palladium |
| PE | Petroleum ether |
| $POCl_3$ | Phosphoric trichloride |
| $T_3P$ | 1,3,5,2,4,6-Trioxatriphosphorinane,2,4,6-tripropyl-,2,4,6-trioxide |
| TEA | Triethylamine |
| TFA | Trifluoroacetic acid |
| THF | Tetrahydrofuran |
| Xphos | 2-Dicyclohexylphosphino-2',4',6'-triisopropylbiphenyl |
| $ZnCl_2$ | Zinc chloride |

Pharmaceutical Composition

The present disclosure provides pharmaceutical compositions comprising at least one compound of the present disclosure, or a pharmaceutically acceptable salt thereof. In some embodiments, the pharmaceutical composition comprises more than one compound of the present disclosure, or a pharmaceutically acceptable salt thereof. In some embodiments, the pharmaceutical composition comprises one or more compounds of the present disclosure, or a pharmaceutically acceptable salt thereof, and a pharmaceutical acceptable carrier.

In general, the pharmaceutically acceptable carriers are conventional medicinal carriers in the art which can be prepared in a manner well known in the pharmaceutical art. In some embodiments, the compounds of the present disclosure, or a pharmaceutically acceptable salt thereof, may be admixed with pharmaceutically acceptable carrier for the preparation of pharmaceutical composition.

The form of pharmaceutical compositions depends on a number of criteria, including, but not limited to, route of administration, extent of disease, or dose to be administered. The pharmaceutical compositions can be formulated for oral, nasal, rectal, percutaneous, intravenous, or intramuscular administration. In accordance to the desired route of administration, the pharmaceutical compositions can be formulated in the form of tablets, capsule, pill, powder, granule, sachets, cachets, lozenges, suspensions, emulsions, solutions, syrups, aerosols (as a solid or in a liquid medium), spray, ointment, paste, cream, lotion, gel, patch, inhalant, or suppository.

In certain embodiments, the pharmaceutical compositions comprise about 1 mg to about 500 mg of the compounds of the present disclosure, or a pharmaceutically acceptable salt thereof, particularly 1 mg to about 50 mg.

In some embodiments, the pharmaceutical compositions comprise one or more compounds of the present disclosure, or a pharmaceutically acceptable salt thereof, as a first active ingredient, and further comprise a second active ingredient. The second active ingredient can be any immunomodulator or anti-tumour agent known in the art, including without limitation, chemotherapeutics, immunotherapeutics, cell signal transduction inhibitors, cell signal transduction inhibitors, alkylating agents, topoisomerase inhibitors, mitosis inhibitors, antihormonal agents, etc. Examples of such immunomodulators or anti-tumour agents are, platinum based chemotherapeutics (e.g., Cisplatin (DDP), Carboplatin (CBP), Sulfato-1,2-diaminocyclohexane platinum (SHP), Nedaplatin, Oxaliplatin (OXA), Laboplatin), Docetaxel, Paclitaxel, Doxorubicin, Etoposide, Mitoxantrone, CTLA-4 inhibitors, anti-CTLA-4 antibodies, PD-1 inhibitors, PD-L1 inhibitors, anti-PD-1/PD-L1 antibodies, CD39 inhibitors, anti-CD39 antibodies, CD73 inhibitors, anti-CD73 antibodies, CCR2 inhibitors, anti-CCR2 antibodies, EGFR inhibitors, CDK 4/6 inhibitors, MELK inhibitors, OX40 agonists, antiandrogen inhibitors, IgG4 isotype antibodies, tyrosine kinase inhibitors, DNA methyltransferase inhibitors, Hsp90 inhibitors, FGFR inhibitors, mTOR inhibitors, aromatase inhibitors, VEGF inhibitors, LHRH antagonists, PI3K inhibitors, AKT inhibitors, aurora kinase inhibitors, MEK inhibitors, HDAC inhibitors, BET inhibitors, PIK3CA inhibitors, proteasome inhibitors, other SERDs, farnesyltransferase inhibitors, VEGF-A antibodies, ErbB3 (Her3) antibodies, proteasome inhibitors, protein kinase C inhibitors, anti-IGF-1R antibodies, anti-HER2 antibodies, SERMs, IGF inhibitors, anti-IgG antibodies and the like. Representative examples of the anti tumour agents for treating cancers or tumors may include, but are not limited to, cisplatin, carboplatin, SHP, nedaplatin, oxaliplatin, laboplatin, docetaxel, paclitaxel, doxorubicin, etoposide, mitoxantrone, vincristine, vinblastine, gemcitabine, cyclophosphamide, chlormabucil, carmustine, methotrexate, fluorouracil, actinomycin, epirubicin, anthracycline, bleomycin, mitomycin-C, irinotecan, topotecan, teniposide interleukin, interferon, tremelimumab, ipilimumab, pembrolizumab, nivolumab, avelumab, durvalumab, atezolizumab, IPH 52, IPH 53, CPI-006, plozalizumab, MLN1202, cetuximab, lapatinib, erlotinib, gefitinib, neratinib, trastuzumab, ado-trastuzumab emtansine, pertuzumab, MCLA-128, anastrazole, raloxifene, G1T38, tamoxifen, goserelin, enzalutamide, vorinostat, entinostat, sunitinib, pazopanib, bevacizumab, ranibizumab, pegaptanib, cediranib, dasatinib, GDC-0980, gedatolisib, alpelisib, BKM120, copanlisib, AZD8835, GDC-0941, taselisib, temsirolimus, everolimus, sapanisertib, AZD5363, MK2206, panitumumab, pembrolizumab, sorafenib, palbociclib, abemaciclib, ribociclib, crizotinib, dovitinib, ruxolitinib, azacitidine, CC-486, HSP90 ganetespib, Debio 1347, erdafitinib, vitusertib, alisertib, selumetinib, GS-5829, GSK525762, MLN9708, GDC-0810, AFP464, tipifarnib, seribantumab, bortezomib, enzastaurin, AVE1642, xentuzumab, dalotuzumab, AMG 479, and the like.

The treatment of Adenosine receptor-associated diseases defined hereinafter may be applied as a sole therapy or may involve, in addition to the compound of the invention, conventional surgery or radiotherapy or chemotherapy or immunotherapy. Such chemotherapy may include one or more of the following chemotherapeutics: Cisplatin (DDP), Carboplatin (CBP), Sulfato-1,2-diaminocyclohexane platinum (SHP), Nedaplatin, Oxaliplatin (OXA), Laboplatin, Docetaxel, Paclitaxel, Doxorubicin, Etoposide, or Mitoxantrone. Such immunotherapeutics may include one or more of the following anti-tumour agents: (i) an anti-CTLA-4 antibody; (ii) an anti-PD-1 antibody; (iii) an anti-PD-L1 antibody; (iv) an anti-CD73 antibody; (v) an anti-CD39 antibody; or (vi) an anti-CCR2 antibody.

Particularly an anti-CTLA-4 antibody is tremelimumab (as disclosed in U.S. Pat. No. 6,682,736). In another aspect of the invention, particularly an anti-CTLA-4 antibody is ipilimumab (marketed by Bristol Myers Squib as YER-VOY®).

Particularly an anti-PD-L1 antibody is an antibody as disclosed in US 20130034559 (MedImmune). In another aspect of the invention, particularly an anti-PD-L1 antibody is an antibody as disclosed US 2010/0203056 (Genentech/Roche). In another aspect of the invention, particularly an anti-PD-L1 antibody is an antibody as disclosed US 20090055944 (Medarex). In another aspect of the invention, particularly an anti-PD-L1 antibody is an antibody as disclosed US 20130323249 (Sorrento Therapeutics).

Particularly an anti-PD-1 antibody is MRK-3475 (Merck). In another aspect of the invention, particularly an anti-PD-1 antibody is Nivolumab, or an anti-PD-1 antibody as disclosed in WO 2006/121168 or U.S. Pat. No. 8,008,449 (Medarex). In another aspect of the invention, particularly an anti-PD-1 antibody is an antibody as disclosed in WO2009/101611 (CureTech). In another aspect of the invention, particularly an anti-PD-1 antibody is an antibody as disclosed in WO2012/145493 (Amplimmune). In another aspect of the invention, particularly an anti-PD-1 antibody is an antibody as disclosed in U.S. Pat. No. 7,488,802 (Wyeth/MedImmune). In another aspect of the invention, particularly an anti-PD-1 antibody is an antibody as disclosed in US 20130280275 (Board of Regents, Univ. of Texas). In another aspect of the invention, particularly an anti-PD-1 antibody is an antibody as disclosed in WO 99/42585 (Agonox), WO 95/12673 and WO 95/21915.

Particularly an anti-CD39 antibody is IPH52 (Innate Pharmaceuticals).

Particularly an anti-CD73 antibody is CPI-006 (Corvus Pharmaceuticals) or IPH53 (Innate Pharmaceuticals).

Particularly an anti-CCR2 antibody is plozalizumab (Takeda Pharmaceuticals International Co.) or MLN1202 (Millennium Pharmaceuticals).

According to this aspect of the invention, there is provided a combination suitable for use in the treatment of an Adenosine receptor-associated disease, especially cancer, comprising a compound of formula (I) as defined hereinbefore or a pharmaceutically acceptable salt thereof and any one or more of the chemotherapeutics listed above and/or any one or more of the immonotherapeutics listed under (i)-(vi) above.

For example, the compounds of present disclosure may be provided in combination with an anti-PD1/PD-L1 antibody. In some specific embodiments, the compounds of present disclosure may be provided in combination with an anti-PD1/PD-L1 antibody and further in combination of an anti-CTLA-4, CD38, CD73, or CCR2 antibody.

According to this aspect of the present disclosure, there is provided a combination suitable for use in the treatment of cancer comprising a compound of formula (I) as defined hereinbefore or a pharmaceutically acceptable salt thereof and any one of the immunomodulators or anti tumour agents listed above.

Therefore in a further aspect of the present disclosure, there is provided a compound of formula (I) or a pharmaceutically acceptable salt thereof in combination with an immunomodulator or chemotherapeutics selected from one listed above.

Herein, where the term "combination" is used, it is to be understood that this refers to simultaneous, separate or sequential administration. In some embodiments, "combination" refers to simultaneous administration. In another aspect of the present disclosure, "combination" refers to separate administration. In a further aspect of the present disclosure, "combination" refers to sequential administration. Where the administration is sequential or separate, the delay in administering the second component should not be such as to lose the beneficial effect of the combination.

According to a further aspect of the present disclosure, there is provided a pharmaceutical composition which comprises a compound of formula (I) or a pharmaceutically acceptable salt thereof in combination with an immunomodulator or anti-tumour agent selected from those listed above, in association with a pharmaceutically acceptable diluent or carrier.

According to a further aspect of the present disclosure, there is provided a pharmaceutical composition which comprises a compound of formula (I) or a pharmaceutically acceptable salt thereof in combination with an immunomodulator or anti-tumour agent selected from one listed above, in association with a pharmaceutically acceptable diluent or carrier for use in producing an immunomodulating or anti-cancer effect.

According to a further aspect of the present disclosure, there is provided a pharmaceutical composition which comprises a compound of formula (I) or a pharmaceutically acceptable salt thereof in combination with an immunomodulator or anti-tumour agent selected from one listed above, in association with a pharmaceutically acceptable diluent or carrier for use in treating NSCLC, RCC, prostate cancer, or breast cancer (etc.).

According to a further aspect of the present disclosure, there is provided a kit comprising a compound of formula (I) or a pharmaceutically acceptable salt thereof in combination with an immunomodulator or anti-tumour agent selected from one listed above.

According to a further aspect of the present disclosure, there is provided a kit comprising:

a) a compound of formula (I) or a pharmaceutically acceptable salt thereof in a first unit dosage form;

b) an immunomodulator or anti-tumour agent selected from one listed above in a second unit dosage form; and c) container for containing said first and second dosage forms.

In addition to their use in therapeutic medicine, the compounds of formula (I), or a pharmaceutically acceptable salt thereof, are also useful as pharmacological tools in the development and standardisation of in vitro and in vivo test systems for the evaluation of the activity or the expression of adenosine receptors in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the present disclosure, described herein also apply.

Method for Treatment

The present disclosure provides a method of treating a disease associated with adenosine receptors (including, for example, A1, A2a, and/or A2b, particularly A2a) by administering to a subject a therapeutically effective amount of one or more compounds, pharmaceutically acceptable salts thereof or the pharmaceutical composition of the present disclosure.

As used herein, the term "disease associated with adenosine receptors" or "AR associated disease" refers to a disease whose onset or development or both is associated with the genomic alterations, expression, over-expression, degradation or activity of AR (including, for example, A1, A2a, and/or A2b, especially A2a), as the case may be. Examples include but are not limited to, inflammatory disorders, cancer, Parkinson disease, epilepsy, cerebral ischemia and stroke, sepression, cognitive impairment, HIV, ADA-SCID, acute heart failure (AHF) and chronic heart failure, chronic obstructive pulmonary disease (COPD), asthma, and other diseases. In certain embodiments, AR associated disease refers to a disease that will be treated by inhibition of the effect of Adenosine receptor.

In some embodiments, the AR associated disease is cancer, preferably an AR-expressing cancer, or AR-overexpressing cancer. An "AR-expressing cancer" is one that involves cancer cells or tumor cells having AR protein, such as A2a, A1 and/or A2b, present at their cell surface. An "AR-overexpressing cancer" is one which has significantly higher levels of AR protein, such as A2a, A1 and/or A2b, at the cell surface of a cancer or tumor cell, compared to a noncancerous cell of the same tissue type. Such overexpression may be caused by gene amplification or by increased transcription or translation. Adenosine receptor expression or overexpression may be determined in a diagnostic or prognostic assay by evaluating increased levels of the AR proteins present on the surface of a cell (e.g. via an immunohistochemistry assay; IHC). Alternatively, or additionally, one may measure levels of AR-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR)(Methods 132: 73-80 (1990)). Aside from the above assays, various in vivo assays are available to one skilled in the art. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

In particular, the cancers include but are not limited to, lung cancer (e.g. non-small cell lung cancer (NSCLC), small cell lung cancer, lung adenocarcinoma, large cell lung cancer, squamous cell lung cancer), renal cell carcinoma (RCC), prostate cancer, breast cancer, ovarian cancer, endometrial cancer, cervical cancer, bone cancer, uterine cancer, colon cancer, leukemia, glioblastoma, melanoma, chondrosarcoma, brain cancer, cholangiocarcinoma, osteosarcoma, lymphoma, adenoma, myeloma, hepatocellular carcinoma, adrenocortical carcinoma, pancreatic cancer, bladder cancer, liver cancer, gastric cancer, colorectal cancer, esophageal cancer, testicular cancer, skin cancer, kidney cancers, mesothelioma, neuroblastoma, thyroid cancer, head and neck cancers, esophageal cancers, eye cancers, nasopharyngeal cancer, or oral cancer. In some embodiments, the cancer is NSCLC, RCC, prostate cancer, or breast cancer. The cancer as mentioned herein can be at any stage, unless otherwise specified. In some embodiments, the cancer is early stage cancer. In some embodiments the cancer is locally advanced cancer. In some embodiments the cancer is locally advanced and/or metastatic cancer. In some embodiments the cancer is invasive cancer. In some embodiments the cancer is a cancer resistant to existing therapies.

In some embodiments, the compounds, or pharmaceutically acceptable salts thereof, of the present disclosure possess potency of treating cancer (e.g., NSCLC, RCC, prostate cancer, breast cancer). In addition, the compounds of the present disclosure, or pharmaceutically acceptable salts thereof may also be useful in the treatment of other Adenosine receptor-associated diseases, for example Parkinson disease, epilepsy, cerebral ischemia and stroke, sepression, cognitive impairment, HIV, ADA-SCID, AHF and chronic heart failure, Chronic obstructive pulmonary disease (COPD), or Asthma.

As used herein, the terms "treatment" and "treat" refer to reversing, alleviating, delaying the onset of, or inhibiting the progress of a disease or disorder, or one or more symptoms thereof, as described herein. In some embodiments, treatment may be conducted after one or more symptoms have developed. In other embodiments, treatment may be conducted in the absence of symptoms. For example, treatment may be conducted to a susceptible individual prior to the onset of symptoms (e.g. in light of a history of symptoms and/or in light of genetic or other susceptibility factors). Treatment may also be continued after symptoms have resolved, for example to present or delay their recurrence.

The therapeutically effective amount of a compound or a pharmaceutically acceptable salts thereof as provided herein will depend on various factors known in the art, such as body weight, age, past medical history, present medications, state of health of the subject and potential for cross-reaction, allergies, sensitivities and adverse side-effects, as well as the administration route and extent of disease development. Dosages may be proportionally reduced or increased by one skilled in the art (e.g. physician or veterinarian) as indicated by these and other circumstances or requirements.

Use of Compounds

In certain embodiments, the present disclosure provides use of the compounds, pharmaceutically acceptable salts thereof, or pharmaceutical composition of the present disclosure in the manufacture of medicaments for the treatment of AR associated diseases. Exemplary AR associated diseases include but are not limited to cancer (e.g. NSCLC, RCC, prostate, or breast cancer), and other diseases.

In such situation, the present disclosure also provides a method of screening patient suitable for treating with the compounds or pharmaceutical composition of the present disclosure alone or combined with other ingredients (e.g. a second active ingredient, e.g. anti-tumour agent). The method includes sequencing the tumor samples from patients and detecting the accumulation or activation of AR.

According to another aspect of the present disclosure, there is therefore provided a compound of formula (I), or a pharmaceutically acceptable salt thereof, as defined hereinbefore for use as a medicament.

According to a further aspect of the present disclosure, there is provided the use of a compound of formula (I), or a pharmaceutically acceptable salt thereof, as defined hereinbefore in the manufacture of a medicament for modulating adenosine receptors in a warm-blooded animal such as man.

The term "modulate", "modulating" or "modulation" when used in connection with adenosine receptors, refers to an action or result of changing the expression, degradation, and/or activity of the adenosine receptors.

According to a further aspect of the present disclosure, there is provided the use of a compound of formula (I), or a pharmaceutically acceptable salt thereof, as defined hereinbefore in the manufacture of a medicament for the treatment of AR associated diseases in a warm-blooded animal such as man.

According to this aspect of the present disclosure, there is provided the use of a compound of formula (I), or a pharmaceutically acceptable salt thereof, as defined hereinbefore in the manufacture of a medicament for the production of an anti-cancer effect in a warm-blooded animal such as man.

According to a further feature of the present disclosure, there is provided the use of a compound of formula (I), or a pharmaceutically acceptable salt thereof, as defined hereinbefore in the manufacture of a medicament for use in the treatment of NSCLC, RCC, prostate, or breast cancer According to a further feature of the present disclosure, there is provided the use of a compound of formula (I), or a pharmaceutically acceptable salt thereof, as defined hereinbefore in the manufacture of a medicament for use in the treatment of breast cancer.

According to a further feature of this aspect of the present disclosure, there is provided a method of modulating adenosine receptors in a warm-blooded animal, such as man, in need of such treatment, which comprises administering to said animal an effective amount of a compound of formula (I), or a pharmaceutically acceptable salt thereof, as defined hereinbefore.

According to a further feature of this aspect of the present disclosure, there is provided a method of treating AR associated diseases in a warm-blooded animal, such as man, in need of such treatment, which comprises administering to said animal an effective amount of a compound of formula (I), or a pharmaceutically acceptable salt thereof, as defined hereinbefore.

According to a further feature of this aspect of the present disclosure, there is provided a method for producing an anti-cancer effect in a warm-blooded animal, such as man, in need of such treatment, which comprises administering to said animal an effective amount of a compound of formula (I), or a pharmaceutically acceptable salt thereof, as defined hereinbefore.

According to a further feature of this aspect of the present disclosure, there is provided a method of producing an anti-cancer effect in a warm-blooded animal, such as man, in need of such treatment, which comprises (1) determining whether or not the warm blooded animal has an AR-expressing cancer and (2) if so administering to said animal an effective amount of the compound of formula (I), or a pharmaceutically acceptable salt thereof, as defined hereinbefore.

According to an additional feature of this aspect of the present disclosure, there is provided a method of treating NSCLC, RCC, prostate, or breast cancer, in a warm-blooded animal, such as man, in need of such treatment, which comprises administering to said animal an effective amount of a compound of formula (I), or a pharmaceutically acceptable salt thereof, as defined hereinbefore.

According to a further aspect of the present disclosure, there is provided a compound of formula (I), or a pharmaceutically acceptable salt thereof, as defined hereinbefore, for use in modulating AR in a warm-blooded animal such as man.

According to a further aspect of the present disclosure, there is provided a compound of formula (I), or a pharmaceutically acceptable salt thereof, as defined hereinbefore, for use in the treatment of AR associated diseases in a warm-blooded animal such as man.

According to this aspect of the present disclosure, there is provided a compound of formula (I), or a pharmaceutically acceptable salt thereof, as defined hereinbefore, for use in the production of an anti-cancer effect in a warm-blooded animal such as man.

According to a further feature of the present disclosure, there is provided a compound of formula (I), or a pharmaceutically acceptable salt thereof, as defined hereinbefore, for use in the treatment of NSCLC, RCC, prostate, or breast cancer.

EXAMPLES

The followings further explain the general methods of the present disclosure. The compounds of the present disclosure may be prepared by the methods known in the art. The following illustrates the detailed preparation methods of the preferred compounds of the present disclosure. However, they are by no means limiting the preparation methods of the compounds of the present disclosure.

Example 01. Preparation of 3-amino-6-(2,6-dimethylpyridin-4-yl)-5-(4-fluorophenyl)-N-((3-fluoropyridin-2-yl)methyl)pyrazine-2-carboxamide (Cmpd. 01)

SCHEME 01

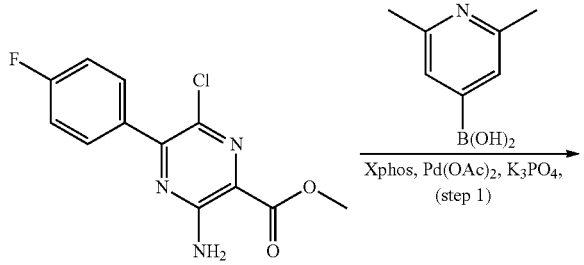

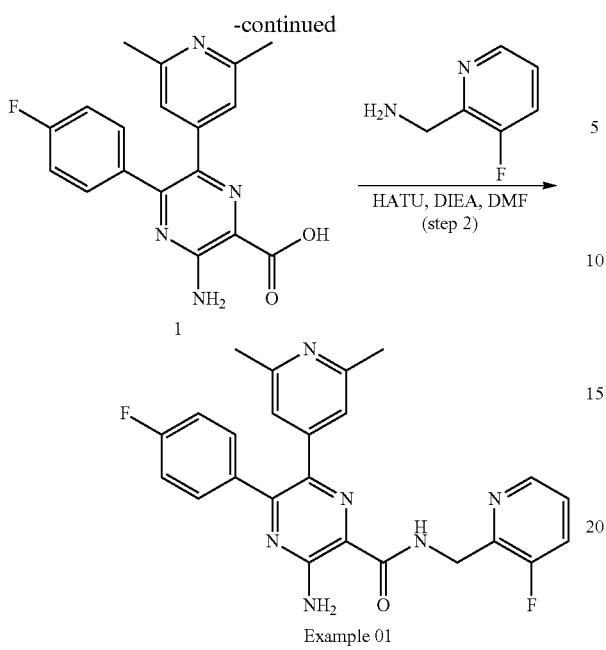

Step 1. methyl 3-amino-6-(2,6-dimethylpyridin-4-yl)-5-(4-fluorophenyl)pyrazine-2-carboxylate To a solution of methyl 3-amino-6-chloro-5-(4-fluorophenyl)pyrazine-2-carboxylate (200 mg, 0.71 mmol, 1 equiv) and (2,6-dimethylpyridin-4-yl)boronic acid (214.4 mg, 1.42 mmol, 2 equiv) in n-BuOH (25 mL) were added xPhos (67.7 mg, 0.14 mmol, 0.2 equiv) and Pd(OAc)$_2$ (31.9 mg, 0.14 mmol, 0.2 equiv), K$_3$PO$_4$ (301.4 mg, 1.42 mmol, 2 equiv). After stirring for 2 h at 100° C. under a nitrogen atmosphere. The resulted mixture was concentrated under reduced pressure. The residue was purified by Prep-TLC (CH$_2$Cl$_2$/MeOH 10:1) to afford methyl 3-amino-6-(2,6-dimethylpyridin-4-yl)-5-(4-fluorophenyl)pyrazine-2-carboxylate (230 mg, 36.8%) as a yellow solid. LCMS: m/z (ESI), M+=339.2

Step 2. 3-amino-6-(2,6-dimethylpyridin-4-yl)-5-(4-fluorophenyl)-N-[(3-fluoropyridin-2-yl)methyl]pyrazine-2-carboxamide (Cmpd. 01)

A solution/mixture of 3-amino-6-(2,6-dimethylpyridin-4-yl)-5-(4-fluorophenyl) pyrazine-2-carboxylic acid (215 mg, 0.64 mmol, 1 equiv) and 1-(3-fluoropyridin-2-yl)methanamine (96.2 mg, 0.76 mmol, 1.20 equiv), HATU (483.2 mg, 1.3 mmol, 2.0 equiv), DIEA (246.4 mg, 1.9 mmol, 3.0 equiv) in DMF (10 mL) was stirred for 2 h at 20° C. under air atmosphere. The resulted mixture was concentrated under reduced pressure. The crude product (215 mg) was purified by Prep-HPLC with the following conditions (Column: XBridge Prep OBD C18 Column 19*250 mm, 5 um; Mobile Phase A: Water (10 MMOL/L NH$_4$HCO$_3$+0.1% NH$_3$.H$_2$O), Mobile Phase B: ACN; Flow rate: 20 mL/min; Gradient: 53% B to 62% B in 7 min; 220/254 nm; Rt: 6.1 min) to afford 3-amino-6-(2,6-dimethylpyridin-4-yl)-5-(4-fluorophenyl)-N-[(3-fluoropyridin-2-yl)methyl]pyrazine-2-carboxamide (Cmpd. 01) (83.3 mg, 29.3%) as a light yellow solid. LCMS: m/z (ESI), M+=447.2. $^1$H NMR (400 MHz, Methanol-d$_4$): δ2.4 (s, 6H), 4.8 (d, J=1.7 Hz, 2H), 7.1-7.2 (m, 4H), 7.4 (dt, J=8.6, 4.4 Hz, 1H), 7.4-7.5 (m, 2H), 7.6 (ddd, J=9.9, 8.4, 1.3 Hz, 1H), 8.4 (dt, J=4.8, 1.4 Hz, 1H).

Example 02. Preparation of 3-amino-N-[(2,6-difluorophenyl)methyl]-6-(1-methyl-6-oxo-1,6-dihydropyridin-3-yl)-5-(5-methylfuran-2-yl)pyrazine-2-carboxamide (Cmpd. 02)

SCHEME 02

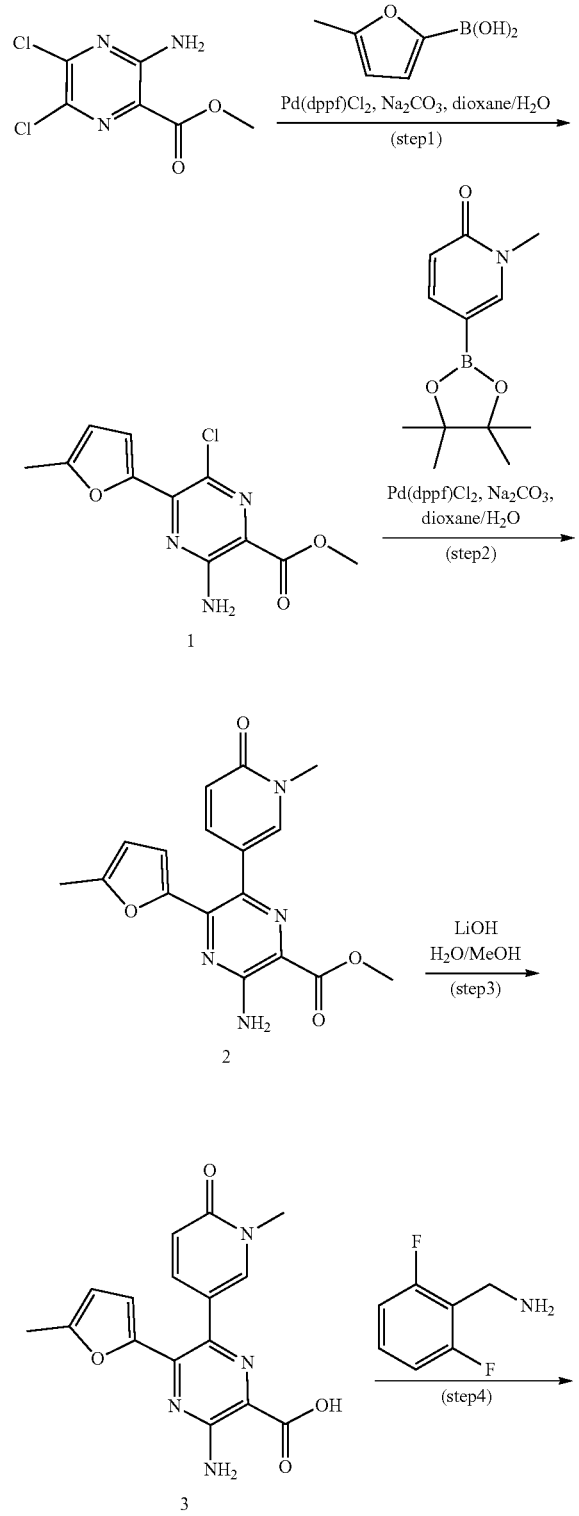

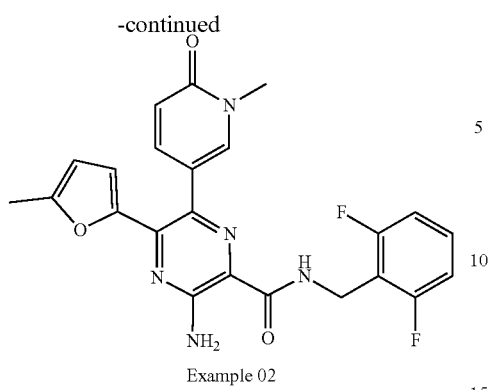

Example 02

Step 1. methyl 6-chloro-3-methyl-5-(5-methylfuran-3-yl)pyrazine-2-carboxylate A mixture of methyl 3-amino-5,6-dichloropyrazine-2-carboxylate (1 g, 4.5 mmol, 1 equiv) and (5-methylfuran-2-yl) boronic acid (0.6 g, 4.8 mmol) and Pd(dppf)Cl$_2$ (0.3 g, 0.5 mmol) and Na$_2$CO$_3$ (1.0 g, 9.0 mmol) in dioxane/H$_2$O (40 mL) was stirred for 4 hours at 90° C. under nitrogen atmosphere. The resulted mixture was filtered, the filter cake was washed with DCM:MeOH (1:1) (3×10 mL). The filtrate was extracted with CH$_2$Cl$_2$ (3×10 mL). Then the organic layer was dried by Na$_2$SO$_4$, and the solution concentrated under reduced pressure. The crude product was purified by Prep-HPLC with the following conditions (CH$_2$Cl$_2$:EtOAc (1:1)) to afford methyl 6-chloro-3-methyl-5-(5-methylfuran-3-yl) pyrazine-2-carboxylate (125 mg, 7.1%) as a yellow solid. LCMS: m/z (ESI), [M+H]$^+$=268.2.

Step 2. methyl 3-methyl-6-(1-methyl-2-oxo-1,2-dihydropyridin-4-yl)-5-(5-methylfuran-3-yl)pyrazine-2-carboxylate A mixture of methyl 6-chloro-3-methyl-5-(5-methyl-furan-3-yl)pyrazine-2-carboxylate (65 mg, 0.24 mmol, 1 equiv) and 1-methyl-5-(4,4,5,5-tetramethyl-1,3,2-dioxaborolan-2-yl)-1,2-dihydropyridin-2-one (56.4 mg, 0.24 mmol, 1.00 equiv) and Pd(dppf)Cl$_2$ (17.5 mg, 0.024 mmol, 0.10 equiv) and Na$_2$CO$_3$ (50.88 mg, 0.48 mmol, 2 equiv) in dioxane/H$_2$O (6/1, 3 mL) was stirred for 10 hours at 90° C. under nitrogen atmosphere. The resulted mixture was filtered, the filter cake was washed with CH$_2$Cl$_2$:MeOH (1:1) (3×10 mL). The filtrate was washed with 20 mL of H$_2$O and extracted with CH$_2$Cl$_2$ (3×20 mL). The aqueous layer was dried with Na$_2$SO$_4$, and was concentrated under reduced pressure. Then the residue was dissolved in ethyl acetate (10 mL). The precipitated solids were collected by filtration and washed with diethyl ether (3×3 mL), and the resulting solid was dried under vacuum to afford methyl 3-methyl-6-(1-methyl-2-oxo-1,2-dihydropyridin-4-yl)-5-(5-methylfuran-3-yl)pyrazine-2-carboxylate (55 mg, 63.2%) as a yellow solid. LCMS: m/z (ESI), [M+H]$^+$=341.2.

Step 3. 3-methyl-6-(1-methyl-2-oxo-1,2-dihydropyridin-4-yl)-5-(5-methylfuran-3-yl)pyrazine-2-carboxylic Acid The methyl 3-methyl-6-(1-methyl-2-oxo-1,2-dihydropyridin-4-yl)-5-(5-methylfuran-3-yl)pyrazine-2-carboxylate (90 mg, 0.3 mmol, 1 equiv) in MeOH (9 mL) and take 1 ml for reaction. The LiOH (25.2 mg, 1.1 mmol, 4.0 equiv) and H$_2$O (1.8 mL) were added to the solution at 0° C. and stirred for 6 hours at room temperature. The mixture was basified to pH 6 with HCl (aq.). The solution was concentrated under reduced pressure and gave 3-methyl-6-(1-methyl-2-oxo-1,2-dihydropyridin-4-yl)-5-(5-methylfuran-3-yl)pyrazine-2-carboxylic acid (85 mg, 96.6%) as a yellow solid. LCMS: m/z (ESI), [M+H]$^+$=327.1.

Step 4. 3-amino-N-[(2,6-difluorophenyl)methyl]-6-(1-methyl-6-oxo-1,6-dihydropyridin-3-yl)-5-(5-methylfuran-2-yl)pyrazine-2-carboxamide (Cmpd. 02)

To a stirred solution of 3-amino-6-(1-methyl-6-oxo-1,6-dihydropyridin-3-yl)-5-(5-methylfuran-2-yl)pyrazine-2-carboxylic acid (80 mg, 0.3 mmol, 1 equiv) and DIEA (116.1 mg, 0.9 mmol, 3.00 equiv) in DMSO (4 mL), was added HAUT (342 mg, 0.9 mmol, 3.0 equiv) in portions at room temperature. The resulted mixture was stirred for 10 mins at room temperature. Then 1-(2,6-difluorophenyl)methanamine (107.3 mg, 0.75 mmol, 2.5 equiv) was added dropwise and stirred for 10 hours at room temperature. The reaction was quenched by the addition of brine (30 mL) at room temperature. The resulting solid was collected by filtration and purified by Prep-TLC (CH$_2$Cl$_2$/EtOAc 1:1) to afford 30 mg of crude product which was purified by Prep-HPLC (Column: XBridge Prep C18 OBD Column, 5 um, 19*150 mm; Mobile Phase A: Water (10 MMOL/L NH$_4$HCO$_3$+0.1% NH$_3$.H$_2$O), Mobile Phase B: ACN; Flow rate: 20 mL/min; Gradient: 37% B to 37% B in 8 min; 220,254 nm; Rt: 7.33 min) to afford 3-amino-N-[(2,6-difluorophenyl)methyl]-6-(1-methyl-6-oxo-1,6-dihydropyridin-3-yl)-5-(5-methylfuran-2-yl)pyrazine-2-carboxamide (Cmpd. 02) (7.4 mg, 6.49%) as a yellow solid. LCMS m/z (ESI) [M+H]$^+$=452.3. $^1$H NMR (400 MHz, Methanol-d$_4$) δ 2.25 (s, 3H), 3.64 (s, 3H), 4.70 (s, 2H), 6.18 (d, J=3.4 Hz, 1H), 6.55 (d, J=9.2 Hz, 1H), 6.81 (d, J=3.3 Hz, 1H), 6.98 (t, J=7.9 Hz, 2H), 7.39-7.28 (m, 1H), 7.52 (dd, J=9.2, 2.5 Hz, 1H), 7.92 (d, J=2.5 Hz, 1H).

Example 04: Preparation of N-((3-amino-6-(1-methyl-6-oxo-1,6-dihydropyridin-3-yl)-5-(5-methylfuran-2-yl)pyrazin-2-yl)methyl)-2,6-difluorobenzamide (Cmpd. 04)

SCHEME 3

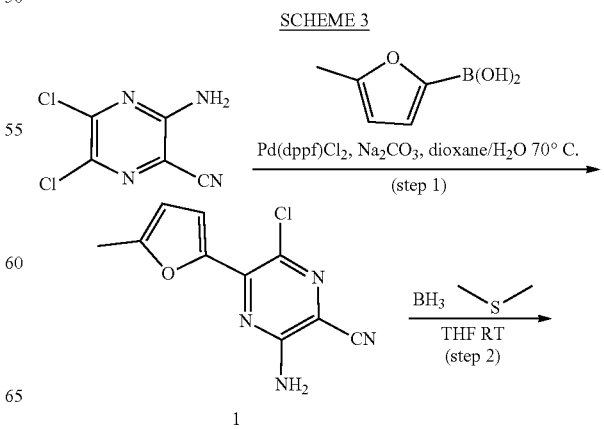

-continued

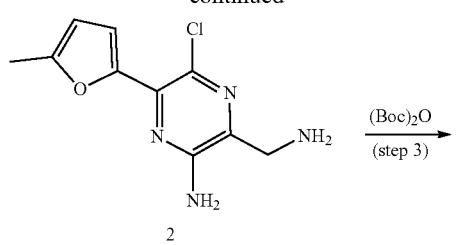

2

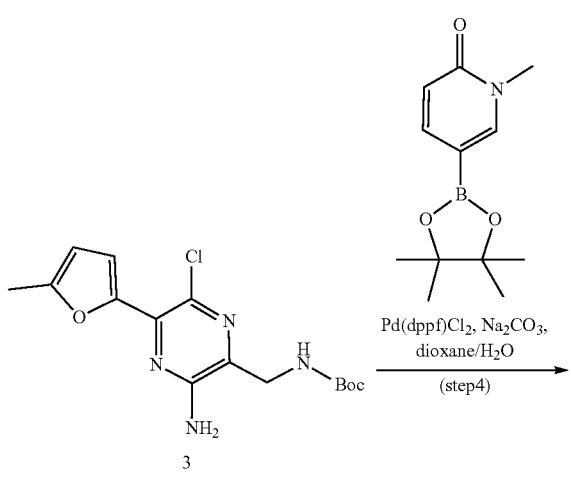

3

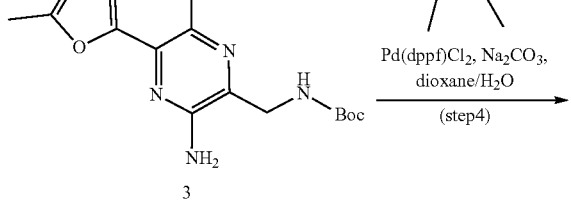

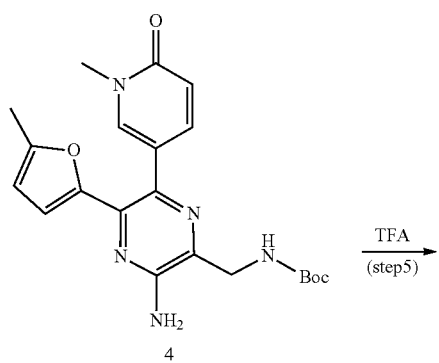

4

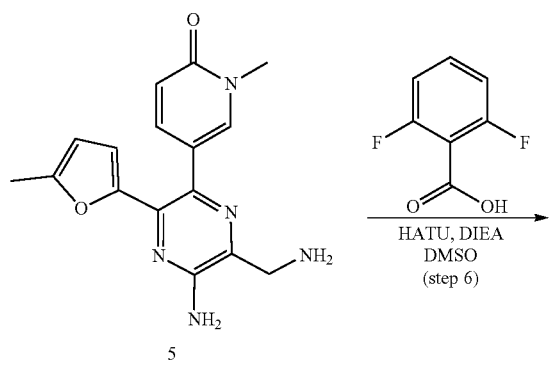

5

-continued

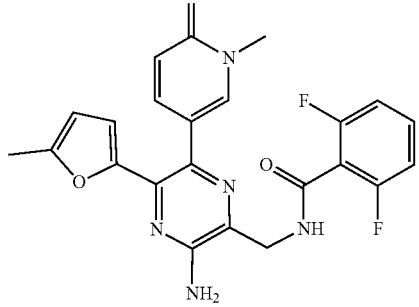

Example 04

Step 1. 3-amino-5-chloro-6-(5-methylfuran-2-yl)pyrazine-2-carbonitrile

A mixture of 3-amino-5,6-dichloropyrazine-2-carbonitrile (250 mg, 1.3 mmol, 1 equiv) and (5-methylfuran-2-yl)boronic acid (166.6 mg, 1.3 mmol, 1.00 equiv) and Pd(dppf)Cl$_2$ (96.8 mg, 0.1 mmol, 0.1 equiv) and Na$_2$CO$_3$ (280.4 mg, 2.7 mmol, 2 equiv) in dioxane/H$_2$O (15 mL) was stirred for 6 hours at 70° C. under nitrogen atmosphere.

The resulted mixture was filtered, the filter cake was washed with CH$_2$Cl$_2$:MeOH (1:1) (3×10 mL). The filtrate was washed with 20 mL of H$_2$O and extracted with CH$_2$Cl$_2$ (3×20 mL). The organic layer was dried with Na$_2$SO$_4$, and concentrated under reduced pressure. The residue was purified by silica gel column chromatography, eluted with PE:(CH$_2$Cl$_2$/EtOAc (1:1)) (1:1) to afford 3-amino-5-chloro-6-(5-methylfuran-2-yl)pyrazine-2-carbonitrile (130 mg, 28.9%) as a yellow solid. LCMS: m/z (ESI), [M+H]$^+$=235.1.

Step 2. 3-(aminomethyl)-6-chloro-5-(5-methylfuran-2-yl)pyrazin-2-amine

A mixture of 3-amino-5-chloro-6-(5-methylfuran-2-yl)pyrazine-2-carbonitrile (240 mg, 1.0 mmol, 1 equiv) in THF (12 mL) was stirred and the DMSB (155.4 mg, 2.1 mmol, 2.0 equiv) slowly added to the mixture solution at 0° C. and stirred for 6 hours at room temperature. The reaction was quenched by the addition of H$_2$O (2 mL) at 0° C., then added the solution of Na$_2$CO$_3$ and stirred for 30 mins at room temperature to afford 3-(aminomethyl)-6-chloro-5-(5-methylfuran-2-yl)pyrazin-2-amine (240 mg, 96.34%) as a yellow liquid. The crude product was used in the next step directly without further purification. LCMS: m/z (ESI), [M+H]$^+$=239.2.

Step 3. tert-butyl N-[[3-amino-5-chloro-6-(5-methylfuran-3-yl)pyrazin-2-yl]methyl]carbamate To the 3-(aminomethyl)-6-chloro-5-(5-methylfuran-2-yl)pyrazin-2-amine (238 mg, 1.0 mmol, 1.0 equiv) in DCM (10 mL) was added (BOC)$_2$O (438.9 mg, 2.0 mmol, 2.0 equiv) at room temperature. The resulted mixture was stirred for 10 hours at room temperature. The resulted mixture was quenched with water (20 mL) and extracted with CH$_2$Cl$_2$ (3×20 mL). The combined organic layers were washed with H$_2$O (3×10 mL), dried over anhydrous Na$_2$SO$_4$. After filtration, the filtrate was concentrated under reduced pressure and gave tert-butyl N-[[3-amino-5-chloro-6-(5-methylfuran- 3-yl)pyrazin-2-yl]methyl]carbamate (150 mg, 41.83%) as a yellow solid. LCMS: m/z (ESI), [M+H]$^+$=339.2.

Step 4. tert-butyl N-[[3-amino-5-(1-methyl-6-oxo-1, 6-dihydropyridin-3-yl)-6-(5-methylfuran-3-yl) pyrazin-2-yl]methyl]carbamate The tert-butyl N-[[3-amino-5-chloro-6-(5-methylfuran-3-yl)pyrazin-2-yl] methyl] carbamate (120 mg, 0.34 mmol, 1 equiv) added into dioxane/H$_2$O (10 mL), then the 1-methyl-5-(4,4,5,5-tetramethyl-1,3,2-dioxaborolan-2-yl)-1,2-dihydropyridin-2-one (124.9 mg, 0.5 mmol, 1.50 equiv) and Pd(dppf)Cl$_2$ (25.9 mg, 0.1 mmol) and Na$_2$CO$_3$ (75.1 mg, 0.7 mmol, 2 equiv) was added under N$_2$, and stirred for 10 hours at 90° C. under nitrogen atmosphere. The reaction solution was concentrated and purified by Prep-TLC (CH$_2$Cl$_2$/EtOAc 1:1) to afford tert-butyl N-[[3-amino-5-(1-methyl-6-oxo-1, 6-dihydropyridin-3-yl)-6-(5-methylfuran-3-yl)pyrazin-2-yl] methyl]carbamate (35 mg, 23.53%) as a yellow solid. LCMS: m/z (ESI), [M+H]$^+$=412.3.

Step 5. 5-[6-amino-5-(aminomethyl)-3-(5-methylfuran-3-yl)pyrazin-2-yl]-1-methyl-1,2-dihydropyridin-2-one The tert-butyl N-[[3-amino-5-(1-methyl-6-oxo-1,6-dihydropyridin-3-yl)-6-(5-methylfuran-3-yl)pyrazin-2-yl]methyl]carbamate (120 mg, 1 equiv) was added into DCM (5 mL) and TFA (2.5 mL). The resulting solution was stirred for 10 hours at room temperature under air atmosphere. The mixture was acidified to pH 7 with saturated Na$_2$CO$_3$ (aq.). The resulted mixture was extracted with CH$_2$Cl$_2$ (3×30 mL). The combined organic layers were washed with H$_2$O (2×10 mL), dried over anhydrous Na$_2$SO$_4$. After filtration, the filtrate was concentrated under reduced pressure. This resulted in 5-[6-amino-5-(aminomethyl)-3-(5-methylfuran-3-yl) pyrazin-2-yl]-1-methyl-1,2-dihydropyridin-2-one (80 mg, 84.58%) as a yellow solid. LCMS: m/z (ESI), [M+H]$^+$= 312.2.

Step 6. N-((3-amino-6-(1-methyl-6-oxo-1,6-dihydropyridin-3-yl)-5-(5-methylfuran-2-yl)pyrazin-2-yl) methyl)-2,6-difluorobenzamide (Cmpd. 04)

To a stirred solution of 5-[6-amino-5-(aminomethyl)-3-(5-methylfuran-3-yl)pyrazin-2-yl]-1-methyl-1,2-dihydropyridin-2-one (80 mg, 0.26 mmol, 1 equiv) and 2,6-difluorobenzoic acid (60.9 mg, 0.39 mmol, 1.5 equiv) in DMSO (1 mL), was added HAUT (197 mg, 0.52 mmol, 2.0 equiv) and DIEA (67 mg, 0.52 mmol, 2.0 equiv) in portion at room temperature under air atmosphere. The resulting solution was stirred for 10 hours at room temperature. The resulted mixture was quenched with brine (20 mL), the aqueous solution was extracted with CH$_2$Cl$_2$ (3×10 mL). The organic layers were dried over anhydrous Na$_2$SO$_4$, filtered and concentrated under reduced pressure. The resulting crude product was purified by Prep-TLC (DCM:MeOH=20:1) to afford N-[[3-amino-5-(1-methyl-6-oxo-1,6-dihydropyridin-3-yl)-6-(5-methylfuran-3-yl)pyrazin-2-yl]methyl]-2,6-difluorobenzamide (Cmpd. 04) (112 mg, 93.7%) as a light yellow solid. LCMS: m/z (ESI) [M+H]$^+$=452.2. $^1$H NMR (400 MHz, Methanol-d$_4$) δ2.22-2.33 (m, 3H), 3.36 (s, 14H), 3.63 (s, 3H), 4.66 (s, 2H), 6.12-6.20 (m, 1H), 6.67 (d, J=3.3 Hz, 1H), 7.09 (t, J=8.2 Hz, 2H), 7.41-7.58 (m, 2H), 7.85 (d, J=2.6 Hz, 1H).

Example 05: Preparation of 3-amino-N-(2,6-difluorobenzyl)-6-(2,6-dimethylpyridin-4-yl)-5-(oxazol-2-yl)pyrazine-2-carboxamide (Cmpd. 05)

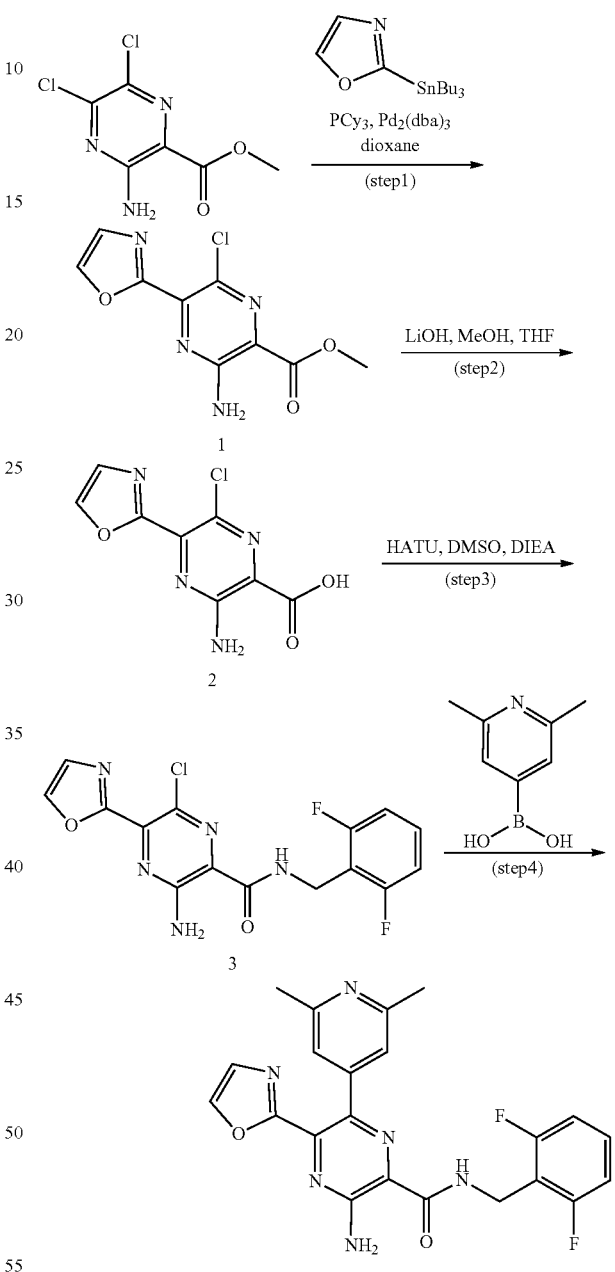

Step 1. methyl 3-amino-6-chloro-5-(oxazol-2-yl) pyrazine-2-carboxylate

To a stirred solution of methyl 3-amino-5,6-dichloropyrazine-2-carboxylate (500 mg, 2.25 mol, 1 equiv) and 2-(tributylstannyl)-1,3-oxazole (806.5 mg, 2.25 mol, 1.00 equiv) in 1,4-dioxane (20 mL) were added LiCl (190.9 mg, 4.50 mmol, 2 equiv), tricyclohexylphosphane (126.3 mg, 0.45 mmol, 0.2 equiv) and Pd$_2$(dba)$_3$. CHCl$_3$ (466.2 mg, 0.45 mmol, 0.20 equiv) in portions at room temperature under nitrogen atmosphere. The resulted mixture was stirred for 4h at 140° C. under nitrogen atmosphere with microwave irritation. The resulted mixture was concentrated under reduced pressure. The residue was purified by Prep-TLC (CH$_2$Cl$_2$/MeOH 20:1) to afford methyl 3-amino-6-chloro-5-(1,3-oxazol-2-yl)pyrazine-2-carboxylate (160 mg, 27.9%) as a yellow solid. LCMS: m/z (ESI), [M+H]$^+$=255.1.

Step 2. 3-amino-6-chloro-5-(oxazol-2-yl)pyrazine-2-carboxylic Acid

To a stirred solution of methyl 3-amino-6-chloro-5-(1,3-oxazol-2-yl)pyrazine-2-carboxylate (100 mg, 0.4 mmol, 1 equiv) in MeOH (10 mL) and water (1 mL) was added LiOH.H$_2$O (49.4 mg, 1.2 mmol, 2.0 equiv) in portions at room temperature. The resulted mixture was stirred for 4h at room temperature. The resulted mixture was concentrated under vacuum. The residue was purified by reverse flash chromatography with the following conditions: column, C18 silica gel; mobile phase, MeOH in water, 10% to 50% gradient in 35 min; detector, UV 254 nm to afford 3-amino-6-chloro-5-(1,3-oxazol-2-yl)pyrazine-2-carboxylic acid (50 mg, 52.9%) as a yellow solid. LCMS: m/z (ESI), [M+H]$^+$=241.1, H NMR (300 MHz, DMSO-d$_6$) δ7.50 (d, J=0.8 Hz, 1H), 8.34 (d, J=0.8 Hz, 1H).

Step 3. 3-amino-6-chloro-N-(2,6-difluorobenzyl)-5-(oxazol-2-yl)pyrazine-2-carboxamide To a stirred mixture of 3-amino-6-chloro-5-(1,3-oxazol-2-yl)pyrazine-2-carboxylic acid (150 mg, 0.62 mmol, 1 equiv) and DIEA (241.7 mg, 1.87 mmol, 3 equiv) in DMSO (10 mL) were added 1-(2,6difluorophenyl)methanamine (133.9 mg, 0.94 mmol, 1.50 equiv) and HATU (355.6 mg, 0.94 mmol, 1.5 equiv) in portions at room temperature atmosphere. The resulted mixture was stirred for 3h at room temperature. The resulted mixture was concentrated under reduced pressure. The residue was purified by Prep-TLC (CH$_2$Cl$_2$/MeOH 20:1) to afford 3-amino-6-chloro-N-[(2,6-difluorophenyl)methyl]-5-(1,3-oxazol-2-yl)pyrazine-2-carboxamide (Cmpd. 05) (140 mg, 48.51%) as a yellow solid. LCMS: m/z (ESI), [M+H]$^+$=366.1, H NMR (300 MHz, DMSO-d$_6$) δ 9.10 (t, J=5.7 Hz, 1H), 8.42 (s, 1H), 7.88 (s, 2H), 7.58 (s, 1H), 7.49-7.28 (m, 1H), 7.10 (t, J=8.0 Hz, 2H), 4.57 (d, J=5.8 Hz, 2H).

Step 4. 3-amino-N-(2,6-difluorobenzyl)-6-(2,6-dimethylpyridin-4-yl)-5-(oxazol-2-yl)pyrazine-2-carboxamide (Cmpd. 05)

To a stirred mixture of (2,6-dimethylpyridin-4-yl)boronic acid (82.6 mg, 550 mmol, 2.00 equiv) and 3-amino-6-chloro-N-[(2,6-difluorophenyl)methyl]-5-(1,3-oxazol-2-yl) pyrazine-2-carboxamide (100 mg, 270 mmol, 1 equiv) in dioxane (10 mL) were added Pd(dppf)Cl$_2$CH$_2$Cl$_2$ (44.7 mg, 0.05 mmol, 0.2 equiv) and K$_3$PO$_4$ (232.2 mg, 1.09 mmol, 4 equiv) in portions at room temperature under nitrogen atmosphere. The resulted mixture was stirred for overnight at 90° C. under nitrogen atmosphere. The resulted mixture was concentrated under vacuum. The residue was purified by PrepTLC (CH$_2$Cl$_2$/MeOH 20:1) to afford 3-amino-N-[(2, 6-difluorophenyl)methyl]-6-(2,6-dimethylpyridin-4-yl)-5-(1,3-oxazol-2-yl)pyrazine-2-carboxamide (Cmpd. 05) (40 mg, 33.2 as a yellow solid. LCMS: m/z (ESI), [M+H]$^+$=437.3; $^1$H NMR (300 MHz, DMSO-d$_6$) δ 9.12 (t, J=5.8 Hz, 1H), 8.26 (s, 1H), 7.95 (s, 2H), 7.46-7.31 (m, 2H), 7.09 (t, J=8.0 Hz, 2H), 7.00 (s, 2H), 4.62 (d, J=5.9 Hz, 2H), 2.40 (s, 6H).

Compounds listed in the table below were prepared using methods described in Cmpd. 05.

| Example/Cmpd number | Structure | LCMS [M + H]$^+$ | $^1$H NMR |
|---|---|---|---|
| 03 | 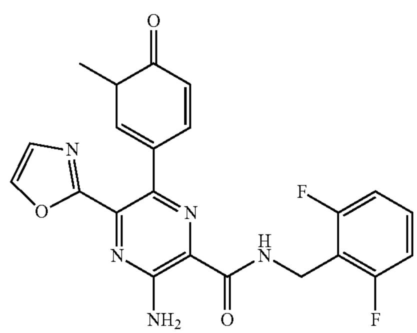 [SMILES: CC1C=C(c2nc(C(=O)NCc3c(F)cccc3F)c(N)nc2-c2ncco2)C=CC1=O] | 439.2 | $^1$H NMR (300 MHz, DMSO-d$_6$) δ3.43 (s, 3H), 4.58 (d, J = 5.8 Hz, 2H), 6.30 (d, J = 9.4 Hz, 1H), 7.07 (t, J = 7.9 Hz, 2H), 7.25-7.45 (m, 3H), 7.75 (s, 2H), 7.96 (d, J = 2.6 Hz, 1H), 8.27 (s, 1H), 9.11 (t, J = 5.9 Hz, 1H). |
| 10 | 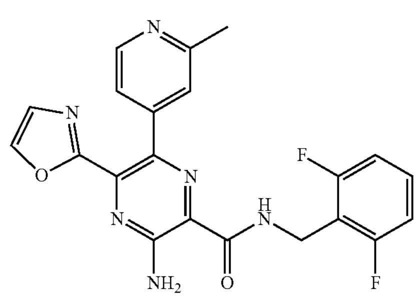 [SMILES: Cc1cc(-c2nc(C(=O)NCc3c(F)cccc3F)c(N)nc2-c2ncco2)ccn1] | 423.0 | $^1$H NMR: (300 MHz, MeOD) δ 2.55 (s, 3H), 4.74 (s, 2H), 7.00 (t, 2H), 7.22 (d, 1H), 7.36 (m, 3H), 8.01 (d, 1H), 8.39 (d, 1H). |

| Example/Cmpd number | Structure | LCMS [M + H]+ | 1H NMR |
|---|---|---|---|
| 34 | 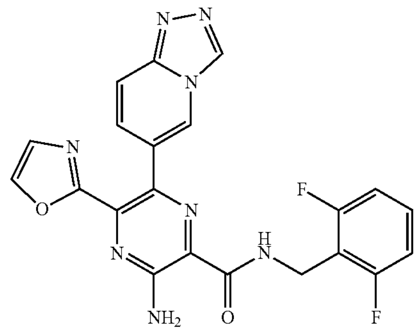 [SMILES: Nc1nc(-c2ncco2)c(-c2ccc3nncn3c2)nc1C(=O)NCc1c(F)cccc1F] | 449.0 | 1H NMR (400 MHz, DMSO-d6) δ 4.60 (d, J = 5.9 Hz, 2H), 7.08 (t, J = 7.9 Hz, 2H), 7.34~7.43 (m, 3H), 7.73 (d, J = 9.5 Hz, 1H), 7.94 (s, 2H), 8.29 (s, 1H), 8.75 (s, 1H), 9.18 (t, J = 5.9 Hz, 1H), 9.28 (s, 1H). |
| 37 | 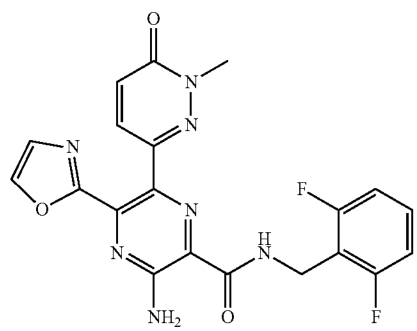 [SMILES: Cn1nc(-c2nc(C(=O)NCc3c(F)cccc3F)c(N)nc2-c2ncco2)ccc1=O] | 440.1 | 1H NMR (400 MHz, DMSO-d6) δ 3.40 (3H, s), 4.60 (2H, d), 6.98-7.16 (3H, m), 7.35-7.47 (2H, m), 8.07 (2H, s), 8.25 (2H, d), 9.29 (1H, t). |
| 105 | 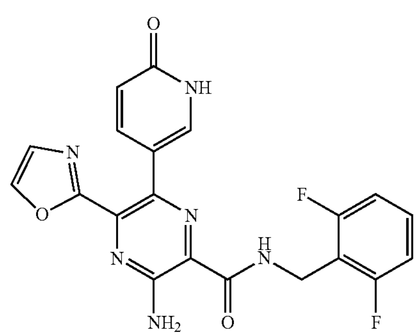 [SMILES: Nc1nc(-c2ncco2)c(-c2ccc(=O)[nH]c2)nc1C(=O)NCc1c(F)cccc1F] | 425.2 | 1H NMR (400 MHz, DMSO-d6) δ 4.59 (d, J = 5.8 Hz, 2H), 6.27 (d, J = 9.5 Hz, 1H), 7.09 (t, J = 8.0 Hz, 2H), 7.34~7.48 (m, 3H), 7.61 (s, 1H), 7.74 (s, 2H), 8.30 (d, J = 0.8 Hz, 1H), 9.17 (t, J = 5.9 Hz, 1H), 11.79 (s, 1H). |

Example 06. Preparation of 3-amino-N-(2,6-difluorobenzyl)-6-(2,6-dimethylmorpholino)-5-(4-fluorophenyl)pyrazine-2-carboxamide (Cmpd. 06)

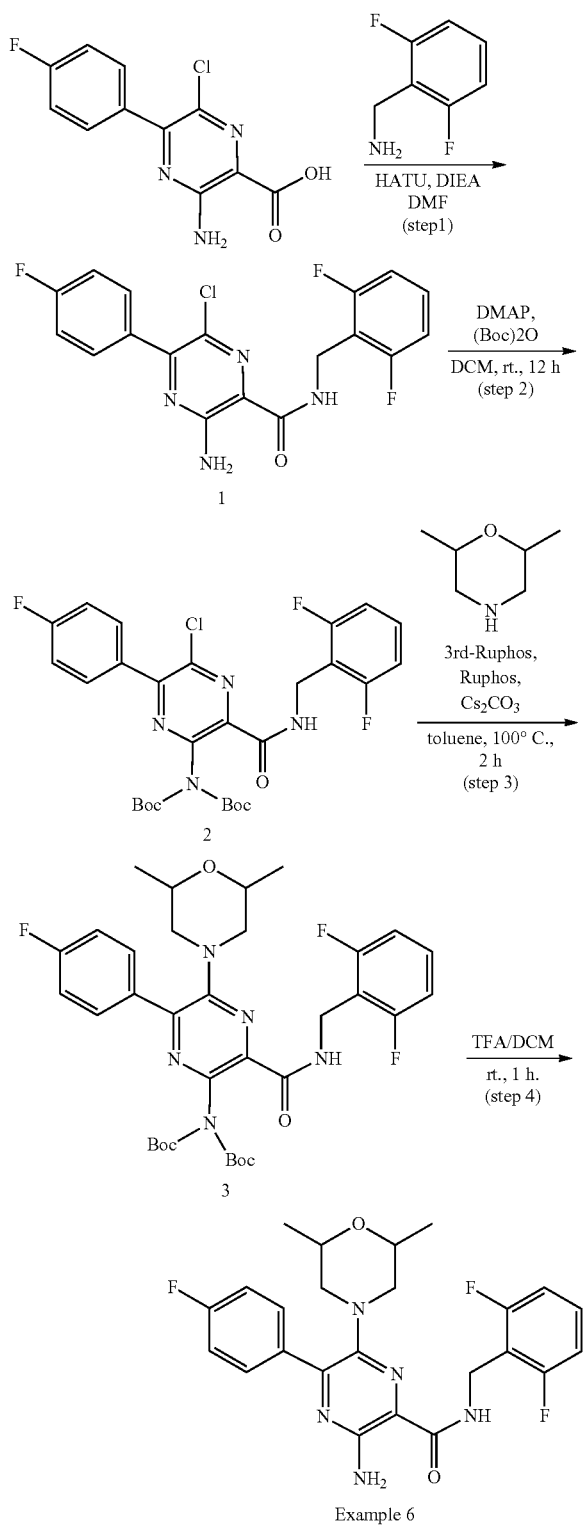

Example 6

Step 1. 3-amino-6-chloro-N-[(2,6-difluorophenyl)methyl]-5-(4-fluorophenyl)pyrazine-2-carboxamide A solution/mixture of 3-amino-6-chloro-5-(4-fluorophenyl)pyrazine-2-carboxylic acid (1.2 g, 4.48 mmol, 1 equiv) and 1-(2,6-difluorophenyl)methanamine (1.0 g, 6.99 mmol, 1.56 equiv) in DMF (25 mL) was stirred for 2 h at 15° C. under air atmosphere. The resulted mixture was washed with 3×10 Volume of water. The precipitated solids were collected by filtration and washed with ethyl ether (3×10 mL), to afford 3-amino-6-chloro-N-[(2,6-difluorophenyl)methyl]-5-(4-fluorophenyl)pyrazine-2-carboxamide (1.3 g, 73.82%) as a Brown yellow solid. LCMS: m/z (ESI), [M+H]$^+$=393.2.

Step 2. tert-butyl N-[(tert-butoxy)carbonyl]-N-(5-chloro-3-[[(2,6-difluorophenyl)methyl]carbamoyl]-6-(4-fluorophenyl)pyrazin-2-yl)carbamate Into a 40 mL sealed tube were added tert-butyl N-[(tert-butoxy)carbonyl]-N-(3-[[(2,6-difluorophenyl)methyl]carbamoyl]-5-(2,6-dimethylmorpholin-4-yl)-6-(4-methylphenyl)pyrazin-2-yl)carbamate (500 mg, 1.27 mmol, 1 equiv), DMAP (13 mg, 0.127 mmol, 0.1 equiv) and di-tert-butyl dicarbonate (687 mg, 3.18 mmol, 2.5 equiv) in DCM (30 mL) at room temperature. The resulting solution was stirred for 12 hours at room temperature. The resulted mixture was concentrated under reduced pressure.

The residue was purified by Prep-TLC (PE/EtOAc 1:2) to afford tert-butyl N-[(tert-butoxy)carbonyl]-N-(5-chloro-3-[[(2,6-difluorophenyl)methyl]carbamoyl]-6-(4-fluorophenyl)pyrazin-2-yl)carbamate (600 mg, 79%) as a yellow solid. LCMS: m/z (ESI), [M+H]$^+$=593.3

Step 3. Preparation of tert-butyl N-[(tert-butoxy)carbonyl]-N-(3-[[(2,6-difluorophenyl) methyl]carbamoyl]-5-(2,6-dimethylmorpholin-4-yl)-6-(4-fluorophenyl)pyrazin-2-yl) carbamate Into a 10 mL sealed tube were added tert-butyl N-[(tert-butoxy)carbonyl]-N-(5-chloro-3-[[(2,6-difluorophenyl)methyl]carbamoyl]-6-(4-fluorophenyl)pyrazin-2-yl)carbamate (230 mg, 0.39 mmol, 1 equiv), 2,6-dimethylmorpholine (134.0 mg, 1.16 mmol, 3 equiv), Cs$_2$CO$_3$ (252.7 mg, 0.78 mmol, 2 equiv), RuPhos (36.2 mg, 0.08 mmol, 0.2 equiv), RuPhos-Palladacycle Gen.3 (32.4 mg, 0.04 mmol, 0.1 equiv) and Toluene (15 mL) at 100° C. for 12h. The resulted mixture was concentrated under reduced pressure. The residue was purified by Prep-TLC (PE/EtOAc 1:2) to afford tert-butyl N-[(tert-butoxy)carbonyl]-N-(3-[[(2,6-difluorophenyl)methyl]carbamoyl]-5-(2,6-dimethylmorpholin-4-yl)-6-(4-fluorophenyl)pyrazin-2-yl)carbamate (30 mg, 11.51%) as a yellow solid. LCMS: m/z (ESI), [M-Boc+H]$^+$=572.3.

Step 4. 3-amino-N-(2,6-difluorobenzyl)-6-(2,6-dimethylmorpholino)-5-(4-fluorophenyl)pyrazine-2-carboxamide (Cmpd. 06)

Into a 50 mL round-bottom flask were added tert-butyl N-[(tert-butoxy)carbonyl]-N-(3-[[(2,6-difluorophenyl)methyl]carbamoyl]-5-(2,6-dimethylmorpholin-4-yl)-6-(4-methylphenyl)pyrazin-2-yl)carbamate (50 mg, 0.07 mmol, 1 equiv) and TFA (2 mL) in DCM (10 mL) at room temperature. The resulted mixture was concentrated under reduced pressure. The crude product (30 mg) was purified by Prep-HPLC with the following conditions (Column: XBridge Prep OBD C18 Column 19*250 mm, 5 um; Mobile Phase A: Water (10 MMOL/L NH₄HCOO₃+0.1% NH₃.H₂O), Mobile Phase B: ACN; Flow rate: 20 mL/min; Gradient: 78% B to 78% B in 7 min; 220/254 nm; Rt: 6.68 min) to afford 3-amino-N-[(2,6-difluorophenyl)methyl]-6-(2,6-dimethylmorpholin-4-yl)-5-(4-fluorophenyl) pyrazine-2-carboxamide (Cmpd. 06) (2 mg, 5.6%) as a yellow solid. LCMS: m/z (ESI), [M+H]⁺=472.3. H (300 MHz, DMSO-d₆) δ 1.08 (6H, s), 2.35 (2H, t), 3.03 (2H, d), 3.60 (2H, d), 4.60 (2H, d), 7.03-7.15 (4H, m), 7.29 (2H, t), 7.39 (1H, q), 8.07 (2H, t), 8.57 (1H, t).

Example 07. Preparation of N-[[3-amino-5-(4-fluorophenyl)-6-(1-methyl-6-oxo-1,6-dihydropyridin-3-yl)pyrazin-2-yl]methyl]-2-fluoro-6-(trifluoromethyl) benzamide (Cmpd. 07)

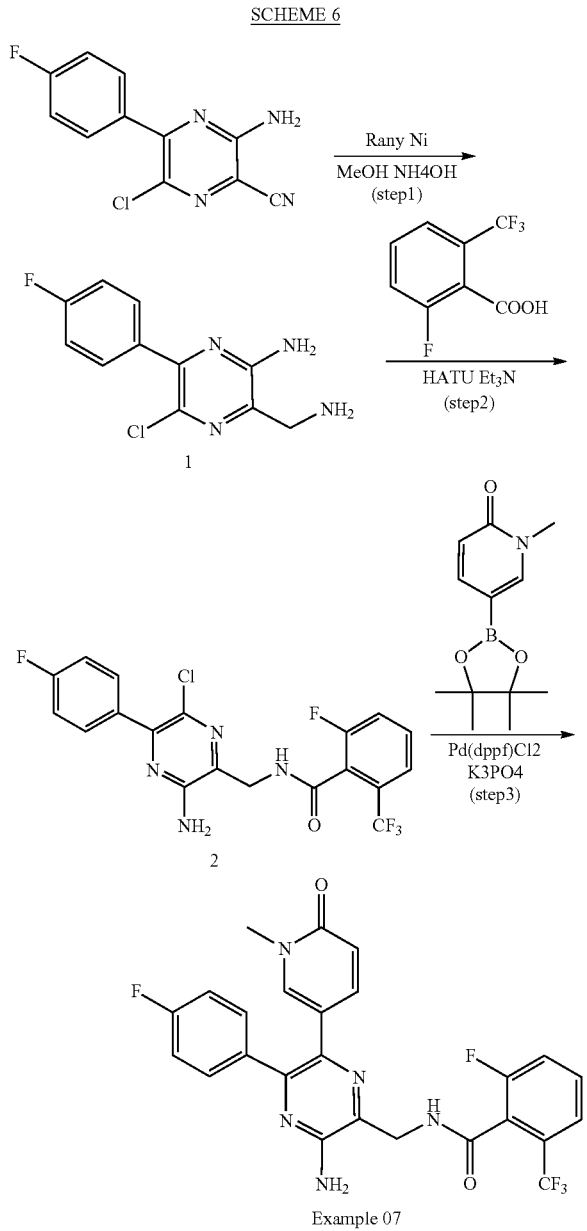

Example 07

Step 1. 3-(aminomethyl)-5-chloro-6-(4-fluorophenyl)pyrazin-2-amine

To a mixture of 3-amino-6-chloro-5-(4-fluorophenyl) pyrazine-2-carbonitrile (500 mg, 2.0 mmol, 1 equiv) in MeOH (100 mL), NH₄OH (2 mL) and Raney-Ni (10 mg, 0.1 mmol, 0.1 equiv) were added in portions. The mixture was stirred for 10 hours at room temperature under hydrogen atmosphere. The resulted mixture was filtered and the filtrate concentrated under reduced pressure. This resulted in 3-(aminomethyl)-5-chloro-6-(4-fluorophenyl)pyrazin-2-amine (560 mg, 87.1%) as a yellow solid. LCMS: m/z (ESI), [M+H]⁺=253.1.

Step 2. N-[[3-amino-6-chloro-5-(4-fluorophenyl) pyrazin-2-yl]methyl]-2-fluoro-6-(trifluoromethyl) benzamide To a mixture of 3-(aminomethyl)-5-chloro-6-(4-fluorophenyl)pyrazin-2-amine (210 mg, 0.8 mmol, 1 equiv) and 2-fluoro-6-(trifluoromethyl)benzoic acid (259.4 mg, 1.3 mmol, 1.5 equiv) in DCM (5 mL), HATU (632.0 mg, 1.7 mmol, 2 equiv) and Et₃N (252.3 mg, 2.5 mmol, 3 equiv) were added in portions. The mixture was stirred for 4 hours at room temperature under air atmosphere and quenched with water (10 mL). The resulted mixture was extracted with CH₂Cl2 (3×20 mL). The combined organic layers were washed with H₂O (3×10 mL), dried over anhydrous Na₂SO₄. After filtration, the filtrate was concentrated under reduced pressure. Then the residue was purified by Prep-TLC (PE/EtOAc 2:1) to afford N-[[3-amino-6-chloro-5-(4-fluorophenyl)pyrazin-2-yl]methyl]-2-fluoro-6-(trifluoromethyl)benzamide (457 mg, 49.7%) as a yellow solid. LCMS: m/z (ESI), [M+H]⁺=443.1.

Step 3. N-[[3-amino-5-(4-fluorophenyl)-6-(1-methyl-6-oxo-1,6-dihydropyridin-3-yl)pyrazin-2-yl] methyl]-2-fluoro-6-(trifluoromethyl)benzamide (Cmpd. 07)

To a mixture of N-[[3-amino-6-chloro-5-(4-fluorophenyl)pyrazin-2-yl]methyl]-2-fluoro-6-(trifluoromethyl)benzamide (90 mg, 200 mmol, 1 equiv) and 1-methyl-5-(4,4,5,5-tetramethyl-1,3,2-dioxaborolan-2-yl)-1,2-dihydropyridin-2-one (167.3 mg, 0.7 mmol, 3.5 equiv) in dioxane/H₂O (10 mL), Pd(dppf)Cl₂ (44.6 mg, 0.06 mmol, 0.30 equiv) and K₃PO₄ (258.9 mg, 1.2 mmol, 6.0 equiv) were added in portions under nitrogen atmosphere. The mixture was stirred for 10 hours at 110° C. under nitrogen atmosphere and concentrated under vacuum. The resulting residue was purified by Prep-TLC (PE/EtOAc 5:4) to afford the residue products then the crude product was purified by Prep-HPLC (Column: XBridge Prep OBD C18 Column 19*250 mm, 5 um; Mobile Phase A: Water (10 MMOL/L NH₄HCOO₃+ 0.1% NH₃.H₂O), Mobile Phase B: ACN; Flow rate: 20 mL/min; Gradient: 34% B to 54% B in 7 min; 220/254 nm; Rt: 7.08 min) to afford N-[[3-amino-5-(4-fluorophenyl)-6-(1-methyl-6-oxo-1,6-dihydropyridin-3-yl)pyrazin-2-yl] methyl]-2-fluoro-6-(trifluoromethyl)benzamide (Cmpd. 07) (29 mg, 27.1%) as a white solid. LCMS m/z (ESI) [M+H]⁺= 516.1. ¹H NMR (400 MHz, Methanol-d₄) δ 3.53 (s, 2H), 4.71 (s, 1H), 6.37 (d, J=9.4 Hz, 1H), 7.13 (t, J=8.8 Hz, 2H), 7.31 (dd, J=9.4, 2.6 Hz, 1H), 7.53 (dt, J=8.8, 6.0 Hz, 2H), 7.63 (d, J=7.6 Hz, 1H), 7.66-7.71 (m, 1H), 7.76 (d, J=2.5 Hz, 1H).

Example 08. Preparation of N-[[3-amino-6-(2,6-dimethylpyridin-4-yl)-5-(4-fluorophenyl)pyrazin-2-yl]methyl]pyridine-2-carboxamide (Cmpd. 08)

SCHEME 7

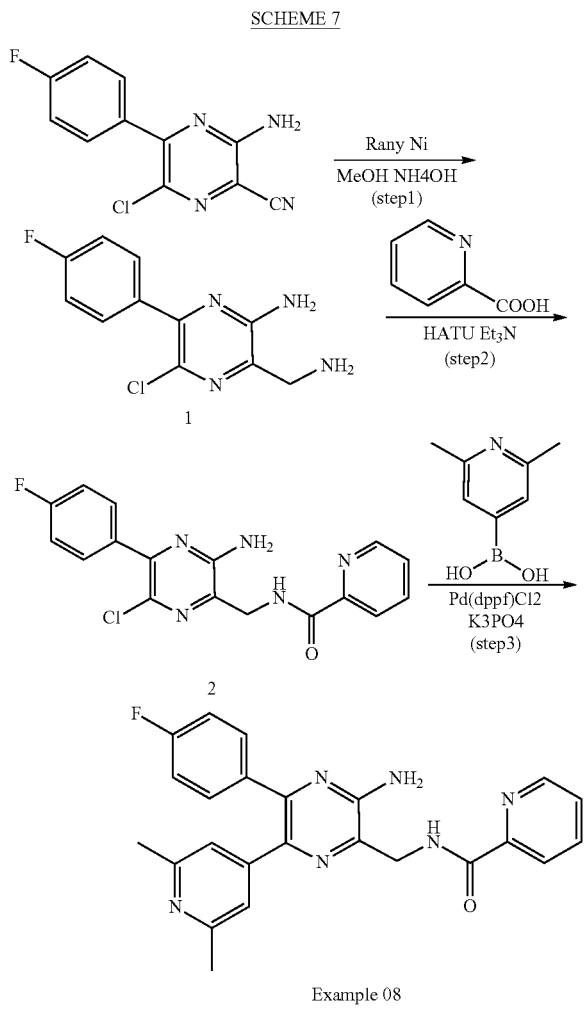

Example 08

Step 1. 3-(aminomethyl)-5-chloro-6-(4-fluorophenyl)pyrazin-2-amine

The 3-amino-6-chloro-5-(4-fluorophenyl)pyrazine-2-carbonitrile (500 mg, 2.0 mmol, 1 equiv) added into MeOH (100 mL), and NH₄OH (2 mL) was added, then the Raney-Ni (10 mg, 0.1 mmol, 0.1 equiv) slowly added into the above mixture and stirred for 10 hours at room temperature under hydrogen atmosphere. The resulted mixture was concentrated under reduced pressure. This resulted in 3-(aminomethyl)-5-chloro-6-(4-fluorophenyl)pyrazin-2-amine (560 mg, 87.1%) as a yellow solid. LCMS: m/z (ESI), $[M+H]^+ = 253.2$.

Step 2. N-[[3-amino-6-(2,6-dimethylpyridin-4-yl)-5-(4-fluorophenyl)pyrazin-2-yl]methyl]pyridine-2-carboxamide A mixture of 3-(aminomethyl)-5-chloro-6-(4-fluorophenyl)pyrazin-2-amine (45 mg, 0.2 mmol, 1 equiv) and pyridine-2-carboxylic acid (32.9 mg, 0.3 mmol, 1.5 equiv) and HAUT (135.4 mg, 0.4 mmol, 2.0 equiv) and TEA (60.9 mg, 0.5 mmol, 3.0 equiv) in DCM (3 mL) was stirred for 4 hours at room temperature under air atmosphere.

The resulted mixture was quenched with water (10 mL) and extracted with CH₂Cl₂ (3×20 mL). The combined organic layers were washed with H₂O (3×10 mL), dried over anhydrous Na₂SO₄. After filtration, the filtrate was concentrated under reduced pressure. Then the residue was purified by Prep-TLC (PE/EtOAc 1:2) to afford N-[[3-amino-6-chloro-5-(4-fluorophenyl)pyrazin-2-yl]methyl]pyridine-2-carboxamide (53 mg, 79.02%) as a yellow solid. LCMS: m/z (ESI), $[M+H]^+ = 358.2$.

Step 3. Preparation of N-[[3-amino-6-(2,6-dimethylpyridin-4-yl)-5-(4-fluorophenyl) pyrazin-2-yl]methyl]pyridine-2-carboxamide (Cmpd. 08)

To a mixture of N-[[3-amino-6-chloro-5-(4-fluorophenyl)pyrazin-2-yl]methyl]pyridine-2-carboxamide (25 mg, 0.1 mmol, 1 equiv) and (2,6-dimethylpyridin-4-yl)boronic acid (16.2 mg, 0.1 mmol, 1.5 equiv) in dioxane/H₂O (2.0 mL), Pd(dppf)Cl₂ (5.1 mg, 0.01 mmol, 0.1 equiv) and K₃PO₄ (44.5 mg, 0.21 mmol, 3 equiv) were added under nitrogen atmosphere. The mixture was stirred for 10 hours at 90° C. under nitrogen atmosphere. The residue was purified by Prep-TLC (PE/EtOAc 1:1) to afford the residue products then the crude product was purified by Prep-HPLC (Column: XBridge Prep OBD C18 Column 19*250 mm, 5 um; Mobile Phase A: Water (10 MMOL/L NH₄HCO₃+0.1% NH₃.H₂O), Mobile Phase B: ACN; Flow rate: 20 mL/min; Gradient: 36% B to 64% B in 7 min; 220/254 nm; Rt: 6.97 min) to afford N-[[3-amino-6-(2,6-dimethylpyridin-4-yl)-5-(4-fluorophenyl)pyrazin-2-yl]methyl]pyridine-2-carboxamide (Cmpd. 08) (6.7 mg, 9.4%) as a white solid. LCMS m/z (ESI) $[M+H]^+ = 429.2$. ¹H NMR (400 MHz, Methanol-d₄) δ 2.37 (s, 4H), 4.74 (s, 1H), 7.01-7.20 (m, 2H), 7.43 (s, 1H), 7.60 (s, 1H), 8.02 (d, J=7.9 Hz, 1H), 8.18 (d, J=7.8 Hz, 1H), 8.69 (s, 1H).

Example 09. Preparation of 3-amino-N-[[6-(dimethylamino)pyridin-2-yl]methyl]-6-(2,6-dimethylpyridin-4-yl)-5-(4-fluorophenyl)pyrazine-2-carboxamide (Cmpd. 09)

SCHEME 8

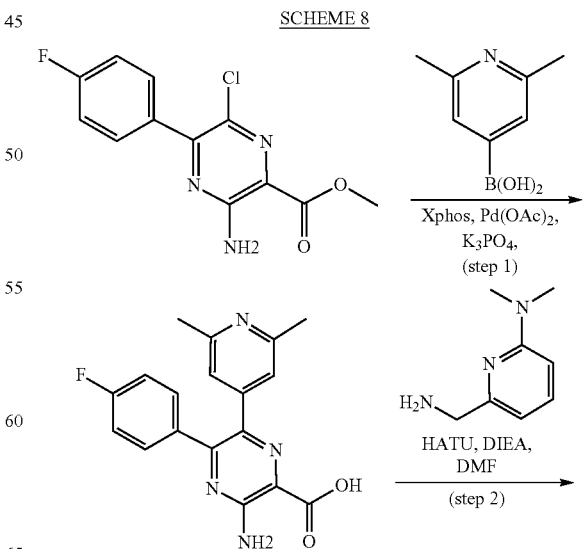

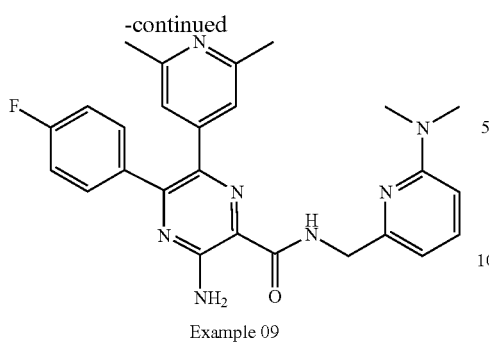

Example 09

Step 1. 3-amino-6-(2,6-dimethylpyridin-4-yl)-5-(4-fluorophenyl)pyrazine-2-carboxylic Acid To a solution of methyl 3-amino-6-chloro-5-(4-fluorophenyl)pyrazine-2-carboxylate (1 g, 3.55 mol, 1 equiv) and (2,6-dimethylpyridin-4-yl)boronic acid (1.1 g, 7.3 mol, 2.1 equiv) in n-BuOH (25 mL) were added x-Phos (0.3 g, 0.7 mmol, 0.2 equiv) and Pd(OAc)$_2$ (0.2 g, 0.7 mmol, 0.2 equiv), K$_3$PO$_4$ (301.4 mg, 1.42 mmol, 2 equiv) under nitrogen atmosphere. The mixture was stirring for 2 h at 100° C. under a nitrogen atmosphere. The resulted mixture was concentrated under reduced pressure. The residue was purified by Prep-TLC (CH$_2$Cl$_2$/MeOH 10:1) to afford 3-amino-6-(2,6-dimethylpyridin-4-yl)-5-(4-fluorophenyl)pyrazine-2-carboxylic acid (400 mg, 33.30%) as a yellow solid. LCMS: m/z (ESI), [M+H]$^+$=339.0.

Step 2. 3-amino-N-[[6-(dimethylamino)pyridin-2-yl]methyl]-6-(2,6-dimethylpyridin-4-yl)-5-(4-fluorophenyl)pyrazine-2-carboxamide (Cmpd. 09)

To a solution of 3-amino-6-(2,6-dimethylpyridin-4-yl)-5-(4-fluorophenyl)pyrazine-2-carboxylic acid (150 mg, 0.4 mmol, 1 equiv), 6-(aminomethyl)-N,N-dimethylpyridin-2-amine (134.1 mg, 0.9 mmol, 2.0 equiv), HATU (337.1 mg, 0.9 mmol, 2 equiv) in DMF (5 mL) was added DIEA (171.9 mg, 1.3 mmol, 3 equiv) dropwise over 1 min at 15° C. The resulted mixture was stirred for additional 2 h at 15° C. The resulted mixture was concentrated under reduced pressure. The crude product (150 mg) was purified by Prep-HPLC with the following conditions (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 49% B to 69% B in 7 min; 254/220 nm; Rt: 5.8 min) to afford 3-amino-N-[[6-(dimethylamino)pyridin-2-yl]methyl]-6-(2,6-dimethylpyridin-4-yl)-5-(4-fluorophenyl)pyrazine-2-carboxamide (Cmpd. 09) (39.0 mg, 18.6%) as a light yellow solid. LCMS: m/z (ESI), [M+H]$^+$= 472.3, $^1$H NMR (400 MHz, DMSO-d$_6$) δ2.33 (s, 6H), 2.97 (s, 6H), 4.48 (d, J=5.6 Hz, 2H), 6.52 (dd, J=10.2, 7.9 Hz, 2H), 6.99 (s, 2H), 7.16-7.26 (m, 2H), 7.37-7.51 (m, 3H), 9.20 (t, J=5.7 Hz, 1H).

Example 11. Preparation of 3-amino-6-(1-methyl-6-oxo-1,6-dihydropyridin-3-yl)-5-(oxazol-2-yl)-N-((3-(trifluoromethyl) pyridin-2-yl)methyl)pyrazine-2-carboxamide (Cmpd. 11)

SCHEME 9

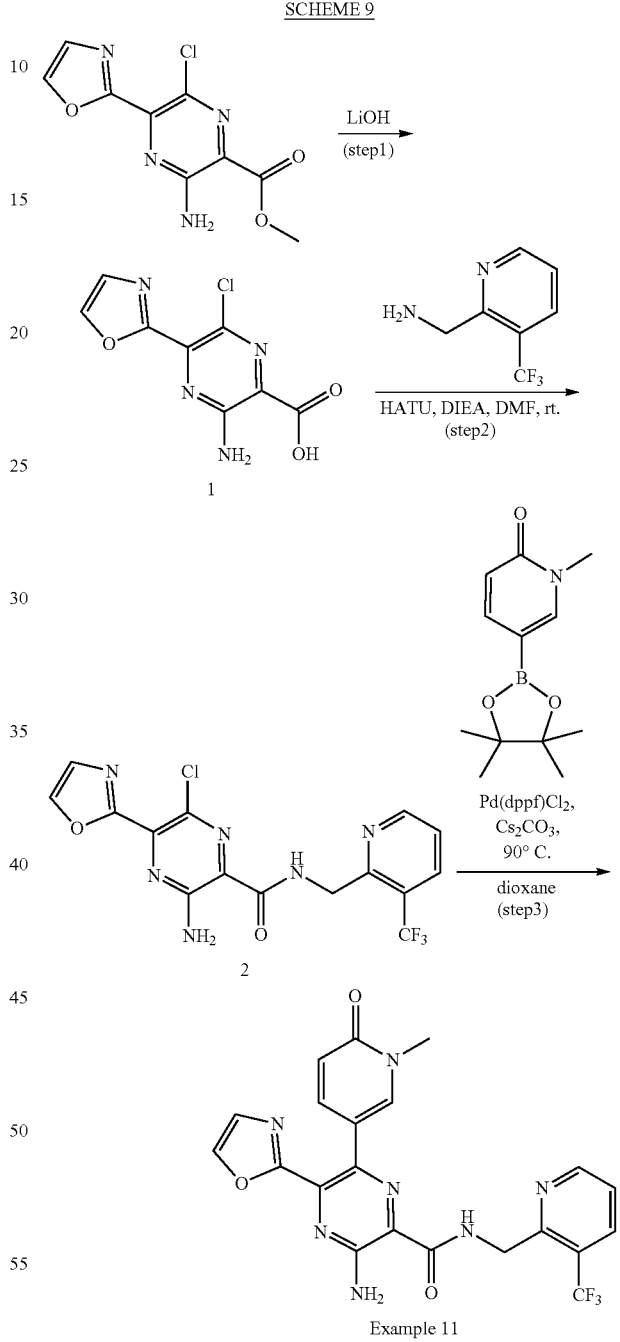

Example 11

Step 1. 3-amino-6-chloro-5-(1,3-oxazol-2-yl)pyrazine-2-carboxylic Acid

To a solution of methyl 3-amino-6-chloro-5-(1,3-oxazol-2-yl)pyrazine-2-carboxylate (400 mg, 1.57 mmol, 1 equiv) in MeOH (2 mL) and THF (8 mL) was added LiOH.H$_2$O (131.8 mg, 3.14 mmol, 2 equiv). The resulted mixture was stirred for 2h at 40° C. under nitrogen atmosphere. The mixture was adjusted to pH=8 with HCl.H$_2$O. The solvent was removed under reduced pressure. The residue afford 3-amino-6-chloro-5-(1,3-oxazol-2-yl)pyrazine-2carboxylic acid (350 mg, 92.6%) as a yellow solid. LCMS: m/z (ESI), [M+H]$^+$=241.1, $^1$H NMR: (300 MHz, DMSO-d$_6$) δ 7.60 (s, 1H), 7.76 (s, 2H), 8.44 (s, 1H), 13.68 (s, 1H).

Step 2. 3-amino-6-chloro-5-(1,3-oxazol-2-yl)-N-[[3-(trifluoromethyl)pyridin-2-yl]methyl]pyrazine-2-carboxamide A solution of 3-amino-6-chloro-5-(1,3-oxazol-2-yl)pyrazine-2-carboxylic acid (150 mg, 0.62 mmol, 1 equiv) in DCM (15 mL) was added 1-[3-(trifluoromethyl)pyridin-2-yl]methanamine (219.6 mg, 1.25 mmol, 2 equiv), HOBT (168.5 mg, 1.25 mmol, 2 equiv) and EDC.HCl (239.0 mg, 1.25 mmol, 2 equiv) in portions for 5 min at room temperature. The resulted mixture was stirred for 2h at room temperature under air atmosphere. The solvent was removed under reduced pressure. The residue was purified by Prep-TLC (PE/EtOAc 1:1) to afford 3-amino-6-chloro-5-(1,3-oxazol-2-yl)-N-[[3-(trifluoromethyl)pyridin-2-yl]methyl]pyrazine-2-carboxamide (20 mg, 8.1%) as a yellow solid. LCMS: m/z (ESI), [M+H]$^+$=399.1; $^1$H NMR: (300 MHz, MeOD) δ 4.93 (s, 2H), 7.53 (d, 2H), 8.19 (m, 2H), 8.83 (d, 1H).

Step 3. 3-amino-6-(1-methyl-6-oxo-1,6-dihydropyridin-3-yl)-5-(1,3-oxazol-2-yl)-N-[[3-(trifluoromethyl)pyridin-2-yl]methyl]pyrazine-2-carboxamide (Cmpd. 11)

To a mixture of 3-amino-6-chloro-5-(1,3-oxazol-2-yl)-N-[[3-(trifluoromethyl) pyridin-2-yl]methyl]pyrazine-2-carboxamide (20 mg, 0.05 mmol, 1 equiv) and 1-methyl-5-(4,4,5,5-tetramethyl-1,3,2-dioxaborolan-2-yl)-1,2-dihydropyridin-2-one (23.6 mg, 0.10 mmol, 2.00 equiv) in 1,4-dioxane (5 mL), Pd(dppf)Cl$_2$ (7.3 mg, 0.01 mmol, 0.20 equiv) and Cs$_2$CO$_3$ (32.7 mg, 0.10 mmol, 2 equiv) were added in portions. The mixture was stirred for 5 min at room temperature under nitrogen atmosphere. The resulted mixture was stirred for 2h at 90° C. under nitrogen atmosphere and concentrated under vacuum. The crude product (40 mg) was purified by Prep-HPLC with the following conditions (Column: XBridge Prep C18 OBD Column, 5 um, 19*150 mm; Mobile Phase A: Water (10 MMOL/L NH$_4$HCO$_3$+ 0.1% NH$_3$.H$_2$O), Mobile Phase B: ACN; Flow rate: 20 mL/min; Gradient: 30% B to 40% B in 7 min; 254, 220 nm; Rt: 6.55 min) to afford 3-amino-6-(1-methyl-6-oxo-1,6-dihydropyridin-3-yl)-5-(1,3-oxazol-2-yl)-N-[[3-(trifluoromethyl)pyridin-2-yl]methyl]pyrazine-2-carboxamide (Cmpd. 11) (2 mg, 8.5%) as a yellow solid. LCMS: m/z (ESI), [M+H]$^+$=472.3, $^1$H NMR: (300 MHz, MeOD) δ 3.66 (s, 3H), 4.95 (s, 2H), 6.55 (d, 1H), 7.39 (d, 1H), 7.54 (m, 2H), 8.07 (m, 2H), 8.19 (d, 1H), 8.79 (d, 1H).

Example 13. Preparation of 3-amino-N-[[6-(dimethylamino)pyridin-2-yl]methyl]-5-(4-fluorophenyl)-6-(1-methyl-6-oxo-1,6-dihydropyridin-3-yl)pyrazine-2-carboxamide (Cmpd. 13)

SCHEME 10

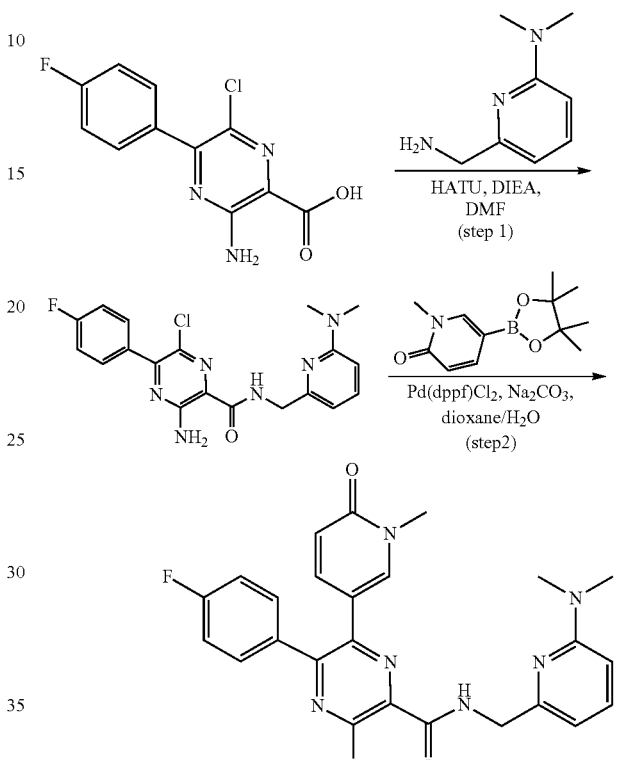

Example 13

Step 1. Preparation of 3-amino-N-[[6-(dimethylamino)pyridin-2-yl]methyl]-5-(4-fluorophenyl)-6-(1-methyl-6-oxo-1,6-dihydropyridin-3-yl)pyrazine-2-carboxamide To a stirred mixture of 3-amino-6-chloro-5-(4-fluorophenyl)pyrazine-2-carboxylic acid (350 mg, 1.308 mmol, 1 equiv) and 6-(aminomethyl)-N,N-dimethylpyridin-2-amine (296.62 mg, 1.962 mmol, 1.5 equiv) in DMF (20 mL) was added HATU (994.47 mg, 2.615 mmol, 2 equiv) and DIEA (338.03 mg, 2.615 mmol, 2 equiv) in portions at 15° C. under air atmosphere. The resulted mixture was stirred for 3 hours and quenched with 50 mL of water. The resulting solid was collected by filtration and dried under reduced pressure to afford 3-amino-6-chloro-N-[[6-(dimethylamino)pyridin-2-yl]methyl]-5-(4-fluorophenyl)pyrazine-2-carboxamide (300 mg, 57.23%) as a light yellow solid. LCMS: m/z (ESI), [M+H]$^+$=401.2.

Step 2. Preparation of 3-amino-N-[[6-(dimethylamino)pyridin-2-yl]methyl]-5-(4-fluorophenyl)-6-(1-methyl-6-oxo-1,6-dihydropyridin-3-yl)pyrazine-2-carboxamide (Cmpd. 13)

To a solution of 3-amino-6-chloro-N-[[6-(dimethylamino) pyridin-2-yl]methyl]-5-(4-fluorophenyl)pyrazine-2-carboxamide (50 mg, 0.12 mmol, 1 equiv) and (1-methyl-6-oxo-1,6-dihydropyridin-3-yl)boronic acid (28.6 mg, 0.19 mmol, 1.50 equiv) in water (0.2 mL) and dioxane (1.8 mL) were added Cs$_2$CO$_3$ (81.3 mg, 0.25 mmol, 2 equiv) and Pd(dppf)Cl$_2$ (9.1 mg, 0.01 mmol, 0.1 equiv) under nitrogen atmosphere, the resulted mixture was stirred for 2 h at 90° C. under a nitrogen atmosphere and concentrated under reduced pressure. The crude product (50 mg) was purified by Prep-HPLC with the following conditions (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 40% B to 48% B in 7 min; 254/220 nm; Rt: 5.37 min) to afford 3-amino-N-[[6-(dimethylamino)pyridin-2-yl]methyl]-5-(4-fluorophenyl)-6-(1-methyl-6-oxo-1,6-dihydropyridin-3-yl)pyrazine-2-carboxamide (Cmpd. 13) (12 mg, 20.3%) as a light yellow solid. LCMS: m/z (ESI), [M+H]$^+$=474.2, $^1$H NMR (400 MHz, DMSO-d$_6$) δ 3.0 (s, 5H), 3.4 (s, 2H), 4.5 (d, J=5.9 Hz, 1H), 6.2 (d, J=9.3 Hz, 1H), 6.4-6.5 (m, 1H), 7.3 (t, J=8.8 Hz, 1H), 7.5 (t, J=7.9 Hz, 1H), 7.5 (t, J=7.1 Hz, 2H), 7.9 (d, J=2.5 Hz, 1H), 9.3 (s, 1H).

Compounds listed in the table below were prepared using methods described in Cmpd. 13.

| Example/Cmpd number | Structure | LCMS [M + H]$^+$ | $^1$H NMR |
|---|---|---|---|
| 12 | 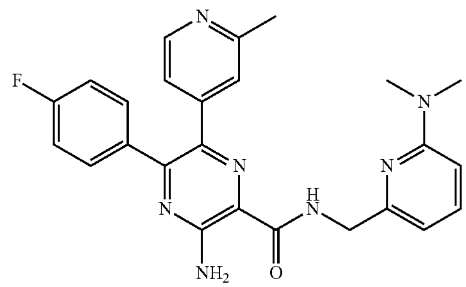 [SMILES: Cc1cc(-c2nc(C(=O)NCc3cccc(N(C)C)n3)c(N)nc2-c2ccc(F)cc2)ccn1] | 458.3 | $^1$H NMR (400 MHz, DMSO-d$_6$) δ 2.4 (s, 3H), 2.9 (s, 5H), 4.5 (d, J = 5.6 Hz, 2H), 6.5 (dd, J = 11.1, 7.8 Hz, 2H), 7.0 (d, J = 5.2 Hz, 1H), 7.2 (t, J = 8.7 Hz, 2H), 7.3 (s, 1H), 7.4-7.5 (m, 3H), 8.3 (d, J = 5.3 Hz, 1H), 9.2 (s, 1H). |

Example 14. Preparation of 3-amino-N-((3-fluoropyridin-2-yl)methyl)-6-(1-methyl-6-oxo-1,6-dihydropyridin-3-yl)-5-(oxazol-2-yl)pyrazine-2-carboxamide (Cmpd. 14)

SCHEME 11

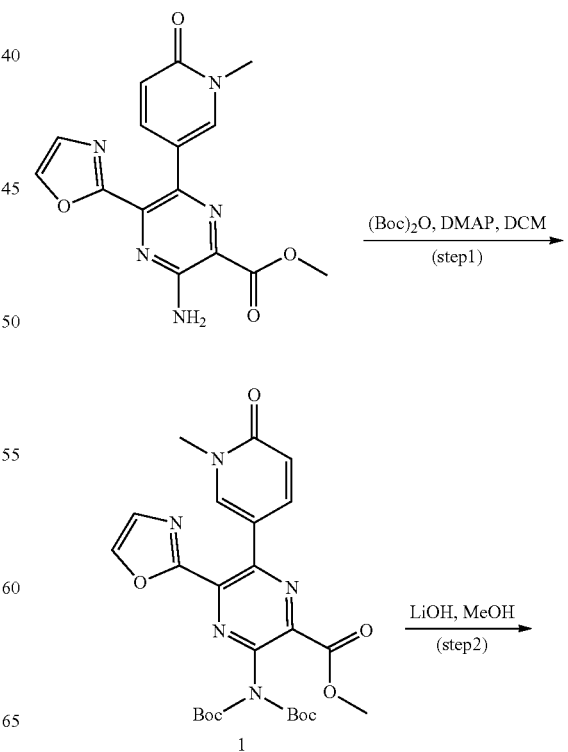

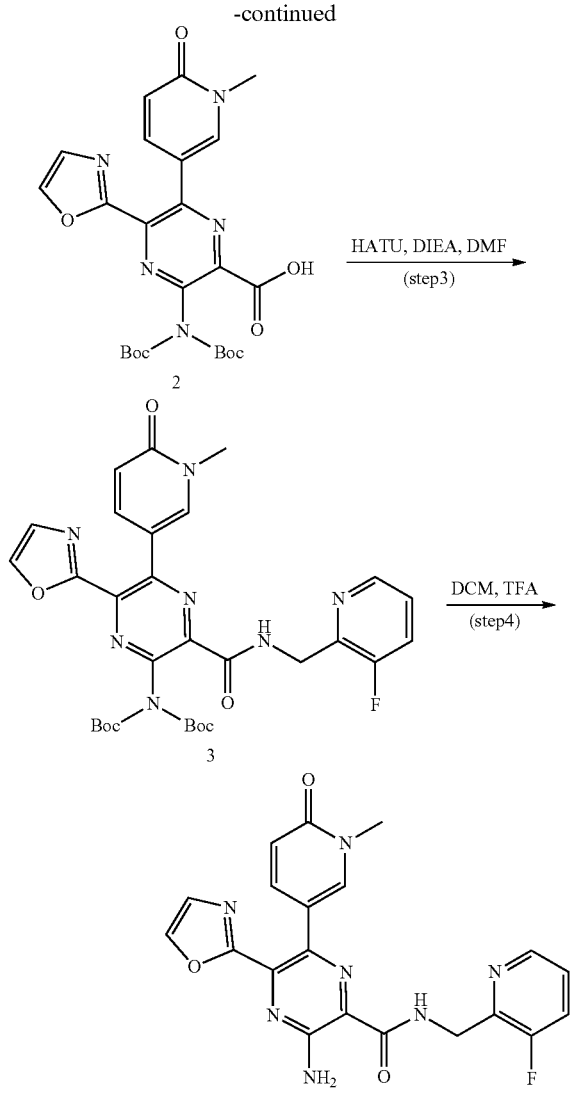

Example 14

Step 1. methyl 3-((ditert-butoxycarbonyl)amino)-6-(1-methyl-6-oxo-1,6-dihydropyridin-3-yl)-5-(oxazol-2-yl)pyrazine-2-carboxylate To a stirred mixture of methyl 3-amino-6-(1-methyl-6-oxo-1,6-dihydropyridin-3-yl)-5-(1,3-oxazol-2-yl)pyrazine-2-carboxylate (80 mg, 0.2 mmol, 1 equiv) and (Boc)$_2$O (160.0 mg, 0.7 mmol, 3.0 equiv) in DCM (2 mL) were added DMAP (5.97 mg, 0.049 mmol, 0.2 equiv) in portions at room temperature under air atmosphere. The resulted mixture was stirred for additional 2 h at room temperature. The resulted mixture was concentrated under reduced pressure. The residue was purified by Prep-TLC (DCM/MeOH 20:1) to afford methyl 3-[bis[(tert-butoxy)carbonyl]amino]-6-(1-methyl-6-oxo-1,6-dihydropyridin-3-yl)-5-(1,3-oxazol-2-yl)pyrazine-2-carboxylate (84 mg, 65.2%) as a light yellow oil. LCMS: m/z (ESI), [M+H]$^+$=528.

Step 2. 3-((ditert-butoxycarbonyl)amino)-6-(1-methyl-6-oxo-1,6-dihydropyridin-3-yl)-5-(oxazol-2-yl)pyrazine-2-carboxylic Acid To a stirred mixture of methyl 3-[bis[(tert-butoxy)carbonyl]amino]-6-(1-methyl-6-oxo-1,6-dihydropyridin-3-yl)-5-(1,3-oxazol-2-yl)pyrazine-2-carboxylate (84 mg, 0.2 mmol, 1 equiv) in MeOH (5 mL), LiOH (7.6 mg, 0.3 mmol, 2 equiv) was added in portions at room temperature under air atmosphere. The resulted mixture was stirred for additional 1 h at 50° C. The mixture was allowed to cool down to room temperature. The resulted mixture was concentrated under reduced pressure.

The residue was purified by Prep-TLC (DCM/MeOH 20:1) to afford 3-[bis[(tert-butoxy)carbonyl]amino]-6-(1-methyl-6-oxo-1,6-dihydropyridin-3-yl)-5-(1,3-oxazol-2-yl)pyrazine-2-carboxylic acid (75 mg, 91.7%) as a yellow solid. LCMS: m/z (ESI), [M+H]$^+$=514.1.

Step 3. ditert-butyl (3-(((3-fluoropyridin-2-yl)methyl)carbamoyl)-5-(1-methyl-6-oxo-1,6-dihydropyridin-3-yl)-6-(oxazol-2-yl)pyrazin-2-yl)carbamate To a stirred mixture of 3-[bis[(tert-butoxy)carbonyl]amino]-6-(1-methyl-6-oxo-1,6-dihydropyridin-3-yl)-5-(1,3-oxazol-2-yl)pyrazine-2-carboxylic acid (81 mg, 0.16 mmol, 1 equiv) and 1-(3-fluoropyridin-2-yl)methanamine (39.8 mg, 0.3 mmol, 2.0 equiv) in DMF (2 mL) were added HATU (120.0 mg, 0.3 mmol, 2 equiv) and DIEA (61.2 mg, 0.47 mmol, 3 equiv) in portions at room temperature under air atmosphere. The resulted mixture was stirred for additional 6 h at room temperature. The resulted mixture was quenched with water (20 mL) and extracted with EtOAc (3×50 mL). The combined organic layers were washed with water (3×50 mL), dried over anhydrous Na$_2$SO$_4$. After filtration, the filtrate was concentrated under reduced pressure. This resulted in tert-butyl N-[(tert-butoxy)carbonyl]-N-(3-[[(3-fluoropyridin-2-yl)methyl]carbamoyl]-5-(1-methyl-6-oxo-1,6-dihydropyridin-3-yl)-6-(1,3-oxazol-2-yl)pyrazin-2-yl)carbamate (80 mg, 81.6%) as a yellow solid which was used in the next step directly without further purification. LCMS: m/z (ESI), [M-Boc+H]$^+$=522.3.

Step 4. 3-amino-N-((3-fluoropyridin-2-yl)methyl)-6-(1-methyl-6-oxo-1,6-dihydropyridin-3-yl)-5-(oxazol-2-yl)pyrazine-2-carboxamide (Cmpd. 14)

To a stirred solution/mixture of tert-butyl N-[(tert-butoxy)carbonyl]-N-(3-[[(3-fluoropyridin-2-yl)methyl]carbamoyl]-5-(1-methyl-6-oxo-1,6-dihydropyridin-3-yl)-6-(1,3-oxazol-2-yl)pyrazin-2-yl)carbamate (70 mg, 0.11 mmol, 1 equiv) and TFA (2 mL) in DCM (2 mL) were added in portions at room temperature under air atmosphere. The resulted mixture was stirred for additional 0.5 h at room temperature. The resulted mixture was concentrated under reduced pressure. The residue was dissolved in MeOH (4 mL). NH$_3$.H$_2$O (4 mL) were added in portions at room temperature under air atmosphere. The resulted mixture was concentrated under reduced pressure. The residue was dissolved in MeOH (4 mL). The residue was purified by Prep-TLC (DCM/MeOH 20:1) to afford 3-amino-N-[(3-fluoropyridin-2-yl)methyl]-6-(1-methyl-6-oxo-1,6-dihydropyridin-3-yl)-5-(1,3-oxazol-2-yl)pyrazine-2-carboxamide (Cmpd. 14) (22 mg, 45.9%) as a yellow solid. LCMS: m/z (ESI), [M+H]$^+$=422.2. $^1$H NMR (DMSO-d$_6$, 400 MHz) δ 3.5 (3H, s), 4.7 (2H, dd), 6.3 (1H, d), 7.3-7.5 (3H, m), 7.7-7.9 (3H, m), 8.0 (1H, d), 8.3 (1H, s), 8.4 (1H, dt), 9.3 (1H, t).

Example 15. Preparation of 3-amino-N-[[6-(dimethylamino)pyridin-2-yl]methyl]-6-(1-methyl-6-oxo-1,6-dihydropyridin-3-yl)-5-(1,3-oxazol-2-yl)pyrazine-2-carboxamide (Cmpd. 15)

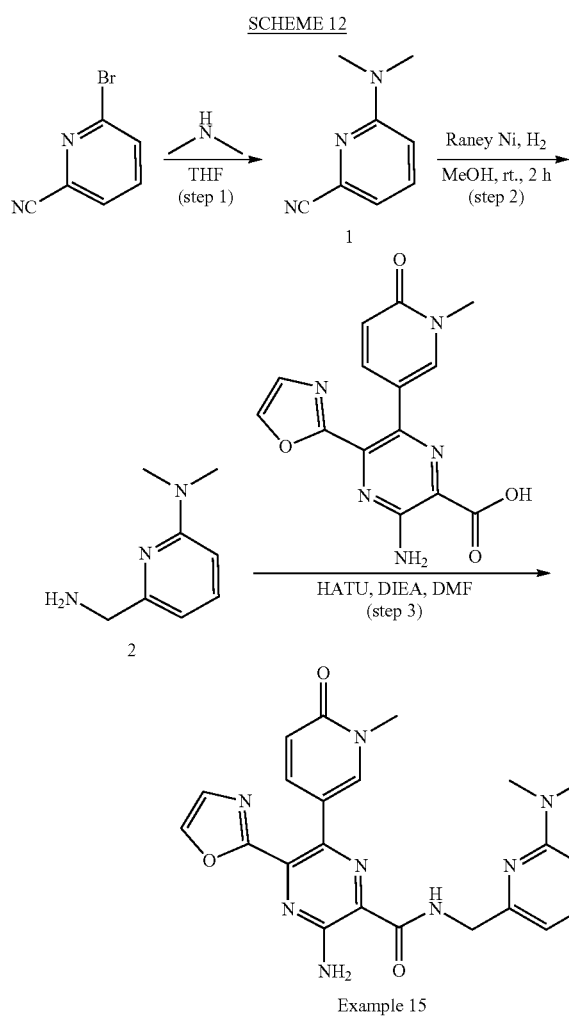

Step 1. 6-(dimethylamino)pyridine-2-carbonitrile

To a solution of 6-bromopyridine-2-carbonitrile (2 g, 10.9 mmol, 1 equiv) in THF (25 mL), dimethylamine (3.0 g, 65.6 mmol, 6 equiv) was added. The solution was stirred for 12 h at 80° C. under air atmosphere. The resulted mixture was concentrated under reduced pressure. The residue was purified by silica gel column chromatography, eluted with PE/EtOAc (5:1) to afford 6-(dimethylamino)pyridine-2-carbonitrile (1.1 g, 68.4%) as a light yellow solid. LCMS: m/z (ESI), $[M+H]^+=148.2$

Step 2. 6-(aminomethyl)-N,N-dimethylpyridin-2-amine

To a mixture of 6-(dimethylamino)pyridine-2-carbonitrile (1.1 g, 7.5 mmol, 1 equiv) in MeOH (50 mL), $NH_3 \cdot H_2O$ (0.3 g, 7.5 mmol, 1 equiv) was added Raney Ni (64.03 mg, 0.747 mmol, 0.10 equiv) at room temperature. The mixture was stirred for 30 min at 20° C. under hydrogen atmosphere. The resulted mixture was filtered and the filtrate was concentrated under reduced pressure to afford 6-(aminomethyl)-N,N-dimethylpyridin-2-amine (1 g, 88.5%) as a yellow oil. LCMS: m/z (ESI), $[M+H]^+=152.2$.

Step 3. 3-amino-N-[[6-(dimethylamino)pyridin-2-yl]methyl]-6-(1-methyl-6-oxo-1,6-dihydropyridin-3-yl)-5-(1,3-oxazol-2-yl)pyrazine-2-carboxamide (Cmpd. 15)

To a mixture of 3-amino-6-(1-methyl-6-oxo-1,6-dihydropyridin-3-yl)-5-(1,3-oxazol-2-yl)pyrazine-2-carboxylic acid (100 mg, 0.32 mmol, 1 equiv) and 6-(aminomethyl)-N,N-dimethylpyridin-2-amine (72.4 mg, 0.48 mmol, 1.5 equiv) in DMF (3 mL), HATU (243 mg, 0.64 mmol, 2 equiv) and DIEA (118 mg, 0.96 mmol, 3 equiv) were added in portions at room temperature. The mixture was stirred for 10 min at 15° C. under air atmosphere. The precipitated solids were collected by filtration and washed with water (3×10 mL). The resulting solid was dried under infrared light to afford 3-amino-N-[[6-(dimethylamino)pyridin-2-yl]methyl]-6-(1-methyl-6-oxo-1,6-dihydropyridin-3-yl)-5-(1,3-oxazol-2-yl)pyrazine-2-carboxamide (Cmpd. 15) (66.1 mg, 46.4%) as a light yellow solid. LCMS: m/z (ESI), $[M+H]^+=447.2$. $^1$H NMR (400 MHz, DMSO-$d_6$) δ 2.9 (s, 5H), 3.3 (s, 2H), 4.4 (d, J=5.7 Hz, 2H), 6.3 (d, J=9.3 Hz, 1H), 6.5 (dd, J=9.2, 7.9 Hz, 2H), 7.3-7.4 (m, 2H), 7.46 (dd, J=8.5, 7.3 Hz, 1H), 7.8 (s, 1H), 8.0 (d, J=2.6 Hz, 1H), 8.3 (d, J=0.8 Hz, 1H), 9.3 (t, J=5.7 Hz, 1H).

Example 16. Preparation of 3-amino-N-((3-(dimethylamino)pyridin-2-yl)methyl)-6-(1-methyl-6-oxo-1,6-dihydropyridin-3-yl)-5-(oxazol-2-yl)pyrazine-2-carboxamide (Cmpd. 16)

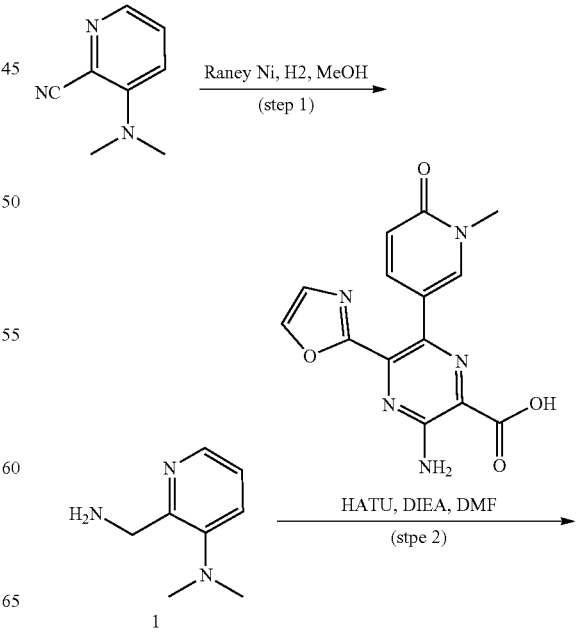

213

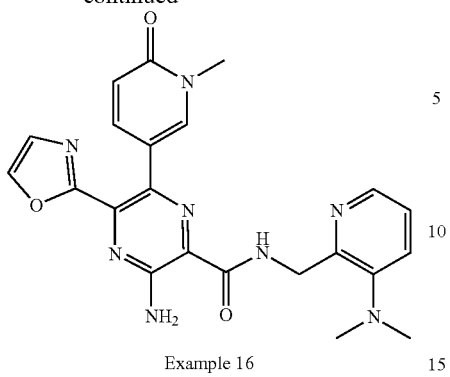

Example 16

Step 1. 2-(aminomethyl)-N,N-dimethylpyridin-4-amine

To a solution of 4-(dimethylamino)pyridine-2-carbonitrile (200 mg, 1.4 mmol, 1 equiv) in MeOH (5 mL), NH$_3$.H$_2$O (0.1 mL, 2.6 mmol, 1.9 equiv) was added. The resulted mixture was stirred for 30 min at 15° C. under hydrogen atmosphere. The resulted mixture was filtered, the filtrate was concentrated under reduced pressure to afford 2-(aminomethyl)-N,N-dimethylpyridin-4-amine (190 mg, 92.5%) as a brown solid. LCMS: m/z (ESI), [M+H]$^+$=152.2.

Step 2. 3-amino-N-((3-(dimethylamino)pyridin-2-yl)methyl)-6-(1-methyl-6-oxo-1,6-dihydropyridin-3-yl)-5-(oxazol-2-yl)pyrazine-2-carboxamide (Cmpd. 16)

To a mixture of 3-amino-6-(1-methyl-6-oxo-1,6-dihydropyridin-3-yl)-5-(1,3-oxazol-2-yl)pyrazine-2-carboxylic acid (100 mg, 0.32 mmol, 1 equiv) and 2-(aminomethyl)-N,N-dimethylpyridin-3-amine (72.4 mg, 0.48 mmol, 1.5 equiv) in DMF (5 mL), HATU (242.7 mg, 0.64 mmol, 2 equiv) and DIEA (165.12 mg, 1.28 mmol, 4 equiv) were added in portions. The mixture was stirred for 60 min at 15° C. under air atmosphere and quenched with water (15 mL). The precipitated solids were collected by filtration and washed with water (3×100 mL). The resulted mixture was concentrated under vacuum to afford 3-amino-N-((3-(dimethylamino)pyridin-2-yl)methyl)-6-(1-methyl-6-oxo-1,6-dihydropyridin-3-yl)-5-(oxazol-2-yl)pyrazine-2-carboxamide (Cmpd. 16) (50.6 mg, 35.5%) as a yellow solid. LCMS: m/z (ESI), [M+H]$^+$=447.2, H NMR (400 MHz, Methanol-d$_4$) δ −0.05 (s, 1H), 1.2 (s, 1H), 2.7 (s, 6H), 3.3 (s, 3H), 4.7 (d, J=5.5 Hz, 2H), 6.3 (d, J=9.4 Hz, 1H), 7.3 (dd, J=8.1, 4.7 Hz, 1H), 7.3-7.4 (m, 2H), 7.5 (dd, J=8.1, 1.5 Hz, 1H), 7.8 (s, 1H), 8.0 (d, J=2.6 Hz, 1H), 8.2 (dd, J=4.7, 1.5 Hz, 1H), 8.3 (d, J=0.7 Hz, 1H), 9.3 (t, J=5.5 Hz, 1H).

214

Example 17. Preparation of 3-amino-N-((6-methoxypyridin-2-yl)methyl)-6-(1-methyl-6-oxo-1,6-dihydropyridin-3-yl)-5-(oxazol-2-yl)pyrazine-2-carboxamide (Cmpd. 17)

SCHEME 14

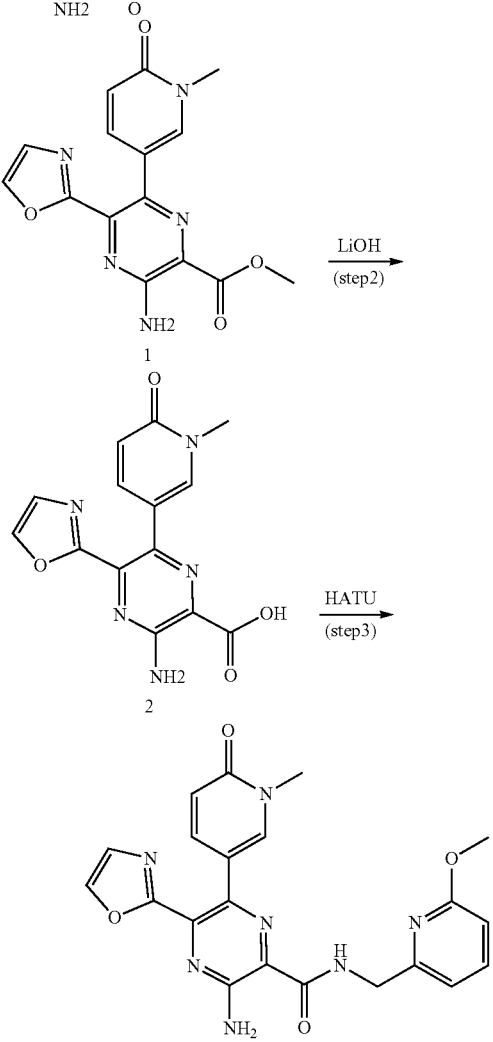

Step 1. 3-amino-6-(1-methyl-6-oxo-1,6-dihydropyridin-3-yl)-5-(1,3-oxazol-2-yl)pyrazine-2-carboxylate To a stirred mixture of methyl 3-amino-6-chloro-5-(1,3-oxazol-2-yl)pyrazine-2-carboxylate (1 g, 3.93 mmol, 1 equiv) and 1-methyl-5-(4,4,5,5-tetramethyl-1,3,2-dioxaborolan-2-yl)-1,2-dihydropyridin-2-one (1.8 g, 7.85 mmol, 2 equiv) in 1,4-dioxane (50 mL) were added Cs$_2$CO$_3$ (2.6 g, 7.85 mmol, 2 equiv) and Pd(dppf)Cl$_2$CH$_2$Cl$_2$ (0.5 g, 0.59 mmol, 0.15 equiv) in portions at room temperature under nitrogen atmosphere. The resulted mixture was stirred for 3 hours at 90° C. under nitrogen atmosphere. The resulted mixture was filtered, the filter cake was washed with CH$_2$Cl$_2$ (1×200 mL). The filtrate was concentrated under reduced pressure. The residue was purified by silica gel column chromatography, eluted with DCM/PE (0-100%) following EA/DCM (0-10%) to afford methyl 3-amino-6-(1-methyl-6-oxo-1,6-dihydropyridin-3-yl)-5-(1,3-oxazol-2-yl)pyrazine-2-carboxylate (1.1 g, 85.58%) as a yellow solid. LCMS: m/z (ESI), [M+H]$^+$=328.0. $^1$H NMR (300 MHz, DMSO-d$_6$) δ3.47 (s, 3H), 3.91 (s, 3H), 6.36 (d, J=9.4 Hz, 1H), 7.35 (dd, J=9.3, 2.6 Hz, 1H), 7.43 (d, J=0.8 Hz, 1H), 7.63 (s, 2H), 7.85 (d, J=2.6 Hz, 1H), 8.32 (d, J=0.8 Hz, 1H)

Step 2. 3-amino-6-(1-methyl-6-oxo-1,6-dihydropyridin-3-yl)-5-(1,3-oxazol-2-yl)pyrazine-2-carboxylic Acid To a stirred mixture of methyl 3-amino-6-(1-methyl-6-oxo-1,6-dihydropyridin-3-yl)-5-(1,3-oxazol-2-yl)pyrazine-2-carboxylate (7 g, 21.39 mmol, 1 equiv) in THF (500 mL) and methanol (100 mL) was added LiOH (1024.4 mg, 42.77 mmol, 2 equiv) solution in water (20 mL) in portions at 35° C. under air atmosphere. The resulted mixture was stirred for 3h at 35° C. under air atmosphere. The mixture was neutralized to pH 6 with HCl (aq.). The resulted mixture was concentrated under reduced pressure to afford 3-amino-6-(1-methyl-6-oxo-1,6-dihydropyridin-3-yl)-5-(1,3-oxazol-2-yl)pyrazine-2-carboxylic acid (6.3 g, 94.03%) as a yellow solid. LCMS: m/z (ESI), [M+H]$^+$=314.0.

Step 3. 3-amino-N-[(6-methoxypyridin-2-yl)methyl]-6-(1-methyl-6-oxo-1,6-dihydro pyridin-3-yl)-5-(1,3-oxazol-2-yl)pyrazine-2-carboxamide (Cmpd. 17)

To a stirred mixture of HATU (24.3 mg, 0.06 mmol, 2 equiv) and 3-amino-6-(1-methyl-6-oxo-1,6-dihydropyridin-3-yl)-5-(1,3-oxazol-2-yl)pyrazine-2-carboxylic acid (10 mg, 0.03 mmol, 1 equiv) in DMF (5 mL) was added DIEA (10.3 mg, 0.08 mmol, 2.5 equiv) in portions at room temperature. The resulted mixture was stirred for 5 min at room temperature. 1-(6-methoxypyridin-2-yl)methanamine (6.6 mg, 0.05 mmol, 1.5 equiv) was added in portions. The resulted mixture was stirred for 3 hours at room temperature. The reaction was quenched with water at room temperature. The precipitated solids were collected by filtration and purified by Prep-TLC (CH$_2$Cl$_2$/MeOH 3:1) to afford 3-amino-N-[(6-methoxypyridin-2-yl)methyl]-6-(1-methyl-6-oxo-1,6-dihydropyridin-3-yl)-5-(1,3-oxazol-2-yl)pyrazine-2-carboxamide (Cmpd. 17) (30 mg, 27.10%) as a yellow solid. LCMS: m/z (ESI), [M+H]$^+$=434.0, $^1$H NMR (300 MHz, DMSO-d$_6$) δ 9.36 (t, J=6.1 Hz, 1H), 8.29 (d, J=0.8 Hz, 1H), 8.02 (d, J=2.6 Hz, 1H), 7.79 (s, 2H), 7.65 (t, J=7.8 Hz, 1H), 7.48-7.32 (m, 2H), 6.90 (d, J=7.3 Hz, 1H), 6.68 (d, J=8.2 Hz, 1H), 6.31 (d, J=9.4 Hz, 1H), 4.53 (d, J=6.0 Hz, 2H), 3.81 (s, 3H), 3.45 (s, 3H).

Example 18. Preparation of 3-amino-6-(1-methyl-6-oxo-1,6-dihydropyridin-3-yl)-N-[(6-methylpyridin-2-yl)methyl]-5-(1,3-oxazol-2-yl)pyrazine-2-carboxamide (Cmpd. 18)

SCHEME 15

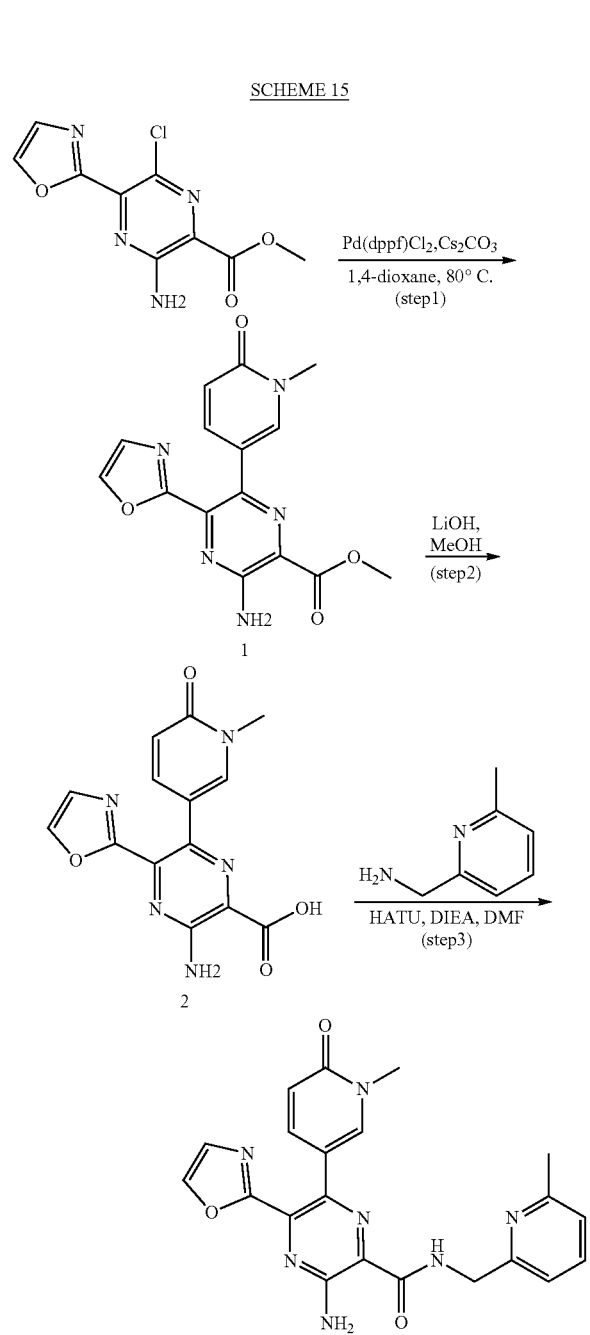

Example 18

Step 1. methyl 3-amino-6-(1-methyl-6-oxo-1,6-dihydropyridin-3-yl)-5-(1,3-oxazol-2-yl) pyrazine-2-carboxylate To a mixture of methyl 3-amino-6-chloro-5-(1,3-oxazol-2-yl)pyrazine-2-carboxylate (1.1 g, 4.32 mmol, 1 equiv) and 1-methyl-5-(4,4,5,5-tetramethyl-1,3,2-dioxaborolan-2-yl)-1,2-dihydropyridin-2-one (2.0 g, 8.64 mmol, 2 equiv) in 1,4-dioxane (40 mL), Pd(dppf)Cl$_2$ (0.3 g, 0.43 mmol, 0.1 equiv) and Cs₂CO₃ (2.8 g, 8.64 mmol, 2 equiv) were added at room temperature under nitrogen atmosphere. The resulted mixture was stirred for 2h at 90° C. under nitrogen atmosphere and concentrated under vacuum. The residue was purified by silica gel column chromatography, eluted with CH$_2$Cl$_2$/MeOH (4%) to afford methyl 3-amino-6-(1-methyl-6-oxo-1,6-dihydropyridin-3-yl)-5-(1,3-oxazol-2-yl) pyrazine-2-carboxylate (1 g, 70.72%) as a yellow solid. LCMS: m/z (ESI), [M+H]⁺=328.0. ¹H NMR: (400 MHz, DMSO-d$_6$) δ 3.46 (s, 3H), 3.90 (s, 3H), 6.35 (d, 1H), 7.34 (dd, 1H), 7.43 (d, 1H), 7.64 (s, 2H), 7.85 (d, 1H), 8.32 (d, 1H).

Step 2. 3-amino-6-(1-methyl-6-oxo-1,6-dihydropyridin-3-yl)-5-(1,3-oxazol-2-yl) pyrazine-2-carboxylic Acid To a solution of methyl 3-amino-6-(1-methyl-6-oxo-1,6-dihydropyridin-3-yl)-5-(1,3-oxazol-2-yl)pyrazine-2-carboxylate (1 g, 3.06 mmol, 1 equiv) in MeOH (30 mL) THF (10 mL), LiOH (0.1 g, 6.11 mmol, 2.00 equiv) was added at room temperature. The resulted mixture was stirred for 2h at 40° C. under air atmosphere. The mixture was adjusted to pH=5 with HCl. The solvent was removed under reduced pressure to afford 3-amino-6-(1-methyl-6-oxo-1,6-dihydropyridin-3-yl)-5-(1,3-oxazol-2-yl)pyrazine-2-carboxylic acid (800 mg, 83.58%) as a yellow solid. LCMS: m/z (ESI), [M+H]⁺=314.0. ¹H NMR: (400 MHz, DMSO-d$_6$) δ 3.46 (s, 3H), 6.30 (d, 1H), 7.28 (dd, 1H), 7.39 (d, 1H), 7.83 (s, 2H), 7.97 (d, 1H), 8.30 (d, 1H).

Step 3. 3-amino-6-(1-methyl-6-oxo-1,6-dihydropyridin-3-yl)-N-[(6-methylpyridin-2-yl) methyl]-5-(1,3-oxazol-2-yl)pyrazine-2-carboxamide (Cmpd. 18)

To a stirred mixture of 3-amino-6-(1-methyl-6-oxo-1,6-dihydropyridin-3-yl)-5-(1,3-oxazol-2-yl)pyrazine-2-carboxylic acid (100 mg, 0.32 mmol, 1 equiv) and HATU (242.7 mg, 0.64 mmol, 2 equiv) and DIEA (123.8 mg, 0.96 mmol, 3 equiv) in DMF (5 mL) was added 1-(6-methylpyridin-2-yl)methanamine (58.5 mg, 0.48 mmol, 1.5 equiv) in portions at room temperature under air atmosphere. The resulted mixture was stirred for 1 h at room temperature under air atmosphere. The mixture was poured into water, filtered, the solid was collected by filtration and washed by MeOH (10 mL), Dried under vacuum to afford 3-amino-6-(1-methyl-6-oxo-1,6-dihydropyridin-3-yl)-N-[(6-methylpyridin-2-yl) methyl]-5-(1,3-oxazol-2-yl)pyrazine-2-carboxamide (Cmpd. 18) (24 mg, 18.01%) as a yellow solid. LCMS: m/z (ESI), [M+H]⁺=418.3. ¹H NMR (400 MHz, DMSO-d$_6$) δ 3.48 (s, 3H), 4.58 (d, J=6.1 Hz, 2H), 6.33 (d, J=9.4 Hz, 1H), 7.15 (d, J=7.7 Hz, 2H), 7.36-7.47 (m, 2H), 7.65 (t, J=7.7 Hz, 1H), 7.81 (s, 2H), 8.06 (d, J=2.6 Hz, 1H), 31 (d, J=0.8 Hz, 1H), 82.47 (s, 3H), 9.45 (t, J=6.1 Hz, 1H).

Compounds listed in the table below were prepared using methods described in Cmpd. 18.

| Example/ Cmpd number | Structure | LCMS [M + H]⁺ | ¹H NMR |
|---|---|---|---|
| 20 | 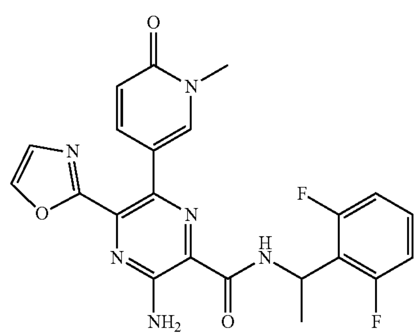 [SMILES: CC(NC(=O)c1nc(-c2ccc(=O)n(C)c2)c(-c2ncco2)nc1N)c1c(F)cccc1F] | 453.3 | ¹H NMR (400 MHz, DMSO-d$_6$) δ 1.60 (d, J = 7.3 Hz 3H), 3.48 (s, 3H), 5.47~5.56 (m, 1H), 6.37 (d, J = 9.3 Hz, 1H), 7.12 (t, J = 8.4 Hz, 2H), 7.29~7.51 (m, 3H), 7.73 (s, 2H), 7.99 (d, J = 2.6 Hz, 1H), 8.30 (d, J = 0.8 Hz, 1H), 8.78 (d, J = 8.3 Hz, 1H) |
| 22 | 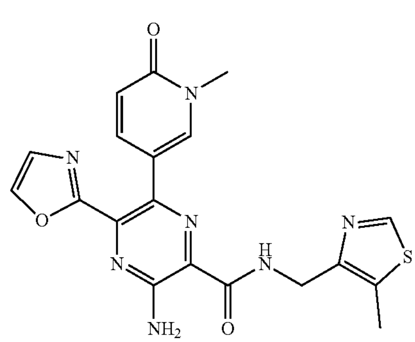 [SMILES: Cc1scnc1CNC(=O)c1nc(-c2ccc(=O)n(C)c2)c(-c2ncco2)nc1N] | 424.2 | ¹H NMR (400 MHz, DMSO-d$_6$) δ 2.46 (s, 3H), 3.47 (s, 2H), 4.56 (d, J = 6.1 Hz, 1H), 6.31 (d, J = 9.4 Hz, 1H), 7.33-7.43 (m, 1H), 7.79 (s, 1H), 8.02 (d, J = 2.6 Hz, 1H), 8.29 (s, 1H), 8.82 (s, 1H), 9.18 (t, J = 6.0 Hz, 1H). |

| Example/Cmpd number | Structure | LCMS [M + H]+ | 1H NMR |
|---|---|---|---|
| 97 | 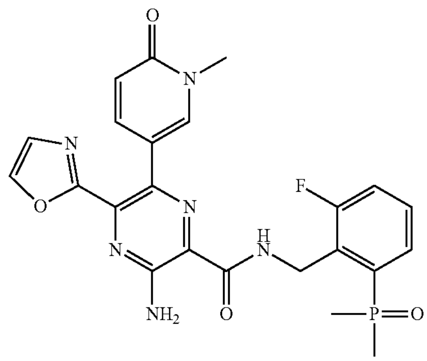 [SMILES: Cn1cc(-c2nc(C(=O)NCc3c(F)cccc3P(C)(C)=O)c(N)nc2-c2ncco2)ccc1=O] | 497.2 | 1H NMR: (300 MHz, DMSO-d6) δ 1.88 (d, 6H), 3.53 (s, 3H), 4.87 (d, 2H), 6.28 (m, 1H), 7.21 (dd, 1H), 7.47 (m, 4H), 7.74 (s, 2H), 8.28 (dd, 2H), 10.08 (t, 1H). |
| 98 | 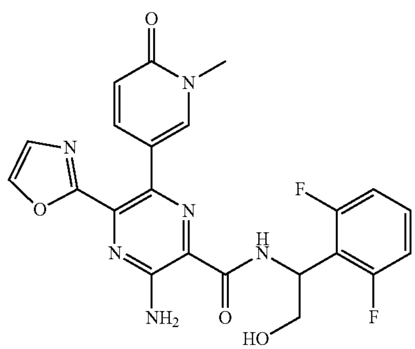 [SMILES: Cn1cc(-c2nc(C(=O)NC(CO)c3c(F)cccc3F)c(N)nc2-c2ncco2)ccc1=O] | 469.2 | 1H NMR: (300 MHz, DMSO-d6) δ 3.47 (s, 3H), 3.78 (qt, 2H), 5.30 (t, 1H), 5.48 (q, 1H), 6.39 (d, 1H), 7.11 (t, 2H), 7.42 (m, 3H), 7.76 (s, 2H), 7.94 (d, 1H), 8.31 (d, 1H), 8.78 (d, 1H). |
| 109 | 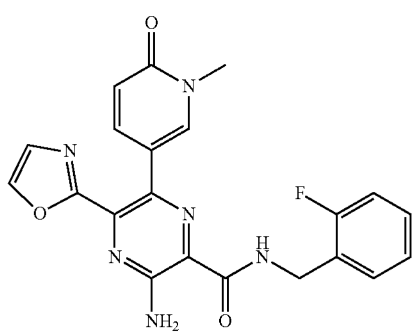 [SMILES: Cn1cc(-c2nc(C(=O)NCc3ccccc3F)c(N)nc2-c2ncco2)ccc1=O] | 421.2 | 1H NMR (300 MHz, DMSO-$d_6$) δ 3.45 (s, 3H), 4.56 (d, J = 6.3 Hz, 2H), 6.31 (d, J = 9.4 Hz, 1H), 7.06-7.23 (m, 2H), 7.26-7.45 (m, 3H), 7.77 (s, 2H), 8.01 (d, J = 2.6 Hz, 1H), 8.28 (d, J = 0.8 Hz, 1H), 9.31 (t, J = 6.3 Hz, 1H). |
| 110 | 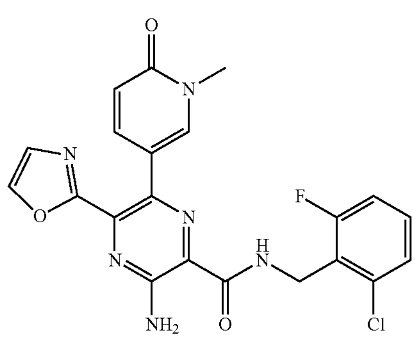 | 455.1 | 1H NMR (400 MHz, DMSO-$d_6$) δ 3.44 (s, 3H), 4.56-4.73 (m, 2H), 6.32 (d, J = 9.4 Hz, 1H), 7.23 (ddd, J = 9.6, 8.0, 1.5 Hz, 1H), 7.30-7.45 (m, 4H), 7.76 (s, 2H), 7.97 (d, J = 2.6 Hz, 1H), 8.29 (d, J = 0.9 Hz, 1H), 9.02 (t, J = 5.8 Hz, 1H). |

Example 19. Preparation of 3-amino-N-[[3-(difluoromethoxy)pyridin-2-yl]methyl]-6-(1-methyl-6-oxo-1,6-dihydropyridin-3-yl)-5-(1,3-oxazol-2-yl)pyrazine-2-carboxamide (Cmpd. 19)

SCHEME 16

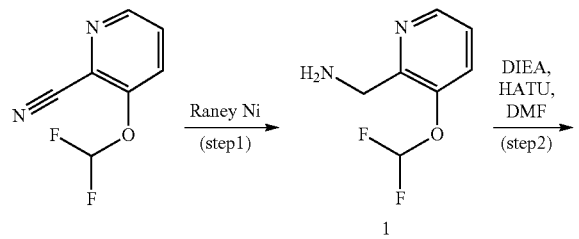

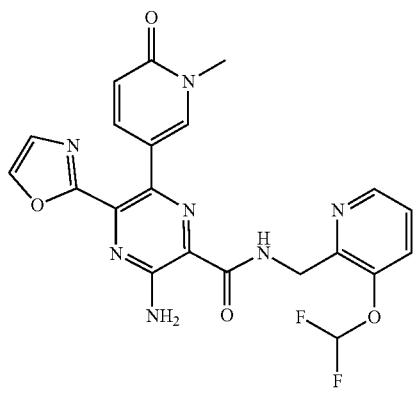

Example 19

Step 1. 1-[3-(difluoromethoxy)pyridin-2-yl]methanamine

To a stirred mixture of 3-(difluoromethoxy)pyridine-2-carbonitrile (70 mg, 0.41 mmol, 1 equiv) and Raney Ni (7.1 mg, 0.1 mmol, 0.2 equiv) in MeOH (5 mL) was added $NH_3 \cdot H_2O$ (1 mL) in portions at room temperature. The resulted mixture was stirred for additional 3 hours at room temperature under hydrogen atmosphere. The resulted mixture was filtered, the filter cake was washed with MeOH (3×10 mL). The filtrate was concentrated under reduced pressure. This resulted in 1-[3-(difluoromethoxy)pyridin-2-yl]methanamine (50 mg, 69.7%) as a purple oil. The crude product was used in the next step directly without further purification. LCMS: m/z (ESI), $[M+H]^+=175.2$.

Step 2. 3-amino-N-[[3-(difluoromethoxy)pyridin-2-yl]methyl]-6-(1-methyl-6-oxo-1,6-dihydropyridin-3-yl)-5-(1,3-oxazol-2-yl)pyrazine-2-carboxamide (Cmpd. 19)

To a stirred solution/mixture of 1-[3-(difluoromethoxy)pyridin-2-yl]methanamine (41.7 mg, 0.24 mmol, 1.5 equiv) and 3-amino-6-(1-methyl-6-oxo-1,6-dihydropyridin-3-yl)-5-(1,3-oxazol-2-yl)pyrazine-2-carboxylic acid (50 mg, 0.16 mmol, 1 equiv) in DMF (4 mL) were added HATU (242.7 mg, 0.64 mmol, 4 equiv) and DIEA (82.5 mg, 0.64 mmol, 4 equiv) dropwise at room temperature under air atmosphere. The resulted mixture was stirred for additional 0.5 h at room temperature. The resulted mixture was dropwise in water (200 mL), The resulted mixture was filtered, the filter cake was washed with MeOH (3×10 mL). This resulted in [3-(difluoromethoxy)pyridin-2-yl]methyl 3-amino-6-(1-methyl-6-oxo-1,6-dihydropyridin-3-yl)-5-(1,3-oxazol-2-yl)pyrazine-2-carboxylate (Cmpd. 19) (18 mg, 23.7%) as a yellow solid. LCMS: m/z (ESI), $[M+H]^+=470.2$. $^1$H NMR (DMSO, 400 MHz) δ 3.5 (3H, s), 4.7 (2H, d), 6.3 (1H, d), 7.3-7.5 (3H, m), 7.7 (1H, d), 7.8 (1H, s), 8.0 (1H, d), 8.3 (1H, s), 8.4 (1H, dd), 9.3 (1H, t).

Example 21: Preparation of N-[[3-amino-5-(4-fluorophenyl)-6-(1-methyl-6-oxo-1,6-dihydropyridin-3-yl)pyrazin-2-yl]methyl]-3-(difluoromethoxy)pyridine-2-carboxamide (Cmpd. 21)

SCHEME 17

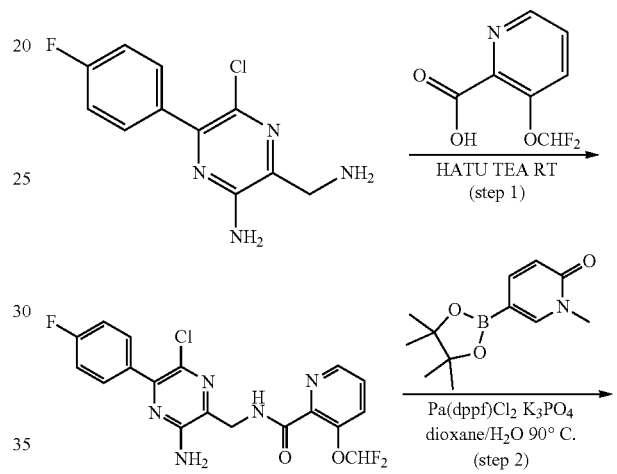

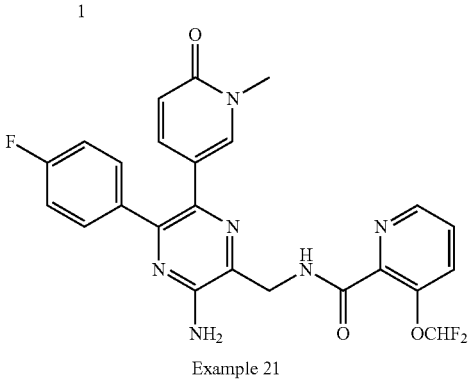

Example 21

Step 1. N-[[3-amino-6-chloro-5-(4-fluorophenyl)pyrazin-2-yl]methyl]-3-(difluoromethoxy)pyridine-2-carboxamide To a mixture of 3-(aminomethyl)-5-chloro-6-(4-fluorophenyl)pyrazin-2-amine (40 mg, 0.16 mmol, 1 equiv) and 3-(difluoromethoxy)pyridine-2-carboxylic acid (59.9 mg, 0.32 mmol, 2.0 equiv) in DCM (2.5 mL), HATU (120.4 mg, 0.32 mmol, 2 equiv) and TEA (48.1 mg, 0.5 mmol, 3 equiv) were added and stirred for 6 hours at room temperature under air atmosphere. The resulted mixture was quenched with water (20 mL) and extracted with $CH_2Cl_2$ (3×20 mL). The combined organic layers were washed with $H_2O$ (3×3 10 mL), dried over anhydrous $Na_2SO_4$. After filtration, the filtrate was concentrated under reduced pressure. The residue was purified by Prep-TLC (PE/EtOAc 1:1) to afford N-[[3-amino-6-chloro-5-(4-fluorophenyl)pyrazin-2-yl]methyl]-3-(difluoromethoxy) pyridine-2-carboxamide (30 mg, 42.5%) as a yellow solid. LCMS: m/z (ESI), [M+H]$^+$= 424.1.

Step 2. N-[[3-amino-5-(4-fluorophenyl)-6-(1-methyl-6-oxo-1,6-dihydropyridin-3-yl)pyrazin-2-yl]methyl]-3-(difluoromethoxy)pyridine-2-carboxamide (Cmpd. 21)

To a mixture of N-[[3-amino-6-chloro-5-(4-fluorophenyl)pyrazin-2-yl]methyl]-3-(difluoromethoxy)pyridine-2-carboxamide (30 mg, 0.07 mmol, 1 equiv) and 1-methyl-5-(4,4,5,5-tetramethyl-1,3,2-dioxaborolan-2-yl)-1,2-dihydropyridin-2-one (33.3 mg, 0.14 mmol, 2.0 equiv) in dioxane/H$_2$O (1 mL), Pd(dppf)Cl$_2$ (10.4 mg, 0.01 mmol, 0.2 equiv) and K$_3$PO$_4$ (45.1 mg, 0.21 mmol, 3 equiv) were added and stirred for 10 hours at 90° C. under nitrogen atmosphere. The residue was purified by Prep-TLC (PE/EtOAc 1:1) then the crude product (25 mg) was purified by Prep-HPLC (Column: XBridge Prep C18 OBD Column, 5 um, 19*150 mm; Mobile Phase A: Water (10 MMOL/L NH$_4$HCOO$_3$+0.1% NH$_3$.H$_2$O), Mobile Phase B: ACN; Flow rate: 20 mL/min; Gradient: 25% B to 27% B in 8 min; 254, 220 nm; Rt: 7.32 min) to afford N-[[3-amino-5-(4-fluorophenyl)-6-(1-methyl-6-oxo-1,6-dihydropyridin-3-yl)pyrazin-2-yl]methyl]-3-(difluoromethoxy)pyridine-2-carboxamide (Cmpd. 21) (2.7 mg, 7.61%) as a white solid. LCMS m/z (ESI) [M+H]$^+$=497.2. $^1$H NMR (400 MHz, Methanol-d$_4$) δ 3.52 (s, 2H), 4.70 (s, 1H), 7.08-7.23 (m, 1H), 7.33 (dd, J=9.4, 2.6 Hz, 1H), 7.45-7.55 (m, 1H), 7.65 (dd, J=8.4, 4.6 Hz, 1H), 7.74-7.84 (m, 1H), 8.56 (dd, J=4.6, 1.3 Hz, 1H).

Example 23. Preparation of 3-amino-6-(1-methyl-6-oxo-1,6-dihydropyridin-3-yl)-N-[[6-(methylamino)pyridin-2-yl]methyl]-5-(1,3-oxazol-2-yl)pyrazine-2-carboxamide (Cmpd. 23)

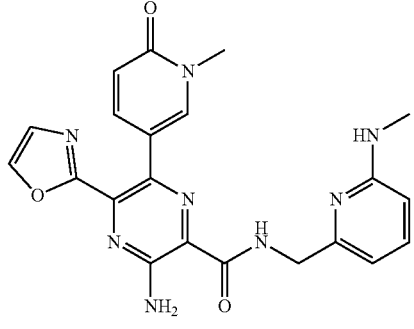

Example 23

Step 1. 6-(methylamino)pyridine-2-carbonitrile

To a solution of 6-bromopyridine-2-carbonitrile (500 mg, 2.7 mmol, 1 equiv) in THF (10 mL), methanamine (424.3 mg, 13.6 mmol, 5.0 equiv) was added at room temperature and stirred for 6 hours at 80° C. under air atmosphere. The residue was purified by Prep-TLC (PE/EtOAc 5:1) to afford 6-(methylamino)pyridine-2-carbonitrile (80 mg, 21.9%) as a white solid. LCMS: m/z (ESI), [M+H]$^+$=134.3.

Step 2. 6-(aminomethyl)-N-methylpyridin-2-amine

To a stirred mixture of 6-(methylamino)pyridine-2-carbonitrile (80 mg, 0.6 mmol, 1 equiv) and Raney Ni (51.5 mg, 0.6 mmol, 1.0 equiv) in MeOH (5 mL) was added NH$_3$.H$_2$O (21.1 mg, 0.60 mmol, 1 equiv) in portions at RT. The resulted mixture was stirred for 30 min at 15° C. under hydrogen atmosphere and concentrated under reduced pressure to afford 6-(aminomethyl)-N-methylpyridin-2-amine (60 mg, 72.8%) as a white solid. LCMS: m/z (ESI), [M+H]$^+$= 137.1.

Step 3. 3-amino-6-(1-methyl-6-oxo-1,6-dihydropyridin-3-yl)-N-[[6-(methylamino)pyridin-2-yl]methyl]-5-(1,3-oxazol-2-yl)pyrazine-2-carboxamide (Cmpd. 23)

To a stirred solution/mixture of 3-amino-6-(1-methyl-6-oxo-1,6-dihydropyridin-3-yl)-5-(1,3-oxazol-2-yl)pyrazine-2-carboxylic acid (70 mg, 0.22 mmol, 1 equiv) and 6-(aminomethyl)-N-methylpyridin-2-amine (46.0 mg, 0.3 mmol, 1.5 equiv) in DMF (3 mL) were added HATU (169.9 mg, 0.5 mmol, 2 equiv) and DIEA (86.6 mg, 0.6 mmol, 3 equiv) dropwise/in portions was stirred for 10 min at 15° C. under air atmosphere. The crude product (60 mg) was purified by Prep-HPLC with the following conditions (Column: XBridge Prep OBD C18 Column 30*150 mm 5 um; Mobile Phase A: Water (0.05% NH$_3$H$_2$O), Mobile Phase B: ACN; Flow rate: 60 mL/min; Gradient: 20% B to 28% B in 7 min; 254/220 nm; Rt: 6.5 min) to afford 3-amino-6-(1-methyl-6-oxo-1,6-dihydropyridin-3-yl)-N-[[6-(methylamino)pyridin-2-yl]methyl]-5-(1,3-oxazol-2-yl)pyrazine-2-carboxamide (Cmpd. 23) (8 mg, 8.3%) as a yellow solid. LCMS: m/z (ESI), [M+H]$^+$=433.2. $^1$H NMR (400 MHz, Methanol-d$_4$) δ 2.8 (s, 2H), 3.6 (s, 2H), 4.5 (s, 1H), 6.4 (d, J=8.2 Hz, 1H), 6.4-6.6 (m, 1H), 7.3-7.4 (m, 1H), 7.5 (dd, J=9.3, 2.6 Hz, 1H), 8.0 (d, J=2.5 Hz, 1H), 8.0 (d, J=0.8 Hz, 1H).

SCHEME 18

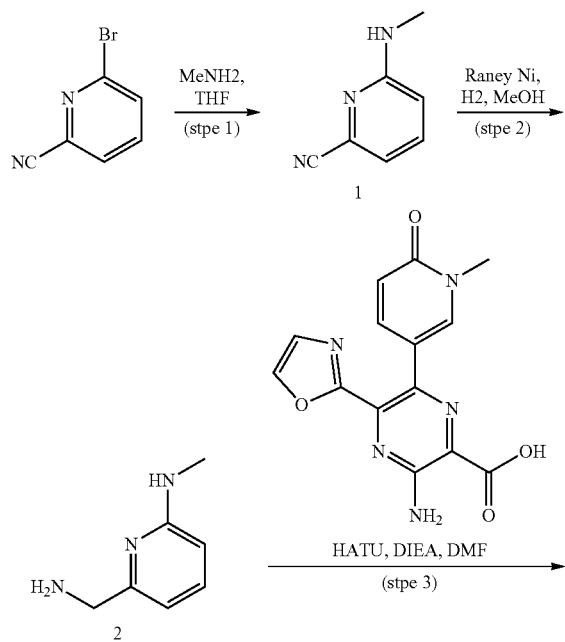

225

Example 24. Preparation of 3-amino-N-[(6-amino-pyridin-2-yl)methyl]-6-(1-methyl-6-oxo-1,6-dihydropyridin-3-yl)-5-(1,3-oxazol-2-yl)pyrazine-2-carboxamide (Cmpd. 24)

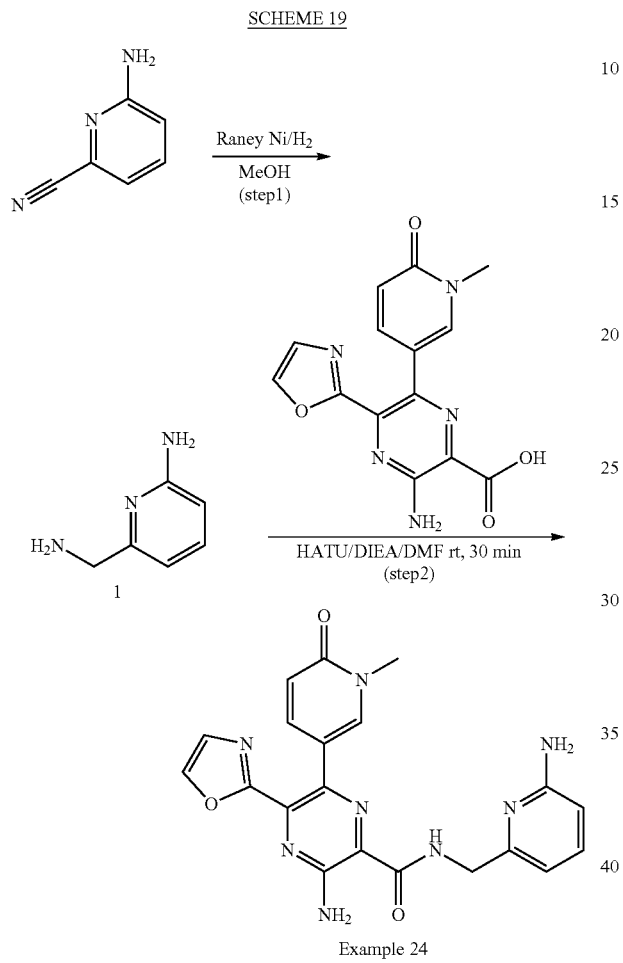

Example 24

Step 1. 6-(aminomethyl)pyridin-2-amine

To a solution of 6-aminopyridinecarbonitrile (100 mg, 0.84 mmol, 1 equiv) in 20 mL MeOH in a 50 mL round-bottom flask was added Raney Ni (10 mg, 0.12 mmol, 0.14 equiv) under nitrogen atmosphere. The mixture was hydrogenated at room temperature for 1.5 hours under hydrogen atmosphere using a hydrogen balloon. The resulted mixture was filtered, the filtrate was concentrated under reduced pressure to afford 6-(aminomethyl)pyridin-2-amine (100 mg, 96.73%) as a brown oil. The crude product was used in the next step directly without further purification. LCMS: m/z (ESI), [M+H]$^+$=124.0.

Step 2. 3-amino-N-[(6-aminopyridin-2-yl)methyl]-6-(1-methyl-6-oxo-1,6-dihydropyridin-3-yl)-5-(1,3-oxazol-2-yl)pyrazine-2-carboxamide (Cmpd. 24)

To a stirred mixture of 3-amino-6-(1-methyl-6-oxo-1,6-dihydropyridin-3-yl)-5-(1,3-oxazol-2-yl)pyrazine-2-carboxylic acid (381.5 mg, 1.22 mmol, 1.5 equiv) and HATU (617.5 mg, 1.62 mmol, 2 equiv) in DMF (15.0 mL) were added DIEA (314.8 mg, 2.44 mmol, 3 equiv) and 6-(aminomethyl)pyridin-2-amine (100 mg, 0.81 mmol, 1 equiv) in portions at room temperature under air atmosphere. The resulted mixture was stirred for 30 mins at room temperature under air atmosphere. The resulted mixture was concentrated under reduced pressure. The residue was purified by Prep-TLC/silica gel column chromatography, eluted with CH$_2$Cl$_2$/MeOH (20:1) to afford 3-amino-N-[(6-aminopyridin-2-yl)methyl]-6-(1-methyl-6-oxo-1,6-dihydropyridin-3-yl)-5-(1,3-oxazol-2-yl)pyrazine-2-carboxamide (Cmpd. 24) (57 mg, 16.43%) as a yellow solid. LCMS: m/z (ESI), [M+H]$^+$=419.0. $^1$H NMR (400 MHz, DMSO-d$_6$) δ 3.48 (s, 3H), 4.39 (d, J=6.2 Hz, 2H), 5.92 (s, 2H), 6.32 (dd, J=8.8, 3.8 Hz, 2H), 6.42 (d, J=7.3 Hz, 1H), 7.28~7.40 (m, 2H), 7.42 (s, 1H), 7.83 (s, 2H), 8.07 (d, J=2.6 Hz, 1H), 8.31 (s, 1H), 9.26 (t, J=6.2 Hz, 1H).

Example 25. Preparation of 3-amino-N-((4-(dimethylamino)pyrimidin-2-yl)methyl)-6-(1-methyl-6-oxo-1,6-dihydropyridin-3-yl)-5-(oxazol-2-yl)pyrazine-2-carboxamide (Cmpd. 25)

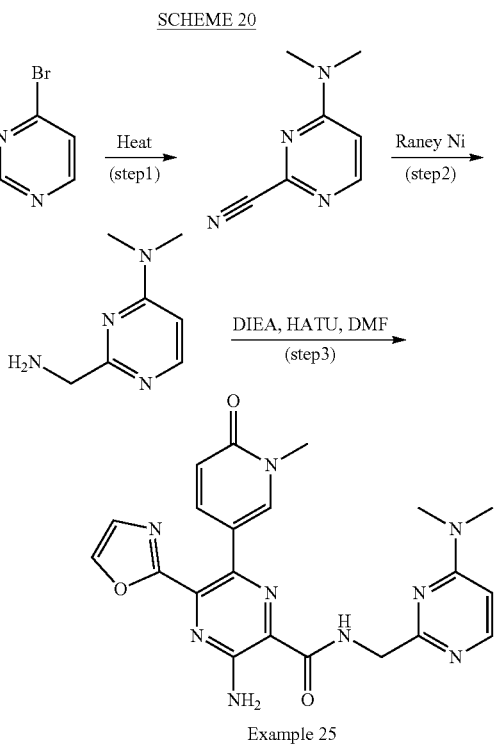

Example 25

Step 1. 4-(dimethylamino)pyrimidine-2-carbonitrile

Into a 40 mL sealed tube were added 4-bromopyrimidine-2-carbonitrile (980 mg, 5.3 mmol, 1 equiv) and NHMe$_2$ (15 mL, 30.00 mmol, 5.6 equiv) in THF (10 mg) at 80° C. for 6 h. The resulted mixture was concentrated under reduced pressure. The residue was purified by silica gel column chromatography, eluted with hexane/EtOAc (1:1) to afford 4-(dimethylamino)pyrimidine-2-carbonitrile (700 mg, 88.7%) as a white solid. LCMS: m/z (ESI), [M+H]$^+$=149.2.

Step 2.
2-(aminomethyl)-N,N-dimethylpyrimidin-4-amine

To a stirred mixture of 4-(dimethylamino)pyrimidine-2-carbonitrile (80 mg, 0.5 mmol, 1 equiv) and Raney Ni (9.3 mg, 0.1 mmol, 0.2 equiv) in MeOH (5 mL) were added NH₄OH (1 mL) dropwise at room temperature. The resulted mixture was stirred for additional 1 h at room temperature under hydrogen atmosphere. The resulted mixture was filtered, the filter cake was washed with MeOH (3×10 mL). The filtrate was concentrated under reduced pressure to afford 70 mg brown oil. The crude product was used in the next step directly without further purification. LCMS: m/z (ESI), [M+H]⁺=153.2.

Step 3. 3-amino-N-[[4-(dimethylamino)pyrimidin-2-yl]methyl]-6-(1-methyl-6-oxo-1,6-dihydropyridin-3-yl)-5-(1,3-oxazol-2-yl)pyrazine-2-carboxamide (Cmpd. 25)

To a stirred mixture of 3-amino-6-(1-methyl-6-oxo-1,6-dihydropyridin-3-yl)-5-(1,3-oxazol-2-yl)pyrazine-2-carboxylic acid (50 mg, 0.16 mmol, 1 equiv) and 2-(aminomethyl)-N,N-dimethylpyrimidin-4-amine (36.4 mg, 0.2 mmol, 1.5 equiv) in DMF (5 mL) were added DIEA (82.5 mg, 0.64 mmol, 4 equiv) and HATU (242.7 mg, 0.6 mmol, 4 equiv) in portions at room temperature under air atmosphere. The resulted mixture was stirred for additional 30 min at room temperature. The resulted mixture was added in water and filtered, the filter cake was washed with EtOAc (3×5 mL) and MeOH (2×5 mL). The crude product was re-crystallized from water/DMF (5:1 mL) to afford 3-amino-N-[[4-(dimethylamino)pyrimidin-2-yl]methyl]-6-(1-methyl-6-oxo-1,6-dihydropyridin-3-yl)-5-(1,3-oxazol-2-yl)pyrazine-2-carboxamide (Cmpd. 25) (14 mg, 19.41%) as a yellow solid. LCMS: m/z (ESI), [M+H]⁺=448.3. ¹H NMR (DMSO, 400 MHz) δ 3.0 (6H, s), 3.5 (3H, s), 4.5 (2H, d), 6.3 (1H, d), 6.6 (1H, d), 7.4-7.4 (2H, m), 7.8 (1H, s), 8.0 (1H, d), 8.1 (1H, d), 8.3 (1H, d), 9.2 (1H, t).

Example 26. Preparation of 3-amino-N-[[6-(azetidin-1-yl)pyridin-2-yl]methyl]-6-(1-methyl-6-oxo-1,6-dihydropyridin-3-yl)-5-(1,3-oxazol-2-yl)pyrazine-2-carboxamide (Cmpd. 26)

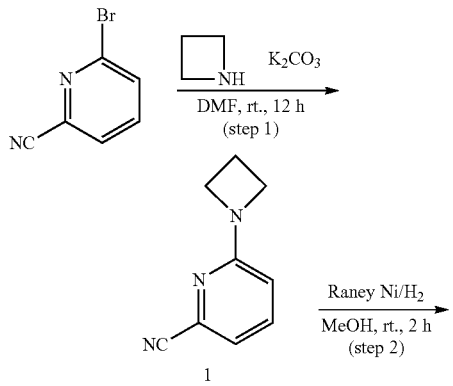

SCHEME 21

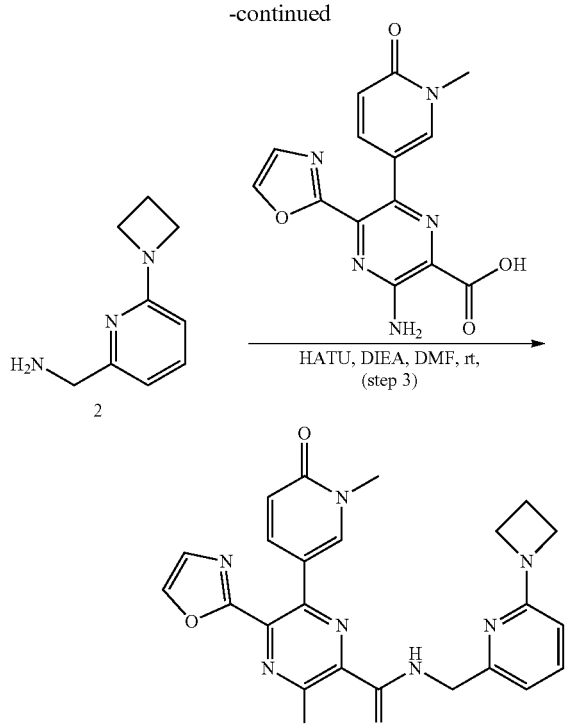

Example 26

Step 1. 6-(azetidin-1-yl)pyridine-2-carbonitrile

Into a 40 mL sealed tube were added 6-bromopyridine-2-carbonitrile (500 mg, 2.732 mmol, 1 equiv), azetidine (202.79 mg, 3.552 mmol, 1.30 equiv) and K₂CO₃ (755.19 mg, 5.464 mmol, 2.00 equiv) in DMF (20 mL) at room temperature. The mixture was stirred for 2 hours at 80° C. and concentrated under vacuum. The residue was purified by silica gel column chromatography, eluted with PE/EtOAc (1:1) to afford 6-(azetidin-1-yl)pyridine-2-carbonitrile (400 mg, 91.97%) as a white solid. LCMS: m/z (ESI), [M+H]⁺= 160.2.

Step 2. 1-[6-(azetidin-1-yl)pyridin-2-yl]methanamine

Into a 50 mL round-bottom flask were added Raney Ni (40 mg, 0.47 mmol, 0.32 equiv) and 6-(azetidin-1-yl)pyridine-2-carbonitrile (230 mg, 1.44 mmol, 1 equiv) in MeOH (20 mL) at room temperature. The mixture was stirred for 2h under H₂ atmosphere. Raney Ni was removed by filtration. The filtrate was concentrated under reduced pressure to afford 1-[6-(azetidin-1-yl)pyridin-2-yl]methanamine (200 mg, 84.81%) as a yellow oil which was used next step without further purification. LCMS: m/z (ESI), [M+H]⁺= 164.2.

Step 3. 3-amino-N-[[6-(azetidin-1-yl)pyridin-2-yl]methyl]-6-(1-methyl-6-oxo-1,6-dihydropyridin-3-yl)-5-(1,3-oxazol-2-yl)pyrazine-2-carboxamide (Cmpd. 26)

To a mixture of 3-amino-6-(1-methyl-6-oxo-1,6-dihydropyridin-3-yl)-5-(1,3-oxazol-2-yl)pyrazine-2-carboxylic acid (80 mg, 0.26 mmol, 1 equiv) and 1-[6-(azetidin-1-yl)pyridin-2-yl]methanamine (62.9 mg, 0.39 mmol, 1.5 equiv) in DMF (5 mL), HATU (195.4 mg, 0.51 mmol, 2 equiv) and DIEA (99.6 mg, 0.77 mmol, 3 equiv) were added at room temperature. The resulted mixture was stirred for 60 min and concentrated under vacuum. The crude product (50 mg) was purified by Prep-HPLC with the following conditions (Column: XBridge Prep C18 OBD Column, 5 um, 19*150 mm; Mobile Phase A: water (10 MMOL/L NH$_4$HCO$_3$+0.1% NH$_3$.H$_2$O), Mobile Phase B: ACN; Flow rate: 20 mL/min; Gradient: 25% B to 43% B in 7 min; 254, 220 nm; Rt: 6.68 min) to afford 3-amino-N-[[6-(azetidin-1-yl)pyridin-2-yl]methyl]-6-(1-methyl-6-oxo-1,6-dihydropyridin-3-yl)-5-(1,3-oxazol-2-yl)pyrazine-2-carboxamide (Cmpd. 26) (11 mg, 9.40%) as a yellow solid. LCMS: m/z (ESI), [M+H]$^+$=459.3. $^1$H NMR (300 MHz, DMSO-d$_6$) δ 2.28 (2H, p), 3.47 (3H, s), 3.89 (4H, t), 4.45 (2H, d), 6.22 (1H, d), 6.33 (1H, d), 6.58 (1H, d), 7.34-7.53 (3H, m), 7.83 (2H, s), 8.02 (1H, d), 8.31 (1H, s), 9.35 (1H, t).

Example 27. Preparation of 3-amino-N-(5-(dimethylamino)-2-fluorobenzyl)-6-(1-methyl-6-oxo-1,6-dihydropyridin-3-yl)-5-(oxazol-2-yl)pyrazine-2-carboxamide (Cmpd. 27)

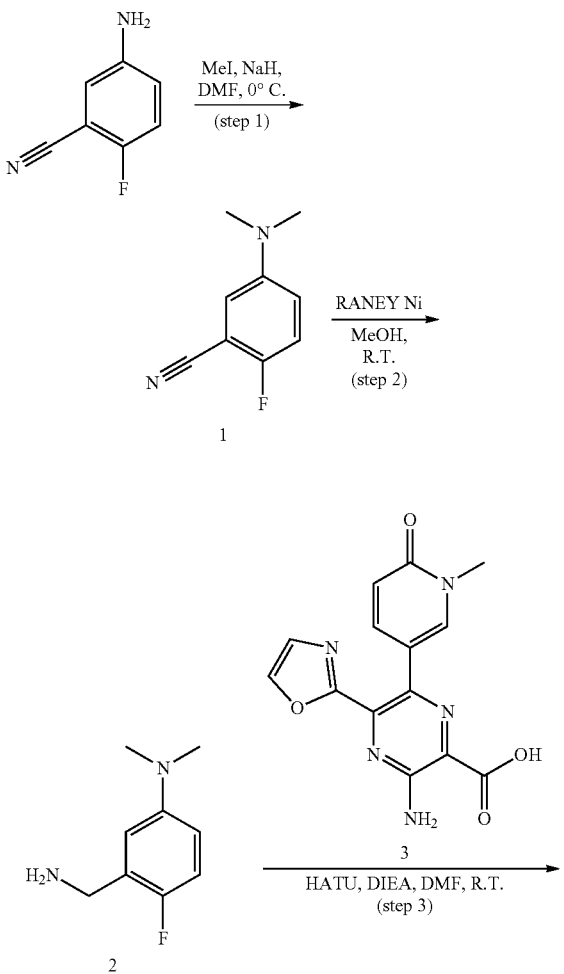

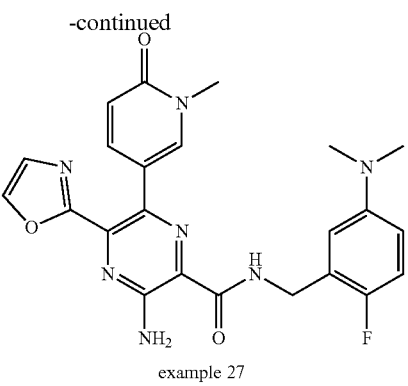

example 27

Step 1. Preparation of 5-(dimethylamino)-2-fluorocyclohexa-1,3-diene-1-carbonitrile To a solution of 5-amino-2-fluorobenzonitrile (2 g, 14.69 mmol, 1 equiv) in DMF (40 mL), NaH (1057.7 mg, 44.08 mmol, 3 equiv) was added at 0° C. After stirring for 5 mins, MeI (8341.4 mg, 58.77 mmol, 4 equiv) was added dropwise at 0° C. The resulting solution was stirred for 2 hr at 0° C. and quenched with saturated aq. NH$_4$Cl (50 mL). The resulting solution was extracted with 3×50 mL of ethyl acetate, dried over anhydrous sodium sulfate and concentrated under vacuum. The residue was applied onto a silica gel column with dichloromethane/methanol (40:1). This resulted in 1.2 g (49.75%) of 5-(dimethylamino)-2-fluorocyclohexa-1,3-diene-1-carbonitrile as a light yellow solid. LCMS: m/z (ESI), [M+H]$^+$=165.2. $^1$HNMR (400 MHz, DMSO-d$_6$) δ 2.89 (6H, s), 7.01-7.07 (2H, m), 7.25-7.32 (1H, m).

Step 2. 3-(aminomethyl)-4-fluoro-N,N-dimethylaniline

To a mixture of Raney Ni (52.18 mg, 0.609 mmol, 0.20 equiv) and 5-(dimethylamino)-2-fluorobenzonitrile (500 mg, 3.045 mmol, 1 equiv) in MeOH (50 mL) in a 250-mL round-bottom flask, NH$_4$OH (2 mL, 51.361 mmol, 16.87 equiv) was added. The resulting solution was stirred for 2 hours at room temperature under hydrogen atmosphere. The Raney Ni was filtered out. The filtrate was concentrated to result in 400 mg (78.08%) of 3-(aminomethyl)-4-fluoro-N,N-dimethylaniline as a solid. LCMS: m/z (ESI), [M-NH$_2$]$^+$=152.3. $^1$HNMR (400 MHz, DMSO-d$_6$) δ 2.83 (6H, s), 3.70 (2H, d), 6.52-6.57 (1H, m), 6.75-6.88 (1H, m), 7.06-7.13 (1H, m)

Step 3. 3-amino-N-(5-(dimethylamino)-2-fluorobenzyl)-6-(1-methyl-6-oxo-1,6-dihydropyridin-3-yl)-5-(oxazol-2-yl)pyrazine-2-carboxamide (Cmpd. 27)

To a mixture of 3-amino-6-(1-methyl-6-oxo-1,6-dihydropyridin-3-yl)-5-(1,3-oxazol-2-yl)pyrazine-2-carboxylic acid (50 mg, 0.16 mmol, 1 equiv) and 3-(aminomethyl)-4-fluoro-N,N-dimethylaniline (32.2 mg, 0.19 mmol, 1.20 equiv) in DMF (10 mL) in a 25-mL round-bottom flask, TEA (48.5 mg, 0.48 mmol, 3.0 equiv) and HATU (66.8 mg, 0.18 mmol, 1.1 equiv) were added. The resulting solution was stirred for 1 hour at room temperature. The reaction was then quenched with 50 mL of water. The resulting solid was collected by filtration and dried under vacuum to afford 17.2 mg (23.25%) of 3-amino-N-[[5-(dimethylamino)-2-fluorophenyl]methyl]-6-(1-methyl-6-oxo-1,6-dihydropyridin-3-yl)-5-(1,3-oxazol-2-yl)pyrazine-2-carboxamide (Cmpd. 27) as a yellow solid. LCMS: m/z (ESI), [M+H]+=464.2. 1HNMR (300 MHz, DMSO-d6) δ 2.80 (6H, s), 3.45 (3H, s), 4.52 (2H, d), 6.30-6.33 (1H, m), 6.59-6.62 (1H, m), 6.63-6.64 (1H, m), 6.73-6.76 (1H, m), 7.00-7.03 (1H, m), 7.36-7.39 (2H, m), 7.76-7.78 (2H, m), 8.02-8.03 (1H, m), 8.29 (1H, s), 9.20-9.24 (1H, m).

Example 28. Preparation of 3-amino-6-(1-methyl-6-oxo-1,6-dihydropyridin-3-yl)-5-(oxazol-2-yl)-N-((6-(pyrrolidin-1-yl) pyridin-2-yl)methyl)pyrazine-2-carboxamide (Cmpd. 28)

SCHEME 23

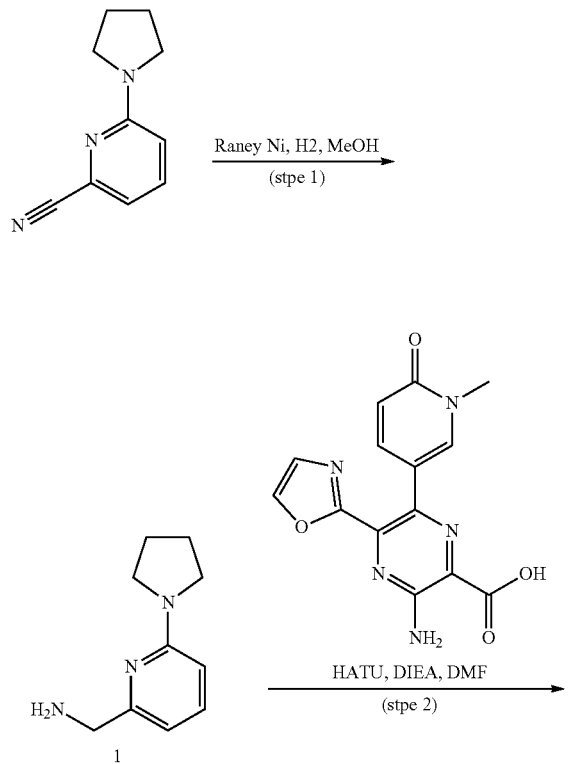

Step 1. 1-[6-(pyrrolidin-1-yl)pyridin-2-yl]methanamine

To a mixture of 6-(pyrrolidin-1-yl)pyridine-2-carbonitrile (200 mg, 1.1 mmol, 1 equiv) and Raney Ni (98.9 mg, 1.1 mmol, 1.0 equiv) in MeOH (10 mL), NH3.H2O (40.5 mg, 1.1 mmol, 1 equiv) was added and stirred for 30 min at 15° C. under hydrogen atmosphere. The resulted mixture was filtered and the filtrate was concentrated under reduced pressure to afford 1-[6-(pyrrolidin-1-yl)pyridin-2-yl]methanamine (120 mg, 58.6%) as a white solid. LCMS: m/z (ESI), [M+H]+=178.3.

Step 2. 3-amino-6-(1-methyl-6-oxo-1,6-dihydropyridin-3-yl)-5-(1,3-oxazol-2-yl)-N-[[6-(pyrrolidin-1-yl)pyridin-2-yl]methyl]pyrazine-2-carboxamide (Cmpd. 28)

To a mixture of 1-[6-(pyrrolidin-1-yl)pyridin-2-yl]methanamine (100 mg, 0.56 mmol, 1 equiv) and 3-amino-6-(1-methyl-6-oxo-1,6-dihydropyridin-3-yl)-5-(1,3-oxazol-2-yl)pyrazine-2-carboxylic acid (176.7 mg, 0.56 mmol, 1.00 equiv) in DMF (3 mL), HATU (429.0 mg, 1.13 mmol, 2 equiv) and DIEA (218.7 mg, 1.69 mmol, 3 equiv) were added at room temperature. The mixture was stirred for 60 min at 15° C. under air atmosphere. The resulted mixture was concentrated under reduced pressure. The crude product (100 mg) was purified by Prep-HPLC with the following conditions (Column: XBridge Prep OBD C18 Column 19*250 mm, 5 um; Mobile Phase A: Water (10 MMOL/L NH4HCOO3+0.1% NH3.H2O), Mobile Phase B: ACN; Flow rate: 20 mL/min; Gradient: 39% B to 40% B in 9 min; 254, 220 nm; Rt: 8.3 min) to afford 3-amino-6-(1-methyl-6-oxo-1,6-dihydropyridin-3-yl)-5-(1,3-oxazol-2-yl)-N-[[6-(pyrrolidin-1-yl)pyridin-2-yl]methyl]pyrazine-2-carboxamide (Cmpd. 28) (36.7 mg, 13.17%) as a yellow solid. LCMS: m/z (ESI), [M+H]+=473.3, 1H NMR (400 MHz, Methanol-d4) δ 1.8-1.9 (m, 4H), 3.3 (d, J=6.6 Hz, 4H), 4.5 (d, J=5.5 Hz, 2H), 6.3 (dd, J=13.3, 8.9 Hz, 2H), 6.5 (d, J=7.3 Hz, 1H), 7.4-7.5 (m, 3H), 7.8 (s, 1H), 7.9 (d, J=2.6 Hz, 1H), 8.3 (d, J=0.8 Hz, 1H), 9.3 (t, J=5.6 Hz, 1H).

Example 29. Preparation of 3-amino-N-[(2,6-difluorophenyl)methyl]-5-(4-fluorophenyl)-6-(1-methyl-6-oxo-1,6-dihydropyridin-3-yl)pyrazine-2-carboxamide (Cmpd. 29)

SCHEME 24

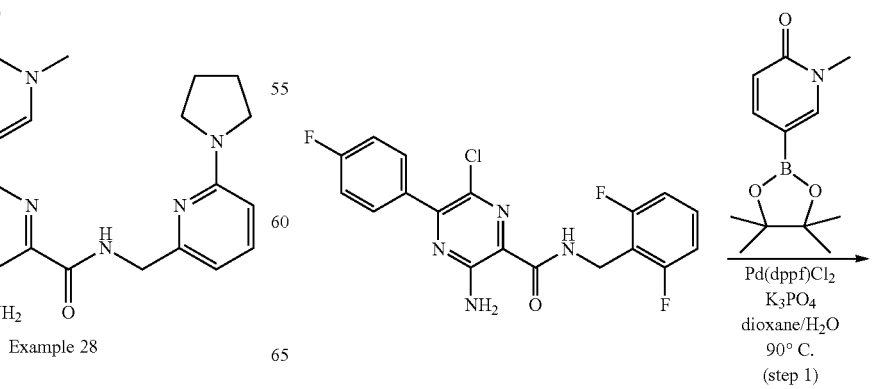

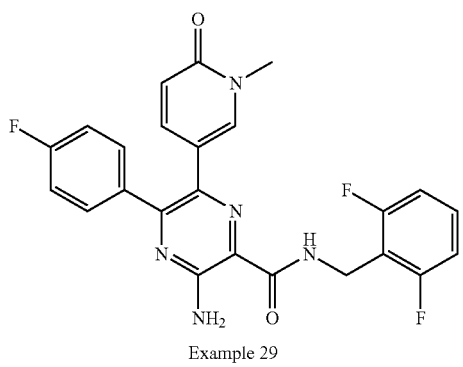

Example 29

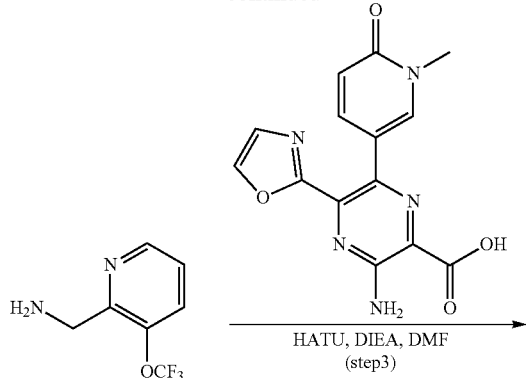

Step 1. Preparation of 3-amino-N-[(2,6-difluorophenyl)methyl]-5-(4-fluorophenyl)-6-(1-methyl-6-oxo-1,6-dihydropyridin-3-yl)pyrazine-2-carboxamide (Cmpd. 29)

To a mixture of 3-amino-6-chloro-N-[(2,6-difluorophenyl)methyl]-5-(4-fluorophenyl)pyrazine-2-carboxamide (100 mg, 0.25 mmol, 1 equiv) and 1-methyl-5-(4,4,5,5-tetramethyl-1,3,2-dioxaborolan-2-yl)-1,2-dihydropyridin-2-one (119.7 mg, 0.5 mmol, 2.0 equiv) in dioxane/$H_2O$ (2 mL), Pd(dppf)$Cl_2$ (37.3 mg, 0.1 mmol, 0.2 equiv) and $K_3PO_4$ (162.1 mg, 0.8 mmol, 3 equiv) were added under nitrogen atmosphere at room temperature. The mixture was stirred for 10 hours at 90° C. under nitrogen atmosphere. The residue was purified by Prep-TLC (PE/EtOAc 1:2) then the crude product was purified by Prep-HPLC (Column: XBridge Prep OBD C18 Column 30×150 mm 5 um; Mobile Phase A: Water (0.05% $NH_3H_2O$), Mobile Phase B: ACN; Flow rate: 60 mL/min; Gradient: 39% B to 49% B in 7 min; 254/220 nm; Rt: 6.18 min) to afford 3-amino-N-[(2,6-difluorophenyl)methyl]-5-(4-fluorophenyl)-6-(1-methyl-6-oxo-1,6-dihydro pyridin-3-yl)pyrazine-2-carboxamide (Cmpd. 29) (7 mg, 5.85%) as a yellow solid. LCMS m/z (ESI) [M+H]$^+$=466.2. $^1$H NMR (400 MHz, Methanol-$d_4$) δ 3.55 (s, 2H), 4.73 (s, 2H), 6.38 (d, J=9.2 Hz, 1H), 6.93-7.05 (m, 2H), 7.10-7.19 (m, 2H), 7.30 (dd, J=9.4, 2.6 Hz, 1H), 7.32-7.42 (m, 1H), 7.50-7.61 (m, 2H), 7.88 (d, J=2.5 Hz, 1H).

Example 30. Preparation of 3-amino-6-(1-methyl-6-oxo-1,6-dihydropyridin-3-yl)-5-(1,3-oxazol-2-yl)-N-[[3-(trifluoromethoxy)pyridin-2-yl]methyl]pyrazine-2-carboxamide. (Cmpd. 30)

SCHEME 25

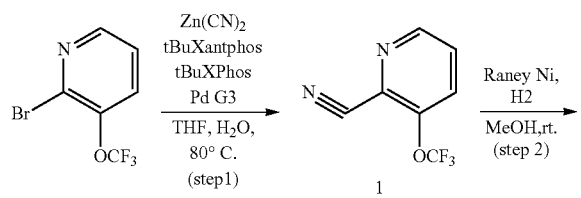

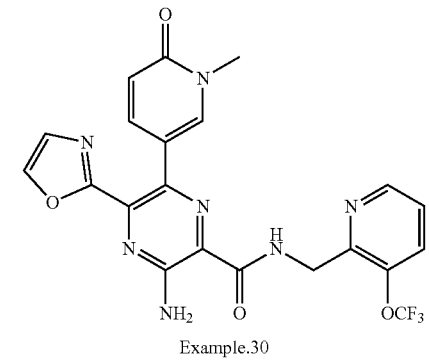

Example.30

Step 1. 3-(trifluoromethoxy)pyridine-2-carbonitrile

To a stirred mixture of 2-bromo-3-(trifluoromethoxy)pyridine (300 mg, 1.24 mmol, 1 equiv) and Zn(CN)$_2$ (291.2 mg, 2.48 mmol, 2 equiv) in THF (15 mL) and $H_2O$ (3 mL), t-BuXantPhos-Pd-G3 (197.0 mg, 0.25 mmol, 0.2 equiv) and t-BuXantPhos (171.3 mg, 0.25 mmol, 0.2 equiv) under nitrogen atmosphere at RT. The resulted mixture was stirred for 2h at 80° C. under nitrogen atmosphere. The solvent was removed under reduced pressure. The residue was purified by Prep-TLC ($CH_2Cl_2$/MeOH 20:1) to afford 3-(trifluoromethoxy)pyridine-2-carbonitrile (200 mg, 85.76%) as a white solid. LCMS: m/z (ESI), [M+H]$^+$=188.9.

Step 2. 1-[3-(trifluoromethoxy)pyridin-2-yl]methanamine

To a solution of 3-(trifluoromethoxy)pyridine-2-carbonitrile (100 mg, 0.53 mmol, 1 equiv) and $NH_3.H_2O$ (1.0 mL, 28.54 mmol, 48.31 equiv) in MeOH (10 mL), Raney Ni (22.8 mg, 0.27 mmol, 0.5 equiv) was added under nitrogen atmosphere. The resulted mixture was stirred for 2 hours at room temperature under hydrogen atmosphere. The resulted mixture was filtered, the filter cake was washed with MeOH (3×10 mL). The filtrate was concentrated under reduced pressure. This resulted in 1-[3-(trifluoromethoxy)pyridin-2-yl]methanamine (80 mg, 78.32%) as a purple oil. The crude product was used in the next step directly without further purification LCMS: m/z (ESI), [M+H]$^+$=193.2.

Step 3. 3-amino-6-(1-methyl-6-oxo-1,6-dihydropyridin-3-yl)-5-(1,3-oxazol-2-yl)-N-[[3-(trifluoromethoxy)pyridin-2-yl]methyl]pyrazine-2-carboxamide (Cmpd. 30)

To a solution of 3-amino-6-(1-methyl-6-oxo-1,6-dihydropyridin-3-yl)-5-(1,3-oxazol-2-yl)pyrazine-2-carboxylic acid (80 mg, 0.26 mmol, 1 equiv) and 1-[3-(trifluoromethoxy)pyridin-2-yl]methanamine (98.1 mg, 0.51 mmol, 2 equiv) in DMF (10 mL), HATU (194.2 mg, 0.51 mmol, 2 equiv) and DIEA (66.0 mg, 0.51 mmol, 2 equiv) were added at room temperature. The resulted mixture was stirred for 30 min at room temperature under air atmosphere. The solvent was removed under reduced pressure. The crude product (80 mg) was purified by Prep-HPLC with the following conditions (Column: XBridge Prep C18 OBD Column, 5 um, 19*150 mm; Mobile Phase A: Water (10 MMOL/L $NH_4HCO_3$+ 0.1% $NH_3.H_2O$), Mobile Phase B: ACN; Flow rate: 20 mL/min; Gradient: 25% B to 46% B in 7 min; 254/220 nm; Rt: 6.83 min) to afford 3-amino-6-(1-methyl-6-oxo-1,6-dihydropyridin-3-yl)-5-(1,3-oxazol-2-yl)-N-[[3-(trifluoromethoxy)pyridin-2-yl]methyl]pyrazine-2-carboxamide (Cmpd. 30) (10 mg, 8.03%) as a yellow solid. LCMS: m/z (ESI), [M+H]$^+$=488.2. $^1$H NMR: (400 MHz, MeOD) δ 3.65 (s, 3H), 4.85 (s, 2H), 6.53 (d, 1H), 7.38 (d, 1H), 7.51 (m, 2H), 7.84 (d, 1H), 8.07 (dd, 2H), 8.54 (d, 1H).

Example 31. Preparation of 3-amino-6-[1-(difluoromethyl)-6-oxo-1,6-dihydropyridin-3-yl]-N-[(3-fluoropyridin-2-yl)methyl]-5-(1,3-oxazol-2-yl)pyrazine-2-carboxamide. (Cmpd. 31)

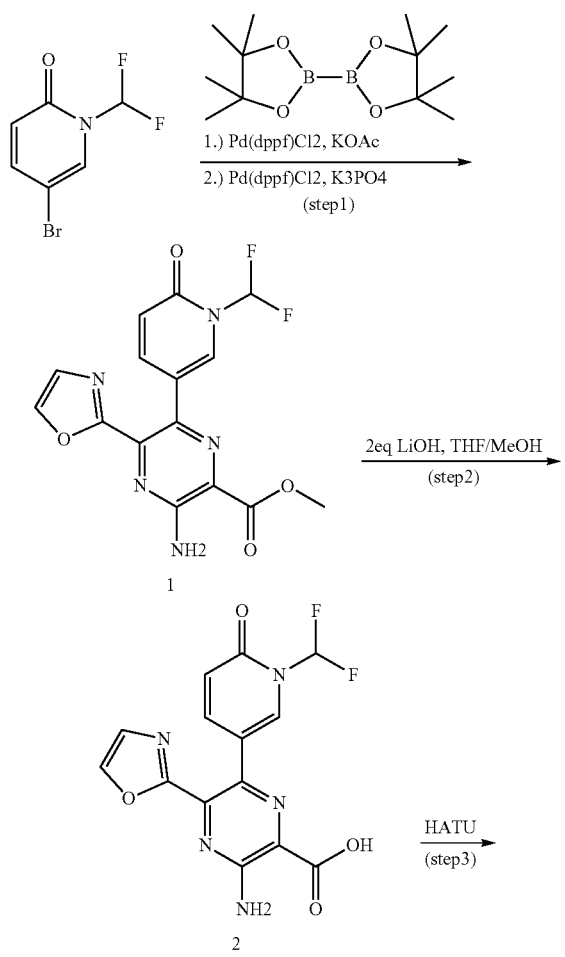

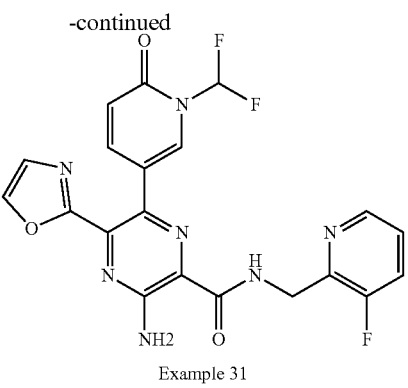

Example 31

Step 1. methyl 3-amino-6-[1-(difluoromethyl)-6-oxo-1,6-dihydropyridin-3-yl]-5-(1,3-oxazol-2-yl)pyrazine-2-carboxylate To a stirred solution of 4,4,5,5-tetramethyl-2-(4,4,5,5-tetramethyl-1,3,2-dioxaborolan-2-yl)-1,3,2-dioxaborolane (340.1 mg, 1.34 mmol, 2 equiv) and 5-bromo-1-(difluoromethyl)-1,2-dihydropyridin-2-one (150 mg, 0.67 mmol, 1 equiv) in THF (20 mL) was added KOAc (197.2 mg, 2.01 mmol, 3.00 equiv) and Pd(dppf)Cl$_2$CH$_2$Cl$_2$ (82.0 mg, 0.10 mmol, 0.15 equiv) in portions at room temperature under nitrogen atmosphere. The resulted mixture was stirred for 3h at 75° C. under nitrogen atmosphere. To this resulting mixture of 1-(difluoromethyl)-5-(4,4,5,5-tetramethyl-1,3,2-dioxaborolan-2-yl)-1,2-dihydropyridin-2-one in THF (20 mL) were added methyl 3-amino-6-chloro-5-(1,3-oxazol-2-yl)pyrazine-2-carboxylate (84.5 mg, 0.33 mmol, 0.50 equiv), Cs$_2$CO$_3$ (432.7 mg, 1.33 mmol, 2 equiv) and Pd(dppf)Cl$_2$CH$_2$Cl$_2$ (70.5 mg, 0.09 mmol, 0.13 equiv) in portions at room temperature under nitrogen atmosphere. The resulted mixture was stirred for 4h at 75° C. under nitrogen atmosphere. The resulted mixture was filtered, the filter cake was washed with CH$_2$Cl$_2$ (2×20 mL). The filtrate was concentrated under reduced pressure. The residue was purified by Prep-TLC (CH$_2$Cl$_2$/MeOH 30:1) to afford methyl 3-amino-6-[1-(difluoromethyl)-6-oxo-1,6-dihydropyridin-3-yl]-5-(1,3-oxazol-2-yl)pyrazine-2-carboxylate (100 mg, 18.65%) as a yellow solid. LCMS: m/z (ESI), [M+H]$^+$=364.1. $^1$H NMR (300 MHz, DMSO-d$_6$) δ3.87 (s, 3H), 6.51 (d, J=9.7 Hz, 1H), 7.41 (s, 1H), 7.59 (dd, J=9.6, 2.5 Hz, 1H), 7.69 (s, 1H), 7.80 (d, J=2.5 Hz, 1H), 7.90 (d, J=8.8 Hz, 1H), 8.32 (d, J=0.8 Hz, 1H).

Step 2. 3-amino-6-[1-(difluoromethyl)-6-oxo-1,6-dihydropyridin-3-yl]-5-(1,3-oxazol-2-yl)pyrazine-2-carboxylic Acid To a stirred solution of methyl 3-amino-6-[1-(difluoromethyl)-6-oxo-1,6-dihydropyridin-3-yl]-5-(1,3-oxazol-2-yl)pyrazine-2-carboxylate (90 mg, 0.25 mmol, 1 equiv) in THF (15 mL) were added LiOH (11.9 mg, 0.50 mmol, 2.01 equiv) in water (1 mL) dropwise at room temperature. The resulted mixture was stirred for 3h at room temperature under air atmosphere. The mixture was neutralized to pH 6 with 1N aq. HCl and concentrated under vacuum to afford crude 3-amino-6-[1-(difluoromethyl)-6-oxo-1,6-dihydropyridin-3-yl]-5-(1,3-oxazol-2-yl)pyrazine-2-carboxylic acid (85 mg, 98.24%) as a yellow solid which was directly used to next step without further purification. LCMS: m/z (ESI), [M+H]$^+$= 350.0.

Step 3. 3-amino-6-[1-(difluoromethyl)-6-oxo-1,6-dihydropyridin-3-yl]-N-[(3-fluoropyridin-2-yl)methyl]-5-(1,3-oxazol-2-yl)pyrazine-2-carboxamide (Cmpd. 31)

To a stirred mixture of 3-amino-6-[1-(difluoromethyl)-6-oxo-1,6-dihydropyridin-3-yl]-5-(1,3-oxazol-2-yl)pyrazine-2-carboxylic acid (10 mg, 0.03 mmol, 1 equiv), DIEA (11.1 mg, 0.09 mmol, 3.00 equiv) and HATU (21.8 mg, 0.06 mmol, 2.00 equiv) in DMF (8 mL) were added 1-(3-fluoropyridin-2-yl)methanamine (5.4 mg, 0.04 mmol, 1.50 equiv) dropwise at room temperature under air atmosphere. The resulted mixture was stirred for 3h at room temperature under air atmosphere. The reaction was quenched with water at room temperature. The precipitated solids were collected by filtration and purified by Prep-TLC (CH$_2$Cl$_2$/MeOH 20:1) to afford 3-amino-6-[1-(difluoromethyl)-6-oxo-1,6-dihydropyridin-3-yl]-N-[(3-fluoropyridin-2-yl)methyl]-5-(1,3-oxazol-2-yl)pyrazine-2-carboxamide (Cmpd. 31) (30 mg, 28.64%) as a yellow solid. LCMS: m/z (ESI), [M+H]$^+$= 458.2, $^1$H NMR (300 MHz, DMSO-d$_6$) δ 9.30 (t, J=5.9 Hz, 1H), 8.35 (dd, J=4.0, 2.3 Hz, 1H), 8.30 (d, J=0.8 Hz, 1H), 8.10 (s, OH), 7.97 (d, J=2.5 Hz, 1H), 7.87 (d, J=13.8 Hz, 2H), 7.75 ? 7.64 (m, 2H), 7.41 (q, J=4.3 Hz, 2H), 6.50 (d, J=9.7 Hz, 1H), 4.68 (dd, J=5.7, 1.5 Hz, 2H).

Example 32. Preparation of 3-amino-N-[(2,6-difluorophenyl)methyl]-6-[imidazo[1,2-a]pyridin-6-yl]-5-(1,3-oxazol-2-yl)pyrazine-2-carboxamide (Cmpd. 32)

SCHEME 27

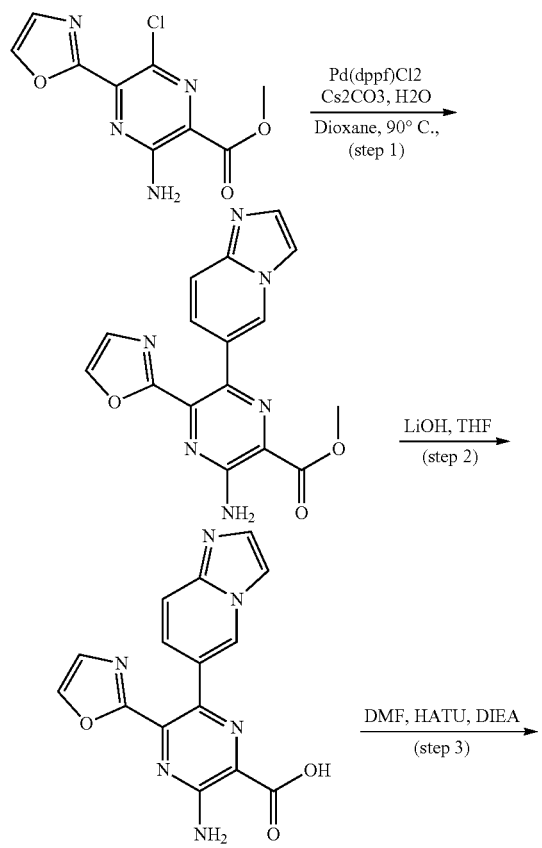

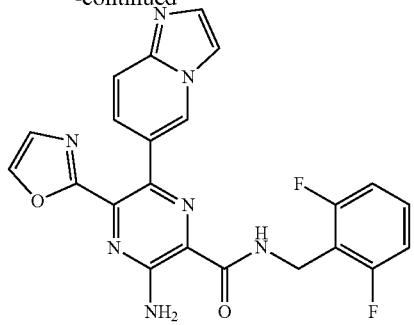

Example 32

Step 1. methyl 3-amino-6-(imidazo[1,2-a]pyridin-6-yl)-5-(oxazol-2-yl)pyrazine-2-carboxylate To a stirred mixture of methyl 3-amino-6-chloro-5-(1,3-oxazol-2-yl)pyrazine-2-carboxylate (300 mg, 1.18 mmol, 1 equiv) and 6-(4,4,5,5-tetramethyl-1,3,2-dioxaborolan-2-yl)imidazo[1,2-a]pyridine (431.4 mg, 1.77 mmol, 1.5 equiv) in dioxane (18 mL) and H$_2$O (2 mL) were added Cs$_2$CO$_3$ (767.7 mg, 2.36 mmol, 2 equiv) and Pd(dppf)Cl$_2$ (172.4 mg, 0.24 mmol, 0.2 equiv) in portions at room temperature under nitrogen atmosphere. The resulted mixture was stirred overnight at 90° C. The mixture was allowed to cool down to room temperature. The resulted mixture was filtered, the filter cake was washed with DCM (3×10 mL). The filtrate was concentrated under reduced pressure. The residue was purified by Prep-TLC (DCM/MeOH 20:1) to afford methyl 3-amino-6-[imidazo[1,2-a]pyridin-6-yl]-5-(1,3-oxazol-2-yl)pyrazine-2-carboxylate (165 mg, 41.6%) as a yellow solid. LCMS: m/z (ESI), [M+H]$^+$=337.2. $^1$H NMR (DMSO-d$_6$, 400 MHz) δ 3.9 (3H, s), 7.1 (1H, dd, J=9.4, 1.8 Hz), 7.4 (1H, s), 7.5 (1H, d, J=9.3 Hz), 7.6 (1H, d, J=1.2 Hz), 7.7 (1H, d, J=19.0 Hz), 8.0 (1H, d, J=1.1 Hz), 8.3 (1H, s), 8.7 (1H, t, J=1.4 Hz)

Step 2. 3-amino-6-(imidazo[1,2-a]pyridin-6-yl)-5-(oxazol-2-yl)pyrazine-2-carboxylic Acid To a stirred solution of methyl 3-amino-6-[imidazo[1,2-a]pyridin-7-yl]-5-(1,3-oxazol-2-yl)pyrazine-2-carboxylate (160 mg, 0.48 mmol, 1 equiv) in THF (20 mL) and water (2 mL), LiOH (13.7 mg, 0.57 mmol, 1.2 equiv) was added in portions at room temperature. The resulted mixture was stirred for 4 hours at room temperature and adjusted PH=5 with 1N aq.HCl. The resulted mixture was concentrated under vacuum and used to the next step directly without further purification. LCMS: m/z (ESI), [M+H]$^+$=323.2.

Step 3. 3-amino-N-[(2,6-difluorophenyl)methyl]-6-[imidazo[1,2-a]pyridin-6-yl]-5-(1,3-oxazol-2-yl)pyrazine-2-carboxamide (Cmpd. 32)

To a stirred mixture of 3-amino-6-[imidazo[1,2-a]pyridin-6-yl]-5-(1,3-oxazol-2-yl)pyrazine-2-carboxylic acid (80 mg, 0.25 mmol, 1 equiv) and 1-(2,6-difluorophenyl)methanamine (71.1 mg, 0.50 mmol, 2 equiv) in DMF (5 mL) were added HATU (377.5 mg, 1 mmol, 4 equiv) and DIEA (128.3 mg, 1 mmol, 4 equiv) in portions at room temperature under air atmosphere. The resulted mixture was stirred for 0.5 h at room temperature. The resulted mixture was quenched with water, the resulting solid was collected by filtration and slurried with MeOH (5 mL). This resulted solid was collected by filtration and dried under vacuum to afford 3-amino-N-[(2,6-difluorophenyl)methyl]-6-[imidazo[1,2-a]pyridin-6-yl]-5-(1,3-oxazol-2-yl)pyrazine-2-carboxamide (Cmpd. 32) (30 mg, 25.8%) as a yellow solid. LCMS: m/z (ESI), [M+H]$^+$=448.2. $^1$H NMR (DMSO-d$_6$, 400 MHz) δ 4.6 (2H, d, J=5.8 Hz), 7.1 (2H, t, J=7.9 Hz), 7.2 (1H, dd, J=9.4, 1.8 Hz), 7.3-7.4 (2H, m), 7.5 (1H, d, J=9.3 Hz), 7.6 (1H, d, J=1.3 Hz), 7.9 (3H, d, J=23.3 Hz), 8.3 (1H, s), 8.7 (1H, t, J=1.3 Hz), 9.2 (1H, t, J=5.9 Hz).

Example 33. Preparation of 3-amino-N-(3-(dimethylamino)-2-fluorobenzyl)-6-(1-methyl-6-oxo-1,6-dihydropyridin-3-yl)-5-(oxazol-2-yl)pyrazine-2-carboxamide (Cmpd. 33)

SCHEME 28

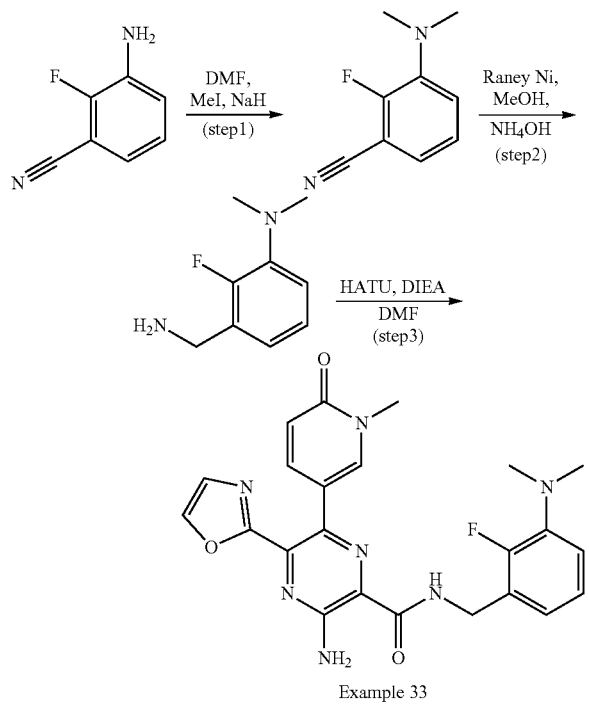

Example 33

Step 1. 3-(dimethylamino)-2-fluorobenzonitrile

To a stirred mixture of 3-amino-2-fluorobenzonitrile (300 mg, 2.20 mmol, 1 equiv) and NaH (158.7 mg, 6.61 mmol, 3.00 equiv) in DMF (10 mL) was added iodomethane (938.4 mg, 6.61 mmol, 3.00 equiv) in portions at room temperature under air atmosphere. The resulted mixture was stirred for 4 hours at room temperature. The resulted mixture was quenched with water (30 mL) and extracted with EtOAc (3×50 mL). The combined organic layers were washed with water (3×10 mL), dried over anhydrous Na$_2$SO$_4$. After filtration, the filtrate was concentrated under reduced pressure and purified by Prep-TLC (PE/EtOAc 5:1) to afford 3-(dimethylamino)-2-fluorobenzonitrile (160 mg, 44.2%) as a light yellow crude solid. LCMS: m/z (ESI), [M+H]$^+$=165.2. $^1$H NMR (Chloroform-d, 400 MHz) δ 2.9 (6H, d, J=1.3 Hz), 7.1-7.1 (3H, m).

Step 2. 3-(aminomethyl)-2-fluoro-N,N-dimethylaniline

To a stirred mixture of 3-(dimethylamino)-2-fluorobenzonitrile (160 mg, 0.97 mmol, 1 equiv) and Raney Ni (16.7 mg, 0.19 mmol, 0.20 equiv) in MeOH (20 mL) was added NH$_4$OH (2 mL) in portions at room temperature. The resulted mixture was stirred for additional 1 h at room temperature under hydrogen atmosphere. The resulted mixture was filtered, the filter cake was washed with MeOH (3×10 mL). The filtrate was concentrated under reduced pressure. The resulting crude product was directly used into the next step without further purification. LCMS: m/z (ESI), [M+H]$^+$=169.0.

Step 3. 3-amino-N-(3-(dimethylamino)-2-fluorobenzyl)-6-(1-methyl-6-oxo-1,6-dihydropyridin-3-yl)-5-(oxazol-2-yl)pyrazine-2-carboxamide (Cmpd. 33)

To a stirred mixture of 3-amino-6-(1-methyl-6-oxo-1,6-dihydropyridin-3-yl)-5-(1,3-oxazol-2-yl)pyrazine-2-carboxylic acid (80 mg, 0.26 mmol, 1 equiv) and 3-(aminomethyl)-2-fluoro-N,N-dimethylaniline (85.9 mg, 0.5 mmol, 2.0 equiv) in DMF (5 mL) were added HATU (194.2 mg, 0.51 mmol, 2.00 equiv) and DIEA (132.0 mL, 1.02 mmol, 4.00 equiv) in portions at room temperature under ir atmosphere. The resulted mixture was stirred for 3 hours at room temperature and concentrated under reduced pressure. The residue was purified by Prep-TLC (DCM/MeOH 20:1) to afford crude product 3-amino-N-(3-(dimethylamino)-2-fluorobenzyl)-6-(1-methyl-6-oxo-1,6-dihydropyridin-3-yl)-5-(oxazol-2-yl)pyrazine-2-carboxamide (100 mg) as a Brown yellow oil. The crude product (100 mg) was purified by Prep-HPLC with the following conditions (Column: Xselect CSH OBD Column 30*150 mm 5 um; Mobile Phase A: Water (0.05% TFA), Mobile Phase B: ACN; Flow rate: 60 mL/min; Gradient: 16% B to 27% B in 7 min; 254; 220 nm; Rt: 4.40 min) to afford 3-amino-N-(3-(dimethylamino)-2-fluorobenzyl)-6-(1-methyl-6-oxo-1,6-dihydropyridin-3-yl)-5-(oxazol-2-yl)pyrazine-2-carboxamide (Cmpd. 33) (44 mg, 37.06%) as a brown yellow solid. LCMS: m/z (ESI), [M+H]$^+$=464.2. $^1$H NMR (DMSO-d$_6$, 400 MHz) δ 2.8 (5H, s), 4.6 (2H, d, J=6.3 Hz), 6.3 (1H, d, J=9.4 Hz), 6.9-7.0 (2H, m), 7.1 (1H, t, J=7.8 Hz), 7.4-7.4 (2H, m), 7.8 (1H, s), 8.0 (1H, d, J=2.6 Hz), 8.3 (1H, d, J=0.8 Hz), 9.3 (1H, t, J=6.4 Hz).

Example 35. Preparation of 3-amino-N-(2,6-difluorobenzyl)-6-(1-methyl-6-oxo-1,6-dihydropyridin-3-yl)-5-(2H-1,2,3-triazol-2-yl)pyrazine-2-carboxamide (Cmpd. 35)

SCHEME 29

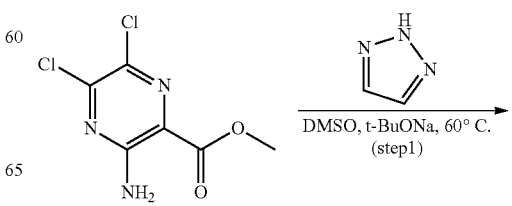

-continued

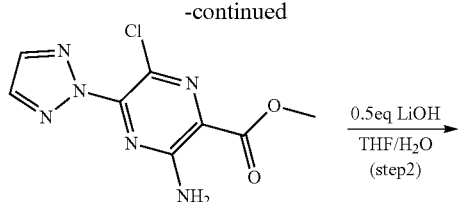

0.5eq LiOH
THF/H₂O
(step2)

1

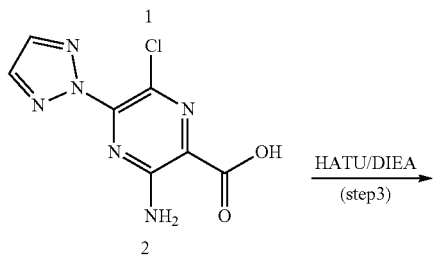

HATU/DIEA
(step3)

2

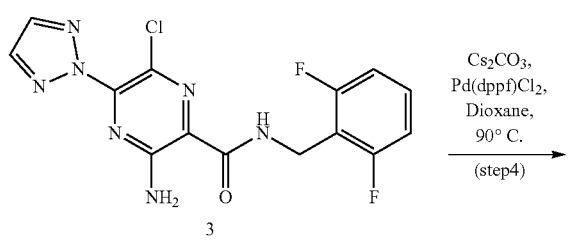

Cs₂CO₃,
Pd(dppf)Cl₂,
Dioxane,
90° C.
(step4)

3

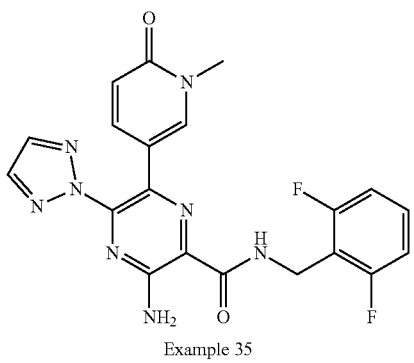

Example 35

Step 1. methyl 3-amino-6-chloro-5-(2H-1,2,3-triazol-2-yl)pyrazine-2-carboxylate

To a stirred solution of methyl 3-amino-5,6-dichloropyrazine-2-carboxylate (2.5 g, 11.26 mmol, 1 equiv) and 2H-1,2,3-triazole (1555.4 mg, 22.52 mmol, 2 equiv) in DMSO (50 mL) was added t-BuONa (1082.1 mg, 11.26 mmol, 1 equiv) in portions at RT. The resulting mixture was stirred for 3 hs at 60° C. in oil bath, cooled to RT and quenched with water (200 mL). The resulting solid was collected by filtration, dried under vacuum and purified by silica gel column (DCM:EA 0-20%) to afford 1.6 g crude product. The crude product was further purified by prep-TLC (DCM:EA 6:1) to afford methyl 3-amino-6-chloro-5-(2H-1,2,3-triazol-2-yl)pyrazine-2-carboxylate (800 mg, 29%). $^1$H NMR (300 MHz, Chloroform-d) δ 4.06 (s, 3H), 8.03 (s, 2H).

Step 2. 3-amino-6-chloro-5-(2H-1,2,3-triazol-2-yl)pyrazine-2-carboxylic Acid

To a stirred mixture of methyl 3-amino-6-chloro-5-(2H-1,2,3-triazol-2-yl)pyrazine-2-carboxylate (200 mg, 0.79 mmol, 1 equiv) in THF (50 mL) was added LiOH (38.0 mg, 1.59 mmol, 2.02 equiv) in water (2 mL) dropwise at room temperature. The resulted mixture was stirred for 3h at 40° C. The resulted mixture was concentrated to 10 mL under vacuum. The mixture was acidified to pH 6 with HCl (aq.). The precipitated solids were collected by filtration and dried under vacuum to afford 3-amino-6-chloro-5-(2H-1,2,3-triazol-2-yl)pyrazine-2-carboxylic acid (120 mg, 52.91%) as a yellow solid which was used to next step without further purification. LCMS: m/z (ESI), [M+H]⁺=240.9.

Step 3. 3-amino-6-chloro-N-[(2,6-difluorophenyl)methyl]-5-(2H-1,2,3-triazol-2-yl)pyrazine-2-carboxamide To a stirred solution of 3-amino-6-chloro-5-(2H-1,2,3-triazol-2-yl)pyrazine-2-carboxylic acid (130 mg, 0.54 mmol, 1 equiv), DIEA (209.5 mg, 1.62 mmol, 3.00 equiv) and 1-(2,6-difluorophenyl)methanamine (116.0 mg, 0.81 mmol, 1.50 equiv) in DMF (10 mL) were added 50% W T₃P (687 mg, 1.08 mmol, 2.00 equiv) dropwise at room temperature. The resulted mixture was stirred for 3h at room temperature. The reaction was quenched with water at room temperature. The precipitated solids were collected by filtration and purified by Prep-TLC (CH₂Cl₂/MeOH 20:1) to afford 3-amino-6-chloro-N-[(2,6-difluorophenyl)methyl]-5-(2H-1,2,3-triazol-2-yl)pyrazine-2-carboxamide (110 mg, 55.67%) as a yellow solid. LCMS: m/z (ESI), [M+H]⁺= 366.0. $^1$H NMR (300 MHz, Chloroform-d) δ 8.00 (s, 3H), 7.38-7.30 (m, 1H), 6.98 (t, J=7.8 Hz, 2H), 4.77 (d, J=6.0 Hz, 2H).

Step 4. 3-amino-N-[(2,6-difluorophenyl)methyl]-6-(1-methyl-6-oxo-1,6-dihydropyridin-3-yl)-5-(2H-1,2,3-triazol-2-yl)pyrazine-2-carboxamide (Cmpd. 35)

To a stirred mixture of 3-amino-6-chloro-N-[(2,6-difluorophenyl)methyl]-5-(2H-1,2,3-triazol-2-yl)pyrazine-2-carboxamide (100 mg, 0.27 mmol, 1 equiv), Cs₂CO₃ (267.3 mg, 0.82 mmol, 3 equiv) and 1-methyl-5-(4,4,5,5-tetramethyl-1,3,2-dioxaborolan-2-yl)-1,2-dihydropyridin-2-one (128.6 mg, 0.55 mmol, 2.00 equiv) in 1,4-dioxane (20 mL) were added Pd(dppf)Cl₂CH₂Cl₂ (44.7 mg, 0.05 mmol, 0.2 equiv) in portions at room temperature under nitrogen atmosphere. The resulted mixture was stirred for 3h at 90° C. under nitrogen atmosphere. The resulted mixture was filtered. The filtrate was concentrated under reduced pressure. The residue was purified by Prep-TLC (CH₂Cl₂/MeOH 20:1) to afford 3-amino-N-[(2,6-difluorophenyl)methyl]-6-(1-methyl-6-oxo-1,6-dihydropyridin-3-yl)-5-(2H-1,2,3-triazol-2-yl)pyrazine-2-carboxamide (Cmpd. 35) (40 mg, 33.04%) as a yellow solid. LCMS: m/z (ESI), [M+H]⁺ =439.2, $^1$H NMR (300 MHz, DMSO-d₆) δ 9.18 (t, J=5.9 Hz, 1H), 8.13 (s, 2H), 7.93 (s, 2H), 7.76 (d, J=2.6 Hz, 1H), 7.48-7.25 (m, 1H), 7.08 (t, J=8.0 Hz, 2H), 6.73 (dd, J=9.5, 2.7 Hz, 1H), 6.20 (d, J=9.5 Hz, 1H), 4.61 (d, J=5.9 Hz, 2H), 3.39 (s, 3H).

243

Example 36. Preparation of 3-amino-N-((3-(hydroxymethyl)pyridin-2-yl)methyl)-6-(1-methyl-6-oxo-1,6-dihydropyridin-3-yl)-5-(oxazol-2-yl)pyrazine-2-carboxamide (Cmpd. 36)

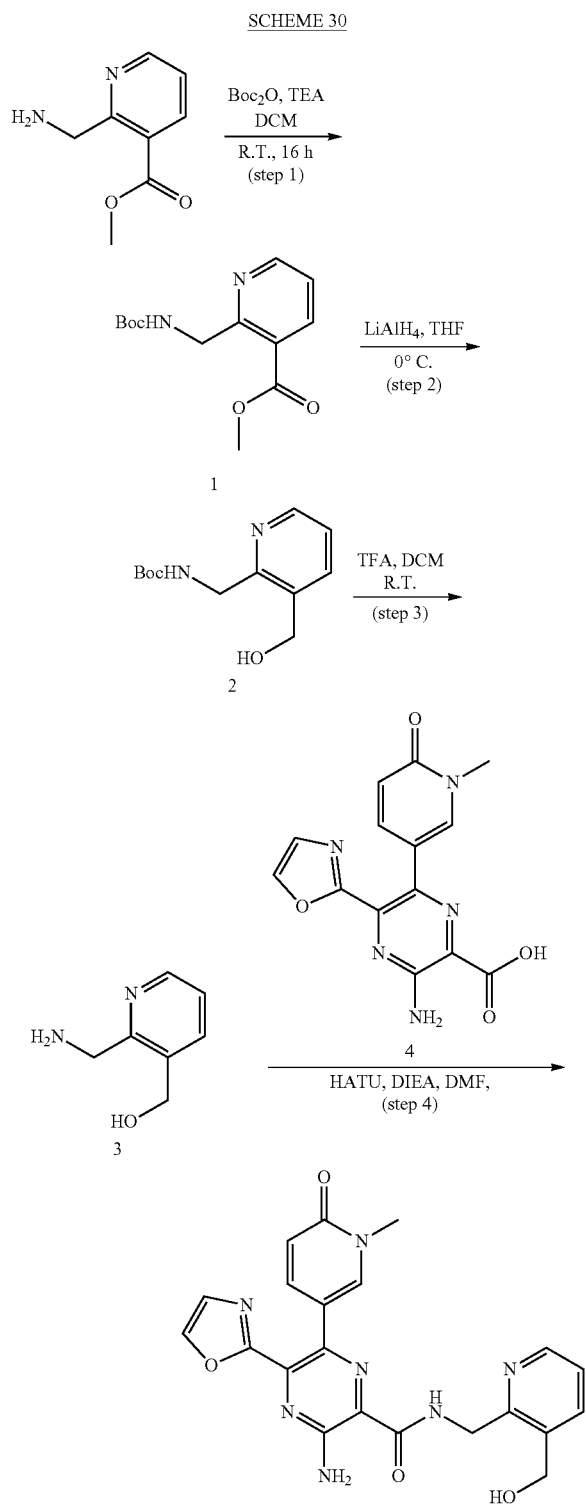

244

Step 1. methyl 2-(((tert-butoxycarbonyl)amino)methyl)nicotinate

To a mixture of methyl 2-(aminomethyl)pyridine-3-carboxylate (1 g, 6.02 mmol, 1 equiv) and TEA (1826.8 mg, 18.05 mmol, 3.0 equiv) in DCM (30 mL) in 250-mL round-bottom flask, was added $Boc_2O$ (1379.0 mg, 6.32 mmol, 1.05 equiv) in portions at room temperature. The resulting solution was stirred for 16 hours at room temperature. The resulting solution was diluted with 50 mL of water. The resulting solution was extracted with 3×50 mL of dichloromethane dried over anhydrous sodium sulfate and concentrated. This resulted in 1.5 g (93.61%) of methyl 2-([[(tert-butoxy)carbonyl]amino]methyl)pyridine-3-carboxylate as a solid. LCMS: m/z (ESI), [M+H]$^+$=267.1.

Step 2. tert-butyl ((3-(hydroxymethyl)pyridin-2-yl)methyl)carbamate

Into a 50-mL round-bottom flask, was placed a solution of methyl 2-([[(tert-butoxy)carbonyl]amino]methyl)pyridine-3-carboxylate (100 mg, 0.38 mmol, 1 equiv) in THF (5 mL). This was followed by the addition of LiAlH$_4$ (42.8 mg, 1.13 mmol, 3 equiv) in portions at 0° C. The resulting solution was stirred for 1 hour at 0° ° C. in a water/ice bath. The reaction was then quenched by the addition of 0.043 mL of water and 0.172 mL NaOH (15% aq). The resulting solids were filtered out. The filtrate was concentrated and resulted in 85 mg (94.9%) of tert-butyl N-[[3-(hydroxymethyl)pyridin-2-yl]methyl]carbamate as a solid. LCMS: m/z (ESI), [M+H]$^+$=239.2. $^1$H NMR (300 MHz, DMSO-d$_6$) δ 1.40 (9H, s), 4.28 (2H, d), 4.58 (2H, d), 5.31-5.33 (1H, m) 7.00 (1H, s), 7.29-7.32 (1H, m), 7.77-7.79 (1H, m).

Step 3. (2-(aminomethyl)pyridin-3-yl)methanol

Into a 10-mL round-bottom flask, was placed a solution of tert-butyl N-[[3-(hydroxymethyl)pyridin-2-yl]methyl]carbamate (50 mg, 0.21 mmol, 1 equiv), TFA (1 mL) in DCM (3 mL). The resulting solution was stirred for 1 hour at room temperature. The resulted mixture was concentrated and resulted in 28 mg (96.6%) of [2-(aminomethyl)pyridin-3-yl]methanol TFA salt as a solid. LCMS: m/z (ESI), [M+H]$^+$= 139.3. $^1$H NMR (300 MHz, DMSO-d$_6$) δ 4.25 (2H, m) 4.58-4.60 (2H, m), 7.44 (1H, m), 7.86-7.88 (1H, m), 8.25 (3H, s), 8.54-8.56 (1H, m).

Step 4. 3-amino-N-((3-(hydroxymethyl)pyridin-2-yl)methyl)-6-(1-methyl-6-oxo-1,6-dihydropyridin-3-yl)-5-(oxazol-2-yl)pyrazine-2-carboxamide (Cmpd. 36)

To a mixture of [2-(aminomethyl)pyridin-3-yl]methanol (52.9 mg, 0.38 mmol, 2.0 equiv), 3-amino-6-(1-methyl-6-oxo-1,6-dihydropyridin-3-yl)-5-(1,3-oxazol-2-yl)pyrazine-2-carboxylic acid (60 mg, 0.19 mmol, 1 equiv) in DMF (15 mL) in a 50-mL round-bottom flask, HATU (87.4 mg, 0.23 mmol, 1.2 equiv) and DIEA (74.3 mg, 0.57 mmol, 3.0 equiv) were added at room temperature. The resulting solution was stirred for 1 hour at room temperature. The reaction was then quenched by the addition of 20 mL of water. The resulting solution was extracted with 3×25 mL of ethyl acetate and the organic layers combined. The resulted mixture was washed with 1×10 mL of saturated salt water. The resulted mixture was concentrated. The crude product was purified by Prep-HPLC with the following conditions (Column: XBridge Prep C18 OBD Column, 5 um, 19*150 mm; Mobile Phase A: water (10 MMOL/L NH₄HCOO₃+0.1% NH₃.H₂O), Mobile Phase B: ACN; Flow rate: 20 mL/min; Gradient: 30% B to 30% B in 7 min; 254, 220 nm; Rt: 6.35 min). This resulted in 20 mg (24.09%) of 3-amino-N-[[3-(hydroxymethyl)pyridin-2-yl]methyl]-6-(1-methyl-6-oxo-1,6-dihydropyridin-3-yl)-5-(1,3-oxazol-2-yl)pyrazine-2-carboxamide (Cmpd. 36) as a yellow solid. LCMS: m/z (ESI), [M+H]⁺= 434.2. ¹HNMR (300 MHz, DMSO-d₆) δ 3.47 (3H, s), 4.65 (4H, d), 5.42 (1H, d), 6.32-6.36 (1H, m), 7.29-7.34 (2H, m), 7.35-7.41 (1H, m), 7.75-7.81 (3H, m), 8.01 (1H, s), 8.30-8.43 (1H, s), 8.35-8.38 (1H, m), 9.36-9.38 (1H, m).

Compounds listed in the table below were prepared using methods described in Cmpd. 36.

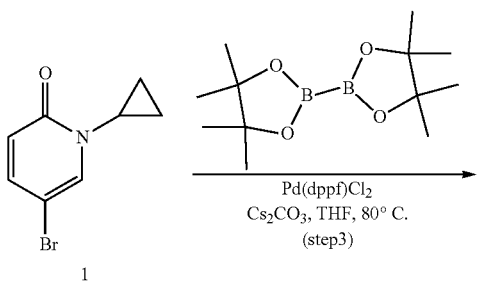

| Example/Cmpd number | Structure | LCMS [M + H]⁺ | ¹H NMR |
|---|---|---|---|
| 37 | 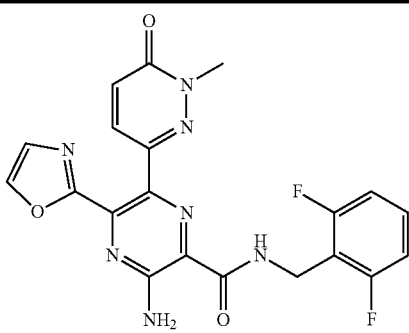 | 440.1 | ¹H NMR (400 MHz, DMSO-d₆) δ 3.40 (3H, s), 4.60 (2H, d), 6.98-7.16 (3H, m), 7.35-7.47 (2H, m), 8.07 (2H, s), 8.25 (2H, d), 9.29 (1H, t). |

Example 38. Preparation of 3-amino-6-(1-cyclopropyl-6-oxo-1,6-dihydropyridin-3-yl)-N-[(2,6-difluorophenyl)methyl]-5-(1,3-oxazol-2-yl)pyrazine-2-carboxamide (Cmpd. 38)

SCHEME 31

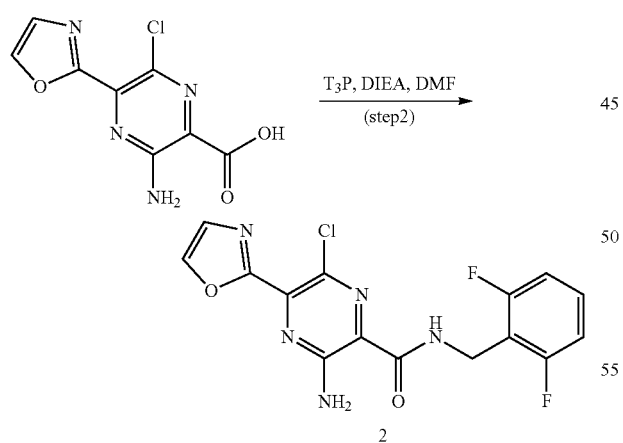

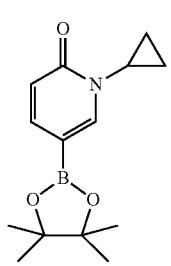

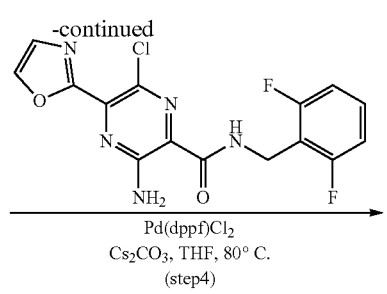

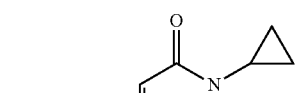

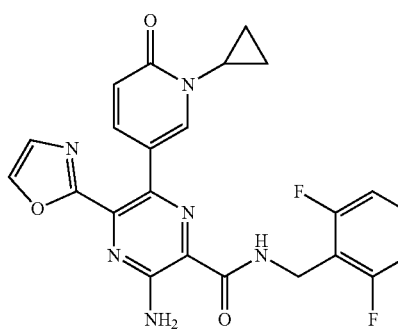

Example 38

Step 1.
5-bromo-1-cyclopropyl-1,2-dihydropyridin-2-one

To a mixture of 5-bromo-1,2-dihydropyridin-2-one (2 g, 11.49 mmol, 1 equiv), cyclopropylboronic acid (2.0 g, 23.28 mmol, 2.03 equiv) and CU (AcO)₂ (2.1 g, 0.01 mmol, 1 equiv) in CH₂ClCH₂Cl (50 mL), Na₂CO₃ (2.4 g, 0.02 mmol, 2 equiv) and 4 4-DI-TERT-BUTYL-2 2-DIPYRIDYL (3.1 g, 0.01 mmol, 1 equiv) were added at room temperature under nitrogen atmosphere. The resulted mixture was stirred for 12 hours at 70° C. under nitrogen atmosphere. The solvent was removed under reduced pressure. The residue was purified by silica gel column chromatography, eluted with $CH_2Cl_2$/MeOH (20:1) to afford 5-bromo-1-cyclopropyl-1,2-dihydropyridin-2-one (600 mg, 24.39%) as a white solid. LCMS: m/z (ESI), [M+H]$^+$=213.9, 215.9. $^1$H NMR: (300 MHz, $CDCl_3$) δ 0.86 (tdd, 2H), 1.13 (m, 2H), 3.31 (tt, 1H), 6.48 (m, 1H), 7.34 (m, 2H).

Step 2. 3-amino-6-chloro-N-[(2,6-difluorophenyl) methyl]-5-(1,3-oxazol-2-yl)pyrazine-2-carboxamide To a solution of 3-amino-6-chloro-5-(1,3-oxazol-2-yl) pyrazine-2-carboxylic acid (50 mg, 0.21 mmol, 1 equiv) and 1-(2,6-difluorophenyl)methanamine (44.6 mg, 0.31 mmol, 1.5 equiv) in DMF (5 mL), $T_3P$ (132.2 mg, 0.42 mmol, 2.00 equiv) and DIEA (80.6 mg, 0.62 mmol, 3 equiv) were added at room temperature. The resulted mixture was stirred for 2h at room temperature under air atmosphere and concentrate under vacuum. The residue was purified by Prep-TLC ($CH_2Cl_2$/MeOH 20:1) to afford 3-amino-6-chloro-N-[(2,6-difluorophenyl)methyl]-5-(1,3-oxazol-2-yl)pyrazine-2-carboxamide (120 mg, 39.47%) as a yellow solid. LCMS: m/z (ESI), [M+H]$^+$=366.0. $^1$H NMR: (300 MHz, DMSO-$d_6$) δ 4.53 (d, 2H), 7.06 (d, 2H), 7.37 (q, 1H), 7.55 (s, 1H), 7.85 (s, 2H), 8.39 (s, 1H), 9.08 (t, 1H).

Step 3. 1-cyclopropyl-5-(4,4,5,5-tetramethyl-1,3,2-dioxaborolan-2-yl)-1,2-dihydropyridin-2-one To a solution of 5-bromo-1-cyclopropyl-1,2-dihydropyridin-2-one (100 mg, 0.47 mmol, 1 equiv) and 4,4,5,5-tetramethyl-2-(4,4,5,5-tetramethyl-1,3,2-dioxaborolan-2-yl)-1,3,2-dioxaborolane (177.9 mg, 0.70 mmol, 1.50 equiv) in THF (10 mL) were added KOAc (137.5 mg, 1.40 mmol, 3.00 equiv) and Pd(dppf)Cl$_2$CH$_2$Cl$_2$ (38.1 mg, 0.05 mmol, 0.1 equiv) under atmosphere at room temperature. The mixture was stirred for 2 hours at 80° C. under nitrogen atmosphere. This resulting solution of 1-cyclopropyl-5-(4,4,5,5-tetramethyl-1,3,2-dioxaborolan-2-yl)-1,2-dihydropyridin-2-one in THF (10 mL) was used into the next step directly without further purification. LCMS: m/z (ESI), [M+H]$^+$=262.1.

Step 4. 3-amino-6-(1-cyclopropyl-6-oxo-1,6-dihydropyridin-3-yl)-N-[(2,6-difluorophenyl) methyl]-5-(1,3-oxazol-2-yl)pyrazine-2-carboxamide (Cmpd. 38)

To a solution of 1-cyclopropyl-5-(4,4,5,5-tetramethyl-1,3,2-dioxaborolan-2-yl)-1,2-dihydropyridin-2-one (100 mg, 0.38 mmol, 1 equiv) in THF (10 mL), was added 3-amino-6-chloro-N-[(2,6-difluorophenyl)methyl]-5-(1,3-oxazol-2-yl)pyrazine-2-carboxamide (280.1 mg, 0.77 mmol, 2 equiv), Cs$_2$CO$_3$ (249.5 mg, 0.77 mmol, 2.00 equiv) and Pd(dppf) Cl$_2$CH$_2$Cl$_2$ (31.3 mg, 0.04 mmol, 0.1 equiv) under nitrogen atmosphere. The mixture was stirring for 2 hours at 80° C. under a nitrogen atmosphere and concentrated under vacuum. The residue was purified by Prep-TLC (CH$_2$Cl$_2$/MeOH 20:1) to afford 3-amino-6-(1-cyclopropyl-6-oxo-1,6-dihydropyridin-3-yl)-N-[(2,6-difluorophenyl)methyl]-5-(1,3-oxazol-2-yl)pyrazine-2-carboxamide (Cmpd. 38) (20 mg, 11.25%) as a yellow solid. LCMS: m/z (ESI), [M+H]$^+$= 465.2. $^1$H NMR: (300 MHz, MeOD) δ 0.93 (dd, 2H), 1.12 (m, 2H), 2.00 (s, 1H), 4.73 (s, 2H), 6.52 (d, 1H), 7.01 (t, 2H), 7.36 (m, 1H), 7.56 (dd, 1H), 7.84 (d, 1H), 8.08 (d, 1H).

Example 39. Preparation of 3-amino-N-[[2-fluoro-6-(morpholin-4-yl)phenyl]methyl]-6-(1-methyl-6-oxo-1,6-dihydropyridin-3-yl)-5-(1,3-oxazol-2-yl) pyrazine-2-carboxamide (Cmpd. 39)

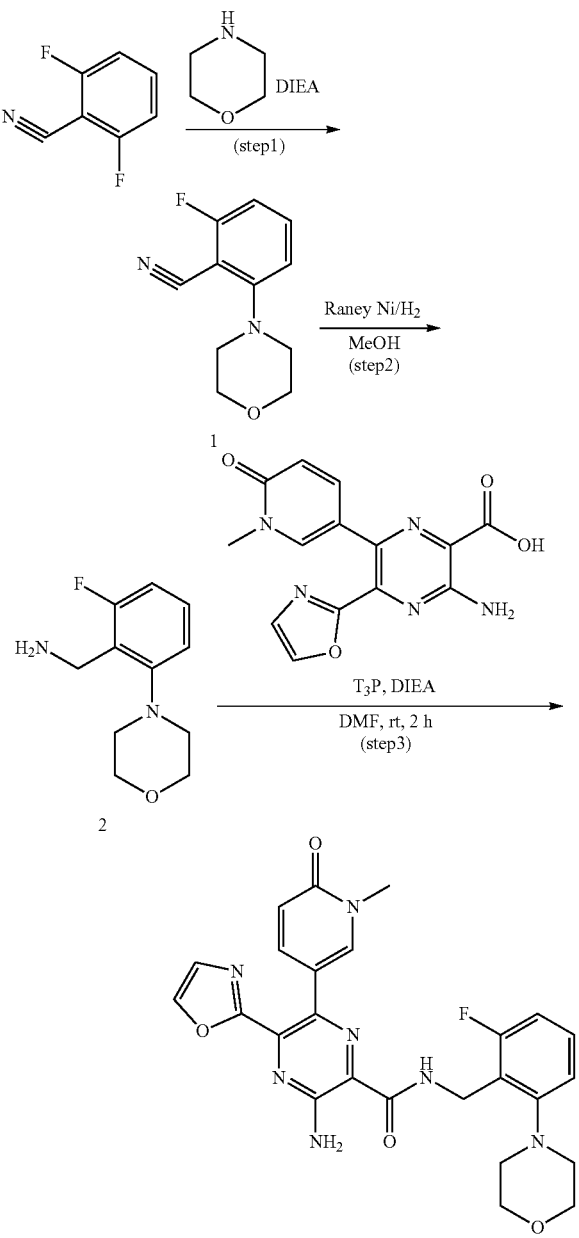

Example 39

Step 1. 2-fluoro-6-(morpholin-4-yl)benzonitrile

To a stirred mixture of 2,6-difluorobenzonitrile (1000 mg, 7.19 mmol, 1 equiv) and morpholine (939.5 mg, 10.78 mmol, 1.5 equiv) in DMSO (10 mL) was added DIEA (1858.2 mg, 14.38 mmol, 2.00 equiv) in portions at room temperature. The resulted mixture was stirred for 2.5 h at 80° C. under air atmosphere. The resulted mixture was diluted with water (200 mL). The resulted mixture was extracted with EtOAc (2×300 mL). The combined organic layers were washed with water (2×100 mL), dried over anhydrous Na$_2$SO$_4$. After filtration, the filtrate was concentrated under reduced pressure to afford 2-fluoro-6-(morpholin-4-yl)benzonitrile (637 mg, 42.97%) as a white solid. LCMS: m/z (ESI), [M+H]$^+$=207.0. $^1$H NMR (400 MHz, Chloroform-d) δ 3.21-3.28 (m, 4H), 3.85-3.92 (m, 4H), 6.78 (dt, J=8.4, 4.2 Hz, 2H), 7.47 (td, J=8.4, 6.6 Hz, 1H).

Step 2. 1-[2-fluoro-6-(morpholin-4-yl)phenyl]methanamine

To a solution of 2-fluoro-6-(morpholin-4-yl)benzonitrile (200 mg, 0.97 mmol, 1 equiv) in MeOH, Raney Ni (166.2 mg, 1.94 mmol, 2 equiv) was added at room temperature. The resulted mixture was stirred for 1.5h at room temperature under hydrogen atmosphere. The resulted mixture was filtered, the filter cake was washed with MeOH (2×10 mL). The filtrate was concentrated under reduced pressure to afford 1-[2-fluoro-6-(morpholin-4-yl)phenyl]methanamine (150 mg, 73.56%) as a white oil which was used in the next step directly without further purification. LCMS: m/z (ESI), [M+H]$^+$=211.2.

Step 3. 3-amino-N-[[2-fluoro-6-(morpholin-4-yl)phenyl]methyl]-6-(1-methyl-6-oxo-1,6-dihydropyridin-3-yl)-5-(1,3-oxazol-2-yl)pyrazine-2-carboxamide (Cmpd. 39)

To a stirred mixture of 3-amino-6-(1-methyl-6-oxo-1,6-dihydropyridin-3-yl)-5-(1,3-oxazol-2-yl)pyrazine-2-carboxylic acid (200 mg, 0.64 mmol, 1 equiv) and 1-[2-fluoro-6-(morpholin-4-yl)phenyl]methanamine (134.2 mg, 0.64 mmol, 1 equiv) in DMF (10 mL) were added T$_3$P (812.5 mg, 2.55 mmol, 4 equiv) and DIEA (247.5 mg, 1.92 mmol, 3 equiv) in portions at room temperature under air atmosphere. The resulted mixture was stirred for 2 hours at room temperature under air atmosphere. The resulted mixture was poured into water (30 mL). The resulting solid was collected by filtration and slurried with MeOH (10 mL). The resulting solid was collected by filtration and dried under reduced pressure to afford 3-amino-N-[[2-fluoro-6-(morpholin-4-yl)phenyl]methyl]-6-(1-methyl-6-oxo-1,6-dihydropyridin-3-yl)-5-(1,3-oxazol-2-yl)pyrazine-2-carboxamide (Cmpd. 39) (120 mg, 37.18%) as a yellow solid. LCMS: m/z (ESI), [M+H]$^+$=506.1. $^1$H NMR (400 MHz, DMSO-d$_6$) δ 2.88 (t, J=4.5 Hz, 4H), 3.34 (s, 3H), 3.64 (t, J=4.5 Hz, 4H), 4.72 (d, J=5.8 Hz, 2H), 6.32 (d, J=9.4 Hz, 1H), 7.00 (dd, J=9.8, 8.4 Hz, 1H), 7.07 (d, J=8.1 Hz, 1H), 7.29 7.43 (m, 3H), 7.83 (s, 2H), 7.97 (d, J=2.6 Hz, 1H), 8.30 (d, J=0.8 Hz, 1H), 9.14 (t, J=5.8 Hz, 1H).

Example 40. Preparation of 3-amino-N-(1-(2,6-difluorophenyl)ethyl)-6-(1-methyl-6-oxo-1,6-dihydropyridin-3-yl)-5-(oxazol-2-yl)pyrazine-2-carboxamide (Cmpd. 40)

SCHEME 33

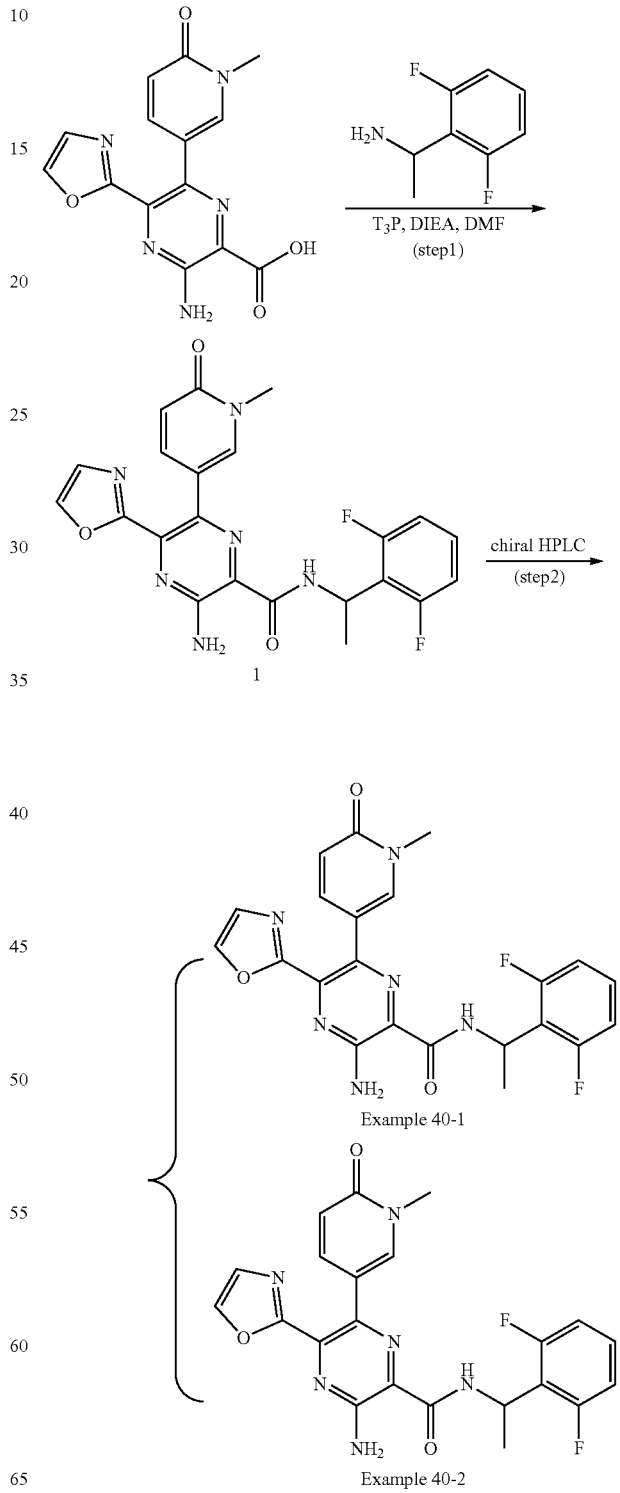

251

Step 1. 3-amino-N-[1-(2,6-difluorophenyl)ethyl]-6-(1-methyl-6-oxo-1,6-dihydropyridin-3-yl)-5-(1,3-oxazol-2-yl)pyrazine-2-carboxamide To a stirred mixture of 3-amino-6-(1-methyl-6-oxo-1,6-dihydropyridin-3-yl)-5-(1,3-oxazol-2-yl)pyrazine-2-carboxylic acid (100 mg, 0.32 mmol, 1 equiv), T₃P (242.7 mg, 0.76 mmol, 2.39 equiv) and DIEA (123.8 mg, 0.96 mmol, 3 equiv) in DMF (10 mL) was added 1-(2,6-difluorophenyl)ethan-1-amine (75.3 mg, 0.48 mmol, 1.5 equiv) in portions at room temperature under air atmosphere. The resulted mixture was stirred for 1 h at room temperature under air atmosphere. The resulted mixture was poured into the water (30 mL). The resulting solid was collected by filtration and slurried MeOH (10 mL). The resulting solid was collected by filtration and dried undue vacuum to afford 3-amino-N-[1-(2,6-difluorophenyl)ethyl]-6-(1-methyl-6-oxo-1,6-dihydropyridin-3-yl)-5-(1,3-oxazol-2-yl)pyrazine-2-carboxamide (40 mg, 27.42%) as a yellow solid. LCMS: m/z (ESI), [M+H]⁺=453.0.

Step 2. 3-amino-N-(1-(2,6-difluorophenyl)ethyl)-6-(1-methyl-6-oxo-1,6-dihydropyridin-3-yl)-5-(oxazol-2-yl)pyrazine-2-carboxamide (Cmpd. 40-1 and Cmpd. 40-2)

The racemate product (60 mg) was purified by preparative chiral-HPLC on a as eluent. Column: CHIRALPAK IG, 20*250 mm, 5 um; Mobile Phase A:Hex:DCM=5:1 (10 mm NH₃-MEOH)-HPLC, Mobile Phase B: EtOH-HPLC; Flow rate: 16 mL/min; Gradient: 50 B to 50 B in 16 min; 220/254 nm; RT1:10.8; RT2:12.8. This resulted in 3-amino-N-(1-(2,6-difluorophenyl)ethyl)-6-(1-methyl-6-oxo-1,6-dihydropyridin-3-yl)-5-(oxazol-2-yl)pyrazine-2-carboxamide (isomer 1) (Cmpd. 40-1) (15 mg) as a yellow solid. LCMS: m/z (ESI), [M+H]⁺=453. ¹H NMR: (400 MHz, MeOD) δ 1.62 (d, 3H), 3.64 (s, 3H), 5.68 (q, 1H), 6.53 (m, 1H), 7.00 (m, 2H), 7.32 (m, 2H), 7.49 (dd, 1H), 7.93 (d, 1H), 8.03 (d, 1H). Chiral: tR=1.967 min. and 3-amino-N-(1-(2,6-difluorophenyl)ethyl)-6-(1-methyl-6-oxo-1,6-dihydropyridin-3-yl)-5-(oxazol-2-yl)pyrazine-2-carboxamide (isomer 2) (Cmpd. 40-2) (15 mg) as a yellow solid. LCMS: m/z (ESI), [M+H]⁺= 453.2. ¹H NMR: (400 MHz, MeOD) δ 1.62 (d, 3H), 3.64 (s, 3H), 5.68 (q, 1H), 6.53 (dd, 1H), 6.99 (m, 2H), 7.32 (m, 2H), 7.50 (dd, 1H), 7.93 (d, 1H), 8.03 (d, 1H). Chiral: tR=2.500 min, Mix Chiral: tR=1.981 min, 2.480 min.

Example 41. Preparation of 3-amino-N-(2,6-difluorobenzyl)-6-(1-(2-hydroxyethyl)-6-oxo-1,6-dihydropyridin-3-yl)-5-(oxazol-2-yl)pyrazine-2-carboxamide (Cmpd. 41)

SCHEME 34

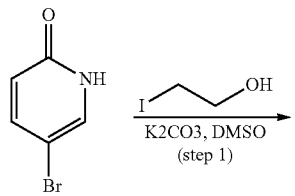

252

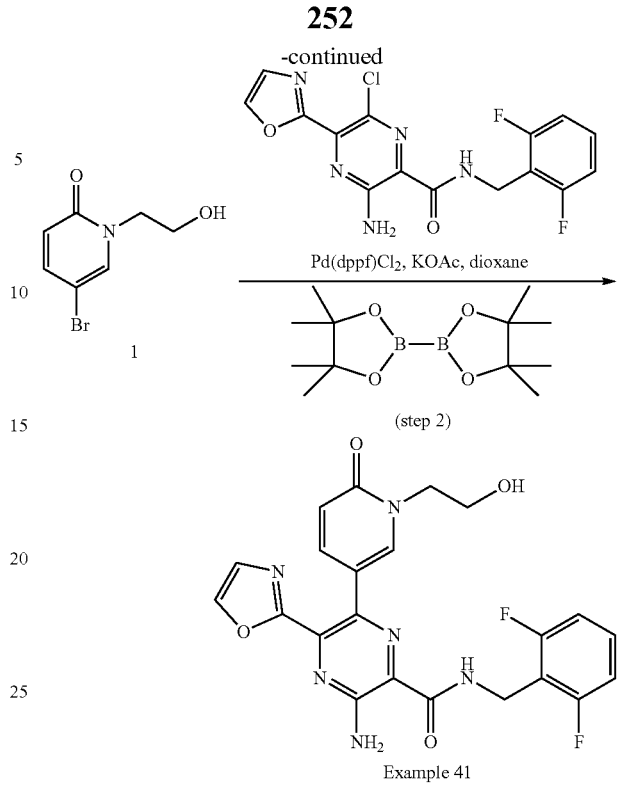

Example 41

Step 1. 5-bromo-1-(2-hydroxyethyl)pyridin-2(1H)-one

To a mixture of 5-bromo-1,2-dihydropyridin-2-one (2 g, 11.49 mmol, 1 equiv), 2-iodoethan-1-ol (4.0 g, 22.98 mmol, 1.999 equiv) in DMSO (30 mL) in a 50-mL round-bottom, was added K₂CO₃ (4.8 g, 34.47 mmol, 2.999 equiv) at room temperature. The resulted mixture was stirred for 16 hours at room temperature. The reaction was then quenched by the addition of 50 mL of water. The resulting solution was extracted with 3×50 mL of ethyl acetate and the organic layers combined. The resulting organic layers was washed with 3×50 mL of sat.NaCl. The combined organic layers was dried over anhydrous sodium sulfate, filtered and concentrated under vacuum. The residue was applied onto a silica gel column with ethyl acetate/petroleum ether (1:2) to afford 330 mg (12%) of 5-bromo-1-(2-hydroxyethyl)-1,2-dihydropyridin-2-one as a white solid. LCMS: m/z (ESI), [M+H]⁺= 218.1. ¹HNMR (400 MHz, Chloroform-d₆) δ 3.93 (2H, s), 4.08 (2H, s), 4.41-4.53 (1H, m), 6.49 (1H, d), 7.66-7.69 (2H, m)

Step 2. 3-amino-N-(2,6-difluorobenzyl)-6-(1-(2-hydroxyethyl)-6-oxo-1,6-dihydropyridin-3-yl)-5-(oxazol-2-yl)pyrazine-2-carboxamide (Cmpd. 41)

Into a 50-mL round-bottom flask, was placed 5-bromo-1-(2-hydroxyethyl)-1,2-dihydropyridin-2-one (298.1 mg, 1.37 mmol, 5 equiv), 4,4,5,5-tetramethyl-2-(4,4,5,5-tetramethyl-1,3,2-dioxaborolan-2-yl)-1,3,2-dioxaborolane (416.6 mg, 1.64 mmol, 6 equiv), Pd(dppf)Cl₂ (120.0 mg, 0.16 mmol, 0.60 equiv), KOAc (80.5 mg, 0.82 mmol, 3 equiv), dioxane (15 mL). The resulting solution was stirred for 2 hours at 80° C. in an oil bath. The resulted mixture was directly used to next step. To this mixture, 3-amino-6-chloro-N-[(2,6-difluorophenyl)methyl]-5-(1,3-oxazol-2-yl)

pyrazine-2-carboxamide (100 mg, 0.27 mmol, 1 equiv), Pd(dppf)Cl$_2$ (100.0 mg, 0.14 mmol, 0.5 equiv), K$_3$PO$_4$ (348.2 mg, 1.64 mmol, 6.00 equiv), dioxane (15 mL) and water (10 mL) were added. The resulting solution was allowed to react, with stirring under atmosphere of N$_2$ for an additional 16 hours at 80° C. in an oil bath. The resulted mixture was concentrated. The resulting solution was extracted with 3×30 mL of ethyl acetate. The organic layers were concentrated. The crude product was purified by Prep-HPLC with the following conditions (Column: XBridge Prep C18 OBD Column, 5 um, 30*150 mm; Mobile Phase A: water (10 MMOL/L NH$_4$HCO$_3$), Mobile Phase B: ACN; Flow rate: 60 mL/min; Gradient: 18% B to 42% B in 7 min; 254, 220 nm; Rt: 6.42 min). This gave 3-amino-N-[(2,6-difluorophenyl)methyl]-6-[1-(2-hydroxyethyl)-6-oxo-1,6-dihydropyridin-3-yl]-5-(1,3-oxazol-2-yl)pyrazine-2-carboxamide (Cmpd. 41) (20 mg, 15.3%) as a yellow solid. LCMS: m/z (ESI), [M+H]$^+$=469.2. $^1$HNMR (300 MHz, DMSO-d$_6$) δ 3.61-3.63 (2H, m), 3.91-3.94 (2H, m), 4.60 (2H, d), 4.86-4.89 (2H, m), 6.32-6.35 (1H, m), 7.04-7.12 (2H, m), 7.34-7.39 (3H, m), 7.40-7.41 (2H, m), 7.45-7.48 (1H, m), 8.28 (1H, s), 9.09-9.11 (1H, m).

Example 42. Preparation of 3-amino-N-[(2,6-difluorophenyl)methyl]-5-(1,3-oxazol-2-yl)-6-[1-(oxetan-3-yl)-6-oxo-1,6-di hydropyridin-3-yl]pyrazine-2-carboxamide (Cmpd. 42)

SCHEME 35

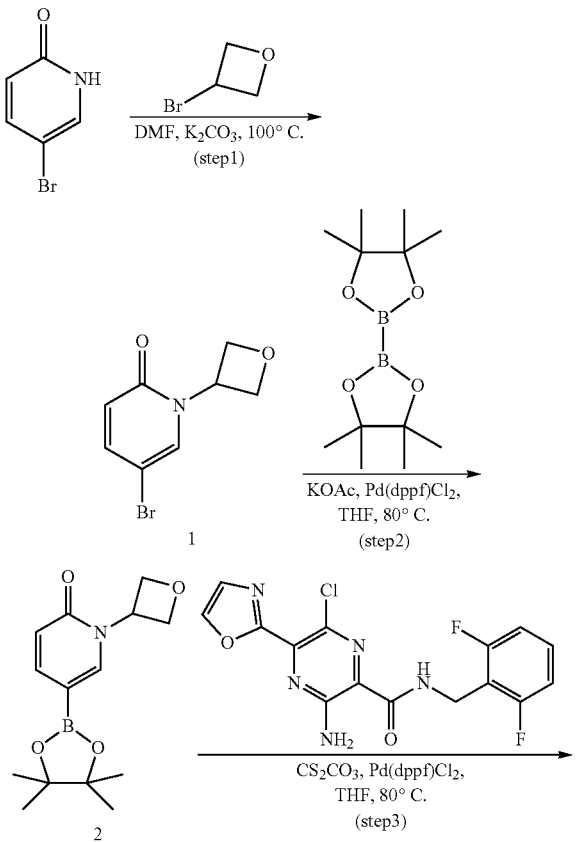

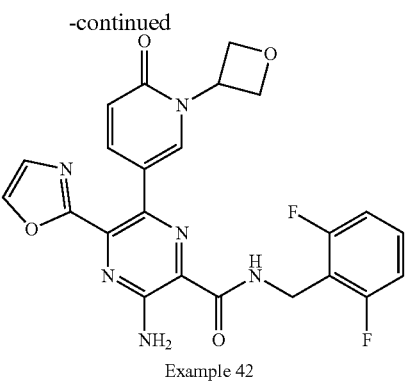

Example 42

Step 1. 5-bromo-1-(oxetan-3-yl)-1,2-dihydropyridin-2-one

To a stirred mixture of 5-bromo-1,2-dihydropyridin-2-one (200 mg, 1.15 mmol, 1 equiv) and 3-bromooxetane (629.8 mg, 4.60 mmol, 4 equiv) in DMF (10 mL) was added K$_2$CO$_3$ (476.6 mg, 3.45 mmol, 3 equiv) in portions at RT under air atmosphere. The resulted mixture was stirred for 3 hours at 100° C. under air atmosphere. The resulted mixture was poured into water. The resulted mixture was extracted with CH$_2$Cl$_2$ (2×100 mL). The combined organic layers were washed with water (1×30 mL), dried over anhydrous Na$_2$SO$_4$. After filtration, the filtrate was concentrated under reduced pressure. The residue was purified by silica gel column chromatography, eluted with PE/EtOAc (10:1) to afford 5-bromo-1-(oxetan-3-yl)-1,2-dihydropyridin-2-one (120 mg, 45.38%) as a white solid. LCMS: m/z (ESI), [M+H]$^+$=230.0. $^1$H NMR (400 MHz, Chloroform-d) δ 4.66-4.74 (m, 2H), 4.96 (ddd, J=7.3, 6.2, 1.0 Hz, 2H), 5.55 (tt, J=6.3, 5.3 Hz, 1H), 6.71 (dd, J=8.8, 0.7 Hz, 1H), 7.67 (dd, J=8.7, 2.5 Hz, 1H), 8.11 (dd, J=2.6, 0.7 Hz, 1H).

Step 2. 1-(oxetan-3-yl)-5-(4,4,5,5-tetramethyl-1,3,2-dioxaborolan-2-yl)pyridin-2(1H)-one To a stirred mixture of 5-bromo-1-(oxetan-3-yl)-1,2-dihydropyridin-2-one (230 mg, 1.00 mmol, 1 equiv) and 4,4,5,5-tetramethyl-2-(4,4,5,5-tetramethyl-1,3,2-dioxaborolan-2-yl)-1,3,2-dioxaborolane (507.7 mg, 2.00 mmol, 2 equiv) in THF (7 mL) were added KOAc (294.3 mg, 3.00 mmol, 3 equiv) and Pd(dppf)Cl$_2$ (146.3 mg, 0.20 mmol, 0.2 equiv) in portions at rt under nitrogen atmosphere. The resulted mixture was stirred for 3 hours at 80° C. under nitrogen atmosphere. The resulted mixture was used in the next step directly without further purification. LCMS: m/z (ESI), [M+H]$^+$=278.2.

Step 3. 3-amino-N-[(2,6-difluorophenyl)methyl]-5-(1,3-oxazol-2-yl)-6-[1-(oxetan-3-yl)-6-oxo-1,6-dihydropyridin-3-yl]pyrazine-2-carboxamide (Cmpd. 42)

To a stirred solution/mixture of 3-amino-6-chloro-N-[(2,6-difluorophenyl)methyl]-5-(1,3-oxazol-2-yl)pyrazine-2-carboxamide (200 mg, 0.55 mmol, 1 equiv) and 1-(oxetan-3-yl)-5-(4,4,5,5-tetramethyl-1,3,2-dioxaborolan-2-yl)-1,2-dihydropyridin-2-one (151.6 mg, 0.55 mmol, 1 equiv) in THF (20 mL) were added Pd(dppf)Cl$_2$ (80.0 mg, 0.11 mmol, 0.20 equiv) and Cs$_2$CO$_3$ (534.5 mg, 1.64 mmol, 3.00 equiv) in portions at rt under nitrogen atmosphere. The resulted mixture was stirred for 3 hours at 80° C. under nitrogen atmosphere. The crude product was purified by Prep-HPLC with the following conditions (Column: XBridge Prep OBD C18 Column 30-150 mm 5 um; Mobile Phase A: Water (0.05% $NH_3H_2O$), Mobile Phase B: ACN; Flow rate: 60 mL/min; Gradient: 25% B to 50% B in 7 min; 254/220 nm; Rt: 5.20 min) to afford 3-amino-N-[(2,6-difluorophenyl)methyl]-5-(1,3-oxazol-2-yl)-6-[1-(oxetan-3-yl)-6-oxo-1,6-di hydropyridin-3-yl]pyrazine-2-carboxamide (5 mg, 1.90%) (Cmpd. 42) as a yellow solid. LCMS: m/z (ESI), $[M+H]^+$=481.2. $^1$H NMR (300 MHz, DMSO-$d_6$) δ 4.58 (d, J=5.8 Hz, 2H), 4.66 (t, J=7.0 Hz, 2H), 4.83 (t, J=7.4 Hz, 2H), 5.56 (p, J=7.3 Hz, 1H), 6.37 (d, J=9.4 Hz, 1H), 7.07 (t, J=8.0 Hz, 2H), 7.28 7.45 (m, 2H), 7.60 (dd, J=9.4, 2.5 Hz, 1H), 7.75 (s, 2H), 7.96 (d, J=2.5 Hz, 1H), 8.29 (d, J=0.8 Hz, 1H), 9.11 (t, J=5.9 Hz, 1H).

Example 45. Preparation of 3-amino-6-[imidazo[1,2-a]pyridin-6-yl]-5-(1,3-oxazol-2-yl)-N-[(1,3-thiazol-4-yl)methyl]pyrazine-2-carboxamide (Cmpd. 45)

SCHEME 36

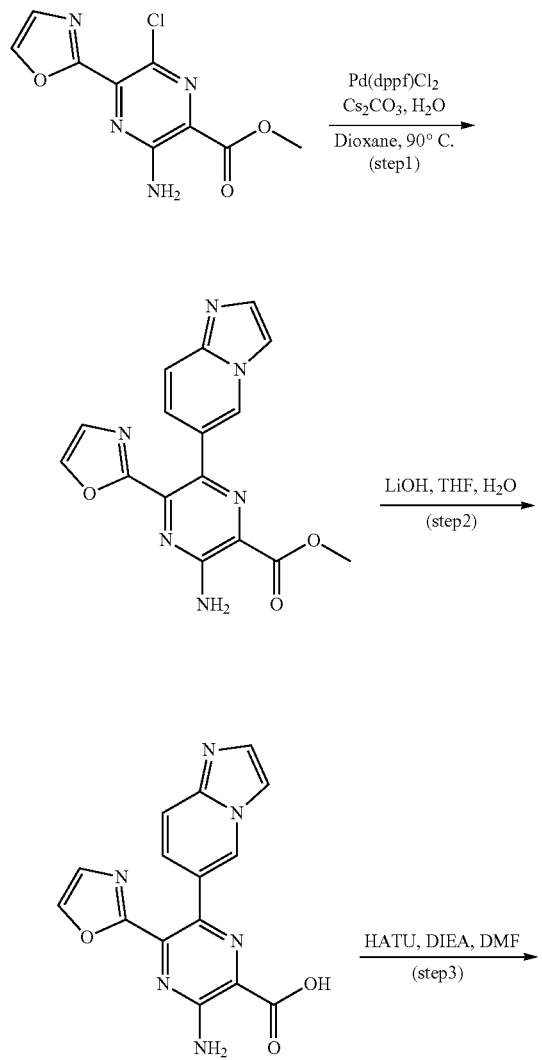

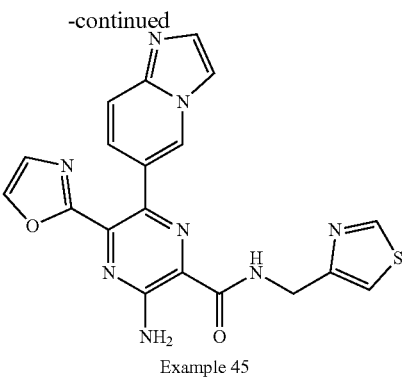

Example 45

Step 1. methyl 3-amino-6-[imidazo[1,2-a]pyridin-6-yl]-5-(1,3-oxazol-2-yl)pyrazine-2-carboxylate To a stirred mixture of methyl 3-amino-6-chloro-5-(1,3-oxazol-2-yl)pyrazine-2-carboxylate (1200 mg, 4.71 mmol, 1 equiv) and 6-(4,4,5,5-tetramethyl-1,3,2-dioxaborolan-2-yl)imidazo[1,2-a]pyridine (1725.6 mg, 7.07 mmol, 1.50 equiv) in dioxane (20 mL) and water (2 mL) was added Pd(dppf)$Cl_2$ (689.7 mg, 0.94 mmol, 0.2 equiv), and $Cs_2CO_3$ (3071.0 mg, 9.43 mmol, 2 equiv) in portions at room temperature under nitrogen atmosphere. The resulted mixture was stirred for overnight at 90° C. The mixture was allowed to cool down to room temperature. The resulted mixture was filtered, the filter cake was washed with DCM (3×10 mL). The filtrate was concentrated under reduced pressure. The residue was purified by silica gel column chromatography, eluted with $CH_2Cl_2$/MeOH (50:1) to afford methyl 3-amino-6-[imidazo[1,2-a]pyridin-6-yl]-5-(1,3-oxazol-2-yl)pyrazine-2-carboxylate (1200 mg, 75.71%) as a yellow solid. LCMS: m/z (ESI), $[M+H]^+$=337. $^1$H NMR (DMSO-$d_6$, 400 MHz) δ 3.9 (3H, s), 7.1 (1H, dd, J=9.4, 1.8 Hz), 7.4 (1H, s), 7.5 (1H, d, J=9.3 Hz), 7.6 (1H, d, J=1.2 Hz), 7.7 (2H, s), 8.0 (1H, s), 8.3 (1H, s), 8.7 (1H, t, J=1.4 Hz)

Step 2. 3-amino-6-[imidazo[1,2-a]pyridin-6-yl]-5-(1,3-oxazol-2-yl)pyrazine-2-carboxylic Acid To a stirred solution of methyl 3-amino-6-[imidazo[1,2-a]pyridin-6-yl]-5-(1,3-oxazol-2-yl)pyrazine-2-carboxylate (2.5 g, 7.4 mmol, 1 equiv) in THF (30 mL) was added LiOH (0.2 g, 8.4 mmol, 1.12 equiv) and $H_2O$ (5 mL) in portions at room temperature under air atmosphere. The resulted mixture was stirred for additional 4 hours at room temperature and acidified to PH=6 with 1N aq.HCl, the resulting solid was collected by filtration and dried under vacuum to afford 3-amino-6-[imidazo[1,2-a]pyridin-6-yl]-5-(1,3-oxazol-2-yl)pyrazine-2-carboxylic acid (2 g, 83.5%) as a yellow solid. LCMS: m/z (ESI), $[M+H]^+$=323.2. $^1$H NMR (DMSO-$d_6$, 400 MHz) δ 3.9 (3H, s), 7.1 (1H, dd, J=9.4, 1.8 Hz), 7.4 (1H, s), 7.5 (1H, d, J=9.3 Hz), 7.6 (1H, d, J=1.2 Hz), 7.7 (2H, s), 8.0 (1H, s), 8.3 (1H, s), 8.7 (1H, t, J=1.4 Hz).

Step 3. 3-amino-6-[imidazo[1,2-a]pyridin-6-yl]-5-(1,3-oxazol-2-yl)-N-[(1,3-thiazol-4-yl)methyl]pyrazine-2-carboxamide (Cmpd. 45)

To a stirred mixture of 3-amino-6-[imidazo[1,2-a]pyridin-6-yl]-5-(1,3-oxazol-2-yl)pyrazine-2-carboxylic acid (100 mg, 0.31 mmol, 1 equiv) and 1-(1,3-thiazol-4-yl)methanamine (70.9 mg, 0.6 mmol, 2.0 equiv) in DMF (3 mL)

were added HATU (471.9 mg, 1.2 mmol, 4.0 equiv) and DIEA (160.4 mg, 1.2 mmol, 4.0 equiv) in portions at room temperature under air atmosphere. The resulted mixture was stirred for additional 60 mins at room temperature. The resulted mixture was poured into water (30 mL), the resulting solid was collected by filtration and slurried with MeOH (16 mL), the resulting solid was collected by filtration and dried under vacuum to afford 3-amino-6-[imidazo[1,2-a]pyridin-6-yl]-5-(1,3-oxazol-2-yl)-N-[(1,3-thiazol-4-yl)methyl]pyrazine-2-carboxamide (Cmpd. 45) (43 mg, 32.8%) as a yellow solid. LCMS: m/z (ESI), [M+H]+=419.2. 1H NMR (DMSO-d6, 400 MHz) δ 2.6 (3H, s), 4.6 (2H, d, J=6.2 Hz), 7.2 (1H, s), 7.3-7.4 (2H, m), 7.6 (1H, d, J=9.3 Hz), 7.8 (1H, s), 8.0 (1H, s), 8.0 (1H, s), 8.3 (1H, s), 8.9 (1H, s), 9.3 (1H, t, J=6.1 Hz).

Compounds listed in the table below were prepared using methods described in Cmpd. 45.

Example 46. Preparation of 3-amino-6-(1-methyl-6-oxo-1,6-dihydropyridin-3-yl)-N-((3-(methylamino)pyridin-2-yl)methyl)-5-(oxazol-2-yl)pyrazine-2-carboxamide (Cmpd. 46)

SCHEME 37

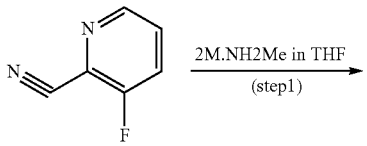

| Example/Cmpd number | Structure | LCMS [M + H]+ | 1H NMR |
|---|---|---|---|
| 43 | 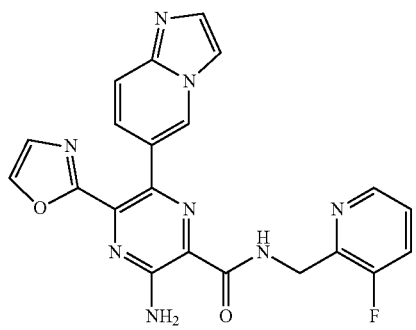 [SMILES: Nc1nc(-c2ncco2)c(-c2ccc3nccn3c2)nc1C(=O)NCc1ncccc1F] | 431.2 | 1H NMR (DMSO-d6, 400 MHz) δ 4.7-4.7 (2H, m), 7.2 (1H, dd, J = 9.4, 1.8 Hz), 7.4-7.4 (2H, m), 7.5 (1H, d, J = 9.3 Hz), 7.6 (1H, d, J = 1.2 Hz), 7.7 (1H, ddd, J = 10.1, 8.4, 1.3 Hz), 7.8-8.0 (2H, m), 8.3 (1H, d, J = 0.8 Hz), 8.4 (1H, dt, J = 4.7, 1.5 Hz), 8.8 (1H, dd, J = 1.8, 1.0 Hz), 9.3 (1H, t, J = 5.9 Hz) |
| 44 | 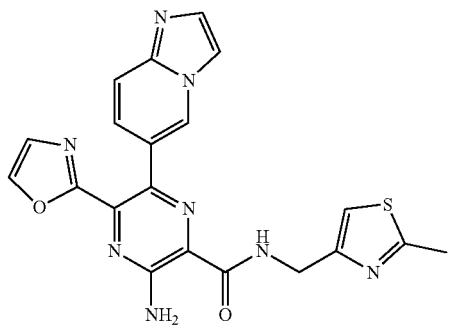 [SMILES: Cc1nc(CNC(=O)c2nc(-c3ccc4nccn4c3)c(-c3ncco3)nc2N)cs1] | 433.2 | 1H NMR (DMSO-d6, 400 MHz) δ 2.6 (3H, s), 4.6 (2H, d, J = 6.2 Hz), 7.2 (1H, s), 7.3-7.4 (2H, m), 7.6 (1H, d, J = 9.3 Hz), 7.8 (1H, s), 8.0 (1H, s), 8.0 (1H, s), 8.3 (1H, s), 8.9 (1H, s), 9.3 (1H, t, J = 6.1 Hz) |
| 99 | 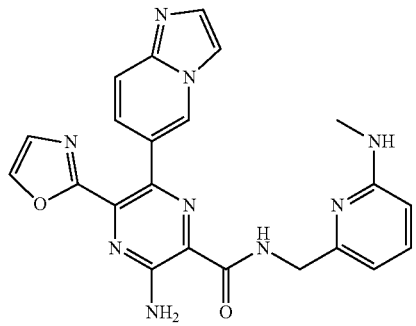 [SMILES: CNc1cccc(CNC(=O)c2nc(-c3ccc4nccn4c3)c(-c3ncco3)nc2N)n1] | 442.3 | 1H NMR (DMSO-d6, 400 MHz) δ 2.6 (3H, d, J = 4.8 Hz), 4.4(2H, d, J = 5.4 Hz), 6.3 (1H, d, J = 8.3 Hz), 6.4 (2H, d, J = 6.7 Hz), 7.2 (1H, dd, J = 9.3, 1.8 Hz), 7.3-7.4 (2H, m), 7.5 (1H, d, J = 9.3 Hz), 7.6 (1H, d, J = 1.2 Hz), 7.9 (2H, s), 8.3 (1H, s), 8.8 (1H, s), 9.4 (1H, t, J = 5.7 Hz). |

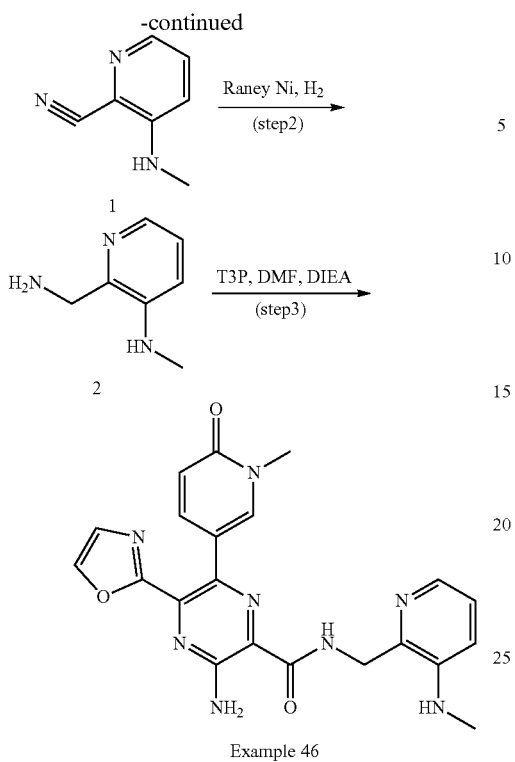

Example 46

Step 1. 3-(methylamino)picolinonitrile

To a solution of 3-fluoropyridine-2-carbonitrile (500 mg, 4.09 mmol, 1 equiv) in THF (20 mL) was added methanamine (190.8 mg, 6.14 mmol, 1.50 equiv) at room temperature. The resulted mixture was stirred for 3 hours at 50° C. The reaction was quenched by the addition of water (10 mL) at room temperature. The precipitated solids were collected by filtration and dried under reduced pressure to afford 3-(methylamino)pyridine-2-carbonitrile (300 mg, 55.02%) as a white solid. LCMS: m/z (ESI), $[M+H]^+=134.0$.

Step 2. 2-(aminomethyl)-N-methylpyridin-3-amine

To a stirred solution of 3-(methylamino)pyridine-2-carbonitrile (100 mg, 0.75 mmol, 1 equiv) in THF (15 mL) were added Raney Ni (128.7 mg, 1.50 mmol, 2.00 equiv) in portions at room temperature under nitrogen atmosphere. The resulted mixture was stirred for 5 hours at room temperature under hydrogen atmosphere. The resulted mixture was filtered, the filter cake was washed with MeOH (20 mL). The filtrate was concentrated under reduced pressure to afford 2-(aminomethyl)-N-methylpyridin-3-amine (90 mg, 87.35%) as a brown semi-solid. LCMS: m/z (ESI), $[M+H]^+=138.0$.

Step 3. 3-amino-6-(1-methyl-6-oxo-1,6-dihydropyridin-3-yl)-N-((3-(methylamino) pyridin-2-yl)methyl)-5-(oxazol-2-yl)pyrazine-2-carboxamide (Cmpd. 46)

To a stirred mixture of 3-amino-6-(1-methyl-6-oxo-1,6-dihydropyridin-3-yl)-5-(1,3-oxazol-2-yl)pyrazine-2-carboxylic acid (70 mg, 0.22 mmol, 1 equiv) and 2-(aminomethyl)-N-methylpyridin-3-amine (36.8 mg, 0.27 mmol, 1.20 equiv) in DMF (10 mL) were added DIEA (86.6 mg, 0.67 mmol, 3 equiv) and T$_3$P (142.2 mg, 0.45 mmol, 2 equiv) in portions at room temperature. The resulted mixture was stirred for 3 hours at room temperature. The reaction was quenched with water (40 mL) at room temperature. The precipitated solids were collected by filtration and washed with water (10 mL). The product was poor solubility and purified by trituration with DMF (5 mL). The resulting yellow solid was collected by filtration, washed with methanol (10 mL) and dried under infrared light to afford 3-amino-6-(1-methyl-6-oxo-1,6-dihydropyridin-3-yl)-N-[[3-(methylamino)pyridin-2-yl]methyl]-5-(1,3-oxazol-2-yl)pyrazine-2-carboxamide (Cmpd. 46) (20 mg, 19.46%) as a yellow solid. LCMS: m/z (ESI), $[M+H]^+=433.2$, $^1$H NMR (300 MHz, DMSO-d$_6$) δ 2.74 (d, J=4.5 Hz, 3H), 3.47 (s, 3H), 4.46 (d, J=5.3 Hz, 2H), 5.68 (d, J=5.0 Hz, 1H), 6.33 (d, J=9.4 Hz, 1H), 6.88 (d, J=7.9 Hz, 1H), 7.13 (dd, J=8.0, 4.8 Hz, 1H), 7.30-7.47 (m, 2H), 7.69-7.90 (m, 3H), 8.01 (d, J=2.6 Hz, 1H), 8.29 (s, 1H), 9.40 (d, J=5.4 Hz, 1H).

Example 47. Preparation of 3-amino-6-(1H-1,3-benzodiazol-5-yl)-N-[(3-fluoropyridin-2-yl)methyl]-5-(1,3-oxazol-2-yl)pyrazine-2-carboxamide (Cmpd. 47)

SCHEME 38

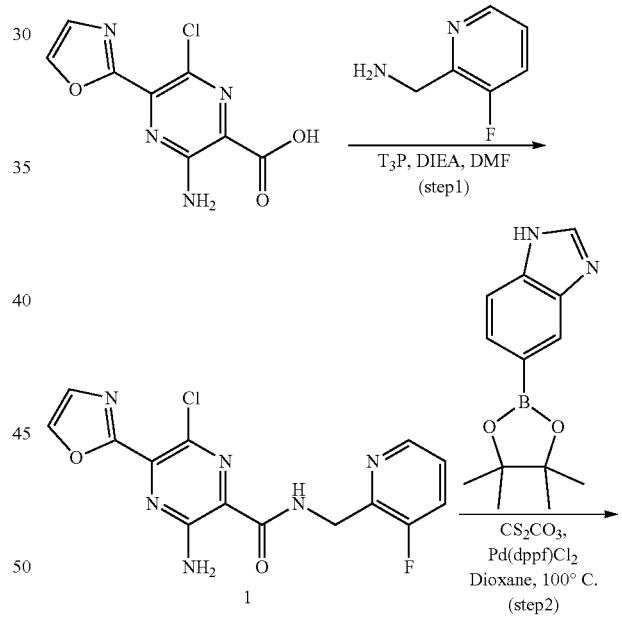

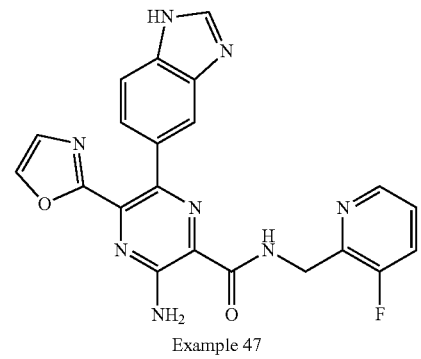

Example 47

Step 1. 3-amino-6-chloro-N-[(3-fluoropyridin-2-yl)methyl]-5-(1,3-oxazol-2-yl)pyrazine-2-carboxamide To a stirred mixture of 3-amino-6-chloro-5-(1,3-oxazol-2-yl)pyrazine-2-carboxylic acid (2000 mg, 8.31 mmol, 1 equiv) and 1-(3-fluoropyridin-2-yl)methanamine (1572.7 mg, 12.47 mmol, 1.5 equiv) in DMF (20 mL) were added DIEA (4297.4 mg, 33.25 mmol, 4 equiv) and $T_3P$ (10579.6 mg, 33.25 mmol, 4 equiv) in portions at room temperature under air atmosphere. The resulted mixture was stirred for 1 h at room temperature under air atmosphere. The resulted mixture was poured into water. The resulting solid was collected by filtration and dried under infrared lamp to afford 3-amino-6-chloro-N-[(3-fluoropyridin-2-yl)methyl]-5-(1,3-oxazol-2-yl)pyrazine-2-carboxamide (2.2 g, 75.89%) as a yellow green solid. LCMS: m/z (ESI), [M+H]$^+$=349.1. $^1$H NMR (400 MHz, DMSO-$d_6$) δ 4.68 (dd, J=5.7, 1.7 Hz, 2H), 7.43 (dt, J=8.6, 4.4 Hz, 1H), 7.59 (s, 1H), 7.73 (ddd, J=10.0, 8.4, 1.3 Hz, 1H), 7.92 (s, 2H), 8.38 8.46 (m, 2H), 9.17 (t, J=5.7 Hz, 1H).

Step 2. 3-amino-6-(1H-1,3-benzodiazol-5-yl)-N-[(3-fluoropyridin-2-yl)methyl]-5-(1,3-oxazol-2-yl)pyrazine-2-carboxamide (Cmpd. 47)

To a solution of 3-amino-6-chloro-N-[(3-fluoropyridin-2-yl)methyl]-5-(1,3-oxazol-2-yl)pyrazine-2-carboxamide (100 mg, 0.29 mmol, 1 equiv) and 5-(4,4,5,5-tetramethyl-1,3,2-dioxaborolan-2-yl)-1H-1,3-benzodiazole (140.0 mg, 0.57 mmol, 2 equiv) in 1,4-dioxane (10 mL) and $H_2O$ (1 mL) were added $Cs_2CO_3$ (186.9 mg, 0.57 mmol, 2 equiv) and Pd(dppf)$Cl_2$ (21.0 mg, 0.03 mmol, 0.1 equiv) under $N_2$. The resulted mixture was stirred for 24 hours at 90° C. under a nitrogen atmosphere and concentrated under vacuum. The crude product was purified by Prep-HPLC with the following conditions (Column: XBridge Prep OBD C18 Column 30×150 mm 5 um; Mobile Phase A: Water (0.05% $NH_3H_2O$), Mobile Phase B: ACN; Flow rate: 60 mL/min; Gradient: 21% B to 31% B in 7 min; 254/220 nm; Rt: 6.45 min) to afford 3-amino-6-(1H-1,3-benzodiazol-5-yl)-N-[(3-fluoropyridin-2-yl)methyl]-5-(1,3-oxazol-2-yl)pyrazine-2-carboxamide (Cmpd. 47) (12 mg, 16.20%) as a yellow solid. LCMS: m/z (ESI), [M+H]$^+$=431.1. $^1$H NMR: (300 MHz, DMSO-$d_6$) δ 4.73 (m, 2H), 7.23 (dd, 1H), 7.34 (s, 1H), 7.41 (dt, 1H), 7.55 (d, 1H), 7.72 (m, 4H), 8.19 (s, 1H), 8.30 (s, 1H), 8.38 (dt, 1H), 9.31 (t, 1H), 13.12 (s, 1H).

Compounds listed in the table below were prepared using methods described in Cmpd. 47.

| Example/Cmpd number | Structure | LCMS [M + H]$^+$ | $^1$H NMR |
|---|---|---|---|
| 51 | 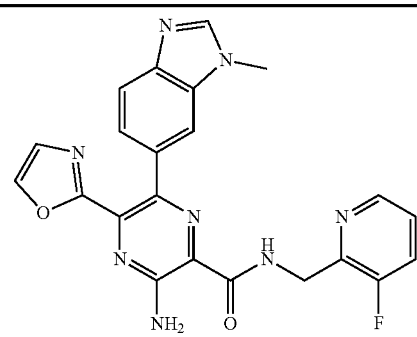 | 445.2 | $^1$H NMR (400 MHz, DMSO-$d_6$) δ 3.82 (s, 3H), 4.77-4.71 (m, 2H), 7.19 (dd, J = 8.4, 1.7 Hz, 1H), 7.35 (s, 1H), 7.41 (dt, J = 8.5, 4.4 Hz, 1H), 7.55~7.65 (m, 2H), 7.73 (ddd, J = 10.1, 8.3, 1.3 Hz, 1H), 7.83 (s, 2H), 8.21 (d, J = 15.9 Hz, 2H), 8.38 (dt, J = 4.6, 1.5 Hz, 1H), 9.31 (t, J = 5.8 Hz, 1H). |
| 100 | 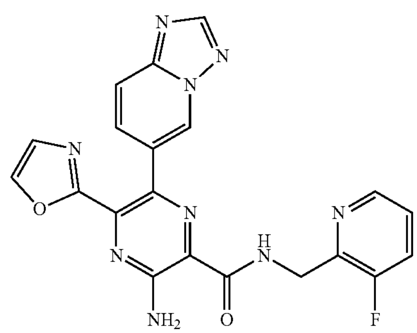 [SMILES: Nc1nc(-c2ncco2)c(-c2ccc3ncnn3c2)nc1C(=O)NCc1ncccc1F] | 432.2 | $^1$H NMR (300 MHz, DMSO-$d_6$) δ 4.69 (dd, J = 6.0, 1.7 Hz, 2H), 7.30-7.43 (m, 2H), 7.60-7.73 (m, 2H), 7.79 (dd, J = 9.3, 0.9 Hz, 1H), 7.95 (d, J = 12.1 Hz, 2H), 8.28 (d, J = 0.8 Hz, 1H), 8.35 (dt, J = 4.7, 1.5 Hz, 1H), 8.53 (s, 1H), 9.29 (dd, J = 1.8, 0.9 Hz, 1H), 9.40 (t, J = 6.0 Hz, 1H). |

Example 48. Preparation of 5-(2,6-dimethylpyridin-4-yl)-6-(4-fluorophenyl)-N4-(2-((3-fluoropyridin-2-yl)amino)ethyl)pyrimidine-2,4-diamine (Cmpd. 48)

SCHEME 39

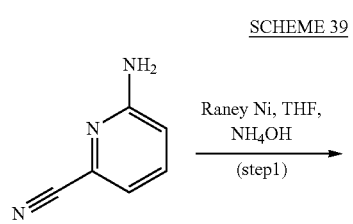

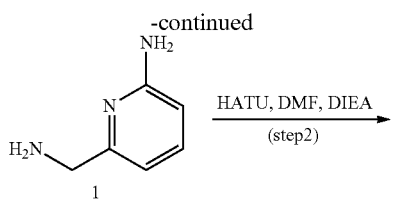

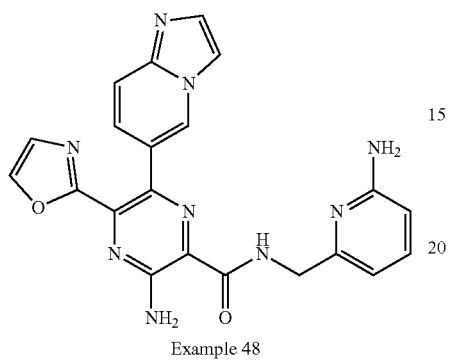

Example 48

Step 1. 6-(aminomethyl)pyridin-2-amine

To a mixture of 6-aminopyridine-2-carbonitrile (100 mg, 0.8 mmol, 1 equiv) and Raney Ni (21.6 mg, 0.3 mmol, 0.3 equiv) in THF (10 mL) were added NH₄OH (1 mL) dropwise at room temperature. The resulted mixture was stirred for additional 40 min at room temperature under hydrogen atmosphere. The resulted mixture was filtered and the filtrate was concentrated under reduced pressure to afford 6-(aminomethyl)pyridin-2-amine (80 mg, 77.4%) as a light brown oil which was used in the next step directly without further purification. LCMS: m/z (ESI), [M+H]$^+$=124.3.

Step 2. 3-amino-N-[(6-aminopyridin-2-yl)methyl]-6-[imidazo[1,2-a]pyridin-6-yl]-5-(1,3-oxazol-2-yl)pyrazine-2-carboxamide (Cmpd. 48)

To a stirred solution/mixture of 3-amino-6-[imidazo[1,2-a]pyridin-6-yl]-5-(1,3-oxazol-2-yl)pyrazine-2-carboxylic acid (100 mg, 0.3 mmol, 1 equiv) and 6-(aminomethyl)pyridin-2-amine (76.4 mg, 0.6 mmol, 2.0 equiv) in DMF (3 mL) were added HATU (471.9 mg, 1.2 mmol, 4.0 equiv) and DIEA (160.4 mg, 1.2 mmol, 4.0 equiv) dropwise/in portions at room temperature under air atmosphere. The resulted mixture was stirred for additional 30 min at room temperature. The resulted mixture was dropwised into water. The resulted mixture was filtered, the filter cake was washed with water (3×10 mL). The crude product was re-crystallized from DCM/MeOH (5:1 6 mL) to afford 3-amino-N-[(6-aminopyridin-2-yl)methyl]-6-[imidazo[1,2-a]pyridin-6-yl]-5-(1,3-oxazol-2-yl)pyrazine-2-carboxamide (Cmpd. 48) (89 mg, 66.1%) as a yellow solid. LCMS: m/z (ESI), [M+H]$^+$= 428.1. $^1$H NMR (DMSO-d₆, 400 MHz) δ 4.4 (2H, d, J=6.1 Hz), 5.9 (2H, d, J=6.0 Hz), 6.3 (1H, d, J=8.1 Hz), 6.4 (1H, d, J=7.2 Hz), 7.2 (1H, dd, J=9.4, 1.8 Hz), 7.3 (1H, t, J=7.8 Hz), 7.4 (1H, s), 7.5 (1H, d, J=9.4 Hz), 7.6 (1H, d, J=1.3 Hz), 7.9 (3H, s), 8.3 (1H, s), 8.8 (1H, t, J=1.4 Hz), 9.3 (1H, t, J=6.2 Hz)

Example 49. Preparation of 3-amino-N-((6-amino-3-fluoropyridin-2-yl)methyl)-6-(1-methyl-6-oxo-1,6-dihydropyridin-3-yl)-5-(oxazol-2-yl)pyrazine-2-carboxamide (Cmpd. 49)

SCHEME 40

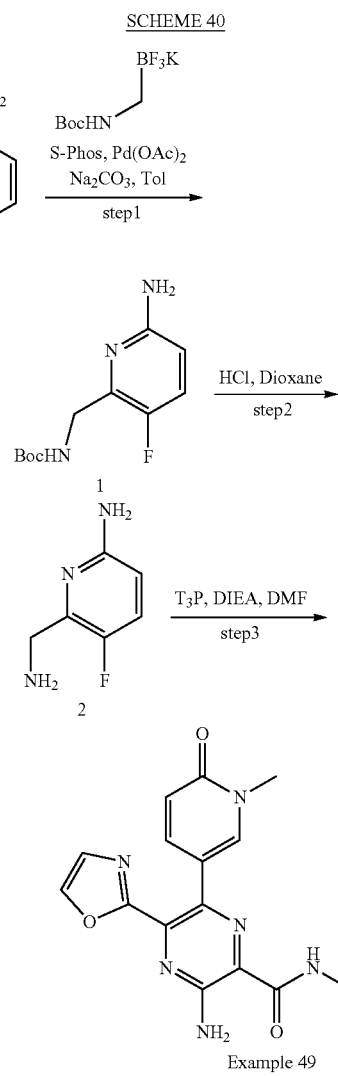

Example 49

Step 1. tert-butyl (6-amino-3-fluoropyridin-2-yl)methylcarbamate

To a stirred mixture of 6-bromo-5-fluoropyridin-2-amine (19 mg, 0.10 mmol, 1 equiv), Na₂CO₃ (42.2 mg, 0.40 mmol, 4 equiv) and potassium tert-butyl N-[(trifluoroboranuidyl)methyl]carbamate (70.7 mg, 0.30 mmol, 3 equiv) in toluene (20 mL) and water (3 mL) were added S-Phos (12.3 mg, 0.03 mmol, 0.3 equiv) and Pd(AcO)₂ (6.7 mg, 0.03 mmol, 0.3 equiv) in portions at room temperature under nitrogen atmosphere. The resulted mixture was stirred for overnight at 100° C. under nitrogen atmosphere. The resulted mixture was concentrated under reduced pressure. The residue was purified by Prep-TLC (CH₂Cl₂/MeOH 30:1) to afford tert-butyl N-[(6-amino-3-fluoropyridin-2-yl)methyl]carbamate (130 mg, 41.17%) as a brown solid. LCMS: m/z (ESI), [M+H]$^+$=242.1.

Step 2. 6-(aminomethyl)-5-fluoropyridin-2-amine

To a stirred solution of tert-butyl N-[(6-amino-3-fluoropyridin-2-yl)methyl]carbamate (120 mg, 0.50 mmol, 1 equiv) in DCM (5 mL) were added HCl (gas) in 1,4-dioxane (362.7 mg, 9.95 mmol, 20 equiv) dropwise at room temperature. The resulted mixture was stirred for 3 hours at room temperature under air atmosphere. The resulted mixture was concentrated to afford 6-(aminomethyl)-5-fluoropyridin-2-amine (100 mg, 142.44%) as a off-white solid which was used to next step without purification. $^1$H NMR (300 MHz, DMSO-$d_6$) δ3.98 (d, J=5.8 Hz, 2H), 6.64 (dd, J=9.1, 3.3 Hz, 1H), 7.53 (t, J=9.1 Hz, 1H).

Step 3. 3-amino-N-((6-amino-3-fluoropyridin-2-yl)methyl)-6-(1-methyl-6-oxo-1,6-dihydropyridin-3-yl)-5-(oxazol-2-yl)pyrazine-2-carboxamide (Cmpd. 49)

To a stirred mixture of 3-amino-6-(1-methyl-6-oxo-1,6-dihydropyridin-3-yl)-5-(1,3-oxazol-2-yl)pyrazine-2-carboxylic acid (90 mg, 0.29 mmol, 1 equiv), 6-(aminomethyl)-5-fluoropyridin-2-amine (61.2 mg, 0.43 mmol, 1.51 equiv) and DIEA (149.3 mg, 1.15 mmol, 4.02 equiv) in DMF (10 mL) was added T$_3$P (182.8 mg, 0.57 mmol, 2.00 equiv) dropwise at room temperature. The resulted mixture was stirred for 3h at room temperature. The reaction was quenched by the addition of water (40 mL) at room temperature. The precipitated solids were collected by filtration and washed with methanol (20 mL) to afford 3-amino-N-[(6-amino-3-fluoropyridin-2-yl)methyl]-6-(1-methyl-6-oxo-1,6-dihydropyridin-3-yl)-5-(1,3-oxazol-2-yl)pyrazine-2-carboxamide (Cmpd. 49) (30 mg, 15.95%) as a yellow solid. LCMS: m/z (ESI), [M+H]$^+$=437.2. $^1$H NMR (300 MHz, DMSO-$d_6$) δ 3.48 (s, 3H), 4.50 (dd, J=5.8, 2.1 Hz, 2H), 5.85 (s, 2H), 6.20-6.47 (m, 2H), 7.20-7.49 (m, 3H), 7.81 (s, 2H), 8.05 (d, J=2.6 Hz, 1H), 8.31 (d, J=0.8 Hz, 1H), 9.09 (t, J=5.8 Hz, 1H).

Example 50. Preparation of 3-amino-N-[[3-fluoro-6-(methylamino)pyridin-2-yl]methyl]-6-(1-methyl-6-oxo-1,6-dihydropyridin-3-yl)-5-(1,3-oxazol-2-yl)pyrazine-2-carboxamide (Cmpd. 50)

SCHEME 41

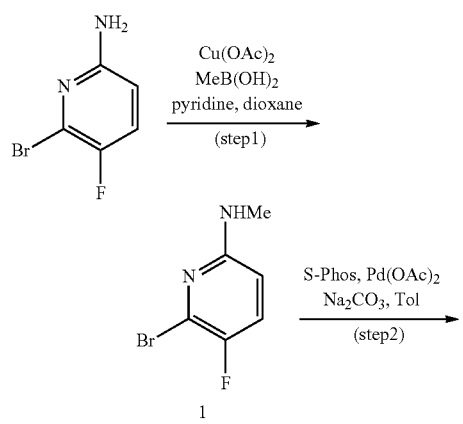

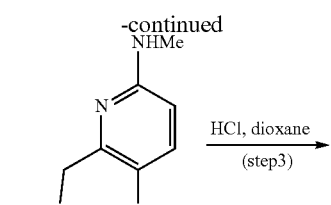

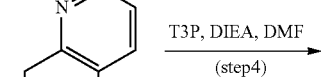

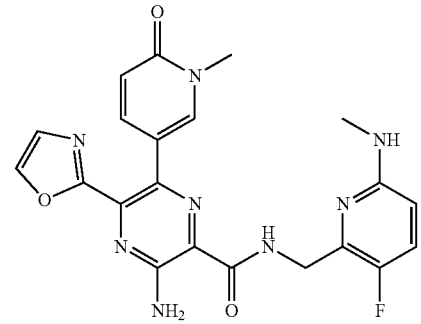

Example 50

Step 1. 6-bromo-5-fluoro-N-methylpyridin-2-amine

To a stirred mixture of (acetyloxy)cuprio acetate (1.64 g, 9.03 mmol, 2.5 equiv) and methylboronic acid (540.6 mg, 9.03 mmol, 2.5 equiv) in dioxane (30 mL) were added pyridine (1 g, 12.64 mmol, 3.5 equiv) and 6-bromo-5-fluoropyridin-2-amine (690 mg, 3.61 mmol, 1 equiv) in portions at room temperature under air atmosphere. The resulted mixture was stirred for 3 hours at 100° C. under air atmosphere. The resulted mixture was filtered, the filter cake was washed with DCM (2×30 mL). The filtrate was concentrated under reduced pressure. The residue was purified by Prep-TLC (PE/EtOAc 4:1) to afford 6-bromo-5-fluoro-N-methylpyridin-2-amine (120 mg, 16.20%) as a brown solid. LCMS: m/z (ESI), [M+H]$^+$=205.1, 207.1.

Step 2. tert-butyl (3-fluoro-6-(methylamino)pyridin-2-yl)methylcarbamate

To a stirred mixture of potassium tert-butyl N-[(trifluoroboranuidyl)methyl]carbamate (346.9 mg, 1.46 mmol, 3 equiv) and 6-bromo-5-fluoro-N-methylpyridin-2-amine (100 mg, 0.49 mmol, 1 equiv) in toluene (20 mL) and water (3 mL) were added S-Phos (60.1 mg, 0.15 mmol, 0.3 equiv), Pd(AcO)$_2$ (32.9 mg, 0.15 mmol, 0.3 equiv) and Na$_2$CO$_3$ (206.8 mg, 1.95 mmol, 4.00 equiv) in portions at room temperature under nitrogen atmosphere. The resulted mixture was stirred for 2 hours at 95° C. under nitrogen atmosphere. The resulted mixture was concentrated under reduced pressure. The residue was purified by Prep-TLC (CH$_2$Cl$_2$/MeOH 30:1) to afford tert-butyl N-[[3-fluoro-6-

(methylamino)pyridin-2-yl]methyl]carbamate (90 mg, 72.28%) as a brown solid. LCMS: m/z (ESI), [M+H]+=256.3.

Step 3. 6-(aminomethyl)-5-fluoro-N-methylpyridin-2-amine

To a stirred solution of tert-butyl N-[[3-fluoro-6-(methylamino)pyridin-2-yl]methyl]carbamate (80 mg, 0.31 mmol, 1 equiv) in DCM (5 mL) was added HCl (6 m) (228.9 mg, 6.28 mmol, 20.03 equiv) dropwise at room temperature. The resulted mixture was stirred for 3 hours at room temperature. The resulted mixture was concentrated under reduced pressure to afford 6-(aminomethyl)-5-fluoro-N-methylpyridin-2-amine (45 mg, 98.71%) as a off-white solid. ¹H NMR (300 MHz, DMSO-d₆) S, 2.82 (d, J=2.5 Hz, 3H), 4.02 (dd, J=5.9, 2.2 Hz, 2H), 6.49 (d, J=9.6 Hz, 1H), 7.40 (t, J=8.3 Hz, 1H).

Step 4. 3-amino-N-((3-fluoro-6-(methylamino)pyridin-2-yl)methyl)-6-(1-methyl-6-oxo-1,6-dihydropyridin-3-yl)-5-(oxazol-2-yl)pyrazine-2-carboxamide (Cmpd. 50)

To a stirred mixture of 3-amino-6-(1-methyl-6-oxo-1,6-dihydropyridin-3-yl)-5-(1,3-oxazol-2-yl)pyrazine-2-carboxylic acid (70 mg, 0.22 mmol, 1 equiv) and 6-(aminomethyl)-5-fluoro-N-methylpyridin-2-amine (38.1 mg, 0.25 mmol, 1.10 equiv) in DMF (10 mL) were added DIEA (86.6 mg, 0.67 mmol, 3 equiv) and (3H3)phosphane (17.9 mg, 0.45 mmol, 2.00 equiv) 50% in EA dropwise at room temperature. The resulted mixture was stirred for 3h at room temperature under air atmosphere. The reaction was quenched with water at room temperature. The precipitated solids were collected by filtration and washed with MeOH (20 mL) to afford 3-amino-N-[[3-fluoro-6-(methylamino)pyridin-2-yl]methyl]-6-(1-methyl-6-oxo-1,6-dihydropyridin-3-yl)-5-(1,3-oxazol-2-yl)pyrazine-2-carboxamide (Cmpd. 50) (25 mg, 24.59%) as a yellow solid. LCMS: m/z (ESI), [M+H]+=451.2. ¹H NMR (300 MHz, DMSO-d₆) δ 2.63 (d, J=4.7 Hz, 3H), 3.43 (s, 3H), 4.51 (dd, J=5.3, 2.1 Hz, 2H), 6.21-6.42 (m, 2H), 6.49 (p, J=4.5, 4.0 Hz, 1H), 7.22-7.46 (m, 3H), 7.82 (s, 2H), 7.95 (d, J=2.6 Hz, 1H), 8.28 (d, J=0.8 Hz, 1H), 9.21 (t, J=5.2 Hz, 1H).

Example 52. Preparation of 3-amino-6-(2,6-dimethylpyridin-4-yl)-N-(4-fluoro-2-methoxybenzyl)-5-(4-fluorophenyl)pyrazine-2-carboxamide (Cmpd. 52)

SCHEME 42

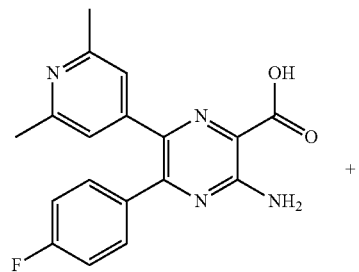

+

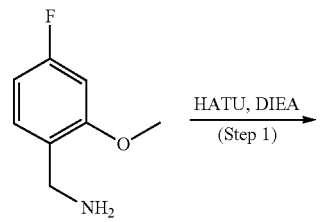

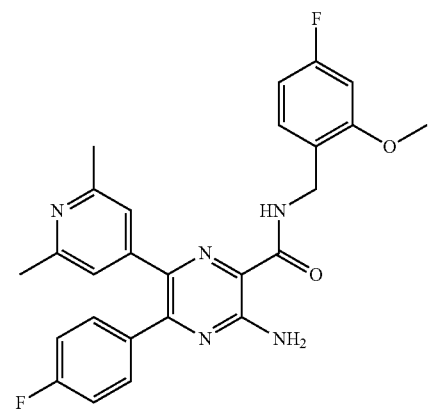

Example 52

Step 1. Preparation of 3-amino-6-(2, 6-dimethylpyridin-4-yl)-N-(4-fluoro-2-methoxy benzyl)-5-(4-fluorophenyl) pyrazine-2-carboxamide (Cmpd. 52)

The mixture of 3-amino-6-(2,6-dimethylpyridin-4-yl)-5-(4-fluorophenyl)pyrazine-2-carboxylic acid (0.05 g, 0.15 mmol), (4-fluoro-2-methoxyphenyl)methanamine (0.03 g, 0.22 mmol) in DMF (5 mL) was added DIEA (0.06 g, 0.44 mmol) and HATU (0.06 g, 0.15 mmol) at 20° C. Then the mixture was stirred at this temperature for 1 h. LCMS showed the reaction was complete. Then the mixture was concentrated and residue was poured to water and then extracted with EA (2×25 mL). The organic solution was then purified with rp-c18 concentrated to give the product 3-amino-6-(2,6-dimethylpyridin-4-yl)-N-(4-fluoro-2-methoxybenzyl)-5-(4-fluorophenyl)pyrazine-2-carboxamide (Cmpd. 52) (0.04 g, yield: 56.9%) as a white solid. LCMS: m/z (ESI), [M+H]+=476.1. ¹H NMR (500 MHz, DMSO-d6) δ ppm 2.3 (s, 6H), 3.9 (s, 3H), 4.5 (d, J=6.3 Hz, 2H), 6.7 (td, J=8.4, 2.4 Hz, 1H), 6.9 (d, J=11.2 Hz, 1H), 7.0 (s, 2H), 7.2-7.2 (m, 3H), 7.4 (dd, J=8.8, 5.7 Hz, 2H), 9.1 (t, J=6.3 Hz, 1H).

Compounds listed in the table below were prepared using methods described in Cmpd. 52

| Example/ Cmpd number | Structure | LCMS [M + H]+ | 1H NMR |
|---|---|---|---|
| 53 | 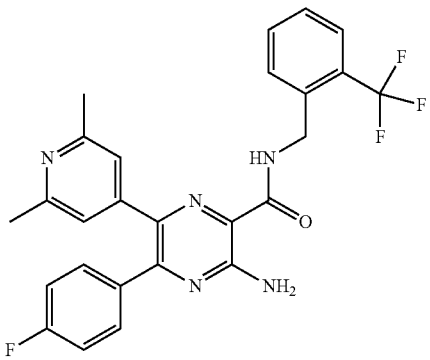 [SMILES: Cc1cc(-c2nc(C(=O)NCc3ccccc3C(F)(F)F)c(N)nc2-c2ccc(F)cc2)cc(C)n1] | 496.2 | 1H NMR (500 MHz, DMSO-d6) δ ppm 2.3 (s, 6H), 4.7 (br d, J = 6.0 Hz, 2H), 7.0 (s, 2H), 7.2 (t, J = 9.0 Hz, 2H), 7.4-7.5 (m, 4H), 7.7 (t, J = 7.7 Hz, 1H), 9.3 (t, J = 6.3 Hz, 1H) |
| 54 | 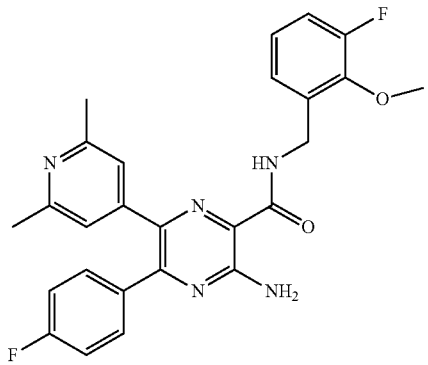 | 478.3 | 1H NMR (500 MHz, DMSO-d6) δ ppm 2.3 (s, 6H), 3.9 (d, J = 1.3 Hz, 3H), 4.6 (d, J = 6.3 Hz, 2H), 7.0 (s, 2H), 7.0-7.1 (m, 2H), 7.1-7.2 (m, 1H), 7.2 (t, J = 8.8 Hz, 3H), 7.4 (dd, J = 8.8, 5.7 Hz, 3H), 9.2 (t, J = 6.5 Hz, 1H) |
| 55 | 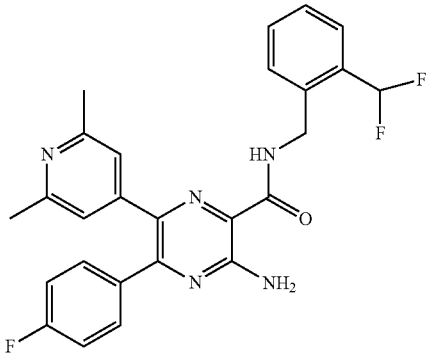 [SMILES: Cc1cc(-c2nc(C(=O)NCc3ccccc3C(F)F)c(N)nc2-c2ccc(F)cc2)cc(C)n1] | 476.4 | 1H NMR (500 MHz, DMSO-d6) δ ppm 2.3 (s, 6H), 4.7 (br d, J = 6.0 Hz, 2H), 7.0 (s, 2H), 7.1-7.3 (m, 2H), 7.4-7.5 (m, 5H), 7.5-7.5 (m, 1H), 7.6 (d, J = 7.6 Hz,1H), 7.7-7.9 (m, 1H), 9.3 (t, J = 6.3 Hz, 1H) |

Example 56. Preparation of 3-amino-6-(2, 6-dimethylpyridin-4-yl)-N-(2-methoxybenzyl)-5-(1H-pyrazol-1-yl)pyrazine-2-carboxamide (Cmpd. 56)

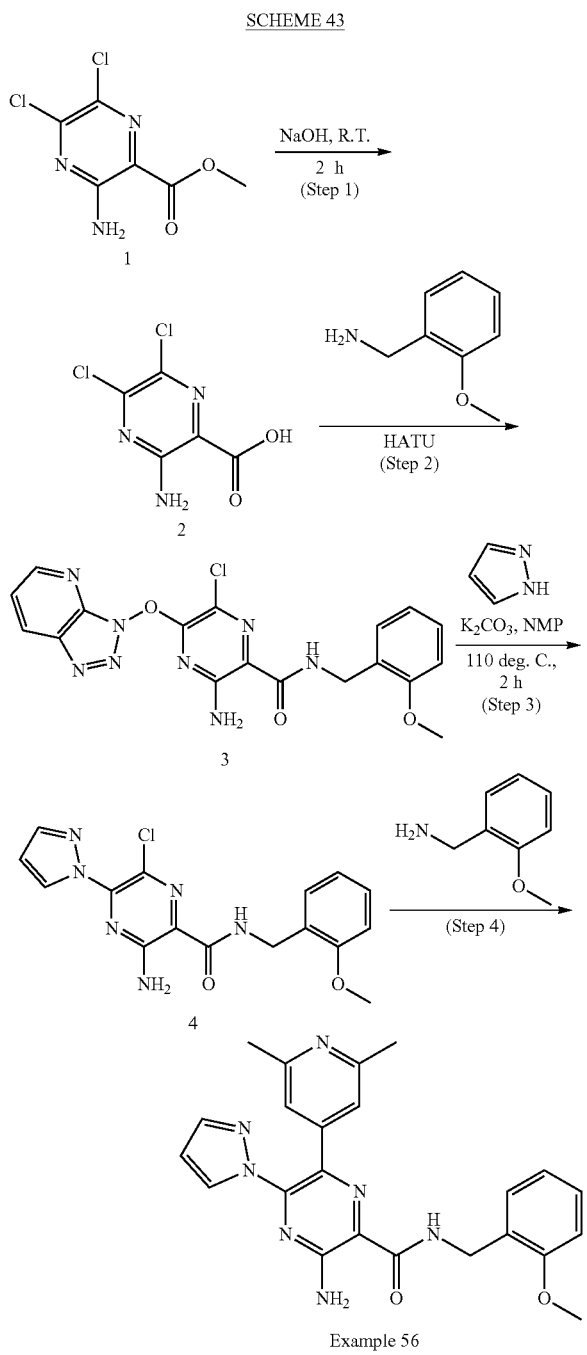

Example 56

Step 1. Preparation of 3-amino-5,6-dichloropyrazine-2-carboxylic Acid

To a stirring solution of methyl 3-amino-5,6-dichloropyrazine-2-carboxylate (3.6 g, 16.29 mmol) in MeOH (20 mL) was added NaOH (1.3 g, 32.58 mmol) at 25° C. Then the mixture was stirred at this temperature for 16 h. LCMS showed the reaction was complete. Then the mixture was concentrated and residue was poured to water and then extracted with EA (2×25 mL). The organic solution was then concentrated to give the crude product 3-amino-5,6-dichloropyrazine-2-carboxylic acid (2.6 g, yield: 77.1%) as a yellow solid. LCMS: m/z (ESI), [M+H]$^+$=208.1.

Step 2. Preparation of 5-((3H-[1,2,3]triazolo[4,5-b]pyridin-3-yl)oxy)-3-amino-6-chloro-N-(2-methoxybenzyl)pyrazine-2-carboxamide The mixture of 3-amino-5,6-dichloropyrazine-2-carboxylic acid (2.5 g, 12.08 mmol), (2-methoxyphenyl)methanamine (1.99 g, 14.5 mmol) in DMF (20 mL) was added DIEA (4.67 g, 36.24 mmol) and HATU (4.59 g, 12.08 mmol) at 20° C. Then the mixture was stirred at this temperature for 1 h. LCMS showed the reaction was complete. Then the mixture was concentrated and residue was poured to water and then extracted with EA (2×25 mL). The organic solution was then purified with silica gel chromatography and concentrated to give the product 5-((3H-[1,2,3]triazolo[4,5-b]pyridin-3-yl)oxy)-3-amino-6-chloro-N-(2-methoxybenzyl)pyrazine-2-carboxamide (5 g, yield: 97.1%) as a white solid. LCMS: m/z (ESI), [M+H]$^+$=427.2.

Step 3. Preparation of 3-amino-6-chloro-N-(2-methoxybenzyl)-5-(1H-pyrazol-1-yl)pyrazine-2-carboxamide To a stirring solution of 5-((3H-[1,2,3]triazolo[4,5-b]pyridin-3-yl)oxy)-3-amino-6-chloro-N-(2-methoxybenzyl)pyrazine-2-carboxamide (0.2 g, 0.47 mmol) in DMF (5 mL) was added 1H-pyrazole (0.05 g, 0.7 mmol) and K$_2$CO$_3$ (0.33 g, 2.35 mmol) at 110° C. Then the mixture was stirred at 110° C. for 3 h. LCMS showed the reaction was complete. Then the mixture was concentrated and residue was poured to water and then extracted with EA (2×25 mL). The organic solution was then purified with silica gel chromatography and concentrated to give the product 3-amino-6-chloro-N-(2-methoxybenzyl)-5-(1H-pyrazol-1-yl)pyrazine-2-carboxamide (0.14 g, yield: 83.3%) as a white solid. LCMS: m/z (ESI), [M+H]$^+$=359.1.

Step 4. Preparation of 3-amino-6-(2,6-dimethylpyridin-4-yl)-N-(2-methoxybenzyl)-5-(1H-pyrazol-1-yl)pyrazine-2-carboxamide (Cmpd. 56)

The mixture of 3-amino-6-chloro-N-(2-methoxybenzyl)-5-(1H-pyrazol-1-yl)pyrazine-2-carboxamide (0.07 g, 0.2 mmol), (2-methoxyphenyl)methanamine (0.07 g, 0.29 mmol) in dioxane (10 mL) was added K$_3$PO$_4$ (0.12 g, 0.59 mmol) and Pd$_2$dba$_3$ (0.02 g, 0.02 mmol) at 120° C. Then the mixture was stirred at this temperature for 0.5 h. LCMS showed the reaction was complete. Then the mixture was concentrated and residue was poured to water and then extracted with EA (2×25 mL). The organic solution was then concentrated and purified with rp-c18 to give the product 3-amino-6-(2,6-dimethylpyridin-4-yl)-N-(2-methoxybenzyl)-5-(1H-pyrazol-1-yl)pyrazine-2-carboxamide (Cmpd. 56) (0.017 g, yield: 20.3%) as a white solid. LCMS: m/z (ESI), [M+H]$^+$=429.5. $^1$H NMR (500 MHz, DMSO-d6) δ ppm 2.3 (s, 6H), 2.7-2.8 (m, 2H), 3.5 (br d, J=6.0 Hz, 2H), 3.7 (s, 3H), 5.6-5.7 (m, 1H), 6.3 (br s, 2H), 6.6 (s, 2H) 6.7-6.9 (m, 3H), 7.0 (br t, J=8.7 Hz, 2H), 7.2 (br t, J=7.1 Hz, 3H).

Example 57. Preparation of 3-amino-6-(2,6-dimethylpyridin-4-yl)-N-(2-methoxybenzyl)-5-(1H-pyrazol-1-yl)pyrazine-2-carboxamide (Cmpd. 57)

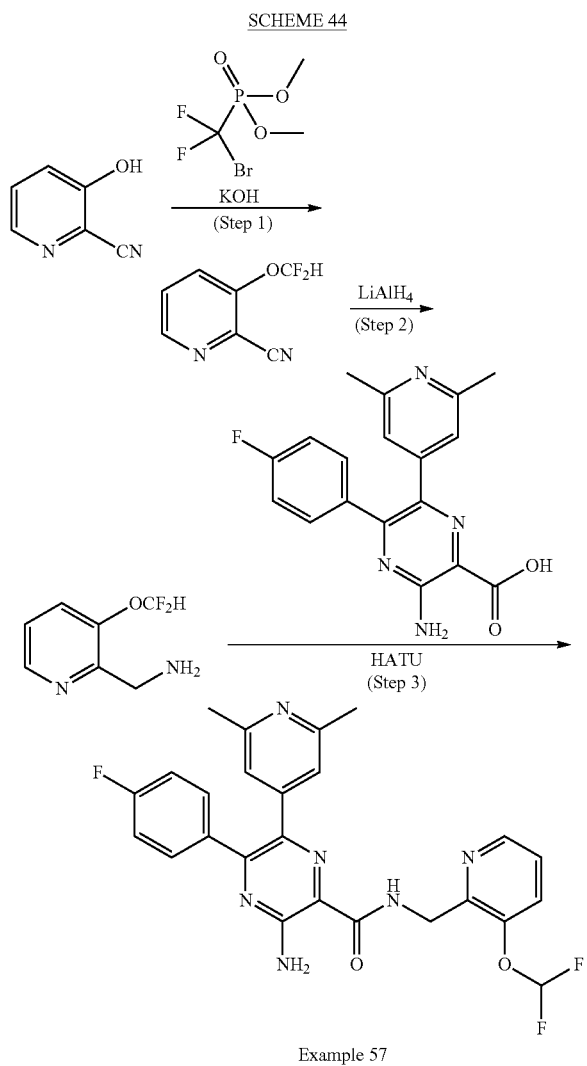

Example 57

Step 1. Preparation of 3-(difluoromethoxy)picolinonitrile

To a stirring solution of 3-hydroxypicolinonitrile (2.2 g, 18.33 mmol) in ACN (10 mL) and WATER was added dimethyl(bromodifluoromethyl)phosphonate (8.72 g, 36.66 mmol) and KOH (3.08 g, 54.99 mmol) at −78° C. Then the mixture was stirred at −78° C. for 16 h. LCMS showed the reaction was complete. Water was added and extracted with EA and concentrated to give a dark oil 3-(difluoromethoxy)picolinonitrile. LCMS: m/z (ESI), [M+H]+=171.4.

Step 2. Preparation of (3-(difluoromethoxy)pyridin-2-yl)methanamine

To a stirring solution of 3-(difluoromethoxy)picolinonitrile (1.5 g, 8.82 mmol) in THF (20 mL) was added LiAlH₄ (0.5 g, 13.23 mmol) at 0° C. Then the mixture was stirred at 0° C. for 1 h. LCMS showed desired product. Water was added and extracted with EA. Concentrated to give a yellow oil. LCMS: m/z (ESI), [M+H]+=175.1.

Step 3. Preparation of 3-amino-N-((3-(difluoromethoxy)pyridin-2-yl)methyl)-6-(2,6-dimethylpyridin-4-yl)-5-(4-fluorophenyl)pyrazine-2-carboxamide (Cmpd. 57)

The mixture of 3-amino-6-(2,6-dimethylpyridin-4-yl)-5-(4-fluorophenyl)pyrazine-2-carboxylic acid (0.03 g, 0.09 mmol), (3-(difluoromethoxy)pyridin-2-yl)methanamine (0.02 g, 0.13 mmol) in DMF (5 mL) was added DIEA (0.03 g, 0.27 mmol) and HATU (0.03 g, 0.09 mmol) at 20° C. Then the mixture was stirred at this temperature for 1 h. LCMS showed the reaction was completed. Then the mixture was concentrated and residue was poured to water and then extracted with EA (2×25 mL). The organic solution was then purified with rp-c18 concentrated to give the product 3-amino-N-((3-(difluoromethoxy)pyridin-2-yl)methyl)-6-(2,6-dimethylpyridin-4-yl)-5-(4-fluorophenyl)pyrazine-2-carboxamide (Cmpd. 57) (0.03 g, yield: 68.4%) as a white solid. LCMS: m/z (ESI), [M+H]+=495.6. ¹H NMR (500 MHz, DMSO-d6) δ ppm 2.3 (s, 6H), 4.7 (d, J=6.0 Hz, 2H), 7.0 (s, 2H), 7.2-7.3 (m, 3H), 7.3-7.5 (m, 4H), 7.7 (d, J=8.5 Hz, 1H), 8.4 (d, J=3.5 Hz, 1H), 9.2 (t, J=5.7 Hz, 1H).

Example 58. Preparation of 3-amino-N-((3-(difluoromethoxy)pyridin-2-yl)methyl)-5-(4-fluorophenyl)-6-(1-methyl-6-oxo-1,6-dihydropyridin-3-yl)pyrazine-2-carboxamide (Cmpd. 58)

SCHEME 45

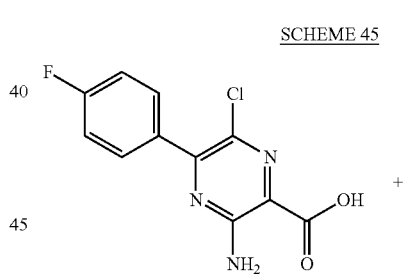

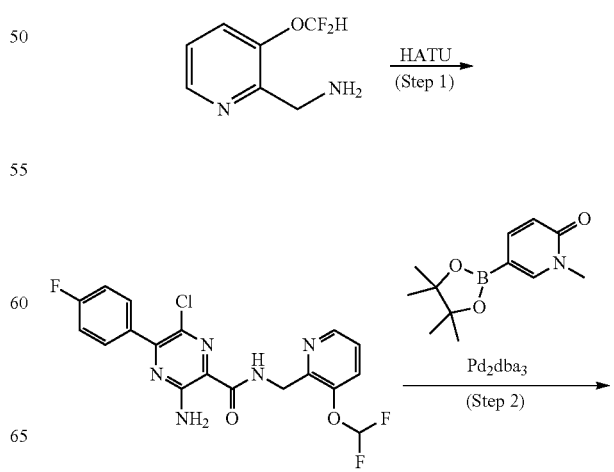

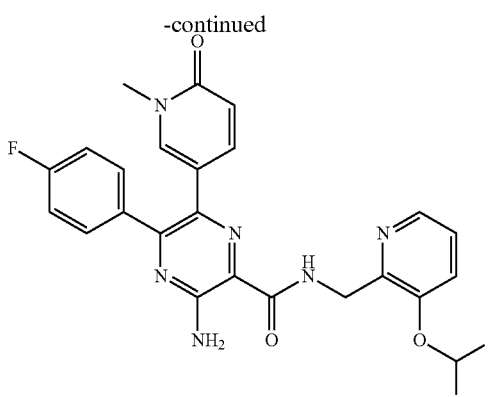

Example 58

Step 1. Preparation of 3-amino-6-chloro-N-((3-(difluoromethoxy)pyridin-2-yl)methyl)-5-(4-fluorophenyl)pyrazine-2-carboxamide The mixture of 3-amino-6-chloro-5-(4-fluorophenyl)pyrazine-2-carboxylic acid (0.12 g, 0.45 mmol), (3-(difluoromethoxy)pyridin-2-yl)methanamine (0.08 g, 0.45 mmol) in DMF (5 mL) was added DIEA (0.17 g, 1.35 mmol) and HATU (0.17 g, 0.45 mmol) at 20° C. Then the mixture was stirred at this temperature for 1 h. LCMS showed the reaction was complete. Then the mixture was concentrated and residue was poured to water and then extracted with EA (2×25 mL). The organic solution was then purified with rp-c18 concentrated to give the product 3-amino-6-chloro-N-((3-(difluoromethoxy)pyridin-2-yl)methyl)-5-(4-fluorophenyl)pyrazine-2-carboxamide (0.07 g, yield: 36.8%) as a white solid. LCMS: m/z (ESI), [M+H]$^+$=424.2.

Step 2. Preparation of 3-amino-N-((3-(difluoromethoxy)pyridin-2-yl)methyl)-5-(4-fluorophenyl)-6-(1-methyl-6-oxo-1,6-dihydropyridin-3-yl)pyrazine-2-carboxamide (Cmpd. 58)

The mixture of 3-amino-6-chloro-N-((3-(difluoromethoxy)pyridin-2-yl)methyl)-5-(4-fluorophenyl)pyrazine-2-carboxamide (0.06 g, 0.14 mmol), 1-methyl-5-(4,4,5,5-tetramethyl-1,3,2-dioxaborolan-2-yl)pyridin-2(1H)-one (0.05 g, 0.21 mmol) in dioxane (3 mL) was added K$_3$PO$_4$ (0.09 g, 0.43 mmol) and Pd$_2$dba$_3$ (0.01 g, 0.01 mmol) at 120° C. Then the mixture was stirred at this temperature for 0.5 h. LCMS showed the reaction was complete. Then the mixture was concentrated and residue was poured to water and then extracted with EA (2×25 mL). The organic solution was then concentrated and purified with RP-C18 to give the product 3-amino-N-((3-(difluoromethoxy)pyridin-2-yl)methyl)-5-(4-fluorophenyl)-6-(1-methyl-6-oxo-1,6-dihydropyridin-3-yl)pyrazine-2-carboxamide (Cmpd. 58) (0.025 g, yield: 35.5%) as a white solid. LCMS: m/z (ESI), [M+H]$^+$=497.2. $^1$H NMR (500 MHz, DMSO-d6) δ ppm 3.4 (s, 3H), 4.7 (d, J=5.7 Hz, 2H), 6.2 (d, J=9.5 Hz, 1H), 7.1 (dd, J=9.5, 2.5 Hz, 1H), 7.2-7.3 (m, 3H), 7.4 (s, 1H), 7.4 (dd, J=8.5, 4.7 Hz, 1H), 7.5-7.6 (m, 3H), 7.7 (d, J=8.2 Hz, 1H), 8.0 (d, J=2.5 Hz, 1H), 8.4 (d, J=4.4 Hz, 1H), 9.2 (t, J=6.0 Hz, 1H).

Example 59. Preparation of 3-amino-N-(2-(difluoromethoxy)phenyl)-5-(3-methyl-1H-pyrazol-1-yl)-6-(1-methyl-6-oxo-1,6-dihydropyridin-3-yl)pyrazine-2-carboxamide (Cmpd. 59)

SCHEME 46

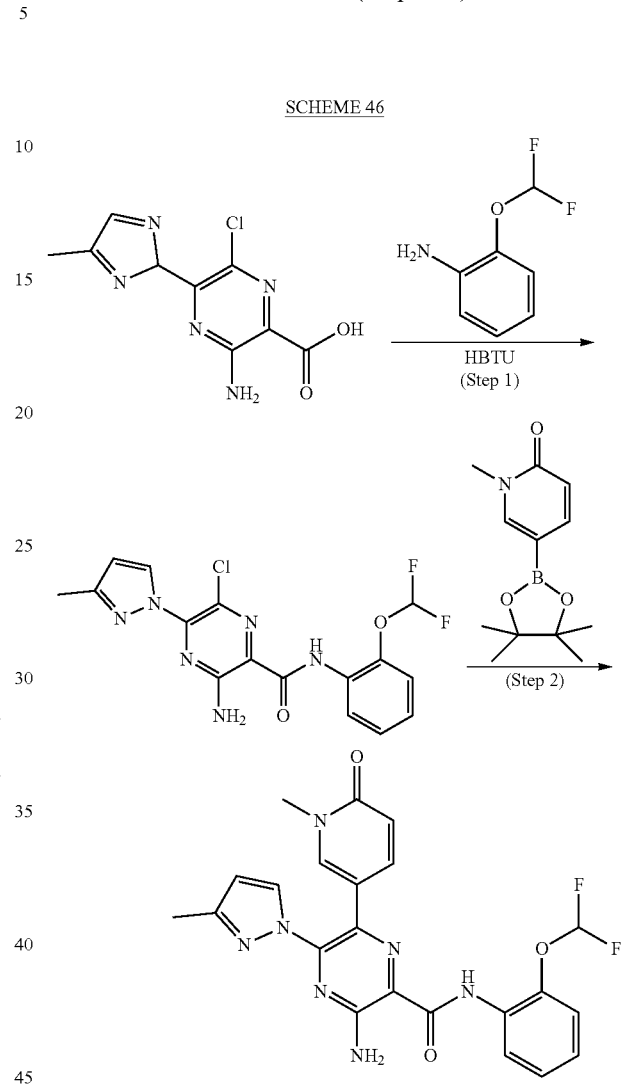

Example 59

Step 1. Preparation of 3-amino-6-chloro-N-(2-(difluoromethoxy)phenyl)-5-(3-methyl-1H-pyrazol-1-yl)pyrazine-2-carboxamide The mixture of 3-amino-6-chloro-5-(3-methyl-1H-pyrazol-1-yl)pyrazine-2-carboxylic acid (0.1 g, 0.4 mmol), 2-(difluoromethoxy)aniline (0.1 g, 0.59 mmol) in DMF (5 mL) was added DIEA (0.15 g, 1.19 mmol) and HATU (0.15 g, 0.4 mmol) at 20° C. Then the mixture was stirred at this temperature for 1 h. LCMS showed the reaction was complete. Then the mixture was concentrated and residue was poured to water and then extracted with EA (2×25 mL). The organic solution was then purified with rp-c18 concentrated to give the product 3-amino-6-chloro-N-(2-(difluoromethoxy)phenyl)-5-(3-methyl-1H-pyrazol-1-yl)pyrazine-2-carboxamide (0.05 g, yield: 30.7%) as a white solid. LCMS: m/z (ESI), [M+H]$^+$=413.4.

Step 2. Preparation of 3-amino-N-(2-(difluoromethoxy)phenyl)-5-(3-methyl-1H-pyrazol-1-yl)-6-(1-methyl-6-oxo-1,6-dihydropyridin-3-yl)pyrazine-2-carboxamide (Cmpd. 59)

The mixture of 3-amino-6-chloro-N-(2-(difluoromethoxy)phenyl)-5-(3-methyl-1H-pyrazol-1-yl)pyrazine-2-carboxamide (0.03 g, 0.07 mmol), 1-methyl-5-(4,4,5,5-tetramethyl-1,3,2-dioxaborolan-2-yl)pyridin-2(1H)-one (0.03 g, 0.11 mmol) in dioxane (3 mL) was added $K_3PO_4$ (0.05 g, 0.22 mmol) and $Pd_2dba_3$ (0.01 g, 0.01 mmol) at 120° C. Then the mixture was stirred at this temperature for 0.5 h. LCMS showed the reaction was completed. Then the mixture was concentrated and residue was poured to water and then extracted with EA (2×25 mL). The organic solution was then concentrated and purified with rp-c18 to give the product 3-amino-N-(2-(difluoromethoxy)phenyl)-5-(3-methyl-1H-pyrazol-1-yl)-6-(1-methyl-6-oxo-1,6-dihydropyridin-3-yl)pyrazine-2-carboxamide (Cmpd. 59) (0.02 g, yield: 56.6%) as a white solid. LCMS: m/z (ESI), $[M+H]^+$= 486.1. $^1$H NMR (500 MHz, DMSO-d6) δ ppm 2.2 (s, 3H), 3.5 (s, 3H), 6.3 (d, J=9.5 Hz, 1H), 6.4 (d, J=2.5 Hz, 1H), 7.0 (dd, J=9.5, 2.5 Hz, 1H), 7.1-7.5 (m, 5H), 7.8-7.9 (m, 2H), 8.1 (d, J=2.2 Hz, 1H), 8.3-8.3 (m, 1H), 10.3 (s, 1H).

Compounds listed in the table below were prepared using methods described in Cmpd. 59.

| Example/ Cmpd number | Structure | LCMS [M + H]+ | $^1$H NMR |
|---|---|---|---|
| 60 | 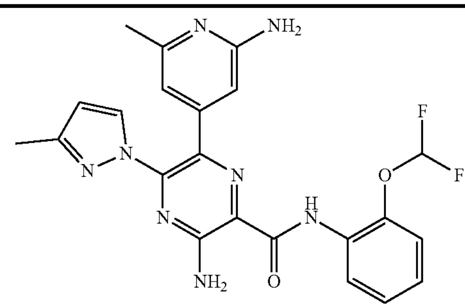 | 467.1 | $^1$H NMR (500 MHz, DMSO-d6) δ ppm 2.1-2.2 (m, 3H), 2.2 (s, 3H), 5.7 (s, 2H), 6.0 (s, 1H), 6.3 (d, J = 2.5 Hz, 1H), 6.4 (s, 1H), 7.2-7.3 (m, 1H), 7.3-7.5 (m, 3H), 7.9 (s, 1H), 8.0 (s, 2H), 8.4 (d, J = 8.2 Hz, 1H), 10.3 (s, 1H). |

Example 61. Preparation of 3-amino-6-(2,6-dimethylpyridin-4-yl)-N-(2-methoxybenzyl)-5-(5-methylfuran-3-yl)pyrazine-2-carboxamide (Cmpd. 61)

SCHEME 47

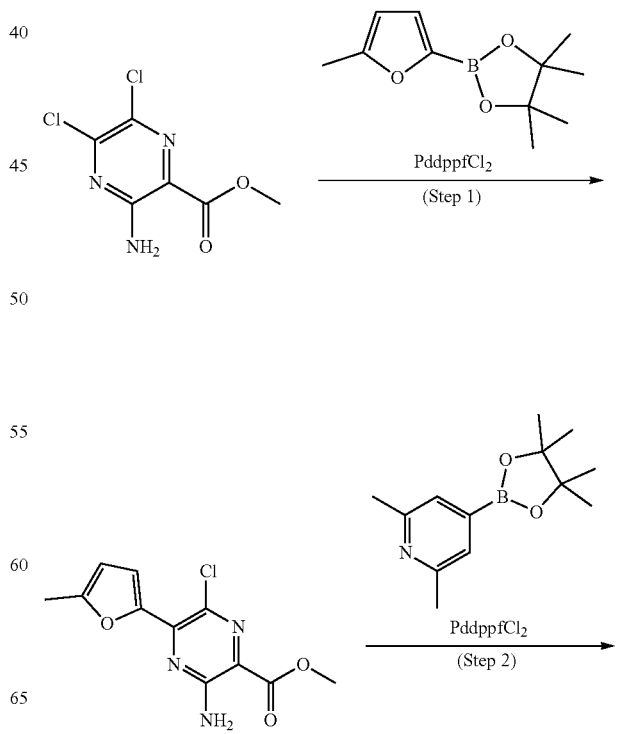

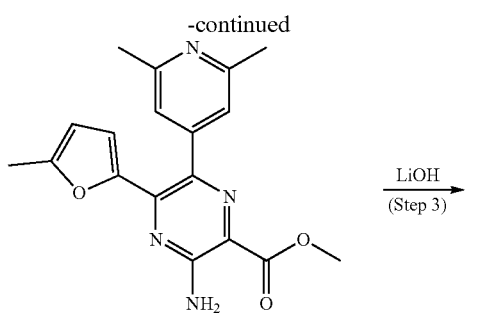

-continued

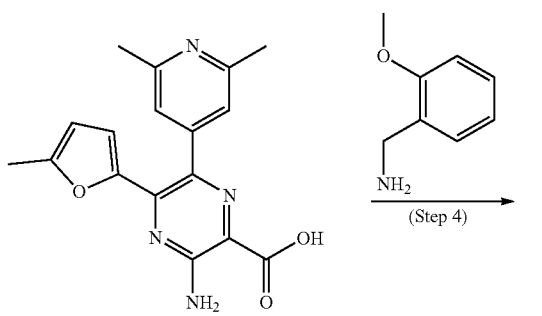

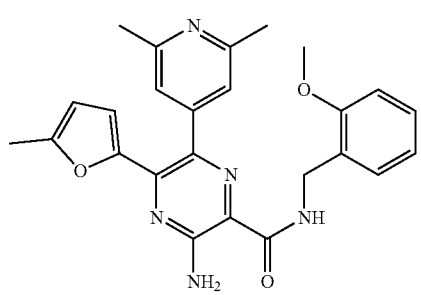

Example 61

Step 1. Preparation of methyl 3-amino-6-chloro-5-(5-methylfuran-3-yl)pyrazine-2-carboxylate The mixture of methyl 3-amino-5,6-dichloropyrazine-2-carboxylate (0.5 g, 2.26 mmol), 4,4,5,5-tetramethyl-2-(5-methylfuran-2-yl)-1,3,2-dioxaborolane (0.71 g, 3.39 mmol) in dioxane (20 mL) was added $Na_2CO_3$ (0.94 g, 4.53 mmol) and $Pd(dppf)Cl_2$ (0.83 g, 1.13 mmol) at 100° C. Then the mixture was stirred at this temperature for 2 h. LCMS showed the reaction was completed and purified with silica gel chromatography to give a desired product methyl 3-amino-6-chloro-5-(5-methylfuran-3-yl)pyrazine-2-carboxylate. LCMS: m/z (ESI), $[M+H]^+=268.4$.

Step 2. Preparation of methyl 3-amino-6-(2,6-dimethylpyridin-4-yl)-5-(5-methylfuran-2-yl)pyrazine-2-carboxylate The mixture of methyl 3-amino-6-chloro-5-(5-methylfuran-3-yl)pyrazine-2-carboxylate (0.26 g, 1 mmol), 2,6-dimethyl-4-(4,4,5,5-tetramethyl-1,3,2-dioxaborolan-2-yl)pyridine (0.23 g, 1 mmol) in dioxane (20 mL) was added $Na_2CO_3$ (0.94 g, 4.53 mmol) and $Pd(dppf)Cl_2$ (0.073 g, 0.1 mmol) at 100° C. Then the mixture was stirred at this temperature for 2 h. LCMS showed the reaction was completed and purified with silica gel chromatography to give a desired product methyl 3-amino-6-(2,6-dimethylpyridin-4-yl)-5-(5-methylfuran-2-yl)pyrazine-2-carboxylate. LCMS: m/z (ESI), $[M+H]^+=339.5$.

Step 3. Preparation of 3-amino-6-(2,6-dimethylpyridin-4-yl)-5-(5-methylfuran-2-yl)pyrazine-2-carboxylic Acid To a stirring solution of methyl 3-amino-6-(2,6-dimethylpyridin-4-yl)-5-(5-methylfuran-2-yl)pyrazine-2-carboxylate (0.4 g, 1.18 mmol) in MeOH (20 mL) was added NaOH (0.09 g, 2.37 mmol) at 25° C. Then the mixture was stirred at this temperature for 16 h. LCMS showed the reaction was complete. Then the mixture was concentrated and residue was poured to water and then extracted with EA (2×10 mL). The organic solution was then concentrated to give the crude product 3-amino-6-(2,6-dimethylpyridin-4-yl)-5-(5-methylfuran-2-yl)pyrazine-2-carboxylic acid (0.3 g, yield: 78.2%) as a yellow solid. LCMS: m/z (ESI), $[M+H]^+=325.2$.

Step 4. Preparation of 3-amino-6-(2,6-dimethylpyridin-4-yl)-N-(2-methoxybenzyl)-5-(5-methylfuran-2-yl)pyrazine-2-carboxamide (Cmpd. 61)

The mixture of 3-amino-6-(2,6-dimethylpyridin-4-yl)-5-(5-methylfuran-2-yl)pyrazine-2-carboxylic acid (0.05 g, 0.15 mmol), (2-methoxyphenyl)methanamine (0.021 g, 0.15 mmol) in DMF (5 mL) was added DIEA (0.058 g, 0.45 mmol) and HATU (0.057 g, 0.15 mmol) at 20° C. Then the mixture was stirred at this temperature for 1 h. LCMS showed the reaction was complete. Then the mixture was concentrated and residue was poured to water and then extracted with EA (2×25 mL). The organic solution was then purified with rp-c18 concentrated to give the product 3-amino-6-(2,6-dimethylpyridin-4-yl)-N-(2-methoxybenzyl)-5-(5-methylfuran-2-yl)pyrazine-2-carboxamide (Cmpd. 61) (0.021 g, yield: 32%) as a white solid. LCMS: m/z (ESI), $[M+H]^+=444.1$. $^1$H NMR (500 MHz, DMSO-d6) δ ppm 2.2 (s, 3H), 2.4 (s, 6H), 3.8 (s, 3H), 4.5 (d, J=6.3 Hz, 2H), 6.2 (d, J=3.2 Hz, 1H), 6.5 (d, J=3.2 Hz, 1H), 6.9 (t, J=7.4 Hz, 1H), 7.0 (d, J=8.2 Hz, 1H), 7.1-7.2 (m, 3H), 7.2 (t, J=7.1 Hz, 1H), 8.9 (t, J=6.3 Hz, 1H).

Compounds listed in the table below were prepared using methods described in Cmpd. 61.

| Example/Cmpd number | Structure | LCMS [M + H]+ | 1H NMR |
|---|---|---|---|
| 62 | 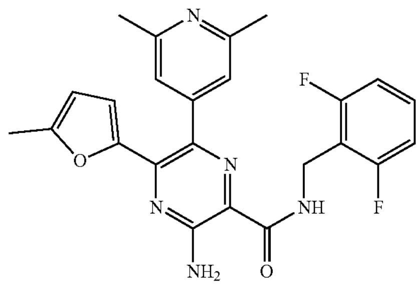 [SMILES: Cc1cc(-c2nc(C(=O)NCc3c(F)cccc3F)c(N)nc2-c2ccc(C)o2)cc(C)n1] | 450.2 | 1H NMR (500 MHz, DMSO-d6) ppm 2.2 (s, 3H), 2.4 (s, 6H), 4.6 (d, J = 6.0 Hz, 2H), 6.2 (d, J = 3.2 Hz, 1H), 6.4 (d, J = 3.5 Hz, 1H), 7.0-7.1 (m, 4H), 7.3-7.4 (m, 1H), 7.7 (brs, 2H), 8.8 (t, J = 5.8 Hz, 1H) |

Example 63. Preparation of 3-amino-6-(2,6-dimethylpyridin-4-yl)-N-(2-methoxybenzyl)-5-(1-methyl-1H-pyrazol-4-yl)pyrazine-2-carboxamide (Cmpd. 63)

SCHEME 48

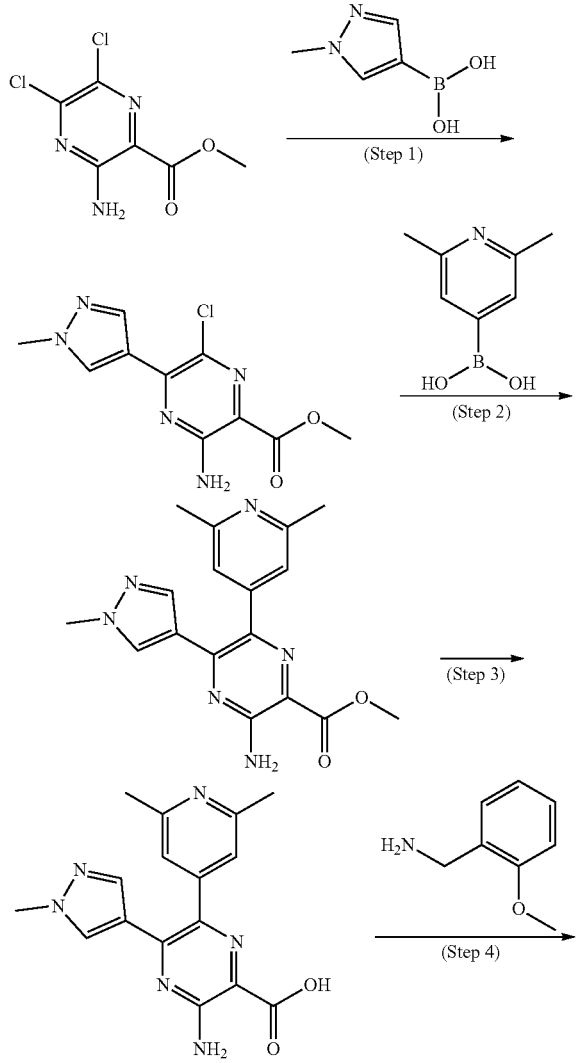

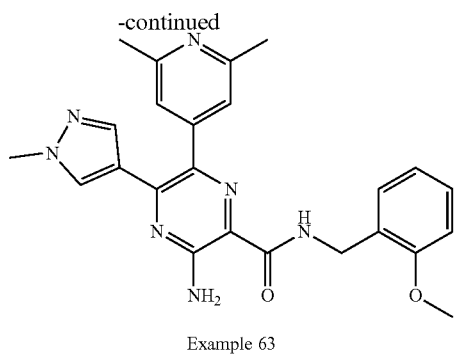

Example 63

Step 1. Preparation of methyl 3-amino-6-chloro-5-(1-methyl-1H-pyrazol-4-yl)pyrazine-2-carboxylate The mixture of methyl 3-amino-5,6-dichloropyrazine-2-carboxylate (0.5 g, 2.26 mmol), (1-methyl-1H-pyrazol-4-yl) boronic acid (0.43 g, 3.39 mmol) in dioxane (20 mL) was added Na$_2$CO$_3$ (0.57 g, 4.53 mmol) and Pd(dppf)Cl$_2$ (0.83 g, 1.13 mmol) at 100° C. Then the mixture was stirred at this temperature for 2h. LCMS showed the reaction was completed and purified with silica gel chromatography to give a desired product methyl 3-amino-6-chloro-5-(1-methyl-1H-pyrazol-4-yl)pyrazine-2-carboxylate. LCMS: m/z (ESI), [M+H]$^+$=268.6.

Step 2. Preparation of methyl 3-amino-6-(2,6-dimethylpyridin-4-yl)-5-(1-methyl-1H-pyrazol-4-yl) pyrazine-2-carboxylate The mixture of methyl 3-amino-6-chloro-5-(1-methyl-1H-pyrazol-4-yl)pyrazine-2-carboxylate (0.4 g, 1.5 mmol), (2,6-dimethylpyridin-4-yl)boronic acid (0.34 g, 2.25 mmol) in dioxane (20 mL) was added Na$_2$CO$_3$ (0.45 g, 3 mmol) and Pd(dppf)Cl$_2$ (0.55 g, 0.75 mmol) at 100° C. Then the mixture was stirred at this temperature for 2 h. LCMS showed the reaction was completed and purified with silica gel chromatography to give a desired product methyl 3-amino-6-(2,6-dimethylpyridin-4-yl)-5-(1-methyl-1H-pyrazol-4-yl)pyrazine-2-carboxylate. LCMS: m/z (ESI), [M+H]$^+$=339.2.

Step 3. Preparation of 3-amino-6-(2,6-dimethylpyridin-4-yl)-5-(1-methyl-1H-pyrazol-4-yl)pyrazine-2-carboxylic Acid To a stirring solution of methyl 3-amino-6-(2,6-dimethylpyridin-4-yl)-5-(1-methyl-1H-pyrazol-4-yl)pyrazine-2-carboxylate (0.4 g, 1.18 mmol) in MeOH (20 mL) was added NaOH (0.09 g, 2.37 mmol) at 25° C. Then the mixture was stirred at this temperature for 16 h. LCMS showed the reaction was complete. Then the mixture was concentrated and residue was poured to water and then extracted with EA (2×10 mL). The organic solution was then concentrated to give the crude product 3-amino-6-(2,6-dimethylpyridin-4-yl)-5-(1-methyl-1H-pyrazol-4-yl)pyrazine-2-carboxylic acid (0.3 g, yield: 78.2%) as a yellow solid. LCMS: m/z (ESI), [M+H]$^+$=325.5.

Step 4. Preparation of 3-amino-6-(2,6-dimethylpyridin-4-yl)-N-(2-methoxybenzyl)-5-(1-methyl-1H-pyrazol-4-yl)pyrazine-2-carboxamide (Cmpd. 63)

The mixture of 3-amino-6-(2,6-dimethylpyridin-4-yl)-5-(1-methyl-1H-pyrazol-4-yl)pyrazine-2-carboxylic acid (0.05 g, 0.15 mmol), (2-methoxyphenyl)methanamine (0.021 g, 0.15 mmol) in DMF (5 mL) was added DIEA (0.058 g, 0.45 mmol) and HATU (0.057 g, 0.15 mmol) at 20° C. Then the mixture was stirred at this temperature for 1 h. LCMS showed the reaction was complete. Then the mixture was concentrated and residue was poured to water and then extracted with EA (2×25 mL). The organic solution was then purified with rp-c18 concentrated to give the product 3-amino-6-(2,6-dimethylpyridin-4-yl)-N-(2-methoxybenzyl)-5-(1-methyl-1H-pyrazol-4-yl)pyrazine-2-carboxamide (Cmpd. 63) (0.004 g, yield: 6%) as a white solid. LCMS: m/z (ESI), [M+H]$^+$=444.2. $^1$H NMR (500 MHz, DMSO-d6) δ ppm 2.2 (s, 3H), 2.4 (s, 6H), 3.8 (s, 3H), 4.5 (d, J=6.3 Hz, 2H), 6.2 (d, J=3.2 Hz, 1H), 6.5 (d, J=3.2 Hz, 1H), 6.9 (t, J=7.4 Hz, 1H), 7.0 (d, J=8.2 Hz, 1H), 7.1-7.2 (m, 3H), 7.2 (t, J=7.1 Hz, 1H), 8.9 (t, J=6.3 Hz, 1H).

Compounds listed in the table below were prepared using methods described in Cmpd. 63.

| Example/ Cmpd number | Structure | LCMS [M + H]$^+$ | $^1$H NMR |
|---|---|---|---|
| 64 | 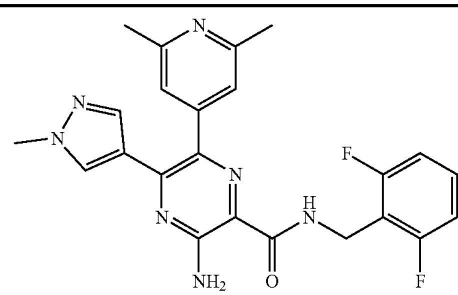 | 450.1 | $^1$H NMR (500 MHz, DMSO-d6) δ ppm 2.4 (s, 6H), 3.8 (s, 3H), 4.6 (d, J = 5.7 Hz, 2H), 7.1 (t, J = 7.3 Hz, 2H), 7.1 (s, 2H), 7.2 (s, 1H), 7.3-7.4 (m, 1H), 7.6 (s, 1H), 8.8 (t, J = 6.0 Hz, 1H) |

Example 72. Preparation of 3-amino-N-(2-(difluoromethoxy)benzyl)-5-(4-fluorophenyl)-6-(1-methyl-6-oxo-1,6-dihydropyridin-3-yl)pyrazine-2-carboxamide (Cmpd. 72)

SCHEME 49

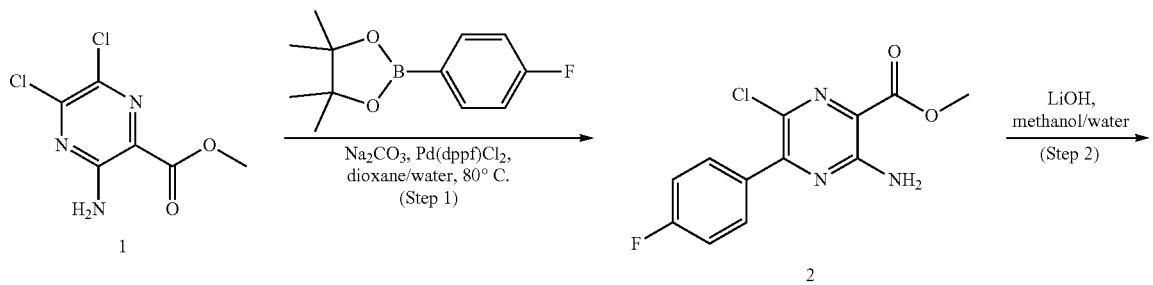

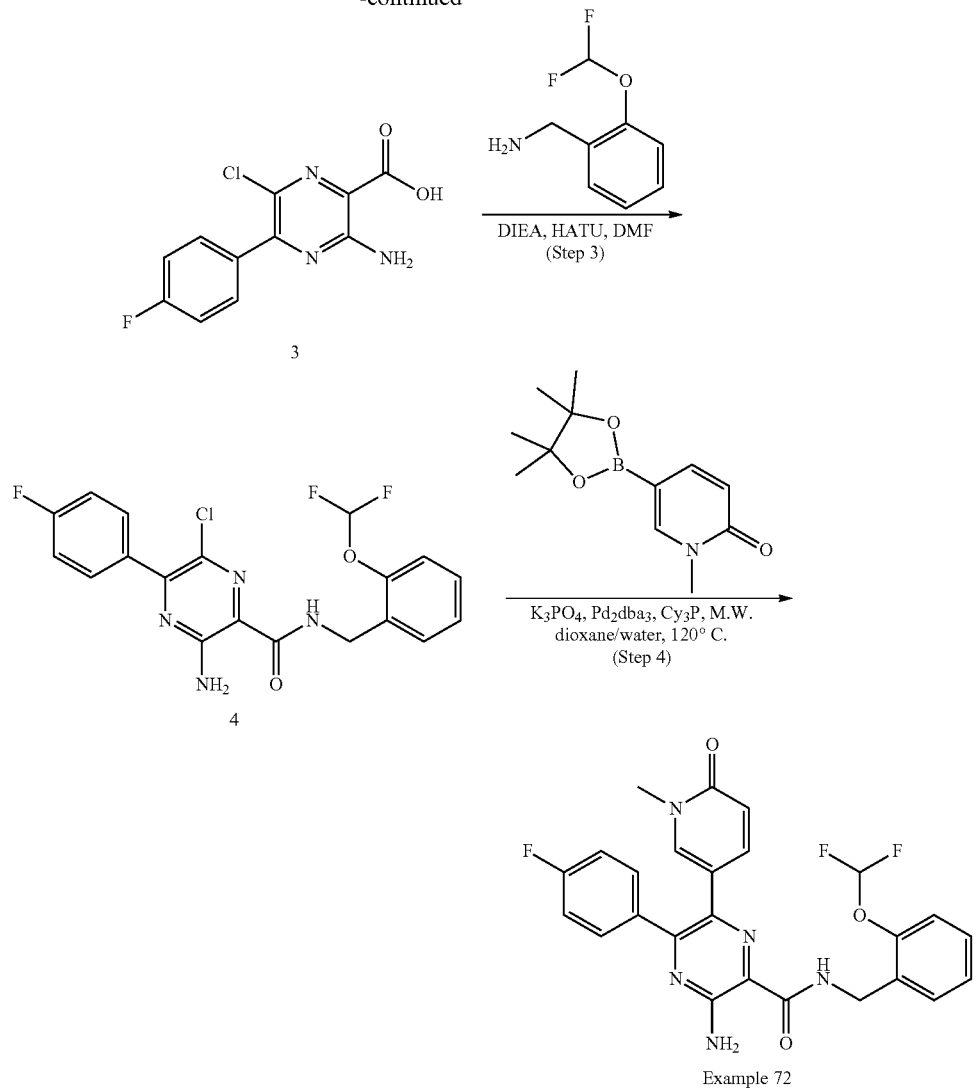

Example 72

Step 1. Preparation of methyl 3-amino-6-chloro-5-(4-fluorophenyl)pyrazine-2-carboxylate The mixture of methyl 3-amino-5,6-dichloropyrazine-2-carboxylate (4.4 g, 19.91 mmol), 2-(4-fluorophenyl)-4,4,5,5-tetramethyl-1,3,2-dioxaborolane (3.07 g, 21.9 mmol) in dioxane (50 mL) and water (5 mL) was added $Na_2CO_3$ (4.22 g, 39.82 mmol) and dppfPdCl$_2$ (2.84 g, 3.98 mmol). Then the mixture was stirred at 100° C. for 1 h under $N_2$ atmosphere. Then the mixture was concentrated and residue was poured to water (100 mL) and then extracted with EA (100 mL×3). The organic solution was then concentrated to afford the crude product (5.5 g, 98% yield) as a yellow solid which was used for next step without further purification. MS m/z (ESI) $[M+H]^+$=282.2.

Step 2. Preparation of 3-amino-6-chloro-5-(4-fluorophenyl)pyrazine-2-carboxylic Acid The mixture of methyl 3-amino-6-chloro-5-(4-fluorophenyl)pyrazine-2-carboxylate (1.1 g, 3.9 mmol) in methanol (5 mL) and water (3 mL) was added LiOH (0.3 g, 12 mmol). Then the mixture was stirred at 20° C. for 3 h. Then the mixture was diluted by citric acid solution (2N, 50 mL) and then filtered. The solid was dried to afford 3-amino-6-chloro-5-(4-fluorophenyl)pyrazine-2-carboxylic acid (0.95 g, 91% yield) as a yellow solid. MS m/z (ESI) $[M+H]^+$=268.2.

Step 3. Preparation of 3-amino-6-chloro-N-(2-(difluoromethoxy)benzyl)-5-(4-fluorophenyl) pyrazine-2-carboxamide To a mixture of 3-amino-6-chloro-5-(4-fluorophenyl)pyrazine-2-carboxylic acid (100 mg, 0.37 mmol), (2-(difluoromethoxy)phenyl)methanamine (80 mg, 0.46 mmol) and DIEA (100 mg, 0.78 mmol) in DMF (3 mL) was added HATU (200 mg, 0.53 mmol) at 20° C. The resulting mixture was stirred at 20° C. for 10 min. The mixture was purified by C18-40 g (MeCN/water=5%-80%) to afford 3-amino-6-chloro-N-(2-(difluoromethoxy) benzyl)-5-(4-fluorophenyl) pyrazine-2-carboxamide (120 mg, 76% yield) as a yellow solid. MS m/z (ESI) $[M+H]^+$=423.3.

Step 4. Preparation of 3-amino-N-(2-(difluoromethoxy)benzyl)-5-(4-fluorophenyl)-6-(1-methyl-6-oxo-1,6-dihydropyridin-3-yl)pyrazine-2-carboxamide (Cmpd. 72)

To a mixture of 3-amino-6-chloro-N-(2-(difluoromethoxy)benzyl)-5-(4-fluorophenyl) pyrazine-2-carboxamide (90 mg, 0.21 mmol), 1-methyl-5-(4,4,5,5-tetramethyl-1,3,2-dioxaborolan-2-yl)pyridin-2(1H)-one (50 mg, 0.21 mmol), Pd$_2$(dba)$_3$ (8 mg, 0.0087 mmol), Tricyclohexylphosphine (11 mg, 0.039 mmol) and K$_3$PO$_4$ (75 mg, 0.35 mmol) in dioxane (3 mL) was added water (1 mL). The resulting mixture was sealed and heated at 120° C. for 15 min in Microwave. The mixture was filtered and the filtrate was purified by C18-40 g (MeCN/water=5%-80%) to afford 3-amino-N-(2-(difluoromethoxy)benzyl)-5-(4-fluorophenyl)-6-(1-methyl-6-oxo-1,6-dihydropyridin-3-yl)pyrazine-2-carboxamide (Cmpd. 72) (82 mg, 78% yield) as a yellow solid. LCMS: m/z (ESI), [M+H]$^+$=496.3. $^1$H NMR (500 MHz, DMSO-d6) δ ppm 3.42 (s, 3H), 4.57 (d, J=6.31 Hz, 2H), 6.20 (d, J=9.46 Hz, 1H), 7.10 (dd, J=9.30, 2.68 Hz, 1H), 7.16-7.30 (m, 5H), 7.30-7.36 (m, 2H), 7.44-7.83 (m, 3H), 7.64 (br d, J=16.08 Hz, 1H), 7.99 (d, J=2.52 Hz, 1H), 9.23 (t, J=6.31 Hz, 1H).

Compounds listed in the table below were prepared using methods described in Cmpd. 72.

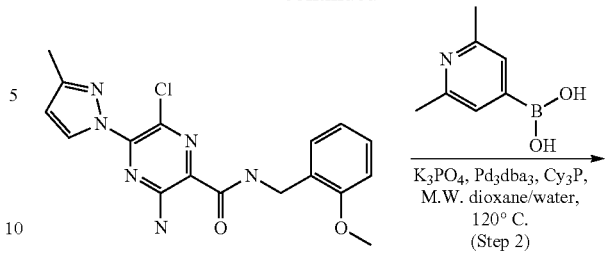

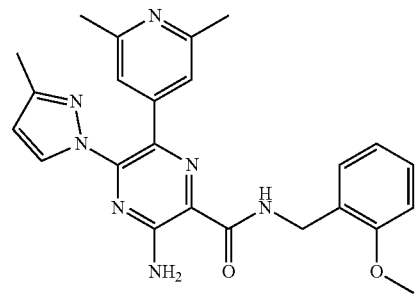

Example 75

| Example/ Cmpd number | Structure | LCMS [M + H]$^+$ | $^1$H NMR |
|---|---|---|---|
| 73 | 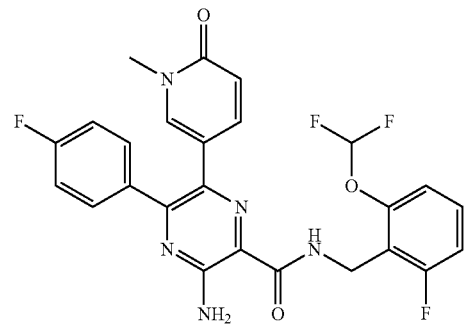 [SMILES: Cn1cc(-c2nc(C(=O)NCc3c(F)cccc3OC(F)F)c(N)nc2-c2ccc(F)cc2)ccc1=O] | 514.3 | $^1$H NMR (500 MHz, DMSO-d6) δ 3.40 (s, 3 H) 4.60 (d, J = 5.99 Hz, 2 H) 6.19 (d, J = 9.46 Hz, 1 H) 7.03-7.09 (m, 2 H) 7.11-7.15 (m, 1 H) 7.23 (t, J = 8.98 Hz, 2 H) 7.28-7.44 (m, 2 H) 7.45-7.77 (m, 4 H) 7.90 (d, J = 2.52 Hz, 1 H) 8.86 (t, J = 5.83 Hz, 1 H) |

Example 75. Preparation of 3-amino-6-(2,6-dimethylpyridin-4-yl)-N-(2-methoxybenzyl)-5-(3-methyl-1H-pyrazol-1-yl)pyrazine-2-carboxamide (Cmpd. 75)

SCHEME 50

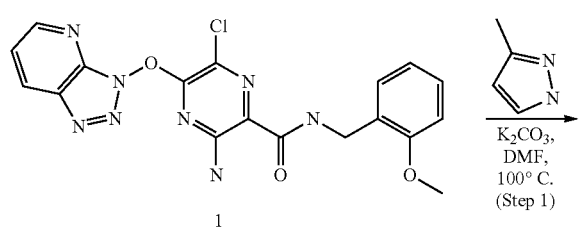

Step 1. Preparation of 3-amino-6-chloro-N-(2-methoxybenzyl)-5-(3-methyl-1H-pyrazol-1-yl)pyrazine-2-carboxamide To a mixture of 5-((3H-[1,2,3]triazolo[4,5-b]pyridin-3-yl)oxy)-3-amino-6-chloro-N-(2-methoxy benzyl)pyrazine-2-carboxamide (500 mg, 1.2 mmol) in DMF (5 mL) was added 3-methyl-1H-pyrazole (120 mg, 1.5 mmol) and K$_2$CO$_3$ (350 mg, 2.5 mmol). The resulting mixture was heated at 120° C. for 1 h. The mixture was purified by C18-40 g (MeCN/water=5%-80%) to afford 3-amino-6-chloro-N-(2-methoxybenzyl)-5-(3-methyl-1H-pyrazol-1-yl)pyrazine-2-carboxamide (200 mg, 46% yield) and 3-amino-6-chloro-N-(2-methoxybenzyl)-5-(5-methyl-1H-pyrazol-1-yl)pyrazine-2-carboxamide (40 mg, 7% yield) as yellow solids. LCMS m/z (ESI) [M+H]$^+$=373.2.

Step 2. Preparation of 3-amino-6-(2,6-dimethylpyridin-4-yl)-N-(2-methoxybenzyl)-5-(3-methyl-1H-pyrazol-1-yl)pyrazine-2-carboxamide (Cmpd. 75)

To a mixture of 3-amino-6-chloro-N-(2-methoxybenzyl)-5-(3-methyl-1H-pyrazol-1-yl)pyrazine-2-carboxamide (45 mg, 0.12 mmol), (2,6-dimethylpyridin-4-yl)boronic acid (20 mg, 0.13 mmol), Pd$_2$(dba)$_3$ (7 mg, 0.0076 mmol), Tricyclohexylphosphine (13 mg, 0.046 mmol) and K$_3$PO$_4$ (45 mg, 0.21 mmol) in dioxane (3 mL) was added water (1 mL). The resulting mixture was sealed and heated at 120° C. for 15 min in Microwave. The mixture was filtered and the filtrate was purified by C18-40 g (MeCN/water=5%-80%) to afford 3-amino-6-(2,6-dimethylpyridin-4-yl)-N-(2-methoxybenzyl)-5-(3-methyl-H-pyrazol-1-yl)pyrazine-2-carboxamide (Cmpd. 75) (36 mg, 67% yield) as a white solid. LCMS: m/z (ESI), [M+H]$^+$=444.3. $^1$H NMR (500 MHz, DMSO-d6) δ ppm 2.10 (s, 3H), 2.34 (s, 6H), 3.84 (s, 3H), 4.50 (d, J=6.31 Hz, 2H), 6.34 (d, J=2.52 Hz, 1H), 6.86 (s, 2H), 6.89 (t, J=7.41 Hz, 1H), 7.00 (d, J=8.20 Hz, 1H), 7.15 (d, J=7.25 Hz, 1H), 7.23 (t, J=7.90 Hz, 1H), 7.98 (d, J=2.21 Hz, 3H), 9.04 (t, J=6.42 Hz, 1H).

Compounds listed in the table below were prepared using methods described in Cmpd. 75.

| Example/Cmpd number | Structure | LCMS [M + H]$^+$ | $^1$H NMR |
|---|---|---|---|
| 74 | 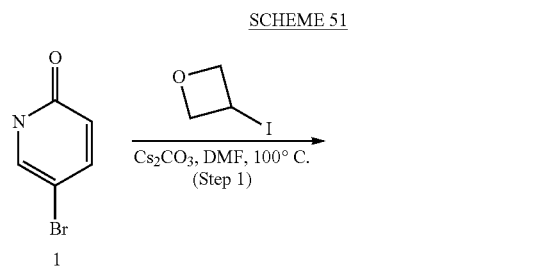 | 444.3 | $^1$H NMR (500 MHz, DMSO-d6) δ 2.18 (s, 3 H), 2.31 (s, 6 H), 3.85 (s, 3 H), 4.52 (br d, J = 6.31 Hz, 2 H), 6.30 (s, 1 H), 6.72 (s, 2 H), 6.88-6.92 (m, 1 H), 7.01 (d, J = 8.20 Hz, 1 H), 7.18 (d, J = 7.25 Hz, 1 H), 7.22-7.26 (m, 1 H), 7.54 (d, J = 1.26 Hz, 1 H), 7.86-8.27 (m, 2 H), 9.16 (t, J = 6.46 Hz, 1H) |

Example 77. Preparation of 3-amino-N-(2-(difluoromethoxy)benzyl)-5-(4-fluorophenyl)-6-(1-methyl-6-oxo-1,6-dihydropyridin-3-yl)pyrazine-2-carboxamide (Cmpd. 77)

SCHEME 51

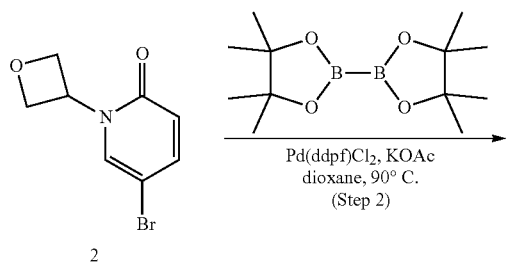

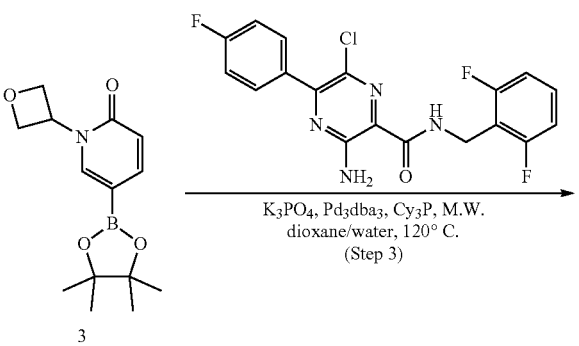

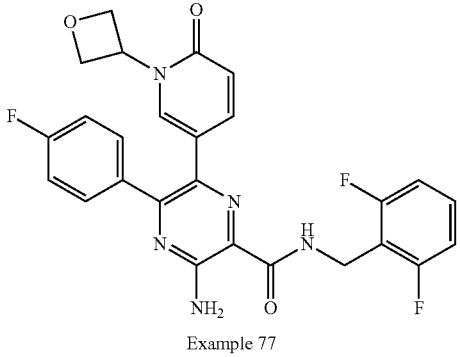

Example 77

Step 1. Preparation of 5-bromo-1-(oxetan-3-yl)pyridin-2(1H)-one

To a mixture of 5-bromopyridin-2(1H)-one (1.2 g, 6.9 mmol) in DMF (10 mL) was added 3-iodooxetane (1.3 g, 7.1 mmol) and Cs$_2$CO$_3$ (2.7 g, 8.3 mmol). The resulting mixture was heated at 100° C. for 4 h. The mixture was filtered and the filtrate was purified by C18-40 g (MeCN/water=5%-40%) to afford 5-bromo-1-(oxetan-3-yl)pyridin-2(1H)-one (310 mg, 20% yield) as a yellow solid. LCMS: m/z (ESI), [M+H]$^+$=230.1.

Step 2. Preparation of 1-(oxetan-3-yl)-5-(4,4,5,5-tetramethyl-1,3,2-dioxaborolan-2-yl)pyridin-2(1H)-one To a mixture of 5-bromo-1-(oxetan-3-yl)pyridin-2(1H)-one (260 mg, 1.1 mmol), 4,4,4',4',5,5,5',5'-octamethyl-2,2'-bi(1,3,2-dioxaborolane) (300 mg, 1.2 mmol) and PdCl$_2$(dppf) (30 mg, 0.041 mmol in dioxane (5 mL) was added KOAc (250 mg, 2.6 mmol). Then the mixture was heated at 90° C. for 30 min in microwave. Then the mixture was diluted by water (50 mL) and extracted by EA (50 mL). The organic layer was dried by brine and anhydrous Na$_2$SO$_4$, then concentrated to afford the crude product (250 mg, 80% yield) as a brown solid. MS m/z (ESI) 278.3 [M+H]+.

Step 3. Preparation of 3-amino-N-(2-(difluoromethoxy)benzyl)-5-(4-fluorophenyl)-6-(1-methyl-6-oxo-1,6-dihydropyridin-3-yl)pyrazine-2-carboxamide (Cmpd. 77)

To a mixture of 1-(oxetan-3-yl)-5-(4,4,5,5-tetramethyl-1,3,2-dioxaborolan-2-yl)pyridin-2(1H)-one (20 mg, 0.072 mmol), 3-amino-6-chloro-N-(2,6-difluorobenzyl)-5-(4-fluorophenyl)pyrazine-2-carboxamide (35 mg, 0.89 mmol), Pd$_2$(dba)$_3$ (7 mg, 0.0076 mmol), Tricyclohexylphosphine (13 mg, 0.046 mmol) and K$_3$PO$_4$ (45 mg, 0.21 mmol) in dioxane (3 mL) was added water (1 mL). The resulting mixture was sealed and heated at 120° C. for 15 min in Microwave. The mixture was filtered and the filtrate was purified by C18-40 g (MeCN/water=5%-80%) to afford 3-amino-N-(2-(difluoromethoxy)benzyl)-5-(4-fluorophenyl)-6-(1-methyl-6-oxo-1,6-dihydropyridin-3-yl)pyrazine-2-carboxamide (Cmpd. 77) (21 mg, 57% yield) as a yellow solid. LCMS: m/z (ESI), [M+H]+=508.3. $^1$H NMR (500 MHz, DMSO-d6) δ ppm 4.30 (s, 2H), 4.64 (t, J=6.94 Hz, 2H), 4.94 (t, J=7.41 Hz, 2H), 5.62 (quin, J=7.01 Hz, 1H), 6.40 (d, J=9.14 Hz, 1H), 6.99 (br t, J=7.72 Hz, 2H), 7.10 (br t, J=8.67 Hz, 2H), 7.24 (dd, J=9.46, 2.21 Hz, 1H), 7.30-7.37 (m, 1H), 7.54 (br dd, J=8.51, 5.36 Hz, 2H), 7.86 (d, J=2.21 Hz, 1H).

Example 78. Preparation of 3-amino-6-(2,6-dimethylpyridin-4-yl)-N-(2-fluorobenzyl)-5-(4-fluorophenyl)pyrazine-2-carboxamide (Cmpd. 78)

SCHEME 52

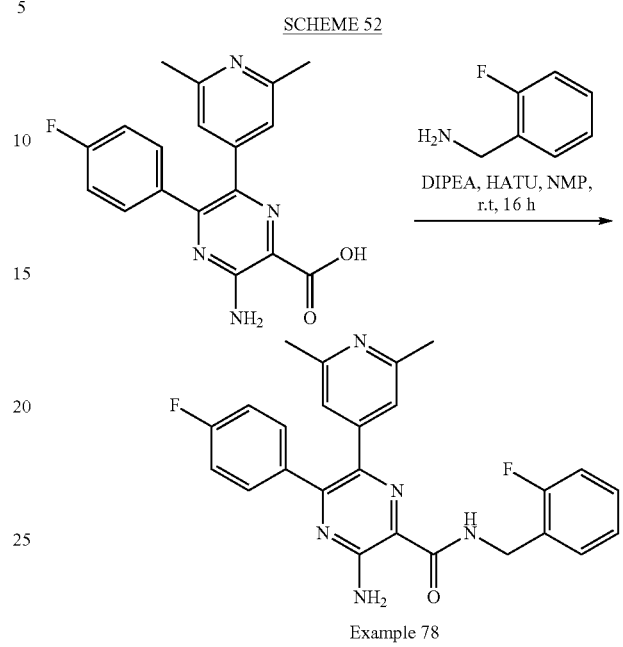

Example 78

Preparation of 3-amino-6-(2,6-dimethylpyridin-4-yl)-N-(2-fluorobenzyl)-5-(4-fluorophenyl) pyrazine-2-carboxamide (Cmpd. 78)

To a stirred mixture of 3-amino-6-(2,6-dimethylpyridin-4-yl)-5-(4-fluorophenyl)pyrazine-2-carboxylic acid (20 mg, 0.059 mmol), (2-fluorophenyl)methanamine (7.4 mg, 0.059 mmol) and DIPEA (15 mg, 0.118 mmol) was added HATU (25 mg, 0.065 mmol) in one portion at room temperature. The resulting mixture was stirred at room temperature for 16 h, under nitrogen atmosphere. The solution was purified by C18-40 g (MeCN/water=0%-80%) to afford 3-amino-6-(2,6-dimethylpyridin-4-yl)-N-(2-fluorobenzyl)-5-(4-fluorophenyl)pyrazine-2-carboxamide (Cmpd. 78) (16.3 mg, 61.94% yield) as an off-white solid. LCMS: m/z (ESI), [M+H]+=446.4. $^1$H NMR (500 MHz, CDCl$_3$) δ ppm 1.9 (brs, 2H), 2.5 (s, 6H), 4.7 (d, J=6.3 Hz, 2H), 6.9 (s, 2H), 7.0 (t, J=8.7 Hz, 2H), 7.1-7.2 (m, 2H), 7.25-7.30 (m, 1H), 7.3-7.4 (m, 3H), 8.3 (brt, J=6.1 Hz, 1H).

Compounds listed in the table below were prepared using methods described in Cmpd. 78.

| Example/Cmpd number | Structure | LCMS [M + H]+ | $^1$H NMR |
|---|---|---|---|
| 65 | 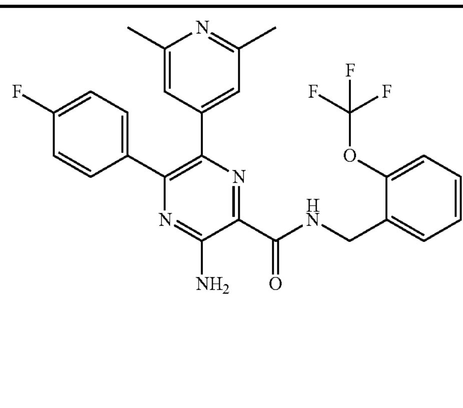 | 512.4 | $^1$H NMR (500 MHz, DMSO-d6) δ 2.31 (s, 6 H), 4.60 (d, J = 6.31 Hz, 2 H), 7.01 (s, 2 H), 7.21 (t, J = 8.83 Hz, 2 H), 7.34-7.45 (m, 6 H), 7.77 (br s, 2 H), 9.23 (t, J = 6.46 Hz, 1H). |

-continued

| Example/ Cmpd number | Structure | LCMS [M + H]+ | 1H NMR |
|---|---|---|---|
| 66 | 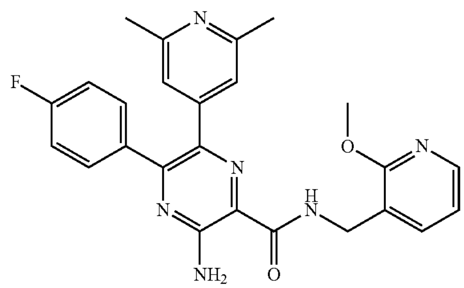 [SMILES: COc1ncccc1CNC(=O)c1nc(-c2cc(C)nc(C)c2)c(-c2ccc(F)cc2)nc1N] | 459.3 | 1H NMR (500 MHz, DMSO-d6) δ 2.31 (br s, H), 3.93 (br s, 3 H), 4.39-4.53 (m, 2 H), 6.90-6.98 (m, 1 H), 7.01 (br s, 2 H), 7.21 (br t, J = 7.88 Hz, 2 H), 7.41 (br s, 2 H), 7.51 (br d, J = 6.31 Hz, 1 H), 7.77 (br s, 2 H), 8.05 (br s, 1 H) 9.15 (br s, 1 H). |
| 71 | 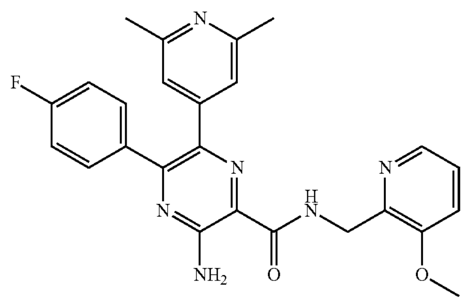 [SMILES: COc1cccnc1CNC(=O)c1nc(-c2cc(C)nc(C)c2)c(-c2ccc(F)cc2)nc1N] | 459.4 | 1H NMR (500 MHz, DMSO-d6) δ 2.28 (s, 6 H), 3.83 (s, 3 H), 4.55 (d, J = 25.36 Hz, 2 H), 6.47-6.75 (m, 1 H), 6.95 (s, 2 H), 7.06 (br s, 1 H), 7.16 (t, J = 8.67 Hz, 2 H), 7.26 (dd, J = 8.20, 4.73 Hz, 1 H), 7.35-7.41 (m, 3 H), 8.03 (d, J = 4.41 Hz, 1 H), 9.16 (t, J = 5.52 Hz, 1 H). |
| 79 | 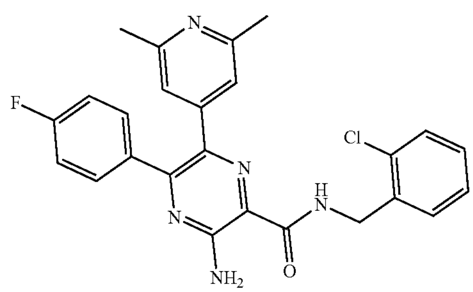 [SMILES: Cc1cc(-c2nc(C(=O)NCc3ccccc3Cl)c(N)nc2-c2ccc(F)cc2)cc(C)n1] | 462.3 | 1H NMR (500 MHz, CDCl3) δ ppm 1.9 (brs, 2H), 2.5 (s, 6 H), 4.8 (d, J = 6.3 Hz, 2H), 6.9 (s, 2H), 7.0 (t, J = 8.5 Hz, 2H), 7.2-7.3 (m, 2H), 7.3-7.5 (m, 4H), 8.4 (brt, J = 6.1 Hz, 1 H) |
| 80 | 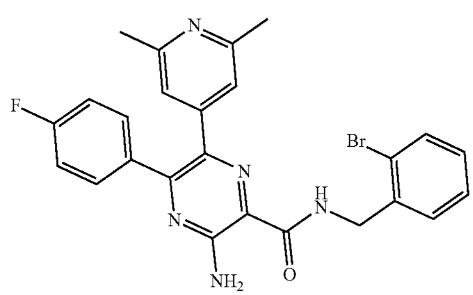 | 506.2 | 1H NMR (500 MHz,CDCl3) δ 1.9 (brs, 2H), 2.5 (s, 6H), 4.7 (d, J = 6.6 Hz, 2H), 6.9 (s, 2H) 7.0 (t, J = 8.7 Hz, 2H), 7.2 (td, J = 7.6, 1.4 Hz, 1H), 7.3 (t, J = 7.3 Hz, 1H), 7.4-7.5 (m, 3H) 7.6 (d, J = 7.6 Hz, 1 H), 8.5 (brt, J = 6.3 Hz, 1 H) |
| 81 | 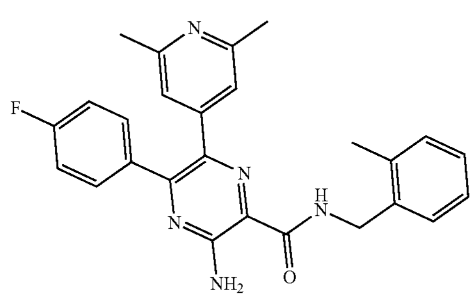 | 442.6 | 1H NMR (500 MHz,CDCl3) δ 1.8 (brs, 2H), 2.4 (s, 3H), 2.4 (s, 6H), 4.7 (d, J = 6.0 Hz, 2H), 6.9 (s, 2H), 7.0 (t, J = 8.5 Hz, 2H), 7.2-7.2 (m, 3H), 7.3-7.3 (m, 1H), 7.3-7.5 (m, 2H), 8.1 (br t, J = 5.8 Hz, 1 H) |

-continued

| Example/ Cmpd number | Structure | LCMS [M + H]+ | 1H NMR |
|---|---|---|---|
| 84 | 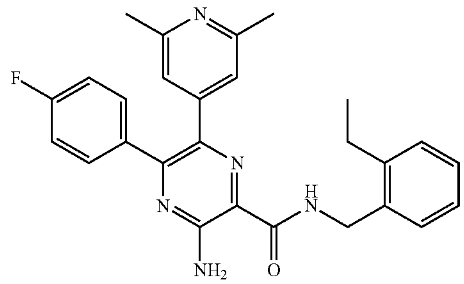 [SMILES: CCc1ccccc1CNC(=O)c1nc(-c2cc(C)nc(C)c2)c(-c2ccc(F)cc2)nc1N] | 456.4 | 1H NMR (500 MHz,CDCl3) δ 1.3 (t, J = 7.6 Hz, 3H), 1.6 (brs, 2H), 2.5 (s, 6H), 2.7 (q, J = 7.6 Hz, 2H), 4.7 (d, J = 6.0 Hz, 2H), 6.9 (s, 2H), 7.0 (t, J = 8.5 Hz, 2H), 7.2-7.2 (m, 1H), 7.3 (s, 1H), 7.3-7.3 (m, 1H), 7.3 (d, J = 7.6 Hz, 1H), 7.4-7.4 (m, 2H), 7.9-8.2 (m, 1H) |
| 85 | 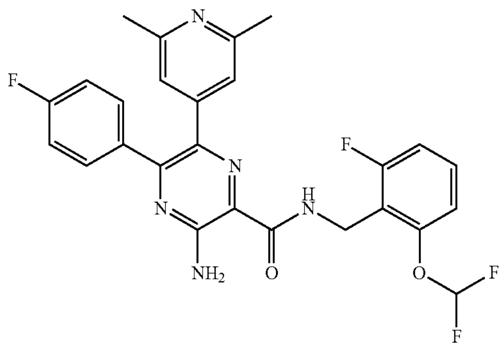 [SMILES: Cc1cc(-c2nc(C(=O)NCc3c(F)cccc3OC(F)F)c(N)nc2-c2ccc(F)cc2)cc(C)n1] | 512.3 | 1H NMR (500 MHz,CDCl3) δ 1.8 (brs, 2H), 2.5 (s, 6H), 4.8 (d, J = 6.3 Hz, 2H), 6.5-6.8 (m, 1H), 6.9 (s, 2H), 6.9-7.1, (m, 4 H), 7.3 (td, J = 8.4, 6.6 Hz, 1H), 7.3-7.4 (m, 2H), 8.4 (br t, J = 6.1 Hz, 1H) |

Example 82. Preparation of 3-amino-6-(1,5-dimethyl-6-oxo-1,6-dihydropyridin-3-yl)-5-(4-fluorophenyl)-N-(2-methoxybenzyl)pyrazine-2-carboxamide (Cmpd. 82)

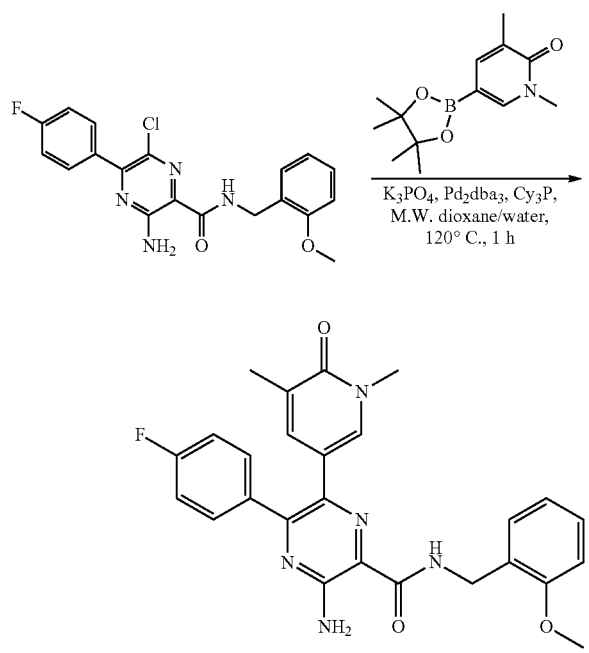

SCHEME 53

Example 82

A suspension of 3-amino-6-chloro-5-(4-fluorophenyl)-N-(2-methoxybenzyl)pyrazine-2-carboxamide (30 mg, 0.078 mmol), 1,3-dimethyl-5-(4,4,5,5-tetramethyl-1,3,2-dioxaborolan-2-yl)pyridin-2(1H)-one (23 mg, 0.093 mmol) and K$_3$PO$_4$ (28 mg, 0.132 mmol) in dioxane (1.50 mL)/water (0.375 mL) was purged and degassed with N$_2$ for 3 times, then added Pcy$_3$ (6.5 mg, 0.023 mmol) and Pd$_2$(dba)$_3$ (7 mg, 0.008 mmol). The resulting mixture was purged and degassed with N$_2$ for 3 times again. The reaction mixture was sealed and heated at 120° C. for 1 h by microwave reactor. The solution was filtered and evaporated under reduced pressure. The residue was purified by C18-40 g flash chromatography, elution gradient from 0% to 60% MeCN in water (0.05% ammonia hydroxide) to afford 3-amino-6-(1,5-dimethyl-6-oxo-1,6-dihydropyridin-3-yl)-5-(4-fluorophenyl)-N-(2-methoxybenzyl)pyrazine-2-carboxamide (Cmpd. 82) (25 mg, 68.08% yield) as a yellow solid. LCMS: m/z (ESI), [M+H]+=474.4. $^1$H NMR (500 MHz, CDCl$_3$) δ ppm 1.7 (s, 2H), 2.1 (s, 3H), 3.5 (s, 3H), 3.9 (s, 3H), 4.7 (d, J=6.3 Hz, 2H), 6.9 (d, J=8.2 Hz, 1H), 6.9 (t, J=7.4 Hz, 1H), 7.1 (t, J=8.7 Hz, 2H), 7.1 (d, J=2.2 Hz, 1H), 7.2 (s, 1H), 7.3-7.3 (m, 1H), 7.3-7.4 (m, 1H) 7.5 (dd, J=8.8, 5.4 Hz, 2H), 8.4 (brt, J=6.0 Hz, 1H).

Compounds listed in the table below were prepared using methods described in Cmpd. 82.

| Example/ Cmpd number | Structure | LCMS [M + H]+ | 1H NMR |
|---|---|---|---|
| 67 | 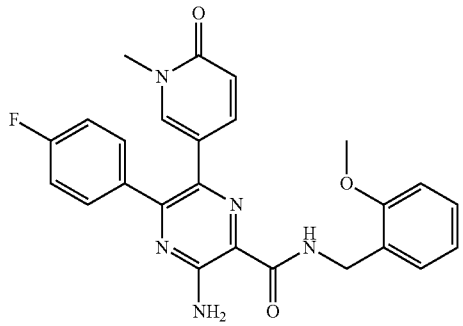 [SMILES: COc1ccccc1CNC(=O)c1nc(-c2ccc(=O)n(C)c2)c(-c2ccc(F)cc2)nc1N] | 460.4 | 1H NMR (500 MHz, DMSO-d6) δ 3.43 (s, 3 H) 3.86 (s, 3 H) 4.52 (d, J = 6.31 Hz, 2 H) 6.22 (d, J = 9.46 Hz, 1 H) 6.91 (t, J = 7.41 Hz, 1 H) 7.01 (d, J = 7.88 Hz, 1 H) 7.11 (d, J = 8.98 Hz, 1 H) 7.17 (d, J = 7.25 Hz, 1 H) 7.21-7.31 (m, 3 H) 7.41-7.91 (m, 4 H) 8.01 (d, J = 2.52 Hz, 1 H) 9.13 (t, J = 6.46 Hz, 1 H). |
| 68 | 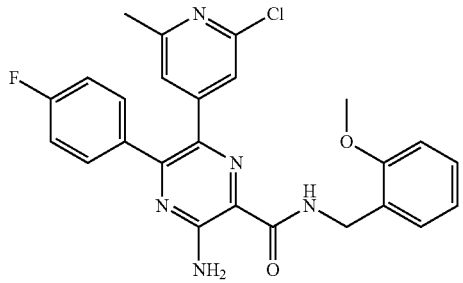 [SMILES: COc1ccccc1CNC(=O)c1nc(-c2cc(C)nc(Cl)c2)c(-c2ccc(F)cc2)nc1N] | 478.4 | 1H NMR (500 MHz, DMSO-d6) δ 2.34 (s, 3 H) 3.86 (s, 3 H) 4.52 (d, J = 6.62 Hz, 2 H) 6.91 (t, J = 7.41 Hz, 1 H) 7.02 (d, J = 7.88 Hz, 1 H) 7.17 (d, J = 6.31 Hz, 1 H) 7.21 (s, 1 H) 7.23-7.29 (m, 3 H) 7.30 (s, 1 H) 7.46 (t, J = 6.61 Hz, 2 H) 7.60-8.27 (m, 2 H) 9.18 (t, J = 6.46 Hz, 1 H). |
| 69 | 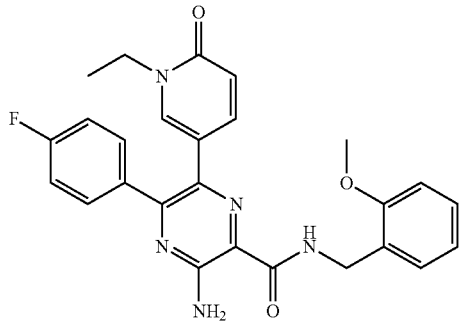 [SMILES: CCn1cc(-c2nc(C(=O)NCc3ccccc3OC)c(N)nc2-c2ccc(F)cc2)ccc1=O] | 474.4 | 1H NMR (500 MHz, DMSO-d6) δ 1.02 (t, J = 7.09 Hz, 3 H) 3.73-3.78 (m, 2 H) 4.44 (d, J = 6.31 Hz, 2 H) 6.22 (d, J = 9.46 Hz, 1 H) 6.84 (t, J = 7.57 Hz, 1H) 6.94 (d, J = 8.20 Hz, 1 H) 7.10 (d, J = 7.25 Hz, 1 H) 7.15-7.23 (m, 3 H) 7.31 (dd, J = 9.46, 2.52 Hz, 1 H) 7.37-7.78 (m, 5 H) 9.04 (t, J = 6.31 Hz, 1 H). |
| 70 | 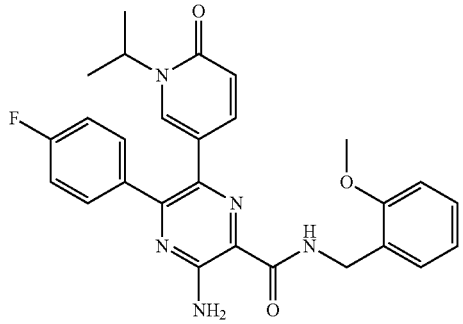 [SMILES: COc1ccccc1CNC(=O)c1nc(-c2ccc(=O)n(C(C)C)c2)c(-c2ccc(F)cc2)nc1N] | 488.4 | 1H NMR (500 MHz, DMSO-d6) δ 0.98 (d, J = 6.62 Hz, 6 H) 3.85 (s, 3 H) 4.51 (d, J = 6.31 Hz, 2 H) 4.90-4.97 (m, J = 6.83 Hz, 1 H) 6.40 (d, J = 9.46 Hz, 1 H) 6.91 (t, J = 7.41 Hz, 1 H) 7.01 (d, J = 8.20 Hz, 1 H) 7.18 (d, J = 7.25 Hz, 1 H) 7.23-7.30 (m, 3 H) 7.33 (d, J = 2.52 Hz, 1 H) 7.41-7.88 (m, 5 H) 9.07 (t, J = 6.46Hz, 1 H). |

| Example/Cmpd number | Structure | LCMS [M + H]+ | 1H NMR |
|---|---|---|---|
| 76 | 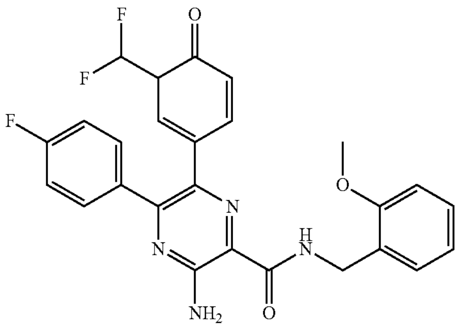 [SMILES: COc1ccccc1CNC(=O)c1nc(C2=CC(C(F)F)C(=O)C=C2)c(-c2ccc(F)cc2)nc1N] | 496.3 | 1H NMR (500 MHz, DMSO-d6) δ 3.84 (s, 3 H) 4.49 (br d, J = 5.99 Hz, 2 H) 6.45 (br d, J = 9.77 Hz, 1 H) 6.90 (br t, J = 7.41 Hz, 1 H) 7.00 (br d, J = 8.20 Hz,1 H) 7.16 (d, J = 7.67 Hz, 1 H) 7.20-7.31 (m, 3 H) 7.50-7.67 (m, 5 H) 7.67-7.95 (m, 2 H) 9.12 (br t, J = 5.99 Hz, 1 H). |

Example 83. Preparation of 3-amino-6-(2-amino-6-methylpyridin-4-yl)-5-(4-fluorophenyl)-N-(2-methoxybenzyl)pyrazine-2-carboxamide (Cmpd. 83)

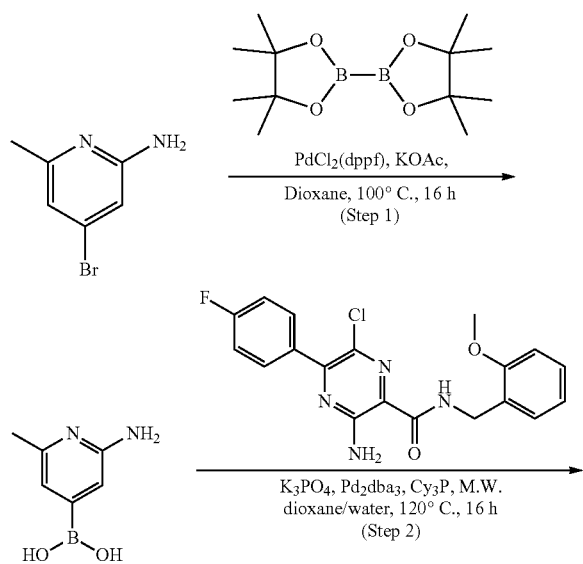

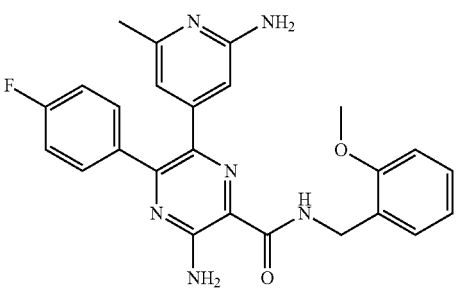

Example 83

Step 1. Preparation of (2-amino-6-methylpyridin-4-yl) boronic Acid

A suspension of 4-bromo-6-methylpyridin-2-amine (80 mg, 0.428 mmol), 4,4,4',4',5,5,5',5'-octamethyl-2,2'-bi(1,3,2-dioxaborolane) (130 mg, 0.513 mmol) and KOAc (50 mg, 0.51 mmol) in dioxane (4 mL) was purged and degassed with $N_2$ for 3 times, then added $PdCl_2$(dppf) (16 mg, 0.021 mmol). The resulting mixture was purged and degassed with $N_2$ for 3 times again. The reaction mixture was sealed and heated at 100° C. for 16 h. The solution was filtered and evaporated under reduced pressure to give (2-amino-6-methylpyridin-4-yl)boronic acid (96 mg, crude) was used the next step without further purification. LCMS: m/z (ESI), $[M+H]^+$=153.3

Step 2. 3-amino-6-(2-amino-6-methylpyridin-4-yl)-5-(4-fluorophenyl)-N-(2-methoxybenzyl) pyrazine-2-carboxamide (Cmpd. 83)

A suspension of 3-amino-6-chloro-5-(4-fluorophenyl)-N-(2-methoxybenzyl)pyrazine-2-carboxamide (30 mg, 0.078 mmol), (2-amino-6-methylpyridin-4-yl)boronic acid (48 mg, 0.093 mmol) and $K_3PO_4$ (48 mg, 0.244 mmol) in dioxane (1.50 mL)/water (0.37 mL) was purged and degassed with $N_2$ for 3 times, then added $Pcy_3$ (6.5 mg, 0.023 mmol) and $Pd_2$(dba)$_3$ (7 mg, 0.008 mmol). The resulting mixture was purged and degassed with $N_2$ for 3 times again. The reaction mixture was sealed and heated at 120° C. for 1 h by microwave reactor. The solution was filtered and evaporated under reduced pressure. The residue was purified by C18-40 g flash chromatography, elution gradient from 0% to 100% MeCN in water (0.05% ammonia hydroxide) to afford 3-amino-6-(2-amino-6-methylpyridin-4-yl)-5-(4-fluorophenyl)-N-(2-methoxybenzyl) pyrazine-2-carboxamide (Cmpd. 83) (7.6 mg, 21.3% yield) as an off-white solid. LCMS: m/z (ESI), $[M+H]^+$=495.3. 1H NMR (500 MHz, CDCl$_3$) δ ppm 1.9 (brs, 2H), 2.3 (s, 3H), 3.9 (s, 3H), 4.7 (d, J=6.3 Hz, 2H), 4.7 (brs, 2H), 6.3 (s, 1H), 6.5 (s, 1H), 6.9 (d, J=8.2 Hz, 1H), 6.9-7.0 (m, 1H), 7.0 (t, J=8.5 Hz, 2H), 7.3-7.4 (m, 2H), 7.4-7.5 (m, 2H), 8.4 (brt, J=6.1 Hz, 1H).

Example 86. Preparation of N-((3-amino-6-(2,6-dimethylpyridin-4-yl)-5-(4-fluorophenyl)pyrazin-2-yl)methyl)-2-methoxybenzamide (Cmpd. 86)

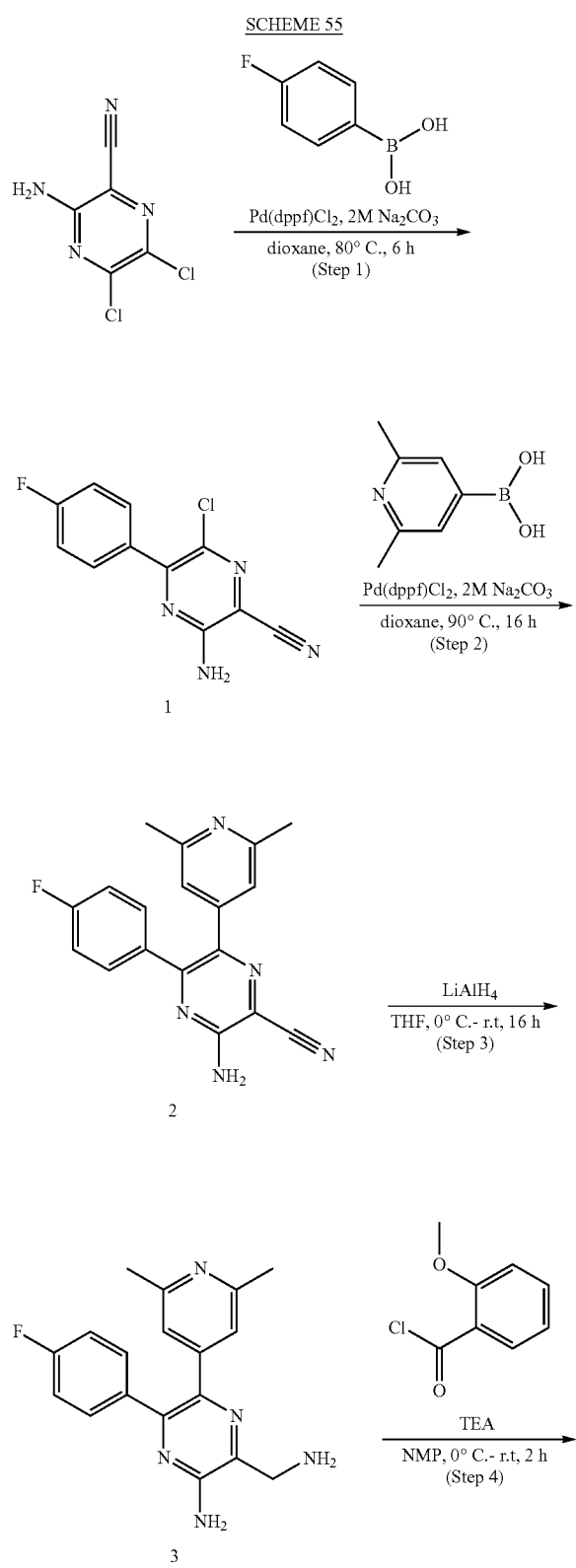

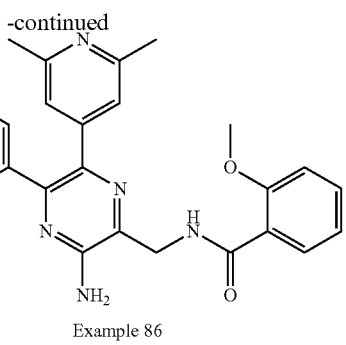

Example 86

Step 1. Preparation of 3-amino-6-chloro-5-(4-fluorophenyl)pyrazine-2-carbonitrile To a solution of 3-amino-5,6-dichloropyrazine-2-carbonitrile (300 mg, 1.5 mmol) and (4-fluorophenyl)boronic acid (233 mg, 1.6 mmol) in dioxane (14 mL) was added 2 M $Na_2CO_3$ (1.6 mL) into the reaction. The resulting mixture was purged and degassed with $N_2$ for 3 times, then added $PdCl_2(dppf)$ (58 mg, 0.079 mmol). The resulting mixture was purged and degassed with $N_2$ for 3 times again. The resulting mixture was heated at 80° C. under nitrogen atmosphere balloon for 6 h. The reaction was diluted with water (20 mL) and extracted with EtOAc (3×20 mL). The combined organics were dried over anhydrous sodium sulfate, filtered and the filtrate was evaporated under reduced pressure to afford 3-amino-6-chloro-5-(4-fluorophenyl)pyrazine-2-carbonitrile (395 mg, crude) as a brown solid. LCMS: m/z (ESI), $[M+H]^+=249.2$.

Step 2. Preparation of 3-amino-6-(2,6-dimethylpyridin-4-yl)-5-(4-fluorophenyl)pyrazine-2-carbonitrile A solution of 3-amino-6-chloro-5-(4-fluorophenyl)pyrazine-2-carbonitrile (395 mg, 1.5 mmol) and (2,6-dimethylpyridin-4-yl)boronic acid (288 mg, 1.9 mmol) in dioxane (14 mL). Then added 2 M $Na_2CO_3$ (1.6 mL) into the reaction. The resulting mixture was purged and degassed with $N_2$ for 3 times, then added $PdCl_2(dppf)$ (58 mg, 0.079 mmol). The resulting mixture was purged and degassed with $N_2$ for 3 times again. The resulting mixture was heated at 90° C. under nitrogen atmosphere balloon for 16 h. The reaction was diluted with water (20 mL) and extracted with EtOAc (3×20 mL). The combined organics were dried over anhydrous sodium sulfate, filtered and the filtrate was evaporated under reduced pressure and purified by column chromatography on silica gel (petroleum ether/EtOAc=10/1-3/1 (v/v)) to give 3-amino-6-(2,6-dimethylpyridin-4-yl)-5-(4-fluorophenyl)pyrazine-2-carbonitrile (311 mg, 61% yield) as a brown solid. LCMS: m/z (ESI), $[M+H]^+=320.3$.

Step 3. Preparation of 3-(aminomethyl)-5-(2,6-dimethylpyridin-4-yl)-6-(4-fluorophenyl)pyrazin-2-amine A solution of 3-amino-6-(2,6-dimethylpyridin-4-yl)-5-(4-fluorophenyl)pyrazine-2-carbonitrile (60 mg, 0.188 mmol) in anhydrous THF (0.5 mL) was added dropwise into a stirred suspension of LiAlH4 (14 mg, 0.376 mmol) in anhydrous THF (1.5 mL) at 0° C. by ice/water bath. The reaction was warmed slowly to room temperature and stirred at room temperature for 16 h. The reaction was diluted with anhydrous THF (10 mL) and cooled and stirred at 0° C. by ice/water bath. Then added sodium sulfate decahydrate (500 mg, three portion) and The resulting mixture was stirred at this temperature for 30 min. then filtered and the filtrate was concentrated in vacuum to give 3-(aminomethyl)-5-(2,6-dimethylpyridin-4-yl)-6-(4-fluorophenyl)pyrazin-2-amine (50 mg, 82% yield) as a brown oil. LCMS: m/z (ESI), [M+H]+=324.4

Step 4. Preparation of N-((3-amino-6-(2,6-dimethylpyridin-4-yl)-5-(4-fluorophenyl)pyrazin-2-yl)methyl)-2-methoxybenzamide (Cmpd. 86)

A solution of 3-(aminomethyl)-5-(2,6-dimethylpyridin-4-yl)-6-(4-fluorophenyl)pyrazin-2-amine (50 mg, 0.15 mmol) and TEA (47 mg, 0.46 mmol) in NMP (1 mL) was cooled by ice/water bath at 0° C., then a solution of 2-methoxybenzoyl chloride (26 mg, 0.155 mmol) in NMP (1.0 mL) was added dropwise into the reaction. The resulting mixture was stirred and warmed slowly to room temperature for 2 h. The solution was purified by C18-40 g flash chromatography, elution gradient from 0% to 50% MeCN in water (0.05% ammonia hydroxide) to afford N-((3-amino-6-(2,6-dimethylpyridin-4-yl)-5-(4-fluorophenyl)pyrazin-2-yl)methyl)-2-methoxybenzamide (Cmpd. 86) (15 mg, 46% yield) as an off-white solid. LCMS: m/z (ESI), [M+H]+=458.3. $^1$H NMR (500 MHz, CDCl$_3$) δ ppm 2.5 (s, 6H), 3.9 (s, 3H), 4.8 (d, J=6.3 Hz, 2H), 6.0 (brs, 2H), 6.9 (s, 2H), 7.0-7.0 (m, 3H), 7.1-7.1 (m, 1H), 7.3-7.4 (m, 2H), 7.5-7.5 (m, 1H), 8.3 (dd, J=7.9, 1.6 Hz, 1H), 8.7 (brt, J=6.0 Hz, 1H)

Example 87. Preparation of 3-amino-6-(1-cyclopropyl-6-oxo-1,6-dihydropyridin-3-yl)-N-(2,6-difluorobenzyl)-5-(4-fluorophenyl)pyrazine-2-carboxamide (Cmpd. 87)

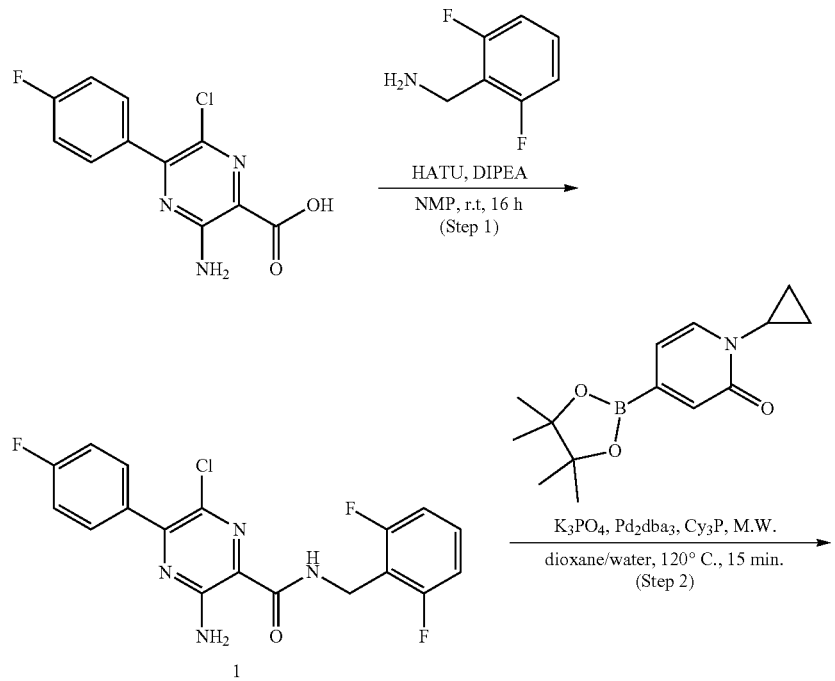

SCHEME 56

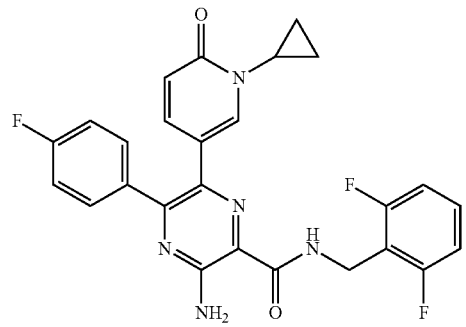

Example 87

Step 1. Preparation of 3-amino-6-chloro-N-(2,6-difluorobenzyl)-5-(4-fluorophenyl)pyrazine-2-carboxamide To a stirred mixture of 3-amino-6-chloro-5-(4-fluorophenyl)pyrazine-2-carboxylic acid (200 mg, 0.74 mmol), (2,6-difluorophenyl)methanamine (107 mg, 0.74 mmol) and DIPEA (93 mg, 1.49 mmol) was added HATU (313 mg, 0.82 mmol) in one portion at room temperature. The resulting mixture was stirred at room temperature for 16 under nitrogen atmosphere. The solution was purified by C18-40 g (MeCN/water=0%-60%) to afford 3-amino-6-chloro-N-(2,6-difluorobenzyl)-5-(4-fluorophenyl)pyrazine-2-carboxamide (290 mg, 99% yield) as a yellow solid. LCMS: m/z (ESI), [M+H]$^+$=393.2.

Step 2. Preparation of 3-amino-6-(1-cyclopropyl-6-oxo-1,6-dihydropyridin-3-yl)-N-(2,6-difluorobenzyl)-5-(4-fluorophenyl)pyrazine-2-carboxamide (Cmpd. 87)

A suspension of 3-amino-6-chloro-N-(2,6-difluorobenzyl)-5-(4-fluorophenyl)pyrazine-2-carboxamide (50 mg, 0.12 mmol), 1-cyclopropyl-4-(4,4,5,5-tetramethyl-1,3,2-dioxaborolan-2-yl)pyridin-2(1H)-one (40 mg, 0.15 mmol) and K$_3$PO$_4$ (46 mg, 0.21 mmol) in dioxane (2.0 mL)/water (0.4 mL) was purged and degassed with N$_2$ for 3 times, then added Pcy$_3$ (11 mg, 0.039 mmol) and Pd$_2$(dba)$_3$ (12 mg, 0.013 mmol). The resulting mixture was purged and degassed with N$_2$ for 3 times again. The reaction mixture was sealed and heated at 120° C. for 15 min. by Microwave reactor. The solution was filtered and evaporated under reduced pressure. The residue was purified by C18-40 g flash chromatography, elution gradient from 0% to 70% MeCN in water (0.05% ammonia hydroxide) to afford 3-amino-6-(1-cyclopropyl-6-oxo-1,6-dihydropyridin-3-yl)-N-(2,6-difluorobenzyl)-5-(4-fluorophenyl)pyrazine-2-carboxamide (Cmpd. 87) (40 mg, 64% yield) as a yellow solid. LCMS: m/z (ESI), [M+H]$^+$=492.3 $^1$H NMR (500 MHz, CDCl$_3$) δ ppm 0.5-0.7 (m, 2H), 0.9-1.2 (m, 2H) 1.6 (brs, 2H), 3.2-3.4 (m, 1H), 4.8 (d, J=6.3 Hz, 2H), 6.5 (d, J=9.1 Hz, 1H), 6.9 (t, J=7.9 Hz, 2H), 7.1 (t, J=8.5 Hz, 2H), 7.2-7.3 (m, 1H), 7.3-7.3 (m, 2H), 7.4-7.5 (m, 2H), 8.2 (brt, J=6.3 Hz, 1H).

Example 88. Preparation of N-((3-amino-5-(4-fluorophenyl)-6-(1-methyl-6-oxo-1,6-dihydropyridin-3-yl)pyrazin-2-yl)methyl)-2,6-difluorobenzamide (Cmpd. 88)

SCHEME 57

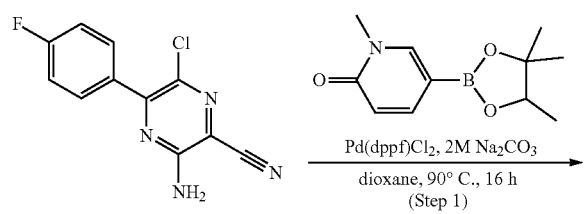

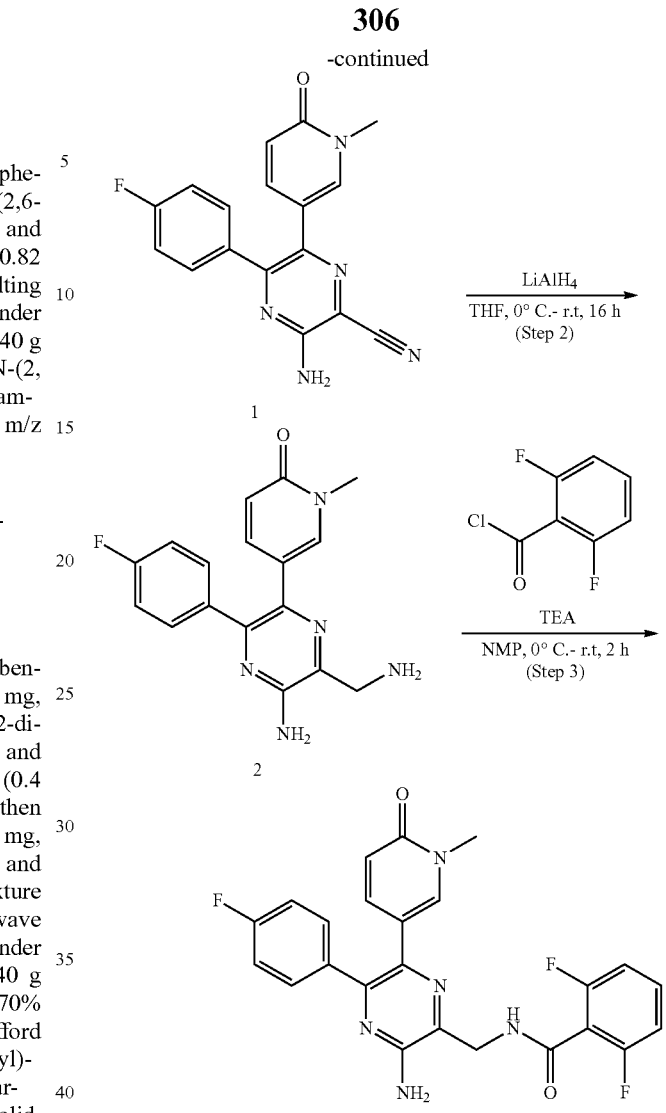

Example 88

Step 1. Preparation of 3-amino-5-(4-fluorophenyl)-6-(1-methyl-6-oxo-1,6-dihydropyridin-3-yl)pyrazine-2-carbonitrile A solution of 3-amino-6-chloro-5-(4-fluorophenyl)pyrazine-2-carbonitrile (395 mg, 1.587 mmol) and 1-methyl-5-(4,4,5,5-tetramethyl-1,3,2-dioxaborolan-2-yl)pyridin-2(1H)-one (448 mg, 1.905 mmol) in dioxane (14 mL) was added 2 M Na$_2$CO$_3$ (336 mg, 1.6 mL) into the reaction. The resulting mixture was purged and degassed with N$_2$ for 3 times, then added PdCl$_2$(dppf) (58 mg, 0.079 mmol). The resulting mixture was purged and degassed with N$_2$ for 3 times again. The resulting mixture was heated at 90° C. under nitrogen atmosphere balloon for 16 h. The reaction was diluted with water (20 mL) and extracted with EtOAc (3×20 mL). The combined organics were dried over anhydrous sodium sulfate, filtered and the filtrate was evaporated under reduced pressure and purified by column chromatography on silica gel (petroleum ether/EtOAc=10/1-3/1 (v/v)) to give 3-amino-5-(4-fluorophenyl)-6-(1-methyl-6-oxo-1,6-dihydropyridin-3-yl)pyrazine-2-carbonitrile (235 mg, 46% yield) as a brown solid. LCMS: m/z (ESI), [M+H]$^+$=322.3.

Step 2. Preparation of 5-(5-amino-6-(aminomethyl)-3-(4-fluorophenyl)pyrazin-2-yl)-1-methylpyridin-2(1H)-one A solution of 3-amino-5-(4-fluorophenyl)-6-(1-methyl-6-oxo-1,6-dihydropyridin-3-yl)pyrazine-2-carbonitrile (51 mg, 0.159 mmol) in anhydrous THF (0.5 mL) was added dropwise into a stirred suspension of LiAlH$_4$ (12 mg, 0.317 mmol) in anhydrous THF (1.5 mL) at 0° C. by ice/water bath. The reaction was warmed slowly to room temperature and stirred at room temperature for 16 h. The reaction was diluted with anhydrous THF (10 mL) and cooled and stirred at 0° C. by ice/water bath. Then added sodium sulfate decahydrate (500 mg, three portion) and The resulting mixture was stirred at this temperature for 30 min. then filtered and the filtrate was concentrated in vacuum to give 5-(5-amino-6-(aminomethyl)-3-(4-fluorophenyl)pyrazin-2-yl)-1-methylpyridin-2(1H)-one (52 mg, 100% yield) as a brown oil. LCMS: m/z (ESI), [M+H]$^+$=326.5

Step 3. Preparation of N-((3-amino-5-(4-fluorophenyl)-6-(1-methyl-6-oxo-1,6-dihydropyridin-3-yl)pyrazin-2-yl)methyl)-2,6-difluorobenzamide (Cmpd. 88)

A solution of 5-(5-amino-6-(aminomethyl)-3-(4-fluorophenyl)pyrazin-2-yl)-1-methylpyridin-2(1H)-one (52 mg, 0.16 mmol) and TEA (49 mg, 0.48 mmol) in NMP (1 mL) was cooled by ice/water bath at 0° C., then a solution of 2,6-difluorobenzoyl chloride (34 mg, 0.19 mmol) in NMP (1.0 mL) was added dropwise into the reaction. The resulting mixture was stirred and warmed slowly to room temperature for 2 h. The solution was purified by C18-40 g flash chromatography, elution gradient from 0% to 60% MeCN in water (0.05% ammonia hydroxide) to afford N-((3-amino-5-(4-fluorophenyl)-6-(1-methyl-6-oxo-1,6-dihydropyridin-3-yl)pyrazin-2-yl)methyl)-2,6-difluorobenzamide (Cmpd. 88) (8 mg, 11% yield) as an off-white solid. LCMS: m/z (ESI), [M+H]$^+$=466.3. $^1$H NMR (500 MHz, CDCl$_3$) δ ppm 3.5 (s, 3H), 4.8 (d, J=6.3 Hz, 2H), 5.5 (brs, 2H), 6.4 (d, J=9.5 Hz, 1H), 7.0-7.0 (m, 3H), 7.1 (t, J=8.7 Hz, 2H), 7.1 (dd, J=9.5, 2.5 Hz, 1H), 7.4-7.5 (m, 4H).

Example 89. Preparation of 3-amino-6-(2,6-dimethylpyridin-4-yl)-5-(4-fluorophenyl)-N-(2-methoxybenzyl)pyrazine-2-carboxamide (Cmpd. 89)

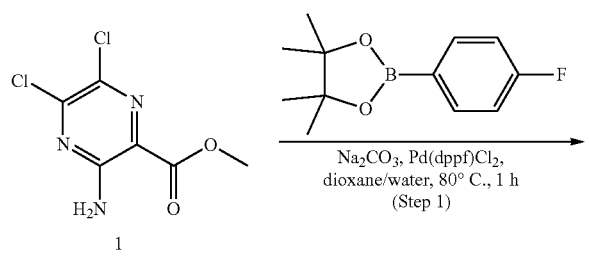

EXAMPLE 58

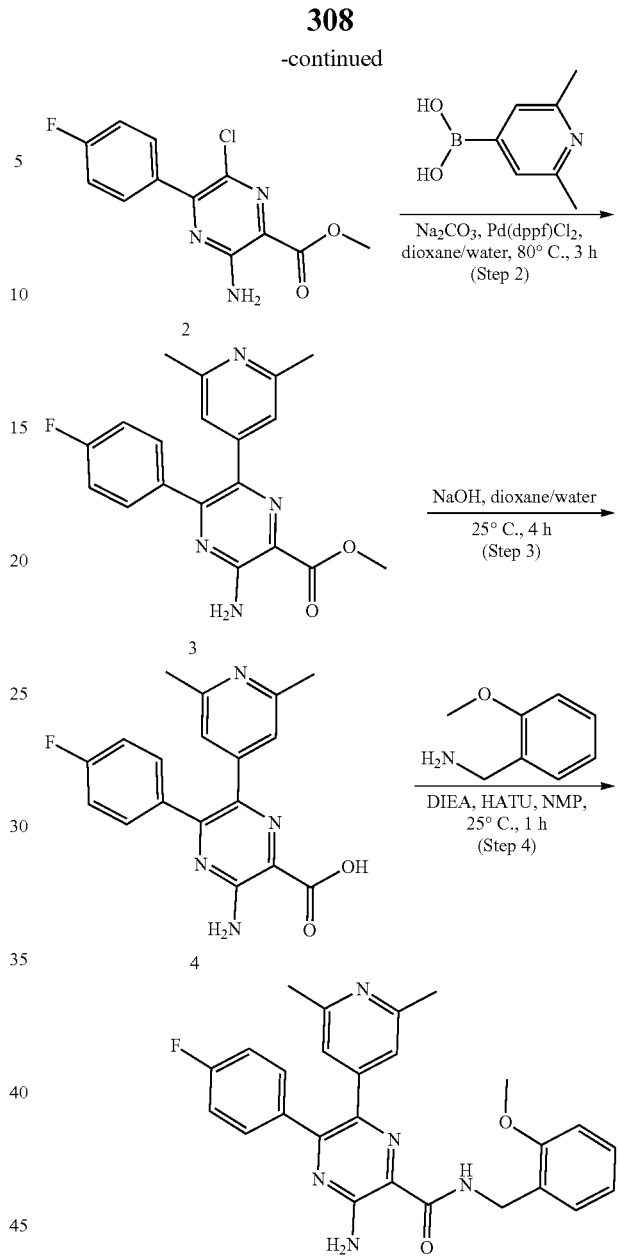

Example 89

Step 1. Preparation of methyl 3-amino-6-chloro-5-(4-fluorophenyl)pyrazine-2-carboxylate The mixture of methyl 3-amino-5,6-dichloropyrazine-2-carboxylate (4.4 g, 19.91 mmol), 2-(4-fluorophenyl)-4,4,5,5-tetramethyl-1,3,2-dioxaborolane (3.07 g, 21.9 mmol) in dioxane (50 mL) and water (5 mL) was added Na$_2$CO$_3$ (4.22 g, 39.82 mmol) and DppfPdCl$_2$ (2.84 g, 3.98 mmol). Then the mixture was stirred at 100° C. for 1 h under N$_2$ atmosphere. Then the mixture was concentrated and residue was poured to water (100 mL) and then extracted with EA (100 mL×3). The organic solution was then concentrated to give the crude product (5.5 g, 98% yield) as a yellow solid which was used for next step without further purification. MS m/z (ESI) [M+H]$^+$=282.2.

Step 2. Preparation of methyl 3-amino-6-(2,6-dimethylpyridin-4-yl)-5-(4-fluorophenyl)pyrazine-2-carboxylate The mixture of methyl 3-amino-6-chloro-5-(4-fluorophenyl)pyrazine-2-carboxylate (2.8 g, 9.96 mmol), (2,6-dimethylpyridin-4-yl)boronic acid (1.51 g, 9.96 mmol) in dioxane (50 mL) and water (5 mL) was added $Na_2CO_3$ (3.01 g, 19.93 mmol) and $Pd(PPh_3)_4$ (1.42 g, 1.99 mmol). Then the mixture was stirred at 80° C. for 8 h under $N_2$ atmosphere. Then the mixture was concentrated and residue was poured to water (100 mL) and then extracted with EA (100 mL×3). The organic solution was then concentrated to give the crude product which was further purified by flash column to give desired methyl 3-amino-6-(2,6-dimethylpyridin-4-yl)-5-(4-fluorophenyl)pyrazine-2-carboxylate (2.5 g, 71% yield) as a yellow solid. MS m/z (ESI) [M+H]$^+$=353.4. $^1$H NMR (500 MHz, DMSO-d6) δ ppm 2.33 (s, 6H), 3.89 (s, 3H), 6.89 (s, 2H), 7.22 (t, J=8.29 Hz, 2H), 7.43 (t, J=6.58 Hz, 2H), 7.61 (br s, 2H).

Step 3. Preparation of 3-amino-6-(2,6-dimethylpyridin-4-yl)-5-(4-fluorophenyl)pyrazine-2-carboxylic Acid To a stirring solution of methyl 3-amino-6-(2,6-dimethylpyridin-4-yl)-5-(4-fluorophenyl)pyrazine-2-carboxylate (2.3 g, 6.53 mmol) in methanol (25 mL) and water (5 mL) was added sodium hydroxide (1.3 g, 32.66 mmol). Then the mixture was stirred a 45° C. for 2 hours. The solution was then concentrated and the residue was suspend in 25 mL water. The solution was washed with 15 mL DCM twice. The inorganic layer was then acidified with 0.5N HCl to pH 3. The solid which formed was collected and dried to give the desired product (1.70 g, 77% yield) as a white solid. MS m/z (ESI) [M+H]$^+$=339.4. 1H NMR (500 MHz, DMSO-d6) δ ppm 2.31-2.38 (m, 6H), 6.94 (s, 2H), 7.22 (t, J=8.41 Hz, 2H), 7.43 (t, J=6.73 Hz, 2H), 7.64 (br s, 2H), 12.56-13.99 (m, 1H).

Step 4. Preparation of 3-amino-6-(2,6-dimethylpyridin-4-yl)-5-(4-fluorophenyl)-N-(2-methoxybenzyl)pyrazine-2-carboxamide (Cmpd. 89)

To a stirring solution of 3-amino-6-(2,6-dimethylpyridin-4-yl)-5-(4-fluorophenyl)pyrazine-2-carboxylic acid (25 mg, 0.07 mmol), (2-methoxyphenyl)methanamine (20 mg, 0.15 mmol) and DIEA (15 mg, 0.118 mmol) in DMF (2 mL) was added HATU (40 mg, 0.11 mmol) in one portion at room temperature. The resulting mixture was stirred at room temperature for 1 h under nitrogen atmosphere. The solution was purified by C18-40 g (MeCN/water=5%-60%) to afford 3-amino-6-(2,6-dimethylpyridin-4-yl)-5-(4-fluorophenyl)-N-(2-methoxybenzyl)pyrazine-2-carboxamide (Cmpd. 89) (19.8 mg, 59.2% yield) as an off-white solid. MS m/z (ESI) [M+H]$^+$=458.4. $^1$H NMR (500 MHz, CDCl$_3$) δ ppm 2.33 (s, 6H), 3.86 (s, 3H), 4.46-4.57 (m, 2H), 6.87-6.95 (m, 1H), 7.02 (s, 3H), 7.13-7.30 (m, 4H), 7.38-7.48 (m, 2H), 7.51-8.20 (m, 2H), 9.02-9.13 (m, 1H).

Compounds listed in the table below were prepared using methods described in Cmpd. 89.

| Example/Cmpd number | Structure | LCMS [M + H]$^+$ | $^1$H NMR |
| --- | --- | --- | --- |
| 90 | 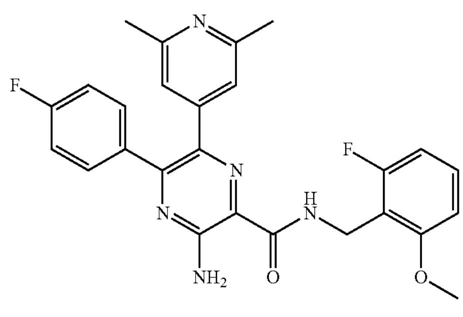 [SMILES: COc1cccc(F)c1CNC(=O)c1nc(-c2cc(C)nc(C)c2)c(-c2ccc(F)cc2)nc1N] | 476.4 | 1H NMR (500 MHz, DMSO-d6) δ ppm 2.26 (s, 6 H) 3.83 (s, 3 H) 4.53 (d, J = 5.99 Hz, 2 H) 6.70-6.89 (m, 4 H) 7.11-7.27(m, 3 H) 7.33 (dd, J = 8.67, 5.52 Hz,2 H) 7.73 (br s, 2 H) 8.63 (t, J = 5.99 Hz, 1 H) |
| 91 | 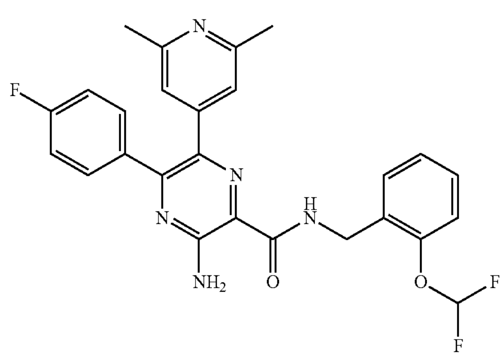 [SMILES: Cc1cc(-c2nc(C(=O)NCc3ccccc3OC(F)F)c(N)nc2-c2ccc(F)cc2)cc(C)n1] | 494.4 | 1H NMR (500 MHz, DMSO-d6) δ ppm 2.08 (s, 1 H) 2.30-2.37 (m, 6 H) 4.58 (d, J = 6.31 Hz, 2 H) 7.02 (s, 2 H) 7.19 -7.25 (m, 4H) 7.31-7.37 (m, 2 H) 7.41 -7.46 (m, 2 H) 7.80 (br s, 2H) 9.16 (t, J = 6.31 Hz, 1 H) |

| Example/Cmpd number | Structure | LCMS [M + H]+ | 1H NMR |
|---|---|---|---|
| 92 | 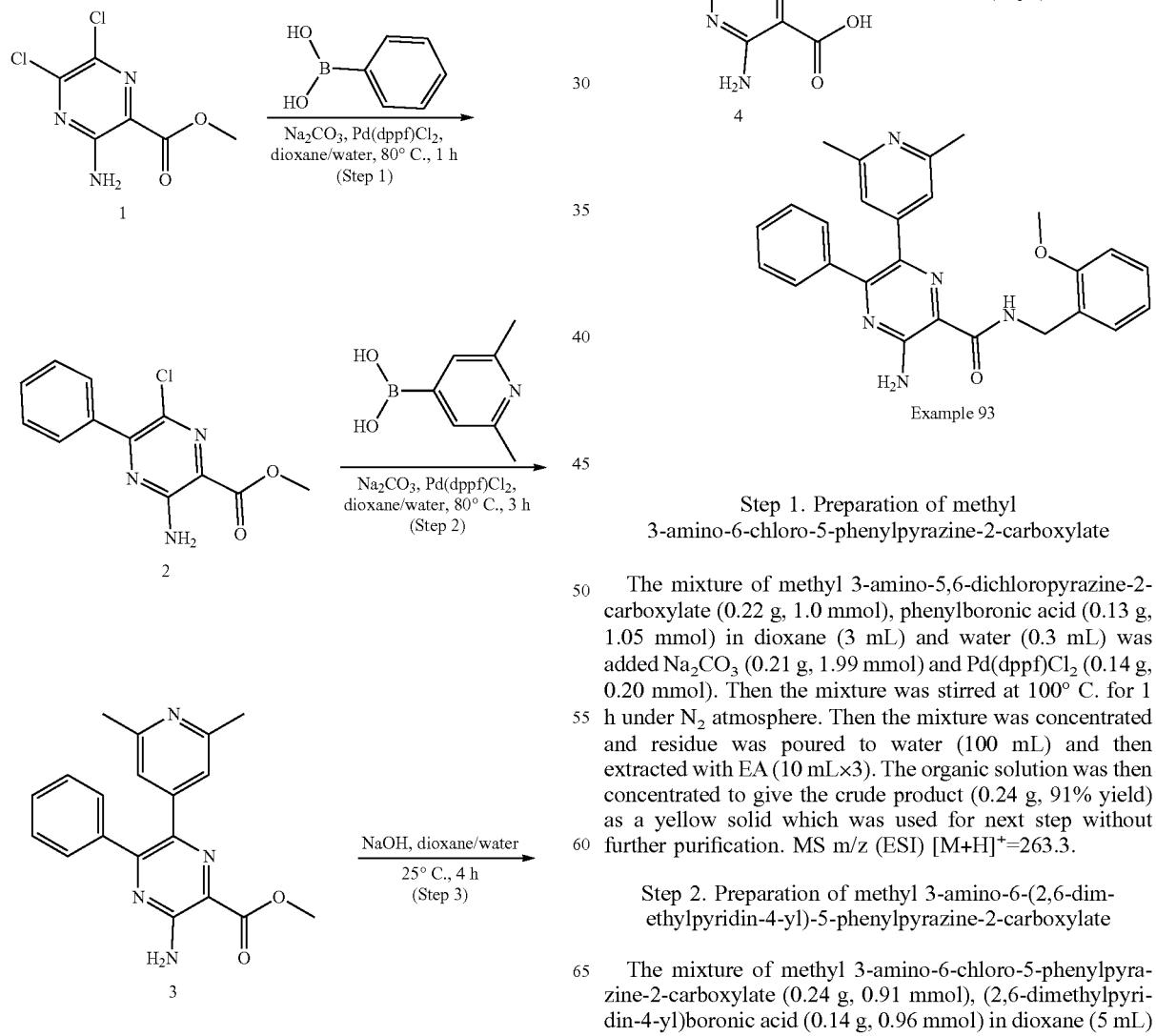 | 476.4 | 1H NMR (500 MHz, DMSO-d6) δ ppm 2.30-2.39 (m, 6 H) 3.85 (s, 3 H) 4.49 (d, J = 6.31 Hz, 2 H) 6.93-7.09 (m, 5 H) 7.19-7.26 (m, 2 H) 7.43 (t, J = 6.43 Hz, 2 H) 7.78 (br s, 2 H) 9.12 (t, J = 6.31 Hz, 1 H) |

Example 93. Preparation of 3-amino-6-(2,6-dimethylpyridin-4-yl)-N-(2-methoxybenzyl)-5-phenylpyrazine-2-carboxamide (Cmpd. 93)

SCHEME 59

Step 1. Preparation of methyl 3-amino-6-chloro-5-phenylpyrazine-2-carboxylate

The mixture of methyl 3-amino-5,6-dichloropyrazine-2-carboxylate (0.22 g, 1.0 mmol), phenylboronic acid (0.13 g, 1.05 mmol) in dioxane (3 mL) and water (0.3 mL) was added Na$_2$CO$_3$ (0.21 g, 1.99 mmol) and Pd(dppf)Cl$_2$ (0.14 g, 0.20 mmol). Then the mixture was stirred at 100° C. for 1 h under N$_2$ atmosphere. Then the mixture was concentrated and residue was poured to water (100 mL) and then extracted with EA (10 mL×3). The organic solution was then concentrated to give the crude product (0.24 g, 91% yield) as a yellow solid which was used for next step without further purification. MS m/z (ESI) [M+H]+=263.3.

Step 2. Preparation of methyl 3-amino-6-(2,6-dimethylpyridin-4-yl)-5-phenylpyrazine-2-carboxylate The mixture of methyl 3-amino-6-chloro-5-phenylpyrazine-2-carboxylate (0.24 g, 0.91 mmol), (2,6-dimethylpyridin-4-yl)boronic acid (0.14 g, 0.96 mmol) in dioxane (5 mL)

and water (0.5 mL) was added Na₂CO₃ (0.19 g, 1.82 mmol) and Pd(PPh₃)₄ (0.14 g, 0.20 mmol). Then the mixture was stirred at 80° C. for 8 h under N₂ atmosphere. Then the mixture was concentrated and residue was poured to water (10 mL) and then extracted with EA (10 mL×3). The organic solution was then concentrated to give the crude product which was further purified by flash column to give desired methyl 3-amino-6-(2,6-dimethylpyridin-4-yl)-5-phenylpyrazine-2-carboxylate (0.30 g, 98% yield) as a yellow solid. MS m/z (ESI) [M+H]⁺=335.4.

Step 3. Preparation of 3-amino-6-(2,6-dimethylpyridin-4-yl)-5-phenylpyrazine-2-carboxylic Acid To a stirring solution of methyl 3-amino-6-(2,6-dimethylpyridin-4-yl)-5-phenylpyrazine-2-carboxylate (0.30 g, 0.90 mmol) in methanol (10 mL) and water (2 mL) was added sodium hydroxide (0.18 g, 4.49 mmol). Then the mixture was stirred a 45° C. for 2 hours. The solution was then concentrated and the residue was suspend in 5 mL water. The solution was washed with DCM (2×5 mL). The inorganic layer was then acidified with 0.5N HCl to pH 3. The solid which formed was collected and dried to give the desired product (0.14 g, 49% yield) as a white solid. MS m/z (ESI) [M+H]⁺=321.4.

Step 4. Preparation of 3-amino-6-(2,6-dimethylpyridin-4-yl)-N-(2-methoxybenzyl)-5-phenylpyrazine-2-carboxamide (Cmpd. 93)

To a stirring solution of 3-amino-6-(2,6-dimethylpyridin-4-yl)-5-phenylpyrazine-2-carboxylic acid (35 mg, 0.11 mmol), (2-methoxyphenyl)methanamine (22 mg, 0.16 mmol) and DIEA (28 mg, 0.22 mmol) in DMF (2 mL) was added HATU (50 mg, 0.13 mmol) in one portion at room temperature. The resulting mixture was stirred at room temperature for 1 h under nitrogen atmosphere. The solution was purified by C18-40 g (MeCN/water=5%-60%) to afford 3-amino-6-(2,6-dimethylpyridin-4-yl)-N-(2-methoxybenzyl)-5-phenylpyrazine-2-carboxamide (Cmpd. 93) (23.0 mg, 48% yield) as an off-white solid. MS m/z (ESI) [M+H]⁺=440.4. ¹H NMR (500 MHz, CDCl₃) δ ppm 2.30 (s, 6H), 3.86 (s, 3H), 4.52 (d, J=6.31 Hz, 2H), 6.91 (t, J=7.36 Hz, 1H), 6.99-7.04 (m, 3H), 7.18 (d, J=7.57 Hz, 1H), 7.25 (t, J=7.87 Hz, 1H), 7.35-7.45 (m, 5H), 7.82 (br s, 2H), 9.06 (t, J=6.31 Hz, 1H).

Example 94. Preparation of 3-amino-6-[imidazo[1,2-a]pyridin-6-yl]-N-[(5-methyl-1,3-thiazol-4-yl)methyl]-5-(1,3-oxazol-2-yl)pyrazine-2-carboxamide (Cmpd. 94)

SCHEME 60

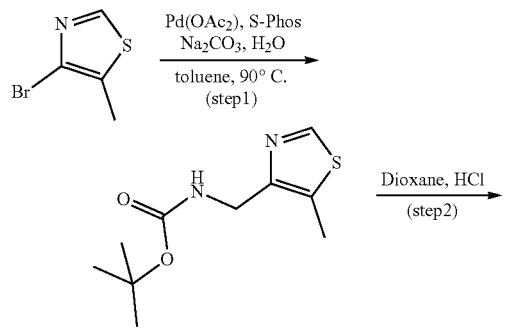

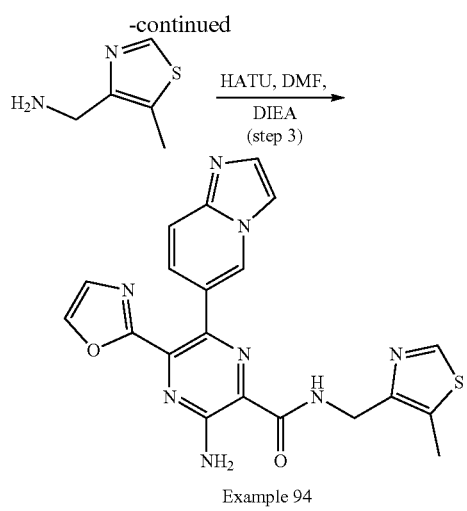

Example 94

Step 1. tert-butyl N-[(5-methyl-1,3-thiazol-4-yl)methyl]carbamate

To a stirred mixture of 4-bromo-5-methyl-1,3-thiazole (400 mg, 2.3 mmol, 1 equiv) and tert-butyl N-[(trifluoro-lambda4-boranyl)methyl]carbamate potassium (639.11 mg, 2.7 mmol, 1.2 equiv) in Toluene (16 mL) were added Na₂CO₃ (714.3 mg, 6.7 mmol, 3.0 equiv), S-Phos (368.9 mg, 0.9 mmol, 0.4 equiv), water (2 mL) and Pd(AcO)₂ (100.9 mg, 0.45 mmol, 0.2 equiv) in portions at room temperature under nitrogen atmosphere. The resulted mixture was stirred for overnight at 90° C. The mixture was allowed to cool down to room temperature. The resulted mixture was filtered, the filter cake was washed with EtOAc (3×10 mL). The filtrate was concentrated under reduced pressure. The residue was purified by Prep-TLC (PE/EtOAc 5:1) to afford tert-butyl N-[(5-methyl-1,3-thiazol-4-yl)methyl]carbamate (280 mg, 54.6%) as a yellow crude solid. LCMS: m/z (ESI), [M+H]⁺=229.2.

Step 2. 1-(5-methyl-1,3-thiazol-4-yl)methanamine

To a stirred solution of tert-butyl N-[(5-methyl-1,3-thiazol-4-yl)methyl]carbamate (270 mg, 1.2 mmol, 1 equiv) in DCM (5 mL) were added 4N HCl in dioxane (5 mL) dropwise at room temperature under air atmosphere. The resulted mixture was stirred for additional 3 hours at room temperature. The resulted mixture was concentrated under reduced pressure. This resulted in 1-(5-methyl-1,3-thiazol-4-yl)methanamine (150 mg, 91.0%) as a brown crude solid which was used into the next step directly without further purification. LCMS: m/z (ESI), [M+H]⁺=129.3.

Step 3. 3-amino-6-[imidazo[1,2-a]pyridin-6-yl]-N-[(5-methyl-1,3-thiazol-4-yl)methyl]-5-(1,3-oxazol-2-yl)pyrazine-2-carboxamide (Cmpd. 94)

To a stirred mixture of 3-amino-6-[imidazo[1,2-a]pyridin-6-yl]-5-(1,3-oxazol-2-yl)pyrazine-2-carboxylic acid (100 mg, 0.3 mmol, 1 equiv) and 1-(5-methyl-1,3-thiazol-4-yl)methanamine (79.6 mg, 0.6 mmol, 2.0 equiv) in DMF (5 mL) were added HATU (471.9 mg, 1.24 mmol, 4.0 equiv) and DIEA (160.4 mg, 1.2 mmol, 4.0 equiv) in portions at room temperature under air atmosphere. The resulted mixture was stirred for additional 60 mins at room temperature.

The resulted mixture was poured into water (20 mL), the resulting solid was collected by filtration and washed with water (10 mL). The crude product was slurried with MeOH (5 mL) to afford 3-amino-6-[imidazo[1,2-a]pyridin-6-yl]-N-[(5-methyl-1,3-thiazol-4-yl)methyl]-5-(1,3-oxazol-2-yl)pyrazine-2-carboxamide (Cmpd. 94) (106 mg, 77.9%) as a yellow solid. LCMS: m/z (ESI), [M+H]$^+$=433.2. $^1$H NMR (Methanol-d$_4$, 400 MHz) δ 2.6 (3H, s), 4.7 (2H, s), 7.2 (1H, dd, J=9.3, 1.8 Hz), 7.3 (1H, s), 7.5 (1H, d, J=9.3 Hz), 7.6 (1H, d, J=1.3 Hz), 7.9 (1H, s), 8.0 (1H, s), 8.7 (1H, d, J=1.5 Hz), 8.8 (1H, s).

Example 95. Preparation of 3-amino-N-[(4-aminopyrimidin-2-yl)methyl]-6-[imidazo[1,2-a]pyridin-6-yl]-5-(1,3-oxazol-2-yl)pyrazine-2-carboxamide (Cmpd. 95)

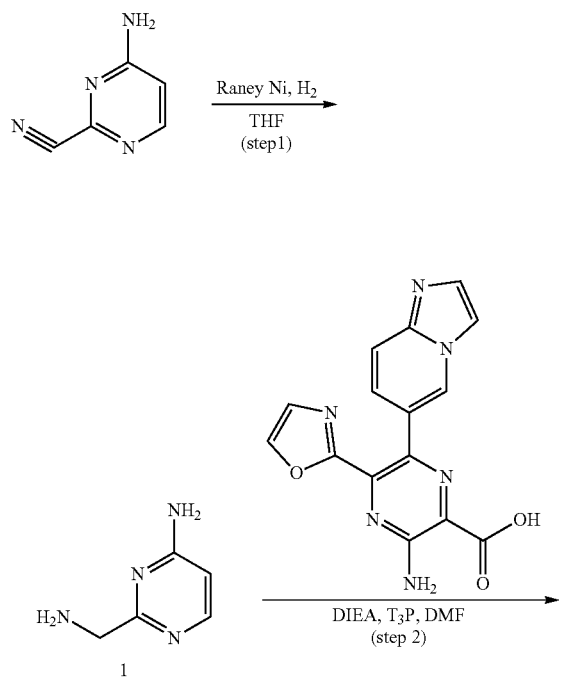

Step 1. 2-(aminomethyl)pyrimidin-4-amine

To a stirred mixture of 4-aminopyrimidine-2-carbonitrile (200 mg, 1.67 mmol, 1 equiv) in THF (10 mL) was added Raney Ni (71.3 mg, 0.83 mmol, 0.5 equiv) at room temperature under nitrogen atmosphere. The resulted mixture was stirred for 1.5 h at room temperature under hydrogen atmosphere. The resulted mixture was filtered, the filter cake was washed with THF (2×5 mL). The filtrate was concentrated under reduced pressure to afford 2-(aminomethyl)pyrimidin-4-amine (200 mg, 96.75%) as a light yellow solid which was used in the next step directly without further purification. LCMS: m/z (ESI), [M+H]$^+$=125.1.

Step 2. 3-amino-N-[(4-aminopyrimidin-2-yl)methyl]-6-[imidazo[1,2-a]pyridin-6-yl]-5-(1,3-oxazol-2-yl)pyrazine-2-carboxamide (Cmpd. 95)

To a stirred mixture of 3-amino-6-[imidazo[1,2-a]pyridin-6-yl]-5-(1,3-oxazol-2-yl)pyrazine-2-carboxylic acid (100 mg, 0.31 mmol, 1 equiv) and 2-(aminomethyl)pyrimidin-4-amine (77.0 mg, 0.62 mmol, 2 equiv) in DMF (10 mL) were added T$_3$P (394.9 mg, 1.24 mmol, 4 equiv) and DIEA (120.3 mg, 0.93 mmol, 3 equiv) in portions at room temperature under air atmosphere. The resulted mixture was stirred for overnight at room temperature under air atmosphere. The resulted mixture was concentrated under reduced pressure. The crude product (60 mg) was purified by Prep-HPLC with the following conditions (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 15% B to 25% B in 7 min; 254/220 nm; Rt: 5.77 min) to afford 3-amino-N-[(4-aminopyrimidin-2-yl)methyl]-6-[imidazo[1,2-a]pyridin-6-yl]-5-(1,3-oxazol-2-yl)pyrazine-2-carboxamide (Cmpd. 95) (13 mg, 9.78%) as a yellow solid. LCMS: m/z (ESI), [M+H]$^+$=429.2, H NMR (400 MHz, DMSO-d$_6$) δ 4.33 4.77 (m, 2H), 6.29 (d, J=5.9 Hz, 1H), 7.18 (dd, J=9.3, 1.8 Hz, 2H), 7.37 (d, J=0.8 Hz, 1H), 7.52 (d, J=9.3 Hz, 1H), 7.61 (d, J=1.2 Hz, 1H), 7.96 (d, J=1.1 Hz, 1H), 8.00 (d, J=5.9 Hz, 4H), 8.28 (d, J=0.8 Hz, 1H), 8.80 (t, J=1.4 Hz, 1H), 9.18 (t, J=5.8 Hz, 1H).

Example 96. Preparation of 3-amino-N-[[2-(dimethylphosphoryl)-6-fluorophenyl]methyl]-6-[imidazo[1,2-a]pyridin-6-yl]-5-(1,3-oxazol-2-yl)pyrazine-2-carboxamide (Cmpd. 96)

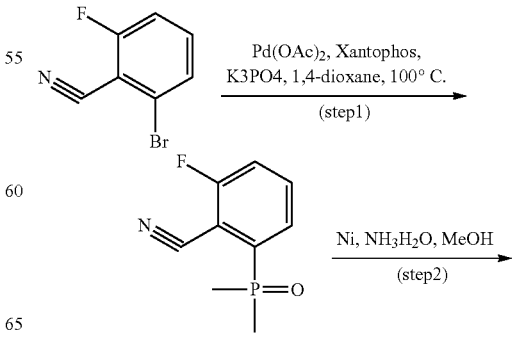

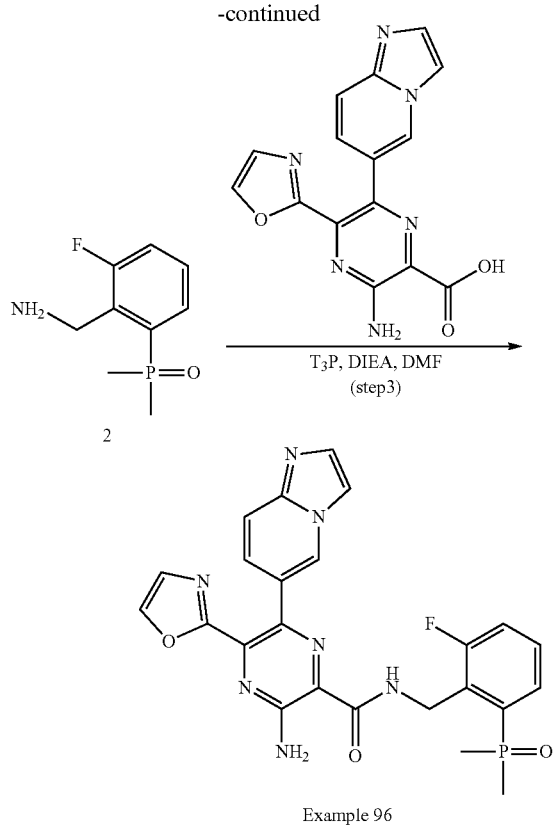

Example 96

Step 1. 2-(dimethylphosphoryl)-6-fluorobenzonitrile

To a mixture of 2-bromo-6-fluorobenzonitrile (1 g, 5.00 mmol, 1 equiv) and (methylphosphonoyl)methane (0.4 g, 1.00 equiv) in 1,4-dioxane (15 mL) was added Pd(AcO)$_2$ (0.1 g, 0.1 equiv), XantPhos (0.6 g, 0.2 equiv) and K$_3$PO$_4$ (2.1 g, 0.01 mmol, 2.00 equiv) under nitrogen atmosphere. The resulted mixture was stirred for 2 hours at 100° C. under nitrogen atmosphere. The resulted mixture was concentrated under reduced pressure. The residue was purified by Prep-TLC (CH$_2$Cl$_2$/MeOH 20:1) to afford 2-(dimethylphosphoryl)-6-fluorobenzonitrile (620 mg, 62.90%) as a white solid. LCMS: m/z (ESI), [M+H]$^+$=198.0. $^1$H NMR: (300 MHz, DMSO-d$_6$) δ 1.83 (s, 3H), 1.87 (s, 3H), 7.80 (m, 2H), 7.95 (m, 1H).

Step 2. 1-[2-(dimethylphosphoryl)-6-fluorophenyl]methanamine

To a solution of 2-(dimethylphosphoryl)-6-fluorobenzonitrile (600 mg, 3.04 mmol, 1 equiv) and NH$_3$.H$_2$O (0.1 mL, 3.82 mmol, 1.13 equiv) in MeOH (10 mL) was added Raney Ni (130.4 mg, 1.52 mmol, 0.5 equiv) at room temperature under nitrogen atmosphere. The resulted mixture was stirred for 2 hours at room temperature under hydrogen atmosphere. The resulted mixture was filtered, the filter cake was washed with MeOH (3×10 mL). The filtrate was concentrated under reduced pressure to afford 1-[2-(dimethylphosphoryl)-6-fluorophenyl]methanamine (550 mg, 89.83%) as a purple oil which was used in the next step directly without further purification. LCMS: m/z (ESI), [M+H]$^+$=202.2, $^1$H NMR: (300 MHz, DMSO-d$_6$) δ 1.82 (m, 6H), 3.17 (s, 3H), 4.02 (d, 2H), 7.45 (s, 3H).

Step 3. 3-amino-N-[[2-(dimethylphosphoryl)-6-fluorophenyl]methyl]-6-[imidazo[1,2-a]pyridin-6-yl]-5-(1,3-oxazol-2-yl)pyrazine-2-carboxamide (Cmpd. 96)

To a solution of 1-[2-(dimethylphosphoryl)-6-fluorophenyl]methanamine (10 mg, 0.05 mmol, 1 equiv) and 3-amino-6-[imidazo[1,2-a]pyridin-6-yl]-5-(1,3-oxazol-2-yl)pyrazine-2-carboxylic acid (16.0 mg, 0.05 mmol, 1.00 equiv) in DMF (5 mL) was added T$_3$P (31.6 mg, 0.10 mmol, 2 equiv) and DIEA (19.3 mg, 0.15 mmol, 3 equiv) at room temperature. The resulting solution was stirred for 60 mins at room temperature under air atmosphere. The resulted mixture was concentrated under reduced pressure. The crude product was purified by Prep-HPLC with the following conditions (Column: XBridge Shield RP18 OBD Column, 5 um, 19*150 mm; Mobile Phase A: Water (10 MMOL/L NH$_4$HCO$_3$), Mobile Phase B: ACN; Flow rate: 20 mL/min; Gradient: 25% B to 35% B in 8 min; 254/220 nm; Rt: 6.27 min) to 3-amino-N-[[2-(dimethylphosphoryl)-6-fluorophenyl]methyl]-6-[imidazo[1,2-a]pyridin-6-yl]-5-(1,3-oxazol-2-yl)pyrazine-2-carboxamide (Cmpd. 96) (95 mg, 37.81%) afford as a yellow solid. LCMS: m/z (ESI), [M+H]$^+$=506.2. $^1$H NMR: (300 MHz, DMSO-d$_6$) δ 1.85 (d, 6H), 4.90 (d, 2H), 7.12 (dd, 1H), 7.37 (d, 1H), 7.49 (m, 4H), 7.62 (m, 1H), 7.86 (s, 2H), 7.91 (s, 1H), 8.28 (d, 1H), 8.88 (d, 1H), 9.98 (t, 1H).

Example 101. Preparation of 3-amino-N-((3-fluoropyridin-2-yl)methyl)-6-(3-methylimidazo[1,2-a]pyridin-6-yl)-5-(oxazol-2-yl)pyrazine-2-carboxamide (Cmpd. 101)

SCHEME 63

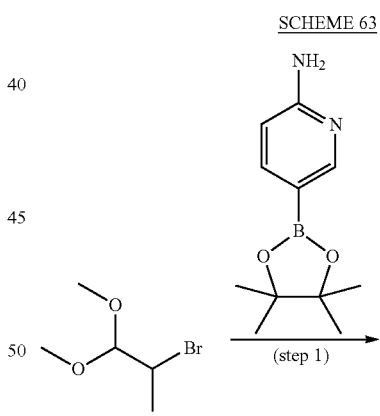

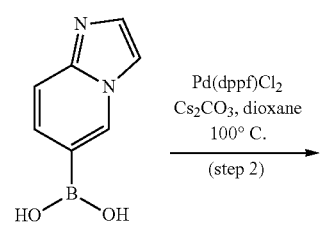

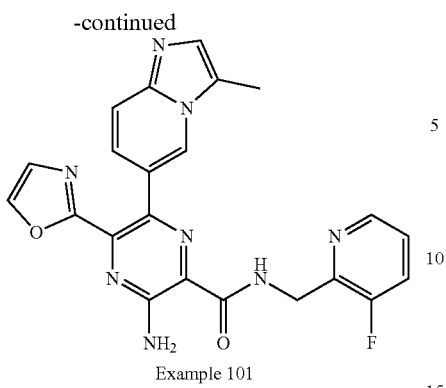

Example 101

Step 1. 3-methylimidazo[1,2-a]pyridin-6-ylboronic Acid

A mixture of 2-bromo-1,1-dimethoxypropane (500 mg, 2.73 mmol, 1 equiv) in 2.5 mL 1N aq.HCl was stirred for 1 h at 80° C. The mixture was cooled to RT and neutralized to pH 7 with NaHCO$_3$ (solid). The aqueous layer was extracted with CHCl$_3$ (3×5 mL). To the resulting CHCl$_3$ solution was added 5-(4,4,5,5-tetramethyl-1,3,2-dioxaborolan-2-yl)pyridin-2-amine (180.3 mg, 0.82 mmol, 0.30 equiv) in portions at room temperature. The resulted mixture was stirred for overnight at 80° C. The resulted mixture was concentrated under reduced pressure to afford crude Products as a crude oil which was directly used to next step without further purification. LCMS: m/z (ESI), [M+H]$^+$=177.0.

Step 2. 3-amino-N-((3-fluoropyridin-2-yl)methyl)-6-(3-methylimidazo[1,2-a]pyridin-6-yl)-5-(oxazol-2-yl)pyrazine-2-carboxamide (Cmpd. 101)

To a stirred mixture of 3-amino-6-chloro-N-[(3-fluoropyridin-2-yl)methyl]-5-(1,3-oxazol-2-yl)pyrazine-2-carboxamide (100 mg, 0.29 mmol, 1 equiv) and [3-methylimidazo[1,2-a]pyridin-6-yl]boronic acid (100.9 mg, 0.57 mmol, 2.00 equiv) in 1,4-dioxane (20 mL) were added Cs$_2$CO$_3$ (467.2 mg, 1.43 mmol, 5 equiv) and Pd(dppf)Cl$_2$CH$_2$Cl$_2$ (70.3 mg, 0.09 mmol, 0.3 equiv) in portions at room temperature under nitrogen atmosphere. The resulted mixture was stirred for overnight at 105° C. under nitrogen atmosphere. The resulted mixture was concentrated under reduced pressure. The residue was purified by Prep-TLC (CH$_2$Cl$_2$/MeOH 20:1) to afford 3-amino-N-[(3-fluoropyridin-2-yl)methyl]-6-[3-methylimidazo[1,2-a]pyridin-6-yl]-5-(1,3-oxazol-2-yl)pyrazine-2-carboxamide (Cmpd. 101) (23 mg, 18.05%) as a yellow solid. LCMS: m/z (ESI), [M+H]$^+$=445.2. $^1$H NMR (400 MHz, DMSO-d$_6$) δ 2.44 (d, J=0.9 Hz, 3H), 4.72 (dd, J=5.8, 1.7 Hz, 2H), 7.25 (dd, J=9.4, 1.8 Hz, 1H), 7.31-7.47 (m, 3H), 7.50 (dd, J=9.4, 1.0 Hz, 1H), 7.72 (ddd, J=10.0, 8.3, 1.3 Hz, 1H), 7.90 (s, 2H), 8.29 (d, J=0.8 Hz, 1H), 8.33-8.42 (m, 2H), 9.36 (t, J=5.9 Hz, 1H).

Example 102. Preparation of 3-amino-N-[(2,6-difluorophenyl)methyl]-6-[1-(3-hydroxypropyl)-6-oxo-1,6-dihydropyridin-3-yl]-5-(1,3-oxazol-2-yl)pyrazine-2-carboxamide (Ex 102)

SCHEME 64

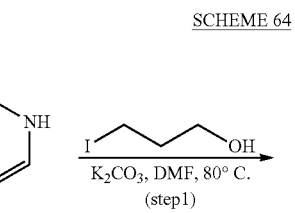

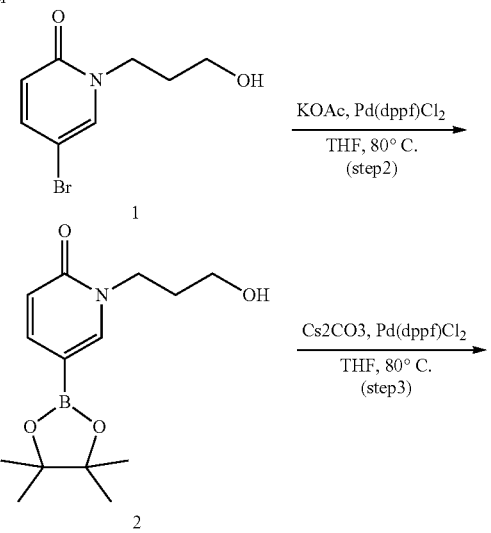

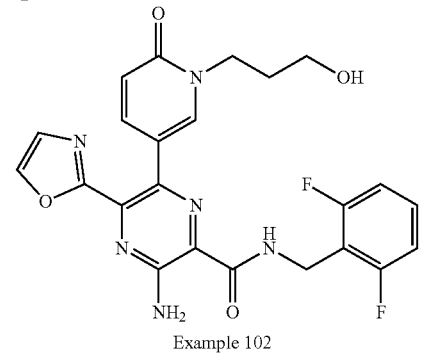

Example 102

Step 1. 5-bromo-1-(3-hydroxypropyl)-1,2-dihydropyridin-2-one

To a solution of 5-bromo-1,2-dihydropyridin-2-one (1 g, 5.75 mmol, 1 equiv) and 3-iodopropan-1-ol (2.1 g, 11.49 mmol, 2 equiv) in DMF (15 mL) was added K$_2$CO$_3$ (1.6 g, 11.49 mmol, 2 equiv) at room temperature. The mixture was stirred for 4 hours at 80° C. under air atmosphere. The resulted mixture was concentrated under reduced pressure. The residue was purified by Prep-TLC (CHCl$_3$/MeOH 20:1) to afford 5-bromo-1-(3-hydroxypropyl)-1,2-dihydropyridin-2-one (300 mg, 22.49%) as a yellow solid. LCMS: m/z (ESI), [M+H]$^+$=232.1, 234.1. $^1$H NMR: (300 MHz, DMSO-d$_6$) δ 1.12 (q, 2H), 2.79 (m, 2H), 3.27 (t, 2H), 4.03 (s, 1H), 5.69 (d, 1H), 6.78 (dd, 1H), 7.09 (d, 1H).

Step 2. 1-(3-hydroxypropyl)-5-(4,4,5,5-tetramethyl-1,3,2-dioxaborolan-2-yl)-1,2-dihydropyridin-2-one To a solution of 5-bromo-1-(3-hydroxypropyl)-1,2-dihydropyridin-2-one (200 mg, 0.86 mmol, 1 equiv) and 4,4,5,5-tetramethyl-2-(4,4,5,5-tetramethyl-1,3,2-dioxaborolan-2-yl)-1,3,2-dioxaborolane (437.7 mg, 1.72 mmol, 2 equiv) in THF (15 mL) were added KOAc (137.5 mg, 1.40 mmol, 3.00 equiv) and Pd(dppf)Cl$_2$ (63.1 mg, 0.09 mmol, 0.1 equiv) at room temperature under nitrogen atmosphere. The mixture was stirred for 2 hours at 80° C. under a nitrogen atmosphere. The mixture was used into the next step directly without further purification. LCMS: m/z (ESI), [M+H]$^+$= 280.3.

Step 3. 3-amino-N-[(2,6-difluorophenyl)methyl]-6-[1-(3-hydroxypropyl)-6-oxo-1,6-dihydropyridin-3-yl]-5-(1,3-oxazol-2-yl)pyrazine-2-carboxamide (Cmpd. 102)

To a solution of 1-(3-hydroxypropyl)-5-(4,4,5,5-tetramethyl-1,3,2-dioxaborolan-2-yl)-1,2-dihydropyridin-2-one (305.3 mg, 1.09 mmol, 2.00 equiv) in THF (15 mL) was added 3-amino-6-chloro-N-[(2,6-difluorophenyl)methyl]-5-(1,3-oxazol-2-yl)pyrazine-2-carboxamide (200 mg, 0.55 mmol, 1 equiv), Cs$_2$CO$_3$ (356.4 mg, 1.09 mmol, 2.00 equiv) and Pd(dppf)Cl$_2$ (40.0 mg, 0.05 mmol, 0.10 equiv) under nitrogen atmosphere at room temperature. The mixture was stirred for 2 hours at 80° C. under a nitrogen atmosphere, the residue was purified by Prep-TLC (CH$_2$Cl$_2$/MeOH 20:1) to afford 3-amino-N-[(2,6-difluorophenyl)methyl]-6-[1-(3-hydroxypropyl)-6-oxo-1,6-dihydropyridin-3-yl]-5-(1,3-oxazol-2-yl)pyrazine-2-carboxamide (Cmpd. 102) (60 mg, 22.74%) as a yellow solid. LCMS: m/z (ESI), [M+H]$^+$= 483.3. $^1$H NMR: (300 MHz, DMSO-d$_6$) δ 1.76 (p, 2H), 3.40 (q, 2H), 3.91 (t, 2H), 4.58 (m, 3H), 6.36 (d, 1H), 7.08 (t, 2H), 7.38 (m, 2H), 7.51 (dd, 1H), 7.75 (s, 2H), 7.85 (d, 1H), 8.28 (s, 1H), 9.10 (t, 1H).

Example 103. Preparation of 3-amino-N-[(2,6-difluorophenyl)methyl]-6-[1-(2-methoxyethyl)-6-oxo-1,6-dihydropyridin-3-yl]-5-(1,3-oxazol-2-yl)pyrazine-2-carboxamide (Cmpd. 103)

SCHEME 65

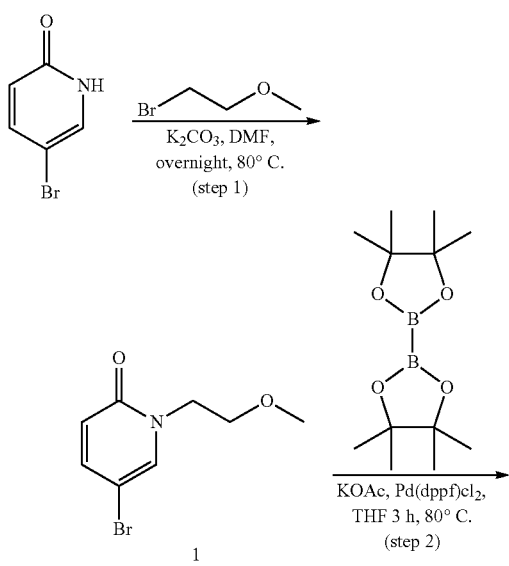

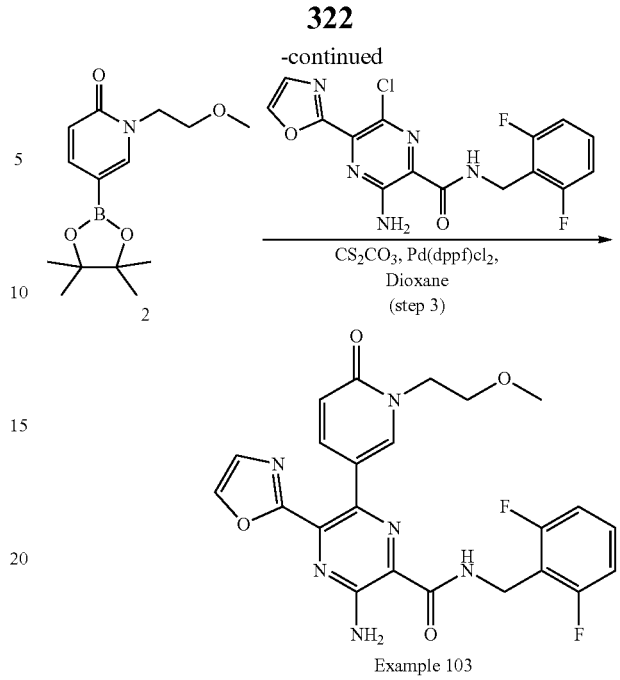

Example 103

Step 1. 5-bromo-1-(2-methoxyethyl)-1,2-dihydropyridin-2-one

To a stirred mixture of 5-bromo-1,2-dihydropyridin-2-one (500 mg, 2.87 mmol, 1 equiv) and 1-bromo-2-methoxyethane (1597.6 mg, 11.49 mmol, 4 equiv) in DMF (15 mL) was added K$_2$CO$_3$ (1191.4 mg, 8.62 mmol, 3 equiv) in portions at 80° C. under air atmosphere. The resulted mixture was stirred for 5 hours at 80° C. under air atmosphere. The resulted mixture was poured into water. The resulted mixture was extracted with EtOAc (2×100 mL). The combined organic layers were washed with water (1×40 mL), dried over anhydrous Na$_2$SO$_4$. After filtration, the filtrate was concentrated under reduced pressure. The residue was purified by silica gel column chromatography, eluted with PE/EtOAc (5:1) to afford 5-bromo-1-(2-methoxyethyl)-1,2-dihydropyridin-2-one (200 mg, 29.99%) as a white solid. LCMS: m/z (ESI), [M+H]$^+$=231.9. $^1$H NMR (400 MHz, DMSO-d$_6$) δ 3.24 (s, 3H), 3.56 (t, J=5.3 Hz, 2H), 4.04 (t, J=5.3 Hz, 2H), 6.38 (d, J=9.6 Hz, 1H), 7.53 (dd, J=9.7, 2.8 Hz, 1H), 7.91 (d, J=2.8 Hz, 1H).

Step 2. 1-(2-methoxyethyl)-5-(4,4,5,5-tetramethyl-1,3,2-dioxaborolan-2-yl)pyridin-2(1H)-one To a stirred mixture of 5-bromo-1-(2-methoxyethyl)-1,2-dihydropyridin-2-one (150 mg, 0.65 mmol, 1 equiv) and 4,4,5,5-tetramethyl-2-(4,4,5,5-tetramethyl-1,3,2-dioxaborolan-2-yl)-1,3,2-dioxaborolane (328.3 mg, 1.29 mmol, 2 equiv) in THF (5 mL) were added Pd(dppf)Cl$_2$ (94.6 mg, 0.13 mmol, 0.2 equiv) and KOAc (190.3 mg, 1.94 mmol, 3 equiv) in portions at 80° C. under nitrogen atmosphere. The resulted mixture was stirred for 3 hours at 80° C. under nitrogen atmosphere. The resulted mixture was concentrated under reduced pressure. The crude product was used in the next step directly without further purification. LCMS: m/z (ESI), [M+H]$^+$=280.3.

Step 3. 3-amino-N-[(2,6-difluorophenyl)methyl]-6-[1-(2-methoxyethyl)-6-oxo-1,6-dihydropyridin-3-yl]-5-(1,3-oxazol-2-yl)pyrazine-2-carboxamide (Cmpd. 103)

To a stirred mixture of 3-amino-6-chloro-N-[(2,6-difluorophenyl)methyl]-5-(1,3-oxazol-2-yl)pyrazine-2-carboxamide (100 mg, 0.27 mmol, 1 equiv) and 1-(2-methoxyethyl)-5-(4,4,5,5-tetramethyl-1,3,2-dioxaborolan-2-yl)-1,2-dihydropyridin-2-on e (152.7 mg, 0.55 mmol, 2.00 equiv) in TH (8 mL) were added Pd(dppf)Cl$_2$ (40.0 mg, 0.05 mmol, 0.2 equiv) and Cs$_2$CO$_3$ (356.4 mg, 1.09 mmol, 4 equiv) in portions at 100° C. under nitrogen atmosphere. The resulted mixture was stirred for overnight at 100° C. under nitrogen atmosphere. The resulted mixture was concentrated under reduced pressure. The residue was purified by silica gel column chromatography, eluted with CH$_2$Cl$_2$/MeOH (20:1) to afford 3-amino-N-[(2,6-difluorophenyl)methyl]-6-[1-(2-methoxyethyl)-6-oxo-1,6-dihydropyridin-3-yl]-5-(1,3-oxazol-2-yl)pyrazine-2-carboxamide (Cmpd. 103) (33 mg, 24.77%) as a yellow green solid. LCMS: m/z (ESI), [M+H]$^+$= 483.2. $^1$H NMR (400 MHz, DMSO-d$_6$) δ 3.22 (s, 3H), 3.57 (t, J=5.4 Hz, 2H), 4.04 (t, J=5.5 Hz, 2H), 4.61 (d, J=5.9 Hz, 2H), 6.35 (d, J=9.4 Hz, 1H), 7.10 (t, J=8.0 Hz, 2H), 7.34 7.46 (m, 2H), 7.47 (dd, J=9.4, 2.6 Hz, 1H), 7.75~7.80 (m, 2H), 7.88 (d, J=2.6 Hz, 1H), 8.30 (d, J=0.8 Hz, 1H), 9.07 (t, J=5.9 Hz, 1H).

Example 104. Preparation of 3-amino-N-[(3-fluoropyridin-2-yl)methyl]-6-[imidazo[1,2-a]pyridin-6-yl]-5-(2H-1,2,3-triazol-2-yl)pyrazine-2-carboxamide (Cmpd. 104)

SCHEME 66

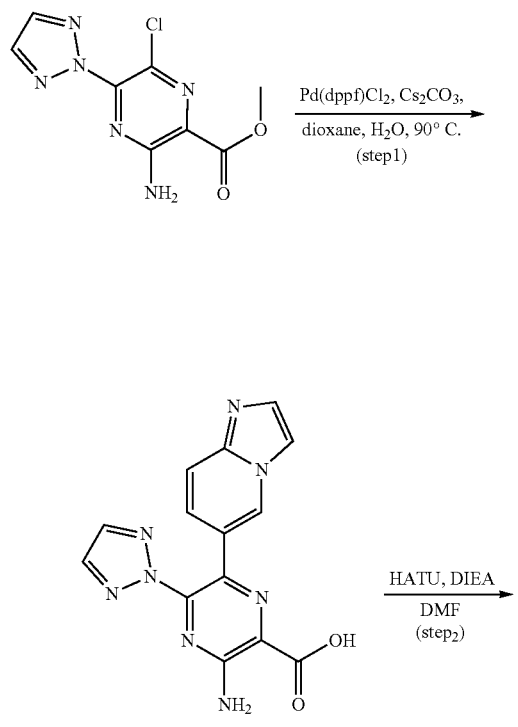

-continued

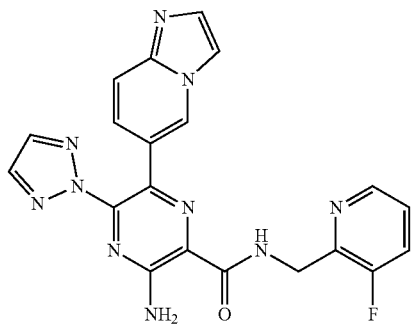

Example 104

Step 1. 3-amino-6-[imidazo[1,2-a]pyridin-6-yl]-5-(2H-1,2,3-triazol-2-yl)pyrazine-2-carboxylic Acid To a stirred mixture of methyl 3-amino-6-chloro-5-(2H-1,2,3-triazol-2-yl)pyrazine-2-carboxylate (300 mg, 1.178 mmol, 1 equiv) and 6-(4,4,5,5-tetramethyl-1,3,2-dioxaborolan-2-yl)imidazo[1,2-a]pyridine (431.39 mg, 1.767 mmol, 1.5 equiv) in dioxane (20 mL) were added Pd(dppf)Cl$_2$ (172.41 mg, 0.236 mmol, 0.2 equiv), water (2 mL) and Cs$_2$CO$_3$ (1151.62 mg, 3.535 mmol, 3 equiv) in portions at room temperature under nitrogen atmosphere. The resulted mixture was stirred for overnight at 90° C. The resulted mixture was filtered, the filter cake was washed with DCM (3×10 mL). The filtrate was acidified to PH=5 with 2N aq.HCl. The resulting solid was collected by filtration and dried under vacuum to afford 3-amino-6-[imidazo[1,2-a]pyridin-6-yl]-5-(2H-1,2,3-triazol-2-yl)pyrazine-2-carboxylic acid (290 mg, 76.37%) as a brown crude solid which was used in the next step directly without further purification. LCMS: m/z (ESI), [M+H]$^+$=323.2.

Step 2. 3-amino-N-[(3-fluoropyridin-2-yl)methyl]-6-[imidazo[1,2-a]pyridin-6-yl]-5-(2H-1,2,3-triazol-2-yl)pyrazine-2-carboxamide (Cmpd. 104)

To a stirred mixture of 3-amino-6-[imidazo[1,2-a]pyridin-6-yl]-5-(2H-1,2,3-triazol-2-yl)pyrazine-2-carboxylic acid (100 mg, 0.31 mmol, 1 equiv) and 1-(3-fluoropyridin-2-yl)methanamine (67.1 mg, 0.62 mmol, 2 equiv) in DMF (3 mL) were added HATU (471.9 mg, 1.24 mmol, 4 equiv) and DIEA (160.4 mg, 1.24 mmol, 4 equiv) in portions at room temperature under air atmosphere. The resulted mixture was stirred for 2 hours at room temperature. The resulted mixture was quenched by water (10 mL), the resulting solid was collected by filtration and washed with water (3×10 mL). The crude product was slurried with MeOH (6 mL), the resulting solid was collected by filtration and dried under vacuum to afford 3-amino-N-[(3-fluoropyridin-2-yl)methyl]-6-[imidazo[1,2-a]pyridin-6-yl]-5-(2H-1,2,3-triazol-2-yl)pyrazine-2-carboxamide (Cmpd. 104) (48 mg, 35.5%) as a yellow solid. LCMS: m/z (ESI), [M+H]$^+$=431.2. $^1$H NMR (DMSO-d$_6$, 400 MHz) δ 4.7 (2H, d, J=5.9 Hz), 6.7 (1H, dd, J=9.4, 1.8 Hz), 7.4 (2H, dd, J=8.8, 4.4 Hz), 7.6 (1H, d, J=1.2 Hz), 7.7 (1H, ddd, J=10.0, 8.3, 1.3 Hz), 7.9 (1H, s), 8.1 (3H, s), 8.4 (1H, dt, J=4.7, 1.5 Hz), 8.6-8.7 (1H, m), 9.4 (1H, t, J=6.0 Hz).

Example 107. Preparation of 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide

Example 108. Preparation of 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide

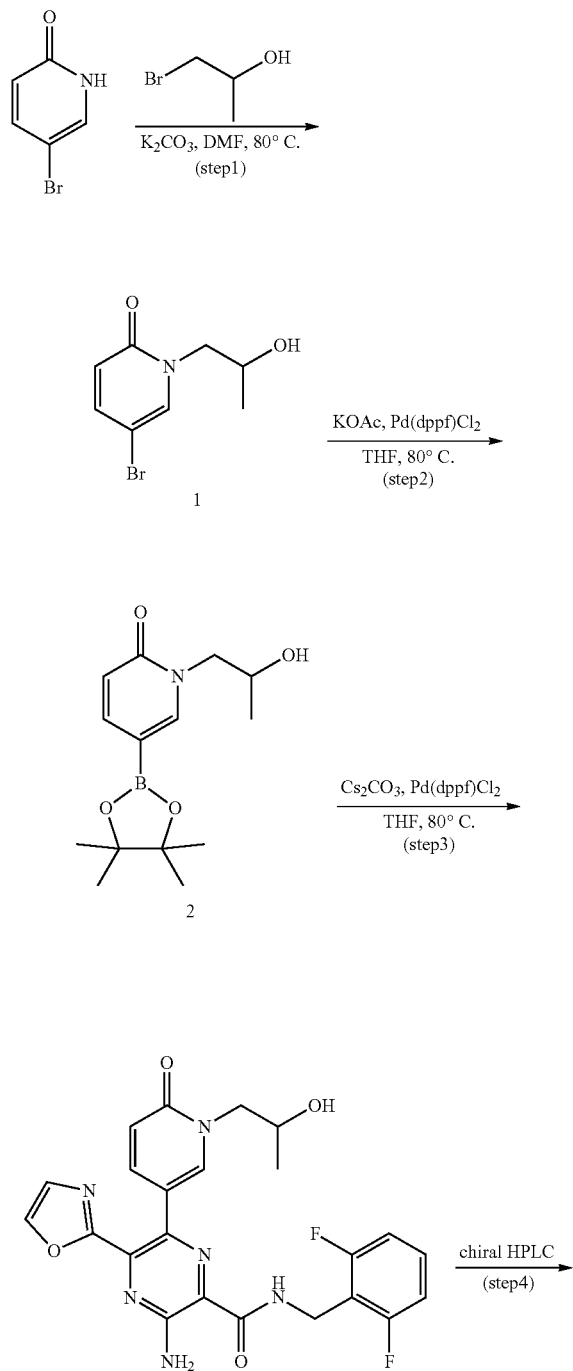

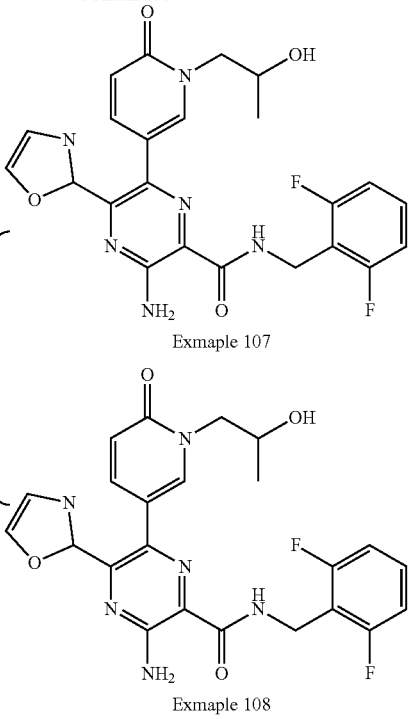

Step 1. 5-bromo-1-(2-hydroxypropyl)-1,2-dihydropyridin-2-one

A solution of 5-bromo-1,2-dihydropyridin-2-one (1 g, 5.75 mmol, 1 equiv) and 1-bromopropan-2-ol (1.6 g, 0.01 mmol, 2.00 equiv) $K_2CO_3$ (1.6 g, 0.01 mmol, 2.00 equiv) in DMF (15 mL) was stirred for 4h at 80° C. under air atmosphere. The resulted mixture was concentrated under reduced pressure. The residue was purified by Prep-TLC ($CH_2Cl_2$/MeOH 20:1) to afford 5-bromo-1-(2-hydroxypropyl)-1,2-dihydropyridin-2-one (0.9 g, 67.48%) as a white solid. LCMS: m/z (ESI), [M+H]$^+$=232.1, 234.1. $^1$H NMR: (300 MHz, DMSO-d$_6$) δ 1.05 (dd, 3H), 3.55 (ddd, 1H), 3.85 (dddd, 1H), 3.96 (ddd, 1H), 4.89 (dd, 1H), 6.35 (dd, 1H), 7.50 (m, 1H), 7.82 (t, 1H).

Step 2. 1-(2-hydroxypropyl)-5-(4,4,5,5-tetramethyl-1,3,2-dioxaborolan-2-yl)-1,2-dihydropyridin-2-one To a solution of 5-bromo-1-(2-hydroxypropyl)-1,2-dihydropyridin-2-one (300 mg, 1.29 mmol, 1 equiv) and 4,4,5,5-tetramethyl-2-(4,4,5,5-tetramethyl-1,3,2-dioxaborolan-2-yl)-1,3,2-dioxaborolane (656.5 mg, 2.59 mmol, 2 equiv) in THF (15 mL) were added KOAc (137.5 mg, 1.40 mmol, 3.00 equiv) and Pd(dppf)Cl$_2$ (94.6 mg, 0.13 mmol, 0.10 equiv). The mixture was stirred for 2 hours at 80° C. under a nitrogen atmosphere. The resulted mixture was used in the next step directly without further purification. LCMS: m/z (ESI), [M+H]$^+$=280.1.

Step 3. 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide To a solution of methyl 3-amino-6-bromo-5-(2H-1,2,3-triazol-2-yl)pyrazine-2-carboxylate (200 mg, 0.67 mmol, 1 equiv) and 1-methyl-5-(4,4,5,5-tetramethyl-1,3,2-dioxaborolan-2-yl)-1,2-dihydropyridin-2-one (314.4 mg, 1.34 mmol, 2.00 equiv) in THF (15 mL) were added $Cs_2CO_3$ (435.8 mg, 1.34 mmol, 2 equiv) and $Pd(dppf)Cl_2$ (48.9 mg, 0.07 mmol, 0.1 equiv). After stirring for 2h at 80° C. under a nitrogen atmosphere, the residue was purified by Prep-TLC ($CH_2Cl_2$/MeOH 20:1) to afford 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide (racemate, 10 mg, 4.77%) as a yellow solid. LCMS: m/z (ESI), $[M+H]^+$=483.3. $^1$H NMR: (300 MHz, DMSO-$d_6$) δ 1.05 (d, 3H), 3.62 (m, 1H), 3.93 (m, 2H), 4.60 (s, 2H), 4.83 (d, 1H), 6.35 (d, 1H), 7.08 (t, 2H), 7.38 (m, 2H), 7.49 (dd, 1H), 7.74 (s, 2H), 7.80 (d, 1H), 8.27 (d, 1H), 9.05 (t, 1H).

Step 4. 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide (Unknown Absolute, Peak 1, Cmpd. 107) and 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide (Unknown Absolute, Peak 2, Cmpd. 108)

The racemate product (100 mg) was purified by preparative chiral-HPLC on a as eluent. Column: Column: (R,R) Whelk-O 1, 21.1*250 mm, 5 um; Mobile Phase A: Hex (8 mmol/L $NH_3$.MeOH)-HPLC, Mobile Phase B: EtOH-HPLC; Flow rate: 20 mL/min; Gradient: 50 B to 50 B in 26 min; 254/220 nm; RT1:16.649; RT2:19.223. This resulted in 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide (isomer 1) (Cmpd. 107) (30 mg, 30%) as a yellow solid LCMS: m/z (ESI), $[M+H]^+$=483.3. $^1$H NMR: (300 MHz, DMSO-$d_6$) δ 1.05 (d, 3H), 3.62 (m, 1H), 3.93 (m, 2H), 4.60 (s, 2H), 4.83 (d, 1H), 6.35 (d, 1H), 7.08 (t, 2H), 7.38 (m, 2H), 7.49 (dd, 1H), 7.74 (s, 2H), 7.80 (d, 1H), 8.27 (d, 1H), 9.05 (t, 1H). Chiral: tR=2.59 min. and 3-amino-N-(2,6-difluorobenzyl)-6-(1-(2-hydroxypropyl)-6-oxo-1,6-dihydropyridin-3-yl)-5-(oxazol-2-yl)pyrazine-2-carboxamide (isomer 2) (Cmpd. 108) (30 mg, 30%) as a yellow solid. LCMS: m/z (ESI), $[M+H]^+$=483.3. $^1$H NMR: (300 MHz, DMSO-$d_6$) δ 1.05 (d, 3H), 3.62 (m, 1H), 3.93 (m, 2H), 4.60 (s, 2H), 4.83 (d, 1H), 6.35 (d, 1H), 7.08 (t, 2H), 7.38 (m, 2H), 7.49 (dd, 1H), 7.74 (s, 2H), 7.80 (d, 1H), 8.27 (d, 1H), 9.05 (t, 1H). Chiral: tR=3.03 min, Mix Chiral: tR=2.59 min, 3.03 min.

Example 111. Preparation of 3-amino-N-((6-(3-(dimethylamino)azetidin-1-yl)pyridin-2-yl)methyl)-6-(3-methylimidazo[1,2-a]pyridin-6-yl)-5-(oxazol-2-yl)pyrazine-2-carboxamide (Cmpd. 111)

SCHEME 67

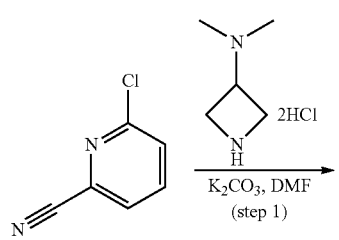

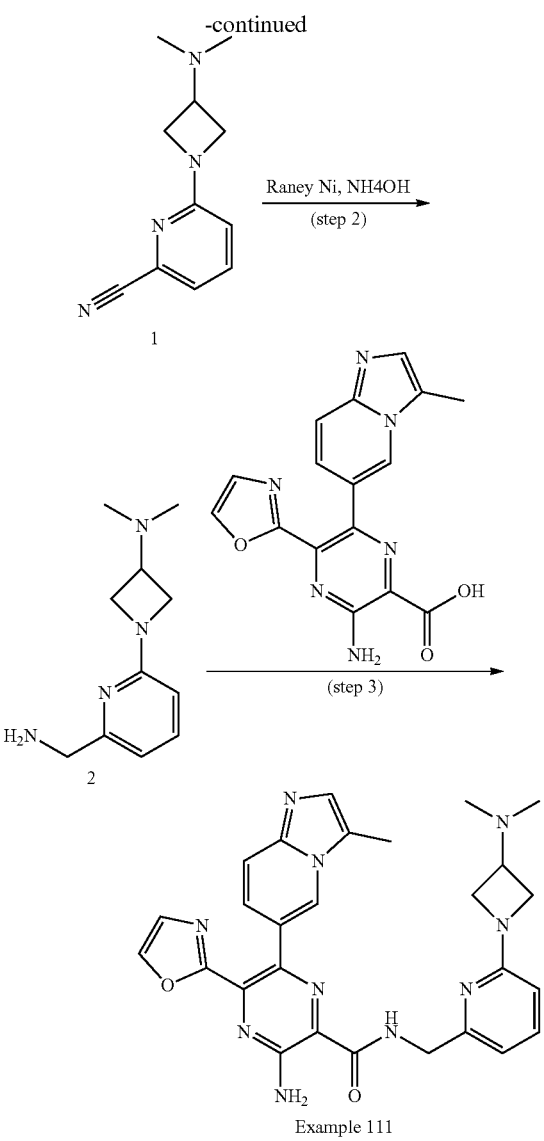

Example 111

Step 1.
6-(3-(dimethylamino)azetidin-1-yl)picolinonitrile

Into a 50-mL round-bottom flask, was placed 6-chloropyridine-2-carbonitrile (1.5 g, 10.826 mmol, 1 equiv), N,N-dimethylazetidin-3-amine-dihydrochloride (1.87 g, 10.826 mmol, 1 equiv), DMF (10 mL, 129.218 mmol, 11.94 equiv), $K_2CO_3$ (4.49 g, 32.479 mmol, 3 equiv). The resulting solution was stirred for 16 hours at 80° C. The resulting solution was extracted with 3×20 mL of dichloromethane. The residue was applied onto a silica gel column with dichloromethane/methanol (50:1). This resulted in (475 mg, 21.69%) of 6-[3-(dimethylamino)azetidin-1-yl]pyridine-2-carbonitrile (Cmpd. 111) as alight brown solid. $^1$H NMR (400 MHz, Chloroform-d) δ 3.96 (1H, s), 6.20 (6H, s), 7.22-7.33 (6H, m), 7.83 (2H, dd), 8.05-8.14 (2H, m), 8.81 (6H, s), 10.62 (1H, dd), 11.02 (1H, dd), 11.57 (1H, dd)

Step 2. 1-(6-(aminomethyl)pyridin-2-yl)-N,N-dimethylazetidin-3-amine

Into a 25-mL round-bottom flask, was placed 6-(3-(dimethylamino)azetidin-1-yl)picolinonitrile. This was followed by the addition of MeOH (10 mL, 246.989 mmol, 111.01 equiv), NH₄OH (2 mL, 51.361 mmol, 23.09 equiv) and Raney Ni at rt. The resulting mixture was stirred for 1 hour at room temperature. The solids were filtered out. The resulting mixture was concentrated. This resulted in 290 mg (63.18%) of 1-[6-(aminomethyl)pyridin-2-yl]-N,N-dimethylazetidin-3-amine as a solid. LCMS: m/z (ESI), [M+H]⁺= 207.1 ¹H NMR (300 MHz, Methanol-d₄) δ 2.24 (6H, s), 3.27 (1H, d), 3.77 (2H, s), 3.79-3.89 (2H, m), 4.12 (2H, t), 6.32 (1H, s), 6.66 (1H, d), 7.51 (1H, t)

Step 3. 3-amino-N-((6-(3-(dimethylamino)azetidin-1-yl)pyridin-2-yl)methyl)-6-(3-methylimidazo[1,2-a]pyridin-6-yl)-5-(oxazol-2-yl)pyrazine-2-carboxamide (Cmpd. 111)

Into a 25-mL round-bottom flask, was placed 3-amino-6-[3-methylimidazo[1,2-a]pyridin-6-yl]-5-(1,3-oxazol-2-yl)pyrazine-2-carboxylic acid (130 mg), DMF (5 mL), T₃P (750 mg), DIEA (530 mg), 1-[6-(aminomethyl)pyridin-2-yl]-N,N-dimethylazetidin-3-amine (130 mg). The resulting solution was stirred for 16 hours at room temperature. The resulting solution was extracted with 3×10 mL of ethyl acetate and the organic layers combined and concentrated. The residue was applied onto a silica gel column with dichloromethane/methanol (8:1). The crude product was purified by Prep-HPLC with the following conditions (Column: XBridge Prep OBD C18 Column 30×150 mm 5 um; Mobile Phase A: Water (0.05% NH₃H₂O), Mobile Phase B: ACN; Flow rate: 60 mL/min; Gradient: 31% B to 41% B in 7 min; 254/220 nm; Rt: 5.10 min) and the product was obtained. This resulted in (51.6 mg) of 3-amino-N-([6-[3-(dimethylamino)azetidin-1-yl]pyridin-2-yl]methyl)-6-[3-methylimidazo[1,2-a]pyridin-6-yl]-5-(1,3-oxazol-2-yl)pyrazine-2-carboxamide (Cmpd. 111) as a yellow solid. LCMS: m/z (ESI), [M+H]⁺=525.3 ¹H-NMR (300 MHz, Methanol-d₄) δ 2.03 (6H, s), 2.49 (3H, d), 3.03 (1H, t), 3.66 (2H, dd), 3.88-3.99 (2H, m), 4.55 (2H, s), 6.29 (1H, d), 6.67 (1H, d), 7.25-7.35 (2H, m), 7.39 (1H, s), 7.43-7.54 (2H, m), 7.99 (1H, d), 8.37 (1H, s)

Example 112. Preparation of 3-amino-6-(3-methylimidazo[1,2-a]pyridin-6-yl)-N-((6-(4-methylpiperazin-1-yl)pyridin-2-yl)methyl)-5-(oxazol-2-yl)pyrazine-2-carboxamide (Cmpd. 112)

SCHEME 68

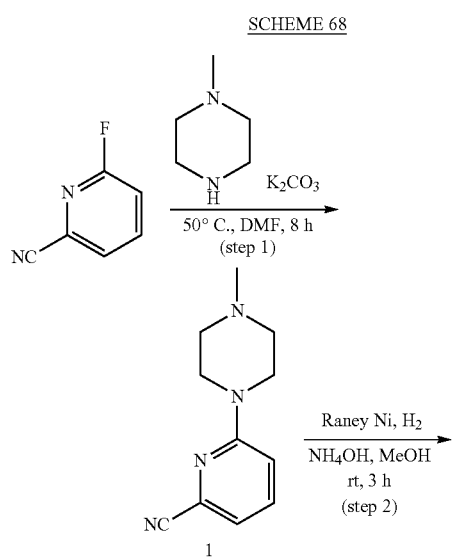

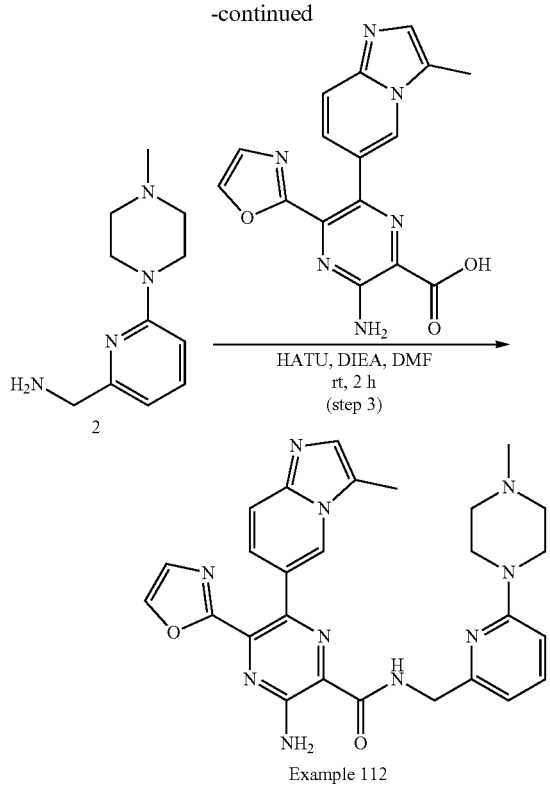

Example 112

Step 1. 6-(4-methylpiperazin-1-yl)picolinonitrile 6-fluoropyridine-2-carbonitrile (500 mg, 4.095 mmol, 1 equiv), 1-methylpiperazine (615.25 mg, 6.142 mmol, 1.5 equiv), K₂CO₃ (1131.89 mg, 8.190 mmol, 2 equiv) were dissolved in 3 mL of DMF. The mixture was stirred at 50° C. for 8 hours. LCMS showed the reaction was OK. The crude product was purified by silica gel column, eluting with DCM:CH₃OH (15:1), the product was further purified by prep-HPLC to give 6-(4-methylpiperazin-1-yl)picolinonitrile (158 mg, 19.08%) as a brown oil. LCMS: m/z (ESI), [M+H]⁺=203.3.

Step 2. (6-(4-methylpiperazin-1-yl)pyridin-2-yl)methanamine 6-(4-methylpiperazin-1-yl)pyridine-2-carbonitrile (140 mg, 0.692 mmol, 1 equiv), Raney Ni (118.60 mg, 1.384 mmol, 2.00 equiv), were dissolved in 3 mL of NH₄OH and MeOH. The mixture was stirred at room temperature under H₂ for 3 hours). LCMS showed the reaction was OK. The crude product was purified by silica gel column, eluting with DCM:CH₃OH (15:1), the product was further purified by prep-HPLC to give (6-(4-methylpiperazin-1-yl)pyridin-2-yl)methanamine (40 mg, 28.01%) as a grey oil. LCMS: m/z (ESI), [M+H]⁺=207.3.

Step 3. 3-amino-6-(3-methylimidazo[1,2-a]pyridin-6-yl)-N-((6-(4-methylpiperazin-1-yl)pyridin-2-yl)methyl)-5-(oxazol-2-yl)pyrazine-2-carboxamide (Cmpd. 112)

1-[6-(4-methylpiperazin-1-yl)pyridin-2-yl]methanamine (29.44 mg, 0.143 mmol, 1.20 equiv), 3-amino-6-[3-methylimidazo[1,2-a]pyridin-6-yl]-5-(1,3-oxazol-2-yl)pyrazine-2- carboxylic acid (40 mg, 0.119 mmol, 1 equiv), EDCI (45.60 mg, 0.238 mmol, 2.00 equiv), HOBT (32.14 mg, 0.238 mmol, 2.00 equiv), DIEA (92.23 mg, 0.714 mmol, 6.00 equiv) were dissolved in 3 mL of DMF. The mixture was stirred at room temperature for 2 h. LCMS showed the reaction was OK. The crude product was purified by silica gel column, eluting with DCM:CH$_3$OH (15:1), the product was further purified by prep-HPLC to give 3-amino-6-(3-methylimidazo[1,2-a]pyridin-6-yl)-N-((6-(4-methylpiperazin-1-yl)pyridin-2-yl)methyl)-5-(oxazol-2-yl)pyrazine-2-carboxamide (26.5 mg, 42.47%) as a yellow solid. LCMS: m/z (ESI), [M+H]$^+$=525.3. $^1$H-NMR (300 MHz, Methanol-d$_4$) δ: 1.29 (s, 6H), 2.29 (1H, d), 2.49 (3H, d), 3.31-3.48 (4H, m), 4.58 (2H, s), 6.67 (2H, dd), 7.24-7.33 (2H, m), 7.42 (1H, d), 7.46-7.58 (2H, m), 7.99 (1H, d), 8.39 (1H, t).

Example 113. Preparation of 3-amino-5-(4-fluorophenyl)-N-[[3-(2-hydroxyethoxy) pyridin-2-yl]methyl]-6-(1-methyl-1H-1,3-benzodiazol-6-yl)pyrazine-2-carboxamide (Cmpd. 113)

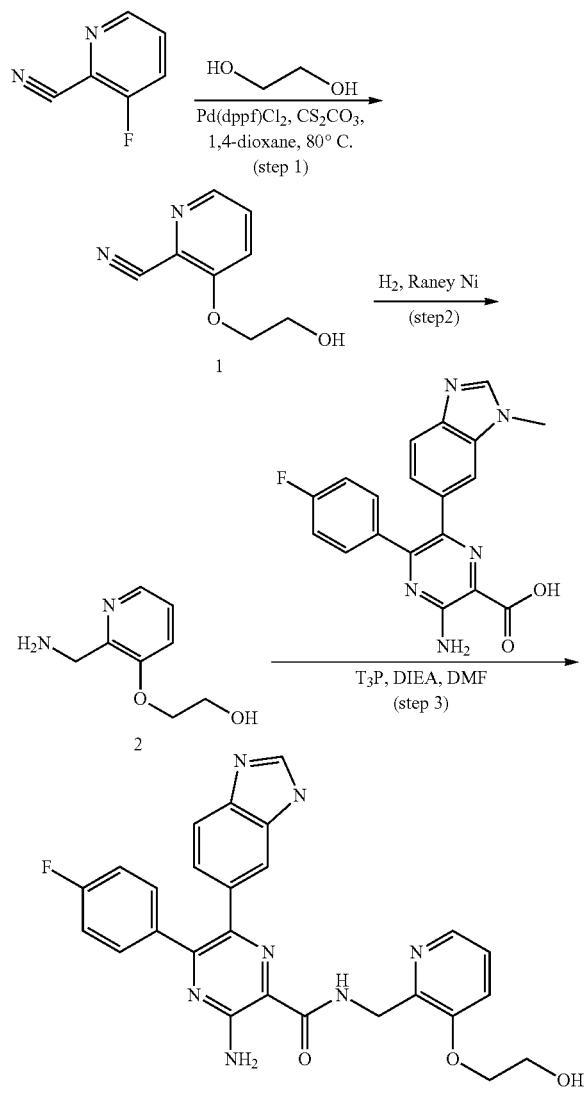

Example 113

Step 1. 3-(2-hydroxyethoxy)pyridine-2-carbonitrile

To a mixture of 3-fluoropyridine-2-carbonitrile (1.5 g, 12.3 mmol, 1 equiv) and ethane-1,2-diol (1.5 g, 24.5 mmol, 2 equiv) in 1,4-dioxane (25 mL) was added Cs$_2$CO$_3$ (8.0 g, 24.5 mmol, 2 equiv). The resulting mixture was stirred for 4 hours at 80° C. under air atmosphere. The resulting mixture was concentrated under reduced pressure. The residue was purified by silica gel column chromatography, eluted with PE/EtOAc (5:1) to afford 3-(2-hydroxyethoxy) pyridine-2-carbonitrile (1 g, 49.6%) as a yellow oil. LCMS: m/z (ESI), [M+H]$^+$=166.1. $^1$H-NMR (300 MHz, DMSO-d$_6$) δ 3.75 (2H, q), 4.23 (2H, m), 4.97 (1H, t), 7.68 (1H, dd), 7.81 (1H, dd), 8.28 (1H, dd).

Step 2. 2-[[2-(aminomethyl)pyridin-3-yl]oxy]ethan-1-ol

To a solution of 3-(2-hydroxyethoxy)pyridine-2-carbonitrile (200 mg, 1.2 mmol, 1 equiv) in MeOH (5 mL) and NH$_3$H$_2$O (1 mL) was added Raney Ni (469.7 mg, 5.5 mmol, 3 equiv). The resulting mixture was stirred for 2 hours at room temperature under hydrogen atmosphere. The resulting mixture was filtered, the filter cake was washed with MeOH (3×10 mL). The filtrate was concentrated under reduced pressure. This resulted in 2-[[2-(aminomethyl)pyridin-3-yl]oxy]ethan-1-ol (200 mg) as a purple oil. The crude product was used in the next step directly without further purification. LCMS: m/z (ESI), [M+H]$^+$=169.3.

Step 3. 3-amino-5-(4-fluorophenyl)-N-[[3-(2-hydroxyethoxy)pyridin-2-yl]methyl]-6-(1-methyl-1H-1,3-benzodiazol-6-yl)pyrazine-2-carboxamide (Cmpd. 113)

To a solution of 2-[[2-(aminomethyl)pyridin-3-yl]oxy]ethan-1-ol (200 mg, 1.2 mmol, 1 equiv) and 3-amino-5-(4-fluorophenyl)-6-(1-methyl-H-1,3-benzodiazol-6-yl)pyrazine-2-carboxylic acid (302.4 mg, 0.8 mmol, 0.7 equiv) in DMF (15 mL) was added T$_3$P (756.7 mg, 2.4 mmol, 2 equiv), DIEA (307.4 mg, 2.4 mmol, 2 equiv) in portions. The resulting mixture was stirred for 1 h at room temperature under air atmosphere. The resulting mixture was concentrated under reduced pressure. The crude product (60 mg) was purified by Prep-HPLC with the following conditions (Column: Xselect CSH OBD Column 30*150 mm 5 um n; Mobile Phase A: Water (0.05% TFA), Mobile Phase B: ACN; Flow rate: 60 mL/min; Gradient: 35% B to 45% B in 7 min; 254; 220 nm; Rt: 7.02 min) to afford 3-amino-5-(4-fluorophenyl)-N-[[3-(2-hydroxyethoxy)pyridin-2-yl]methyl]-6-(1-methyl-1H-1,3-benzodiazol-6-yl)pyrazine-2-carboxamide (Cmpd. 113) (20 mg, 6.55%) as a yellow solid. LCMS: m/z (ESI), [M+H]$^+$=514.3. $^1$H NMR (300 MHz, DMSO-d$_6$) δ 3.76 (2H, t), 3.98 (3H, s), 4.12 (2H, t), 4.69 (2H, d), 7.15 (2H, q), 7.37 (4H, m), 7.51 (1H, d), 7.67 (1H, d), 7.76 (2H, s), 8.04 (1H, d), 8.10 (1H, dd), 9.22 (2H, d). F NMR (282 MHz, DMSO-d$_6$) δ −74.48, −112.25.

Compounds listed in the table below were prepared using methods described in Cmpd. 113.

| Example/Cmpd number | Structure | LCMS [M + H]+ | 1H NMR |
|---|---|---|---|
| 300 | 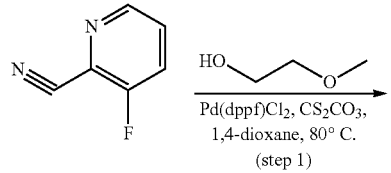 | 487.1 | 1H-NMR (300 MHz, Methanol-d4) δ 2.50 (3H, s), 3.87-3.93 (2H, m), 4.12-4.19 (2H, m), 4.51-4.71 (2H, m), 7.24-7.34 (3H, m), 7.38 (1H, s), 7.42-7.51 (2H, m), 8.00 (1H, d), 8.07 (1H, d), 8.39 (1H, s). |

Example 114. Preparation of 3-amino-5-(4-fluoro-phenyl)-N-[[3-(2-methoxyethoxy) pyridin-2-yl]methyl]-6-(1-methyl-1H-1,3-benzodiazol-6-yl)pyrazine-2-carboxamide (Cmpd. 114)

SCHEME 70

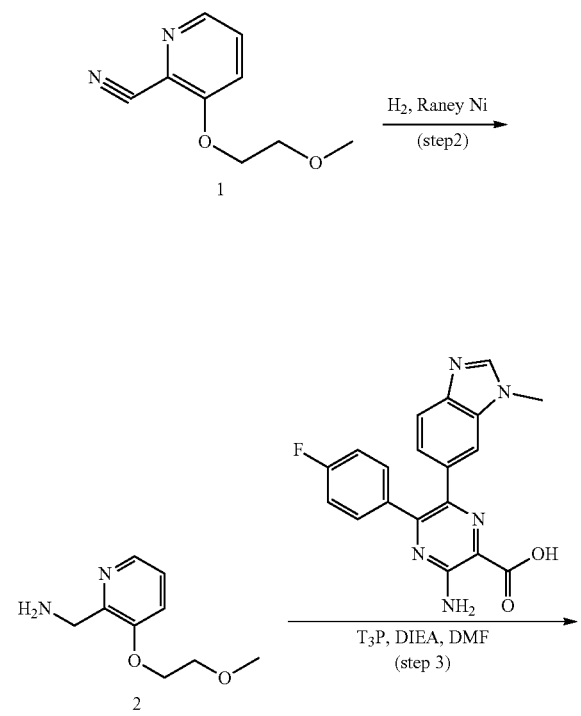

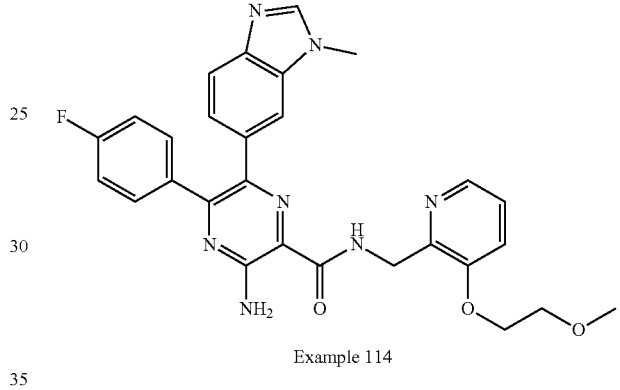

Example 114

Step 1. N-[2-[(2-cyanopyridin-3-yl)oxy]ethyl]-N-methylcarbamate

To a mixture of 3-fluoropyridine-2-carbonitrile (1.5 g, 12.2 mmol, 1 equiv) and tert-butyl N-(2-hydroxyethyl)-N-methylcarbamate (4.3 g, 24.5 mmol, 2 equiv) in 1,4-dioxane (25 mL) was added $Cs_2CO_3$ (8.01 g, 24.6 mmol, 2.0 equiv) at room temperature. The resulting mixture was stirred for 4 hours at 80° C. under air atmosphere. The resulting mixture was concentrated under reduced pressure. The residue was purified by silica gel column chromatography, eluted with PE/EtOAc (10:1) to afford tert-butyl N-[2-[(2-cyanopyridin-3-yl)oxy]ethyl]-N-methylcarbamate (1.8 g, 52.8%) as a yellow solid. LCMS: m/z (ESI), [M+H]+=179.0. 1H-NMR (300 MHz, DMSO-d6) δ 1.36 (9H, s), 2.90 (3H, d), 3.57 (2H, t), 4.33 (2H, q), 7.69 (1H, dd), 7.82 (1H, d), 8.29 (1H, dd).

Step 2. 1-[3-(2-methoxyethoxy)pyridin-2-yl]methanamine

To a solution of 3-(2-methoxyethoxy)pyridine-2-carbonitrile (300 mg, 1.7 mmol, 1 equiv) in MeOH (5 mL) and $NH_3H_2O$ (1 mL) was added Raney Ni (288.4 mg, 3.3 mmol, 2 equiv) in portions at room temperature. The resulting mixture was stirred for 2h at room temperature under hydrogen atmosphere. The resulting mixture was filtered, the filter cake was washed with MeOH (3×10 mL). The filtrate was concentrated under reduced pressure. This resulted in 1-[3-(2-methoxyethoxy)pyridin-2-yl]methanamine (200 mg, 65.2%) as a purple oil. The crude product was used in the next step directly without further purification. LCMS: m/z (ESI), [M+H]$^+$=183.1.

Step 3. 3-amino-5-(4-fluorophenyl)-N-[[3-(2-methoxyethoxy)pyridin-2-yl]methyl]-6-(1-methyl-1H-1,3-benzodiazol-6-yl)pyrazine-2-carboxamide (Cmpd. 114)

To a solution of 1-[3-(2-methoxyethoxy)pyridin-2-yl]methanamine (180 mg, 1 mmol, 1 equiv) and 3-amino-5-(4-fluorophenyl)-6-(1-methyl-1H-1,3-benzodiazol-6-yl)pyrazine-2-carboxylic acid (251.2 mg, 0.7 mmol, 0.7 equiv) in DMF (15 mL) was added T$_3$P (628.6 mg, 2 mmol, 2 equiv) and DIEA (255.3 mg, 2 mmol, 2 equiv) in portions at room temperature. The resulting mixture was stirred for 1 h at room temperature under air atmosphere. The resulting mixture was concentrated under reduced pressure. The crude product (60 mg) was purified by Prep-HPLC with the following conditions (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 35% B to 45% B in 7 min; 254/220 nm; Rt: 6.83 min) to afford 3-amino-5-(4-fluorophenyl)-N-[[3-(2-methoxyethoxy)pyridin-2-yl]methyl]-6-(1-methyl-1H-1,3-benzodiazol-6-yl)pyrazine-2-carbox-amide (Cmpd. 114) (48.1 mg, 9.2%) as a yellow solid. LCMS: m/z (ESI), [M+H]$^+$=528.3. $^1$H NMR (300 MHz, DMSO-d$_6$) δ 3.29 (3H, s), 3.69 (2H, dd), 3.78 (3H, s), 4.20 (2H, dd), 4.62 (2H, d), 7.10 (1H, d), 7.15 (2H, t), 7.28 (1H, dd), 7.44 (4H, m), 7.69 (2H, m), 8.08 (1H, dd), 8.19 (1H, s), 9.18 (1H, t).

Example 115. Preparation of 3-amino-5-(4-fluorophenyl)-6-(1-methyl-1H-1,3-benzodiazol-6-yl)-N-([3-[2-(methylamino)ethoxy]pyridin-2-yl]methyl)pyrazine-2-carboxamide (Cmpd. 115)

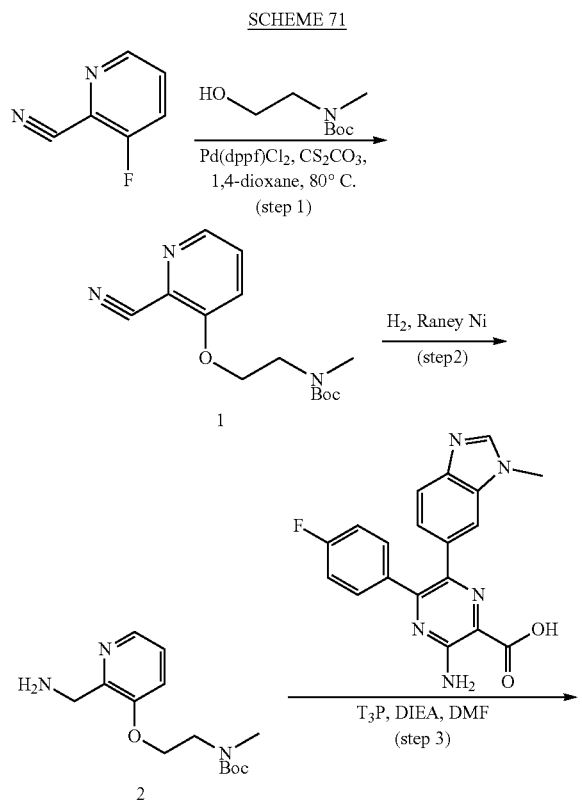

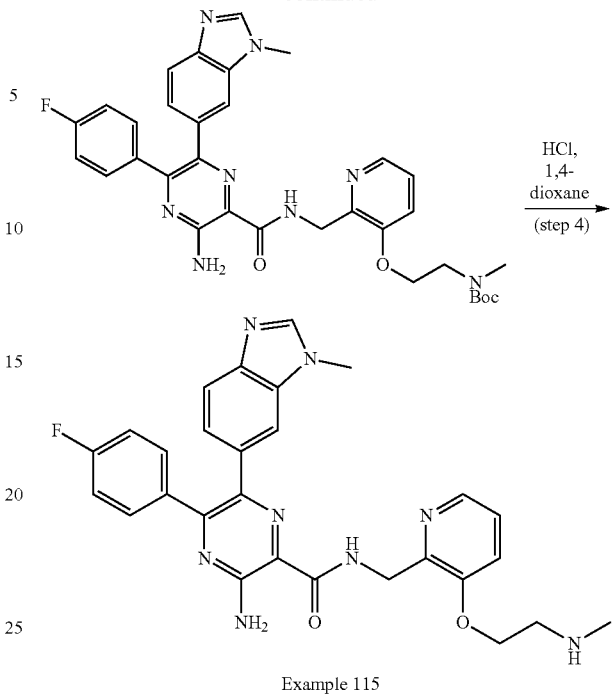

Example 115

Step 1. tert-butyl N-[2-[(2-cyanopyridin-3-yl)oxy]ethyl]-N-methylcarbamate

To a mixture of 3-fluoropyridine-2-carbonitrile (1.5 g, 12.2 mmol, 1 equiv) and tert-but-yl N-(2-hydroxyethyl)-N-methylcarbamate (4.3 g, 24.5 mmol, 2 equiv) in 1,4-dioxane (25 mL) was added Cs$_2$CO$_3$ (8.01 g, 24.5 mmol, 2 equiv) in portions at room temperature. The resulting mixture was stirred for 4h at 80° C. under air atmosphere. The resulting mixture was concentrated under reduced pressure. The residue was purified by silica gel column chromatography, eluted with PE/EtOAc (10:1) to afford tert-butyl N-[2-[(2-cyanopyridin-3-yl)oxy]ethyl]-N-methylcarbamate (1.8 g, 52.8%) as a yellow solid. LCMS: m/z (ESI), [M+H]$^+$=278.0. $^1$H-NMR (300 MHz, DMSO-d$_6$) δ 1.36 (9H, s), 2.90 (3H, d), 3.57 (2H, t), 4.33 (2H, q), 7.69 (1H, dd), 7.82 (1H, d), 8.29 (1H, dd).

Step 2. tert-butyl N-(2-[[2-(aminomethyl)pyridin-3-yl]oxy]ethyl)-N-methylcarbamate To a solution of tert-butyl N-[2-[(2-cyanopyridin-3-yl)oxy]ethyl]-N-methylcarbamate (300 mg, 1.08 mmol, 1 equiv) in MeOH (5 mL) and NH$_3$H$_2$O (1 mL) was added Raney Ni (185.3 mg, 2.1 mmol, 2 equiv) at room temperature. The resulting mixture was stirred for 2h at room temperature under hydrogen atmosphere. The resulting mixture was filtered, the filter cake was washed with MeOH (3×10 mL). The filtrate was concentrated under reduced pressure. This resulted in tert-butyl N-(2-[[2-(aminomethyl)pyridin-3-yl]oxy]ethyl)-N-methylcarbamate (200 mg, 65.7%) as a purple oil. The crude product was used in the next step directly without further purification. LCMS: m/z (ESI), [M+H]$^+$=282.3.

Step 3. N-(2-[[2-([[3-amino-5-(4-fluorophenyl)-6-(1-methyl-1H-1,3-benzodiazol-6-yl) pyrazin-2-yl]formamido]methyl)pyridin-3-yl]oxy]ethyl)-N-methylcarbamate To a solution of tert-butyl N-(2-[[2-(aminomethyl)pyridin-3-yl]oxy]ethyl)-N-methylcarbamate 200 mg, 0.7 mmol, 1 equiv) and 3-amino-5-(4-fluorophenyl)-6-(1-methyl-1H-1,3-benzodiazol-6-yl)pyrazine-2-carboxylic acid (180.8 mg, 0.5 mmol, 0.7 equiv) in DMF (15 mL) was added T₃P (452.3 mg, 1.4 mmol, 2 equiv) and DIEA (183.7 mg, 1.4 mmol, 2.0 equiv) in portions at room temperature. The resulting mixture was stirred for 1 h at room temperature under air atmosphere. The resulting mixture was concentrated under reduced pressure. The residue was purified by Prep-TLC (CH₂Cl₂/MeOH 20:1) to afford tert-butyl N-(2-[[2-([[3-amino-5-(4-fluorophenyl)-6-(1-methyl-1H-1,3-benzodiazol-6-yl)pyrazin-2-yl]formamido]methyl)pyridin-3-yl]oxy]ethyl)-N-methylcarbamate (150 mg, 33.6%) as a yellow solid. LCMS: m/z (ESI), [M+H]⁺=627.4.

Step 4. 3-amino-5-(4-fluorophenyl)-6-(1-methyl-1H-1,3-benzodiazol-6-yl)-N-([3-[2-(methylamino)ethoxy]pyridin-2-yl]methyl)pyrazine-2-carboxamide (Cmpd. 115)

To a solution 4N.HCl (gas) in 1,4-dioxane (10 mL) was added tert-butyl N-(2-[[2-([[3-amino-5-(4-fluorophenyl)-6-(1-methyl-1H-1,3-benzodiazol-6-yl)pyrazin-2-yl]formamido]methyl)pyridin-3-yl]oxy]ethyl)-N-methylcarbamate (150 mg, 0.2 mmol, 1 equiv) in portions at room temperature. The resulting mixture was stirred for 1 h at room temperatu-re under air atmosphere. The crude product (100 mg) was purified by Prep-HPLC with the following conditions (Column: XBridge Prep OBD C18 Column 30×150 mm 5 um; Mobile Phase A: Water (0.05% NH₃H₂O), Mobile Phase B: ACN; Flow rate: 60 mL/min; Gradient: 33% B to 43% B in 7 min; 254/220 nm; Rt: 5.8 min) to afford 3-amino-5-(4-fluorophenyl)-6-(1-methyl-1H-1,3-benzodiazol-6-yl)-N-([3-[2-(methylamino)ethoxy]pyridin-2-yl]methyl)pyrazine-2-carboxamide (Cmpd. 115) (51 mg, 40.5%) as a yellow solid. LCMS: m/z (ESI), [M+H]⁺=527.3. ¹H NMR (300 MHz, DMSO-d₆) δ 2.31 (3H, s), 2.85 (2H, t), 3.79 (3H, s), 4.11 (2H, t), 4.66 (2H, d), 7.09 (3H, m), 7.28 (1H, dd), 7.44 (5H, m), 7.69 (2H, d), 8.08 (1H, dd), 8.20 (1H, s), 9.18 (1H, t).

Example 116. Preparation of 3-amino-N-([3-[2-(dimethylamino)ethoxy]pyridin-2-yl]methyl)-5-(4-fluorophenyl)-6-(1-methyl-1H-1,3-benzodiazol-6-yl)pyrazine-2-carboxamide (Cmpd. 116)

SCHEME 72

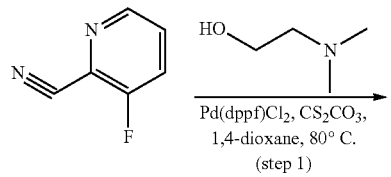

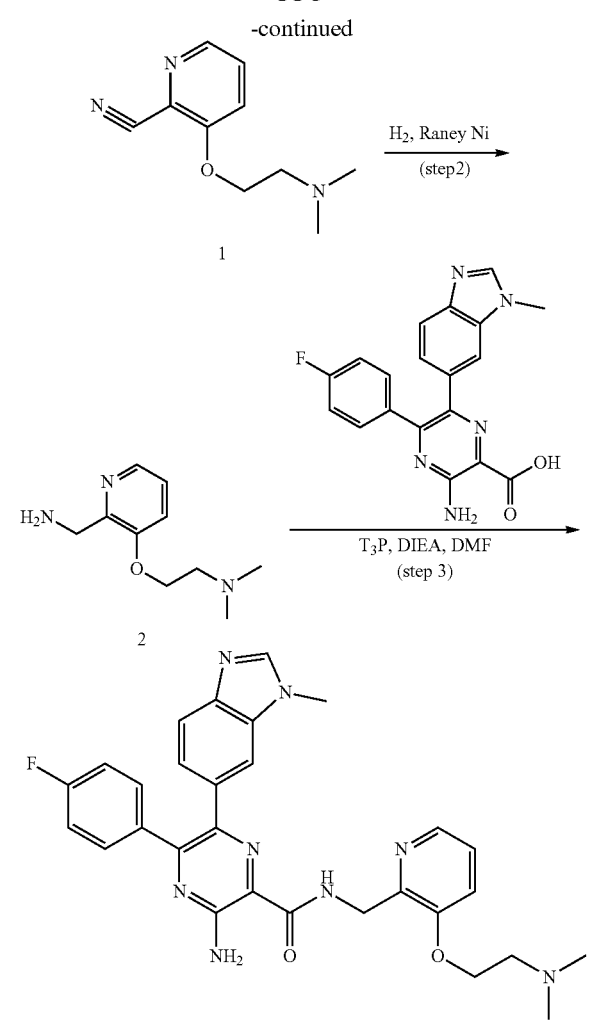

Example 116

Step 1. 3-[2-(dimethylamino)ethoxy]pyridine-2-carbonitrile

To a mixture of 3-fluoropyridine-2-carbonitrile (1 g, 8.1 mmol, 1 equiv) and 2-(dimethylamino)ethan-1-ol (1.4 g, 0.02 mmol, 2.0 equiv) in 1,4-dioxane (25 mL) was added Cs₂CO₃ (5.3 g, 0.02 mmol, 2 equiv) at room temperature. The resulting mixture was stirred for 4h at 80° C. under air atmosphere. The resulting mixture was concentrated under reduced pressure. The residue was purified by silica gel column chromatography, eluted with PE/EtOAc (2:3) to afford 3-[2-(dimethylamino)ethoxy]pyridine-2-carbonitrile (1.2 g, 76.6%) as a yellow oil. LCMS: m/z (ESI), [M+H]⁺= 192.1. ¹H-NMR (300 MHz, DMSO-d₆) δ 2.21 (6H, s), 2.66 (2H, t), 4.26 (2H, t), 7.68 (1H, ddd), 7.79 (1H, dt), 8.27 (1H, dt).

Step 2. 1-[3-[2-(dimethylamino)ethoxy]pyridin-2-yl]methanamine

To a solution of 3-[2-(dimethylamino)ethoxy]pyridine-2-carbonitrile (300 mg, 1.5 mmol, 1 equiv) in MeOH (5 mL) and NH₃H₂O (1 mL) was added Raney Ni (403.2 mg, 4.7 mmol, 3 equiv) at room temperature. The resulting mixture was stirred for 2 hs at room temperature under hydrogen atmosphere. The resulting mixture was filtered, the filter cake was washed with MeOH (3×10 mL). The filtrate was concentrated under reduced pressure. This resulted in 1-[3-[2-(dimethylamino)ethoxy]pyridin-2-yl]methanamine (200 mg, 65.3%) as a purple oil. The crude product was used in the next step directly without further purification. LCMS: m/z (ESI), [M+H]⁺=196.1.

Step 3. 3-amino-N-([3-[2-(dimethylamino)ethoxy]pyridin-2-yl]methyl)-5-(4-fluorophenyl)-6-(1-methyl-1H-1,3-benzodiazol-6-yl)pyrazine-2-carboxamide (Cmpd. 116)

To a solution of 1-[3-[2-(dimethylamino)ethoxy]pyridin-2-yl]methanamine (200 mg, 1.02 mmol, 1 equiv) and 3-amino-5-(4-fluorophenyl)-6-(1-methyl-1H-1,3-benzodiazol-6-yl)pyrazine-2-carboxylic acid (260.5 mg, 0.7 mmol, 0.7 equiv) in DMF (15 mL) was added $T_3P$ (651.8 mg, 2.04 mmol, 2 equiv) and DIEA (264.7 mg, 2.04 mmol, 2 equiv) in portions at room temperature.

The resulting mixture was stirred for 1 h at room temperature under air atmosphere. The resulting mixture was concentrated under reduced pressure. The crude product was purified by Prep-HPLC with the following conditions (Column: XBridge Prep OBD C18 Column 30×150 mm 5 um; Mobile Phase A: Water (0.05% $NH_3H_2O$), Mobile Phase B: ACN; Flow rate: 60 mL/min; Gradient: 33% B to 43% B in 7 min; 254/220 nm; Rt: 7.08 min) to afford 3-amino-N-([3-[2-(dimethylamino)ethoxy]pyridin-2-yl]methyl)-5-(4-fluorophenyl)-6-(1-methyl-1H-1,3-benzodiazol-6-yl)pyrazine-2-carboxamide (Cmpd. 116) (46.5 mg, 8.40%) as a yellow solid. LCMS: m/z (ESI), [M+H]⁺=541.4. ¹H NMR (300 MHz, DMSO-d₆) δ 2.20 (6H, s), 2.66 (2H, t), 3.79 (3H, s), 4.15 (2H, t), 4.63 (2H, d), 7.10 (3H, m), 7.29 (1H, dd), 7.46 (4H, m), 7.58 (2H, s), 7.69 (1H, d), 8.08 (1H, dd), 8.20 (1H, s), 9.18 (1H, t).

Example 117. Preparation of 3-amino-5-(4-fluorophenyl)-N-([3-[(2-hydroxyethyl) amino]pyridin-2-yl]methyl)-6-(1-methyl-1H-1,3-benzodiazol-6-yl)pyrazine-2-carboxamide (Cmpd. 117)

SCHEME 73

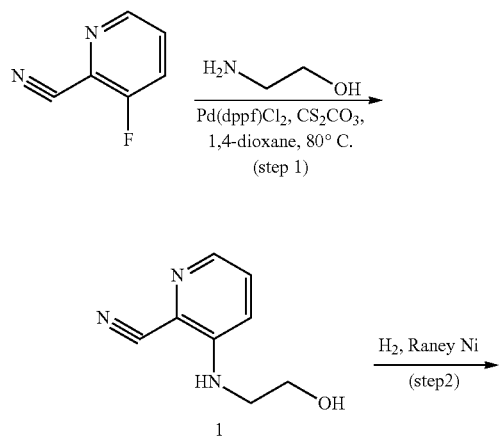

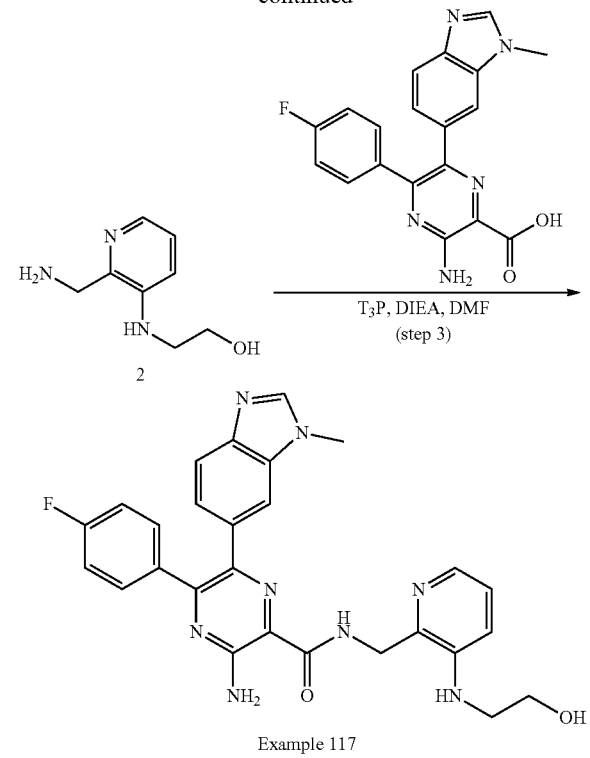

Example 117

Step 1. 3-[(2-hydroxyethyl)amino]pyridine-2-carbonitrile

To a mixture of 3-fluoropyridine-2-carbonitrile (1.5 g, 12.3 mmol, 1 equiv) and 2-aminoethan-1-ol (1.5 g, 24.5 mmol, 2 equiv) in DMSO (25 mL) was added $Cs_2CO_3$ (8.01 g, 24.5 mmol, 2 equiv) in portions at room temperature. The resulting mixture was stirred for 4h at 80° C. under air atmosphere. The resulting mixture was concentrated under reduced pressure. The residue was purified by silica gel column chromatography, eluted with PE/EtOAc (1:1) to afford 3-[(2-hydroxyethyl)amino]pyridine-2-carbonitrile (1 g, 49.8%) as a yellow oil. LCMS: m/z (ESI), [M+H]⁺=164.2. ¹H-NMR (300 MHz, DMSO-d₆) δ 3.25 (2H, q), 3.54 (2H, t), 4.83 (1H, s), 6.18 (1H, t), 7.29 (1H, dd), 7.39 (1H, ddd), 7.86 (1H, dd).

Step 2. 2-[[2-(aminomethyl)pyridin-3-yl]amino]ethan-1-ol

To a solution of 3-[(2-hydroxyethyl)amino]pyridine-2-carbonitrile (300 mg, 1.8 mmol, 1 equiv) in MeOH (5 mL) and $NH_3H_2O$ (1 mL) was added Raney Ni (472.5 mg, 5.5 mmol, 3 equiv) at room temperature. The resulting mixture was stirred for 2 h at room temperature under hydrogen atmosphere. The resulting mixture was filtered, the filter cake was washed with MeOH (3×10 mL). The filtrate was concentrated under reduced pressure. This resulted in 2-[[2-(aminomethyl)pyridin-3-yl]amino]ethan-1-ol (230 mg, 74.8%) as a purple oil. The crude product was used in the next step directly without further purification. LCMS: m/z (ESI), [M+H]⁺=168.1.

Step 3. 3-amino-5-(4-fluorophenyl)-N-([3-[(2-hy-droxyethyl)amino]pyridin-2-yl]methyl)-6-(1-methyl-1H-1,3-benzodiazol-6-yl)pyrazine-2-carboxamide (Cmpd. 117)

To a solution of 2-[[2-(aminomethyl)pyridin-3-yl]amino]ethan-1-ol (200 mg, 1.2 mmol, 1 equiv) and 3-amino-5-(4-fluorophenyl)-6-(1-methyl-1H-1,3-benzodiazol-6-yl)pyrazine-2-carboxylic acid (304.2 mg, 0.8 mmol, 0.7 equiv) in DMF (15 mL) was added T$_3$P (761.1 mg, 2.3 mmol, 2 equiv) and DIEA (309.1 mg, 2.4 mmol, 2 equiv) in portions. The resulting mixture was stirred for 1 h at room temperature under air atmosphere. The resulting mixture was concentrated under reduced pressure. The reaction mixture (60 mg) was purified by Prep-HPLC with the following conditions (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 35% B to 36% B in 7 min; 254/220 nm; Rt: 5.57 min) to afford 3-amino-5-(4-fluorophenyl)-N-([3-[(2-hydroxyethyl)amino]pyridin-2-yl]methyl)-6-(1-methyl-1H-1,3-benzodiazol-6-yl)pyrazine-2-carboxamide (Cmpd. 117) (33.3 mg, 5.4%) as a yellow solid. LCMS: m/z (ESI), [M+H]$^+$=513.4. $^1$H NMR (300 MHz, DMSO-d$_6$) δ 3.17 (2H, d), 3.60 (2H, q), 3.78 (3H, s), 4.50 (2H, d), 4.78 (1H, t), 5.47 (1H, t), 6.98 (1H, d), 7.09 (4H, m), 7.44 (3H, m), 7.74 (4H, m), 8.19 (1H, s), 9.40 (1H, t).

Example 118. Preparation of 3-amino-N-((4-(dimethylamino)pyridin-3-yl)methyl)-6-(3-methylimidazo[1,2-a]pyridin-6-yl)-5-(oxazol-2-yl)pyrazine-2-carboxamide (Cmpd. 118)

SCHEME 74

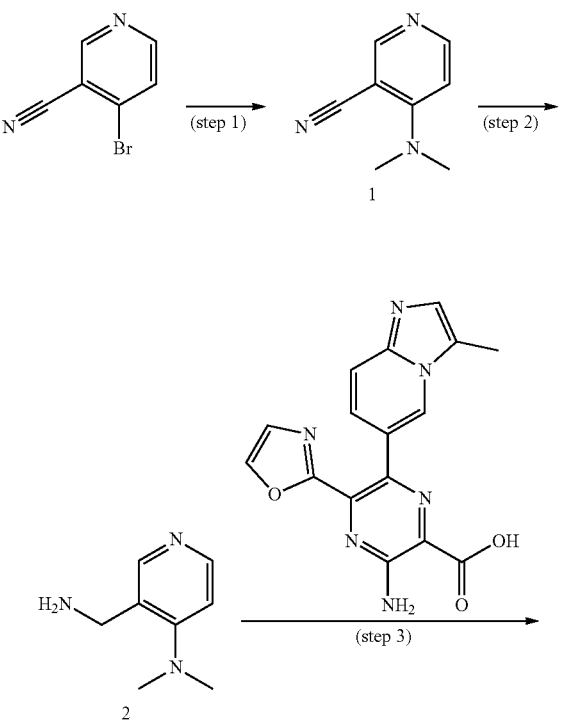

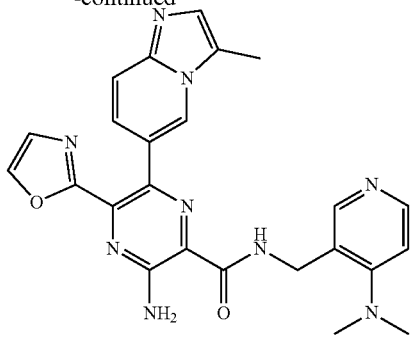

Example 118

Step 1. 4-(dimethylamino)nicotinonitrile

Into a 20 mL vial were added dimethylamine (295.63 mg, 6.557 mmol, 2.00 equiv), 4-bromopyridine-3-carbonitrile (600 mg, 3.279 mmol, 1 equiv) and K$_2$CO$_3$ (1.36 g, 9.836 mmol, 3.00 equiv) at room temperature. The resulting mixture was stirred for 2 h at 40° C.

The resulting mixture was filtered, the filter cake was washed with DCM (2×20 mL). The filtrate was concentrated under reduced pressure. The residue was purified by Prep-TLC (EtOAc) to afford 4-(dimethylamino)pyridine-3-carbonitrile (470 mg, 97.40%) as an off-white solid (crude). 1H-NMR (400 MHz, CDCl$_3$) δ 3.26 (6H, s), 6.55 (1H, d), 8.23 (1H, d), 8.47 (1H, s)

Step 2. 3-(aminomethyl)-N,N-dimethylpyridin-4-amine

A solution of 4-(dimethylamino)pyridine-3-carbonitrile (470 mg, 3.193 mmol, 1 equiv) and raney nickel (957.56 mg, 11.177 mmol, 3.50 equiv), NH$_3$H2O (1.12 g, 31.958 mmol, 10.01 equiv) in MeOH was stirred for 7 h at room temperature under hydrogen atmosphere. The resulting mixture was filtered, the filtrate cake was washed with DCM (2×10 mL). The filtrate was concentrated under reduced pressure. This resulted in 3-(aminomethyl)-N,N-dimethylpyridin-4-amine (467 mg, 96.71%) as a green oil. LCMS: m/z (ESI), [M+H]$^+$= 152.3. $^1$H-NMR (300 MHz, MeOD-d$_4$) δ 2.75-3.05 (6H, m), 3.93 (2H, s), 6.95 (1H, s), 7.90-8.51 (2H, m).

Step 3. 3-amino-N-((4-(dimethylamino)pyridin-3-yl)methyl)-6-(3-methylimidazo[1,2-a]pyridin-6-yl)-5-(oxazol-2-yl)pyrazine-2-carboxamide (Cmpd. 118)

To a stirred solution of 3-amino-6-[3-methylimidazo[1,2-a]pyridin-6-yl]-5-(1,3-oxazol-2-yl)pyrazine-2-carboxylic acid (70 mg, 0.208 mmol, 1 equiv) and DIEA (80.70 mg, 0.624 mmol, 3.00 equiv), T$_3$P (132.45 mg, 0.416 mmol, 2.00 equiv) in DMF was added 3-(aminomethyl)-N,N-dimethylpyridin-4-amine (62.95 mg, 0.416 mmol, 2.00 equiv) dropwise at room temperature. The resulting mixture was stirred for 1 h at room temperature. The residue was purified by Prep-TLC (CH$_2$Cl$_2$/MeOH 20:1) to afford a yellow solid. The crude product (90 mg) was purified by Prep-HPLC with the following conditions (Column: XBridge Prep OBD C18 Column 30×150 mm 5 um; Mobile Phase A: Water (10 MMOL/L NH$_4$HCO$_3$), Mobile Phase B: ACN; Flow rate: 60 mL/min; Gradient: 15% B to 50% B in 7 min; 254/220 nm; Rt: 5.82 min) to afford 3-amino-N-[[4-(dimethylamino)pyridin-3-yl]methyl]-6-[3-methylimidazo[1,2-a]pyridin-6-yl]-

5-(1,3-oxazol-2-yl)pyrazine-2-carboxamide (Cmpd. 118) (45 mg, 46.05%) as a yellow solid. LCMS: m/z (ESI), [M+H]$^+$=470.3. $^1$H-NMR (400 MHz, DMSO-d$_6$) δ 2.42 (3H, d), 2.80 (6H, s), 4.57 (2H, d), 6.89 (1H, d), 7.26 (1H, dd), 7.38 (2H, dd), 7.48 (1H, dd), 7.89 (2H, s), 8.19-8.30 (3H, m), 8.34 (1H, dd), 9.39 (1H, t).

Example 119. Preparation of 3-amino-N-[[3-(carbamoylmethoxy)pyridin-2-yl]methyl]-5-(4-fluorophenyl)-6-(1-methyl-1H-1,3-benzodiazol-6-yl)pyrazine-2-carboxamide (Cmpd. 119)

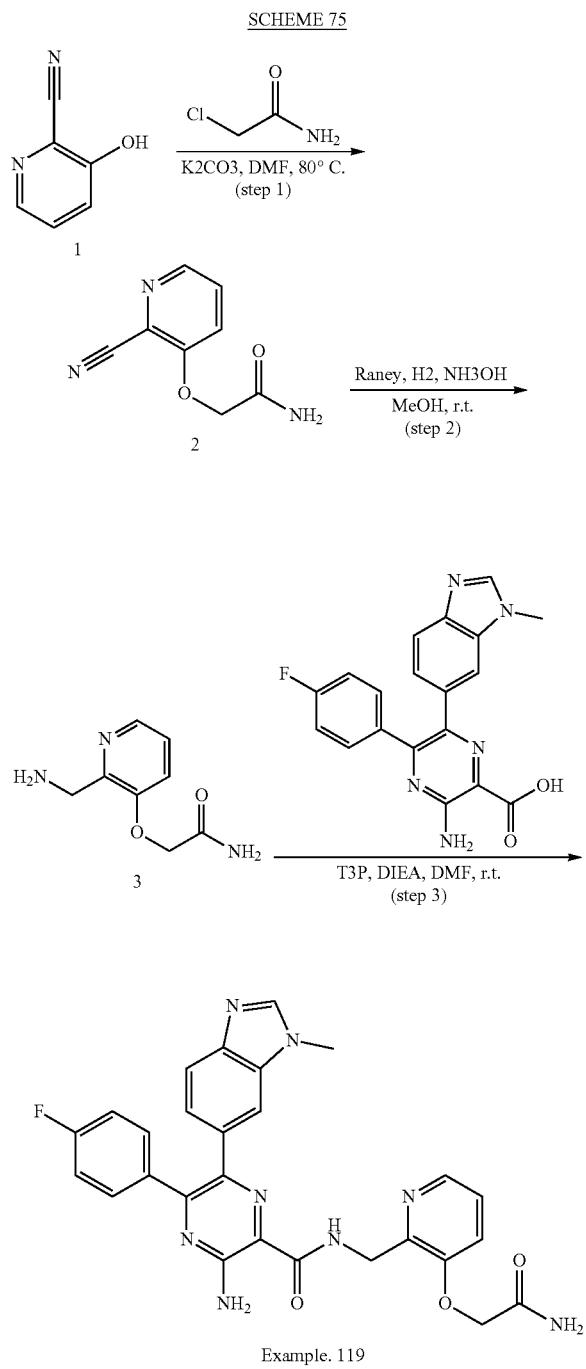

Step 1. 2-[(2-cyanopyridin-3-yl)oxy]acetamide

A mixture of K$_2$CO$_3$ (448.75 mg, 3.247 mmol, 3 equiv), 2-chloroacetamide (121.45 mg, 1.299 mmol, 1.2 equiv) and 3-hydroxypyridine-2-carbonitrile (130 mg, 1.082 mmol, 1 equiv) in DMF (6 mL) was stirred for 16 hours at 80° C. under air atmosphere. The resulting mixture was diluted with water (30 mL) and extracted with EtOAc (3×20 mL). The combined organic layers were washed with brine (3×30 mL), dried over anhydrous Na$_2$SO$_4$. After filtration, the filtrate was concentrated under reduced pressure. The residue was purified by Prep-TLC (CH$_2$Cl$_2$/MeOH 12:1) to afford 2-[(2-cyanopyridin-3-yl)oxy]acetamide (100 mg, 52.15%) as a white solid. LCMS: m/z (ESI), [M+H]$^+$=178.0. $^1$H-NMR (300 MHz, CDCl$_3$) δ: 4.78 (2H, s), 7.47 (1H, d), 7.61 (2H, d), 7.70 (1H, d), 8.32 (1H, d)

Step 2. 2-[[2-(aminomethyl)pyridin-3-yl]oxy]acetamide

A mixture of raney nickel (26.98 mg, 0.315 mmol, 0.62 equiv) and 2-[(2-cyanopyridin-3-yl)oxy]acetamide (90 mg, 0.508 mmol, 1 equiv) in MeOH (5 mL) was stirred for 1 h at room temperature under hydrogen atmosphere. The precipitated solids were collected by filtration and washed with MeOH (3×10 mL). The resulting mixture was concentrated under reduced pressure to afford 2-[[2-(aminomethyl)pyridin-3-yl]oxy]acetamide (60 mg, 65.18%) as a purple solid. LCMS: m/z (ESI), [M+H]$^+$=182.1

Step 3. 3-amino-N-[[3-(carbamoylmethoxy)pyridin-2-yl]methyl]-5-(4-fluorophenyl)-6-(1-methyl-1H-1,3-benzodiazol-6-yl)pyrazine-2-carboxamide (Cmpd. 119)

A mixture of T$_3$P (100 mg, 1.344 mmol, 4 equiv), DIEA (470.5 mg, 1.344 mmol, 4.00 equiv), 3-amino-5-(4-fluorophenyl)-6-(1-methyl-1H-1,3-benzodiazol-6-yl)pyrazine-2-carboxylic acid (120 mg, 0.336 mmol, 1.00 equiv) and 2-[[2-(aminomethyl)pyridin-3-yl]oxy]acetamide (59.8 mg, 0.336 mmol, 1 equiv) in DMF (0.2 mL) was stirred for 4 hours at room temperature under air atmosphere. The crude product (70 mg) was purified by Prep-HPLC with the following conditions (Column: XBridge Prep OBD C18 Column 19*250 mm, 5 um; Mobile Phase A: Water (0.05% NH$_3$H$_2$O), Mobile Phase B: ACN; Flow rate: 20 mL/min; Gradient: 31% B to 45% B in 8 min; 254/220 nm; Rt: 7.30 min) to afford 3-amino-N-[[3-(carbamoylmethoxy)pyridin-2-yl]methyl]-5-(4-fluorophenyl)-6-(1-methyl-1H-1,3-benzodiazol-6-yl)pyrazine-2-carboxamide (Cmpd. 119) (20 mg, 12.14%) as a yellow solid. LCMS: m/z (ESI), [M+H]$^+$=527.3. $^1$H-NMR (300 MHz, DMSO-d$_6$) δ 3.80 (3H, s), 4.61 (2H, s), 4.75 (2H, d), 7.08 (1H, d), 7.15 (2H, t), 7.27-7.38 (2H, m), 7.43 (2H, d), 7.50 (2H, d), 7.64 (2H, s), 7.72 (1H, s), 8.13 (1H, d), 8.21 (1H, s), 9.23 (1H, d). $^{19}$F NMR (282 MHz, DMSO-d$_6$) δ: −112.591

345

Examples 120/121. Preparation of (R/S)-3-amino-6-(3-methylimidazo[1,2-a]pyridin-6-yl)-N-((1-methylpyrrolidin-2-yl)methyl)-5-(oxazol-2-yl)pyrazine-2-carboxamide (Cmpd. 120/121)

SCHEME 76

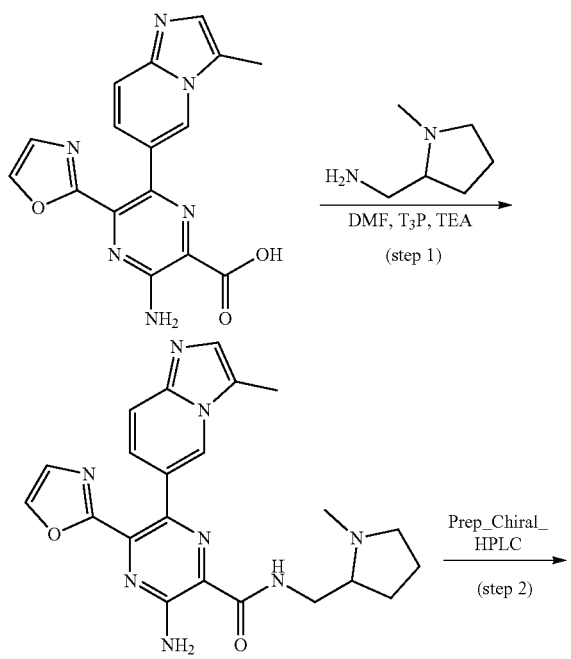

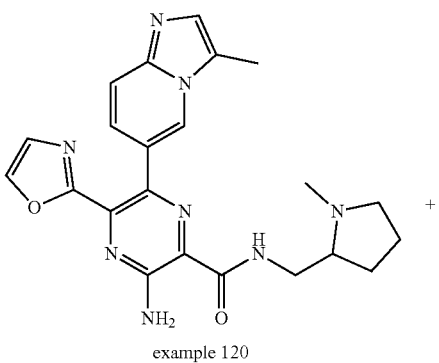

example 120

+

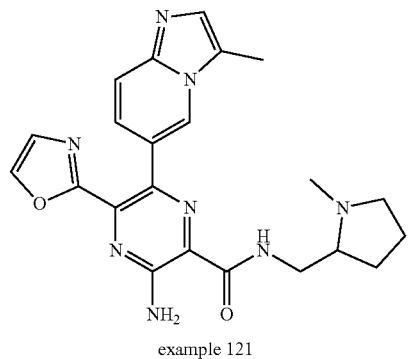

example 121

346

Step 1. 3-amino-6-(3-methylimidazo[1,2-a]pyridin-6-yl)-N-((1-methylpyrrolidin-2-yl) methyl)-5-(oxazol-2-yl)pyrazine-2-carboxamide To a stirred solution of 3-amino-6-[3-methylimidazo[1,2-a]pyridin-6-yl]-5-(1,3-oxazol-2-yl)pyrazine-2-carboxylic acid (300 mg, 0.892 mmol, 1 equiv) Et$_3$N (270.79 mg, 2.676 mmol, 3.00 equiv) and T$_3$P (851.48 mg, 2.676 mmol, 3.00 equiv) in DMF was added 1-(1-methylpyrrolidin-2-yl)methanamine (203.73 mg, 1.784 mmol, 2.00 equiv) dropwise at room temperature. The resulting mixture was stirred for overnight at room temperature. The residue was purified by Prep-TLC (CH$_2$Cl$_2$/MeOH 20:1) to afford a yellow solid. The crude product (260 mg) was purified by Prep-HPLC with the following conditions (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 23% B to 38% B in 7 min; 254/220 nm; Rt: 6.33 min) to afford 3-amino-6-[3-methylimidazo[1,2-a]pyridin-6-yl]-N-[(1-methylpyrrolidin-2-yl)methyl]-5-(1,3-oxazol-2-yl)pyrazine-2-carboxamide (120 mg, 31.10%) as a yellow solid. LCMS: m/z (ESI), [M+H]$^+$=433.3. 1H-NMR (400 MHz, DMSO-d$_6$) δ 1.55-1.67 (3H, m), 1.78-1.88 (1H, m), 2.14 (1H, q), 2.31 (3H, s), 2.42 (4H, d), 2.94 (1H, dd), 3.20-3.29 (1H, m), 3.48 (1H, ddd), 7.19 (1H, dd), 7.36 (1H, d), 7.40 (1H, d), 7.49 (1H, dd), 7.90 (2H, s), 8.27 (1H, d), 8.31-8.36 (1H, m), 8.66 (1H, t).

Step 2. (R/S)-3-amino-6-(3-methylimidazo[1,2-a] pyridin-6-yl)-N-((1-methylpyrrolidin-2-yl)methyl)-5-(oxazol-2-yl)pyrazine-2-carboxamide (Cmpd. 120/121)

The crude product was purified by Prep-HPLC with the following conditions (Column: CHIRALPAK IG, 20*250 mm, 5 um; Mobile Phase A:Hex:DCM=3:1 (10 mM NH$_3$-MEOH)-HPLC, Mobile Phase B: EtOH-HPLC; Flow rate: 18 mL/min; Gradient: 50 B to 50 B in 25 min; 220/254 nm; RT1:13.303; RT2:19.802) to afford 3-amino-6-[3-methylimidazo[1,2-a]pyridin-6-yl]-N-[[(2R)-1-methylpyrrolidin-2-yl]methyl]-5-(1,3-oxazol-2-yl)pyrazine-2-carboxamide (isomer 1) (Cmpd. 120) (42 mg, 42.00%), LCMS: m/z (ESI), [M+H]$^+$=433.2. 1H-NMR (400 MHz, DMSO-d$_6$) δ1.60 (3H, dp), 1.76-1.89 (1H, m), 2.15 (1H, q), 2.30 (3H, s), 2.42 (4H, d), 2.93 (1H, dd), 3.24 (1H, dd), 3.48 (1H, dd), 7.19 (1H, dd), 7.35 (1H, d), 7.40 (1H, d), 7.48 (1H, dd), 8.24 (1H, d), 8.35 (1H, dd). 3-amino-6-[3-methylimidazo[1,2-a]pyridin-6-yl]-N-[[(2R)-1-methylpyrrolidin-2-yl]methyl]-5-(1,3-oxazol-2-yl)pyrazine-2-carboxamide (isomer 2) (Cmpd. 121) (40 mg, 40%) as a yellow solid. LCMS: m/z (ESI), [M+H]$^+$=433.2. $^1$H-NMR (400 MHz, DMSO-d$_6$) δ1.59 (3H, ddt), 1.77-1.90 (1H, m), 2.14 (1H, q), 2.29 (3H, s), 2.42 (4H, d), 2.89-2.96 (1H, m), 3.24 (1H, dd), 3.48 (1H, dd), 7.19 (1H, dd), 7.34 (1H, d), 7.40 (1H, d), 7.48 (1H, dd), 8.24 (1H, d), 8.35 (1H, dd)

Example 122. Preparation of (R)-3-amino-6-(3-methylimidazo[1,2-a]pyridin-6-yl)-5-(oxazol-2-yl)-N-(pyrrolidin-2-ylmethyl)pyrazine-2-carboxamide (Cmpd. 122)

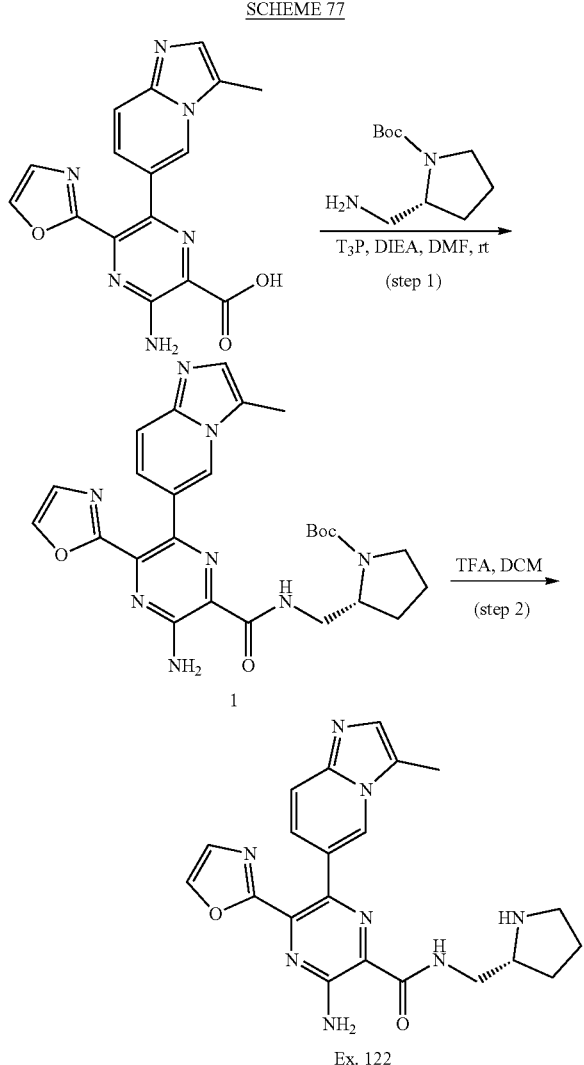

Step 1. (R)-tert-butyl 2-((3-amino-6-(3-methylimidazo[1,2-a]pyridin-6-yl)-5-(oxazol-2-yl)pyrazine-2-carboxamido)methyl)pyrrolidine-1-carboxylate To a stirred solution of 3-amino-6-[3-methylimidazo[1,2-a]pyridin-6-yl]-5-(1,3-oxazol-2-yl)pyrazine-2-carboxylic acid (140 mg, 0.416 mmol, 1 equiv) and tert-butyl (2R)-2-(aminomethyl)pyrrolidine-1-carboxylate (125.06 mg, 0.624 mmol, 1.50 equiv), DIEA (161.40 mg, 1.249 mmol, 3.00 equiv) in DMF were added $T_3P$ (264.91 mg, 0.833 mmol, 2.00 equiv) dropwise at room temperature. The resulting mixture was stirred for 1 h at room temperature. The resulting mixture was diluted with water (100 mL). The resulting mixture was extracted with $CH_2Cl_2$ (4×100 mL). The combined organic layers were dried over anhydrous $Na_2SO_4$. After filtration, the filtrate was concentrated under reduced pressure.

The residue was purified by Prep-TLC ($CH_2Cl_2$/MeOH 20:1) to afford tert-butyl (2R)-2-[[(3-amino-6-[3-methylimidazo[1,2-a]pyridin-6-yl]-5-(1,3-oxazol-2-yl)pyrazin-2-yl)formamido]methyl]pyrrolidine-1-carboxylate (156 mg, 72.26%) as a yellow solid. LCMS: m/z (ESI), $[M+H]^+$=519.2.

Step 2. (R)-3-amino-6-(3-methylimidazo[1,2-a]pyridin-6-yl)-5-(oxazol-2-yl)-N-(pyrolidin-2-ylmethyl)pyrazine-2-carboxamide (Cmpd. 122)

Into a 50 mL round-bottom flask were added tert-butyl (2R)-2-[[(3-amino-6-[3-methylimidazo[1,2-a]pyridin-6-yl]-5-(1,3-oxazol-2-yl)pyrazin-2-yl)formamido]methyl]pyrrolidine-1-carboxylate (140 mg, 0.270 mmol, 1 equiv) and TFA (2.00 mL, 17.541 mmol, 99.74 equiv) at room temperature. The resulting mixture was stirred for 1 h at room temperature. The resulting mixture was concentrated under reduced pressure. The resulting mixture was diluted with DCM (100 mL). The reaction was quenched with saturated $NaHCO_3$ at room temperature. The resulting mixture was extracted with $CH_2Cl_2$ (3×100 mL). The combined organic layers were dried over anhydrous $Na_2SO_4$. After filtration, the filtrate was concentrated under reduced pressure. The crude product (100 mg) was purified by Prep-HPLC with the following conditions (Column: XBridge Prep OBD C18 Column 30×150 mm 5 um; Mobile Phase A: Water (10 MMOL/L $NH_4HCO_3$+0.1% $NH_3H_2O$), Mobile Phase B: ACN; Flow rate: 60 mL/min; Gradient: 10% B to 30% B in 7 min; 254/220 nm; Rt: 6.82 min) to afford 3-amino-6-[3-methylimidazo[1,2-a]pyridin-6-yl]-5-(1,3-oxazol-2-yl)-N-[[(2R)-pyrrolidin-2-yl]methyl]pyrazine-2-carboxamide (Cmpd. 122) (60 mg, 53.11%) as a yellow solid. LCMS: m/z (ESI), $[M+H]^+$=419.2. $^1$H-NMR (400 MHz, DMSO-$d_6$) δ 1.32-1.44 (1H, m), 1.54-1.82 (3H, m), 2.43 (3H, d), 2.71-2.86 (2H, m), 3.23 (3H, ddt), 7.21 (1H, dd), 7.38 (2H, dd), 7.49 (1H, dd), 7.91 (2H, s), 8.27 (1H, d), 8.34 (1H, t), 8.75 (1H, t)

Example 123. Preparation of (S)-3-amino-6-(3-methylimidazo[1,2-a]pyridin-6-yl)-5-(oxazol-2-yl)-N-(pyrrolidin-2-ylmethyl)pyrazine-2-carboxamide (Cmpd. 123)

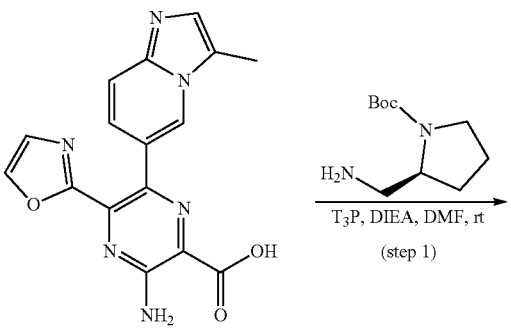

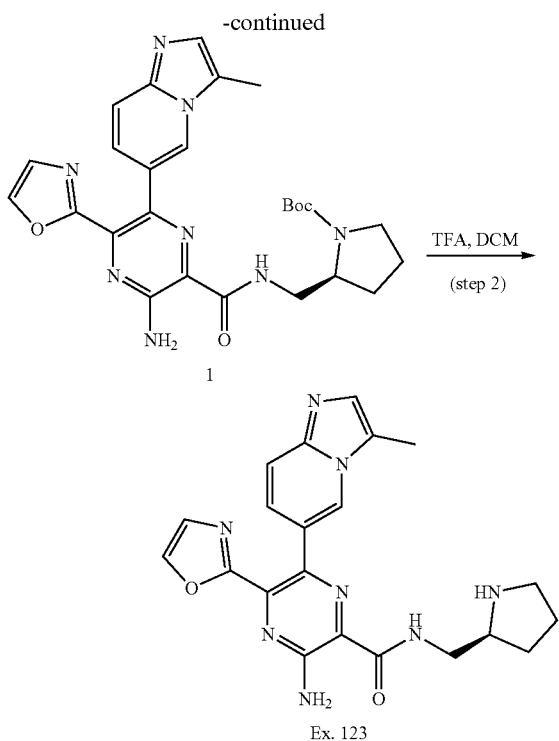

Step 1. (S)-tert-butyl 2-((3-amino-6-(3-methylimidazo[1,2-a]pyridin-6-yl)-5-(oxazol-2-yl)pyrazine-2-carboxamido)methyl)pyrrolidine-1-carboxylate Into a 8 mL vial were added 3-amino-6-[3-methylimidazo[1,2-a]pyridin-6-yl]-5-(1,3-oxazol-2-yl)pyrazine-2-carboxylic acid (140 mg, 0.416 mmol, 1 equiv) and tert-butyl (2S)-2-(aminomethyl)pyrrolidine-1-carboxylate (125.06 mg, 0.624 mmol, 1.50 equiv) and DIEA (161.40 mg, 1.249 mmol, 3.00 equiv), $T_3P$ (264.91 mg, 0.833 mmol, 2.0 equiv) at room temperature. The resulting mixture was stirred for 2 h at room temperature. The resulting mixture was diluted with water (100 mL). The resulting mixture was extracted with $CH_2Cl_2$ (4×100 mL). The combined organic layers were dried over anhydrous $Na_2SO_4$. After filtration, the filtrate was concentrated under reduced pressure. The residue was purified by Prep-TLC ($CH_2Cl_2$/MeOH 20:1) to afford tert-butyl (2S)-2-[[(3-amino-6-[3-methylimidazo[1,2-a]pyridin-6-yl]-5-(1,3-oxazol-2-yl)pyrazin-2-yl)formamido]methyl]pyrrolidine-1-carboxylate (170 mg, 78.75%) as a yellow solid. LCMS: m/z (ESI), [M+H]$^+$=519.4.

Step 2. (S)-3-amino-6-(3-methylimidazo[1,2-a]pyridin-6-yl)-5-(oxazol-2-yl)-N-(pyrrolidin-2-ylmethyl)pyrazine-2-carboxamide (Cmpd. 123)

Into a 50 mL round-bottom flask were added tert-butyl (2S)-2-[[(3-amino-6-[3-methylimidazo[1,2-a]pyridin-6-yl]-5-(1,3-oxazol-2-yl)pyrazin-2-yl)formamido]methyl]pyrrolidine-1-carboxylate (170 mg, 0.328 mmol, 1 equiv) and TFA (3 mL, 40.389 mmol, 123.21 equiv) at room temperature. The resulting mixture was stirred for 1 h at room temperature. The resulting mixture was concentrated under reduced pressure. The resulting mixture was diluted with DCM (100 mL). The reaction was quenched with saturated $NaHCO_3$ at room temperature and extracted with $CH_2Cl_2$ (3×100 mL). The combined organic layers were dried over anhydrous $Na_2SO_4$. After filtration, the filtrate was concentrated under reduced pressure. The crude product (100 mg) was purified by Prep-HPLC with the following conditions (Column: XBridge Prep OBD C18 Column 30×150 mm 5 um; Mobile Phase A: Water (0.05% $NH_3H_2O$), Mobile Phase B: ACN; Flow rate: 60 mL/min; Gradient: 17% B to 37% B in 7 min; 254/220 nm; Rt: 5.73 min) to afford 3-amino-6-[3-methylimidazo[1,2-a]pyridin-6-yl]-5-(1,3-oxazol-2-yl)-N-[[(2S)-pyrrolidin-2-yl]methyl]pyrazine-2-carboxamide (Cmpd. 123) (60 mg, Y=43.74%) as a yellow solid. LCMS: m/z (ESI), [M+H]$^+$=419.2. $^1$H-NMR (400 MHz, DMSO-d$_6$) δ 1.38 (1H, ddt), 1.51-1.81 (3H, m), 2.43 (3H, d), 2.71-2.84 (2H, m), 3.22 (3H, ddt), 7.20 (1H, dd), 7.38 (2H, dd), 7.49 (1H, dd), 7.91 (2H, s), 8.27 (1H, d), 8.34 (1H, dd), 8.74 (1H, t).

Example 128. Preparation of (R)-3-amino-6-(3-ethylpyrazolo[1,5-a]pyridin-5-yl)-N-((1-methylpyrrolidin-2-yl)methyl)-5-(oxazol-2-yl)pyrazine-2-carboxamide (Cmpd. 128)

SCHEME 79

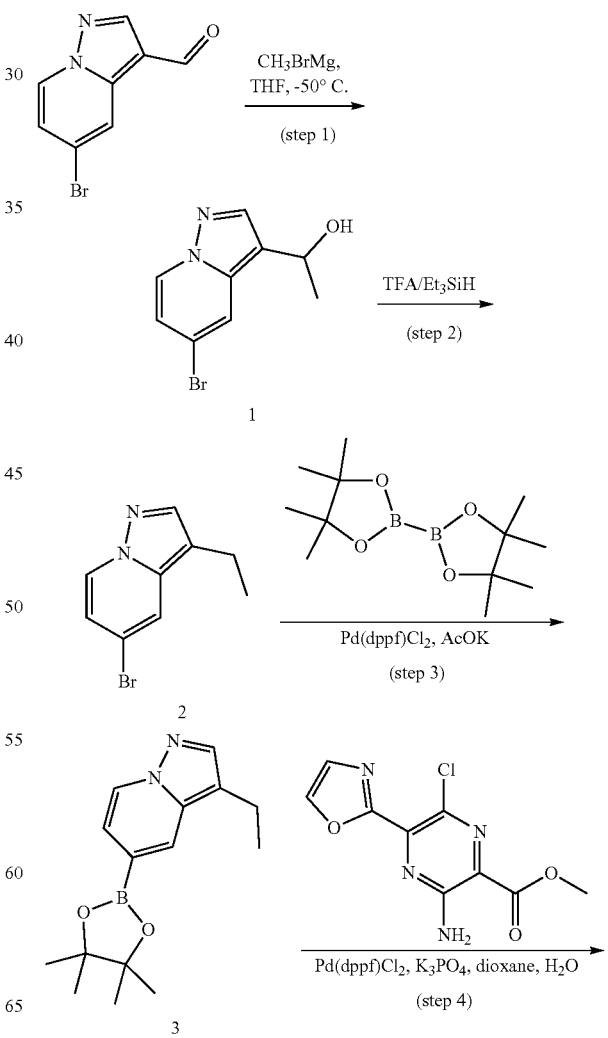

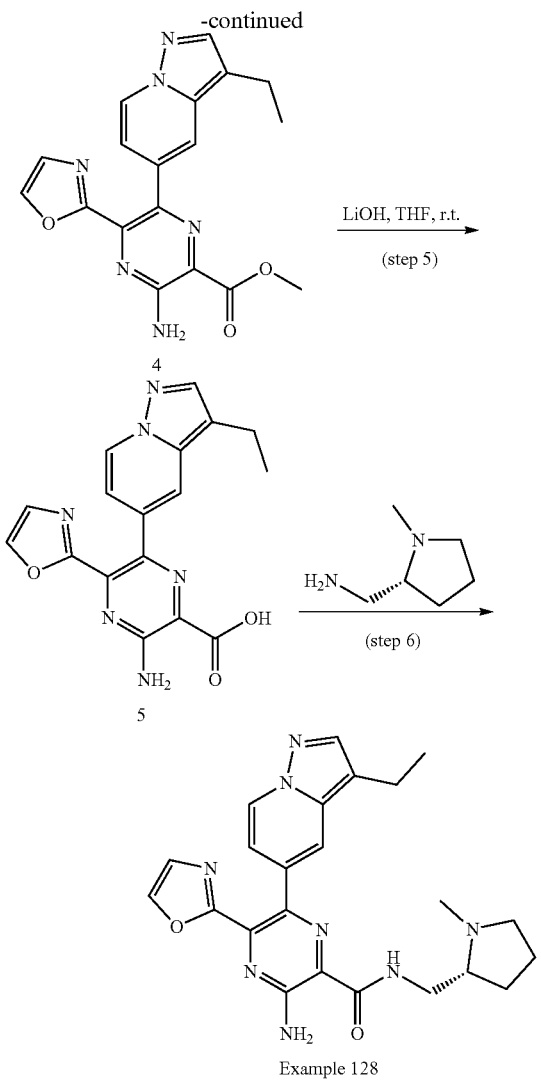

Example 128

Step 1. 1-[5-bromopyrazolo[1,5-a]pyridin-3-yl]ethan-1-ol

To a stirred solution of 5-bromopyrazolo[1,5-a]pyridine-3-carbaldehyde (1 g, 4.444 mmol, 1 equiv) and CH$_3$MgBr (2.12 g, 17.8 mmol, 4.00 equiv) in THF (20 mL) at −50° C. under nitrogen atmosphere. The reaction was quenched by the addition of sat. NH$_4$Cl (aq.) (5 mL) at 0° C. The aqueous layer was extracted with CH$_2$Cl$_2$ (3×30 mL). The residue was purified by silica gel column chromatography, eluted with PE/EtOAc (5:1) to afford 1-[5-bromopyrazolo[1,5-a]pyridin-3-yl]ethan-1-ol (600 mg, 56.01%) as a white solid. LCMS: m/z (ESI), [M+H]$^+$=241.2.

Step 2. 5-bromo-3-ethylpyrazolo[1,5-a]pyridine

To a stirred solution of 1-[5-bromopyrazolo[1,5-a]pyridin-3-yl]ethan-1-ol (640 mg, 2.65 mmol, 1 equiv) and triethylsilane (1852.03 mg, 15.93 mmol, 6.0 equiv) in TFA (10 mL) at room temperature under air atmosphere. The resulting mixture was concentrated under reduced pressure. The residue was purified by Prep-TLC (PE/EtOAc 5:1) to afford 5-bromo-3-ethylpyrazolo[1,5-a]pyridine (490 mg, 82.0%) as a white solid. LCMS: m/z (ESI), [M+H]$^+$=225.1.

Step 3. 3-ethyl-5-(4,4,5,5-tetramethyl-1,3,2-dioxaborolan-2-yl)pyrazolo[1,5-a]pyridine To a solution of 5-bromo-3-ethylpyrazolo[1,5-a]pyridine (430 mg, 1.9 mmol, 1 equiv) and 4,4,5,5-tetramethyl-2-(4,4,5,5-tetramethyl-1,3,2-dioxaborolan-2-yl)-1,3,2-dioxaborolane (970.2 mg, 3.81 mmol, 2.0 equiv) in dioxane (10 mL) were added K$_3$PO$_4$ (1216.5 mg, 5.73 mmol, 3.0 equiv) and Pd(dppf)Cl$_2$ (279.6 mg, 0.38 mmol, 0.2 equiv). After stirring for 2 h at 90° C. under a nitrogen atmosphere, the resulting mixture was concentrated under reduced pressure. The residue was purified by Prep-TLC (CH$_2$Cl$_2$/MeOH 12:1) to afford 3-ethyl-5-(4,4,5,5-tetramethyl-1,3,2-dioxaborolan-2-yl)pyrazolo[1,5-a]pyridine (420 mg, 80.78%) as a white solid. LCMS: m/z (ESI), [M+H]$^+$=273.2.

Step 4. methyl 3-amino-6-[3-ethylpyrazolo[1,5-a]pyridin-5-yl]-5-(1,3-oxazol-2-yl)pyrazine-2-carboxylate To a solution of methyl 3-amino-6-chloro-5-(1,3-oxazol-2-yl)pyrazine-2-carboxylate (400 mg, 1.571 mmol, 1 equiv) and 3-ethyl-5-(4,4,5,5-tetramethyl-1,3,2-dioxaborolan-2-yl)pyrazolo[1,5-a]pyridine (641.31 mg, 2.356 mmol, 1.50 equiv) in dioxane (10 mL) and water (1 mL) were added K$_3$PO$_4$ (1000.35 mg, 4.713 mmol, 3 equiv) and Pd(dppf)Cl$_2$ (229.89 mg, 0.314 mmol, 0.2 equiv). After stirring for 2 h at 85° C. under a nitrogen atmosphere, The residue was purified by Prep-TLC (CH$_2$Cl$_2$/MeOH 15:1) to afford methyl 3-amino-6-[3-ethylpyrazolo[1,5-a]pyridin-5-yl]-5-(1,3-oxazol-2-yl)pyrazine-2-carboxylate (300 mg, 52.4%) as a Brown yellow solid. LCMS: m/z (ESI), [M+H]$^+$=365.3.

Step 5. 3-amino-6-(3-ethylpyrazolo[1,5-a]pyridin-5-yl)-5-(oxazol-2-yl)pyrazine-2-carboxylic Acid A solution of methyl 3-amino-6-[3-ethylpyrazolo[1,5-a]pyridin-5-yl]-5-(1,3-oxazol-2-yl)pyrazine-2-carboxylate (280 mg, 0.77 mmol, 1 equiv) and LiOH (36.8 mg, 1.54 mmol, 2.0 equiv) in THF (20 mL) was stirred for 1 h at room temperature under air atmosphere. The resulting mixture was concentrated under reduced pressure. The mixture/residue was acidified to pH 5 with HCl (1 aq.). The precipitated solids were collected by filtration and concentrated under vacuum to afford 3-amino-6-[3-ethylpyrazolo[1,5-a]pyridin-5-yl]-5-(1,3-oxazol-2-yl)pyrazine-2-carboxylic acid (240 mg, 89.15%) as a Brown yellow solid. LCMS: m/z (ESI), [M+H]$^+$=351.3.

Step 6. 3-amino-6-[3-ethylpyrazolo[1,5-a]pyridin-5-yl]-N-[[(2R)-1-methylpyrrolidin-2-yl]methyl]-5-(1,3-oxazol-2-yl)pyrazine-2-carboxamide (Cmpd. 128)

A solution of 3-amino-6-[3-ethylpyrazolo[1,5-a]pyridin-5-yl]-5-(1,3-oxazol-2-yl)pyrazine-2-carboxylic acid (70 mg, 0.2 mmol, 1 equiv), 1-[(2R)-1-methylpyrrolidin-2-yl]methanamine (34.22 mg, 0.3 mmol, 1.5 equiv), HATU (151.95 mg, 0.4 mmol, 2 equiv), DIEA (77.5 mg, 0.6 mmol, 3 equiv) in DMF (2 mL) was stirred for 30 min at room temperature under air atmosphere. The reaction mixture was purified by Prep-HPLC with the following conditions (Column: XBridge Prep OBD C18 Column 19*250 mm, 5 um; Mobile Phase A: Water (0.05% NH$_3$H$_2$O), Mobile Phase B: ACN; Flow rate: 20 mL/min; Gradient: 40% B to 50% B in 8 min; 254/220 nm; Rt: 7.25 min) to afford 3-amino-6-[3-ethylpyrazolo[1,5-a]pyridin-5-yl]-N-[[(2R)-1-methylpyrrolidin-2-yl]methyl]-5-(1,3-oxazol-2-yl)pyrazine-2-carboxamide (Cmpd. 128) (20.1 mg, 22.42%) as a yellow solid. LCMS: m/z (ESI), [M+H]$^+$=447.3. $^1$H NMR (400 MHz, DMSO-d$_6$) δ 1.2 (3H, t), 1.6 (3H, dt), 1.8 (1H, q), 2.2 (1H, q), 2.3 (3H, s), 2.4 (1H, s), 2.7 (2H, q), 2.9-3.0 (1H, m), 3.2-3.3 (m, 1H), 3.4-3.5 (m, 1H), 6.8 (1H, dd), 7.4 (1H, d), 7.6 (1H, dd), 7.9 (1H, s), 7.9 (1H, s), 8.3 (1H, d), 8.6 (1H, dd), 8.6 (1H, t).

Example 129. Preparation of (S)-3-amino-6-(3-ethylpyrazolo[1,5-a]pyridin-5-yl)-N-((1-methylpyrrolidin-2-yl)methyl)-5-(oxazol-2-yl)pyrazine-2-carboxamide (Cmpd. 129)

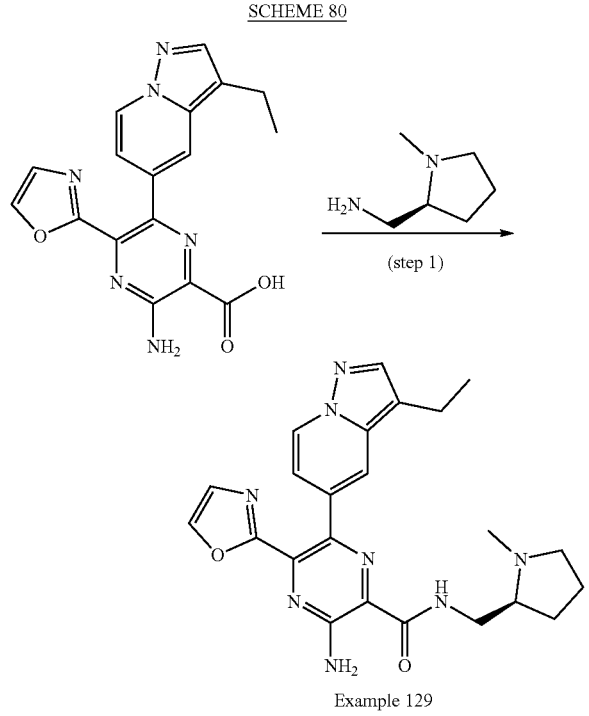

Example 129

Step 1. 3-amino-6-[3-ethylpyrazolo[1,5-a]pyridin-5-yl]-N-[[(2R)-1-methylpyrrolidin-2-yl]methyl]-5-(1,3-oxazol-2-yl)pyrazine-2-carboxamide (Cmpd. 129)

A solution of 3-amino-6-[3-ethylpyrazolo[1,5-a]pyridin-5-yl]-5-(1,3-oxazol-2-yl)pyrazine-2-carboxylic acid (70 mg, 0.200 mmol, 1 equiv), 1-[(2S)-1-methylpyrrolidin-2-yl]methanamine (34.22 mg, 0.300 mmol, 1.5 equiv), HATU (151.95 mg, 0.400 mmol, 2.00 equiv), DIEA (77.47 mg, 0.599 mmol, 3 equiv) in DMF (2 mL) was stirred for 30 min at room temperature under air atmosphere. The crude product (70 mg) was purified by Prep-HPLC with the following conditions (Column: XBridge Prep OBD C18 Column 19*250 mm, 5 um; Mobile Phase A: Water (0.05% NH$_3$H2), Mobile Phase B: ACN; Flow rate: 20 mL/min; Gradient: 39% B to 51% B in 8 min; 254/220 nm; Rt: 7.67 min) to afford 3-amino-6-[3-ethylpyrazolo[1,5-a]pyridin-5-yl]-N-[[(2S)-1-methylpyrrolidin-2-yl]methyl]-5-(1,3-oxazol-2-yl)pyrazine-2-carboxamide (Cmpd. 129) (29.8 mg, 22.42%) as a yellow solid. LCMS: m/z (ESI), [M+H]$^+$=447.3. $^1$H NMR (400 MHz, DMSO-d$_6$) δ 1.2 (3H, t), 1.5-1.7 (3H, m), 1.8-1.9 (1H, m), 2.2 (1H, q), 2.3 (3H, s), 2.4 (1H, s), 2.7 (2H, q), 2.9-3.0 (1H, m), 3.2-3.3 (1H, m), 3.5 (1H, ddd), 6.8 (1H, dd), 7.4 (1H, s), 7.5-7.6 (1H, m), 7.9 (1H, s), 7.9 (1H, s), 8.3 (1H, s), 8.6 (1H, d), 8.6 (1H, t).

Example 130. Preparation of 3-amino-6-(1-methyl-1H-1,3-benzodiazol-6-yl)-N-[[(2S)-1-methylpyrrolidin-2-yl]methyl]-5-(2H-1,2,3-triazol-2-yl)pyrazine-2-carboxamide (Cmpd. 130)

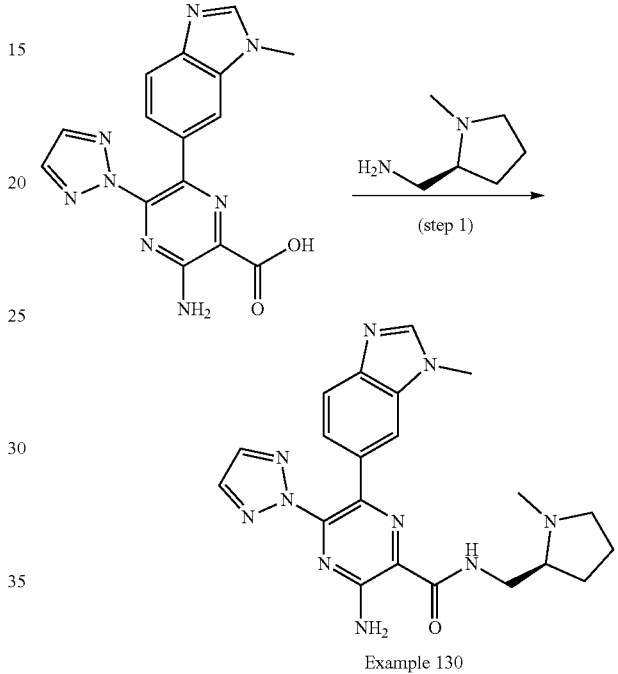

Example 130

Step 1. 3-amino-6-(1-methyl-1H-1,3-benzodiazol-6-yl)-5-(1,3-oxazol-2-yl)-N-[(1,3-thiazol-4-yl) methyl] pyrazine-2-carboxamide (Cmpd. 130)

To a stirred solution of 3-amino-6-(1-methyl-1H-1,3-benzodiazol-6-yl)-5-(2H-1,2,3-triazol-2-yl)pyrazine-2-carboxylic acid (300 mg, 0.892 mmol, 1 equiv) and 1-[(2S)-1-methylpyrrolidin-2-yl]methanamine (101.86 mg, 0.892 mmol, 1 equiv) in DMF were added T$_3$P (851.47 mg, 2.676 mmol, 3 equiv) and DIEA (576.44 mg, 4.460 mmol, 5 equiv) dropwise/in portions at room temperature under air atmosphere. The resulting mixture was stirred for 4 h at room temperature under air atmosphere. The resulting mixture was extracted with EtOAc (3×20 mL). The combined organic layers were washed with brine (3×10 mL), dried over anhydrous Na$_2$SO$_4$. After filtration, the filtrate was concentrated under reduced pressure. The crude product (300 mg) was purified by Prep-HPLC with the following conditions (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 18% B to 35% B in 7 min; 254/220 nm; Rt: 7.08 min) to afford 3-amino-6-(1-methyl-1H-1,3-benzodiazol-6-yl)-N-[[(2S)-1-methylpyrrolidin-2-yl]methyl]-5-(2H-1,2,3-triazol-2-yl)pyrazine-2-carboxamide (Cmpd. 130) (20 mg, 5.18%) as a yellow solid. LCMS m/z (ESI) [M+H]$^+$=433.2;

H-NMR (400 MHz, MeOD-d₄) δ 1.68-1.81 (2H, m), 1.81 (1H, s), 1.96-2.08 (1H, m), 2.33 (1H, q), 2.47 (3H, d), 2.61 (1H, s), 3.06-3.13 (1H, m), 3.42-3.47 (1H, m), 3.66-3.70 (1H, m), 3.85 (3H, s), 7.03-7.06 (1H, m), 7.40 (1H, s), 7.53 (1H, d), 7.91 (2H, s), 8.14 (1H, s).

Example 131. Preparation of (R)-3-amino-6-(1-methyl-1H-benzo[d]imidazol-6-yl)-N-((1-methylpyrrolidin-2-yl)methyl)-5-(2H-1,2,3-triazol-2-yl)pyrazine-2-carboxamide (Cmpd. 131)

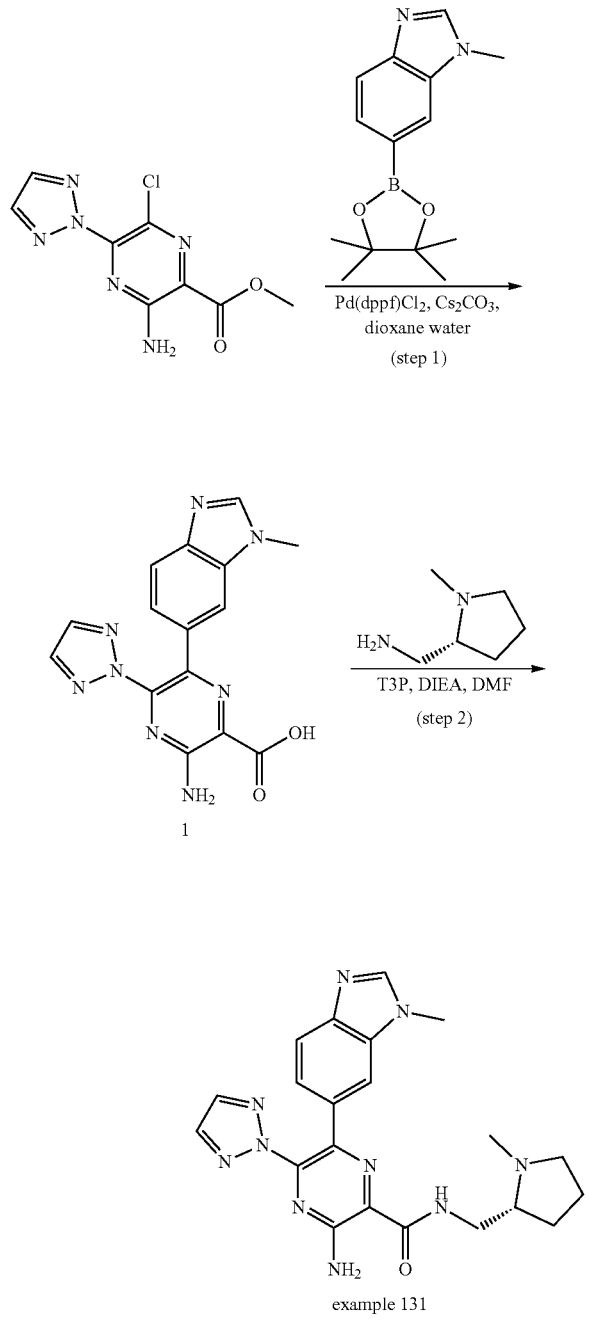

example 131

Step 1. 3-amino-6-(1-methyl-1H-benzo[d]imidazol-6-yl)-5-(2H-1,2,3-triazol-2-yl)pyrazine-2-carboxylic Acid A solution of methyl 3-amino-6-chloro-5-(2H-1,2,3-triazol-2-yl)pyrazine-2-carboxylate (500 mg, 1.964 mmol, 1 equiv), 1-methyl-6-(4,4,5,5-tetramethyl-1,3,2-dioxaborolan-2-yl)-1H-1,3-benzodiazole (608.25 mg, 2.356 mmol, 1.20 equiv), Pd(dppf)Cl₂ (287.36 mg, 0.393 mmol, 0.2 equiv) and Cs₂CO₃ (2559.16 mg, 7.855 mmol, 4.0 equiv) in dioxane (40 mL), water (5 mL) was stirred for 16 h at 100° C. under nitrogen atmosphere. The resulting mixture was extracted with EtOAc (3×40 mL). The water solution was acidified to pH 6 with HCl (1M). The precipitated solids were collected by filtration and washed with water (2×10 mL). This afford 3-amino-6-(1-methyl-1H-1,3-benzodiazol-6-yl)-5-(2H-1,2,3-triazol-2-yl)pyrazine-2-carboxylic acid (240 mg, 36.34%) as a light yellow solid. LCMS: m/z (ESI), [M+H]⁺=337.1. ¹H-NMR (300 MHz, MeOD-d₄) δ 3.93 (3H, s), 7.33-7.35 (2H, m), 7.43-7.46 (1H, m), 7.82-7.84 (2H, m), 8.12 (1H, s)

Step 2. (R)-3-amino-6-(1-methyl-1H-benzo[d]imidazol-6-yl)-N-((1-methylpyrrolidin-2-yl)methyl)-5-(2H-1,2,3-triazol-2-yl)pyrazine-2-carboxamide (Cmpd. 131)

A mixture of 3-amino-6-(1-methyl-1H-1,3-benzodiazol-6-yl)-5-(2H-1,2,3-triazol-2-yl)pyrazine-2-carboxylic acid (100 mg, 0.297 mmol, 1 equiv), 1-[(2R)-1-methylpyrrolidin-2-yl]methanamine (67.91 mg, 0.595 mmol, 2.0 equiv), T3P (473.04 mg, 1.487 mmol, 5 equiv) and DIEA (384.29 mg, 2.973 mmol, 10 equiv) in DMF (5 mL) was stirred for 2 h at room temperature. The resulting mixture was extracted with EtOAc (3×20 mL). The combined organic layers were washed with brine (20 mL), dried over anhydrous Na₂SO₄. After filtration, the filtrate was concentrated under reduced pressure. The crude product was purified by Prep-HPLC with the following conditions (Column: Kinetex EVO C18 Column 30*150.5 um; Mobile Phase A: Water (10 MMOL/L NH₄HCO₃), Mobile Phase B: ACN; Flow rate: 60 mL/min; Gradient: 20% B to 35% B in 7 min; 254/220 nm; Rt: 5.73 min) to afford 3-amino-6-(1-methyl-1H-1,3-benzodiazol-6-yl)-N-[[(2R)-1-methylpyrrolidin-2-yl]methyl]-5-(2H-1,2,3-triazol-2-yl)pyrazine-2-carboxamide (Cmpd. 131) (20 mg, 15.55%) as a yellow solid. LCMS: m/z (ESI), [M+H]⁺= 433.3. ¹H-NMR (300 MHz, DMSO-d₆) S 1.67-1.69 (3H, m), 1.86-1.89 (1H, m), 2.15-2.17 (1H, m), 2.33 (3H, s), 2.45-2.47 (1H, m), 2.96-2.97 (1H, m), 3.31-3.34 (1H, m), 3.74 (3H, m), 6.84-6.87 (1H, m), 7.25 (1H, s), 7.48 (1H, s), 8.01-8.03 (2H, m), 8.07-8.09 (2H, m), 8.20 (1H, s), 8.66-8.68 (1H, m).

Compounds listed in the table below were prepared using methods described in Cmpd. 131.

| Example/ Cmpd number | Structure | LCMS [M + H]+ | 1H NMR |
|---|---|---|---|
| 299 | 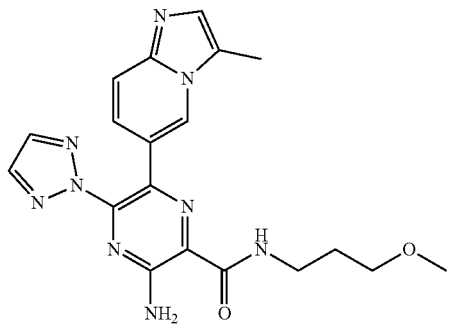 [SMILES: COCCCNC(=O)c1nc(-c2ccc3ncc(C)n3c2)c(-n2nccn2)nc1N] | 408.2 | 1H NMR: (300 MHz, DMSO-d6) δ 1.82 (2H, p), 2.38 (3H, s), 3.25 (3H, s), 3.42 (4H, s), 6.91 (1H, dd), 7.41 (2H, m), 7.90 (1H, s), 8.14 (4H, s), 8.97 (1H, t). |
| 201-1 | 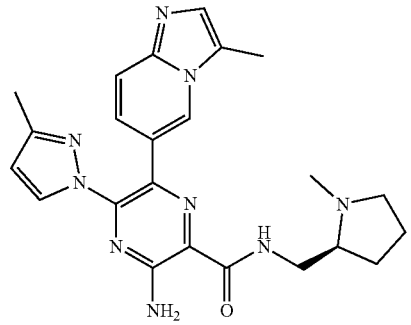 [SMILES: Cc1ccn(-c2nc(N)c(C(=O)NC[C@@H]3CCCN3C)nc2-c2ccc3ncc(C)n3c2)n1] | 446.2 | 1H NMR (300 MHz, Methanol-d4) δ 1.61-1.85 (3H, m), 2.01 (1H, d), 2.15 (3H, s), 2.33 (1H, q), 2.43-2.50 (6H, m), 2.55 (1H, s), 3.09 (1H, dd), 3.31-3.48 (1H, m), 3.65 (1H, dd), 4.61 (1H, s), 6.34 7.44 (2H, m), 8.06 (1H, d), 8.13 (1H, t). |
| 201-2 | 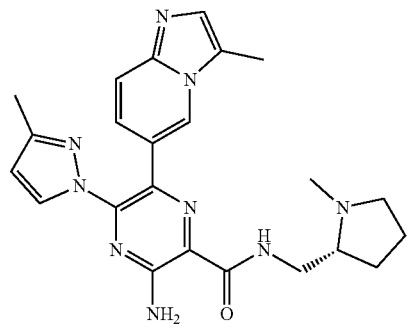 [SMILES: Cc1ccn(-c2nc(N)c(C(=O)NC[C@H]3CCCN3C)nc2-c2ccc3ncc(C)n3c2)n1] | 446.2 | 1H-NMR (300 MHz, Methanol-d4) δ 1.74 (3H, s), 1.99 (1H, d), 2.15 (3H, s), 2.31 (1H, q), 2.45 (6H, d), 2.57 (1H, s), 3.08 (1H, s), 3.38-3.67 (2H, m), 4.88 (1H, m), 6.34 (1H, s), 7.12 (1H, d), 7.31-7.43 (2H, m), 8.06 (1H, s), 8.13 (1H, s). |

Examples 134/135. Preparation of 3-amino-6-[3-methylimidazo[1,2-a]pyridin-6-yl]-5-(1,3-oxazol-2-yl)-N-[[(2R/2S)-oxetan-2-yl]methyl]pyrazine-2-carboxamide (Cmpd. 134/135)

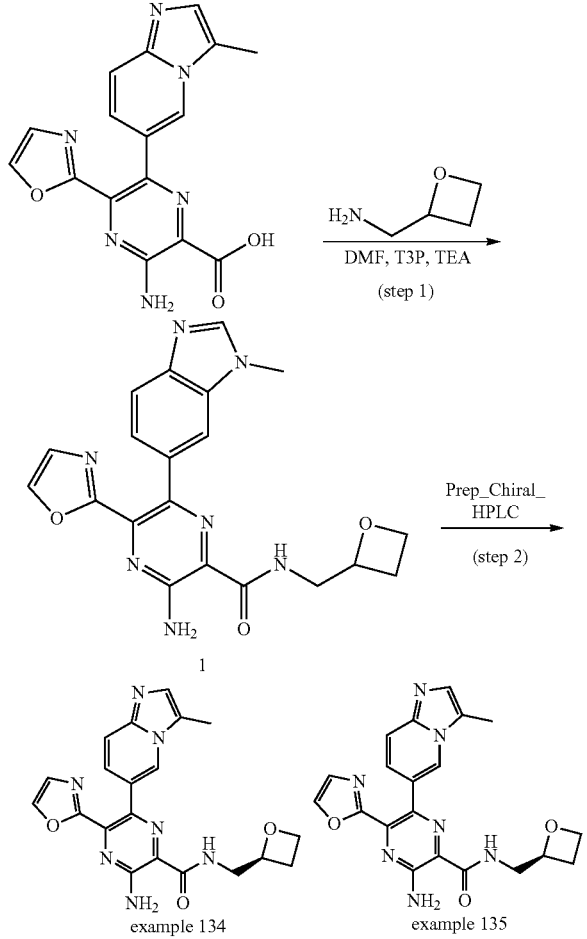

Step 1. 3-amino-6-[3-methylimidazo[1,2-a]pyridin-6-yl]-5-(1,3-oxazol-2-yl)-N-[(oxetan-2-yl)methyl]pyrazine-2-carboxamide To a stirred mixture of T$_3$P (946.09 mg, 2.973 mmol, 5.00 equiv) and 1-(oxetan-2-yl)methanamine (77.72 mg, 0.892 mmol, 1.50 equiv) in DMF (5 mL) were added 3-amino-6-[3-methylimidazo[1,2-a]pyridin-6-yl]-5-(1,3-oxazol-2-yl) pyrazine-2-carboxylic acid (200 mg, 0.595 mmol, 1 equiv) and DIEA (307.44 mg, 2.379 mmol, 4.00 equiv) dropwise at 25° C. under nitrogen atmosphere. The resulting mixture was stirred for 6h at 25° C. under nitrogen atmosphere. The reaction was quenched by the addition of Water (50 mL) at 25° C. The aqueous layer was extracted with EtOAc (3×50 mL). The aqueous layer was evaporated. The crude product (100 mg) was purified by Prep-HPLC with the following conditions (Column: XBridge Prep OBD C18 Column 30×150 mm 5 um; Mobile Phase A: Water (0.05% NH$_3$H2), Mobile Phase B: ACN; Flow rate: 60 mL/min; Gradient: 19% B to 29% B in 7 min; 254/220 nm; Rt: 6.45 min) to afford 3-amino-6-[3-methylimidazo[1,2-a]pyridin-6-yl]-5-(1,3-oxazol-2-yl)-N-[(oxetan-2-yl)methyl]pyrazine-2-carboxamide (90 mg, 37.33%) as a yellow solid. LCMS: m/z (ESI), [M+H]$^+$=406.2.

Step 2. Preparation of 3-amino-6-[3-methylimidazo[1,2-a]pyridin-6-yl]-5-(1,3-oxazol-2-yl)-N-[[(2R/2S)-oxetan-2-yl]methyl]pyrazine-2-carboxamide (Cmpd. 134/135)

The crude product (150 mg) was purified by Prep-HPLC with the following conditions (Column: CHIRALPAK IE, 2*25 cm, 5 um; Mobile Phase A: MTBE (10 mM NH3-MEOH)-HPLC-, Mobile Phase B: EtOH-HPLC; Flow rate: 20 mL/min; Gradient: 20 B to 20 B in 18 min; 220/254 nm; RT1:12.678; RT2:14.094) to afford 3-amino-6-[3-methyl-imidazo[1,2-a]pyridin-6-yl]-5-(1,3-oxazol-2-yl)-N-[[(2R)-oxetan-2-yl]methyl]pyrazine-2-carboxamide (isomer 1) (Cmpd. 134) (60 mg, 40%) as a yellow solid. LCMS: m/z (ESI), [M+H]$^+$=406.1. $^1$H NMR (300 MHz, MeOD-d$_4$) δ 2.50 (3H, d), 2.52-2.61 (1H, m), 2.72 (1H, t), 3.60-3.79 (2H, m), 4.56 (1H, dt), 4.63-4.74 (1H, m), 4.95-5.07 (1H, m), 7.26 (1H, dd), 7.32 (1H, d), 7.38 (1H, d), 7.48 (1H, dd), 8.00 (1H, d), 8.37 (1H, d). and 3-amino-6-[3-methylimidazo[1,2-a]pyridin-6-yl]-5-(1,3-oxazol-2-yl)-N-[[(2R)-oxetan-2-yl]methyl] pyrazine-2-carboxamide (isomer 2) (Cmpd. 135) (60 mg, 40%) as a yellow solid. LCMS: m/z (ESI), [M+H]$^+$=406.1. $^1$H NMR (300 MHz, MeOD-d$_4$) δ 2.50 (3H, d), 2.55 (1H, d), 2.71 (1H, d), 3.64 (1H, dd), 3.74 (2H, dd), 4.56 (1H, dt), 4.63-4.74 (1H, m), 4.95-5.07 (1H, m), 7.26 (1H, dd), 7.32 (1H, d), 7.38 (1H, d), 7.48 (1H, dd), 8.00 (1H, d), 8.37 (1H, s).

Example 136. Preparation of (R)-3-amino-6-(3-methylimidazo[1,2-a]pyridin-6-yl)-5-(oxazol-2-yl)-N-((tetrahydrofuran-3-yl)methyl)pyrazine-2-carboxamide (Cmpd. 136)

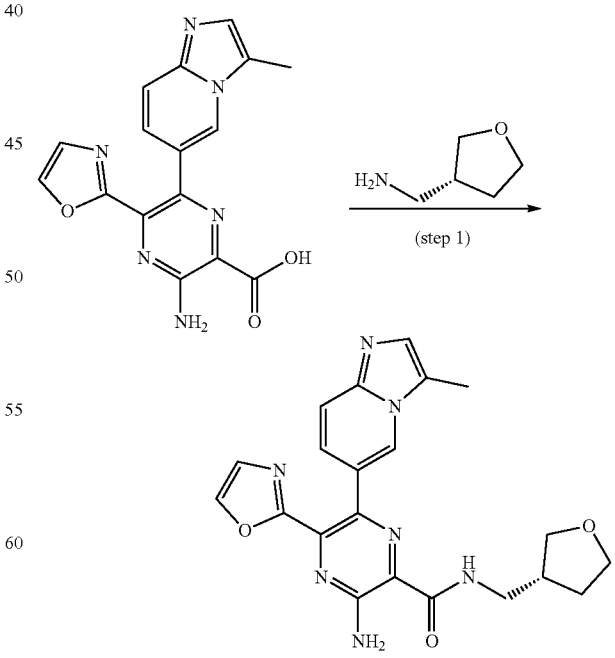

Step 1. (R)-3-amino-6-(3-methylimidazo[1,2-a]pyridin-6-yl)-5-(oxazol-2-yl)-N-((tetrahydrofuran-3-yl)methyl)pyrazine-2-carboxamide (Cmpd. 136)

Into a 25-mL round-bottom flask, was placed 3-amino-6-[3-methylimidazo[1,2-a]pyridin-6-yl]-5-(1,3-oxazol-2-yl)pyrazine-2-carboxylic acid (100 mg, 0.297 mmol, 1 equiv), DIEA (384.30 mg, 2.973 mmol, 10 equiv), and (R)-(tetrahydrofuran-3-yl)methanamine (90.23 mg, 0.892 mmol, 3 equiv) in DMF (4 mL). T$_3$P (378.44 mg, 1.189 mmol, 4 equiv) was added to the above solution at 0° C. The resulting solution was stirred for 1 hr at room temperature. The reaction mixture was purified by Prep-HPLC with the following conditions: (Column: XBridge Prep OBD C18 Column 30×150 mm 5 um; Mobile Phase A: Water (10 MMOL/L NH$_4$HCO$_3$+0.1% NH$_3$.H$_2$O), Mobile Phase B: ACN; Flow rate: 60 mL/min; Gradient: 17% B to 37% B in 7 min; 254/220 nm; Rt: 5.85 min). This resulted in 67 mg (53.72%) of (R)-3-amino-6-(3-methylimidazo[1,2-a]pyridin-6-yl)-5-(oxazol-2-yl)-N-((tetrahydrofuran-3-yl)methyl)pyrazine-2-carboxamide (Cmpd. 136) as a yellow solid. LCMS: m/z (ESI), [M+H]$^+$=420.2. $^1$H-NMR (400 MHz, MeOD-d$_4$) δ 1.75 (1H, dt), 2.02-2.15 (1H, m), 2.53 (3H, d), 2.65 (1H, t), 3.45 (2H, d), 3.65 (1H, dd), 3.76 (1H, q), 3.83 (1H, dd), 3.92 (1H, td), 7.28 (1H, dd), 7.34 (1H, d), 7.41 (1H, s), 7.46-7.53 (1H, m), 8.02 (1H, d), 8.40 (1H, s)

Example 137. Preparation of (S)-3-amino-6-(3-methylimidazo[1,2-a]pyridin-6-yl)-5-(oxazol-2-yl)-N-((tetrahydrofuran-3-yl)methyl)pyrazine-2-carboxamide (Cmpd. 137)

SCHEME 85

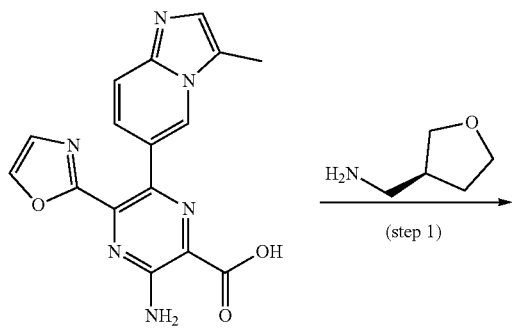

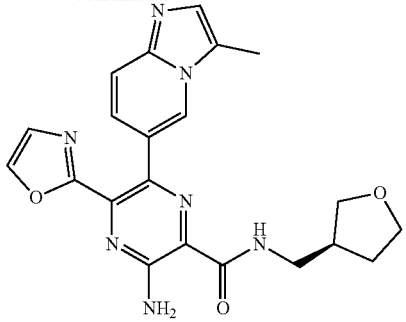

Example. 137

Step 1. (S)-3-amino-6-(3-methylimidazo[1,2-a]pyridin-6-yl)-5-(oxazol-2-yl)-N-((tetrahydrofuran-3-yl)methyl)pyrazine-2-carboxamide (Cmpd. 137)

To a stirred mixture of 3-amino-6-[3-methylimidazo[1,2-a]pyridin-6-yl]-5-(1,3-oxazol-2-yl)pyrazine-2-carboxylic acid (100 mg, 0.297 mmol, 1 equiv) and (S)-(tetrahydrofuran-3-yl)methanamine (130 mg, 1.285 mmol, 4.32 equiv) in DMF were added DIEA (1.04 mL, 5.946 mmol, 20 equiv) and T$_3$P (473.05 mg, 1.487 mmol, 5 equiv) dropwise at room temperature under air atmosphere. The reaction mixture was diluted with water (25 mL). The aqueous layer was extracted with EtOAc (2×25 mL). The combined organic layer was concentrated under reduced pressure. The residue was purified by Prep-HPLC with the following conditions (Column: XBridge Prep OBD C18 Column 30×150 mm 5 um; Mobile Phase A: Water (10 MMOL/L NH$_4$HCO$_3$+0.1% NH$_3$.H$_2$O), Mobile Phase B: ACN; Flow rate: 60 mL/min; Gradient: 15% B to 35% B in 7 min; 254/220 nm; Rt: 6.48 min) to afford (S)-3-amino-6-(3-methylimidazo[1,2-a]pyridin-6-yl)-5-(oxazol-2-yl)-N-((tetrahydrofuran-3-yl)methyl)pyrazine-2-carboxamide (Cmpd. 137) (70 mg, 56.00%) as a yellow solid. LCMS: m/z (ESI), [M+H]$^+$=420.3; H-NMR (400 MHz, MeOD-d$_4$) δ 1.75 (1H, dt), 2.02-2.15 (1H, m), 2.53 (3H, d), 2.65 (1H, t), 3.45 (2H, d), 3.65 (1H, dd), 3.76 (1H, q), 3.83 (1H, dd), 3.92 (1H, td), 7.28 (1H, dd), 7.34 (1H, d), 7.41 (1H, s), 7.46-7.53 (1H, m), 8.02 (1H, d), 8.40 (1H, s).

Compounds listed in the table below were prepared using methods described in Cmpd. 137.

| Example/Cmpd number | Structure | LCMS [M + H]$^+$ | $^1$H NMR |
|---|---|---|---|
| 124 | (structure shown) | 447.2 | $^1$H NMR (400 MHz, MeOD-d$_4$) δ 0.87-1.33 (2H, m), 1.50 (1H, d), 1.55-1.96 (3H, m), 2.48 (3H, d), 2.64 (1H, s), 2.89 (1H, d), 3.09 (1H, d), 3.19 (3H, d), 3.44-3.80 (2H, m), 7.27 (1H, d), 7.32 (1H, d), 7.40 (1H, s), 7.51 (1H, d), 7.99 (1H, d), 8.27 (1H, d) (isomer 1) |

| Example/Cmpd number | Structure | LCMS [M + H]+ | 1H NMR |
|---|---|---|---|
| 125 | 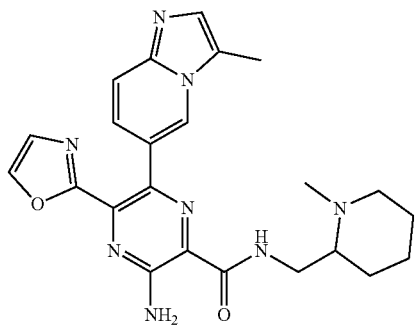 [SMILES: Cc1cnc2ccc(-c3nc(C(=O)NCC4CCCCN4C)c(N)nc3-c3ncco3)cn12] | 447.2 | 1H NMR (400 MHz, MeOD-d4) δ 0.87-1.33 (2H, m), 1.48 (1H, s), 1.55-1.93 (3H, m), 2.48 (3H, d), 2.58 (1H, d), 2.89 (1H, d), 3.01-3.13 (1H, m), 3.19 (3H, d), 3.42-3.80 (2H, m), 7.23-7.35 (2H, m), 7.40 (1H, s), 7.51 (1H, d), 7.99 (1H, d), 8.27 (1H, d) (isomer 2) |
| 126 | 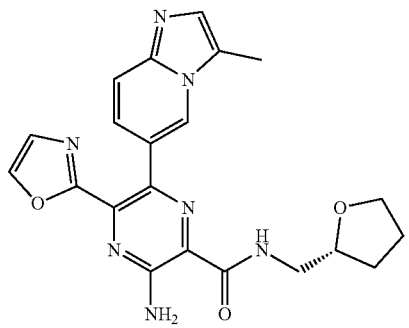 [SMILES: Cc1cnc2ccc(-c3nc(C(=O)NC[C@H]4CCCO4)c(N)nc3-c3ncco3)cn12] | 420.3 | 1H NMR (300 MHz, Methanol-d4)1.64-1.78 (1H, m), 2.00 (3H, ddd), 2.52 (3H, d), 3.45 (1H, dd), 3.59 (1H, dd), 3.78 (1H, q), 3.91 (1H, q), 4.08-4.18 (1H, m), 7.23-7.37 (2H, m), 7.40 (1H, s), 7.50 (1H, d), 8.01 (1H, d), 8.38 (1H, s) |
| 127 | 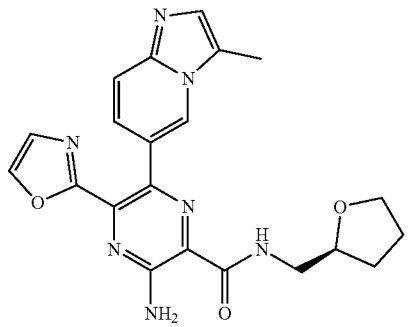 | 420.3 | 1H NMR (300 MHz, DMSO-d6) δ 1.67-1.69 (1H, m), 1.81-1.85 (3H, m), 2.43 (3H, s),3.36-3.39 (2H, m), 3.60-3.65 (1H, m), 3.75- 3.78 (1H, m), 4.02-4.04 (1H, m), 7.20-7.21 (1H, m), 7.23-7.24 (2H, m), 7.35-7.39 (1H, m), 7.90 (2H, m), 8.26-8.27 (1H, m), 8.33 (1H, s) , 8.75-8.79 (1H, m). |
| 132 | 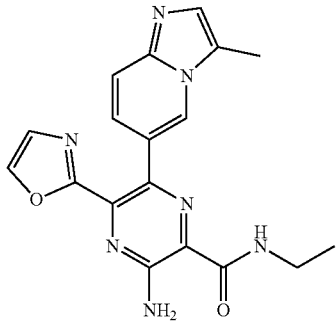 [SMILES: CCNC(=O)c1nc(-c2ccc3ncc(C)n3c2)c(-c2ncco2)nc1N] | 364.2 | 1H NMR (300 MHz, DMSO-d6) 1.15 (3H, t), 2.45 (3H, d), 3.35 (2H, s) 7.23 (1H, dd), 7.38 (2H, dd), 7.44-7.53 (1H, m), 7.92 (2H, s), 8.27-8.34 (2H, m), 8.89 (1H, t) |

| Example/Cmpd number | Structure | LCMS [M + H]+ | 1H NMR |
|---|---|---|---|
| 133 | 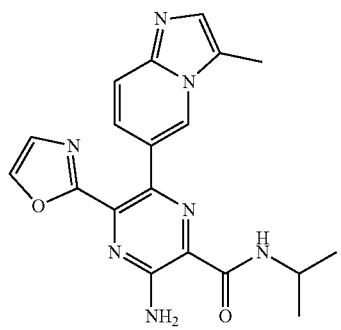 [SMILES: Cc1cnc2ccc(-c3nc(C(=O)NC(C)C)c(N)nc3-c3ncco3)cn12] | 378.2 | 1H NMR (400 MHz, MeOD-d4) δ 1.30 (6H, d), 2.52 (3H, d), 4.24 (1H, p), 7.25 (1H, dd), 7.35 (1H, s), 7.41 (1H, d), 7.51 (1H, dd), 8.01 (1H, d), 8.36-8.41 (1H, m) |
| 142 | 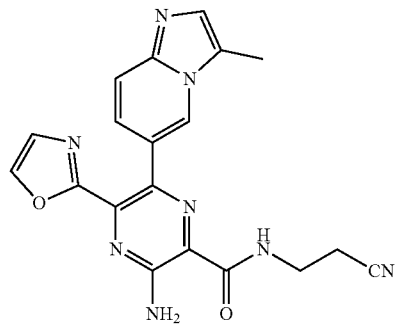 [SMILES: Cc1cnc2ccc(-c3nc(C(=O)NCCC#N)c(N)nc3-c3ncco3)cn12] | 389.3 | 1H NMR (400 MHz, Methanol-d6) δ 2.53 (3H, d), 2.82 (2H, t), 3.70 (2H, t), 7.29 (1H, dd), 7.34 (1H, d), 7.40 (1H, d), 7.50 (1H, dd), 8.02 (1H, d), 8.37-8.42 (1H, m) |
| 143 | 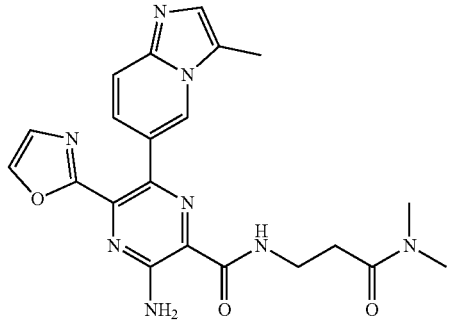 | 435.2 | 1H NMR (300 MHz, DMSO-d6) δ 2.44 (3H, d), 2.57-2.62 (2H, m), 2.80 (3H, s), 2.94 (3H, s), 3.47-3.49 (2H, m), 7.14-7.17 (1H, m), 7.35-7.39 (2H, m), 7.45-7.48 (1H, m), 7.91 (2H, s), 8.23-8.34 (2H, m), 8.90 (1H, d). |
| 145 | 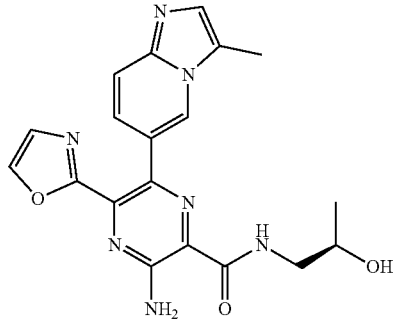 [SMILES: Cc1cnc2ccc(-c3nc(C(=O)NC[C@@H](C)O)c(N)nc3-c3ncco3)cn12] | 394.1 | 1H NMR (300 MHz, MeOD-d4) δ 1.20 (3H, d), 2.49 (3H, d), 3.34 (1H, s), 3.50 (1H, dd), 3.94-4.00 (1H, m), 7.25 (1H, dd), 7.31 (1H, d), 7.38 (1H, d), 7.48 (1H, dd), 7.99 (1H, d), 8.35 (1H, d). |

| Example/Cmpd number | Structure | LCMS [M + H]+ | 1H NMR |
|---|---|---|---|
| 146 | 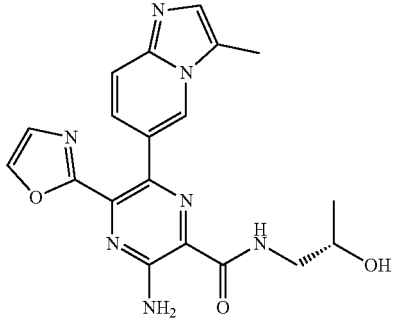 | 394.2 | 1H NMR (300 MHz, MeOD-d4) δ 1.20 (3H, d), 2.49 (3H, d), 3.34 (1H, s), 3.50 (1H, dd), 3.94-4.00 (1H, m), 7.25 (1H, dd), 7.31 (1H, d), 7.38 (1H, d), 7.48 (1H, dd), 7.99 (1H, d), 8.35 (1H, d). |
| 148 | 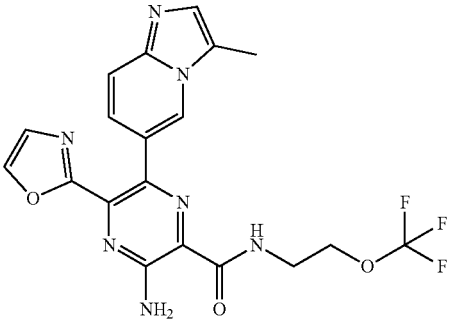 [SMILES: Cc1cnc2ccc(-c3nc(C(=O)NCCOC(F)(F)F)c(N)nc3-c3ncco3)cn12] | 448.2 | 1H NMR (400 MHz, DMSO-d6) δ 2.43 (3H, s), 3.64 (2H, q), 4.25 (2H, t), 7.24 (1H, dd), 7.38 (2H, d), 7.49 (1H, d), 7.90 (2H, s), 8.30 (2H, d), 9.02 (1H, t). |
| 151 | 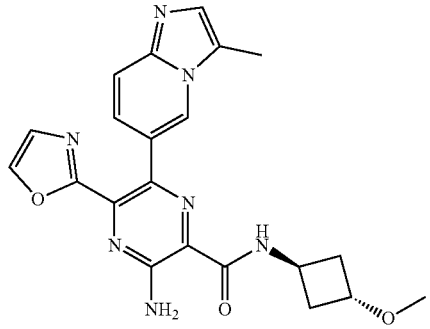 [SMILES: CO[C@H]1C[C@H](NC(=O)c2nc(-c3ccc4ncc(C)n4c3)c(-c3ncco3)nc2N)C1] | 420.3 | 1H NMR (300 MHz, DMSO-d6) δ 2.27 (2H, d), 2.39 (1H, q), 2.41 (1H, s), 2.45 (3H, d), 3.16 (3H, s), 3.98 (1H, d), 4.50 (1H, p), 7.22 (1H, d), 7.38 (2H, d), 7.49 (1H, d), 7.89 (2H, s), 8.28 (1H, d), 8.39 (1H, t), 8.95 (1H, d) |
| 152 | 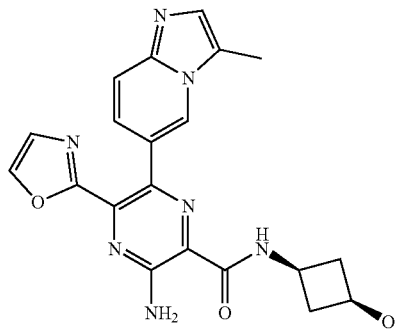 [SMILES: Cc1cnc2ccc(-c3nc(C(=O)N[C@H]4C[C@@H](O)C4)c(N)nc3-c3ncco3)cn12] | 420.3 | 1H NMR (300 MHz, DMSO-d6) δ 2.10 (2H, dt), 2.42-2.48 (3H, m), 2.53-2.65 (2H, m), 3.14 (3H, s), 3.64 (1H, p), 4.06 (1H, h), 7.25 (1H, d), 7.38 (2H, d), 7.49 (1H, d), 7.89 (2H, s), 8.28 (1H, d), 8.36 (1H, t), 8.93 (1H, d) |

-continued

| Example/ Cmpd number | Structure | LCMS [M + H]+ | 1H NMR |
|---|---|---|---|
| 153 | 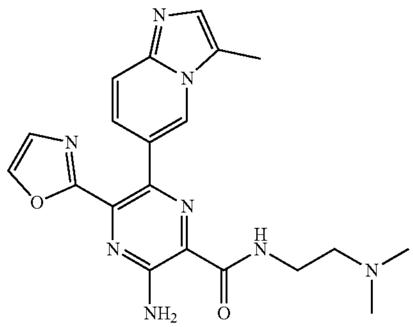 | 407.3 | 1H NMR (300 MHz, DMSO-$d_6$) δ 2.19 (6H, s), 2.35-2.47 (5H, m), 3.41 (2H, q), 7.21 (1H, dd), 7.38 (2H, dd), 7.49 (1H, dd), 7.92 (2H, s), 8.27 (1H, d), 8.33 (1H, t), 8.75 (1H, t) |
| 155 | 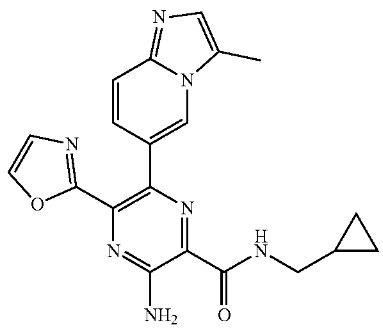 [SMILES: Cc1cnc2ccc(-c3nc(C(=O)NCC4CC4)c(N)nc3-c3ncco3)cn12] | 390.3 | 1H NMR (400 MHz, DMSO-$d_6$) δ 0.23-0.31 (2H, m), 0.39-0.48 (2H, m), 1.05-1.12 (1H, m), 2.41-2.46 (3H, m), 3.19 (2H, t), 7.23 (1H, dd), 7.38 (2H, dd), 7.49 (1H, dd), 7.92 (2H, s), 8.27 (1H, d), 8.32-8.37 (1H, m), 8.92 (1H, t) |

Example 138. Preparation of 3-amino-5-(4-fluorophenyl)-6-[3-methylimidazo[1,2-a]pyridin-6-yl]-N-[[(2R)-1-methylpyrrolidin-2-yl]methyl]pyrazine-2-carboxamide (Cmpd. 138)

SCHEME 86

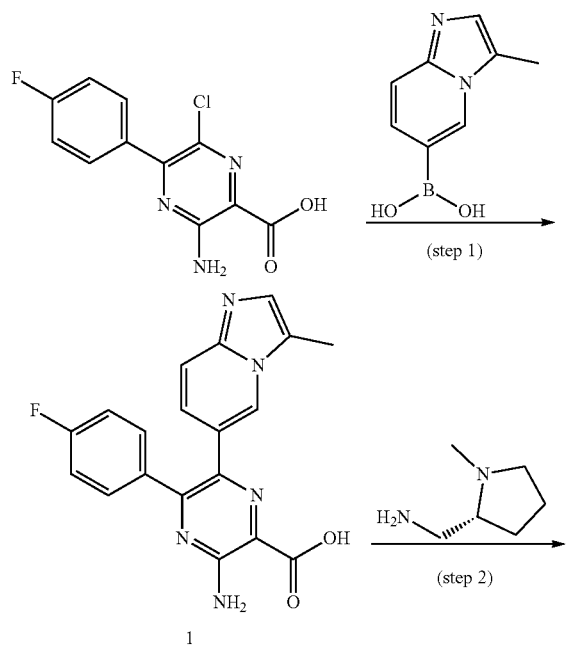

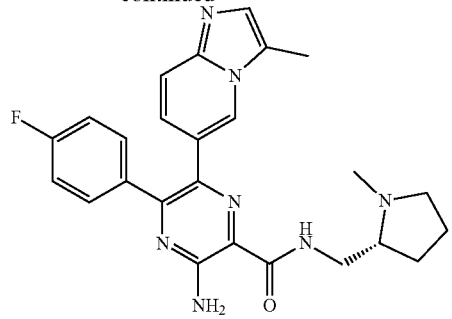

Example 138

Step 1. 3-amino-5-(4-fluorophenyl)-6-[3-methylimidazo[1,2-a]pyridin-6-yl]pyrazine-2-carboxylic Acid Into a 100-mL round-bottom flask purged and maintained with an inert atmosphere of nitrogen, was placed 3-amino-6-chloro-5-(4-fluorophenyl)pyrazine-2-carboxylic acid (1 g, 3.736 mmol, 1 equiv), [3-methylimidazo[1,2-a]pyridin-6-yl] boronic acid (1.12 g, 6.364 mmol, 1.70 equiv), $Cs_2CO_3$ (3.04 g, 9.330 mmol, 2.50 equiv), dioxane (25 mL), Pd(dppf)$Cl_2$ (273.39 mg, 0.374 mmol, 0.10 equiv). The resulting solution was stirred for 16 hours at 100° C. The resulting solution was diluted with 20 mL of $H_2O$. The resulting solution was extracted with 3×20 mL of ethyl acetate and the aqueous layers combined. The pH value of the solution was adjusted to 4 with HCl (1 mol/L). The solids were collected by filtration. This resulted in 500 mg (36.83%) of 3-amino-5-(4-fluorophenyl)-6-[3-methylimidazo[1,2-a]pyridin-6-yl]pyrazine-2-carboxylic acid as a brown solid. LCMS: m/z (ESI), [M+H]$^+$=364. 1H NMR (400 MHz, DMSO-d$_6$) δ 2.37 (3H, s), 6.97 (1H, d), 7.21 (2H, t), 7.38 (2H, t), 7.51 (2H, d), 7.62 (2H, s), 8.26 (1H, s)

Step 2. 3-amino-5-(4-fluorophenyl)-6-[3-methylimidazo[1,2-a]pyridin-6-yl]-N-[[(2R)-1-methylpyrrolidin-2-yl]methyl]pyrazine-2-carboxamide (Cmpd. 138)

Into a 20-mL vial, was placed 3-amino-5-(4-fluorophenyl)-6-[3-methylimidazo[1,2-a]pyridin-6-yl]pyrazine-2-carboxylic acid (130 mg, 0.358 mmol, 1 equiv), 1-[(2R)-1-methylpyrrolidin-2-yl]methanamine (81.71 mg, 0.716 mmol, 2.00 equiv), DMF (6 mL), DIEA (0.31 mL, 2.396 mmol, 3.42 equiv), T$_3$P (569.19 mg, 1.789 mmol, 5.00 equiv). The resulting solution was stirred for 16 hours at 20° C. The resulting mixture was concentrated under vacuum. The crude product was purified by preparative HPLC (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 34% B to 49% B in 7 min; 254/220 nm; Rt: 6.52 min). This resulted in 54.29 mg (33.02%) of 3-amino-5-(4-fluorophenyl)-6-[3-methylimidazo[1,2-a]pyridin-6-yl]-N-[[(2R)-1-methylpyrrolidin-2-yl]methyl]pyrazine-2-carboxamide (Cmpd. 138) as a yellow solid. LCMS: m/z (ESI), [M+H]$^+$=460. $^1$H-NMR (400 MHz, DMSO-d$_6$) δ 1.61 (3H, d), 1.73-1.95 (1H, m), 2.12 (1H, dd), 2.32 (3H, s), 2.37 (3H, d), 2.42 (1H, s), 2.89-3.03 (1H, m), 3.17-3.29 (1H, m), 3.50 (1H, d), 6.99 (1H, d), 7.21 (2H, t), 7.31-7.43 (2H, m), 7.45-7.56 (2H, m), 7.74 (2H, s), 8.24 (1H, d), 8.63 (1H, t). 19F NMR (400 MHz, DMSO-d6) −112.225 (1F)

Example 147. Preparation of 3-amino-N-(2-methoxyethyl)-6-(3-methylimidazo[1,2-a]pyridin-6-yl)-5-(oxazol-2-yl)pyrazine-2-carboxamide (Cmpd. 147)

SCHEME 87

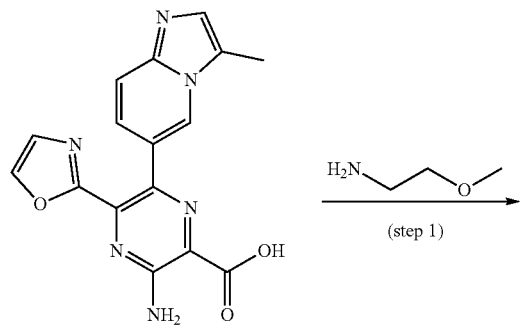

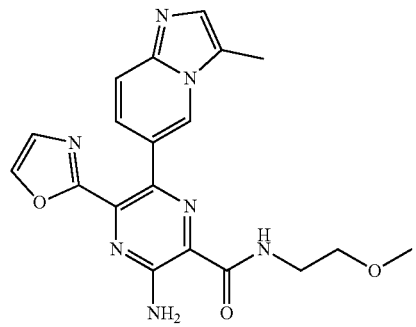

Example. 147

Step 1. 3-amino-N-(2-methoxyethyl)-6-(3-methylimidazo[1,2-a]pyridin-6-yl)-5-(oxazol-2-yl)pyrazine-2-carboxamide (Cmpd. 147)

To a stirred mixture of 3-amino-6-[3-methylimidazo[1,2-a]pyridin-6-yl]-5-(1,3-oxazol-2-yl)pyrazine-2-carboxylic acid (90 mg, 0.268 mmol, 1 equiv) and 2-methoxyethan-1-amine (60.30 mg, 0.803 mmol, 3 equiv) in DMF were added DIEA (164.08 mg, 1.270 mmol, 5 equiv) and T$_3$P (323.16 mg, 1.016 mmol, 4 equiv) dropwise at room temperature under air atmosphere. The resulting solution was stirred for 1 hr at room temperature. Water (25 mL) was added to the reaction mixture. The resulting mixture was extracted with EtOAc (3×25 mL). The combined organic layers were washed with brine (1×15 mL), dried over anhydrous Na$_2$SO$_4$. After filtration, the filtrate was concentrated under reduced pressure. The residue was purified by Prep-HPLC with the following conditions (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 18% B to 32% B in 7 min; 254 nm; Rt: 6.83 min) to afford 3-amino-N-(2-methoxyethyl)-6-[3-methylimidazo[1,2-a]pyridin-6-yl]-5-(1,3-oxazol-2-yl)pyrazine-2-carboxamide (Cmpd. 147) (50 mg, 49.78%) as a yellow solid. LCMS: m/z (ESI), [M+H]$^+$=394.2. $^1$H-NMR (400 MHz, MeOD-d$_4$) δ 2.52 (3H, d), 3.39 (3H, s), 3.55-3.65 (4H, m), 7.26-7.29 (1H, m), 7.33 (1H, d), 7.40 (1H, d), 7.48-7.51 (1H, m), 8.00 (1H, d), 8.36-8.38 (1H, m).

Compounds listed in the table below were prepared using methods described in Cmpd. 147.

| Example/Cmpd number | Structure | LCMS [M + H]+ | 1H NMR |
|---|---|---|---|
| 158 | 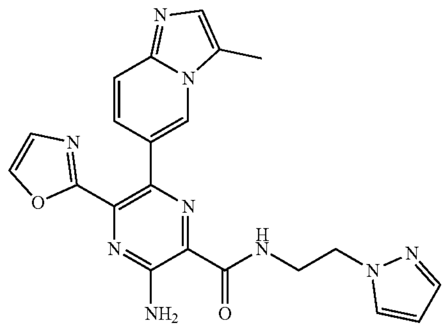 [SMILES: Cc1cnc2ccc(-c3nc(C(=O)NCCn4cccn4)c(N)nc3-c3ncco3)cn12] | 430.2 | 1H-NMR (300 MHz, Methanol-d4) δ 2.50 (3H, d), 3.80 (2H, t), 4.39 (2H, t), 6.26 (1H, t), 7.25 (1H, dd), 7.31 (1H, d), 7.38 (1H, d), 7.43-7.52 (2H, m), 7.64 (1H, d), 7.99 (1H, d), 8.31 (1H, t). |
| 159 | 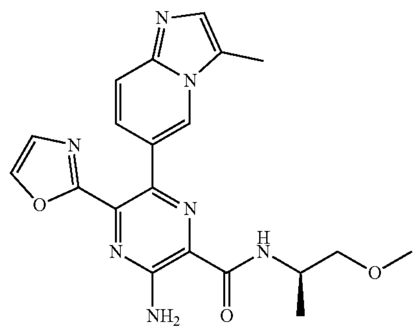 [SMILES: COC[C@@H](C)NC(=O)c1nc(-c2ccc3ncc(C)n3c2)c(-c2ncco2)nc1N] | 408.3 | 1H NMR (400 MHz, DMSO-d6) δ 1.2 (3H, d), 2.4 (3H, s), 3.3 (3H, s), 3.4 (1H, dd), 3.5 (1H, dd), 4.2 (1H, dt), 7.2 (1H, dd), 7.4 (1H, s), 7.4 (1H, s), 7.5 (1H, d), 7.9 (2H, s), 8.3 (1H, s), 8.3 (1H, t), 8.5 (1H, d) |
| 160 | 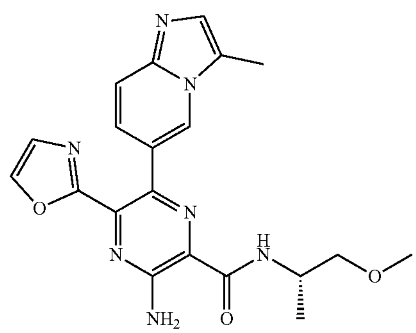 [SMILES: COC[C@H](C)NC(=O)c1nc(-c2ccc3ncc(C)n3c2)c(-c2ncco2)nc1N] | 408.3 | 1H NMR (400 MHz, DMSO-d6) δ 1.2 (3H, d), 2.4 (3H, s), 3.3 (3H, s), 3.4 (1H, dd), 3.5 (1H, dd), 4.2 (1H, dt), 7.2 (1H, dd), 7.4 (1H, s), 7.4 (1H, s), 7.5 (1H, d), 7.9 (2H, s), 8.3 (1H, s), 8.3 (1H, t), 8.5 (1H, d) |
| 163 | 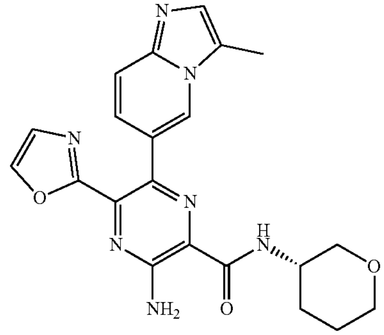 [SMILES: Cc1cnc2ccc(-c3nc(C(=O)N[C@H]4CCCOC4)c(N)nc3-c3ncco3)cn12] | 420.3 | 1H NMR (400 MHz, DMSO-d6) δ 1.5-1.8 (3H, m), 1.9 (1H, s), 2.4 (3H, d), 3.3 (3H, s), 3.4 (1H, d), 3.7-3.8 (2H, m), 4.0 (1H, dd), 7.2 (1H, dd), 7.4 (2H, dd), 7.5 (1H, dd), 7.9 (2H, s), 8.3 (1H, d), 8.3-8.4 (1H, m), 8.5 (1H, d) |

-continued
| Example/ Cmpd number | Structure | LCMS [M + H]+ | 1H NMR |
|---|---|---|---|
| 164 | 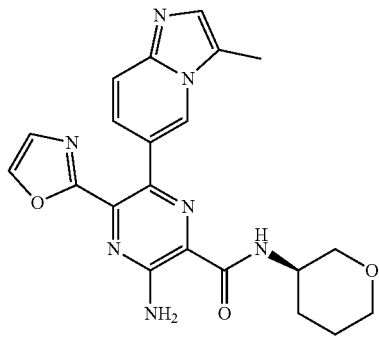 [SMILES: Cc1cnc2ccc(-c3nc(C(=O)N[C@@H]4CCCOC4)c(N)nc3-c3ncco3)cn12] | 420.3 | 1H NMR (300 MHz, DMSO-d$_6$) δ 1.5-1.8 (3H, m), 1.9 (1H, d), 2.4-2.5 (3H, m), 3.3 (1H, s), 3.4 (1H, s), 3.7-3.8 (2H, m), 4.0 (1H, dt), 7.2 (1H, dd), 7.4 (2H, dd), 7.5 (1H, dd), 7.9 (2H, s), 8.3 (1H, d), 8.3-8.4 (1H, m), 8.5 (1H, d). |
| 165 | 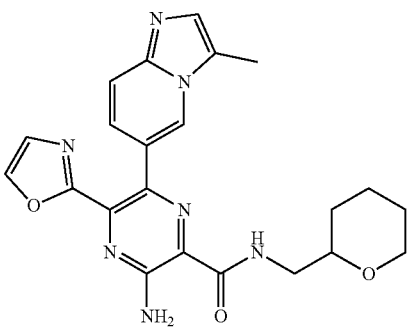<br>isomer 1 | 434.3 | 1H NMR (400 MHz, DMSO-d$_6$) δ 1.16-1.26 (1H, m), 1.44 (3H, s), 1.61 (1H, d), 1.77 (1H, s), 2.44 (3H, d), 3.24-3.53 (4H, m), 3.82-3.89 (1H, m), 7.22 (1H, dd), 7.39 (2H, dd), 7.49 (1H, dd), 7.92 (2H, s), 8.28 (1H, d), 8.32-8.38 (1H, m), 8.77 (1H, t) |
| 166 | 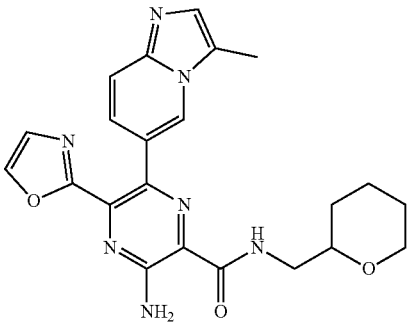<br>isomer 2 | 434.3 | 1H NMR (400 MHz, DMSO-d$_6$) δ 1.15-1.30 (1H, m), 1.45 (3H, s), 1.61 (1H, d), 1.77 (1H, s), 2.40-2.48 (3H, m), 3.27-3.33 (2H, m), 3.30 (1H, s), 3.47 (1H, t), 3.86 (1H, d), 7.22 (1H, dd), 7.39 (2H, dd), 7.49 (1H, dd,), 7.92 (2H, s), 8.28 (1H, d), 8.35 (1H, d), 8.77 (1H, t) |
| 167 | 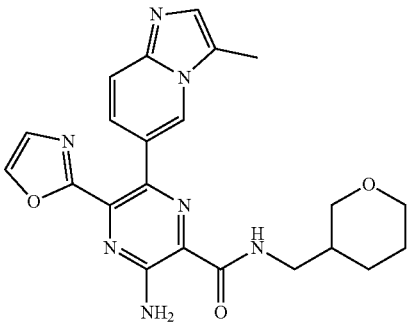<br>isomer 1 | 434.2 | 1H NMR (300 MHz, DMSO-d$_6$) δ 1.14-1.32 (1H m,), 1.37-1.64 (2H m), 1.66-1.91 (2H, m), 2.41 (3H, d), 3.05-3.22 (3H, m), 3.27 (1H, dd), 3.54-3.84 (2H, m), 7.22 (1H,dd), 7.34 (1H, d), 7.37 (1H, d), 7.46 (1H, dd), 7.87 (2H, s), 8.25 (1H, d), 8.32 (1H, dd), 8.86 (1H, t). |

| Example/Cmpd number | Structure | LCMS [M + H]+ | 1H NMR |
|---|---|---|---|
| 168 | 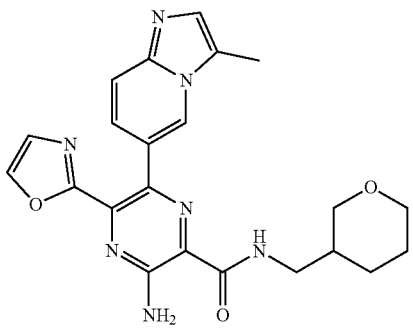 isomer 2 | 434.3 | 1H NMR (300 MHz, DMSO-d6) δ 1.23 (1H, d), 1.32-1.52 (1H, m), 1.52-1.64 (1H, m), 1.71-1.99 (2H, m), 2.41 (3H, d), 3.05-3.19 (3H, m), 3.20-3.31 (1H, m), 3.62-3.80 (2H, m), 7.22 (1H, dd), 7.36 (2H, dd), 7.46 (1H, dd), 7.87 (2H, s), 8.25 (1H, d), 8.32 (1H, dd), 8.86 (1H, t). |
| 205 | 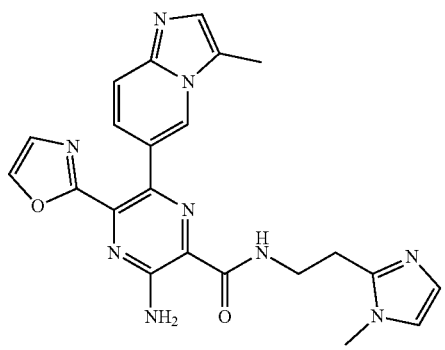 [SMILES: Cc1cnc2ccc(-c3nc(C(=O)NCCc4nccn4C)c(N)nc3-c3ncco3)cn12] | 444.3 | 1H NMR (300 MHz, Methanol-d4) δ 2.50 (3H, s), 3.02 (2H, t), 3.68 (3H, s), 3.74 (2H, t), 6.82 (1H, s), 6.97 (1H, s), 7.21-7.33 (2H, m), 7.38 (1H, s), 7.48 (1H, d), 7.99 (1H, s), 8.32 (1H, s). |
| 207 | 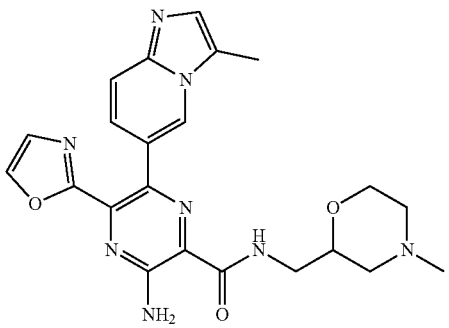 [SMILES: Cc1cnc2ccc(-c3nc(C(=O)NCC4CN(C)CCO4)c(N)nc3-c3ncco3)cn12] | 449.3 | 1H NMR (400 MHz, DMSO-d6) δ 1.7 (1H, t), 1.9-2.0 (1H, m), 2.2 (3H, s), 2.4 (3H, s), 2.6 (1H, d), 2.7 (1H, d), 3.4 (2H, d), 3.5 (1H, td), 3.6 (1H, d), 3.8 (1H, d), 7.2 (1H, dd), 7.3-7.4 (2H, m), 7.5 (1H, d), 7.9 (2H, s), 8.3 (1H, s), 8.3 (1H, d), 8.8 (1H, t) |
| 208 | 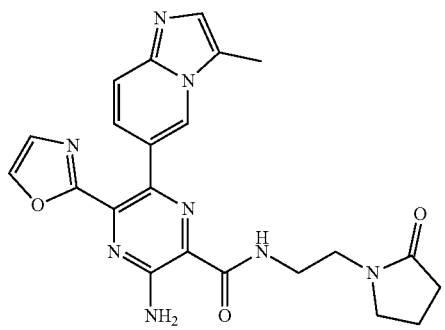 [SMILES: Cc1cnc2ccc(-c3nc(C(=O)NCCN4CCCC4=O)c(N)nc3-c3ncco3)cn12] | 447.3 | 1H-NMR (300 MHz, Methanol-d4) δ 2.02 (2H, p), 2.32 (2H, t), 2.53 (3H, d), 3.50-3.63 (6H, m), 7.24-7.51 (4H, m), 7.99 (1H, d), 8.41 (1H, s). |

| Example/Cmpd number | Structure | LCMS [M + H]+ | 1H NMR |
|---|---|---|---|
| 210 | 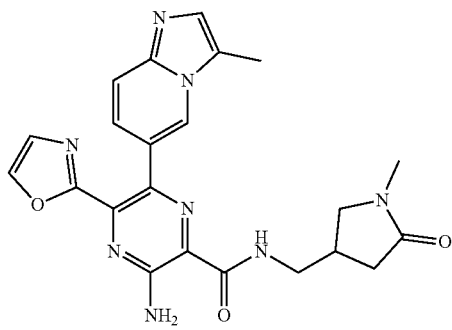<br>isomer 2 | 447.3 | 1H NMR (400 MHz, DMSO-d6) δ 2.10 (1H, dd), 2.33-2.41 (2H, m), 2.45 (3H, d), 2.63 (1H, s), 2.69 (3H, s), 3.17 (1H, dd), 3.36-3.47 (2H, m), 7.24 (1H, dd), 7.39 (2H, dd), 7.46-7.53 (1H, m), 7.91 (2H, s), 8.34 (2H, s), 9.03 (1H, d) |
| 213 | 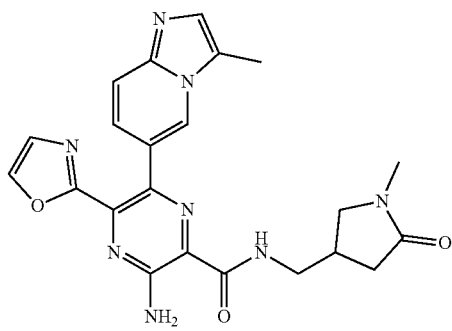<br>isomer 1 | 447.3 | 1H NMR (400 MHz, DMSO-d6) δ 2.10 (1H, dd), 2.33-2.41 (2H, m), 2.45 (3H, d), 2.63-2.69 (4H, m), 3.17 (1H, dd), 3.36 (1H, s), 3.38-3.47 (1H, m), 7.24 (1H, dd), 7.39 (2H, dd), 7.46-7.53 (1H, m), 7.91 (2H, s), 8.28 (1H, d), 8.34 (1H, s), 9.03 (1H, d) |
| 211 | 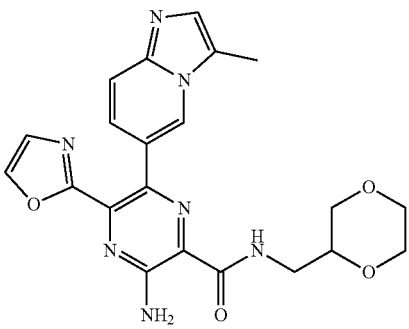 [SMILES: Cc1cnc2ccc(-c3nc(C(=O)NCC4COCCO4)c(N)nc3-c3ncco3)cn12] | 436.3 | 1H NMR (300 MHz, Methanol-d4) δ 2.47-2.57 (3H, m), 3.30-3.48 (3H, m), 3.44-3.60 (1H, m), 3.57-3.76 (2 H, m), 3.71-3.86 (3 H, m), 7.25 (1H, dd), 7.31 (1H, d), 7.38 (1H, d), 7.48 (1H, dd), 7.99 (1H, d), 8.36 (1H, d). |
| 212 | 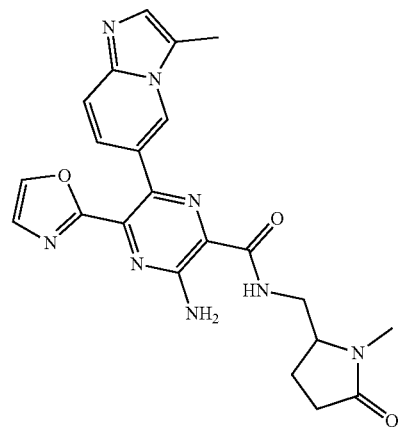 [SMILES: Cc1cnc2ccc(-c3nc(C(=O)NCC4CCC(=O)N4C)c(N)nc3-c3ncco3)cn12] | 447.3 | 1H NMR (300 MHz, DMSO-d6) δ 1.9-2.1 (3H, m), 2.3 (1H, q), 2.4 (3H, s), 2.8 (3H, s), 3.4-3.6 (2H, m), 3.7 (1H, s), 7.2 (1H, dd), 7.4 (2H, dd), 7.5-7.5 (1H, m), 7.9 (2H, s), 8.3 (1H, d), 8.4 (1H, d), 8.9 (1H, t). |

| Example/Cmpd number | Structure | LCMS [M + H]+ | 1H NMR |
|---|---|---|---|
| 215 | 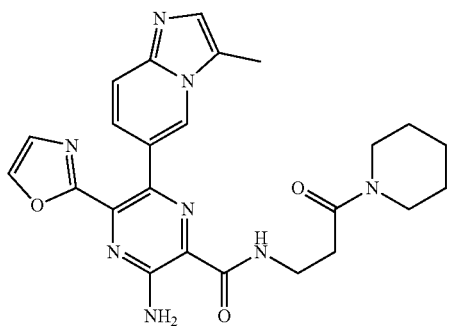 [SMILES: Cc1cnc2ccc(-c3nc(C(=O)NCCC(=O)N4CCCCC4)c(N)nc3-c3ncco3)cn12] | 475.4 | 1H NMR (300 MHz, DMSO-d6) δ 1.34-1.55 (6H, m), 2.58 (5H, d), 3.53 (6H, d), 7.31 (1H, s), 7.84-8.15 (5H, m), 8.30 (1H, s), 8.87 (2H, d) |
| 216 | 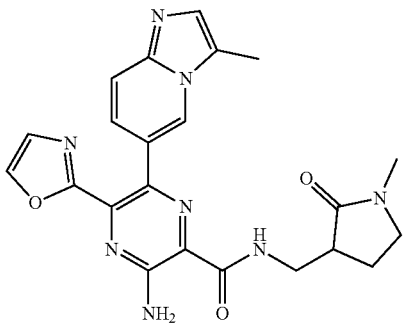<br>isomer 1 | 447.3 | 1H-NMR (400 MHz, DMSO-d6) δ 1.77 (1H, dq), 2.13 (1H, ddd), 2.48 (3H, s), 2.66 (1H, q), 2.73 (3H, s), 3.27 (2H, td), 3.45 (1H, m), 3.56 (1H, dt), 7.19 (1H, dd), 7.37 (1H, s), 7.43 (1H, s), 7.49 (1H, d), 7.91 (2H, s), 8.28 (1H, s), 8.41 (1H, s), 9.18 (1H, dd). |
| 217 | 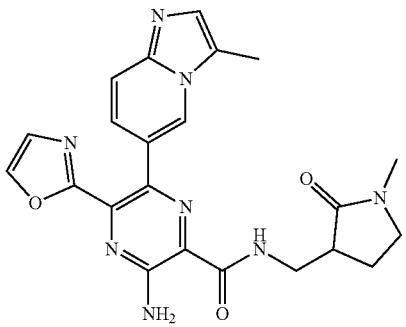<br>isomer 2 | 461.3 | 1H NMR (300 MHz, DMSO-d6) δ 1.65-1.90 (4H, m), 2.45-2.65 (5H, m), 3.20-3.40 (6H, m), 7.31 (1H, s), 7.90-8.20 (5H, m), 8.30 (1H, s), 8.88-8.98 (2H, m) |
| 218 | 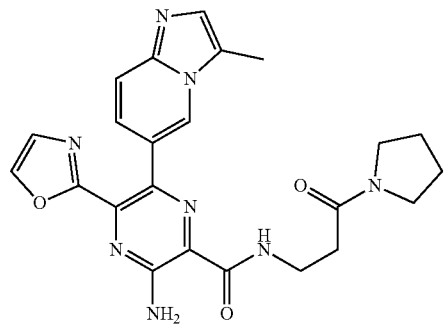 [SMILES: Cc1cnc2ccc(-c3nc(C(=O)NCCC(=O)N4CCCC4)c(N)nc3-c3ncco3)cn12] | 390.2 | 1H NMR (300 MHz, DMSO-d6) δ 1.60-1.69 (2H, m), 2.15-2.23 (4H, m), 2.47-2.56 (3H, m), 4.39-4.47 (1H, m), 7.19-7.20 (1H, m), 7.22-7.23 (2H, m), 7.33-7.38 (1H, m), 7.84-7.86 (2H, m), 8.23-8.25 (1H, m), 8.34-8.36 (1H, m), 8.84-8.87 (1H, m). |

| Example/ Cmpd number | Structure | LCMS [M + H]+ | 1H NMR |
|---|---|---|---|
| 220 | 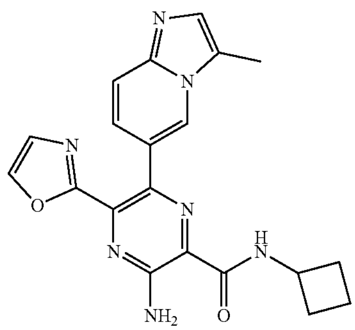 [SMILES: Cc1cnc2ccc(-c3nc(C(=O)NC4CCC4)c(N)nc3-c3ncco3)cn12] | 402.1 | 1H-NMR (400 MHz, DMSO-d6) δ 2.14 (6H, s), 2.44 (3H, s), 2.47 (1H, s), 7.21 (1H, dd), 7.31-7.42 (2H, m), 7.47 (1H, d), 7.87 (2H, s), 8.26 (1H, s), 8.35 (1H, d), 9.22 (1H, s) |
| 222 | 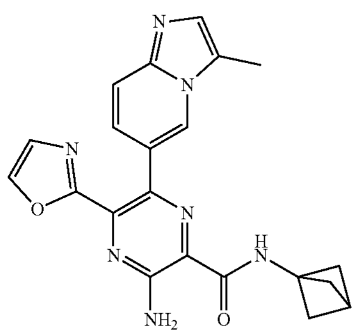 [SMILES: Cc1cnc2ccc(-c3nc(C(=O)NC45CC(C4)C5)c(N)nc3-c3ncco3)cn12] | 447.2 | 1H NMR (400 MHz, DMSO-d6) δ 1.77 (1H, dq), 2.13 (1H, ddd), 2.48 (3H, s), 2.66 (1H, q), 2.73 (3H, s), 3.27 (2H, td), 3.45 (1H, m), 3.56 (1H, dt), 7.19 (1H, dd), 7.37 (1H, s), 7.43 (1H, s), 7.49 (1H, d), 7.91 (2H, s), 8.28 (1H, s), 8.41 (1H, s), 9.18 (1H, dd). |
| 225 | 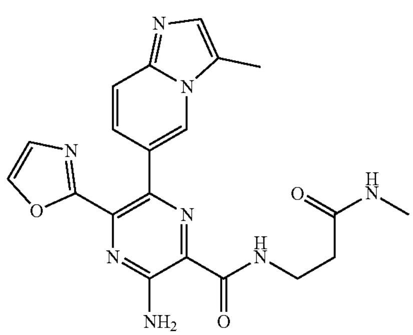 [SMILES: CNC(=O)CCNC(=O)c1nc(-c2ccc3ncc(C)n3c2)c(-c2ncco2)nc1N] | 421.2 | 1H-NMR (300 MHz, Methanol-d4) δ 1.87-2.60 (5H, m), 2.70 (3H, s), 3.66 (2H, t), 7.23 (1H, dd), 7.32 (1H, d), 7.38 (1H, d), 7.43-7.51 (1H, m), 7.99 (1H, d), 8.37 (1H, s). |
| 226 | 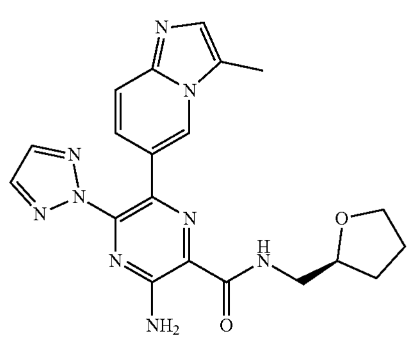 [SMILES: Cc1cnc2ccc(-c3nc(C(=O)NC[C@@H]4CCCO4)c(N)nc3-n3nccn3)cn12] | 420.3 | 1H NMR (300 MHz, DMSO-d6) δ 1.76 (4H, m), 2.36 (3H, d), 3.40 (2H, d), 3.62 (1H, q), 3.78 (1H, q), 4.04 (1H, t), 6.87 (1H, dd), 7.39 (2H, m), 7.92 (1H, m), 8.12 (4H, s), 8.85 (1H, t). |

| Example/Cmpd number | Structure | LCMS [M + H]+ | 1H NMR |
|---|---|---|---|
| 228 | 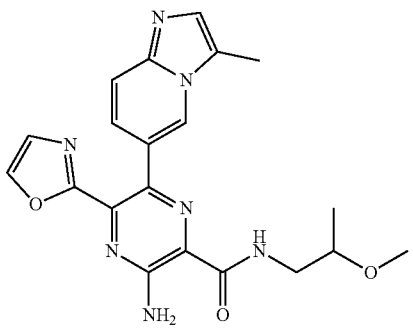 [SMILES: COC(C)CNC(=O)c1nc(-c2ccc3ncc(C)n3c2)c(-c2ncco2)nc1N] | 408.3 | 1H NMR (400 MHz, DMSO-d6) δ 1.1 (3H, d), 2.4 (3H, d), 3.3 (3H, s), 3.3 (1H, s), 3.4 (1H, d), 3.5-3.6 (1H, m), 7.2 (1H, dd), 7.4 (1H, d), 7.4 (1H, d), 7.5 (1H, dd), 7.9 (2H, s), 8.3 (1H, d), 8.3-8.4 (1H, m), 8.8 (1H, t) |
| 237 | 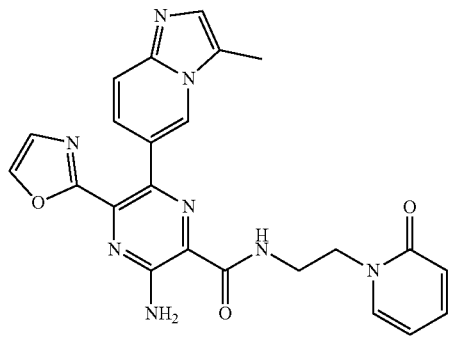 [SMILES: Cc1cnc2ccc(-c3nc(C(=O)NCCn4ccccc4=O)c(N)nc3-c3ncco3)cn12] | | 1H NMR (300 MHz, Methanol-d4) δ 2.51 (3H, d), 3.77 (2H, t), 4.25 (2H, t), 6.26-6.36 (1H, m), 6.53 (1H, d), 7.23 (1H, dd), 7.35 (2H, dd), 7.42-7.53 (2H, m), 7.53-7.61 (1H, m), 7.99 (1H, d), 8.38 (1H, s). |
| 238 | 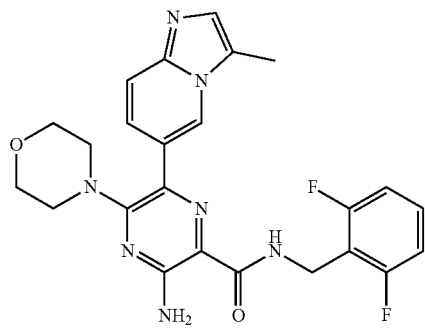 [SMILES: Cc1cnc2ccc(-c3nc(C(=O)NCc4c(F)cccc4F)c(N)nc3N3CCOCC3)cn12] | 480.3 | 1H NMR (300 MHz, Chloroform-d) δ 2.54 (3H, s), 3.26 (4H, t), 3.64-3.73 (4H, m), 4.73 (2H, d), 6.91 (2H, t), 7.47 (1H, s), 7.59-7.74 (2H, m), 8.00 (1H, s), 8.31 (1H, s) |
| 239 | 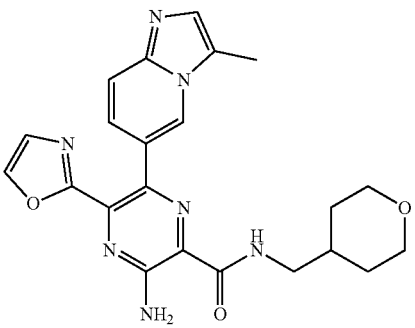 [SMILES: Cc1cnc2ccc(-c3nc(C(=O)NCC4CCOCC4)c(N)nc3-c3ncco3)cn12] | 434.2 | 1H NMR (400 MHz, DMSO-d6) δ 1.21 (2H, qd), 1.58 (2H, d), 1.76-1.91 (1H, m), 2.42 (3H, s), 3.24 (4H, dt), 3.75-3.90 (2H, m), 7.23 (1H, dd), 7.37 (2H, d), 7.48 (1H, d), 7.89 (2H, s), 8.26 (1H, s), 8.33 (1H, s), 8.87 (1H, t) |

| Example/ Cmpd number | Structure | LCMS [M + H]+ | 1H NMR |
|---|---|---|---|
| 240 | 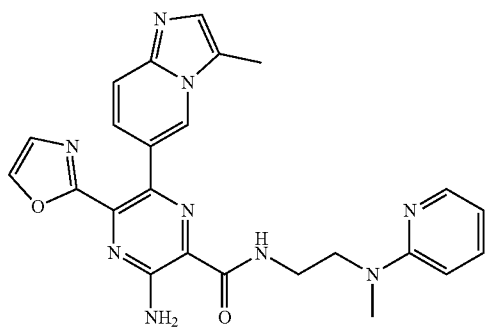 [SMILES: Cc1cnc2ccc(-c3nc(C(=O)NCCN(C)c4ccccn4)c(N)nc3-c3ncco3)cn12] | 470.4 | 1H NMR (300 MHz, DMSO-d6) δ 2.42 (3H, d), 3.02 (3H, s), 3.50 (2H, q), 3.72 (2H, t), 6.27 (1H, d), 6.65 (1H, d), 7.19 (1H, d), 7.35 (1H, d), 7.38-7.45 (2H, m), 7.50 (1H, d), 7.78-7.99 (3H, m), 8.26 (2H, t), 9.04 (1H, t) |
| 241 | 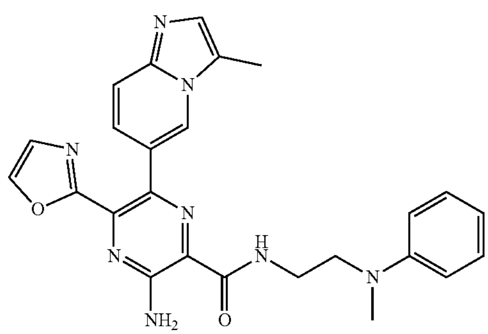 [SMILES: Cc1cnc2ccc(-c3nc(C(=O)NCCN(C)c4ccccc4)c(N)nc3-c3ncco3)cn12] | 408.2 | 1H NMR (400 MHz, DMSO-d6) δ 1.1 (3H, d), 2.4 (3H, s), 3.3 (3H, s), 3.3-3.4 (2H, m), 3.5 (1H, q), 7.2 (1H, dd), 7.4 (1H, s), 7.4 (1H, s), 7.5 (1H, d), 7.9 (2H, s), 8.3 (1H, s), 8.3-8.4 (1H, m), 8.7 (1H, t) |
| 242 | 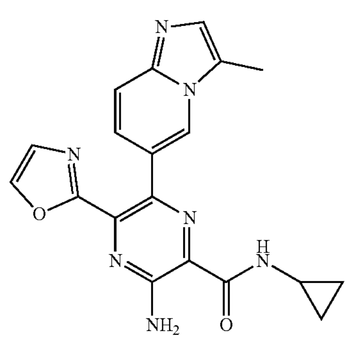 [SMILES: Cc1cnc2ccc(-c3nc(C(=O)NC4CC4)c(N)nc3-c3ncco3)cn12] | 420.2 | 1H NMR (400 MHz, DMSO-d6) δ 1.7 (1H, dq), 1.9-2.0 (1H, m), 2.4 (3H, s), 2.6 (1H, q), 3.3 (2H, t), 3.5 (1H, dd), 3.6-3.7 (2H, m), 3.7-3.8 (1H, m), 6.9 (1H, dd), 7.4 (1H, s), 7.4 (1H, d), 7.9 (1H, s), 8.1 (1H, s), 8.1 (2H, s), 9.0 (1H, t) |
| 243 | Isomer 2 | 394.3 | 1H NMR (400 MHz, DMSO-d6) δ 2.4 (3H, s), 3.3 (3H, s), 3.5 (4H, d), 6.9 (1H, dd), 7.4-7.4 (2H, m), 7.9 (1H, d), 8.1 (4H, s), 8.9 (1H, s) |

| Example/ Cmpd number | Structure | LCMS [M + H]+ | 1H NMR |
|---|---|---|---|
| 244 | 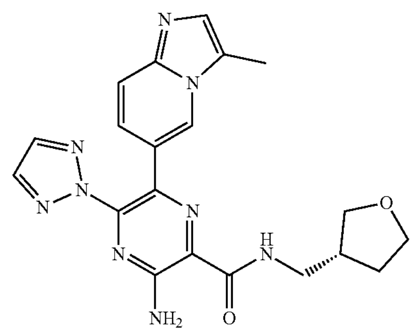 [SMILES: Cc1cnc2ccc(-c3nc(C(=O)NC[C@H]4CCOC4)c(N)nc3-n3nccn3)cn12] | 469.4 | 1H NMR (300 MHz, DMSO-d6) δ 2.42 (3H, d), 2.92 (3H, s), 3.48 (4H, s), 6.54 (1H, t), 6.72-6.81 (2H, m), 7.11 (2H, dd), 7.20 (1H, dd), 7.36 (2H, dd), 7.48 (1H, dd), 7.89 (2H, s), 8.22-8.31 (2H, m), 8.94 (1H, d) |
| 245 | 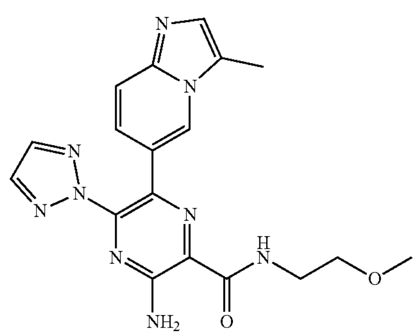 [SMILES: COCCNC(=O)c1nc(-c2ccc3ncc(C)n3c2)c(-n2nccn2)nc1N] | 376.2 | 1H NMR (400 MHz, DMSO-d6) δ 0.6-0.8 (4H, m), 2.4 (3H, s), 2.9 (1H, td), 7.2 (1H, dd), 7.4 (3H, m), 7.9 (2H, s), 8.3 (1H, s), 8.4 (1H, t), 8.7 (1H, d,). |
| 248 | Isomer 1 | 408.2 | 1H NMR (400 MHz, DMSO-d6) δ 1.1 (3H, d), 2.4 (3H, s), 3.3 (3H, s), 3.3-3.4 (2H, m), 3.5 (1H, q), 7.2 (1H, dd), 7.4 (1H, s), 7.4 (1H, s), 7.5 (1H, d), 7.9 (2H, s), 8.3 (1H, s), 8.3 (1H, s), 8.7 (1H, t) |
| 249 | 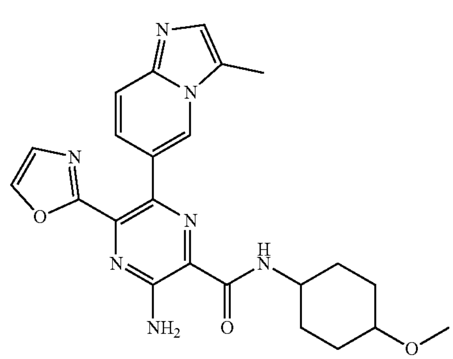 [SMILES: COC1CCC(NC(=O)c2nc(-c3ccc4ncc(C)n4c3)c(-c3ncco3)nc2N)CC1] | 448.3 | 1H NMR (300 MHz, DMSO-d6) (400 MHz, Methanol-d4) δ 1.29-1.43 (2H, m), 1.52 (2H, d), 2.03 (2H, d), 2.14 (2H, d), 2.52 (3H, d), 3.24-3.30 (1H, m), 3.37 (3H, s), 3.80-3.95 (1H, m), 7.28 (1H, d), 7.32 (1H, s), 7.40 (1H, s), 7.50 (1H, d), 8.00 (1H, s), 8.37-8.40 (1H, m). |

| Example/Cmpd number | Structure | LCMS [M + H]+ | 1H NMR |
|---|---|---|---|
| 251 | 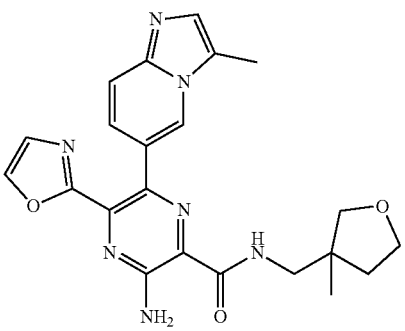 [SMILES: Cc1cnc2ccc(-c3nc(C(=O)NCC4(C)CCOC4)c(N)nc3-c3ncco3)cn12] | 434.3 | 1H NMR (300 MHz, DMSO-d6) δ 1.07 (3H, s), 1.50-1.64 (1H, m), 1.90 (1H, t), 2.43 (3H, d), 3.27 (1H, d), 3.35 (2H, d), 3.64 (1H, s), 3.68-3.87 (2H, m), 7.19 (1H, d), 7.38 (2H, d), 7.48 (1H, d), 7.87 (2H, s), 8.28 (1H, d), 8.40 (1H, d), 8.86 (1H, t) |
| 252 | 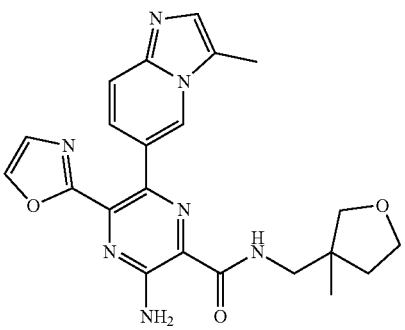 [SMILES: Cc1cnc2ccc(-c3nc(C(=O)NCC4(C)CCOC4)c(N)nc3-c3ncco3)cn12] | 434.3 | 1H NMR (300 MHz, DMSO-d6) 1.07 (3H, s), 1.49-1.63 (1H, m), 1.84-1.96 (1H, m), 2.43 (3H, d), 3.27 (1H, d), 3.35 (2H, d), 3.66 (1H, d), 3.68-3.88 (2H, m), 7.19 (1H, d), 7.38 (2H, d), 7.48 (1H, d), 7.87 (2H, s), 8.28 (1H, d), 8.40 (1H, d), 8.86 (1H, t) |
| 253 | 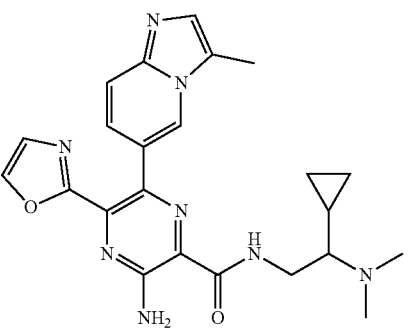<br>isomer 1 | 447.3 | 1H NMR (400 MHz, DMSO-d6) δ 0.1 (1H, dd), 0.3 (1H, dd), 0.3-0.4 (1H, m), 0.5-0.6 (1H, m), 0.7-0.8 (1H, m), 1.9 (1H, d), 2.3 (6H, s), 2.4 (3H, s), 3.4-3.5 (2H, m), 7.2 (1H, dd), 7.4 (2H, d), 7.5 (1H, d), 8.3 (1H, s), 8.3 (1H, s), 8.6 (1H, t). |
| 254 | 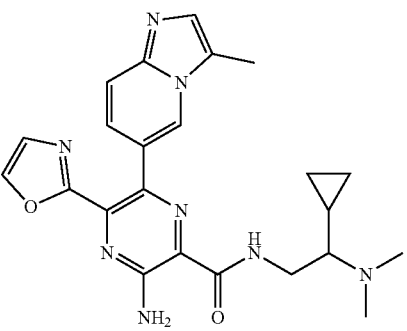<br>isomer 2 | 461.4 | 1H NMR (400 MHz, DMSO-d6) δ 1.54 (1H, d), 1.71 (1H, s), 1.86 (2H, s), 2.48 (4H, s), 2.82 (3H, s), 3.28 (2H, d), 3.48-3.55 (2H, d), 7.17 (1H, d), 7.37 (1H, s), 7.42 (1H, s), 7.49 (1H, d), 7.90 (2H, s), 8.28 (1H, s), 8.39 (1H, s), 9.16 (1H, s) |

| Example/Cmpd number | Structure | LCMS [M + H]+ | 1H NMR |
|---|---|---|---|
| 255 | 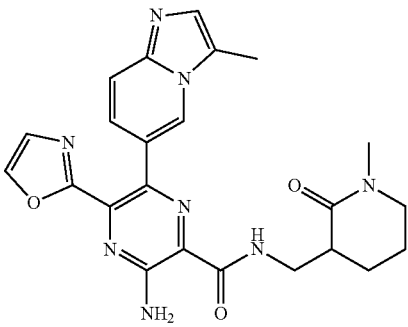 [SMILES: Cc1cnc2ccc(-c3nc(C(=O)NCC4CCCN(C)C4=O)c(N)nc3-c3ncco3)cn12] | 406.1 | 1H NMR (300 MHz, DMSO-d6) δ1.99 (1H, dq), 2.17 (1H, m), 2.42 (3H, d), 3.67 (2H, m), 3.86 (2H, dt), 4.46 (1H, dd), 7.19 (1H, dd), 7.40 (3H, m), 7.85 (2H, s), 8.25 (1H, d), 8.37 (1H, dd), 8.70 (1H, d). |
| 258 | 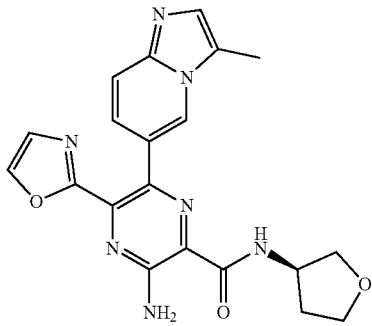 | 434.3 | 1H-NMR DMSO-d6,) 400 MHz) δ 1.19 (3H, d),1.66 (1H, m), 1.82 (2H, m), 1.92(1H, m), 2.42 (3H, s), 3.70 (1H, m), 3.75 (1H, q), 3.98 (1H, m), 4.04 (1H, ddd), 7.22 (1H, dd), 7.35 (1H, s), 7.42-7.52 (2H, dd), 7.90 (2H, s), 8.33 (2H, m), 8.36 (1H, s) |
| 260 | 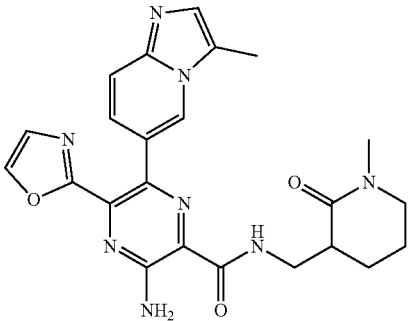 [SMILES: Cc1cnc2ccc(-c3nc(C(=O)NCC4CCCN(C)C4=O)c(N)nc3-c3ncco3)cn12] | 434.3 | 1H NMR (400 MHz, DMSO-d6) δ 1.29 (3H, s), 1.35 (3H, s), 2.22 (1H, dd), 2.33 (1H, dd), 2.42 (3H, s), 3.62 (2H, m), 4.67 (1H, p), 7.24 (1H, dd), 7.35 (1H, s), 7.39 (1H, s), 7.49 (1H, d), 7.90 (2H, s), 8.27 (1H, s), 8.32 (1H, s), 8.83 (1H, t) |
| 262 | 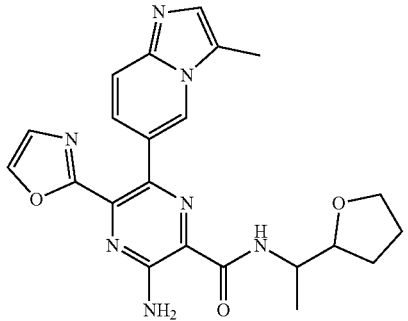 [SMILES: Cc1cnc2ccc(-c3nc(C(=O)NC(C)C4CCCO4)c(N)nc3-c3ncco3)cn12] | 434.3 | 1.19 (3H, d),1.66 (1H, m), 1.82 (2H, m), 1.92(1H, m), 2.42 (3H, s), 3.70 (1H, m), 3.75 (1H, q), 3.98 (1H, m), 4.04 (1H, ddd), 7.22 (1H, dd), 7.35 (1H, s), 7.42 (1H, s), 7.52 (1H, d), 7.90 (2H, s), 8.33 (2H, m), 8.36 (1H, s) |

| Example/Cmpd number | Structure | LCMS [M + H]+ | 1H NMR |
|---|---|---|---|
| 263 | 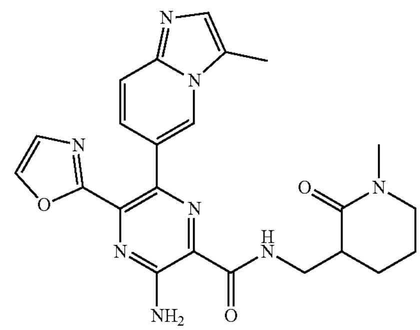 [SMILES: Cc1cnc2ccc(-c3nc(C(=O)NCC4CCCN(C)C4=O)c(N)nc3-c3ncco3)cn12] | 461.4 | 1H NMR (400 MHz, DMSO-d6) δ 1.54 (1H, d), 1.71 (1H, s), 1.86 (2H, s), 2.48 (4H, s), 2.82 (3H, s), 3.29 (2H, d), 3.46-3.60 (2H, m), 7.17 (1H, d), 7.37 (1H, s), 7.42 (1H, s), 7.48 (1H, d), 7.90 (2H, s), 8.28 (1H, s), 8.39 (1H, s), 9.17(1H, s). |
| 266 | 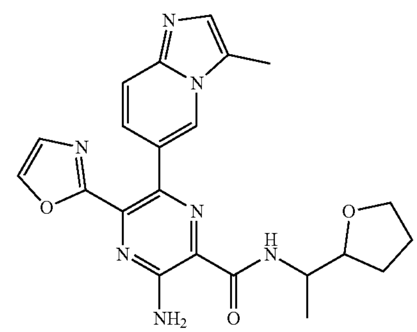 [SMILES: Cc1cnc2ccc(-c3nc(C(=O)NC(C)C4CCCO4)c(N)nc3-c3ncco3)cn12] | 434.3 | 1H-NMR DMSO-d6,) 400 MHz) 1.20 (3H, d), 1.76 (1H, m), 1.95 (3H, m), 2.43 (3H, d), 3.65 (1H, q), 3.83 (1H, m), 3.90 (1H, q), 4.03 (1H, dt), 7.22 (1H, dd), 7.36 (1H, d), 7.41 (1H, d), 7.50 (1H, dd), 7.90 (2H, s), 8.28 (1H, d), 8.36 (1H, dd), 8.48 (1H, d) |
| 269 | isomer 2 | 447.3 | 1H-NMR (400 MHz, DMSO-d6,) δ 0.1 (1H, dd), 0.3-0.3 (1H, m), 0.4-0.4 (1H, m), 0.6 (1H, d), 0.7-0.8 (1H, m), 1.9 (1H, d), 2.3 (6H, s), 2.4 (3H, s), 3.5 (2H, dt), 7.2 (1H, dd), 7.4 (2H, d), 7.5 (1H, d), 7.9 (2H, s), 8.3 (1H, s), 8.3 (1H, s), 8.6 (1H, d) |
| 270 | 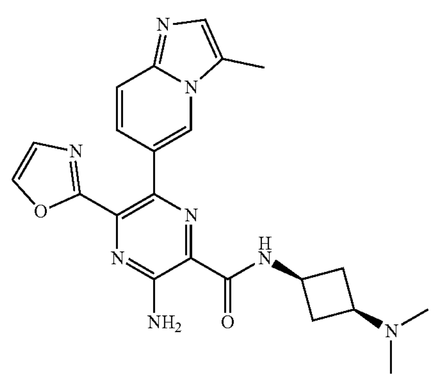 [SMILES: Cc1cnc2ccc(-c3nc(C(=O)N[C@H]4C[C@@H](N(C)C)C4)c(N)nc3-c3ncco3)cn12] | 434.3 | 1H-NMR (400 MHz, DMSO-d6,) δ 1.29 (3H, s), 1.35 (3H, s), 2.22 (1H, dd), 2.33 (1H, dd), 2.42 (3H, s), 3.62 (2H, m), 4.67 (1H, p), 7.24 (1H, dd), 7.35 (1H, s), 7.39 (1H, s), 7.49 (1H, d), 7.90 (2H, s), 8.27 (1H, s), 8.32 (1H, s), 8.83 (1H, t) |

-continued
| Example/ Cmpd number | Structure | LCMS [M + H]+ | 1H NMR |
|---|---|---|---|
| 271-1 | 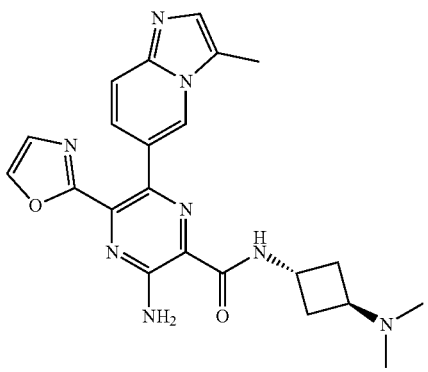 [SMILES: Cc1cnc2ccc(-c3nc(C(=O)N[C@H]4C[C@H](N(C)C)C4)c(N)nc3-c3ncco3)cn12] | 433.2 | 1H-NMR (300 MHz, MeOH-d4) δ 1.88-1.97 (2H, m), 2.17 (6H, s), 2.45-2.62 (3H, m), 2.52 (3H, s), 4.21-4.29 (1H, m), 7.21-7.24 (1H, d), 7.30 (1H, s), 7.39 (1H, s), 7.45-7.49 (1H, d), 7.98 (1H, s), 8.43 (1H, s). |
| 271-2 | 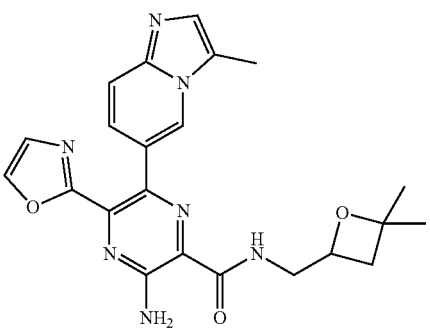 isomer 1 | 433.2 | 1H-NMR (300 MHz, MeOH-d4) δ 2.18 (6H, s), 2.26-2.44 (4H, m), 2.50 (3H, s), 2.92-3.01 (1H, m), 4.43-4.52 (1H, m), 7.27-7.31 (2H, m), 7.38 (1H, s), 7.48-7.51 (1H, d), 7.98 (1H, s), 8.36 (1H, s). |
| 274 | 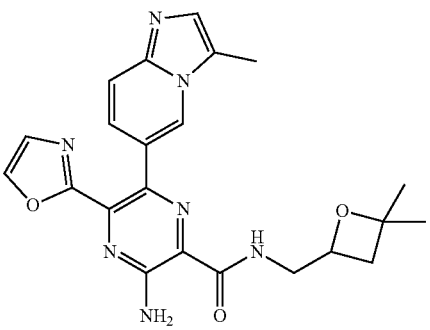 isomer 2 434.2 | | 1H- NMR (DMSO-d6, 400 MHz) 1.20 (3H, d), 1.76 (1H, m), 1.95 (3H, m), 2.43 (3H, d), 3.65 (1H, q), 3.83 (1H, m), 3.90 (1H, q), 4.03 (1H, dt), 7.22 (1H, dd), 7.36 (1H, d), 7.41 (1H, d), 7.50 (1H, dd), 7.90 (2H, s), 8.28 (1H, d), 8.36 (1H, dd), 8.48 (1H, d) |

| Example/ Cmpd number | Structure | LCMS [M + H]+ | 1H NMR |
|---|---|---|---|
| 277 | 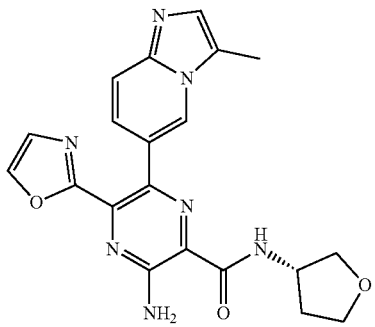 [SMILES: Cc1cnc2ccc(-c3nc(C(=O)N[C@H]4CCOC4)c(N)nc3-c3ncco3)cn12] | 406.1 | 1H- NMR: (300 MHz, DMSO-d6) δ 1.99 (1H ,m), 2.18 (1H, m,), 2.42 (3H, d), 3.67 (2H ,m), 3.86 (2H, dt), 4.47 (1H ,m), 7.18 (1H, dd), 7.36 (2H ,dd), 7.45 (1H ,dd), 7.85 (2H, s), 8.24 (1H, d), 8.37 (1H ,dd), 8.70 (1H, d). |
| 288 | 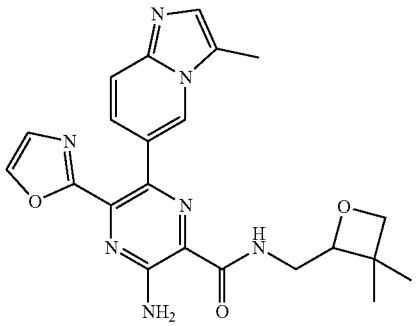 [SMILES: Cc1cnc2ccc(-c3nc(C(=O)NCC4OCC4(C)C)c(N)nc3-c3ncco3)cn12] | 434.3 | 1H- NMR (300 MHz, DMSO-d6) δ 1.20 (6H, s), 2.41-2.44 (3H, m), 3.53-3.57 (2H, m), 4.05-4.07 (1H, m), 4.15-4.17 (1H, m), 4.47-4.51 (1H, m), 7.17-7.20 (1H, m), 7.22-7.25 (2H, m) 7.33-7.34 (1H, m), 7.85-7.89 (2H, m), 8.24-8.26 (1H, m), 8.32-8.35 (1H, m), 8.74-8.76 (1H, m) |
| 289 | 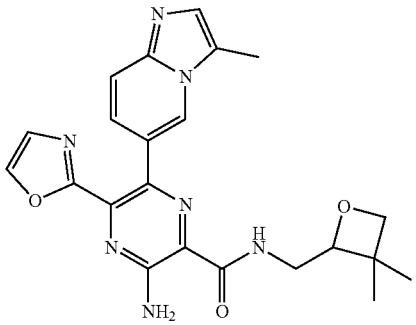 [SMILES: Cc1cnc2ccc(-c3nc(C(=O)NCC4OCC4(C)C)c(N)nc3-c3ncco3)cn12] | 434.3 | 1H- NMR (300 MHz, DMSO-d6) δ 1.20 (6H, s), 2.41-2.44 (3H, m), 3.53-3.57 (2H, m), 4.05-4.07 (1H, m), 4.15-4.17 (1H, m), 4.47-4.51 (1H, m), 7.17-7.20 (1H, m), 7.22-7.25 (2H, m) 7.33-7.34 (1H, m), 7.85-7.89 (2H, m), 8.24-8.26 (1H, m), 8.32-8.35 (1H, m), 8.74-8.76 (1H, m) |
| 292 | 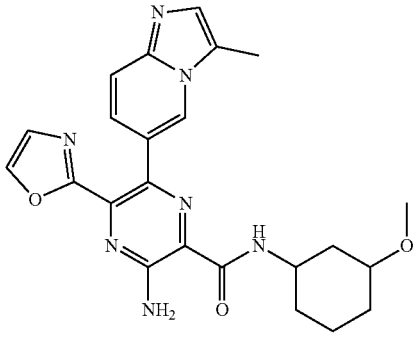<br>isomer 1 | 448.2 | 1H-NMR (400 MHz, DMSO-d6) δ 1.31 (1H, t), 1.44-1.65 (4H, m), 1.77 (2H, d), 1.97 (1H, d), 2.43 (3H, s), 3.24 (3H, s), 3.57 (1H, s), 4.10 (1H, q), 7.21 (1H, dd), 7.34 (1H, d), 7.37-7.41 (1H, m), 7.48 (1H, dd), 7.87 (2H, s), 8.22-8.28 (1H, m), 8.32-8.38 (1H, m), 8.42 (1H, d). |

| Example/Cmpd number | Structure | LCMS [M + H]+ | 1H NMR |
|---|---|---|---|
| 293 | 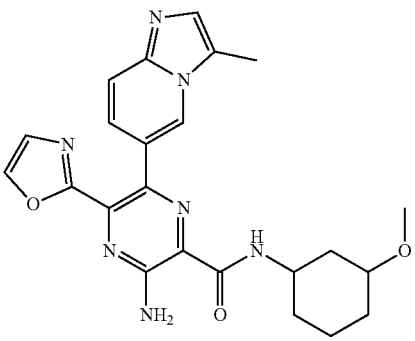<br>isomer 2 | 448.2 | 1H-NMR (400 MHz, DMSO-d6) δ 1.31 (1H, t), 1.43-1.66 (4H, m), 1.77 (2H, d), 1.97 (1H, d), 2.43 (3H, s), 3.24 (3H, s), 3.57 (1H, s), 4.10 (1H, d), 7.22 (1H, dd), 7.35 (1H, s), 7.40 (1H, s), 7.48 (1H, d), 7.88 (2H, s), 8.26 (1H, s), 8.37 (1H, s), 8.42 (1H, d). |
| 294 | 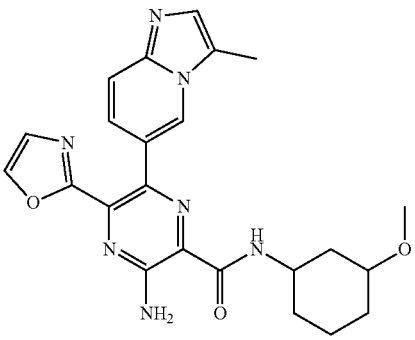<br>isomer 3 | 448.2 | 1H-NMR (400 MHz, DMSO-d6) δ 1.29 (2H, d), 1.51 (2H, d), 1.77 (3H, d), 1.99-2.12 (1H, m), 2.43 (3H, d), 3.21 (3H, s), 3.31(1H, s), 3.95 (1H, s), 7.25 (1H, dd), 7.36 (1H, d), 7.40 (1H, d), 7.47-7.55 (1H, m), 7.92 (2H, s), 8.27 (1H, d), 8.33 (1H, d), 8.80 (1H, d). |
| 295 | 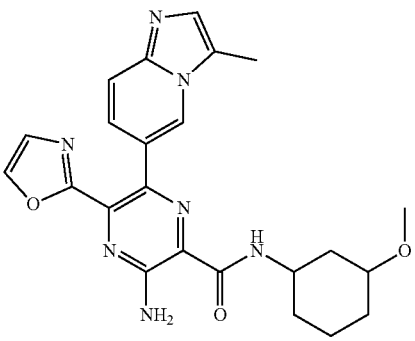<br>isomer 4 | 448.2 | 1H-NMR (400 MHz, DMSO-d6) δ 1.27 (2H, s), 1.38-1.55 (2H, m), 1.75 (3H, d), 2.03 (1H, d), 2.40 (3H, d), 3.18 (3H, s), 3.33 (1H, s), 3.92 (1H, s), 7.22 (1H, dd), 7.31-7.41 (2H, m), 7.44-7.52 (1H, m), 7.89 (2H, s), 8.25 (1H, d), 8.30 (1H, s), 8.77 (1H, d). |
| 306 | 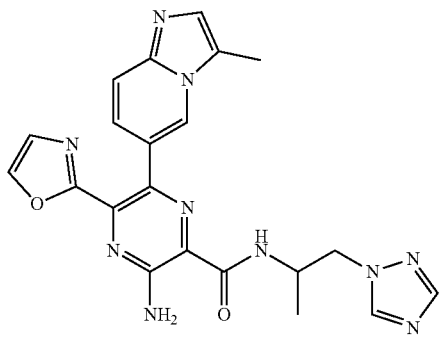 [SMILES: Cc1cnc2ccc(-c3nc(C(=O)NC(C)Cn4cncn4)c(N)nc3-c3ncco3)cn12] | 445.1 | 1H-NMR (300 MHz, Methanol-d4) δ 1.28 (3H, d), 2.50 (3H, d), 4.45 (2H, d), 4.60 (1H, q), 7.26-7.36 (2H, m), 7.39 (1H, d), 7.52 (1H, dd), 7.91-8.02 (2H, m), 8.29-8.36 (1H, m), 8.45 (1H, s). |

Example 149: Preparation of 3-amino-N-(3-methoxypropyl)-6-[3-methylimidazo[1,2-a]pyridin-6-yl]-5-(1,3-oxazol-2-yl)pyrazine-2-carboxamide (Cmpd. 149)

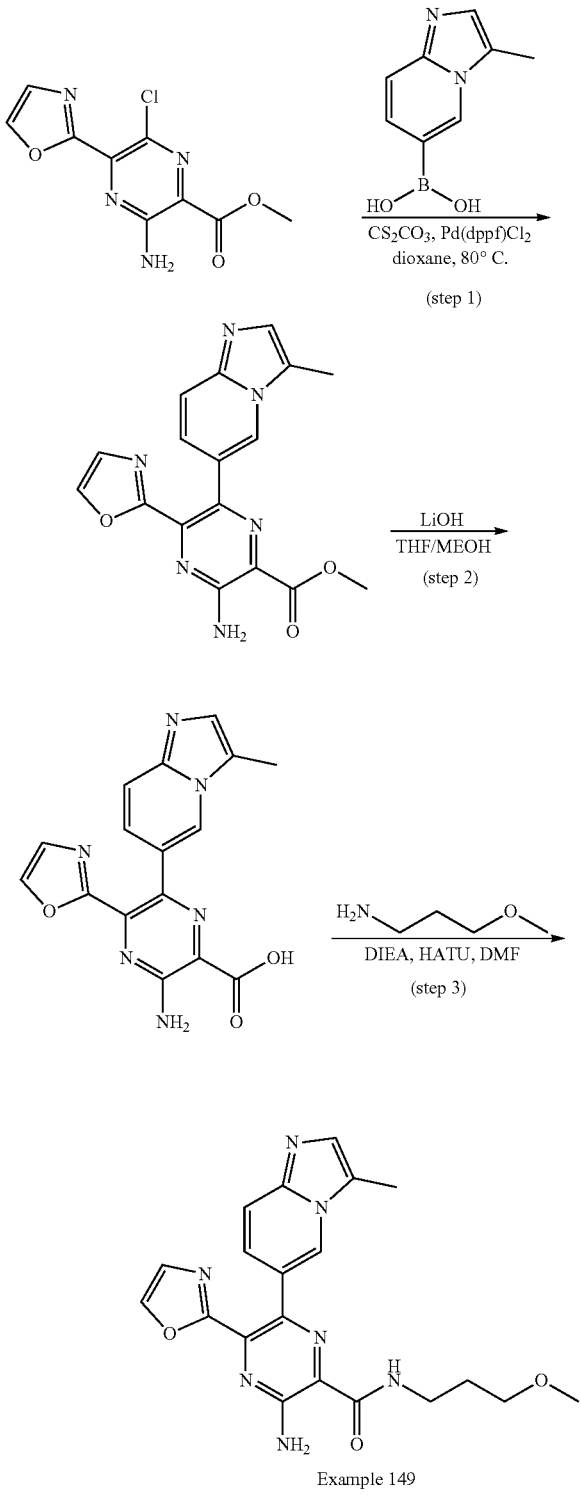

Example 149

Step 1. methyl 3-amino-6-[3-methylimidazo[1,2-a]pyridin-6-yl]-5-(1,3-oxazol-2-yl) pyrazine-2-carboxylate To a stirred mixture of methyl 3-amino-6-chloro-5-(1,3-oxazol-2-yl)pyrazine-2-carboxylate (3000 mg, 11.8 mmol, 1 equiv) and [3-methylimidazo[1,2-a]pyridin-6-yl]boronic acid (4146.7 mg, 23.6 mmol, 2 equiv) in dioxane (300 mL) were added $Cs_2CO_3$ (11516.2 mg, 35.3 mmol, 3 equiv) and Pd(dppf)Cl$_2$ (1724.1 mg, 2.4 mmol, 0.2 equiv) in portions at 80° C. under nitrogen atmosphere. The resulting mixture was stirred for 1.5 h at 95° C. under nitrogen atmosphere. The resulting mixture was concentrated under reduced pressure. The residue was purified by silica gel column chromatography, eluted with $CH_2Cl_2$/EtOAc (1:4) to afford methyl 3-amino-6-[3-methylimidazo[1,2-a]pyridin-6-yl]-5-(1,3-oxazol-2-yl)pyrazine-2-carboxylate (1500 mg, 36.3%) as a yellow solid. LCMS: m/z (ESI), [M+H]$^+$=351.3. $^1$H-NMR (400 MHz, DMSO-d$_6$) δ 2.12 (3H, s), 2.38 (3H, d), 7.04 (1H, dd), 7.36-7.38 (2H, m), 7.46-7.55 (1H, m), 7.71 (2H, s), 8.27 (1H, d), 8.80 (1H, t).

Step 2. 3-amino-6-[3-methylimidazo[1,2-a]pyridin-6-yl]-5-(1,3-oxazol-2-yl)pyrazine-2-carboxylic Acid A mixture of methyl 3-amino-6-[3-methylimidazo[1,2-a]pyridin-6-yl]-5-(1,3-oxazol-2-yl)pyrazine-2-carboxylate (1500 mg, 4.3 mmol, 1 equiv) and LiOH (205.1 mg, 8.6 mmol, 2 equiv) in THF (100 mL) and MeOH (20 mL) was stirred for 1.5 h at 45° C. The resulting mixture was stirred for 2.5 h at 45° C. under air atmosphere. The mixture was acidified to pH 5 with HCl (aq.). The resulting mixture was concentrated under vacuum to afford 3-amino-6-[3-methylimidazo[1,2-a]pyridin-6-yl]-5-(1,3-oxazol-2-yl)pyrazine-2-carboxylic acid (1200 mg, 83.3%) as a yellow solid. The crude product was used in the next step directly without further purification. LCMS: m/z (ESI), [M+H]$^+$=337.3.

Step 3. 3-amino-N-(3-methoxypropyl)-6-[3-methylimidazo[1,2-a]pyridin-6-yl]-5-(1,3-oxazol-2-yl)pyrazine-2-carboxamide (Cmpd. 149)

To a stirred mixture of 3-amino-6-[3-methylimidazo[1,2-a]pyridin-6-yl]-5-(1,3-oxazol-2-yl)pyrazine-2-carboxylic acid (100 mg, 0.3 mmol, 1 equiv) and 3-methoxypropan-1-amine (53 mg, 0.6 mmol, 2 equiv) in DMF (8 mL) were added HATU (226.1 mg, 0.6 mmol, 2 equiv) and DIEA (115.3 mg, 0.9 mmol, 3 equiv) in portions at room temperature under air atmosphere. The resulting mixture was stirred for 2.5 h at room temperature under air atmosphere. The resulting mixture was concentrated under reduced pressure. The crude product (80 mg) was purified by Prep-HPLC with the following conditions (Column: XBridge Prep OBD C18 Column 30×150 mm 5 um; Mobile Phase A: Water (0.05% $NH_3H_2O$), Mobile Phase B: ACN; Flow rate: 60 mL/min; Gradient: 21% B to 34% B in 7 min; 254/220 nm; Rt: 6.67 min) to afford 3-amino-N-(3-methoxypropyl)-6-[3-methylimidazo[1,2-a]pyridin-6-yl]-5-(1,3-oxazol-2-yl)pyrazine-2-carboxamide (Cmpd. 149) (10 mg, 8.3%) as a yellow green solid. LCMS: m/z (ESI), [M+H]$^+$=408.3. $^1$H-NMR (400 MHz, DMSO-d$_6$) δ 1.78 (2H, p), 2.43 (3H, s), 3.22 (3H, s), 3.39 (4H, q), 7.23 (1H, dd), 7.38 (2H, d), 7.48 (1H, d), 7.91 (2H, s), 8.23-8.35 (2H, m), 8.89 (1H, t)

Example 154. Preparation of 3-amino-N-[[1-(dimethylamino)cyclopropyl]methyl]-5-(4-fluorophenyl)-6-[3-methylimidazo[1,2-a]pyridin-6-yl]pyrazine-2-carboxamide (Cmpd. 154)

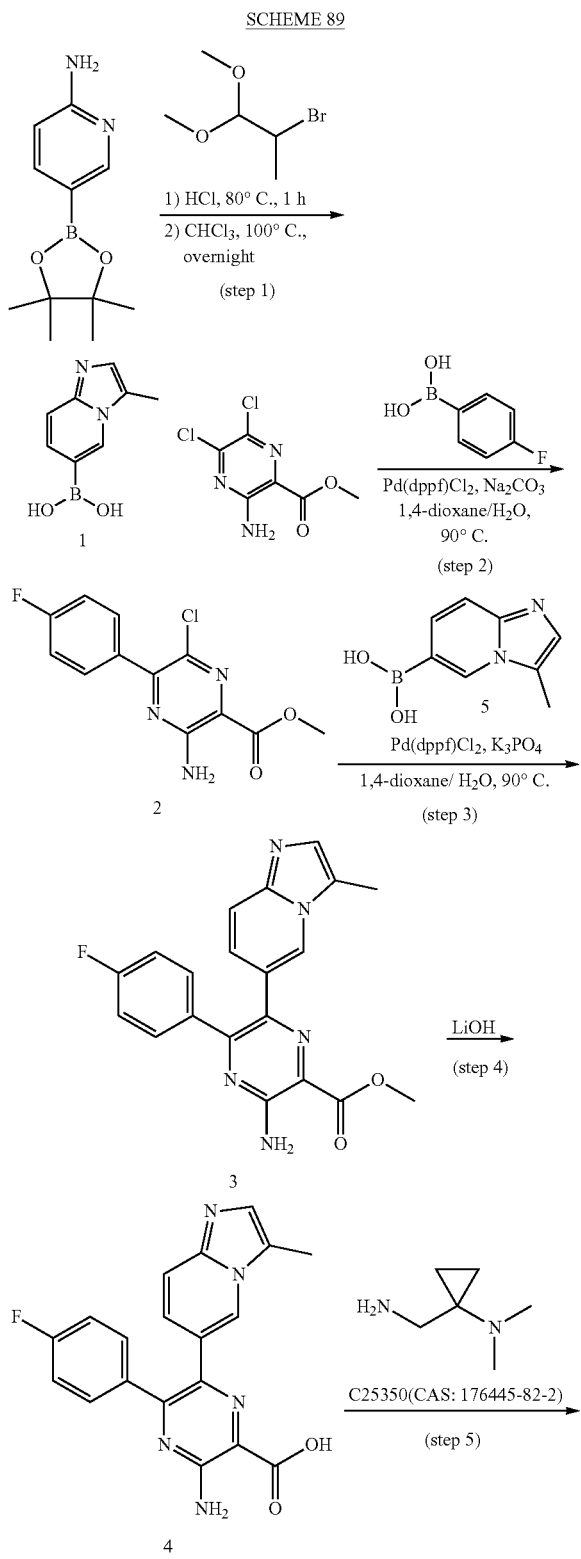

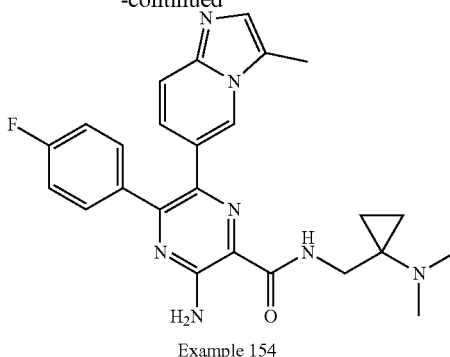

Example 154

Step 1. [3-methylimidazo[1,2-a]pyridin-6-yl]boronic Acid

The 5-(3,3,4,4-tetramethylborolan-1-yl)pyridin-2-amine (20.0 g, 92.5 mmol, 1.0 equiv) was added into HCl (1.0 mol/L) was stirred for 1 h at 80° C. under air atmosphere. The mixture was basified to pH 7 with NaHCO$_3$ (s). The resulting mixture was extracted with CHCl$_3$ (5×40 mL). And dried over anhydrous Na$_2$SO$_4$. After filtration, the 2-bromo-1,1-dimethoxypropane (49.9 g, 272.9 mmol, 2.9 equiv) was added into the above mixture. The resulting mixture was stirred for 10 h at 100° C. under air atmosphere. The resulting mixture was concentrated under reduced pressure. The crude product was re-crystallized from EtOAc/MeOH (20:1 50 mL) to afford [3-methylimidazo[1,2-a]pyridin-6-yl]boronic acid (14.6 g, 87.8%) as a white solid. LCMS: m/z (ESI), [M+H]$^+$=177.2.

Step 2. methyl 3-amino-6-chloro-5-(4-fluorophenyl)pyrazine-2-carboxylate

A mixture of methyl 3-amino-5,6-dichloropyrazine-2-carboxylate (20 g, 90.1 mmol, 1.0 equiv) and (4-fluorophenyl)boronic acid (13.9 g, 99.1 mmol, 1.1 equiv) and Pd(dppf)Cl$_2$ (6.6 g, 9.0 mmol, 0.1 equiv) and Na$_2$CO$_3$ (19.1 g, 180.2 mmol, 2.0 equiv) in 1,4-dioxane/H$_2$O (300 mL) was stirred for 2h at 90° C. under nitrogen atmosphere. The resulting mixture was extracted with EtOAc (3×200 mL). The combined organic layers were washed with H$_2$O (3×80 mL), dried over anhydrous Na$_2$SO$_4$. After filtration, the filtrate was concentrated under reduced pressure. The crude product was re-crystallized from MeOH (100 mL) to afford methyl 3-amino-6-chloro-5-(4-fluorophenyl)pyrazine-2-carboxylate (19.2 g, 74.2%) as a yellow solid. LCMS: m/z (ESI), [M+H]$^+$=282.2.

Step 3. methyl 3-amino-5-(4-fluorophenyl)-6-[3-methylimidazo[1,2-a]pyridin-6-yl]pyrazine-2-carboxylate A mixture of methyl 3-amino-6-chloro-5-(4-fluorophenyl)pyrazine-2-carboxylate (9.2 g, 32.6 mmol, 1.0 equiv) and [3-methylimidazo[1,2-a]pyridin-6-yl]boronic acid (11.5 g, 65.3 mmol, 2.0 equiv) and Pd(dppf)Cl$_2$ (2.4 g, 3.3 mmol, 0.1 equiv) and K$_3$PO$_4$ (13.9 g, 65.3 mmol, 2.0 equiv) in 1,4-dioxane/H$_2$O (200 mL) was stirred for 2 h at 90° C. under nitrogen atmosphere. The resulting mixture was extracted with EtOAc (4×80 mL). The combined organic layers were washed with H$_2$O (3×30 mL), dried over anhydrous Na$_2$SO$_4$. After filtration, the filtrate was concentrated under reduced pressure. The residue was purified by silica gel column chromatography, eluted with CH$_2$Cl$_2$/EtOAc (2:1) to afford methyl 3-amino-5-(4-fluorophenyl)-6-[3-methylimidazo[1,2-a]pyridin-6-yl]pyrazine-2-carboxylate (9.5 g, 76.1%) as a Brown yellow solid. LCMS: m/z (ESI), [M+H]$^+$=378.3.

Step 4. 3-amino-5-(4-fluorophenyl)-6-(3-methylimidazo[1,2-a]pyridin-6-yl)pyrazine-2-carboxylic Acid To a stirred solution of methyl 3-amino-5-(4-fluorophenyl)-6-[3-methylimidazo[1,2-a]pyridin-6-yl]pyrazine-2-carboxylate (3.0 g, 7.9 mmol, 1.0 equiv) and lithiumol (380.8 mg, 15.9 mmol, 2.0 equiv) in THF/H$_2$O=20:1 (82 mL). The resulting mixture was stirred for 4.0 h at room temperature under air atmosphere. Desired product could be detected by LCMS. The mixture was acidified to pH 3 with HCl (in dioxane). The precipitated solids were collected by filtration and washed with water (2×10 mL) to afford 3-amino-5-(4-fluorophenyl)-6-[3-methylimidazo[1,2-a]pyridin-6-yl]pyrazine-2-carboxylic acid (2.1 g, 72.7%) as a light yellow solid. LCMS: m/z (ESI), [M+H]$^+$=364.2. $^1$H-NMR (400 MHz, DMSO-d$_6$) δ 2.35-2.42 (3H, m), 6.97 (1H, dd), 7.14-7.28 (2H, m), 7.34-7.43 (2H, m), 7.45-7.57 (2H, m), 7.65 (2H, s), 8.28 (1H, t).

Step 5. 3-amino-N-[[1-(dimethylamino)cyclopropyl]methyl]-5-(4-fluorophenyl)-6-[3-methylimidazo[1,2-a]pyridin-6-yl]pyrazine-2-carboxamide (Cmpd. 154)

A mixture of 3-amino-5-(4-fluorophenyl)-6-[imidazo[1,2-a]pyridin-6-yl]pyrazine-2-carboxylic acid (100.0 mg, 0.3 mmol, 1.0 equiv) and 1-(aminomethyl)-N,N-dimethylcyclopropan-1-amine (49.0 mg, 0.4 mmol, 1.5 equiv) and HATU (217.6 mg, 0.6 mmol, 2.0 equiv) and DIEA (111.0 mg, 0.9 mmol, 3.0 equiv) in DMF (2.5 mL) was stirred for 1 h at room temperature under air atmosphere. The reaction was quenched with Water at room temperature. The solids was separated out, then the crude product was re-crystallized from EtOH (4 mL) to afford 3-amino-N-[[1-(dimethylamino)cyclopropyl]methyl]-5-(4-fluorophenyl)-6-[3-methylimidazo[1,2-a]pyridin-6-yl]pyrazine-2-carboxamide (Cmpd. 154) (25 mg, 18.6%) as a yellow solid. LCMS: m/z (ESI), [M+H]$^+$=460.3. $^1$H NMR (400 MHz, DMSO-d$_6$) δ 0.43-0.52 (2H, m), 0.61-0.70 (2H, m), 2.39 (9H, d), 3.49 (2H, d), 6.97 (1H, dd), 7.21 (2H, t), 7.33-7.44 (2H, m), 7.46-7.54 (2H, m), 7.72 (2H, s), 8.32 (1H, s), 8.67 (1H, t).

Compounds listed in the table below were prepared using methods described in Cmpd. 154.

| Example/Cmpd number | Structure | LCMS [M + H]$^+$ | $^1$H NMR |
|---|---|---|---|
| 139 | 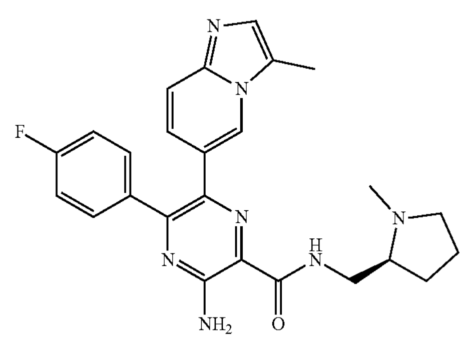 [SMILES: Cc1cnc2ccc(-c3nc(C(=O)NC[C@@H]4CCCN4C)c(N)nc3-c3ccc(F)cc3)cn12] | 460.3 | $^1$H-NMR (300 MHz, DMSO-d$_6$) δ 1.62 (3H, s), 1.76-1.92 (1H, m), 2.14 (1H, t), 2.32 (3H, s), 2.37 (3H, d), 2.40-2.46 (1H, m), 2.87-3.01 (1H, m), 3.24 (1H, t), 3.48 (1H, d), 6.99 (1H, d), 7.21 (2H, t), 7.30-7.43 (2H, m), 7.51 (2H, d), 7.73 (2H, s), 8.24 (1H, d), 8.63 (1H, t). |
| 144 | 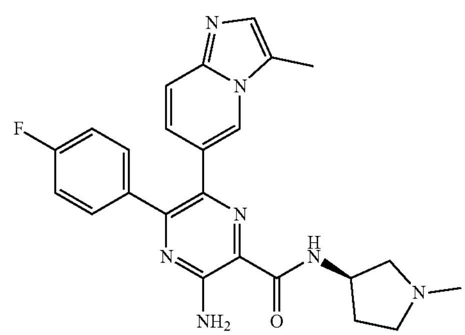 [SMILES: Cc1cnc2ccc(-c3nc(C(=O)N[C@@H]4CCN(C)C4)c(N)nc3-c3ccc(F)cc3)cn12] | 446.3 | $^1$H-NMR (400 MHz, DMSO-d$_6$) δ 1.91-2.04 (1H, m), 2.20-2.31 (4H, m), 2.33-2.51 (4H, m), 2.58-2.62 (1H, m), 2.61-2.72 (2H, m), 4.39-4.48 (1H, m), 7.15-7.30 (2H, m), 7.31-7.42 (2H, m), 7.42-7.55 (2H, m), 7.60-7.90 (2H, s), 8.30 (1H, s), 8.65 (1H, d). |

| Example/Cmpd number | Structure | LCMS [M + H]+ | 1H NMR |
|---|---|---|---|
| 150 | 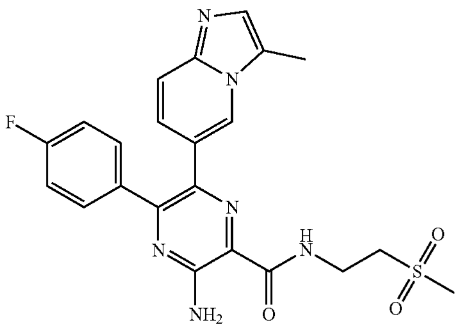 [SMILES: Cc1cnc2ccc(-c3nc(C(=O)NCCS(C)(=O)=O)c(N)nc3-c3ccc(F)cc3)cn12] | 469.2 | 1H-NMR (400 MHz, DMSO-d6) 2.40 (3H, d), 3.09 (3H, s), 3.45 (2H, t), 3.78 (2H, q), 7.01 (1H, dd), 7.15-7.29 (2H, m), 7.34-7.44 (2H, m), 7.46-7.58 (2H, m), 7.74 (2H, s), 8.22-8.29 (1H, m), 9.06 (1H, t) |
| 200-1 | 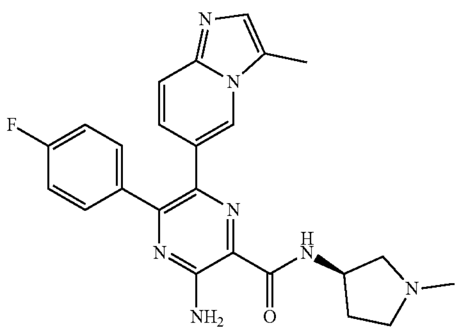 [SMILES: Cc1cnc2ccc(-c3nc(C(=O)N[C@@H]4CCN(C)C4)c(N)nc3-c3ccc(F)cc3)cn12] | 446.3 | 1H-NMR (400 MHz, DMSO-d6) δ 1.83 (1H, d), 2.25 (4H, s), 2.39 (4H, s), 2.53 (1H, d), 2.65 (2H, q), 4.41 (1H, s), 7.00 (1H, dd), 7.20 (2H, t), 7.38 (2H, d), 7.50 (2H, dd), 7.72 (1H, s), 8.33 (1H, s), 8.57 (1H, d). |
| 200-2 | 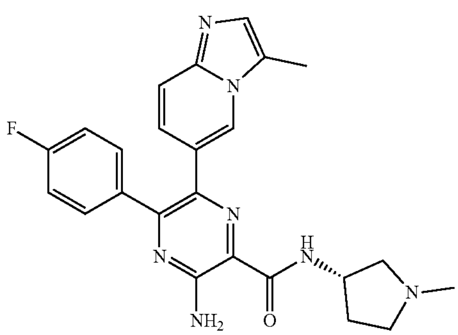 [SMILES: Cc1cnc2ccc(-c3nc(C(=O)N[C@H]4CCN(C)C4)c(N)nc3-c3ccc(F)cc3)cn12] | 446.3 | 1H NMR (400 MHz, DMSO-d6) δ 1.83 (1H, d), 2.38 (1H, s), 2.25 (3H, s), 2.39 (4H, s), 2.53 (1H, d), 2.65 (2H, q), 4.41 (1H, s), 7.00 (1H, dd), 7.20 (2H, t), 7.38 (2H, d), 7.50 (2H, dd), 7.72 (1H, s), 8.33 (1H, s), 8.57 (1H, d). |
| 203-1 | 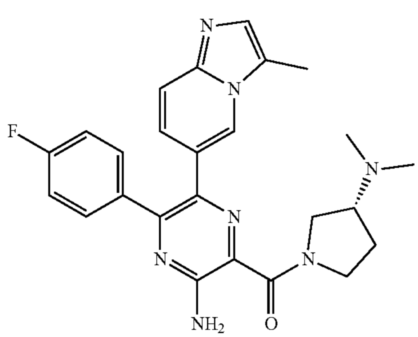 [SMILES: Cc1cnc2ccc(-c3nc(C(=O)N4CC[C@@H](N(C)C)C4)c(N)nc3-c3ccc(F)cc3)cn12] | 460.3 | 1H-NMR (DMSO-d6, 400 MHz) δ 1.74 (1H, dt), 2.08 (1H, s), 2.20 (6H, d), 2.32 (3H, d), 2.71 (1H, p), 3.62-3.95 (1H, m), 3.85-3.95 (2H, m), 4.10-4.35 (1H, m), 7.00 (1H, ddd), 7.21 (2H, t), 7.3-7.53 (4H, m), 7.48-7.58 (2H, m), 8.10 (1H, dd) |

| Example/Cmpd number | Structure | LCMS [M + H]+ | 1H NMR |
|---|---|---|---|
| 203-2 | 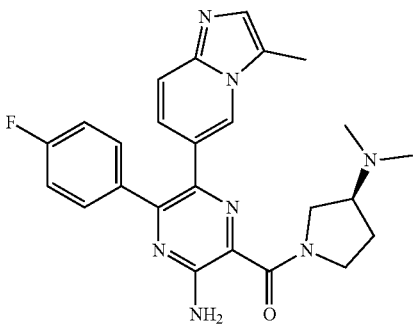 [SMILES: Cc1cnc2ccc(-c3nc(C(=O)N4CC[C@H](N(C)C)C4)c(N)nc3-c3ccc(F)cc3)cn12] | 460.3 | 1H-NMR (400 MHz, DMSO-d6) δ 1.74 (1H, dt), 2.08 (1H, s), 2.19 (6H, d), 2.31 (3H, d), 2.63-2.80 (1H, m), 3.3 (1H, s), 3.61-3.92 (2H, m), 4.01-4.40 (1H, m), 7.00 (1H, ddd), 7.20 (2H, t), 7.3-7.41 (4H, dd), 7.51 (2H, td), 8.09 (1H, d). |
| 204-1 | 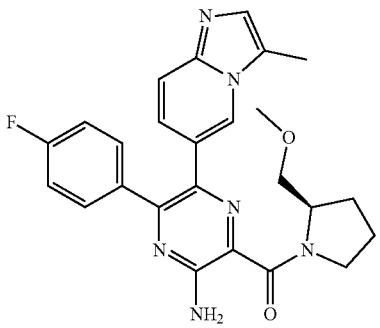 [SMILES: COC[C@H]1CCCN1C(=O)c1nc(-c2ccc3ncc(C)n3c2)c(-c2ccc(F)cc2)nc1N] | 461.2 | 1H-NMR (400 MHz, DMSO-d6) δ 1.77-2.02 (4H, m), 2.32 (3H, dd), 2.55 (1H, s), 2.99 (2H, s), 3.2-3.3 (2H, m) 3.36-3.51 (2H, m), 3.61 (1H, dt), 3.81-3.91 (1H, dt), 4.38-4.92 (1H, dt), 7.02 (1H, ddd), 7.14-7.30 (4H, m), 7.36-7.52 (4H, m), 8.04 (1H, d) |
| 204-2 | 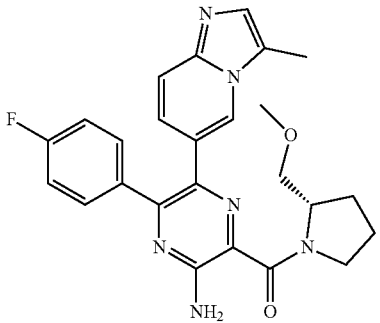 [SMILES: COC[C@@H]1CCCN1C(=O)c1nc(-c2ccc3ncc(C)n3c2)c(-c2ccc(F)cc2)nc1N] | 461.3 | 1H-NMR (400 MHz, DMSO-d6) δ 1.71-2.06 (4H, m), 2.31 (3H, d), 2.98 (1H, s),3.32 (2H, ddd), 3.61 (1H, dd), 3.74 (1H, d), 3.84 (1H, d), 4.29-4.91 (1H, m), 6.93-7.09 (1H, m), 7.12-7.30 (4H, m), 7.35 (1H, s), 7.42 (1H, 0, 7.50 (2H, td), 8.00-8.2 (1H, m) |
| 246 | 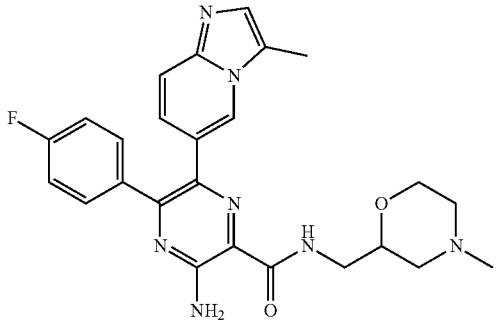 | 476.3 | 1H-NMR (400 MHz, DMSO-d6)δ 1.6 (1H, s), 2.1 (1H, s), 2.3 (3H, s), 2.4 (3H, s), 2.7 (1H, s), 2.9 (1H, dd), 3.3 (1H, t), 3.5 (1H, t), 3.7 (1H, s), 3.8 (1H, t), 7.3 (1H, s), 7.7 (1H, dd), 7.8 (1H, d), 7.9-8.0 (1H, m), 8.2 (1H, s), 8.3 (1H, s), 8.6 (2H, d)H, dd), 7.8 (1H, d), 7.9-8.1 (1H, m), 8.2 (1H, s), 8.3 (1H, s), 8.6 (2H, d) |

| Example/Cmpd number | Structure | LCMS [M + H]+ | 1H NMR |
|---|---|---|---|
| 250 | 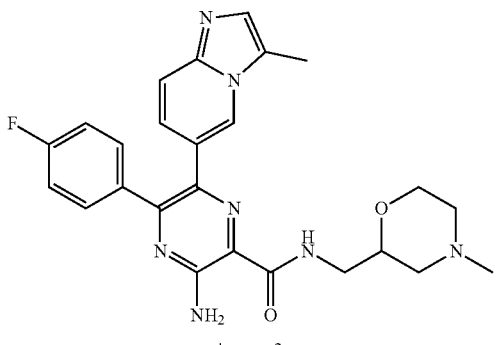 isomer 2 | 476.3 | 1H-NMR (400 MHz, DMSO-d6) δ 1.6 (1H, s), 2.1 (1H, s), 2.3 (3H, s), 2.4 (3H, s), 2.7 (1H, s), 2.9 (1H, dd), 3.3 (1H, t), 3.5 (1H, t), 3.7 (1H, s), 3.8 (1H, t), 7.3 (1H, s), 7.7 (1H, dd), 7.8 (1H, d), 7.9-8.0 (1H, m), 8.2 (1H, s), 8.3 (1H, s), 8.6 (2H, d)H, dd), 7.8 (1H, d), 7.9-8.1 (1H, m), 8.2 (1H, s), 8.3 (1H, s), 8.6 (2H, d) |
| 256 | 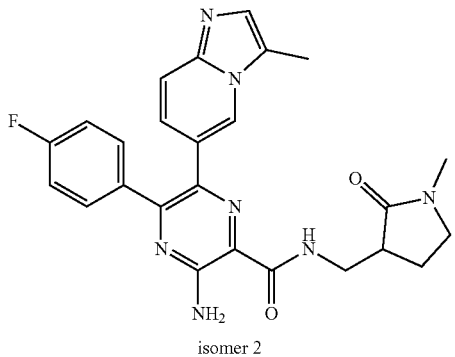 [SMILES: Cc1cnc2ccc(-c3nc(C(=O)NCC4CCN(C)C4=O)c(N)nc3-c3ccc(F)cc3)cn12] isomer 2 | 474.2 | 1H-NMR (300 MHz, DMSO-d6) δ 1.69-1.84 (1H, m), 2.06-2.22 (1H, m), 2.41-2.48 (3H, m), 2.67 (1H, t), 2.75 (3H, s), 3.29 (2H, d), 3.41 (1H, d), 3.61 (1H, t), 6.94 (1H, d), 7.22 (2H, t), 7.37 (2H, d), 7.52 (2H, d), 7.72 (2H, s), 8.36 (1H, d), 9.21 (1H, d) |
| 267 | 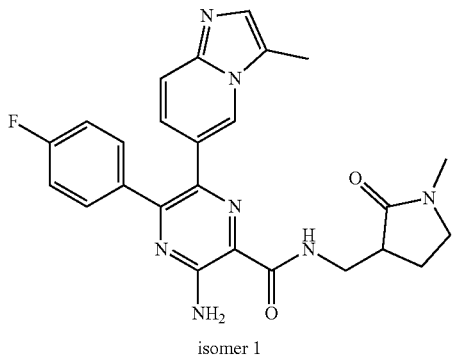 [SMILES: Cc1cnc2ccc(-c3nc(C(=O)NCC4CCN(C)C4=O)c(N)nc3-c3ccc(F)cc3)cn12] isomer 1 | 474.3 | 1H-NMR (300 MHz, DMSO-d6) δ 1.77 (1H, d), 2.05-2.21 (1H, m), 2.43-2.48 (3H, m), 2.67 (1H, t), 2.75 (3H, s), 3.26 (2H, d), 3.41 (1H, d), 3.61 (1H, t), 6.94 (1H, d), 7.16-7.26 (2H, m), 7.31-7.41 (2H, m), 7.46-7.56 (2H, m), 7.72 (2H, s), 8.30-8.41 (1H, m), 9.21 (1H, d) |
| 275 | 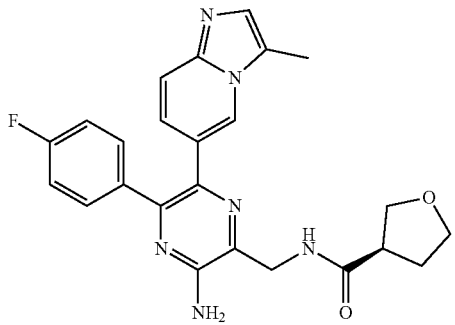 [SMILES: Cc1cnc2ccc(-c3nc(CNC(=O)[C@@H]4CCOC4)c(N)nc3-c3ccc(F)cc3)cn12] | 447.3 | 1H NMR (400 MHz, DMSO-d6) δ 2.04 (2H, q), 2.33 (3H, s), 3.07 (1H, t), 3.70 (3H, m), 3.87 (1H, t), 4.39 (2H, m), 6.66 (2H, s), 6.95 (1H, dd), 7.17 (2H, t), 7.36 (2H, m), 7.44 (2H, m), 8.08 (1H, d), 8.61 (1H, t). |

Example 156. Preparation of (2S)—N-[[3-amino-5-(4-fluorophenyl)-6-[3-methylimidazo[1,2-a]pyridin-6-yl]pyrazin-2-yl]methyl]-1-methylpyrrolidine-2-carboxamide (Cmpd. 156)

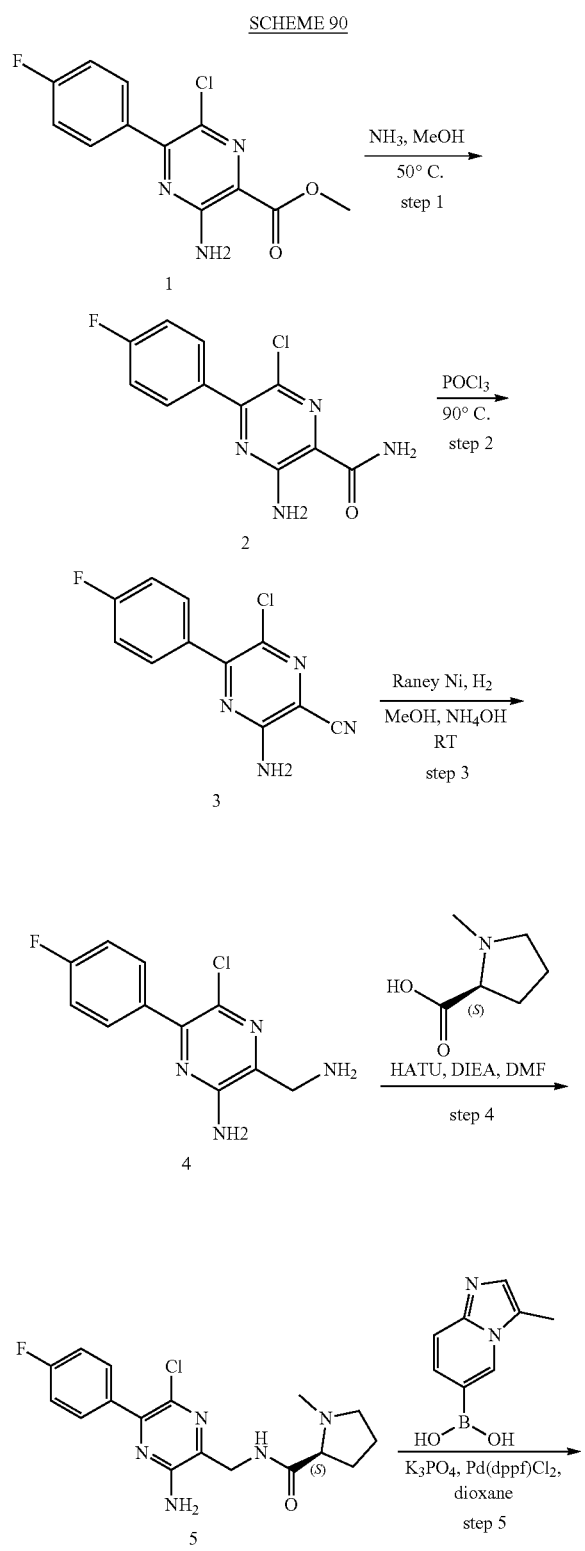

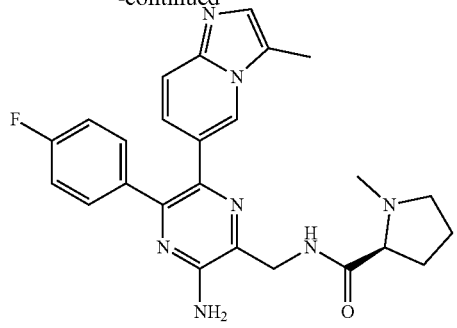

Example 156

Step 1. 3-amino-6-chloro-5-(4-fluorophenyl)pyrazine-2-carboxamide

Into a 50 mL sealed tube were added methyl 3-amino-6-chloro-5-(4-fluorophenyl)pyrazine-2-carboxylate (2.0 g, 7.10 mmol, 1 equiv) and $NH_3$ (g) in MeOH (30 ml, 7.0 mmol/L) at room temperature, heated for 5 h at 50° C., concentrated to afford 3-amino-6-chloro-5-(4-fluorophenyl)pyrazine-2-carboxamide (1.5 g, 79%) as a light yellow solid. LCMS: m/z (ESI), $[M+H]^+=267.1$.

Step 2. 3-amino-6-chloro-5-(4-fluorophenyl)pyrazine-2-carbonitrile

Into a 25 mL round-bottom flask were added 3-amino-6-chloro-5-(4-fluorophenyl)pyrazine-2-carboxamide (1.5 g, 5.63 mmol, 1 equiv) and $POCl_3$ (10 mL, 107.28 mmol, 19.07 equiv) at room temperature, heated for 3 h at 90° C. Cooled to room temperature, poured into $NaHCO_3$ (aq., 200 ml), filtered and dried to give 3-amino-6-chloro-5-(4-fluorophenyl)pyrazine-2-carbonitrile (1.2 g, 86%) as yellow solid. LCMS: m/z (ESI), $[M+H]^+=249.2$.

Step 3. 3-(aminomethyl)-5-chloro-6-(4-fluorophenyl)pyrazin-2-amine

Into a 500 mL round-bottom flask were added 3-amino-6-chloro-5-(4-fluorophenyl)pyrazine-2-carbonitrile (1.4 g, 5.63 mmol, 1 equiv) and Raney Ni (0.3 g, 3.50 mmol, 0.62 equiv) in methanol (150 mL) at room temperature, stirred for 15 h under $H_2$ condition (about 1.5 atm), filtered and concentrated to afford 3-(aminomethyl)-5-chloro-6-(4-fluorophenyl)pyrazin-2-amine (1.1 g, crude) as a light brown solid. LCMS: m/z (ESI), $[M-NH_2]^+=236.2$.

Step 4. (2S)—N-[[3-amino-5-(4-fluorophenyl)-6-[3-methylimidazo[1,2-a]pyridin-6-yl]pyrazin-2-yl]methyl]-1-methylpyrrolidine-2-carboxamide To a stirred mixture of (2S)-1-methylpyrrolidine-2-carboxylic acid (168.68 mg, 1.31 mmol, 1.10 equiv), 3-(aminomethyl)-5-chloro-6-(4-fluorophenyl)pyrazin-2-amine (300 mg, 1.19 mmol, 1 equiv) and HATU (496.58 mg, 1.31 mmol, 1.1 equiv) in DMF (3.0 mL) was added DIEA (306.89 mg, 2.38 mmol, 2.0 equiv) dropwise at 0° C. under nitrogen atmosphere, stirred for 3 h at room temperature, added water (15 ml), filtered and dried to afford (2S)—N-[[3-amino-6-chloro-5-(4-fluorophenyl)pyrazin-2-yl]methyl]-1-methylpyrrolidine-2-carboxamide (250 mg, 57.88%) as a light yellow solid. LCMS: m/z (ESI), [M+H]$^+$=364.2.

Step 5. (2S)—N-[[3-amino-5-(4-fluorophenyl)-6-[3-methylimidazo[1,2-a]pyridin-6-yl]pyrazin-2-yl]methyl]-1-methylpyrrolidine-2-carboxamide (Cmpd. 156)

A mixture of (2S)—N-[[3-amino-6-chloro-5-(4-fluorophenyl)pyrazin-2-yl]methyl]-1-methylpyrrolidine-2-carboxamide (180.0 mg, 0.5 mmol, 1.0 equiv) and [3-methylimidazo[1,2-a]pyridin-6-yl]boronic acid (174.1 mg, 0.9 mmol, 2.0 equiv) and Pd(dppf)Cl$_2$ (36.2 mg, 0.1 mmol, 0.1 equiv) and K$_3$PO$_4$ (315.1 mg, 1.5 mmol, 3.0 equiv) in 1,4-dioxane/H$_2$O (4.0 mL) was stirred for 10 h at 90° C. under nitrogen atmosphere. The residue was purified by Prep-TLC (CH$_2$Cl$_2$/MeOH 40:1), then the crude product (80.0 mg) was purified by Prep-HPLC with following conditions (Column: XBridge Prep OBD C$^{18}$ Column 30×150 mm 5 um; Mobile Phase A: Water (0.05% NH$_3$H2O), Mobile Phase B: ACN; Flow rate: 60 mL/min; Gradient: 30% B to 43% B in 7 min; 254/220 nm; Rt: 6.70 min) to afford (2S)—N-[[3-amino-5-(4-fluorophenyl)-6-[3-methylimidazo[1,2-a]pyridin-6-yl]pyrazin-2-yl]m ethyl]-1-methylpyrrolidine-2-carboxamide (Cmpd. 157) (20.0 mg, 8.6%) as a light yellow solid. LCMS: m/z (ESI), [M+H]$^+$=460.3. $^1$H-NMR (400 MHz, DMSO-d$_6$) δ1.73 (3H, td), 2.10 (1H, dd), 2.19-2.38 (7H, m), 2.80 (1H, dd), 3.04 (1H, dd), 4.30-4.49 (2H, m), 6.68 (2H, s), 6.99 (1H, dd), 7.17 (2H, t), 7.34 (1H, s), 7.37-7.49 (3H, m), 8.01 (1H, s), 8.44 (1H, t).

Example 157. Preparation of (2R)—N-[[3-amino-5-(4-fluorophenyl)-6-[3-methylimidazo[1,2-a]pyridin-6-yl]pyrazin-2-yl]methyl]-1-methylpyrrolidine-2-carboxamide (Cmpd. 157)

SCHEME 91

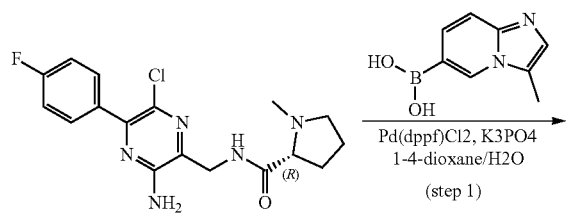

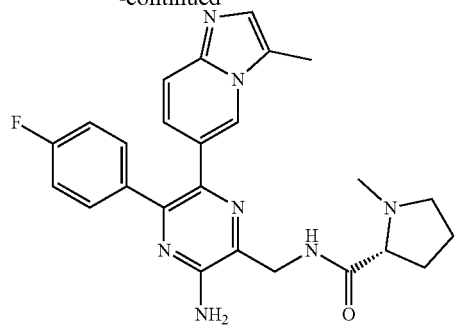

Example 157

Step 1. (2R)—N-[[3-amino-5-(4-fluorophenyl)-6-[3-methylimidazo[1,2-a]pyridin-6-yl]pyrazin-2-yl]methyl]-1-methylpyrrolidine-2-carboxamide (Cmpd. 157)

A mixture of (2R)—N-[[3-amino-6-chloro-5-(4-fluorophenyl)pyrazin-2-yl]methyl]-1-methylpyrrolidine-2-carboxamide (180.0 mg, 0.5 mmol, 1.0 equiv) and [3-methylimidazo[1,2-a]pyridin-6-yl]boronic acid (174.1 mg, 0.9 mmol, 2.0 equiv) and Pd(dppf)Cl$_2$ (36.2 mg, 0.1 mmol, 0.2 equiv) and K$_3$PO$_4$ (315.1 mg, 1.5 mmol, 3.0 equiv) in 1,4-dioxane/H$_2$O (4.0 mL) was stirred for 10 h at 90° C. under nitrogen atmosphere. The residue was purified by Prep-TLC (CH$_2$Cl$_2$/MeOH 40:1), then the crude product (80.0 mg) was purified by Prep-HPLC with following conditions (Column: XBridge Prep OBD C18 Column 30×150 mm 5 um; Mobile Phase A: Water (0.05% NH$_3$H2O), Mobile Phase B: ACN; Flow rate: 60 mL/min; Gradient: 30% B to 43% B in 7 min; 254/220 nm; Rt: 6.70 min) to afford (2R)—N-[[3-amino-5-(4-fluorophenyl)-6-[3-methylimidazo[1,2-a]pyridin-6-yl]pyrazin-2-yl]m ethyl]-1-methylpyrrolidine-2-carboxamide (Cmpd. 157) (20.0 mg, 8.6%) as a light yellow solid. LCMS: m/z (ESI), [M+H]$^+$=460.3. $^1$H-NMR (400 MHz, DMSO-d$_6$) δ1.73 (3H, td), 2.10 (1H, dd), 2.19-2.38 (7H, m), 2.80 (1H, dd), 3.04 (1H, dd), 4.30-4.49 (2H, m), 6.68 (2H, s), 6.99 (1H, dd), 7.17 (2H, t), 7.34-7.49 (4H, m), 8.01 (1H, s), 8.44 (1H, t).

Compounds listed in the table below were prepared using methods described in Cmpd. 157.

| Example/Cmpd number | Structure | LCMS [M + H]$^+$ | $^1$H NMR |
|---|---|---|---|
| 264 | 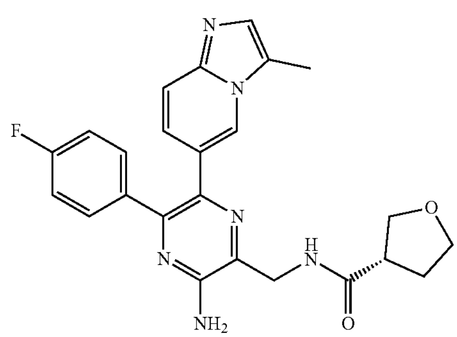 [SMILES: Cc1cnc2ccc(-c3nc(CNC(=O)[C@H]4CCOC4)c(N)nc3-c3ccc(F)cc3)cn12] | 447.2 | $^1$H-NMR (400 MHz, DMSO-d$_6$) δ 2.03 (2H, m), 2.33 (3H, s), 3.07 (1H, p), 3.69 (3H, m), 3.87 (1H, t), 4.40 (2H, dd), 6.66 (2H, s), 6.95 (1H, dd), 7.17 (2H, t), 7.36 (2H, m), 7.44 (2H, m), 8.08 (1H, s), 8.61 (1H, t). |

| Example/Cmpd number | Structure | LCMS [M + H]+ | 1H NMR |
|---|---|---|---|
| 265 | 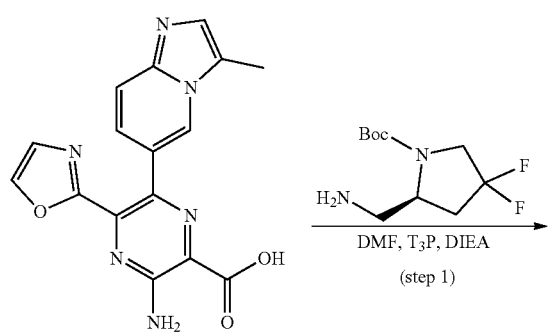 | 447.3 | 1H-NMR (300 MHz, DMSO-d6) δ 1.80 (2H, q), 1.91 (1H, m), 2.14 (1H, dq), 2.32 (3H, d), 3.78 (1H, q), 3.94 (1H, q), 4.37 (3H, m), 6.69 (2H, s), 6.96 (1H, dd), 7.17 (2H, t), 7.35 (2H, dd), 7.42 (2H, m), 8.06 (1H, d), 8.40 (1H, t). |

Example 161. Preparation of (S)-3-amino-N-((4,4-difluoro-1-methylpyrrolidin-2-yl)methyl)-6-(3-methylimidazo[1,2-a]pyridin-6-yl)-5-(oxazol-2-yl)pyrazine-2-carboxamide (Cmpd. 161)

SCHEME 92

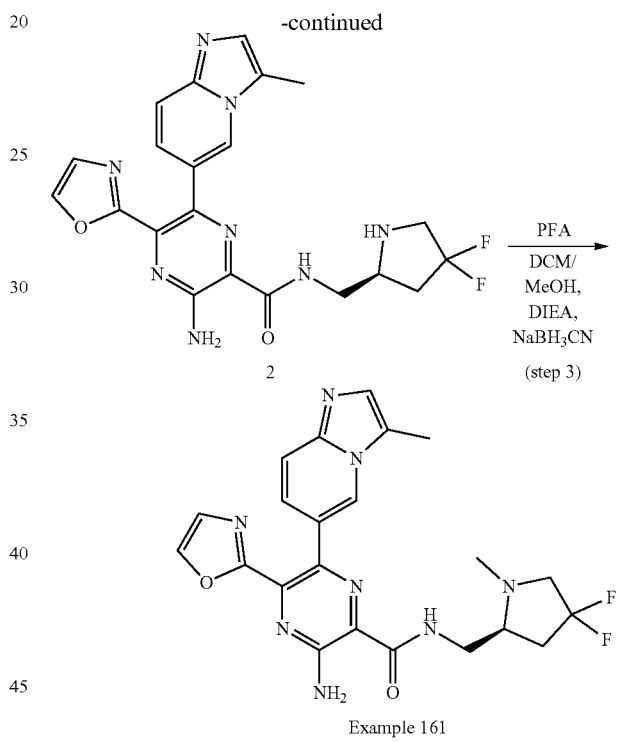

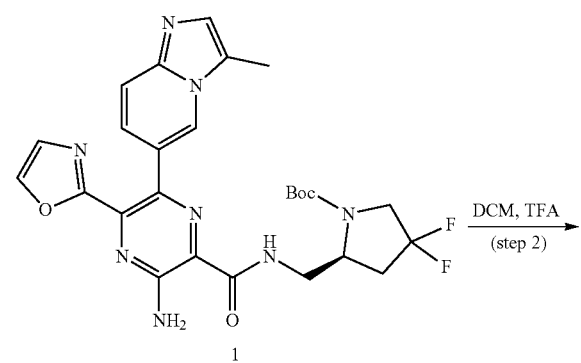

Step 1. (S)-tert-butyl 2-((3-amino-6-(3-methylimidazo[1,2-a]pyridin-6-yl)-5-(oxazol-2-yl)pyrazine-2-carboxamido)methyl)-4,4-difluoropyrrolidine-1-carboxylate To a stirred solution of 3-amino-6-[3-methylimidazo[1,2-a]pyridin-6-yl]-5-(1,3-oxazol-2-yl)pyrazine-2-carboxylic acid (150 mg, 0.446 mmol, 1 equiv) and tert-butyl (2S)-2-(aminomethyl)-4,4-difluoropyrrolidine-1-carboxylate (210.75 mg, 0.892 mmol, 2.00 equiv), DIEA (172.93 mg, 1.338 mmol, 3.00 equiv) in DMF was added T3P (283.83 mg, 0.892 mmol, 2.00 equiv) dropwise at 0° C. under air atmosphere. The resulting mixture was stirred for 1 h at room temperature under air atmosphere. The resulting mixture was diluted with EtOAc (40 mL). The resulting mixture was washed with 2×40 mL of water. The organic layer was dried over anhydrous Na2SO4, and the solid was filtered out, concentrated under vacuum. The residue was purified by Prep-TLC (CH$_2$Cl$_2$/MeOH 200:15) to afford tert-butyl (2S)-2-[[(3-amino-6-[3-methylimidazo[1,2-a]pyridin-6-yl]-5-(1,3-oxazol-2-yl)pyrazin-2-yl)formamido]methyl]-4,4-difluoropyrrolidine-1-carboxylate (220 mg, 88.95%) as a yellow solid. LCMS: m/z (ESI), [M+H]$^+$=555.2.

Step 2. (S)-3-amino-N-((4,4-difluoropyrrolidin-2-yl)methyl)-6-(3-methylimidazo[1,2-a]pyridin-6-yl)-5-(oxazol-2-yl)pyrazine-2-carboxamide Into a 50 mL round-bottom flask were added tert-butyl (2S)-2-[[(3-amino-6-[3-methylimidazo[1,2-a]pyridin-6-yl]-5-(1,3-oxazol-2-yl)pyrazin-2-yl)formamido]methyl]-4,4-difluoropyrrolidine-1-carboxylate (220 mg, 0.397 mmol, 1 equiv) and TFA (2 mL, 26.926 mmol, 67.87 equiv) at room temperature. The resulting mixture was stirred for 1 h at room temperature under air atmosphere. The solvent and TFA was evaporated out to afford 3-amino-N-[(4,4-difluoropyrrolidin-2-yl)methyl]-6-[3-methylimidazo[1,2-a]pyridin-6-yl]-5-(1,3-oxazol-2-yl)pyrazine-2-carboxamide (180 mg, 99.84%) as a yellow solid (crude). LCMS: m/z (ESI), [M+H]$^+$=455.2.

Step 3. (S)-3-amino-N-((4,4-difluoro-1-methylpyrrolidin-2-yl)methyl)-6-(3-methylimidazo[1,2-a]pyridin-6-yl)-5-(oxazol-2-yl)pyrazine-2-carboxamide (Cmpd. 161)

To a stirred mixture of 3-amino-N-[[(2S)-4,4-difluoropyrrolidin-2-yl]methyl]-6-[3-methylimidazo[1,2-a]pyridin-6-yl]-5-(1,3-oxazol-2-yl)pyrazine-2-carboxamide (180 mg, 0.396 mmol, 1 equiv) and HCHO (118.93 mg, 3.961 mmol, 10.00 equiv), DIEA (510.9 mg, 3.961 mmol, 10.00 equiv) in CH$_2$Cl$_2$ (6 mL) and MeOH (3 mL) were added NaBH$_3$CN (149.35 mg, 2.377 mmol, 6.00 equiv) in portions at room temperature under air atmosphere. The reaction mixture was stirred at rt for 2 hours. Quenched by water (50 mL) and extracted by DCM (2×50 mL), the organic layer was combined and dried on anhydrous Na$_2$SO$_4$, the solid was filtered out and the solvent was evaporated out. The residue was purified by Prep-TLC (DCM:MeOH=20:1) to afford a yellow solid. The crude product (100 mg) was purified by Prep-HPLC with the following conditions (Column: Kinetex EVO C18 Column 30*150, 5 um; Mobile Phase A: Water (10 MMOL/L NH$_4$HCO$_3$), Mobile Phase B: ACN; Flow rate: 60 mL/min; Gradient: 27% B to 40% B in 7 min; 254/220 nm; Rt: 6.05 min) to afford 3-amino-N-[[(2S)-4,4-difluoro-1-methylpyrrolidin-2-yl]methyl]-6-[3-methylimidazo[1,2-a]pyridin-6-yl]-5-(1,3-oxazol-2-yl)pyrazine-2-carboxamide (Cmpd. 161) (60 mg, 32.34%) as a yellow solid. LCMS: m/z (ESI), [M+H]$^+$=469.2. 1H NMR (400 MHz, DMSO-d$_6$) δ 2.19 (1H, dt), 2.33 (3H, s), 2.43 (4H, s), 2.61 (1H, ddd), 2.78 (1H, s), 3.38 (1H, d), 3.53 (1H, s), 7.20 (1H, dd), 7.38 (2H, d), 7.49 (1H, d), 7.89 (2H, s), 8.29 (2H, d), 8.77 (1H, t)

Example 162. Preparation of (R)-3-amino-N-((4,4-difluoro-1-methylpyrrolidin-2-yl)methyl)-6-(3-methylimidazo[1,2-a]pyridin-6-yl)-5-(oxazol-2-yl)pyrazine-2-carboxamide (Cmpd. 162)

SCHEME 93

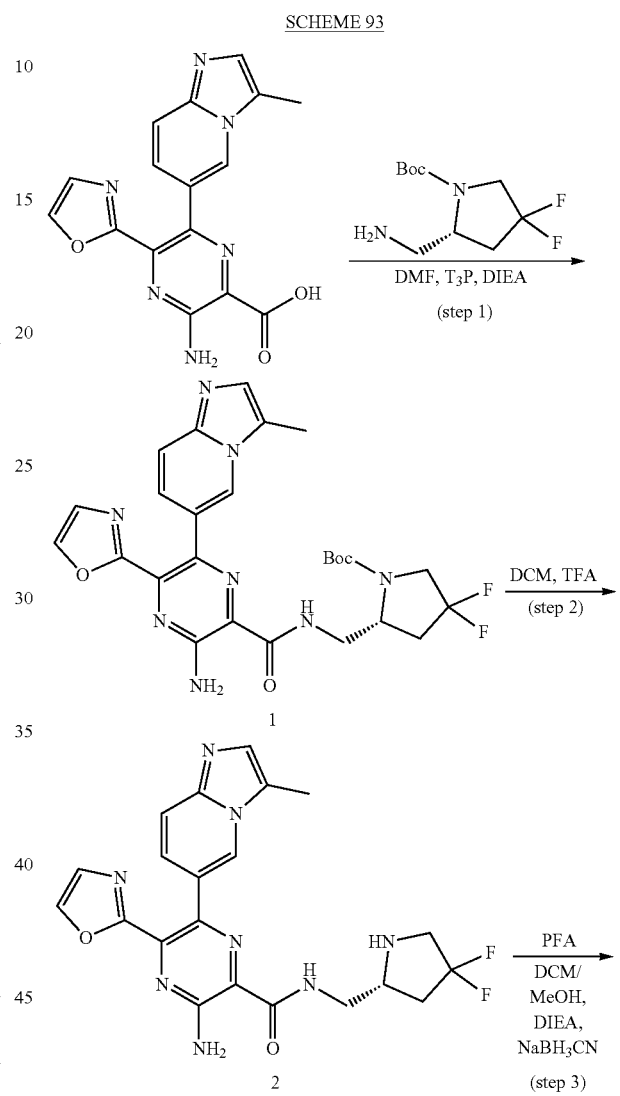

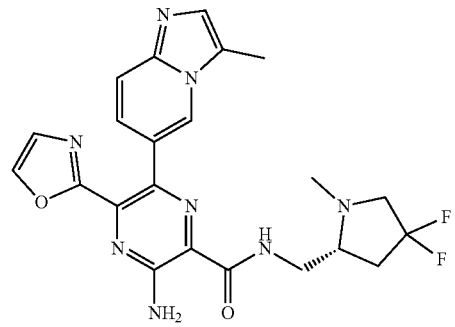

Example 162

Step 1. (R)-tert-butyl 2-((3-amino-6-(3-methylimidazo[1,2-a]pyridin-6-yl)-5-(oxazol-2-yl)pyrazine-2-carboxamido)methyl)-4,4-difluoropyrrolidine-1-carboxylate To a stirred mixture of 3-amino-6-[3-methylimidazo[1,2-a]pyridin-6-yl]-5-(1,3-oxazol-2-yl)pyrazine-2-carboxylic acid (150 mg, 0.446 mmol, 1 equiv) and tert-butyl (2R)-2-(aminomethyl)-4,4-difluoropyrrolidine-1-carboxylate (210.75 mg, 0.892 mmol, 2.00 equiv), DIEA (172.93 mg, 1.338 mmol, 3.00 equiv) in DMF were added $T_3P$ (283.83 mg, 0.892 mmol, 2.00 equiv) dropwise at 0° C. under air atmosphere. The resulting mixture was diluted with EtOAc (50 mL). The resulting mixture was washed with 2×50 mL of water and 2×50 mL of saturated NaCl, the organic layer was dried on anhydrous $Na_2SO_4$, The resulting mixture was concentrated under reduced pressure. The residue was purified by Prep-TLC ($CH_2Cl_2$/MeOH 20:1) to afford tert-butyl (2R)-2-[[(3-amino-6-[3-methylimidazo[1,2-a]pyridin-6-yl]-5-(1,3-oxazol-2-yl)pyrazin-2-yl)formamido]methyl]-4,4-difluoropyrrolidine-1-carboxylate (220 mg, 88.95%) as a yellow solid. LCMS: m/z (ESI), $[M+H]^+=555.2$; H-NMR (400 MHz, DMSO-$d_6$) δ 1.28 (9H, s), 2.43 (4H, s), 2.63 (1H, s), 3.48 (1H, s), 3.64 (1H, s), 3.80 (1H, s), 4.02 (1H, q), 4.29 (1H, s), 7.20 (1H, s), 7.42 (3H, dd), 7.89 (2H, s), 8.31 (2H, d), 9.03 (1H, d)

Step 2. (R)-3-amino-N-((4,4-difluoropyrrolidin-2-yl)methyl)-6-(3-methylimidazo[1,2-a]pyridin-6-yl)-5-(oxazol-2-yl)pyrazine-2-carboxamide To a stirred solution of tert-butyl (2R)-2-[[(3-amino-6-[3-methylimidazo[1,2-a]pyridin-6-yl]-5-(1,3-oxazol-2-yl)pyrazin-2-yl)formamido]methyl]-4,4-difluoropyrrolidine-1-carboxylate (220 mg, 0.397 mmol, 1 equiv) in DCM was added TFA (2 mL, 26.926 mmol, 67.87 equiv) at room temperature under air atmosphere. The resulting mixture was stirred for 1 h at room temperature under air atmosphere. DCM and TFA was evaporated out to afford 3-amino-N-[[(2R)-4,4-difluoropyrrolidin-2-yl]methyl]-6-[3-methylimidazo[1,2-a]pyridin-6-yl]-5-(1,3-oxazol-2-yl)pyrazine-2-carboxamide (99.84%) as a yellow solid (crude). LCMS: m/z (ESI), $[M+H]^+=455$. 2H-NMR (400 MHz, DMSO-$d_6$) δ 2.40 (1H, t), 2.56 (3H, s), 2.73 (1H, dq), 3.75 (3H, d), 3.85 (1H, q), 4.08 (1H, dd), 7.34 (1H, s), 7.92-8.17 (5H, m), 8.34 (1H, s), 8.96 (1H, s), 9.20 (1H, t)

Step 3. (R)-3-amino-N-((4,4-difluoro-1-methylpyrrolidin-2-yl)methyl)-6-(3-methylimidazo[1,2-a]pyridin-6-yl)-5-(oxazol-2-yl)pyrazine-2-carboxamide (Cmpd. 162)

To a stirred mixture of 3-amino-N-[[(2R)-4,4-difluoropyrrolidin-2-yl]methyl]-6-[3-methylimidazo[1,2-a]pyridin-6-yl]-5-(1,3-oxazol-2-yl)pyrazine-2-carboxamide (180 mg, 0.396 mmol, 1 equiv) and HCHO (118.93 mg, 3.961 mmol, 10.00 equiv), DIEA (307.15 mg, 2.377 mmol, 6.00 equiv) in $CH_2Cl_2$ (6 mL)/MeOH (3 mL) was added $NaBH_3CN$ (149.35 mg, 2.377 mmol, 6.00 equiv) dropwise at room temperature under air atmosphere. The resulting mixture was stirred for 2 h at room temperature under air atmosphere. The reaction was quenched by the addition of Water (50 mL) at room temperature. The aqueous layer was extracted with $CH_2Cl_2$ (2×50 mL). The organic layer was combined and dried on anhydrous $Na_2SO_4$ and the solvent was evaporated out to afford a yellow solid. The crude product (160 mg) was purified by Prep-HPLC with the following conditions (Column: XBridge Prep OBD C18 Column 19*250 mm, 5 um; Mobile Phase A: Water (10 MMOL/L $NH_4HCO_3$), Mobile Phase B: ACN; Flow rate: 20 mL/min; Gradient: 32% B to 45% B in 8 min; 254; 220 nm; Rt: 7.67 min) to afford 3-amino-N-[[(2R)-4,4-difluoro-1-methylpyrrolidin-2-yl]methyl]-6-[3-methylimidazo[1,2-a]pyridin-6-yl]-5-(1,3-oxazol-2-yl)pyrazine-2-carboxamide (Cmpd. 162) (40 mg, 21.56%) as a yellow solid. LCMS: m/z (ESI), $[M+H]^+=469.2$ 1H NMR (400 MHz, DMSO-$d_6$) δ 2.19 (1H, dt), 2.33 (3H, s), 2.42 (4H, s), 2.54-2.71 (1H, m), 2.79 (1H, s), 3.55 (1H, d), 7.20 (1H, dd), 7.38 (2H, d), 7.49 (1H, d), 7.90 (2H, s), 8.29 (2H, d), 8.77 (1H, t).

Example 171. Preparation of 3-amino-N-[(6-[1-methyl-1,6-diazaspiro[3.3]heptan-6-yl]pyridin-2-yl)methyl]-6-[3-methylimidazo[1,2-a]pyridin-6-yl]-5-(1,3-oxazol-2-yl)pyrazine-2-carboxamide (Cmpd. 171)

SCHEME 94

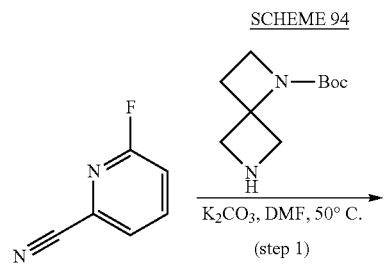

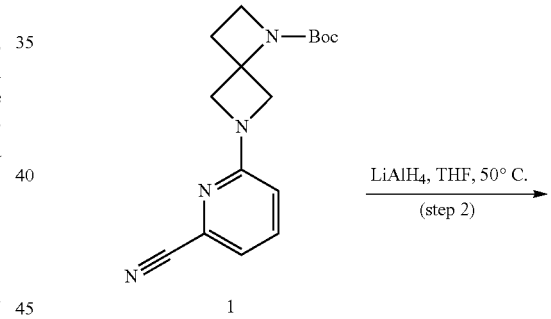

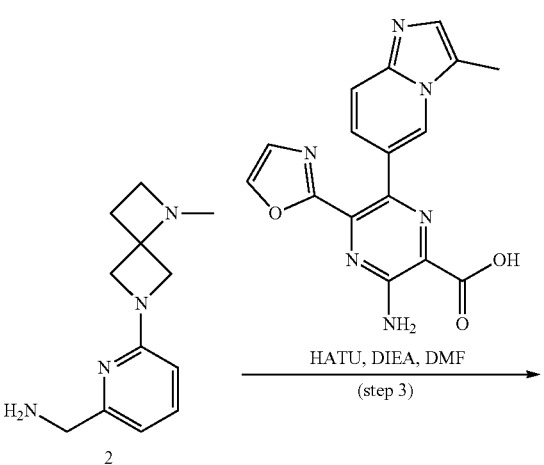

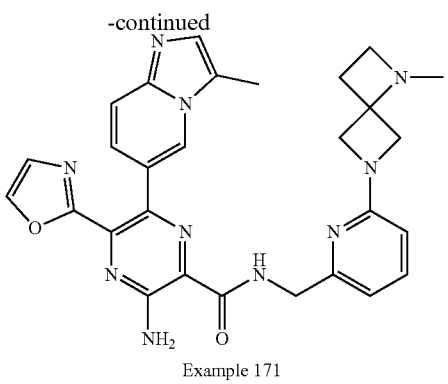

Example 171

Step 1. tert-butyl 6-(6-cyanopyridin-2-yl)-1,6-diazaspiro[3.3]heptane-1-carboxylate A mixture of 6-fluoropyridine-2-carbonitrile (1.5 g, 12.29 mmol, 1 equiv) and tert-butyl 1,6-diazaspiro[3.3]heptane-1-carboxylate (2.92 g, 14.73 mmol, 1.20 equiv) and K$_2$CO$_3$ (5.09 g, 36.829 mmol, 3.00 equiv) in DMF (20 mL) was stirred for 10h at 50° C. under air atmosphere. The resulting mixture was extracted with EtOAc (4×20 mL). The combined organic layers were washed with H$_2$O (2×10 mL), dried over anhydrous Na$_2$SO$_4$. After filtration, the filtrate was concentrated under reduced pressure. The residue was purified by silica gel column chromatography, eluted with PE/EtOAc (6:1) to afford tert-butyl 6-(6-cyanopyridin-2-yl)-1,6-diazaspiro[3.3]heptane-1-carboxylate (2.69 g, 72.17%) as a white solid. LCMS: m/z (ESI), [M+H]$^+$=301.3.

Step 2. 1-(6-[1-methyl-1,6-diazaspiro[3.3]heptan-6-yl]pyridin-2-yl)methanamine A mixture of tert-butyl 6-(6-cyanopyridin-2-yl)-1,6-diazaspiro[3.3]heptane-1-carboxylate (0.5 g, 1.665 mmol, 1 equiv) and LiAlH$_4$ (0.13 g, 3.425 mmol, 2.06 equiv) in THF (10 mL) was stirred for 6h at 50° C. under air atmosphere. The reaction was quenched by the addition of EtOAc (20 mL) at room temperature. And then extracted with EtOAc (4×20 mL). The combined organic layers were washed with water (3×10 mL), dried over anhydrous Na$_2$SO$_4$. After filtration, the filtrate was concentrated under reduced pressure. This resulted in 1-(6-[1-methyl-1,6-diazaspiro[3.3]heptan-6-yl]pyridin-2-yl)methanamine (200 mg, 53.93%) as a white solid. LCMS: m/z (ESI), [M+H]$^+$=219.2.

Step 3. 3-amino-N-[(6-[1-methyl-1,6-diazaspiro[3.3]heptan-6-yl]pyridin-2-yl)methyl]-6-[3-methylimidazo[1,2-a]pyridin-6-yl]-5-(1,3-oxazol-2-yl)pyrazine-2-carboxamide (Cmpd. 171)

To a stirred solution/mixture of 3-amino-6-[imidazo[1,2-a]pyridin-6-yl]-5-(1,3-oxazol-2-yl)pyrazine-2-carboxylic acid (100 mg, 0.31 mmol, 1 equiv) and 1-(6-[1-methyl-1,6-diazaspiro[3.3]heptan-6-yl]pyridin-2-yl)methanamine (101.6 mg, 0.465 mmol, 1.50 equiv) in DMF (3 mL) were added HATU (235.96 mg, 0.621 mmol, 2.00 equiv) and DIEA (120.31 mg, 0.931 mmol, 3.0 equiv) dropwise at room temperature under air atmosphere. The crude product (100 mg) was purified by Prep-HPLC with the following conditions (Column: XBridge Prep OBD C18 Column 30×150 mm 5 um; Mobile Phase A: Mobile Phase B: ACN; Flow rate: 60 mL/min; Gradient: 28% B to 40% B in 7 min; 254; 220 nm; Rt: 6.37 min) to afford 3-amino-N-[(6-[1-methyl-1,6-diazaspiro[3.3]heptan-6-yl]pyridin-2-yl)methyl]-6-[3-methylimidazo[1,2-a]pyridin-6-yl]-5-(1,3-oxazol-2-yl)pyrazine-2-carboxamide (Cmpd. 171) (20 mg, 12.01%) as a yellow solid. LCMS: m/z (ESI), [M+H]$^+$=537.3. $^1$H NMR (400 MHz, DMSO-d$_6$) δ 2.1 (5H, d), 2.4 (3H, s), 2.9 (2H, t), 3.8 (2H, d), 4.0 (2H, d), 4.5 (2H, d), 6.3 (1H, d), 6.6 (1H, d), 7.3 (1H, d), 7.4 (2H, d), 7.4-7.5 (2H, m), 7.9 (1H, s), 8.3 (1H, s), 8.3 (1H, s), 9.4 (1H, t).

Example 172. Preparation of 3-amino-N-((6-((8-methyl-3,8-diazabicyclo[3.2.1]octan-3-yl)pyridin-2-yl)methyl)-6-(3-methylimidazo[1,2-a]pyridin-6-yl)-5-(oxazol-2-yl)pyrazine-2-carboxamide (Cmpd. 172)

SCHEME 95

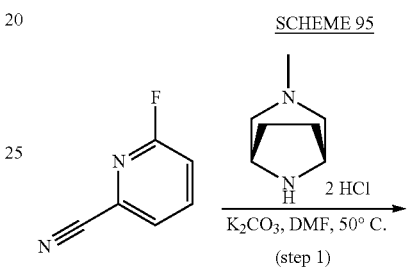

(step 1)

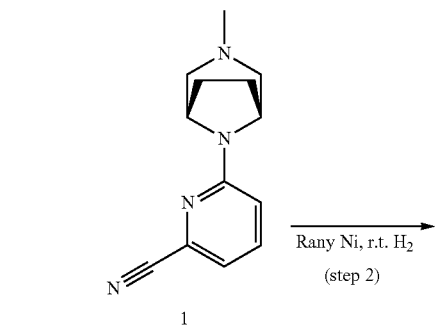

(step 2)

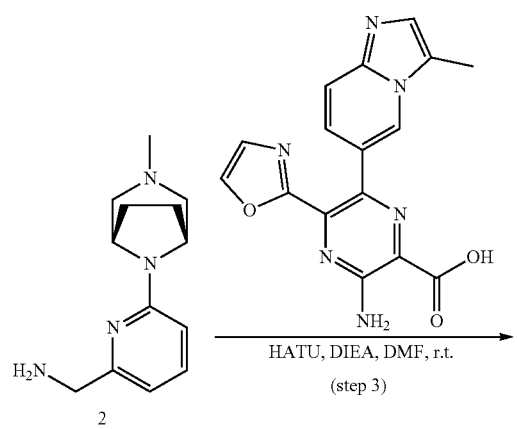

(step 3)

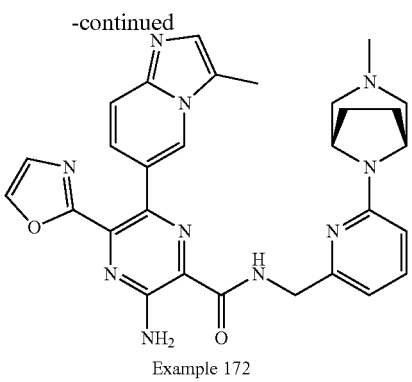

Example 172

Step 1. 6-((1R,5S)-3-methyl-3,8-diazabicyclo[3.2.1]octan-3-yl)picolinonitrile To a stirred solution of 6-fluoropyridine-2-carbonitrile (594 mg, 4.865 mmol, 1 equiv) and 3-methyl-3,8-diazabicyclo[3.2.1]octane (675.35 mg, 5.351 mmol, 1.10 equiv) in DMF (10.5 mL) were added $K_2CO_3$ (2756.59 mg, 19.946 mmol, 4.10 equiv) in portions at room temperature under air atmosphere. The resulting mixture was stirred for 6.0h at 50° C. under air atmosphere. The resulting mixture was concentrated under vacuum. The residue was purified by Prep-TLC (hexane/EtOAc 1:1) to afford 6-[3-methyl-3,8-diazabicyclo[3.2.1]octan-8-yl]pyridine-2-carbonitrile (613 mg, 55.19%) as a light yellow oil. LCMS: m/z (ESI), [M+H]$^+$=229.3

Step 2. (6-((1R,5S)-3-methyl-3,8-diazabicyclo[3.2.1]octan-3-yl)pyridin-2-yl)methanamine To a stirred solution of 6-[8-methyl-3,8-diazabicyclo[3.2.1]octan-3-yl]pyridine-2-carbonitrile (613 mg, 2.685 mmol, 1 equiv) and $NH_3 \cdot H_2O$ (1.2 mL, 190.218 mmol, 65.14 equiv) in MeOH (15 mL) was added Raney-Ni (345.07 mg, 4.028 mmol, 1.50 equiv) dropwise at room temperature under hydrogen atmosphere. The resulting mixture was stirred for 1.0 h at room temperature under hydrogen atmosphere. Desired product could be detected by LCMS. The resulting mixture was concentrated under reduced pressure to afford 1-(6-[8-methyl-3,8-diazabicyclo[3.2.1]octan-3-yl]pyridin-2-yl)methanamine (580 mg, 94.99%) as a yellow oil. LCMS: m/z (ESI), [M+H]$^+$=233.3.

Step 3. 3-amino-N-((6-((1R,5S)-3-methyl-3,8-diazabicyclo[3.2.1]octan-8-yl)pyridin-2-yl)methyl)-6-(3-methylimidazo[1,2-a]pyridin-6-yl)-5-(oxazol-2-yl)pyrazine-2-carboxamide To a stirred solution of 3-amino-6-[3-methylimidazo[1,2-a]pyridin-6-yl]-5-(1,3-oxazol-2-yl)pyrazine-2-carboxamide (200 mg, 0.596 mmol, 1 equiv) and 1-(6-[3-methyl-3,8-diazabicyclo[3.2.1]octan-8-yl]pyridin-2-yl)methanamine (207.85 mg, 0.895 mmol, 1.50 equiv) in DMF (4.00 mL, 205.218 mmol, 324.98 equiv) were added HATU (453.56 mg, 1.193 mmol, 2.00 equiv) and DIEA (308.34 mg, 2.386 mmol, 4.00 equiv) in portions at room temperature under air atmosphere. Desired product could be detected by LCMS. The residue was purified by Prep-TLC ($CH_2Cl_2$/MeOH 20:1) to afford 3-amino-N-[(6-[3-methyl-3,8-diazabicyclo[3.2.1]octan-8-yl]pyridin-2-yl)methyl]-6-[3-methylimidazo[1,2-a]pyridin-6-yl]-5-(1,3-oxazol-2-yl)pyrazine-2-carboxamide (100 mg, 30.45%) as a dark yellow solid. The crude product (100 mg) was purified by Prep-HPLC with the following conditions (Column: X Bridge Prep OBD C18 Column 30×150 mm 5 um; Mobile Phase A: Water (0.05% NH3H2O), Mobile Phase B: ACN; Flow rate: 60 mL/min; Gradient: 31% B to 43% B in 7 min; 254; 220 nm; Rt: 6.77 min) to afford 3-amino-N-[(6-[3-methyl-3,8-diazabicyclo[3.2.1]octan-8-yl]pyridin-2-yl)methyl]-6-[3-methylimidazo[1,2-a]pyridin-6-yl]-5-(1,3-oxazol-2-yl)pyrazine-2-carboxamide (Cmpd. 172) (39 mg, 23.9%) as a yellow solid. LCMS: m/z (ESI), [M+H]$^+$=551.3. $^1$H NMR (400 MHz, DMSO-d$_6$) δ 1.57 (4H, s), 1.92 (3H, s), 2.04 (2H, d), 2.17 (2H, d), 2.43 (3H, d), 4.36 (2H, s), 4.48 (2H, d), 6.57 (2H, t), 7.23 (1H, dd), 7.35 (1H, d), 7.38-7.55 (3H, m), 7.94 (2H, s), 8.27 (1H, d), 8.38 (1H, s), 9.34 (1H, t)

Example 175. Preparation of 3-amino-N-((6-(6-methyl-2,6-diazaspiro[3.4]octan-2-yl)pyridin-2-yl)methyl)-6-(3-methylimidazo[1,2-a]pyridin-6-yl)-5-(oxazol-2-yl)pyrazine-2-carboxamide (Cmpd. 175)

SCHEME 96

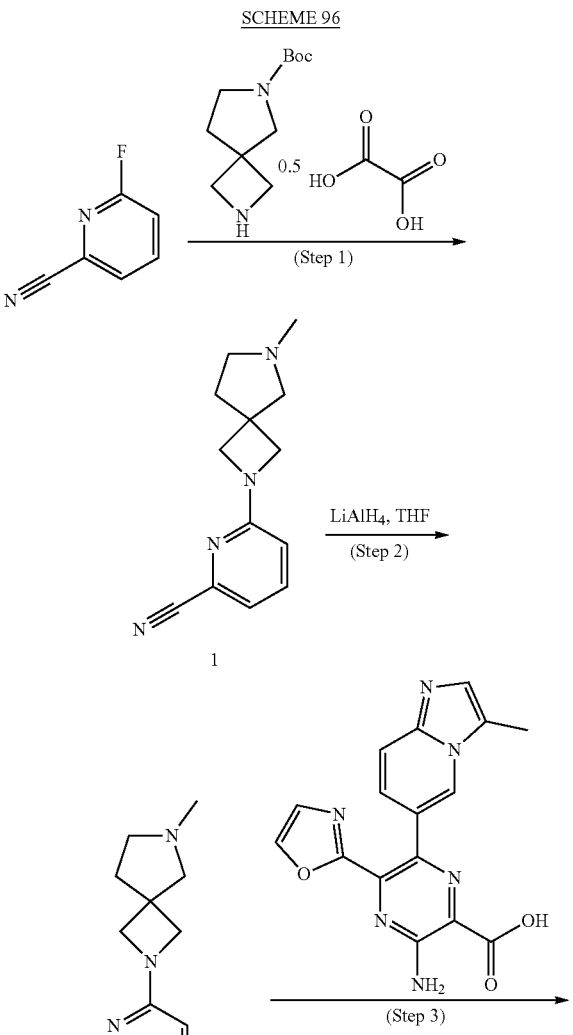

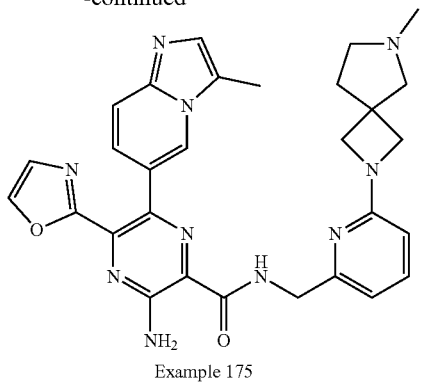

Example 175

Step 1. 6-(6-methyl-2,6-diazaspiro[3.4]octan-2-yl) picolinonitrile

Into a 40 mL sealed tube were added 6-fluoropyridine-2-carbonitrile (500 mg, 4.095 mmol, 1 equiv.) oxalic acid; tert-butyl 2,6-diazaspiro[3.4]octane-6-carboxylate (1609.41 mg, 5.323 mmol, 1.3 equiv) $K_2CO_3$ (1697.83 mg, 12.285 mmol, 3 equiv) and DMF (10 mL) at room temperature. The resulting mixture was stirred for 3 hours at 50° C. The reaction was quenched by the addition of sat. NaCl (aq.) (250 mL) at room temperature. The resulting mixture was extracted with EtOAc (2×125 mL). The combined organic layers were washed with sat. NaCl (aq.) (250 mL), dried over anhydrous $Na_2SO_4$. After filtration, the filtrate was concentrated under reduced pressure. The residue was purified by Prep-TLC ($CH_2Cl_2$/MeOH 30:1) to afford 6-[(1S,4S)-5-methyl-2,5-diazabicyclo[2.2.1]heptan-2-yl]pyridine-2-carbonitrile (700 mg, 79.78%) as a white solid. LCMS: m/z (ESI), [M+H]$^+$=259.2

Step 2. (6-(6-methyl-2,6-diazaspiro[3.4]octan-2-yl) pyridin-2-yl)methanamine Into a 40 mL sealed tube were added tert-butyl 2-(6-cyanopyridin-2-yl)-2,6-diazaspiro[3.4]octane-6-carboxylate (500 mg, 1.590 mmol, 1 equiv) in THF (10 mL) then LiAlH$_4$ (301.81 mg, 7.952 mmol, 5 equiv) was added at 0° C. This solution was stirred at 70° C. for 2h. Desired product could be detected by LCMS. The reaction was quenched by the addition of Water (0.5 mL) at 0° C. The solid was filtered out. The filtrate was concentrated under vacuum to afford 1-(6-[6-methyl-2,6-diazaspiro[3.4]octan-2-yl]pyridin-2-yl)methanamine (250 mg, 67.66%) as a yellow oil. LCMS: m/z (ESI), [M+H]$^+$=233.3.

Step 3. 3-amino-N-((6-(6-methyl-2,6-diazaspiro[3.4]octan-2-yl)pyridin-2-yl)methyl)-6-(3-methylimidazo[1,2-a]pyridin-6-yl)-5-(oxazol-2-yl)pyrazine-2-carboxamide Into a 10 mL sealed tube were added 1-(6-[6-methyl-2,6-diazaspiro[3.4]octan-2-yl]pyridin-2-yl)methanamine (150 mg, 0.646 mmol, 1 equiv) 3-amino-6-[3-methylimidazo[1,2-a]pyridin-6-yl]-5-(1,3-oxazol-2-yl)pyrazine-2-carboxylic acid (65.14 mg, 0.194 mmol, 1.50 equiv) HATU (490.98 mg, 1.291 mmol, 2.00 equiv) and DIEA (333.77 mg, 2.583 mmol, 4 equiv) in DMF (10 mL) at room temperature for 2 h. Desired product could be detected by LCMS. The crude product (100 mg) was purified by Prep-HPLC with the following conditions (Column: XBridge Prep OBD C18 Column 19*250 mm, 5 um; Mobile Phase A: Mobile Phase B: MeOH-HPLC; Flow rate: 20 mL/min; Gradient: 66% B to 70% B in 7 min; 254; 220 nm; Rt: 6.32 min) to afford 3-amino-N-[(6-[6-methyl-2,6-diazaspiro[3.4]octan-2-yl]pyridin-2-yl)methyl]-6-[3-methylimidazo[1,2-a]pyridin-6-yl]-5-(1,3-oxazol-2-yl)pyrazine-2-carboxamide (Cmpd. 175) (15 mg, 14.3%) as a yellow solid. LCMS: m/z (ESI), [M+H]$^+$=551.3. $^1$H NMR (400 mHz, DMSO-d$_6$) δ 1.87 (2H, t), 2.22 (3H, s), 2.36-2.45 (5H, m), 2.48 (2H, s), 3.66-3.80 (4H, m), 4.47 (2H, d), 6.23 (1H, d), 6.61 (1H, d), 7.28 (1H, dd), 7.36 (1H, d), 7.38-7.57 (3H, m), 7.93 (2H, s), 8.25-8.37 (2H, m), 9.38 (1H, d)

Example 198. Preparation of 3-amino-6-(3-(aminomethyl)imidazo[1,2-a]pyridin-6-yl)-N-((3-fluoropyridin-2-yl)methyl)-5-(oxazol-2-yl)pyrazine-2-carboxamide (Cmpd. 198)

SCHEME 97

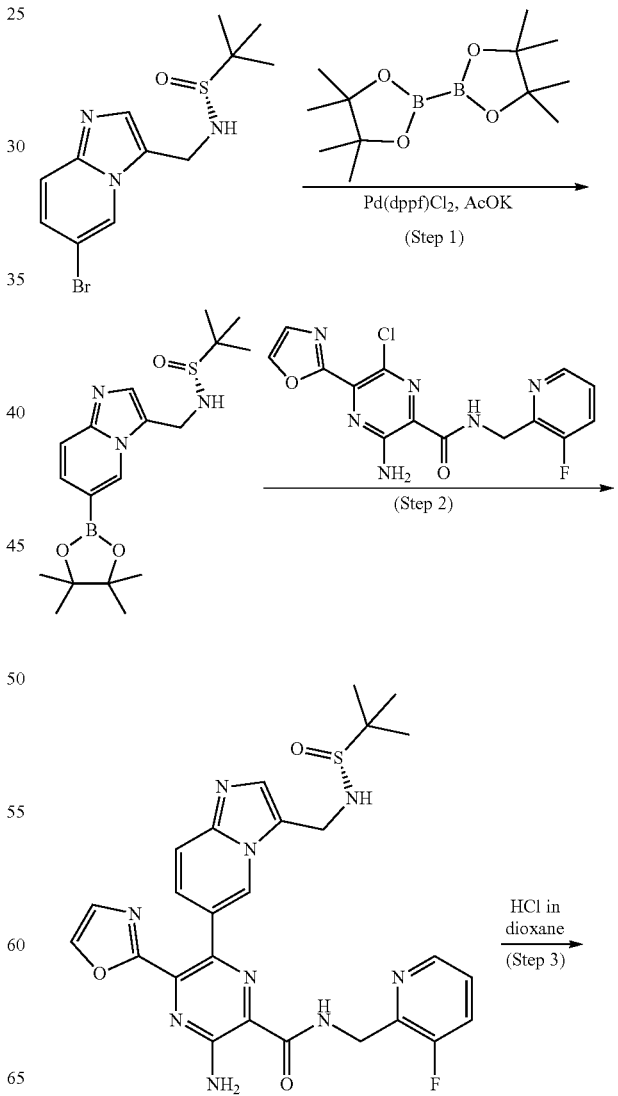

-continued

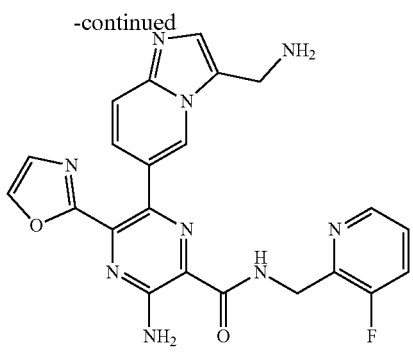

Example 198

Step 1. (S)-2-methyl-N-((6-(4,4,5,5-tetramethyl-1,3,2-dioxaborolan-2-yl)imidazo[1,2-a]pyridin-3-yl)methyl)propane-2-sulfinamide A mixture of tert-butyl N-([6-bromoimidazo[1,2-a]pyridin-3-yl]methyl)carbamate (700 mg, 2.146 mmol, 1 equiv) and 4,4,5,5-tetramethyl-2-(4,4,5,5-tetramethyl-1,3,2-dioxaborolan-2-yl)-1,3,2-dioxaborolane (817. 42 mg, 3.219 mmol, 1.50 equiv) and Pd(dppf)Cl$_2$ (157.02 mg, 0.215 mmol, 0.1 equiv) and AcOK (421.22 mg, 4.292 mmol, 2 equiv) in 1,4-dioxane (10 mL) was stirred for 2 h at 90° C. under nitrogen atmosphere. The residue was purified by Prep-TLC (CH$_2$Cl$_2$/MeOH 30:1) to afford tert-butyl N-[[6-(4,4,5,5-tetramethyl-1,3,2-dioxaborolan-2-yl)imidazo[1,2-a]pyridin-3-yl]methyl]carbamate (500 mg, 49.94%) as a Brown yellow solid. LCMS: m/z (ES$^+$), [M+H]$^+$=432.3

Step 2. (S)-3-amino-6-(3-(((tert-butylsulfinyl)amino)methyl)imidazo[1,2-a]pyridin-6-yl)-N-((3-fluoropyridin-2-yl)methyl)-5-(oxazol-2-yl)pyrazine-2-carboxamide To a stirred solution of (S)-2-methyl-N-[[6-(4,4,5,5-tetramethyl-1,3,2-dioxaborolan-2-yl)imidazo[1,2-a]pyridin-3-yl]methyl]propane-2-sulfinamide (649.19 mg, 1.721 mmol, 2.00 equiv) and 3-amino-6-chloro-N-[(3-fluoropyridin-2-yl)methyl]-5-(1,3-oxazol-2-yl)pyrazine-2-carboxamide (300 mg, 0.860 mmol, 1 equiv) in dioxane/H2O=7:1 (16 mL) were added K$_3$PO$_4$ (547.83 mg, 2.581 mmol, 3.0 equiv) and Pd(dppf)Cl$_2$.CH$_2$Cl$_2$ (147.53 mg, 0.181 mmol, 0.21 equiv) dropwise/in portions at room temperature under hydrogen atmosphere. The resulting mixture was stirred for 2.0 h at 80° C. under nitrogen atmosphere. Desired product could be detected by LCMS: m/z (ES$^+$), [M+H]$^+$=564.3

Step 3. 3-amino-6-(3-(aminomethyl)imidazo[1,2-a]pyridin-6-yl)-N-((3-fluoropyridin-2-yl)methyl)-5-(oxazol-2-yl)pyrazine-2-carboxamide Into a 10.0 mL sealed tube were added 3-amino-N-[(3-fluoropyridin-2-yl)methyl]-6-[3-([[(S)-2-methylpropane-2-sulfinyl]amino]methyl)imidazo[1,2-a]pyridin-6-yl]-5-(1,3-oxazol-2-yl)pyrazine-2-carboxamide (150 mg) and dioxane/HCl (6.0 mL) at room temperature. The resulting mixture was stirred for 60 min at room temperature under air atmosphere. Desired product could be detected by LCMS. The resulting mixture was concentrated under reduced pressure. The resulting mixture was diluted with DMF (4 mL). And submitted to Prep-HPLC The crude product (100 mg) was purified by Prep-HPLC with the following conditions (Column: XBridge Prep OBD C18 Column 19*250 mm, 5 um; Mobile Phase A: Water (0.05% NH$_3$H$_2$O), Mobile Phase B: ACN; Flow rate: 20 mL/min; Gradient: 21% B to 31% B in 8 min; 254/220 nm; Rt: 7.53 min) to afford 3-amino-6-[3-(aminomethyl)imidazo[1,2-a]pyridin-6-yl]-N-[(3-fluoropyridin-2-yl)methyl]-5-(1,3-oxazol-2-yl)pyrazine-2-carboxamide (Cmpd. 198) (20 mg, 6.12%) as a yellow solid. LCMS: m/z (ES$^+$), [M+H]$^+$=460.2. $^1$H-NMR (DMSO-d$_6$, 40 MHz) δ 4.01 (2H, s), 4.67-4.76 (2H, m), 7.29 (1H, dd), 7.33-7.56 (4H, m), 7.72 (1H, ddd), 7.90 (2H, s), 8.28 (1H, d), 8.38 (1H, dt), 8.57 (1H, t), 9.34 (1H, t)

Example 199. 3-amino-5-(4-fluorophenyl)-N-([3-[2-(methylamino)ethoxy]pyridin-2-yl]methyl)-6-[3-methylimidazo[1,2-a]pyridin-6-yl]pyrazine-2-carboxamide (Cmpd. 199)

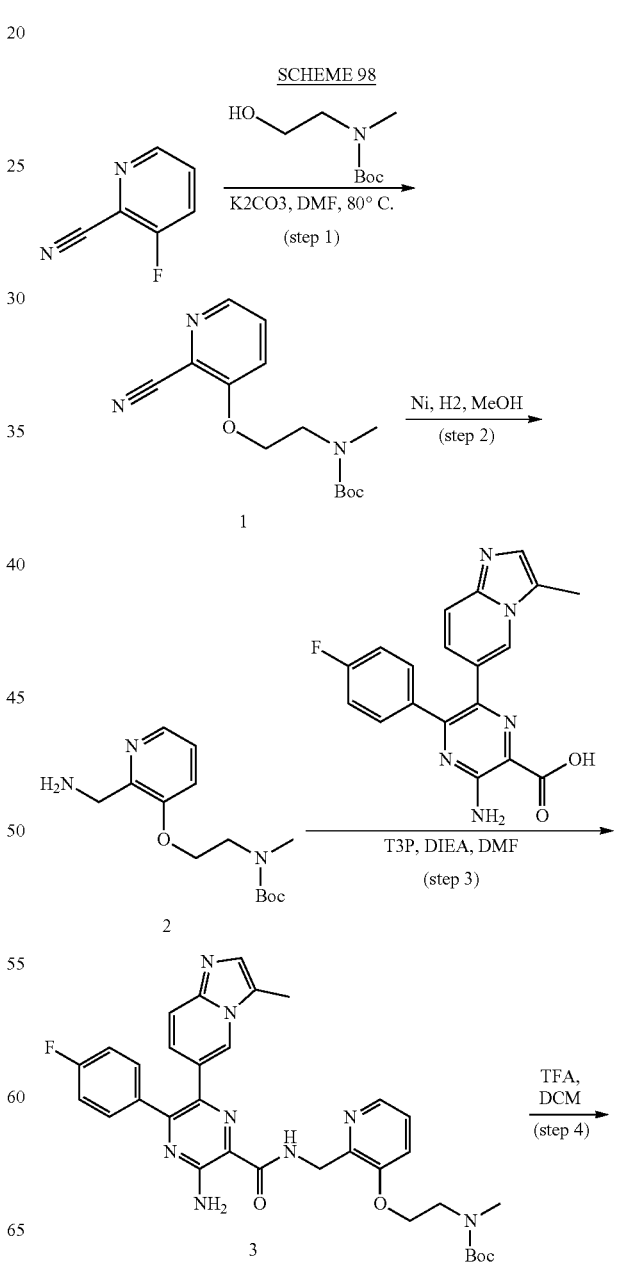

-continued

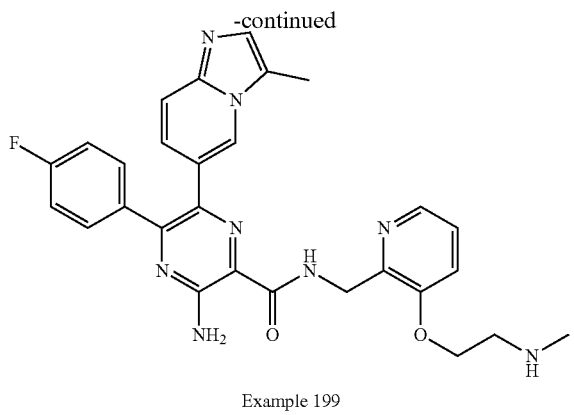

Example 199

Step 1. tert-butyl N-[2-[(2-cyanopyridin-3-yl)oxy]ethyl]-N-methylcarbamate

Into a 20-mL vial, was placed 3-fluoropyridine-2-carbonitrile (800 mg, 6.552 mmol, 1 equiv), tert-butyl N-(2-hydroxyethyl)-N-methylcarbamate (1.38 g, 7.875 mmol, 1.20 equiv), DMF (4 mL), $K_2CO_3$ (2.26 g, 16.352 mmol, 2.50 equiv). The resulting mixture was stirred for 16 hrs at 80° C. The resulting mixture was diluted with 20 mL of $H_2O$. The resulting solution was extracted with 3×8 mL of ethyl acetate and the organic layers combined. The resulting solution was washed with 3×10 mL of brine and the organic layers combined and dried over anhydrous sodium sulfate and concentrated under vacuum. The residue was purified by preparative TLC (EtOAc: petroleum ether=1:1). This resulted in 738 mg (40.62%) of tert-butyl N-[2-[(2-cyanopyridin-3-yl)oxy]ethyl]-N-methylcarbamate as a purple solid. LCMS: m/z (ESI), [M+H−tBu]$^+$=222.1 $^1$H-NMR (300 MHz, DMSO-$d_6$) δ 1.34 (9H, d), 2.91 (3H, d), 3.58 (2H, t), 4.34 (2H, s), 7.71 (1H, d), 7.84 (1H, d), 8.31 (1H, d)

Step 2. tert-butyl N-(2-[[2-(aminomethyl)pyridin-3-yl]oxy]ethyl)-N-methylcarbamate Into a 25-mL round-bottom flask purged and maintained with an inert atmosphere of hydrogen, was placed tert-butyl N-[2-[(2-cyanopyridin-3-yl)oxy]ethyl]-N-methylcarbamate (738 mg, 2.661 mmol, 1 equiv), MeOH (10 mL), $NH_3 \cdot H_2O$ (1 mL, 25.681 mmol, 9.65 equiv), Raney Ni (227.99 mg, 2.661 mmol, 1.00 equiv). The resulting solution was stirred for 2 hrs at 16° C. The solids were filtered out. The resulting mixture was concentrated under vacuum.

This resulted in 700 mg (93.49%) of tert-butyl N-(2-[[2-(aminomethyl)pyridin-3-yl]oxy]ethyl)-N-methylcarbamate as a purple solid. LCMS: m/z (ESI), [M+H]$^+$=282.2

Step 3. tert-butyl N-(2-[[2-([[3-amino-5-(4-fluorophenyl)-6-[3-methylimidazo[1,2-a]pyridin-6-yl]pyrazin-2-yl]formamido]methyl)pyridin-3-yl]oxy]ethyl)-N-methylcarbamate Into a 6-mL vial, was placed tert-butyl N-(2-[[2-(aminomethyl)pyridin-3-yl]oxy]ethyl)-N-methylcarbamate (154.87 mg, 0.550 mmol, 2.00 equiv), 3-amino-5-(4-fluorophenyl)-6-[3-methylimidazo[1,2-a]pyridin-6-yl]pyrazine-2-carboxylic acid (100 mg, 0.275 mmol, 1 equiv), DIEA (0.34 mL, 2.061 mmol, 7.49 equiv), DMF (2.5 mL), $T_3P$ (262.70 mg, 0.826 mmol, 3.00 equiv). The resulting solution was stirred for 16 hrs at 16° C. The resulting solution was diluted with 20 mL of $H_2O$. The resulting solution was extracted with 3×10 mL of ethyl acetate and the organic layers combined. The resulting solution was extracted with 3×10 mL of brine and the organic layers combined and dried over anhydrous sodium sulfate. The residue was purified by preparative TLC (DCM:MeOH=7:1). This resulted in 93 mg (53.92%) of tert-butyl N-(2-[[2-([[3-amino-5-(4-fluorophenyl)-6-[3-methylimidazo[1,2-a]pyridin-6-yl]pyrazin-2-yl]formamido]methyl)pyridin-3-yl]oxy]ethyl)-N-methylcarbamate as a yellow solid. LCMS: m/z (ESI), [M/2+H]$^+$=314. 3

Step 4. 3-amino-5-(4-fluorophenyl)-N-((3-(2-(methylamino)ethoxy)pyridin-2-yl)methyl)-6-(3-methylimidazo[1,2-a]pyridin-6-yl)pyrazine-2-carboxamide 2,2,2-trifluoroacetate (Cmpd. 199)

Into a 6-mL vial, was placed tert-butyl N-(2-[[2-([[3-amino-5-(4-fluorophenyl)-6-[3-methylimidazo[1,2-a]pyridin-6-yl]pyrazin-2-yl]formamido]methyl)pyridin-3-yl]oxy]ethyl)-N-methylcarbamate (80 mg, 0.128 mmol, 1 equiv), DCM (3.00 mL), TFA (1.00 mL, 13.46 mmol, 105.2 equiv). The resulting solution was stirred for 2 hrs at 20° C. The resulting mixture was concentrated under vacuum. The pH value of the solution was adjusted to 9 with Saturated sodium bicarbonate solution. The resulting solution was extracted with 3×10 mL of ethyl acetate and the organic layers combined. The resulting mixture was concentrated under vacuum. The residue was purified by preparative TLC (DCM:MeOH=3:1). The crude product was purified by preparative HPLC (Column: Sunfire Prep C18 OBD Column, 10 um, 19*250 mm; Mobile Phase A: Water (0.05% TFA), Mobile Phase B: ACN; Flow rate: 20 mL/min; Gradient: 10% B to 25% B in 10 min; 254, 220 nm; Rt: 8.7 min). This resulted in 20.22 mg of 3-amino-5-(4-fluorophenyl)-N-((3-(2-(methylamino)ethoxy)pyridin-2-yl)methyl)-6-(3-methylimidazo[1,2-a]pyridin-6-yl)pyrazine-2-carboxamide 2,2,2-trifluoroacetate (Cmpd. 199) as a yellow solid. LCMS: m/z (ESI), [M+H]$^+$=527.3 $^1$H-NMR (300 MHz, DMSO-$d_6$) δ 2.52-2.54 (3H, m), 2.71 (3H, t), 3.43 (2H, s), 4.34 (2H, t), 4.75 (2H, d), 7.23 (2H, t), 7.34 (1H, d), 7.44-7.58 (3H, m), 7.69 (1H, d), 7.79-7.90 (2H, m), 8.03 (1H, d), 8.13 (1H, d), 8.76 (3H, d), 9.34 (1H, t). $^{19}$F NMR (300 MHz, DMSO-$d_6$) δ −111.615 (1F), −74.101 (7.27F)

Examples 202/206. 3-amino-N-[[1-methylpyrrolidin-2-yl]methyl]-5-(1,3-oxazol-2-yl)-6-[3-(trifluoromethyl)imidazo[1,2-a]pyridin-6-yl]pyrazine-2-carboxamide (Cmpd. 202) 3-amino-N-[1-methylpyrrolidin-2-yl]methyl]-5-(1,3-oxazol-2-yl)-6-[3-(trifluoromethyl)imidazo[1,2-a]pyridin-6-yl]pyrazine-2-carboxamide (Cmpd. 206)

SCHEME 99

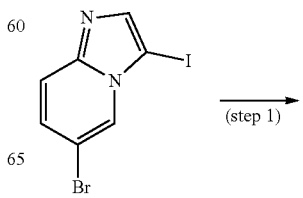

(step 1)

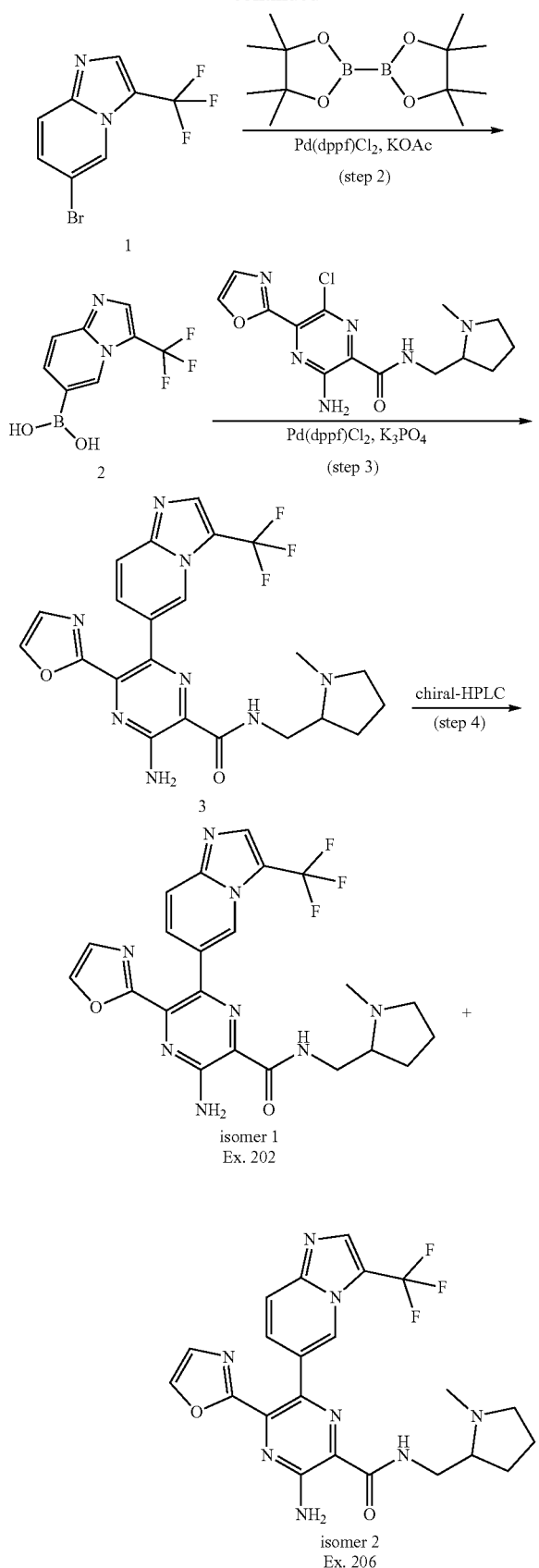

Step 1. 6-bromo-3-(trifluoromethyl)imidazo[1,2-a]pyridine

A mixture of 6-bromo-3-iodoimidazo[1,2-a]pyridine (1.5 g, 4.645 mmol, 1 equiv), 15-(trifluoromethyl)-1lambda4,12lambda4-diaza-15-cupratetracyclo [10.2.1.0ˆ[5,14]. 0ˆ[8,13]]pentadeca-1,3,5(14), 6,8,10,12-heptaen-15-ylium (1.74 g, 5.574 mmol, 1.2 equiv) in DMF (15 mL) was stirred for overnight at 50° C. The resulting mixture was diluted with $CH_2Cl_2$ (100 mL). The resulting mixture was filtered, the filter cake was washed with DCM (2×50 mL). The resulting mixture was washed with 2×150 mL of water. The organic phase was concentrated under reduced pressure. The residue was purified by silica gel column chromatography (detected by mAU 220 nm), eluted with $CH_2Cl_2$/PE (40:60) to afford 6-bromo-3-(trifluoromethyl)imidazo[1,2-a]pyridine (780 mg, 63.36%) as a white solid. LCMS: m/z (ESI), $[M+H]^+$= 267.1. $^1H$ NMR (300 MHz, DMSO-$d_6$) δ 7.7 (1H, dd), 7.7-7.8 (1H, m), 8.2-8.2 (1H, m), 8.6-8.8 (1H, m).

Step 2. [3-(trifluoromethyl)imidazo[1,2-a]pyridin-6-yl]boronic Acid

To a solution of 6-bromo-3-(trifluoromethyl)imidazo[1,2-a]pyridine (500 mg, 1.887 mmol, 1 equiv) and 4,4,5,5-tetramethyl-2-(4,4,5,5-tetramethyl-1,3,2-dioxaborolan-2-yl)-1,3,2-dioxaborolane (958. 14 mg, 3.773 mmol, 2.00 equiv) in dioxane (20 mL) were added AcOK (555.45 mg, 5.660 mmol, 3 equiv) and Pd(dppf)Cl$_2$ (276.08 mg, 0.377 mmol, 0.2 equiv). After stirring for 2 h at 90° C. under a nitrogen atmosphere, The resulting mixture was concentrated under reduced pressure. The residue was purified by reverse flash chromatography with the following conditions: column, C18 silica gel; mobile phase, MeOH in water, 10% to 50% gradient in 10 min; detector, UV 254 nm to afford [3-(trifluoromethyl)imidazo[1,2-a]pyridin-6-yl]boronic acid (370 mg, 85.29%) as a white solid. LCMS: m/z (ESI), $[M+H]^+$=231.1

Step 3. 3-amino-N-[[(2S)-1-methylpyrrolidin-2-yl]methyl]-5-(1,3-oxazol-2-yl)-6-[3-(trifluoromethyl)imidazo[1,2-a]pyridin-6-yl]pyrazine-2-carboxamide To a solution of [3-(trifluoromethyl)imidazo[1,2-a]pyridin-6-yl]boronic acid (350 mg, 1.522 mmol, 1 equiv) and 3-amino-6-chloro-N-[(1-methylpyrrolidin-2-yl)methyl]-5-(1,3-oxazol-2-yl)pyrazine-2-carbox amide (512.60 mg, 1.522 mmol, 1.00 equiv) in dioxane (20 mL) and H$_2$O (2 mL) were added K$_3$PO$_4$ (969.25 mg, 4.566 mmol, 3 equiv) and Pd(dppf)Cl$_2$ (222.74 mg, 0.304 mmol, 0.2 equiv). After stirring for 2 h at 90° C. under a nitrogen atmosphere, the resulting mixture was concentrated under reduced pressure. The residue was purified by Prep-TLC/silica gel column chromatography, eluted with $CH_2Cl_2$/MeOH (15:1) to afford 3-amino-N-[[1-methylpyrrolidin-2-yl]methyl]-5-(1,3-oxazol-2-yl)-6-[3-(trifluoromethyl)imidazo[1,2-a]pyridin-6-yl]pyrazine-2-carboxamide (200 mg, 27.01%) as a light yellow solid. LCMS: m/z (ESI), $[M+H]^+$=487.3

Step 4. 3-amino-N-[[1-methylpyrrolidin-2-yl]methyl]-5-(1,3-oxazol-2-yl)-6-[3-(trifluoromethyl)imidazo[1,2-a]pyridin-6-yl]pyrazine-2-carboxamide (Cmpd. 202)/(Cmpd. 206)

The crude product (100 mg) was purified by Prep-chiral HPLC with the following conditions (Column: CHIRAL-PAK IG, 2.0 cm I.D*25 cm L (5 um); Mobile Phase A:

CO2:75, Mobile Phase B: ETOH:ACN=1:25; Flow rate: 40 mL/min; 220 nm; RT1:10; RT2:12.65) to afford 3-amino-N-[1-methylpyrrolidin-2-yl]methyl]-5-(1,3-oxazol-2-yl)-6-[3-(trifluoromethyl)imidazo[1,2-a]pyridin-6-yl]pyrazine-2-carboxamide (Cmpd. 202) (50 mg, 27.78%) and 3-amino-N-[1-methylpyrrolidin-2-yl]methyl]-5-(1,3-oxazol-2-yl)-6-[3-(trifluoromethyl)imidazo[1,2-a]pyridin-6-yl]pyrazine-2-carboxamide (Cmpd. 206) as a yellow solid. 3-amino-N-[1-methylpyrrolidin-2-yl]methyl]-5-(1,3-oxazol-2-yl)-6-[3-(trifluoromethyl)imidazo[1,2-a]pyridin-6-yl]pyrazine-2-carboxamide. (Cmpd. 202) LCMS: m/z (ESI), [M+H]$^+$=487.3.1H NMR (400 MHz, DMSO-d$_6$) δ 1.6 (3H, ddd), 1.8 (1H, dd), 2.1 (1H, q), 2.3 (3H, s), 2.4 (1H, s), 2.9 (1H, dd), 3.2 (1H, ddd), 3.5 (1H, ddd), 7.3 (1H, s), 7.7 (1H, dd), 7.8 (1H, d), 7.9-8.1 (1H, m), 8.2 (1H, s), 8.3 (1H, s), 8.6 (2H, d). (Cmpd. 206) LCMS: m/z (ESI), [M+H]$^+$=487.3.1H NMR (400 MHz, DMSO-d$_6$) δ 1.6 (3H, ddd), 1.8 (1H, dd), 2.1 (1H, q), 2.3 (3H, s), 2.4 (1H, s), 2.9 (1H, dd), 3.2 (1H, ddd), 3.5 (1H, ddd), 7.3 (1H, s), 7.7 (1H, dd), 7.8 (1H, d), 7.9-8.1 (1H, m), 8.2 (1H, s), 8.3 (1H, s), 8.6 (2H, d).

Examples 214/209. Preparation of 3-amino-6-(3-chloroimidazo[1,2-a]pyridin-6-yl)-N-((1-methylpyrrolidin-2-yl)methyl)-5-(oxazol-2-yl)pyrazine-2-carboxamide (Cmpd. 214/209)

SCHEME 100

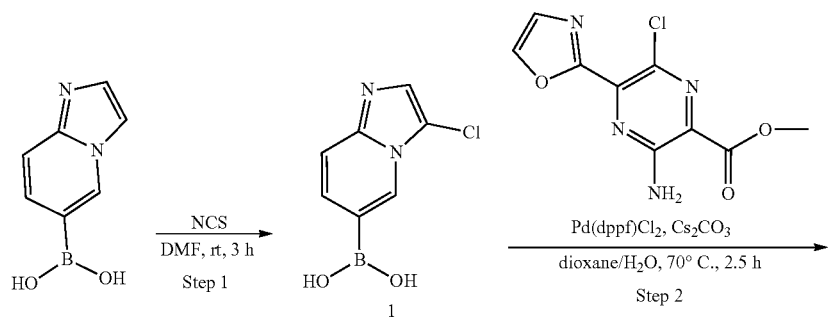

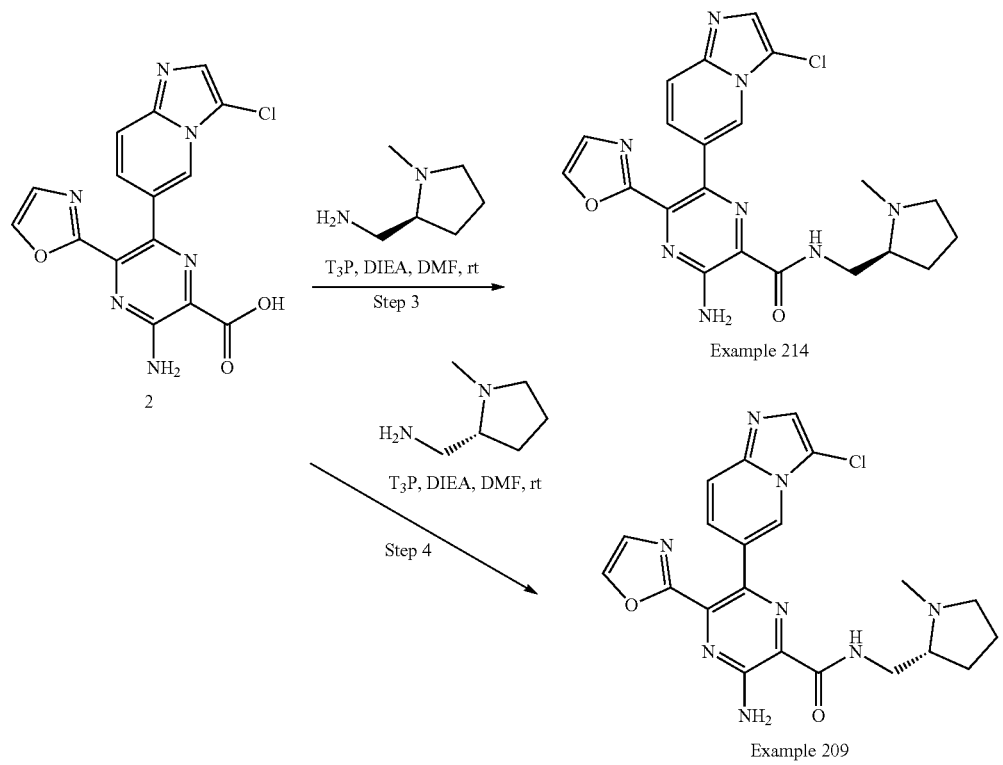

Step 1. (3-chloroimidazo[1,2-a]pyridin-6-yl)boronic Acid

[imidazo[1,2-a]pyridin-6-yl]boronic acid (600 mg, 3.705 mmol, 1 equiv) and NCS (1.24 g, 9.262 mmol, 2.50 equiv) were dissolved in 3 mL of DMF. The mixture was stirred at room temperature for 3 h. LCMS showed the reaction was OK. The crude product was purified by reversed phase HPLC to give [3-chloroimidazo[1,2-a]pyridin-6-yl]boronic acid (235 mg, 32.3%) as a white solid. LCMS: m/z (ESI), $[M+H]^+=197.2$.

Step 2. 3-amino-6-(3-chloroimidazo[1,2-a]pyridin-6-yl)-5-(oxazol-2-yl)pyrazine-2-carboxylic Acid

[3-chloroimidazo[1,2-a]pyridin-6-yl]boronic acid (169.69 mg, 0.864 mmol, 1.00 equiv), methyl 3-amino-6-chloro-5-(1,3-oxazol-2-yl)pyrazine-2-carboxylate (220 mg, 0.864 mmol, 1 equiv), Pd(dppf)Cl2 (126.44 mg, 0.173 mmol, 0.2 equiv) and $Cs_2CO_3$ (1126.03 mg, 3.456 mmol, 4 equiv) were dissolved in 2.4 mL of dioxane/$H_2O$ (5:1). The mixture was stirred at 70° C. for 2 h. LCMS showed the reaction was OK. The mixture was concentrated, acidified with acetic acid and purified by reversed phase HPLC to give methyl 3-amino-6-[3-chloroimidazo[1,2-a]pyridin-6-yl]-5-(1,3-oxazol-2-yl)pyrazine-2-carboxylate (100 mg, 31.22%) as a white solid. LCMS: m/z (ESI), $[M+H]^+=371.2$.

Step 3. 3-amino-6-[3-chloroimidazo[1,2-a]pyridin-6-yl]-N-[[(2R)-1-methylpyrrolidin-2-yl]methyl]-5-(1,3-oxazol-2-yl)pyrazine-2-carboxamide (Cmpd. 214)

3-amino-6-[3-chloroimidazo[1,2-a]pyridin-6-yl]-5-(1,3-oxazol-2-yl)pyrazine-2-carboxylic acid (100 mg, 0.280 mmol, 1 equiv), 1-[(2R)-1-methylpyrrolidin-2-yl]methanamine (48.02 mg, 0.420 mmol, 1.5 equiv), DIEA (253.61 mg, 1.962 mmol, 7 equiv) and $T_3P$ (267.58 mg, 0.841 mmol, 3 equiv) were added in DMF (3 mL). The resulting suspension was stirred at room temperature for 3 h. The reaction mixture was quenched with saturated $NH_4Cl$ (15 mL) and extracted with EtOAc (3×50 mL), the organic layer was dried over $Na_2SO_4$, filtered and evaporated to afford yellow gum. The residue was purified by Prep-HPLC with the following conditions (Column: XBridge Prep OBD C18 Column 19*250 mm, 5 um; Mobile Phase A: water, Mobile Phase B: ACN; Flow rate: 20 mL/min; Gradient: 29% B to 37% B in 8 min; 254; 220 nm; Rt: 6.57/7.42 min) to afford 3-amino-6-[3-chloroimidazo[1,2-a]pyridin-6-yl]-N-[[(2R)-1-methylpyrrolidin-2-yl]methyl]-5-(1,3-oxazol-2-yl)pyrazine-2-carboxamide (Cmpd. 214) (23.9 mg, 18.8%) as a light yellow solid. LCMS: m/z (ESI), $[M+H]^+=453.2$. $^1$H-NMR (400 MHz, Methanol-$d_4$) δ 1.66-1.84 (3H, m), 2.02 (1H, dq), 2.32 (1H, q), 2.46 (3H, s), 2.59 (1H, s), 3.09 (1H, dd), 3.42 (1H, dd), 3.66 (1H, dd), 7.33 (1H, d), 7.43 (1H, dd), 7.59 (1H, dd), 7.66 (1H, s), 8.03 (1H, d), 8.50 (1H, dd).

Step 4. 3-amino-6-[3-chloroimidazo[1,2-a]pyridin-6-yl]-N-[[(2S)-1-methylpyrrolidin-2-yl]methyl]-5-(1,3-oxazol-2-yl)pyrazine-2-carboxamide (Cmpd. 209)

3-amino-6-[3-chloroimidazo[1,2-a]pyridin-6-yl]-5-(1,3-oxazol-2-yl)pyrazine-2-carboxylic acid (100 mg, 0.280 mmol, 1 equiv), 1-[(2R)-1-methylpyrrolidin-2-yl]methanamine (48.02 mg, 0.420 mmol, 1.5 equiv), DIEA (253.61 mg, 1.962 mmol, 7 equiv), $T_3P$ (267.58 mg, 0.841 mmol, 3 equiv) were added in DMF (3 mL). The resulting suspension was stirred at room temperature for 3 h. The reaction mixture was quenched with saturated $NH_4Cl$ (15 mL), extracted with EtOAc (3×50 mL), the organic layer was dried over $Na_2SO_4$, filtered and evaporated to afford yellow gum. The residue was purified by Prep-HPLC with the following conditions (Column: XBridge Prep OBD C18 Column 19*250 mm, 5 um; Mobile Phase A: water, Mobile Phase B: ACN; Flow rate: 20 mL/min; Gradient: 29% B to 37% B in 8 min; 254; 220 nm; Rt: 6.57/7.42 min) to afford 3-amino-6-[3-chloroimidazo[1,2-a]pyridin-6-yl]-N-[[(2S)-1-methylpyrrolidin-2-yl]methyl]-5-(1,3-oxazol-2-yl)pyrazine-2-carboxamide (18.9 mg, 14.8%) as a light yellow solid. LCMS: m/z (ESI), $[M+H]^+=453.2$. $^1$H-NMR (400 MHz, Methanol-$d_4$) δ 1.72-1.84 (3H, m), 2.02 (1H, dq), 2.32 (1H, q), 2.46 (3H, s), 2.59 (1H, s), 3.09 (1H, dt), 3.42 (1H, dd), 3.66 (1H, dd), 7.33 (1H, d), 7.42 (1H, dd), 7.59 (1H, dd), 7.66 (1H, s), 8.03 (1H, d), 8.50 (1H, dd).

Example 219. Preparation of 3-amino-N-[[(3R)-1-cyclopropanecarbonylpyrrolidin-3-yl]methyl]-6-[3-methylimidazo[1,2-a]pyridin-6-yl]-5-(1,3-oxazol-2-yl)pyrazine-2-carboxamide (Cmpd. 219)

SCHEME 101

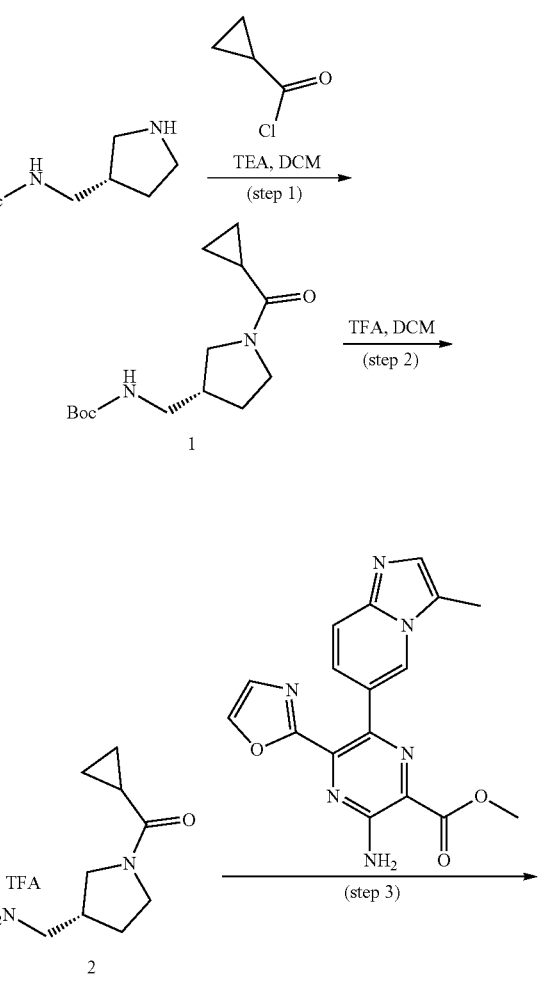

-continued

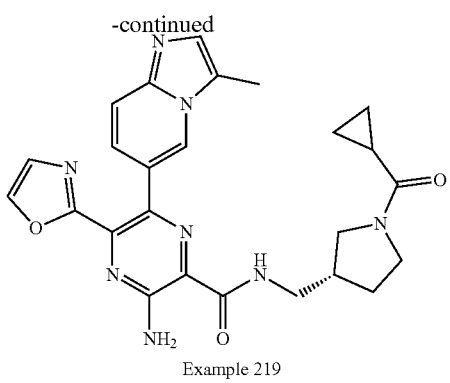

Example 219

Step 1. tert-butyl N-[[(3R)-1-cyclopropanecarbonylpyrrolidin-3-yl]methyl]carbamate A mixture of TEA (757.86 mg, 7.489 mmol, 3 equiv), cyclopropanecarbonyl chloride (391.44 mg, 3.745 mmol, 1.5 equiv) and tert-butyl N-[[(3S)-pyrrolidin-3-yl]methyl]carbamate (500 mg, 2.496 mmol, 1 equiv) in DCM (15 mL) was stirred for 16 hrs at room temperature under air atmosphere. The reaction was diluted with DCM (90 mL), the organic layers were washed with water (2×100 mL), dried over anhydrous $Na_2SO_4$. After filtration, the filtrate was concentrated under reduced pressure to afford tert-butyl N-[[(3R)-1-cyclopropanecarbonylpyrrolidin-3-yl]methyl]carbamate (750 mg, 111.95%) as a brown oil. $^1$H-NMR (300 MHz, Chloroform-d) δ 0.77 (2H, d), 1.01 (2H, d), 1.46 (9H, d), 1.61 (1H, d), 1.68-1.85 (1H, m), 2.07 (1H, d), 2.33-2.58 (1H, m), 3.03-3.28 (2H, m), 3.28-3.49 (1H, m), 3.58-3.72 (1H, m), 3.72-3.87 (1H, m)

Step 2. 1-[(3R)-1-cyclopropanecarbonylpyrrolidin-3-yl]methanamine

A mixture of TFA (1 mL) and tert-butyl N-[[(3R)-1-cyclopropanecarbonylpyrrolidin-3-yl]methyl]carbamate (300 mg, 1.118 mmol, 1 equiv) in DCM (3 mL) was stirred for 1 h at room temperature under air atmosphere. The resulting mixture was concentrated under reduced pressure. The residue was basified to pH 7 with saturated $NaHCO_3$ (aq.). The resulting mixture was extracted with $CH_2Cl_2$ (2×50 mL).

The combined organic layers were washed with water (2×50 mL), dried over anhydrous $Na_2SO_4$. After filtration, the filtrate was concentrated under reduced pressure to afford 1-[(3R)-1-cyclopropanecarbonylpyrrolidin-3-yl]methanamine (180 mg, 95.71%) as a brown oil. LCMS: m/z (ESI), $[M+H]^+$=169.1. $^1$H NMR (300 MHz, DMSO-$d_6$) δ 0.64-0.79 (4H, m), 1.09-1.25 (1H, m), 1.59-1.81 (2H, m), 1.91-2.17 (1H, m), 2.90 (2H, q), 2.98-3.16 (1H, m), 3.23-3.50 (1H, m), 3.52-3.67 (1H, m), 3.69-3.90 (1H, m), 7.85 (2H, s)

Step 3. 3-amino-N-[[(3R)-1-cyclopropanecarbonylpyrrolidin-3-yl]methyl]-6-[3-methylimidazo[1,2-a]pyridin-6-yl]-5-(1,3-oxazol-2-yl)pyrazine-2-carboxamide (Cmpd. 219)

A mixture of DIEA (215.21 mg, 1.665 mmol, 7 equiv), $T_3P$ (378.44 mg, 1.189 mmol, 5 equiv), 1-[(3R)-1-cyclopropanecarbonylpyrrolidin-3-yl]methanamine (160.08 mg, 0.952 mmol, 4 equiv) and 3-amino-6-[3-methylimidazo[1, 2-a]pyridin-6-yl]-5-(1,3-oxazol-2-yl)pyrazine-2-carboxylic acid (80 mg, 0.238 mmol, 1 equiv) in DMF (3 mL) was stirred for overnight at room temperature under air atmosphere. Desired product could be detected by LCMS. The residue was purified by Prep-HPLC with the following conditions (Column: XBridge Prep OBD C18 Column 30×150 mm 5 um; Mobile Phase A: Water (10 MMOL/L $NH_4HCO_3$), Mobile Phase B: ACN; Flow rate: 60 mL/min; Gradient: 28% B to 28% B in 7 min; 254/220 nm; Rt: 5.37 min) to afford 3-amino-N-[[(3R)-1-cyclopropanecarbonylpyrrolidin-3-yl]methyl]-6-[3-methylimidazo[1,2-a]pyridin-6-yl]-5-(1,3-oxazol-2-yl)pyrazine-2-carboxamide (Cmpd. 219) (60 mg, 50.81%) as a yellow solid. LCMS: m/z (ESI), $[M+H]^+$=487.3. $^1$H-NMR (300 MHz, DMSO-$d_6$) δ 0.68 (4H, d), 1.59-1.83 (2H, m), 1.85-2.17 (1H, m), 2.44 (3H, s), 2.61 (1H, s), 3.05-3.32 (1H, m), 3.36-3.53 (3H, m), 3.60 (1H, t), 3.68-3.84 (1H, m), 7.24 (1H, d), 7.33-7.43 (2H, m), 7.49 (1H, d), 7.91 (2H, s), 8.28 (1H, s), 8.35 (1H, d), 8.96-9.10 (1H, m)

Example 221. Preparation of 3-amino-N-[[(3S)-1-cyclopropanecarbonylpyrrolidin-3-yl]methyl]-6-[3-methylimidazo[1,2-a]pyridin-6-yl]-5-(1,3-oxazol-2-yl)pyrazine-2-carboxamide (Cmpd. 221)

SCHEME 102

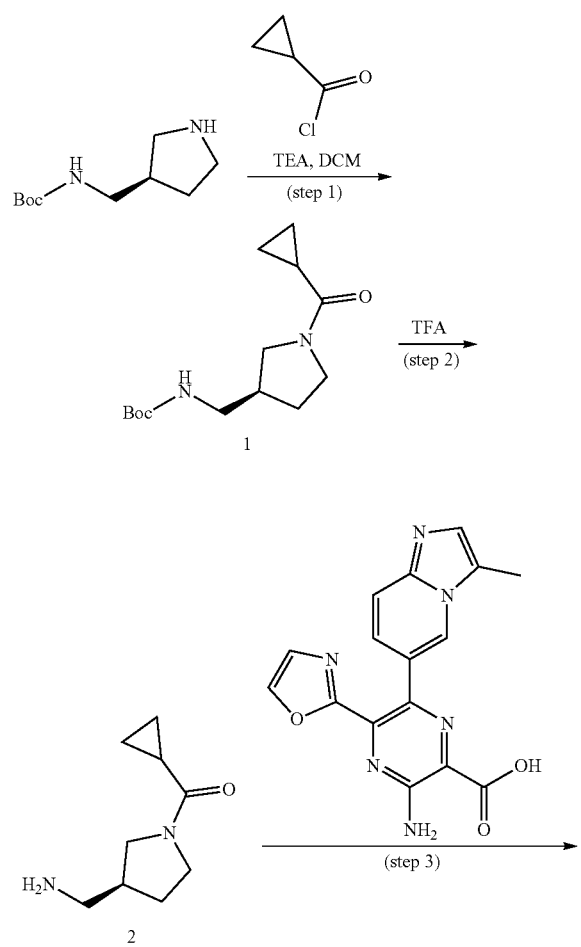

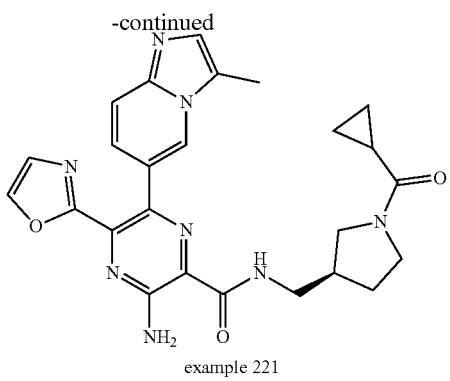

example 221

Step 1. tert-butyl N-[[(3S)-1-cyclopropanecarbonylpyrrolidin-3-yl]methyl]carbamate To a stirred mixture of TEA (1515.71 mg, 14.979 mmol, 6.00 equiv) and cyclopropanecarbonyl chloride (521.91 mg, 4.993 mmol, 2.00 equiv) in DCM (10 mL) were added tert-butyl N-[[(3R)-pyrrolidin-3-yl]methyl]carbamate (500 mg, 2.496 mmol, 1 equiv) in portions at 25° C. under nitrogen atmosphere. The resulting mixture was stirred for 2 h at 25° C. under air atmosphere. The resulting mixture was extracted with $CH_2Cl_2$ (3×20 mL).

And then the organic phase was dried over anhydrous $Na_2SO_4$. After filtration, the filtrate was concentrated under reduced pressure to afford tert-butyl N-[[(3S)-1-cyclopropanecarbonylpyrrolidin-3-yl]methyl]carbamate (670 mg, 100.01%) as yellow solid. $^1$H-NMR (300 MHz, MeOD-$d_4$) δ 0.85 (4H, dt), 1.44 (9H, s), 1.58-1.85 (2H, m), 2.05 (1H, ddq), 2.42 (1H, dp), 3.09 (3H, dd), 3.37 (1H, q), 3.48-3.73 (2H, m), 3.80 (1H, dt).

Step 2. 1-[(3S)-1-cyclopropanecarbonylpyrrolidin-3-yl]methanamine

To a stirred mixture of tert-butyl N-[[(3S)-1-cyclopropanecarbonylpyrrolidin-3-yl]methyl]carbamate (300 mg, 1.118 mmol, 1 equiv) in DCM (3 mL) were added TFA (1 mL) at 25° C. under nitrogen atmosphere. The resulting mixture was stirred for 20 min at 25° C. under nitrogen atmosphere. The resulting mixture was concentrated under reduced pressure to afford 1-[(3S)-1-cyclopropanecarbonylpyrrolidin-3-yl]methanamine (170 mg, 90.39%) as yellow oil. LCMS: m/z (ESI), [2M+H]$^+$=337.2.

Step 3. 3-amino-N-[[(3S)-1-cyclopropanecarbonylpyrrolidin-3-yl]methyl]-6-[3-methylimidazo[1,2-a]pyridin-6-yl]-5-(1,3-oxazol-2-yl)pyrazine-2-carboxamide (Cmpd. 221)

To a stirred mixture of 3-amino-6-[3-methylimidazo[1,2-a]pyridin-6-yl]-5-(1,3-oxazol-2-yl)pyrazine-2-carboxylic acid (99.95 mg, 0.297 mmol, 0.50 equiv) and DIEA (153.64 mg, 1.189 mmol, 2 equiv) in DMF (5 mL) were added $T_3P$ (472.81 mg, 1.486 mmol, 2.50 equiv) and 1-[(3S)-1-cyclopropanecarbonylpyrrolidin-3-yl]methanamine (100 mg, 0.594 mmol, 1 equiv) in portions at 25° C. under nitrogen atmosphere. The resulting mixture was stirred for 4 h at 25° C. under nitrogen atmosphere. The crude product (100 mg) was purified by Prep-HPLC with the following conditions (Column: XBridge Prep OBD C18 Column 30×150 mm 5 um; Mobile Phase A: Water (10 MMOL/L $NH_4HCO_3$), Mobile Phase B: ACN; Flow rate: 60 mL/min; Gradient: 28% B to 28% B in 7 min; 254/220 nm; Rt: 5.37 min) to afford 3-amino-N-[[(3S)-1-cyclopropanecarbonylpyrrolidin-3-yl]methyl]-6-[3-methylimidazo[1,2-a]pyridin-6-yl]-5-(1,3-oxazol-2-yl)pyrazine-2-carboxamide (60 mg, 20.75%) as a yellow solid. LCMS: m/z (ESI), [M+H]$^+$= 487.2. $^1$H-NMR (300 MHz, DMSO-$d_6$) δ 0.69 (4H, d), 1.70-2.10 (3H, m), 2.44 (3H, s), 2.50 (1H, t), 3.10 (1H, dd), 3.52 (4H, d), 3.68-3.80 (1H, m), 7.24 (1H, dd), 7.33-7.43 (2H, m), 7.49 (1H, d), 7.90 (2H, s), 8.28 (1H, s), 8.36 (1H, d), 9.02 (1H, d)

Example 223. Preparation of 3-amino-N-[(3-fluoropyridin-2-yl)methyl]-6-[3-methylimidazo[1,2-a]pyridin-6-yl]-5-(morpholin-4-yl)pyrazine-2-carboxamide (Cmpd. 223)

SCHEME 103

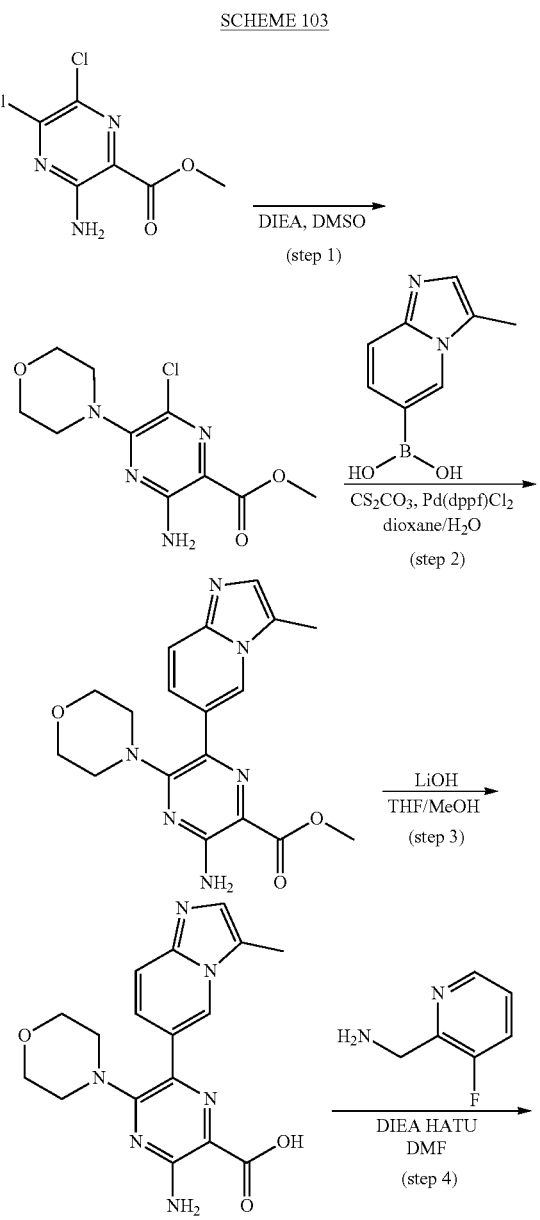

445

-continued

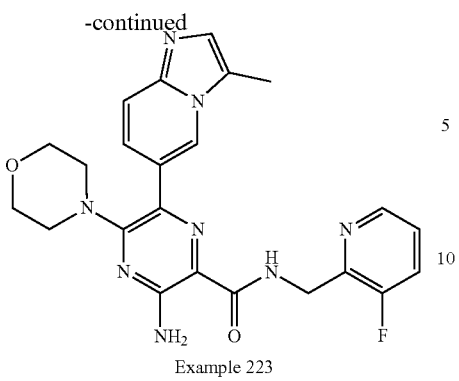

Example 223

Step 1. methyl 3-amino-6-chloro-5-(morpholin-4-yl) pyrazine-2-carboxylate

To a stirred mixture of methyl 3-amino-5,6-dichloropyrazine-2-carboxylate (50 mg, 0.225 mmol, 1 equiv) and DIEA (87.31 mg, 0.676 mmol, 3 equiv) in DMSO was added morpholine (39.24 mg, 0.450 mmol, 2 equiv) in portions at room temperature. The resulting mixture was stirred for overnight at room temperature. The reaction was quenched with Water at room temperature. The precipitated solids were collected by filtration and washed with water (1×100 mL), dried under vacuum to afford methyl 3-amino-6-chloro-5-(morpholin-4-yl)pyrazine-2-carboxylate (1.8 g, 97.71%) as a yellow solid. $^1$H-NMR (400 MHz, Chloroform-d) δ 3.61-3.72 (4H, m), 3.75-3.88 (4H, m), 3.94 (3H, s).

Step 2. methyl 3-amino-6-[3-methylimidazo[1,2-a] pyridin-6-yl]-5-(morpholin-4-yl) pyrazine-2-carboxylate To a stirred mixture of methyl 3-amino-6-chloro-5-(morpholin-4-yl)pyrazine-2-carboxylate (600 mg, 2.200 mmol, 1 equiv) and [3-methylimidazo[1,2-a]pyridin-6-yl]boronic acid (580.81 mg, 3.300 mmol, 1.5 equiv) in dioxane (50 mL) were added Cs2CO3 (2150.70 mg, 6.601 mmol, 3 equiv) and Pd(dppf)Cl$_2$ (321.99 mg, 0.440 mmol, 0.2 equiv) in portions at 95° C. under nitrogen atmosphere. The resulting mixture was stirred for 2h at 95 C under nitrogen atmosphere. The resulting mixture was concentrated under reduced pressure. The residue was purified by silica gel column chromatography, eluted with CH$_2$Cl$_2$/MeOH (20:1) to afford methyl 3-amino-6-[3-methylimidazo[1,2-a]pyridin-6-yl]-5-(morpholin-4-yl)pyrazine-2-carboxylate (400 mg, 49.35%) as a yellow green solid. LCMS: m/z (ESI), [M+H]$^+$=369.3. $^1$H-NMR (400 MHz, DMSO-d$_6$) δ 3.26 (4H, d), 3.58 (4H, d), 3.79 (3H, s), 3.93 (3H, s), 7.30 (2H, s), 7.40 (1H, s), 7.52 (1H, d), 7.60 (1H, d), 8.45 (1H, s)

Step 3. 3-amino-6-[3-methylimidazo[1,2-a]pyridin-6-yl]-5-(morpholin-4-yl)pyrazine-2-carboxylic Acid To a solution of methyl 3-amino-6-[3-methylimidazo[1,2-a]pyridin-6-yl]-5-(morpholin-4-yl)pyrazine-2-carboxylate (400 mg, 1.086 mmol, 1 equiv) in THF (50 mL) and methanol (10 mL) was added LiOH (156.01 mg, 6.515 mmol, 6 equiv) in portions at room temperature. The resulting mixture was stirred for 2 h at room temperature under air atmosphere. The mixture was acidified to pH 6 with HCl (aq.). The resulting mixture was concentrated under vacuum

446 to afford 3-amino-6-[3-methylimidazo[1,2-a]pyridin-6-yl]-5-(morpholin-4-yl)pyrazine-2-carboxylic acid (350 mg, 90.96%) as a yellow solid. The crude product was used in the next step directly without further purification. LCMS: m/z (ESI), [M+H]$^+$=355.1.

Step 4. 3-amino-N-[(3-fluoropyridin-2-yl)methyl]-6-[3-methylimidazo[1,2-a]pyridine-6-yl]-5-(morpholin-4-yl)pyrazine-2-carboxamide (Cmpd. 223)

To a stirred mixture of 3-amino-6-[3-methylimidazo[1,2-a]pyridin-6-yl]-5-(morpholin-4-yl)pyrazine-2-carboxylic acid (100 mg, 0.282 mmol, 1 equiv) and 1-(3-fluoropyridin-2-yl)methanamine (71.19 mg, 0.564 mmol, 2 equiv) in DMF (10 mL) were added HATU (214.59 mg, 0.564 mmol, 2 equiv) and DIEA (109.41 mg, 0.847 mmol, 3 equiv) in portions at room temperature under air atmosphere. The resulting mixture was stirred for 2.5 h at room temperature under air atmosphere. The resulting mixture was concentrated under reduced pressure. The resulting crude product was purified by Prep-HPLC with the following conditions (Column: XBridge Prep OBD C18 Column 19*250 mm, 5 um; Mobile Phase A: 5% ammonia in water, Mobile Phase B: ACN; Flow rate: 20 mL/min; Gradient: 33% B to 48% B in 8 min; 254; 220 nm; Rt: 7.47 min) to afford 3-amino-N-[(3-fluoropyridin-2-yl)methyl]-6-[3-methylimidazo[1,2-a]pyridin-6-yl]-5-(morpholin-4-yl)pyrazine-2-carboxamide (9 mg, 6.83%) (Cmpd. 223) as a white solid. LCMS: m/z (ESI), [M+H]$^+$=463.3. $^1$H NMR (400 MHz, DMSO-d$_6$) δ 2.54 (3H, d), 3.63 (4H, t), 4.61-4.74 (4H, m), 7.36-7.45 (2H, m), 7.57-7.64 (1H, m), 7.66-7.79 (2H, m), 8.36 (1H, dt), 8.63 (1H, s), 8.93 (1H, t)

Examples 227/224. Preparation of Trans/Cis-3-amino-N-((6-((3-(dimethylamino) cyclobutyl)amino) pyridin-2-yl)methyl)-6-(3-methylimidazo[1,2-a]pyridin-6-yl)-5-(oxazol-2-yl)pyrazine-2-carboxamide (Cmpd. 227/224)

SCHEME 104

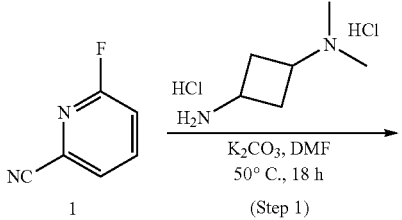

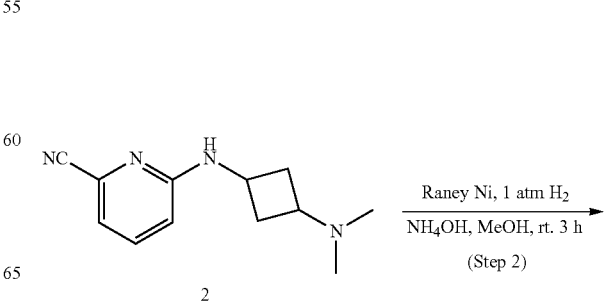

-continued

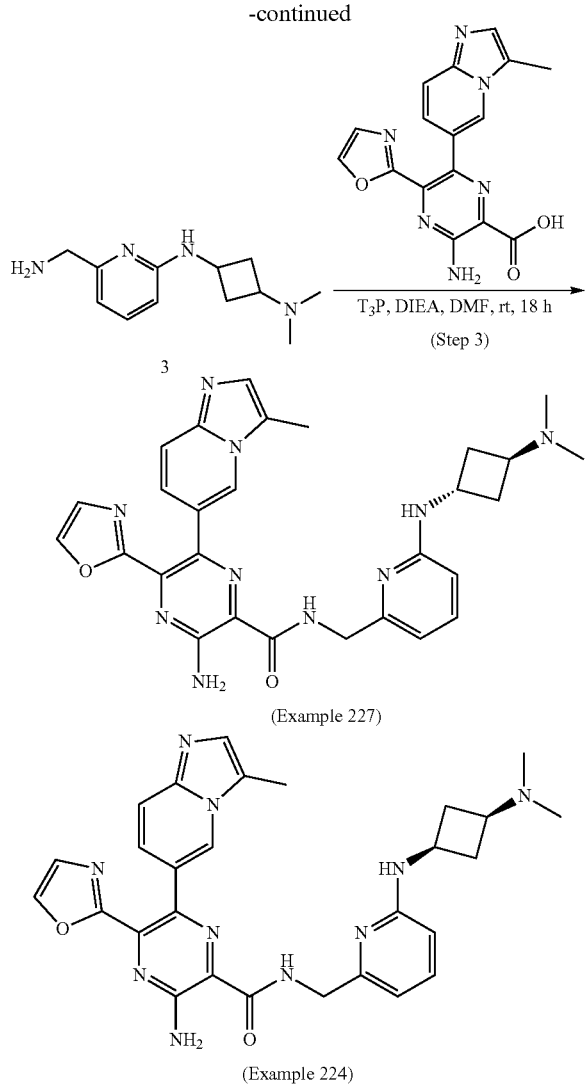

(Example 227)

(Example 224)

Step 1. 6-((3-(dimethylamino)cyclobutyl)amino) picolinonitrile

A mixture of 6-fluoropyridine-2-carbonitrile (136 mg, 1.114 mmol, 1 equiv), N1,N1-dimethylcyclobutane-1,3-diamine dihydrochloride (250 mg, 1.336 mmol, 1.20 equiv) and dipotassium carbonate (462 mg, 3.343 mmol, 3.00 equiv) in 3 mL of DMF was stirred at 50° C. for 18 h. After cooled to room temperature, water was added and extracted with EtOAc (3×100 mL). The combined organic layers were washed with brine, dried over anhydrous $Na_2SO_4$. After filtered and concentrated, the residue was purified by column (DCM/MeOH 3/1) to afford 6-[[3-(dimethylamino) cyclobutyl]amino]pyridine-2-carbonitrile (155 mg, 64.3%) as a white solid. LCMS: m/z (ESI), $[M+H]^+=217.3$.

Step 2. N1-(6-(aminomethyl)pyridin-2-yl)-N3,N3-dimethylcyclobutane-1,3-diamine

A mixture of 6-[[3-(dimethylamino)cyclobutyl]amino] pyridine-2-carbonitrile (155 mg, 0.717 mmol, 1 equiv), 1 mL of ammonia solution and Raney Ni (100 mg) in methanol (10 mL) was hydrogenated under 1 atm $H_2$ at room temperature for 3 h. After filtered through celite, the filtrate was concentrated to dryness under vacuum and the residue was used directly in the next step. LCMS: m/z (ESI), $[M+H]^+=221.2$.

Step 3. Cis/Trans3-amino-N-((6-((3-(dimethylamino)cyclobutyl)amino)pyridin-2-yl) methyl)-6-(3-methylimidazo[1,2-a]pyridin-6-yl)-5-(oxazol-2-yl) pyrazine-2-carboxamide (Cmpd. 224/227)

To a mixture of 3-amino-6-(1-methyl-1H-1, 3-benzodiazol-6-yl)-5-(1,3-oxazol-2-yl)pyrazine-2-carboxylic acid (150 mg, 0.446 mmol, 1 equiv) and N3-[6-(aminomethyl) pyridin-2-yl]N1,N1-dimethylcyclobutane-1,3-diamine (145 mg, 0.66 mmol, 1.48 equiv) in N, N-dimethylformamide (5 mL) were added DIEA (0.39 mL, 2.239 mmol, 5.02 equiv) and 50% wt $T_3P$ solution in ethyl acetate (860 mg, 1.351 mmol, 3.03 equiv). The mixture was stirred at room temperature for 18 h. After concentrated to dryness, the residue was purified by Prep-HPLC with the following conditions: (Column: XBridge Prep OBD C18 Column 19*250 mm, 5 um; Mobile Phase A: water, Mobile Phase B: ACN; Flow rate: 20 mL/min; Gradient: 29% B to 37% B in 8 min; 254; 220 nm; Rt: 6.57/7.42 min) to afford Trans-3-amino-6-[3-methyl-imidazo[1,2-a]pyridin-6-yl]-5-(1,3-oxazol-2-yl)-N-[(6-[[3-(dimethylamino)cyclo-butyl]amino]pyridin-2-yl) methyl]pyrazine-2-carboxamide (Cmpd. 227) (6.6 mg, 2.7%) (Cmpd. 227) LCMS: m/z (ESI), $[M+H]^+=539.4$. $^1$H-NMR (300 MHz, MeOH-d$_4$) δ 1.87-1.95 (2H, m), 2.02-2.14 (8H, m), 2.43 (3H, s), 2.71-2.81 (1H, m), 3.97-4.02 (1H, m), 4.48 (2H, s), 6.26-6.28 (1H, d), 6.55-6.57 (1H, d), 7.22-7.48 (5H, m), 7.99 (1H, s), 8.38 (1H, s), and Cis-3-amino-6-[3-methylimidazo[1,2-a]pyridin-6-yl]-5-(1,3-oxazol-2-yl)-N-[(6-[[3-(di-meth ylamino)cyclobutyl]amino] pyridin-2-yl)methyl]pyrazine-2-carboxamide (Cmpd. 224) (6.1 mg, 2.5%) as yellow solid, (Cmpd. 224) LCMS: m/z (ESI), $[M+H]^+=539.3$. $^1$H-NMR (300 MHz, MeOH-d$_4$) δ 1.39-1.48 (2H, m), 1.56-1.66 (1H, m), 1.89 (6H, s), 2.16-2.24 (2H, m), 2.44 (3H, s), 3.76-3.87 (1H, m), 4.49 (2H, s), 6.29-6.32 (1H, d), 6.50-6.52 (1H, d), 7.25-7.37 (4H, m), 7.48-7.52 (1H, d), 7.97 (1H, s), 8.43 (1H, s).

Example 229. Preparation of 3-amino-6-[3-methyl-imidazo[1,2-a]pyridin-6-yl]-N-[[(2R)-oxolan-2-yl] methyl]-5-(2H-1,2,3-triazol-2-yl)pyrazine-2-carboxamide (Cmpd. 229)

SCHEME 105

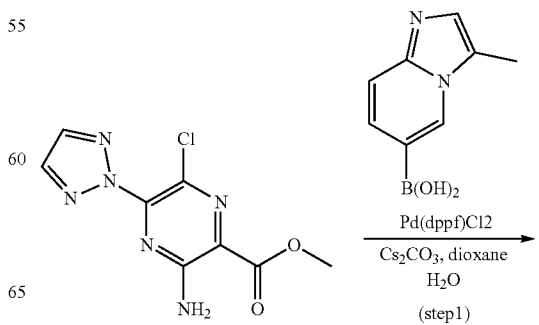

(step1)

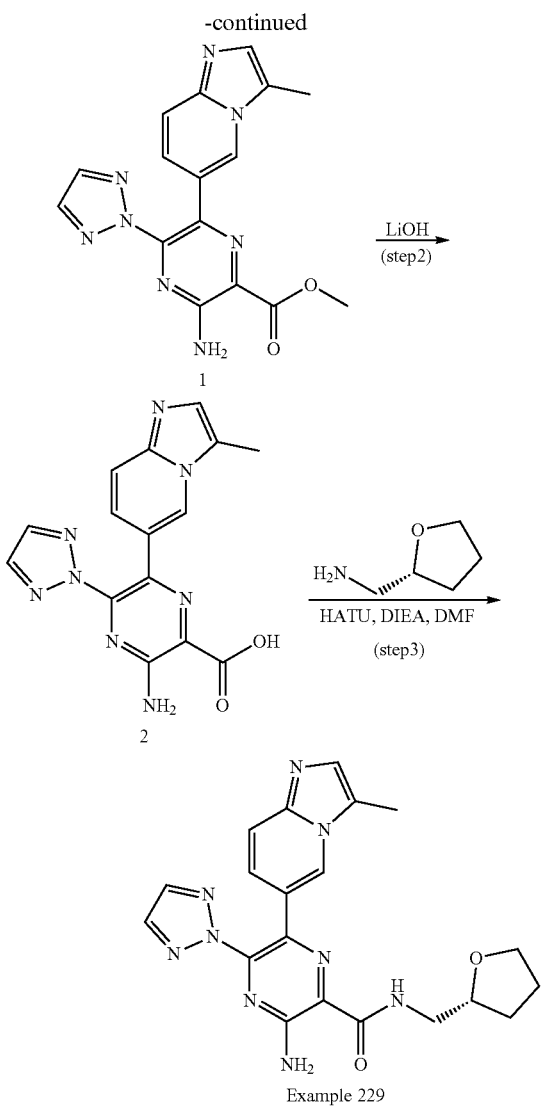

Step 1. methyl 3-amino-6-[3-methylimidazo[1,2-a]pyridin-6-yl]-5-(2H-1,2,3-triazol-2-yl)pyrazine-2-carboxylate To a stirred mixture of methyl 3-amino-6-chloro-5-(2H-1,2,3-triazol-2-yl)pyrazine-2-carboxylate (1 g, 3.927 mmol, 1 equiv) and [3-methylimidazo[1,2-a]pyridin-6-yl]boronic acid (1.38 g, 7.855 mmol, 2 equiv) in 1,4-dioxane (15 mL) and H₂O (1.5 mL) were added Cs₂CO₃ (2.56 g, 7.855 mmol, 2.00 equiv) and Pd(dppf)Cl₂·CH₂Cl₂ (0.64 g, 0.785 mmol, 0.2 equiv) in portions at room temperature under nitrogen atmosphere. The resulting mixture was stirred for overnight at 100° C. under nitrogen atmosphere. The resulting mixture was concentrated under reduced pressure. The residue was purified by Prep-TLC (CH₂Cl₂/MeOH 20:1) to afford methyl 3-amino-6-[3-methylimidazo[1,2-a]pyridin-6-yl]-5-(2H-1,2,3-triazol-2-yl)pyrazine-2-carboxylate (1 g, 72.68%) as a yellow solid. LCMS: m/z (ESI), [M+H]⁺=351.1. ¹H-NMR: (300 MHz, DMSO-d₆) δ 2.31 (3H, s), 3.91 (3H, s), 6.91 (1H, m), 7.42 (2H, m), 7.73 (1H, m), 7.91 (2H, s), 8.12 (2H, s).

Step 2. 3-amino-6-[3-methylimidazo[1,2-a]pyridin-6-yl]-5-(2H-1,2,3-triazol-2-yl)pyrazine-2-carboxylic Acid To a stirred solution of methyl 3-amino-6-[3-methylimidazo[1,2-a]pyridin-6-yl]-5-(2H-1,2,3-triazol-2-yl)pyrazine-2-carboxylate (950 mg, 2.712 mmol, 1 equiv) in MeOH (15 mL) and THF (3 mL) were added LiOH (97.42 mg, 4.067 mmol, 1.5 equiv) in portions at room temperature. The resulting mixture was stirred for 4 hs at room temperature. The residue was acidified to pH=5 with HCl (aq.). The resulting solid was collected by filtration and dried under vacuum to afford 3-amino-6-[3-methylimidazo[1,2-a]pyridin-6-yl]-5-(2H-1,2,3-triazol-2-yl)pyrazine-2-carboxylic acid (400 mg, 43.86%) as a yellow solid. LCMS: m/z (ESI), [M+H]⁺=337.1.

Step 3. 3-amino-6-[3-methylimidazo[1,2-a]pyridin-6-yl]-N-[[(2R)-oxolan-2-yl]methyl]-5-(2H-1,2,3-triazol-2-yl)pyrazine-2-carboxamide (Cmpd. 229)

To a stirred mixture of 1-[(2R)-oxolan-2-yl]methanamine (60.15 mg, 0.595 mmol, 2 equiv) and 3-amino-6-[3-methylimidazo[1,2-a]pyridin-6-yl]-5-(2H-1,2,3-triazol-2-yl)pyrazine-2-carboxylic acid (100 mg, 0.297 mmol, 1 equiv) in DMF (10 mL) were added DIEA (76.86 mg, 0.595 mmol, 2 equiv) and T₃P (23.80 mg, 0.595 mmol, 2 equiv) dropwise at room temperature. The resulting mixture was stirred for 3 hs at room temperature. The reaction was quenched with Water at room temperature. The resulting mixture was concentrated under vacuum. The crude product was purified by Prep-HPLC with the following conditions (Column: XBridge Prep OBD C18 Column 19*250 mm, 5 um; Mobile Phase A: Mobile Phase B: Flow rate: 20 mL/min; Gradient: 30% B to 41% B in 8 min; 254; 220 nm; Rt: 7.17 min) to afford 3-amino-6-[3-methylimidazo[1,2-a]pyridin-6-yl]-N-[[(2R)-oxolan-2-yl]methyl]-5-(2H-1,2,3-triazol-2-yl)pyrazine-2-carboxamide (Cmpd. 229) (43 mg, 34.48%) as a yellow solid. LCMS: m/z (ESI), [M+H]⁺=420.3. ¹H NMR: (300 MHz, DMSO-d₆) δ1.78 (4H, m), 2.36 (3H, d), 3.40 (2H, d), 3.62 (1H, m), 3.78 (1H, m), 4.04 (1H, p), 6.87 (1H, dd), 7.39 (2H, m), 7.92 (1H, m), 8.12 (4H, s), 8.85 (1H, t).

Examples 230-1/230-2. Preparation of 3-amino-6-(3-methylimidazo[1,2-a]pyridin-6-yl)-5-(oxazol-2-yl)-N-((1,4,4-trimethylpyrrolidin-2-yl)methyl)pyrazine-2-carboxamide (Cmpd. 230-1/230-2)

SCHEME 106

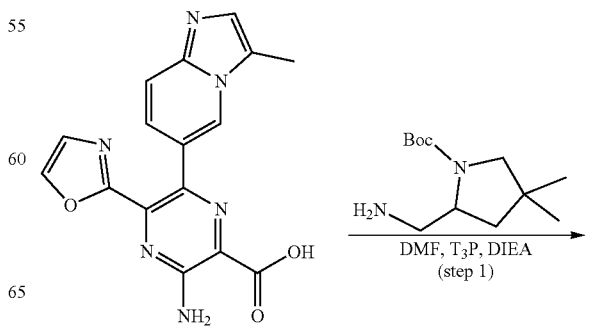

451
-continued

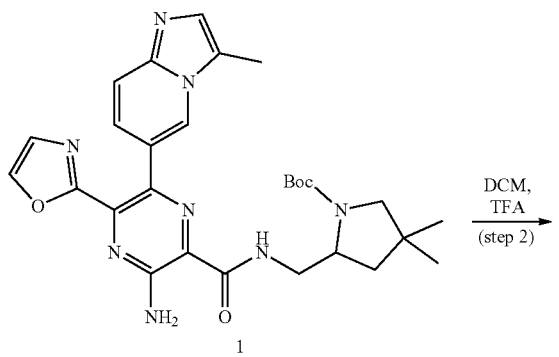

1

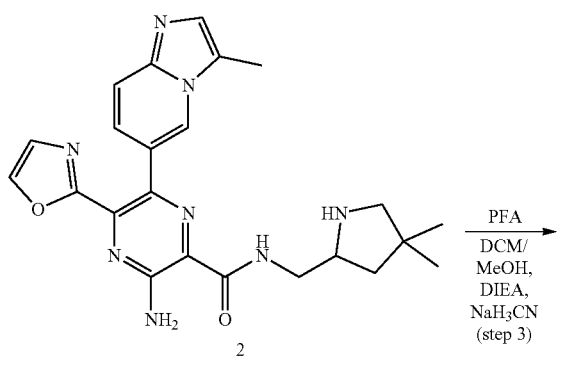

2

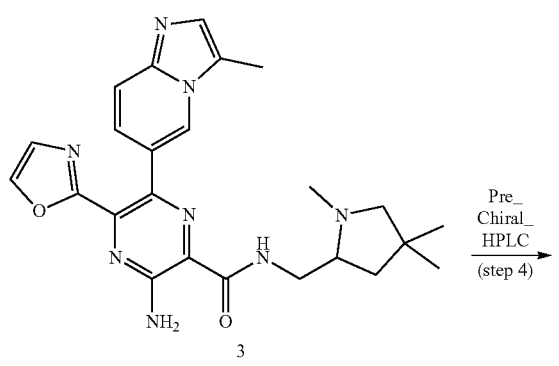

3

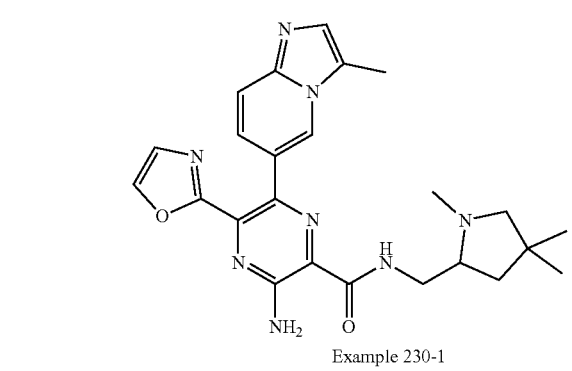

Example 230-1

452
-continued

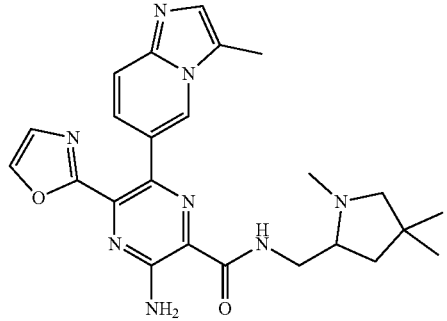

Example 230-2

Step 1. Tert-butyl 2-((3-amino-6-(3-methylimidazo[1,2-a]pyridin-6-yl)-5-(oxazol-2-yl)pyrazine-2-carboxamido)methyl)-4,4-dimethylpyrrolidine-1-carboxylate To a stirred mixture of 3-amino-6-[3-methylimidazo[1,2-a]pyridin-6-yl]-5-(1,3-oxazol-2-yl)pyrazine-2-carboxylic acid (200 mg, 0.595 mmol, 1 equiv), DIEA (230.58 mg, 1.784 mmol, 3 equiv) and tert-butyl 2-(aminomethyl)-4,4-dimethylpyrrolidine-1-carboxylate (271.58 mg, 1.189 mmol, 2 equiv) in DMF (12 mL) was added $T_3P$ (378.44 mg, 1.189 mmol, 2 equiv) dropwise at 0° C. under nitrogen atmosphere. The resulting mixture was stirred for 1 h at room temperature under nitrogen atmosphere. The reaction was quenched by the addition of Water (20 mL) at room temperature. The resulting mixture was extracted with $CH_2Cl_2$ (3×20 mL). The combined organic layers were dried over anhydrous $Na_2SO_4$. After filtration, the filtrate was concentrated under reduced pressure. The residue was purified by Prep-TLC ($CH_2Cl_2$/MeOH 20:1) to afford tert-butyl 2-[[(3-amino-6-[3-methylimidazo[1,2-a]pyridin-6-yl]-5-(1,3-oxazol-2-yl)pyrazin-2-yl)formamido]methyl]-4,4-dimethylpyrrolidine-1-carboxylate (180 mg, 55.37%) as a yellow solid. LCMS: m/z (ESI), [M+H]$^+$=547.4.

Step 2. 3-amino-N-((4,4-dimethylpyrrolidin-2-yl)methyl)-6-(3-methylimidazo[1,2-a]pyridin-6-yl)-5-(oxazol-2-yl)pyrazine-2-carboxamide To a stirred solution of tert-butyl 2-[[(3-amino-6-[3-methylimidazo[1,2-a]pyridin-6-yl]-5-(1,3-oxazol-2-yl)pyrazin-2-yl)formamido]methyl]-4,4-dimethylpyrrolidine-1-carboxylate (160 mg, 0.293 mmol, 1 equiv) in DCM (8 mL) was added TFA (3 mL, 40.389 mmol, 137.99 equiv) dropwise at room temperature under air atmosphere. The resulting mixture was stirred for 30 min at room temperature under air atmosphere. The resulting mixture was concentrated under reduced pressure to afford 3-amino-N-[(4,4-dimethylpyrrolidin-2-yl)methyl]-6-[3-methylimidazo[1,2-a]pyridin-6-yl]-5-(1,3-oxazol-2-yl)pyrazine-2-carboxamide (135 mg, 98.12%) as a yellow oil. LCMS: m/z (ESI), [M+H]$^+$=447.4.

Step 3. 3-amino-6-(3-methylimidazo[1,2-a]pyridin-6-yl)-5-(oxazol-2-yl)-N-((1,4,4-trimethylpyrrolidin-2-yl)methyl)pyrazine-2-carboxamide To a stirred mixture of 3-amino-N-[(4,4-dimethylpyrrolidin-2-yl)methyl]-6-[3-methylimidazo[1,2-a]pyridin-6-yl]-5-(1,3-oxazol-2-yl)pyrazine-2-carboxamide (155 mg, 0.347 mmol, 1 equiv), DIEA (89.73 mg, 0.694 mmol, 2 equiv) and Paraformaldehyde (312.69 mg, 3.471 mmol, 10 equiv) in DCM (12 mL) and MeOH (4 mL) was added NaBH$_3$CN (65.44 mg, 1.041 mmol, 3 equiv) in portions at room temperature under nitrogen atmosphere. The resulting mixture was stirred for 12 h at room temperature under nitrogen atmosphere. The reaction was quenched by the addition of Water (20 mL) at room temperature. The resulting mixture was extracted with CH$_2$Cl$_2$ (3×15 mL). The combined organic layers were dried over anhydrous Na$_2$SO$_4$. After filtration, the filtrate was concentrated under reduced pressure. The residue was purified by Prep-TLC (CH$_2$Cl$_2$/MeOH 10:1) to afford 3-amino-6-[3-methylimidazo[1,2-a]pyridin-6-yl]-5-(1,3-oxazol-2-yl)-N-[(1,4,4-trimethylpyrrolidin-2-yl)methyl]pyrazine-2-carboxamide (130 mg, 81.32%) as a yellow solid. LCMS: m/z (ESI), [M+H]$^+$=461.4.

Step 4. 3-amino-6-(3-methylimidazo[1,2-a]pyridin-6-yl)-5-(oxazol-2-yl)-N-((1,4,4-trimethylpyrrolidin-2-yl)methyl)pyrazine-2-carboxamide (230-1/230-2)

The crude product (100 mg) was purified by Chiral-Prep-HPLC with the following conditions (Column: CHIRAL-PAK ID-03, 2.0 cm I.D*25 cm L (5 um); Mobile Phase A:Hex:DCM=5:1 (10 mM NH$_3$-MEOH)-HPLC, Mobile Phase B: IPA-HPLC; Flow rate: 20 mL/min; Gradient: 25 B to 25 Bin 22 min; 220/254 nm; RT1: 15.342; RT2: 17.566) to afford 3-amino-6-[3-methylimidazo[1,2-a]pyridin-6-yl]-5-(1,3-oxazol-2-yl)-N-[(1,4,4-trimethylpyrrolidin-2-yl)methyl]pyrazine-2-carboxamide (Cmpd. 230-1) (45 mg, 43.41%) LCMS: m/z (ESI), [M+H]$^+$=461.3. $^1$H-NMR (400 MHz, DMSO-d$_6$) δ 1.01 (6H, d), 1.46 (1H, s), 1.68 (1H, s), 2.05 (1H, s), 2.28 (3H, s), 2.42 (3H, s), 2.68 (1H, s), 3.48 (1H, s), 7.19 (1H, dd), 7.40 (2H, d), 7.49 (1H, d), 7.90 (2H, s), 8.31 (2H, d), 8.65 (1H, s). and 3-amino-6-[3-methylimidazo[1,2-a]pyridin-6-yl]-5-(1,3-oxazol-2-yl)-N-[(1,4,4-trimethylpyrrolidin-2-yl)methyl]pyrazine-2-carboxamide (Cmpd. 230-2) (45 mg, 45%), LCMS: m/z (ESI), [M+H]$^+$= 461.3. $^1$H NMR (400 MHz, DMSO-d$_6$) δ 1.01 (6H, d), 1.46 (1H, s), 1.68 (1H, s), 2.05-2.28 (4H, m), 2.42 (3H, s), 2.68 (1H, s), 3.30 (1H, s), 3.48 (1H, s), 7.19 (1H, dd), 7.36 (1H, s), 7.40 (1H, s), 7.49 (1H, d), 7.90 (2H, s), 8.27 (1H, s), 8.31 (1H, s), 8.65 (1H, s).

Example 231. Preparation of (R)-3-amino-5-(3-fluorophenyl)-6-(3-methylimidazo[1,2-a]pyridin-6-yl)-N-((1-methylpyrrolidin-2-yl)methyl)pyrazine-2-carboxamide (Cmpd. 231)

SCHEME 107

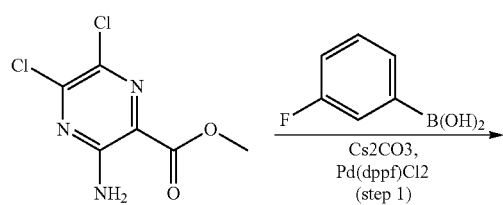

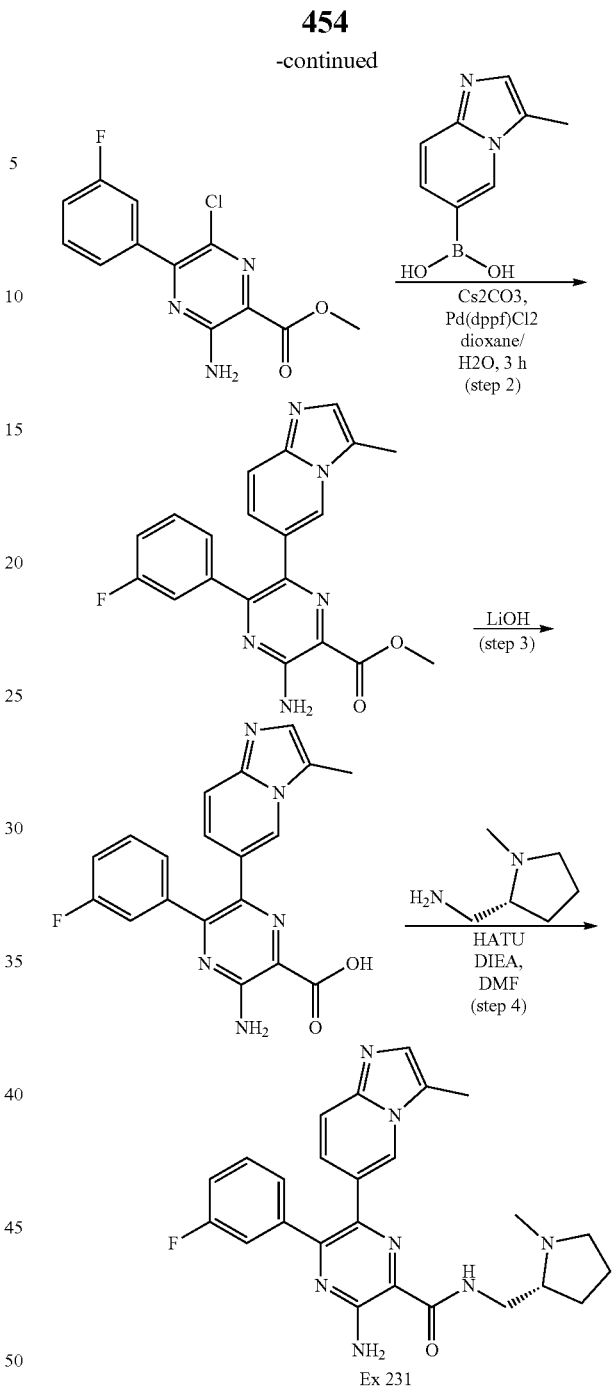

Step 1. Preparation of methyl 3-amino-6-chloro-5-(3-fluorophenyl)pyrazine-2-carboxylate To a stirred mixture of methyl 3-amino-5,6-dichloropyrazine-2-carboxylate (1.5 g, 6.756 mmol, 1 equiv) and (3-fluorophenyl)boronic acid (0.95 g, 6.790 mmol, 1.00 equiv) in 1,4-dioxane (100 mL) and H$_2$O (5 mL) were added Cs$_2$CO$_3$ (6.60 g, 0.020 mmol, 3 equiv) and Pd(dppf)Cl$_2$ (0.74 g, 0.001 mmol, 0.15 equiv) in portions at room temperature under nitrogen atmosphere. The resulting mixture was stirred for 3 h at 70° C. C under nitrogen atmosphere. The resulting mixture was filtered, the filter cake was washed with CH$_2$Cl$_2$ (1×30 mL). The filtrate was concentrated under reduced pressure. The residue was purified by silica gel column chromatography, eluted with CH$_2$Cl$_2$/EtOAc (4:1) to afford methyl 3-amino-6-chloro-5-(3-fluorophenyl)pyrazine-2-carboxylate (900 mg, 47.30%) as a yellow solid. LCMS: m/z (ESI), [M+H]$^+$=282.0. $^1$H-NMR (300 MHz, Chloroform-d) δ 4.03 (3H, s), 7.22 (1H, m), 7.41-7.59 (2H, m), 7.65 (1H, ddd).

Step 2. methyl 3-amino-5-(3-fluorophenyl)-6-(3-methylimidazo[1,2-a]pyridin-6-yl)pyrazine-2-carboxylate To a stirred mixture of methyl 3-amino-6-chloro-5-(3-fluorophenyl)pyrazine-2-carboxylate (400 mg, 1.420 mmol, 1 equiv) and [3-methylimidazo[1,2-a]pyridin-6-yl]boronic acid (324.88 mg, 1.846 mmol, 1.30 equiv) in 1,4-dioxane (20 mL) and H$_2$O (2 mL) were added Cs$_2$CO$_3$ (1388.09 mg, 4.260 mmol, 3 equiv) and Pd(dppf)Cl$_2$ (155.86 mg, 0.213 mmol, 0.15 equiv) in portions at room temperature under nitrogen atmosphere. The resulting mixture was stirred for 3h at 90° C. C under nitrogen atmosphere. The resulting mixture was filtered, the filter cake was washed with CH$_2$Cl$_2$ (1×20 mL). The filtrate was concentrated under reduced pressure. The residue was purified by Prep-TLC (CH$_2$Cl$_2$/MeOH 20:1) to afford methyl 3-amino-5-(3-fluorophenyl)-6-[3-methylimidazo[1,2-a]pyridin-6-yl]pyrazine-2-carboxylate (300 mg, 55.98%) as a yellow solid. LCMS: m/z (ESI), [M+H]$^+$=378.1.
$^1$H-NMR (300 MHz, Chloroform-d) δ 2.22-2.65 (3H, m), 4.04 (3H, s), 6.91-7.05 (1H, m), 7.05-7.23 (2H, m), 7.30 (2H, d), 7.44 (2H, d), 8.11 (1H, t).

Step 3. 3-amino-5-(3-fluorophenyl)-6-(3-methylimidazo[1,2-a]pyridin-6-yl)pyrazine-2-carboxylic Acid To a stirred solution of methyl 3-amino-5-(3-fluorophenyl)-6-[3-methylimidazo[1,2-a]pyridin-6-yl]pyrazine-2-carboxylate (300 mg, 0.795 mmol, 1 equiv) in THF (20 mL) and H$_2$O (4 mL) was added LiOH (38.08 mg, 1.590 mmol, 2.00 equiv) in portions at room temperature. The resulting mixture was stirred for 3h at room temperature. The mixture was acidified to pH 5 with HCl (aq.). The resulting mixture was concentrated under reduced pressure to afford 3-amino-5-(3-fluorophenyl)-6-[3-methylimidazo[1,2-a]pyridin-6-yl]pyrazine-2-carboxylic acid (280 mg, 96.94%) as a yellow solid which was directly used to next step without further purification. LCMS: m/z (ESI), [M+H]$^+$=364.2.

Step 4. (R)-3-amino-5-(3-fluorophenyl)-6-(3-methylimidazo[1,2-a]pyridin-6-yl)-N-((1-methylpyrrolidin-2-yl)methyl)pyrazine-2-carboxamide (Cmpd. 231)

To a stirred mixture of 1-[(2R)-1-methylpyrrolidin-2-yl]methanamine (62.85 mg, 0.550 mmol, 2.00 equiv) and 3-amino-5-(3-fluorophenyl)-6-[3-methylimidazo[1,2-a]pyridin-6-yl]pyrazine-2-carboxylic acid (100 mg, 0.275 mmol, 1 equiv) in DMF (10 mL) were added DIEA (106.71 mg, 0.826 mmol, 3.00 equiv) and T$_3$P (175.14 mg, 0.550 mmol, 2.00 equiv) in portions at room temperature. The resulting mixture was stirred for 3 h at room temperature. The resulting mixture was concentrated under reduced pressure. The crude product was purified by Prep-HPLC with the following conditions (Column: XBridge Prep OBD C18 Column 19*250 mm, 5 um; Mobile Phase A (5% NH$_4$HCO$_3$ in Water): Mobile Phase B: ACN; Flow rate: 20 mL/min; Gradient: 37% B to 51% B in 8 min; 254; 220 nm; Rt: 7.27 min) to afford 3-amino-5-(3-fluorophenyl)-6-[3-methylimidazo[1,2-a]pyridin-6-yl]-N-[[(2R)-1-methylpyrrolidin-2-yl]methyl]pyrazine-2-carboxamide (Cmpd. 231) (20 mg, 15.81%) as a yellow solid. LCMS: m/z (ESI), [M+H]$^+$= 460.3. $^1$H-NMR (400 MHz, DMSO-d$_6$) δ 1.65 (3H, s), 1.86 (1H, s), 2.18 (1H, s), 2.34 (3H, s), 2.37 (3H, d), 2.45 (1H, s), 2.97 (1H, s), 3.31 (1H, s), 3.51 (1H, s), 7.03 (1H, dd), 7.26 (2H, ddd), 7.30-7.35 (1H, m), 7.36-7.43 (3H, m), 7.77 (2H, s), 8.13-8.32 (1H, m), 8.67 (1H, s).

Examples 235/232. Preparation of 3-amino-N-((6-(3-(dimethyl amino)pyrrolidin-1-yl)pyridin-2-yl)methyl)-6-(3-methylimidazo[1,2-a]pyridin-6-yl)-5-(oxazol-2-yl)pyrazine-2-carboxamide (Cmpd. 235/232)

SCHEME 109

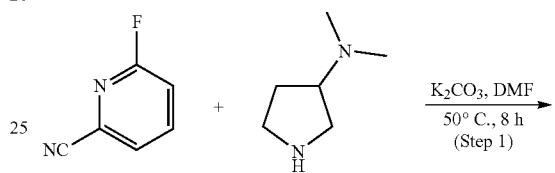

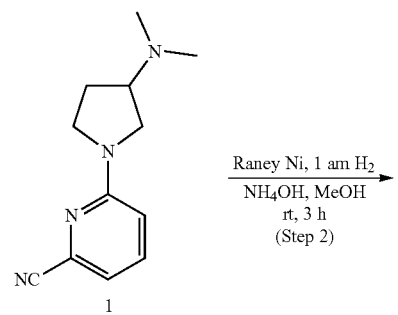

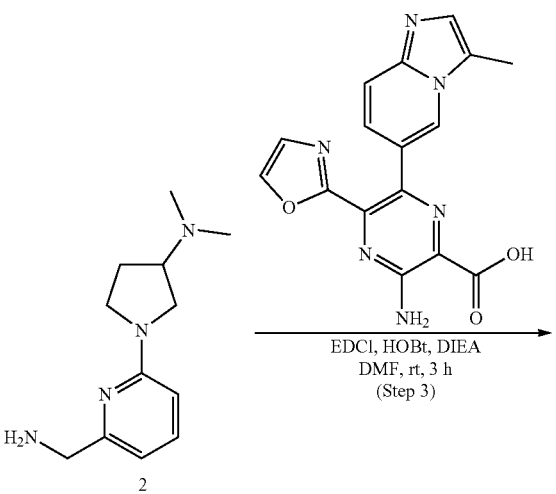

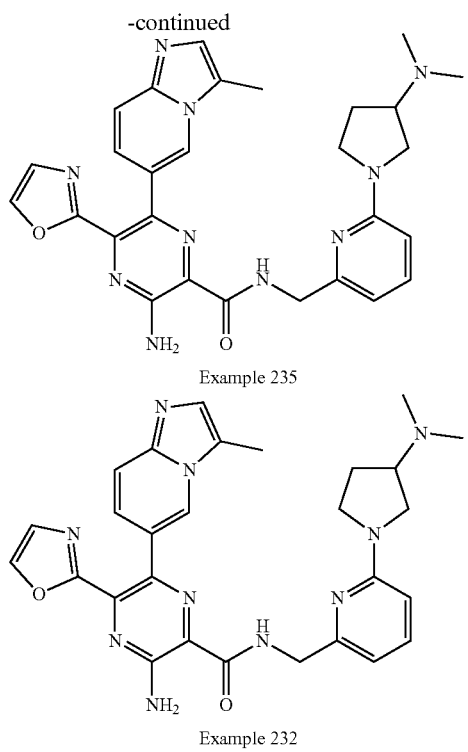

Example 235

Example 232

Step 1. 16-[3-(dimethylamino)pyrrolidin-1-yl]pyridine-2-carbonitrile

To a mixture of 6-fluoropyridine-2-carbonitrile (500 mg, 4.095 mmol, 1 equiv) and N, N-dimethylpyrrolidin-3-amine (701.41 mg, 6.142 mmol, 1.5 equiv) in 2 mL of DMF was added potassium carbonate (1.14 g, 8.190 mmol, 2.00 equiv). The mixture was stirred at 50° C. for 8 h. After concentrated to dryness, the residue was purified by silica gel column chromatography eluting with DCM/CH$_3$OH=10/1 to afford 6-[3-(di-methylamino)pyrrolidin-1-yl]pyridine-2-carbonitrile (810 mg, 80.0%) as a yellow solid. LCMS: m/z (ESI), [M+H]$^+$=217.1.

Step 2.1-[6-(aminomethyl)pyridin-2-yl]-N,N-dimethylpyrrolidin-3-amine

A mixture of 6-[3-(dimethylamino)pyrrolidin-1-yl]pyridine-2-carbonitrile (200 mg, 0.925 mmol, 1 equiv), Raney Ni (158.45 mg, 1.849 mmol, 2 equiv) and NH$_4$OH (50 mg) in methanol (16 mL) was hydrogenated under 1 atm H$_2$ at room temperature for 3 h. After filtered through celite, the filtrate was concentrated to dryness under vacuum and the residue was used directly in the next step. LCMS: m/z (ESI), [M+H]$^+$=221.1.

Step 3. 3-amino-N-([6-[3-(dimethylamino)pyrrolidin-1-yl]pyridin-2-yl]methyl)-6-[3-methylimidazo[1,2-a]pyridin-6-yl]-5-(1,3-oxazol-2-yl)pyrazine-2-carboxamide (Cmpd. 235/232)

To a mixture of 1-[6-(aminomethyl)pyridin-2-yl]-N,N-dimethylpyrrolidin-3-amine (185 mg, 0.840 mmol, 1 equiv), 3-amino-6-[3-methylimidazo[1,2-a]pyridin-6-yl]-5-(1,3-oxazol-2-yl)pyrazine-2-carboxylic acid (423 mg, 1.260 mmol, 1.50 equiv) in N, N-di-Methylformamide (5 mL) were added DIEA (651.14 mg, 5.038 mmol, 6 equiv), HOBt (226.92 mg, 1.679 mmol, 2 equiv) and EDCI (321.94 mg, 1.679 mmol, 2 equiv). The mixture was stirred at room temperature for 3 h. After concentrated to dryness, the residue was purified by Chiral-Prep-HPLC with the following conditions (Column: CHIRAL ART Cellulose-SB S-5 um, 2*25 cm, 5 um; Mobile Phase A: Hex (8 mmol/L NH$_3$.MeOH)-HPLC, Mobile Phase B: MeOH:EtOH=1:1-HPLC; Flow rate: 20 mL/min; Gradient: 50 B to 50 B in 13 min; 220/254 nm; R$_{T1}$: 8.028 min; R$_{T2}$: 10.436 min) to afford 3-amino-N-([6-[3-(dimethylamino)pyrrolidin-1-yl]pyridin-2-yl]methyl)-6-[3-methylimidazo[1,2-a]pyridin-6-yl]-5-(1,3-oxazol-2-yl)pyrazine-2-carboxamide (Cmpd. 235) (77 mg, 17.0%), LCMS: m/z (ESI), [M+H]$^+$=539.4. $^1$H-NMR (300 MHz, Methanol-d$_4$) δ 1.28 (1H, m), 1.48 (1H, m), 2.16 (6H, s), 2.48 (3H, d), 2.55-2.66 (1H, m), 3.09 (2H, dt), 3.52 (2H, dt), 4.54 (2H, s), 6.31 (1H, d), 6.57 (1H, d), 7.22-7.33 (2H, m), 7.38-7.56 (3H, m), 7.98 (1H, d), 8.37 (1H, s) and 3-amino-N-([6-[3-(dimethylamino)pyrrolidin-1-yl]pyridin-2-yl]methyl)-6-[3-methylimidazo[1,2-a]pyridin-6-yl]-5-(1,3-oxazol-2-yl)pyrazine-2-carboxamide (Cmpd. 232) (30 mg, 6.63%) LCMS: m/z (ESI), [M+H]$^+$=539.3. $^1$H-NMR (300 MHz, Methanol-d$_4$) δ 1.39-1.59 (2H, m), 2.16 (6H, s), 2.48 (3H, d), 2.55-2.66 (1H, m), 3.09 (2H, dt), 3.52 (2H, dt), 4.54 (2H, s), 6.31 (1H, d), 6.57 (1H, d), 7.22-7.33 (2H, m), 7.38-7.56 (3H, m), 7.98 (1H, d), 8.37 (1H, s).

Example 233. Preparation of rac-3-amino-N-(2-(methyl(tetrahydrofuran-3-yl)amino)ethyl)-6-(3-methylimidazo[1,2-a]pyridin-6-yl)-5-(oxazol-2-yl)pyrazine-2-carboxamide (Cmpd. 233)

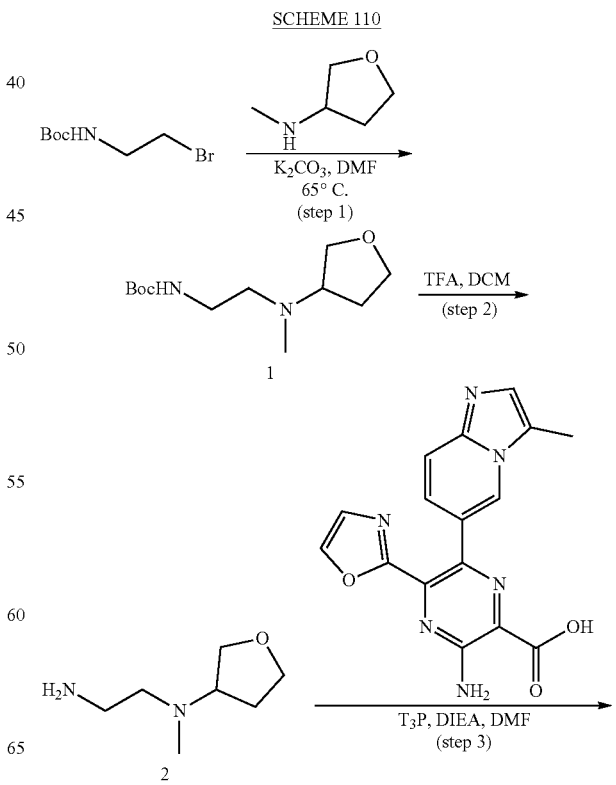

SCHEME 110

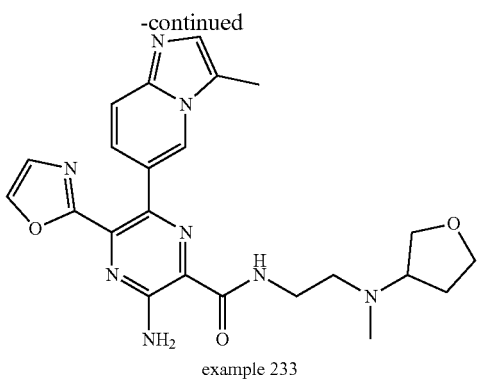

example 233

Step 1. tert-butyl (2-(methyl(tetrahydrofuran-3-yl)amino)ethyl)carbamate

A mixture of tert-butyl N-(2-bromoethyl)carbamate (400 mg, 1.785 mmol, 1 equiv), N-methyloxolan-3-amine (180.54 mg, 1.785 mmol, 1 equiv) and $K_2CO_3$ (740.06 mg, 5.355 mmol, 3.0 equiv) in DMF (30 mL) was stirred for 16 h at 65° C. The resulting mixture was diluted with water (30 mL). The resulting mixture was extracted with EtOAc (3×30 mL). The combined organic layers were washed with saturated brine (20 mL), dried over anhydrous $Na_2SO_4$. After filtration, the filtrate was concentrated under reduced pressure. This gave tert-butyl N-[2-[methyl(oxolan-3-yl)amino]ethyl]carbamate (410 mg, 94.0%) as a light yellow oil. LCMS: m/z (ESI), [M+H]$^+$=245.1. $^1$H-NMR (300 mHz, DMSO-$d_6$) δ 0.62 (9H, s), 1.02-1.05 (1H, m), 1.35-1.18 (1H, m), 1.45 (2H, s), 1.80-1.56 (2H, m, 2H), 2.37-2.39 (3H, m), 2.50-2.53 (1H, m), 2.87-2.69 (1H, m), 2.91-2.94 (1H, m), 3.01-3.05 (1H, m), 3.12-3.15 (1H, m)

Step 2. N1-methyl-N1-(tetrahydrofuran-3-yl)ethane-1,2-diamine

A solution of tert-butyl N-[2-[methyl(oxolan-3-yl)amino]ethyl]carbamate (200 mg, 0.819 mmol, 1 equiv) and TFA (3 mL) in DCM (6 mL) was stirred for 1 h at room temperature. The resulting mixture was concentrated under reduced pressure. The residue was neutralized to pH 7 with saturated $NaHCO_3$ (aq.). The aqueous layer was extracted with EtOAc (3×20 mL). The resulting mixture was concentrated under reduced pressure. This gave N-(2-aminoethyl)-N-methyloxolan-3-amine (105 mg, 88.95%) as light yellow oil. LCMS: m/z (ESI), [M+H]$^+$=145.1. $^1$H-NMR (300 mHz, DMSO-$d_6$) δ 1.41-1.44 (1H, m), 1.60-1.64 (1H, m), 2.05-2.08 (1H, d), 2.16-2.19 (1H, s), 2.50-2.53 (1H, m), 2.65-2.67 (4H, m), 2.89-2.90 (1H, m), 2.97-2.99 (1H, m), 3.30-3.32 (1H, m), 3.37-3.39 (2H, m)

Step 3. rac-3-amino-N-(2-(methyl(tetrahydrofuran-3-yl)amino)ethyl)-6-(3-methylimidazo[1,2-a]pyridin-6-yl)-5-(oxazol-2-yl)pyrazine-2-carboxamide A solution of 3-amino-6-[3-methylimidazo[1,2-a]pyridin-6-yl]-5-(1,3-oxazol-2-yl)pyrazine-2-carboxylic acid (80 mg, 0.238 mmol, 1 equiv), N-(2-aminoethyl)-N-methyloxolan-3-amine (41.17 mg, 0.285 mmol, 1.2 equiv), $T_3P$ (227.06 mg, 0.714 mmol, 3.0 equiv) and DIEA (92.23 mg, 0.714 mmol, 3.0 equiv) in DMF (2 mL) was stirred for 2 h at room temperature. The resulting mixture was diluted with water (30 mL) and extracted with EtOAc (3×30 mL). The combined organic layers were washed with saturated brine (10 mL), dried over anhydrous $Na_2SO_4$. After filtration, the filtrate was concentrated under reduced pressure. The crude product was purified by Prep-HPLC with the following conditions (Column: XBridge Prep C18 OBD Column 19×150 mm 5 um; Mobile Phase A: Mobile Phase B: ACN; Flow rate: 20 mL/min; Gradient: 20% B to 37% B in 7 min; 254/220 nm; Rt: 6.58 min) to afford 3-amino-N-[2-[methyl(oxolan-3-yl)amino]ethyl]-6-[3-methylimidazo[1,2-a]pyridin-6-yl]-5-(1,3-oxazol-2-yl)pyrazine-2-carboxamide (Cmpd. 233) (12.2 mg, 11.09%) as a yellow solid. LCMS: m/z (ESI), [M+H]$^+$=463.4 $^1$H-NMR (300 mHz, MeOD-$d_4$) δ 1.81-1.85 (1H, m), 2.04-2.05 (1H, m), 2.32 (3H, s), 2.49 (3H, s), 2.59-2.63 (2H, m), 3.22-3.24 (1H, m), 3.29-3.34 (2H, m), 3.51-3.55 (2H, m), 3.60-3.65 (2H, m), 7.25-7.30 (2H, m), 7.31-7.38 (1H, s), 7.47-7.50 (1H, m), 8.02 (1H, s), 8.68 (1H, s).

Example 234. Preparation of (3S)-3-[(3-amino-6-[3-methylimidazo[1,2-a]pyridin-6-yl]-5-(1,3-oxazol-2-yl)pyrazin-2-yl)formamido]-N,N-dimethylbutanamide (Cmpd. 234)

SCHEME 111

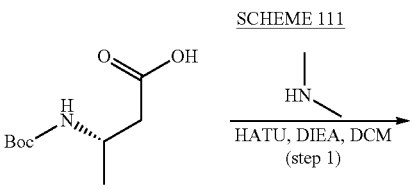

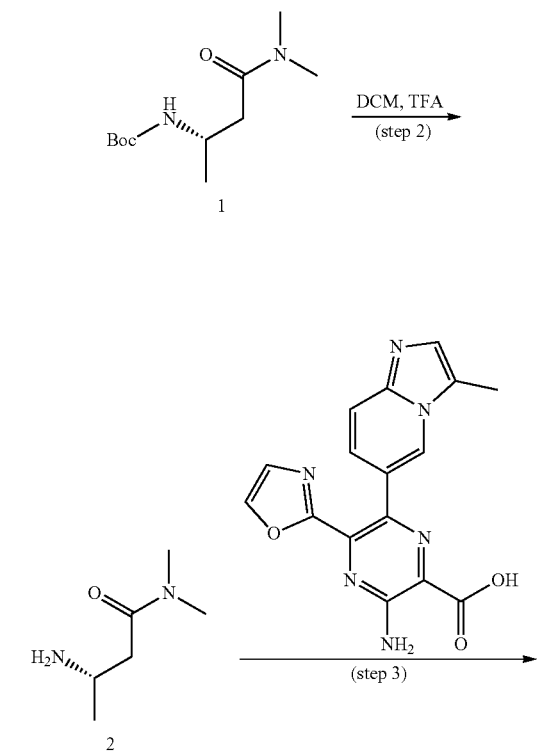

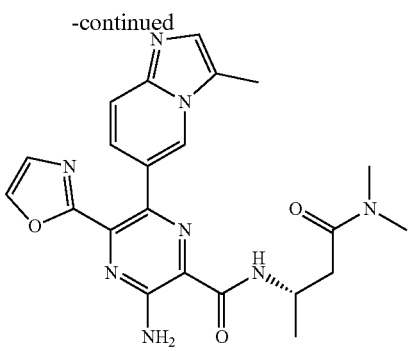

Example. 234

Step 1. (S)-tert-butyl 4-(dimethylamino)-4-oxobutan-2-ylcarbamate

To a stirred mixture of (3S)-3-[[(tert-butoxy)carbonyl]amino]butanoic acid (500 mg, 2.460 mmol, 1 equiv) and dimethylamine (221.83 mg, 4.920 mmol, 2 equiv) in DCM were added HATU (1870.86 mg, 4.920 mmol, 2 equiv) in portions and DIEA (1.59 g, 12.301 mmol, 5 equiv) dropwise at room temperature under air atmosphere. The resulting mixture was stirred for overnight at room temperature under air atmosphere. The residue was purified by reverse flash chromatography with the following conditions: column, C18 silica gel; mobile phase, ACN in water, 5% to 20% gradient in 10 min; detector, UV 220 nm. This resulted in tert-butyl N-[(2S)-1-(dimethylcarbamoyl)propan-2-yl]carbamate (550 mg, 64.07%) as a pink solid. LCMS (ESI) m/z [M+H]$^+$= 231.1; $^1$H-NMR (400 MHz, CDCl$_3$-d) δ 1.27 (3H, d), 1.44 (9H, s), 2.44-2.49 (1H, m), 2.60-2.65 (1H, m), 2.95 (3H, s), 3.04 (3H, s), 4.00-4.05 (1H, m).

Step 2. (S)-3-amino-N,N-dimethylbutanamide

Into a 50 mL round-bottom flask were added tert-butyl N-[(2S)-1-(dimethylcarbamoyl)propan-2-yl]carbamate (200 mg, 0.868 mmol, 1 equiv) and TFA (0.99 g, 8.684 mmol, 10 equiv) at room temperature. The resulting mixture was concentrated under reduced pressure. The crude product was used in the next step directly without further purification. LCMS (ESI) m/z [M+H]$^+$=131.1; $^1$H-NMR (300 MHz, CDCl$_3$-d) δ 1.40 (3H, d), 2.70 (2H, d), 2.95 (3H, s), 3.01 (3H, s), 3.74 (1H, s), 7.78 (3H, s), 11.00 (2H, s).

Step 3. (S)-3-amino-N-(4-(dimethylamino)-4-oxobutan-2-yl)-6-(3-methylimidazo[1,2-a]pyridin-6-yl)-5-(oxazol-2-yl)pyrazine-2-carboxamide (Cmpd. 234)

To a stirred solution/mixture of (3S)-3-amino-N,N-dimethylbutanamide (77.42 mg, 0.595 mmol, 2 equiv) and 3-amino-6-[3-methylimidazo[1,2-a]pyridin-6-yl]-5-(1,3-oxazol-2-yl)pyrazine-2-carboxylic acid (100 mg, 0.297 mmol, 1 equiv) in DMF were added DIEA (768.59 mg, 5.947 mmol, 20.00 equiv) and T$_3$P (946.09 mg, 2.973 mmol, 10.00 equiv) dropwise at room temperature under air atmosphere. The resulting mixture was stirred for overnight at room temperature under air atmosphere. The crude product (100 mg) was purified by Prep-HPLC with the following conditions (Column: XBridge Prep OBD C18 Column 19*250 mm, 5 um; Mobile Phase A: Mobile Phase B: MeOH-HPLC; Flow rate: 20 mL/min; Gradient: 49% B to 59% B in 8 min; 254; 220 nm; Rt: 6.97 min) to afford (3S)-3-[(3-amino-6-[3-methylimidazo[1,2-a]pyridin-6-yl]-5-(1,3-oxazol-2-yl)pyrazin-2-yl)formamido]-N,N-dimethylbutanamide (15 mg, 11.15%) as a yellow solid. LCMS (ESI) [M+H]$^+$=449.3; $^1$H-NMR (400 MHz, DMSO-d$_6$) δ 1.23 (3H, d), 2.48 (3H, d), 2.52-2.60 (1H, m), 2.74-2.79 (1H, m), 2.83 (3H, s), 3.00 (3H, s), 4.38 (1H, s), 7.14-7.17 (1H, m), 7.37-7.41 (2H, m), 7.47-7.49 (1H, m), 8.28 (1H, d), 8.37 (1H, s), 9.01 (1H, d).

Example 236. Preparation of (3R)-3-[(3-amino-6-[3-methylimidazo[1,2-a]pyridin-6-yl]-5-(1,3-oxazol-2-yl)pyrazin-2-yl)formamido]-N,N-dimethylbutanamide (Cmpd. 236)

SCHEME 112

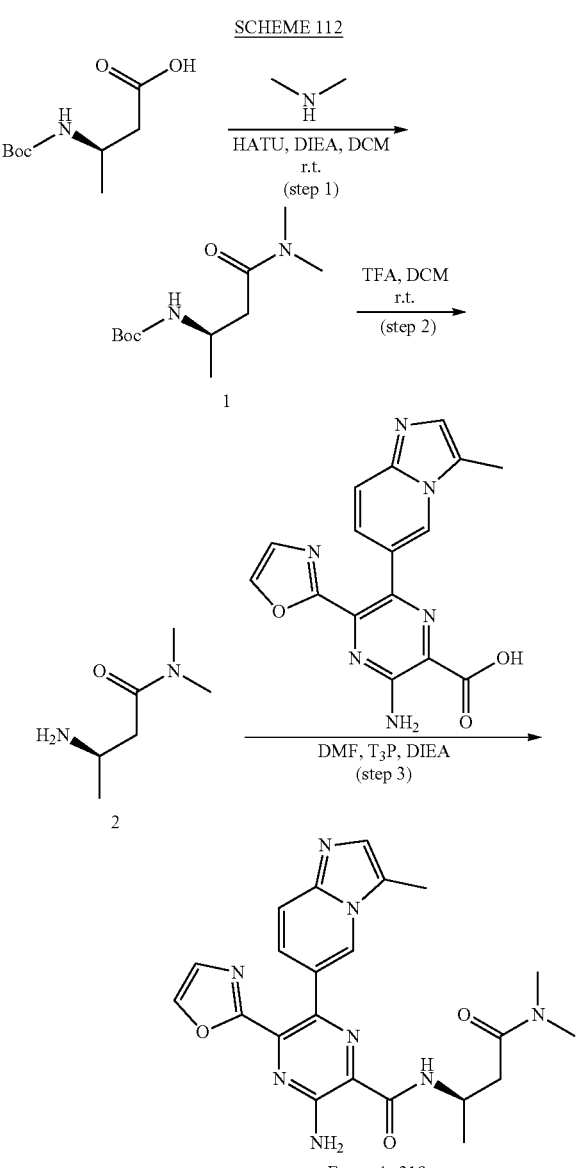

Example 219

Step 1. tert-butyl N-[(2R)-1-(dimethylcarbamoyl)propan-2-yl]carbamate

A mixture of DIEA (1589.80 mg, 12.301 mmol, 5 equiv), HATU (1870.86 mg, 4.920 mmol, 2 equiv), dimethylamine hydrochloride (401.20 mg, 4.920 mmol, 2 equiv) and (3R)-3-[[(tert-butoxy)carbonyl]amino]butanoic acid (500 mg, 2.460 mmol, 1 equiv) in DCM (15 mL, 1 equiv) was stirred for overnight at room temperature under air atmosphere. The resulting mixture was concentrated under reduced pressure. The crude product (1000 mg) was purified by Prep-HPLC with the following conditions (0-20% H$_2$O in ACN) to afford tert-butyl N-[(2R)-1-(dimethylcarbamoyl)propan-2-yl]carbamate (550 mg, 1.35%) as a colorless oil. LCMS: m/z (ESI), [M+H]$^+$=231.0. $^1$H NMR (300 MHz, Chloroform-d) δ 1.27 (3H, d), 1.44 (9H, s), 2.47 (1H, d), 2.64 (1H, d), 2.95 (3H, s), 3.04 (3H, s), 4.02 (1H, d)

Step 2. (3R)-3-amino-N,N-dimethylbutanamide

A mixture of TFA (1.00 mL, 13.463 mmol, 15.50 equiv) and tert-butyl N-[(2R)-1-(dimethylcarbamoyl)propan-2-yl]carbamate (200 mg, 0.868 mmol, 1 equiv) in DCM (3 mL) was stirred for 1 h at room temperature under air atmosphere. The resulting mixture was concentrated under reduced pressure to afford (3R)-3-amino-N,N-dimethylbutanamide (100 mg, 88.45%) as a pink oil. $^1$H NMR (300 MHz, Chloroform-d) δ 1.47 (3H, d), 2.76 (2H, d), 3.00 (3H, s), 3.06 (3H, s), 3.79 (1H, s), 7.81 (2H, s)

Step 3. (3R)-3-[(3-amino-6-[3-methylimidazo[1,2-a]pyridin-6-yl]-5-(1,3-oxazol-2-yl)pyrazin-2-yl)formamido]-N,N-dimethylbutanamide (Cmpd. 236)

A mixture of DIEA (245.95 mg, 1.903 mmol, 8 equiv), T$_3$P (454.12 mg, 1.427 mmol, 6 equiv), (3R)-3-amino-N,N-dimethylbutanamide (123.88 mg, 0.952 mmol, 4 equiv) and 3-amino-6-[3-methylimidazo[1,2-a]pyridin-6-yl]-5-(1,3-oxazol-2-yl)pyrazine-2-carboxylic acid (80 mg, 0.238 mmol, 1 equiv) in DMF (3 mL) was stirred for overnight at room temperature under air atmosphere. Desired product could be detected by LCMS. The crude product (100 mg) was purified by Prep-HPLC with the following conditions (Column: XBridge Prep OBD C18 Column 19*250 mm, 5 um; Mobile Phase A: Mobile Phase B: MeOH-HPLC; Flow rate: 20 mL/min; Gradient: 47% B to 59% B in 8 min; 254; 220 nm; Rt: 7.40 min) to afford (3R)-3-[(3-amino-6-[3-methylimidazo[1,2-a]pyridin-6-yl]-5-(1,3-oxazol-2-yl)pyrazin-2-yl)formamido]-N,N-dimethylbutanamide (Cmpd. 236) (60 mg, 55.12%) as a yellow solid. LCMS: m/z (ESI), [M+H]$^+$=449.3. $^1$H-NMR (300 MHz, DMSO-d$_6$) δ 1.23 (3H, d), 2.46-2.49 (3H, m), 2.58 (1H, d), 2.76-2.83 (4H, m), 3.00 (3H, s), 4.39 (1H, s), 7.15 (1H, d), 7.39 (2H, d), 7.49 (1H, d), 7.93 (2H, s), 8.28 (1H, d), 8.38 (1H, d), 9.02 (1H, d).

Examples 247-1/247-2. Preparation of 3-amino-N-((1,2-dimethylpyrrolidin-2-yl)methyl)-6-(3-methylimidazo[1,2-a]pyridin-6-yl)-5-(oxazol-2-yl)pyrazine-2-carboxamide (Cmpd. 247-1/247-2)

SCHEME 113

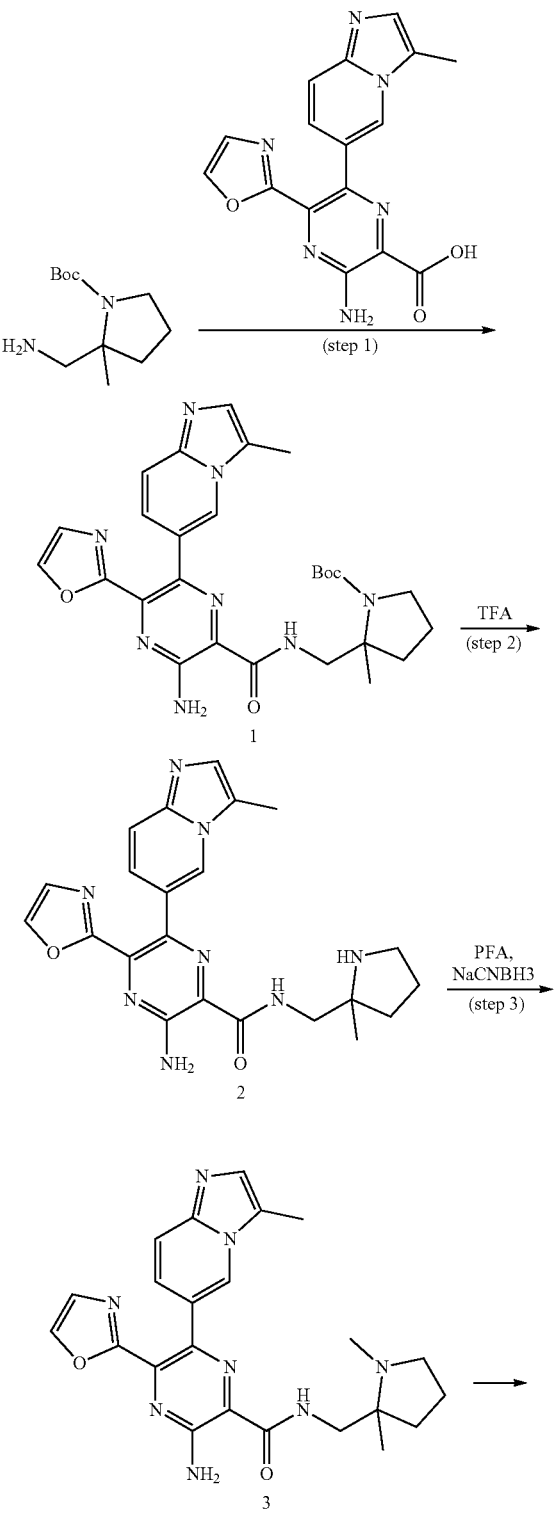

-continued

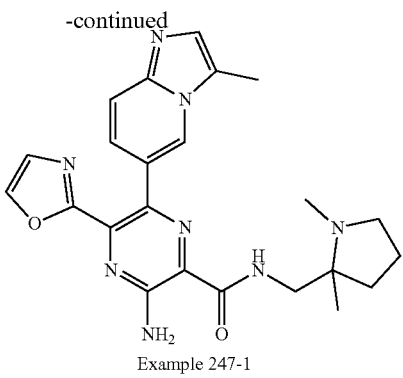

Example 247-1

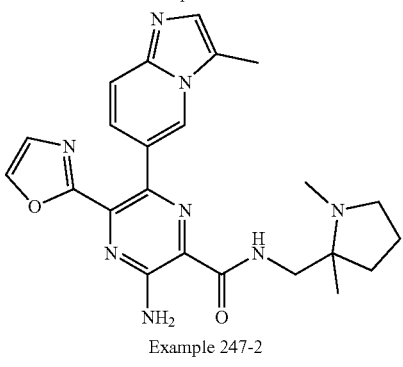

Example 247-2

Step 1. tert-butyl 2-[[(3-amino-6-[3-methylimidazo [1,2-a]pyridin-6-yl]-5-(1,3-oxazol-2-yl)pyrazin-2-yl) formamido]methyl]-2-methylpyrrolidine-1-carboxylate To a stirred mixture of 3-amino-6-[3-methylimidazo[1,2-a]pyridin-6-yl]-5-(1,3-oxazol-2-yl)pyrazine-2-carboxylic acid (200 mg, 0.595 mmol, 1 equiv) and tert-butyl 2-(aminomethyl)-2-methylpyrrolidine-1-carboxylate (254.89 mg, 1.189 mmol, 2 equiv) in DMF were added $T_3P$ (946.09 mg, 2.973 mmol, 5 equiv) and DIEA (307.44 mg, 2.379 mmol, 4 equiv) dropwise at 25° C. C under nitrogen atmosphere. The resulting mixture was stirred for 2 h at 25° C. under nitrogen atmosphere. The resulting mixture was diluted with water (50 mL), extracted with $CH_2Cl_2$ (3×50 mL). The combined organic layers were washed with brine (3×50 mL), dried over anhydrous $Na_2SO_4$. After filtration, the filtrate was concentrated under reduced pressure. The residue was purified by Prep-TLC ($CH_2Cl_2$/MeOH 20:1) to afford tert-butyl 2-[[(3-amino-6-[3-methylimidazo[1,2-a]pyridin-6-yl]-5-(1,3-oxazol-2-yl)pyrazin-2-yl)formamido]methyl]-2-methylpyrrolidine-1-carboxylate (280 mg, 88.40%) as a yellow solid. LCMS: m/z (ESI), $[M+H]^+=$ 533.3. $^1$H-NMR (300 MHz, MeOD-$d_4$) δ1.18 (5H, s), 1.40 (7H, d), 1.81 (2H, d), 2.49 (3H, d), 3.49 (1H, s), 3.63 (1H, t), 3.80 (1H, d), 7.23-7.41 (3H, m), 7.49 (1H, d), 8.00 (1H, s), 8.30 (1H, s).

Step 2. 3-amino-6-[3-methylimidazo[1,2-a]pyridin-6-yl]-N-[(2-methylpyrrolidin-2-yl)methyl]-5-(1,3-oxazol-2-yl)pyrazine-2-carboxamide To a stirred solution of tert-butyl 2-[[(3-amino-6-[3-methylimidazo[1,2-a]pyridin-6-yl]-5-(1,3-oxazol-2-yl)pyrazin-2-yl)formamido]methyl]-2-methylpyrrolidine-1-carboxylate (280 mg) in DCM were added TFA (1.5 mL) at 25° C. under nitrogen atmosphere. The resulting mixture was stirred for 30 min at 25° C. under nitrogen atmosphere. The resulting mixture was concentrated under reduced pressure to afford 3-amino-6-[3-methylimidazo[1,2-a]pyridin-6-yl]-N-[(2-methylpyrrolidin-2-yl)methyl]-5-(1,3-oxazol-2-yl)pyrazine-2-carboxamide (200 mg, 87.96%). LCMS: m/z (ESI), $[M+H]^+=433.2$.

Step 3. tert-butyl 2-[[(3-amino-6-[3-methylimidazo [1,2-a]pyridin-6-yl]-5-(1,3-oxazol-2-yl)pyrazin-2-yl) formamido]methyl]-2-methylpyrrolidine-1-carboxylate To a stirred mixture of 3-amino-6-[3-methylimidazo[1,2-a]pyridin-6-yl]-N-[(2-methylpyrrolidin-2-yl)methyl]-5-(1,3-oxazol-2-yl)pyrazine-2-carboxamide (200 mg, 0.462 mmol, 1 equiv) and PFA (138.73 mg, 4.624 mmol, 10 equiv) in MeOH (8 mL) were added $NaBH_3CN$ (145.30 mg, 2.312 mmol, 5 equiv) and DIEA (239.07 mg, 1.850 mmol, 4 equiv) dropwise at 25° C. under nitrogen atmosphere. The resulting mixture was stirred for 2 h at 25° C. under nitrogen atmosphere. The mixture reaction was purified by Prep-HPLC with the following conditions (Column: Atlantis Prep T3 OBD Column 19*150 mm 5 um; Mobile Phase A: water, Mobile Phase B: ACN; Flow rate: 20 mL/min; Gradient: 10% B to 20.% B in 7 min; 254/220 nm; Rt: 6.08 min) to afford 3-amino-N-[(1,2-dimethylpyrrolidin-2-yl)methyl]-6-[3-methylimidazo[1,2-a]pyridin-6-yl]-5-(1,3-oxazol-2-yl) pyrazine-2-carboxamide (100 mg, 58.12%) as a yellow solid.

Step 4. tert-butyl 2-[[(3-amino-6-[3-methylimidazo [1,2-a]pyridin-6-yl]-5-(1,3-oxazol-2-yl)pyrazin-2-yl) formamido]methyl]-2-methylpyrrolidine-1-carboxylate (Cmpd. 247-1/247-2)

The product (100 mg) was purified by Chiral-Prep-HPLC with the following conditions (Column: CHIRALPAK IG, 5*25 cm, 5 um; Mobile Phase A: Hex:DCM=3:1 (10 mM $NH_3$-MEOH)-HPLC, Mobile Phase B: EtOH-HPLC; Flow rate: 20 mL/min; Gradient: 40 B to 40 B in 10 min; 220/254 nm; RT1:6.193, RT2:7.693) to afford 3-amino-N-[(1,2-dimethylpyrrolidin-2-yl)methyl]-6-[3-methylimidazo[1,2-a] pyridin-6-yl]-5-(1,3-oxazol-2-yl)pyrazine-2-carboxamide (Cmpd. 247-1) (30 mg, 30.0%) and 3-amino-N-[(1,2-dimethylpyrrolidin-2-yl)methyl]-6-[3-methylimidazo[1,2-a] pyridin-6-yl]-5-(1,3-oxazol-2-yl)pyrazine-2-carboxamide (Cmpd. 247-2) (30 mg, 30.0%) as a yellow solid. (Cmpd. 247-1) LCMS: m/z (ESI), $[M+H]^+=447.2$. $^1$H-NMR (300 MHz, MeOD-$d_4$) δ1.05 (3H, s), 1.56-1.68 (1H, m), 1.77 (2H, p), 1.85-1.97 (1H, m), 2.33 (3H, s), 2.49 (3H, d), 2.58-2.69 (1H, m), 2.97 (1H, s), 3.25 (1H, s), 3.53 (1H, d), 7.26 (1H, dd), 7.32 (1H, d), 7.39 (1H, s), 7.49 (1H, d), 8.00 (1H, d), 8.35 (1H, s) (Cmpd. 247-2) LCMS: m/z (ESI), $[M+H]^+=447.4$. $^1$H-NMR (300 MHz, MeOD-$d_4$) δ1.05 (3H, s), 1.56-1.68 (1H, m), 1.77 (2H, p), 1.85-1.97 (1H, m), 2.33 (3H, s), 2.49 (3H, d), 2.58-2.69 (1H, m), 2.97 (1H, s), 3.25 (1H, s), 3.53 (1H, d), 7.26-7.39 (3H, m), 7.49 (1H, d), 8.00 (1H, d), 8.35 (1H, s)

Example 257. Preparation of (2R)—N-[[3-amino-5-(3,4-difluorophenyl)-6-[3-methylimidazo[1,2-a]pyridin-6-yl]pyrazin-2-yl]methyl]-1-methylpyrrolidine-2-carboxamide (Cmpd. 257)

SCHEME 114

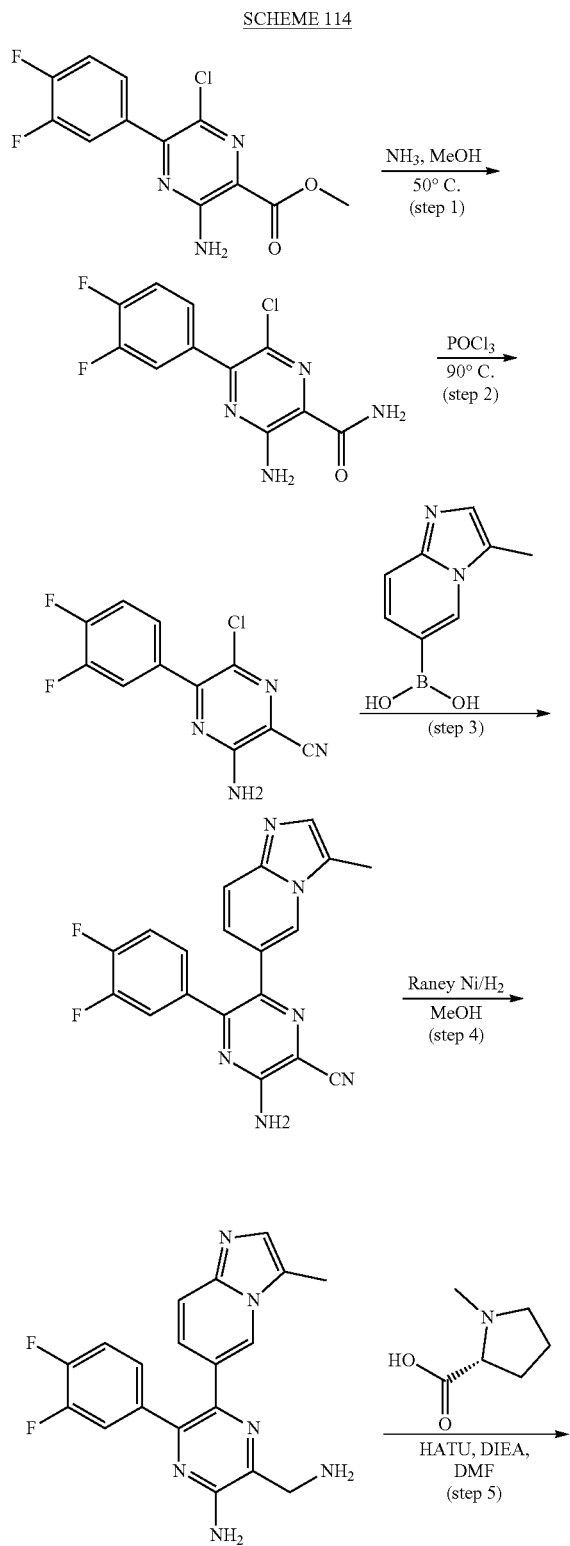

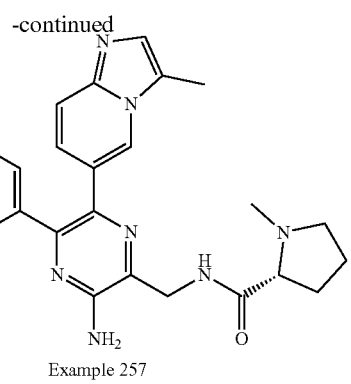

Example 257

Step 1. 3-amino-6-chloro-5-(3,4-difluorophenyl)pyrazine-2-carboxamide

To a solution of $NH_3$ (g) in MeOH (15 mL) was added methyl 3-amino-6-chloro-5-(3,4-difluorophenyl)pyrazine-2-carboxylate (1000 mg, 3.337 mmol, 1 equiv) in portions at room temperature. The mixture was stirred for 5 h at 50° C. under air atmosphere. The resulting mixture was concentrated under vacuum to afford 3-amino-6-chloro-5-(3,4-difluorophenyl)pyrazine-2-carboxamide (930 mg, 97.90%) as a yellow solid. The crude product was used in the next step directly without further purification. LCMS: m/z (ESI), $[M+H]^+=285.2$. $^1$H-NMR (400 MHz, DMSO-$d_6$) δ 7.55-7.67 (3H, m), 7.74-7.85 (3H, m), 8.04 (1H, s)

Step 2. 3-amino-6-chloro-5-(3,4-difluorophenyl)pyrazine-2-carbonitrile

To a solution of phosphoryl trichloride (5 mL) was added 3-amino-6-chloro-5-(3,4-difluorophenyl)pyrazine-2-carboxamide (900 mg, 3.162 mmol, 1 equiv) in portions at room temperature. The resulting mixture was stirred for 2 h at 90° C. under air atmosphere. The resulting mixture was concentrated under reduced pressure. The residue was dissolved with $CH_2Cl_2$ (100 mL) and basified to pH 8 with saturated $NaHCO_3$ (aq.). The resulting mixture was extracted with $CH_2Cl_2$ (2×100 mL). The combined organic layers were washed with water (2×30 mL), dried over anhydrous Na2SO4. After filtration, the filtrate was concentrated under reduced pressure. The residue was purified by silica gel column chromatography, eluted with PE/EtOAc (6:1) to afford 3-amino-6-chloro-5-(3,4-difluorophenyl)pyrazine-2-carbonitrile (550 mg, 65.24%) as a yellow solid. LCMS: m/z (ESI), $[M+H]^+=267.0$. $^1$H NMR (400 MHz, DMSO-$d_6$) δ 7.56-7.68 (2H, m), 7.73 (2H, s), 7.75-7.85 (1H, m)

Step 3. 3-amino-5-(3,4-difluorophenyl)-6-[3-methylimidazo[1,2-a]pyridin-6-yl]pyrazine-2-carbonitrile To a stirred mixture of 3-amino-6-chloro-5-(3,4-difluorophenyl)pyrazine-2-carbonitrile (400 mg, 1.500 mmol, 1 equiv) and [3-methylimidazo[1,2-a]pyridin-6-yl]boronic acid (395.99 mg, 2.250 mmol, 1.5 equiv) in dioxane (50 mL) were added $Cs_2CO_3$ (977.56 mg, 3.000 mmol, 2 equiv) and pd(dppf)cl$_2$ (219.53 mg, 0.300 mmol, 0.2 equiv) in portions at 90° C. under nitrogen atmosphere. The resulting mixture was stirred for 2 h at 90° C. under nitrogen atmosphere. The resulting mixture was concentrated under reduced pressure. The residue was purified by Prep-TLC ($CH_2Cl_2$/MeOH 20:1) to afford 3-amino-5-(3,4-difluorophenyl)-6-[3-methylimidazo[1,2-a]pyridin-6-yl]pyrazine-2-carbonitrile (400 mg, 55.19%) as a yellow solid. LCMS: m/z (ESI), [M+H]+= 363.3.

Step 4. 3-(aminomethyl)-6-(3,4-difluorophenyl)-5-[3-methylimidazo[1,2-a]pyridin-6-yl]pyrazin-2-amine To a solution of 3-amino-5-(3,4-difluorophenyl)-6-[3-methylimidazo[1,2-a]pyridin-6-yl]pyrazine-2-carbonitrile (400 mg, 1.104 mmol, 1 equiv) in MeOH (50 mL) was added Raney Ni (189.16 mg, 2.208 mmol, 2.00 equiv) in portions at room temperature. The mixture was stirred for 2 h at room temperature under hydrogen atmosphere. The resulting mixture was filtered, the filter cake was washed with MeOH (2×50 mL). The filtrate was concentrated under vacuum to afford 3-(aminomethyl)-6-(3,4-difluorophenyl)-5-[3-methylimidazo[1,2-a]pyridin-6-yl]pyrazin-2-amine (300 mg, 74.17%) as a beige solid. The crude product was used in the next step directly without further purification. LCMS: m/z (ESI), [M+H]+=367.3.

Step 5. (2R)—N-[[3-amino-5-(3,4-difluorophenyl)-6-[3-methylimidazo[1,2-a]pyridin-6-yl]pyrazin-2-yl]methyl]-1-methylpyrrolidine-2-carboxamide (Cmpd. 257)

To a stirred mixture of 3-(aminomethyl)-5-chloro-6-(3,4-difluorophenyl)pyrazin-2-amine (100 mg, 0.369 mmol, 1 equiv) and (2R)-1-methylpyrrolidine-2-carboxylic acid (95.44 mg, 0.739 mmol, 2 equiv) in DMF (10 mL) were added HATU (210.72 mg, 0.554 mmol, 1.5 equiv) and DIEA (191.00 mg, 1.478 mmol, 4 equiv) in portions at room temperature under air atmosphere. The resulting mixture was stirred for 2 h at room temperature under air atmosphere. The resulting mixture was concentrated under reduced pressure. The crude product was purified by Prep-HPLC with the following conditions (Column: Kinetex EVO C18 Column 30*150, 5 um; Mobile Phase A: 5% ammonia in water, Mobile Phase B: ACN; Flow rate: 60 mL/min; Gradient: 30% B to 50% B in 7 min; 254; 220 nm; Rt: 5.95 min) to afford (2R)—N-[[3-amino-5-(3,4-difluorophenyl)-6-[3-methylimidazo[1,2-a]pyridin-6-yl]pyrazin-2-yl]methyl]-1-methylpyrrolidine-2-carboxamide (41 mg, 23.17%) (Cmpd. 257) as a white solid. LCMS: m/z (ESI), [M+H]+=478.3. 1H-NMR (400 MHz, DMSO-d6) δ1.64-1.83 (3H, m), 2.03-2.19 (1H, m), 2.21-2.39 (7H, m), 2.81 (1H, dd), 3.04 (1H, dt), 4.32-4.49 (2H, m), 6.75 (2H, s), 6.98 (1H, dd), 7.15-7.24 (1H, m), 7.33-7.44 (3H, m), 7.49 (1H, ddd), 8.07-8.13 (1H, m), 8.45 (1H, t)

Example 259. Preparation of 3-amino-6-[3-methylimidazo[1,2-a]pyridin-6-yl]-N-[[(2R)-1-methylpyrrolidin-2-yl]methyl]-5-phenylpyrazine-2-carboxamide (Cmpd. 259)

SCHEME 115

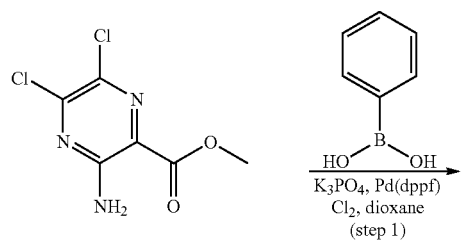

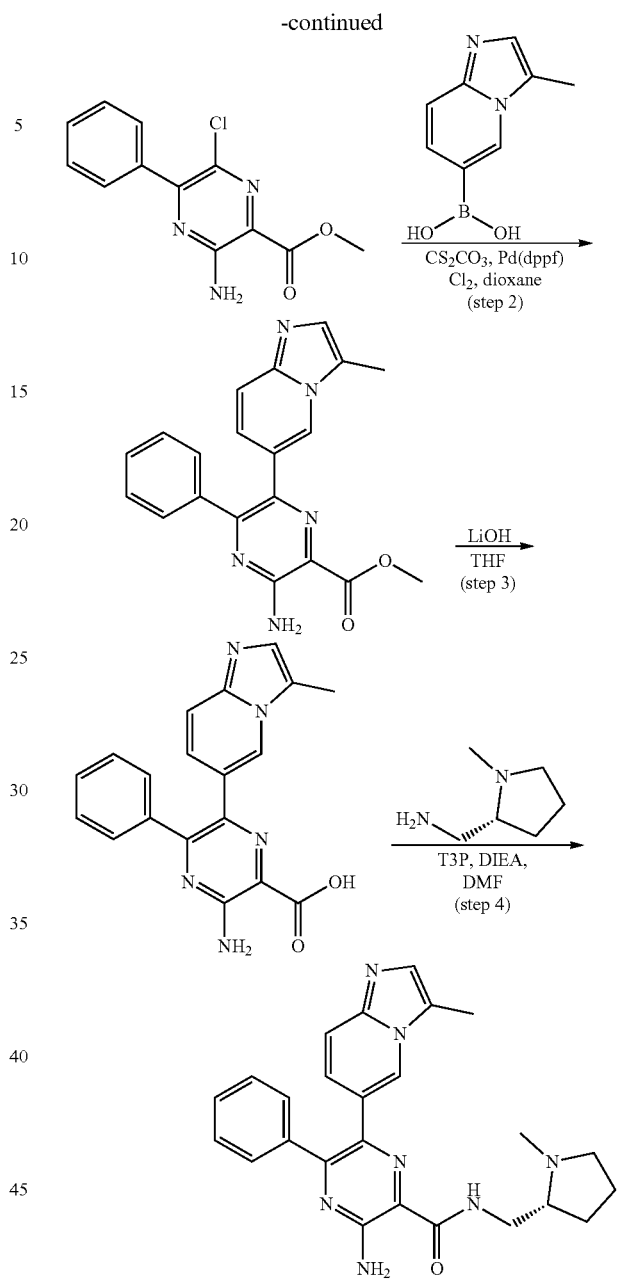

Step 1. methyl 3-amino-6-chloro-5-phenylpyrazine-2-carboxylate

To a stirred mixture of methyl 3-amino-5,6-dichloropyrazine-2-carboxylate (600 mg, 2.702 mmol, 1 equiv) and phenylboronic acid (336.09 mg, 2.756 mmol, 1.02 equiv) in dioxane (20 mL) were added K3PO4 (1147.23 mg, 5.405 mmol, 2 equiv) and Pd(dppf)Cl2 (395.46 mg, 0.540 mmol, 0.2 equiv) in portions at room temperature under nitrogen atmosphere. The resulting mixture was stirred for 3 h at 70° C. under nitrogen atmosphere. The resulting mixture was concentrated under reduced pressure. The residue was purified by Prep-TLC (PE/EtOAc 1:1) to afford methyl 3-amino-6-chloro-5-phenylpyrazine-2-carboxylate (400 mg, 56.14%) as a yellow solid. LCMS: m/z (ESI), [M+H]+=264.3. 1H NMR (400 MHz, DMSO-d₆) δ 3.89 (3H, s), 7.53 (3H, dd), 7.61 (2H, s), 7.71-7.78 (2H, m)

Step 2. 3-amino-6-[3-methylimidazo[1,2-a]pyridin-6-yl]-5-phenylpyrazine-2-carboxylate To a stirred mixture of methyl 3-amino-6-chloro-5-phenylpyrazine-2-carboxylate (150 mg, 0.569 mmol, 1 equiv) and [3-methylimidazo[1,2-a]pyridin-6-yl]boronic acid (200.22 mg, 1.138 mmol, 2 equiv) in dioxane (10 mL) were added CS2CO3 (556.05 mg, 1.707 mmol, 3 equiv) and Pd(dppf)Cl₂ (83.25 mg, 0.114 mmol, 0.2 equiv) in portions at room temperature under nitrogen atmosphere. The resulting mixture was stirred for 2 h at 80° C. under nitrogen atmosphere. The resulting mixture was concentrated under reduced pressure. The residue was purified by Prep-TLC (CH₂Cl₂/MeOH 20:1) to afford methyl 3-amino-6-[3-methylimidazo[1,2-a]pyridin-6-yl]-5-phenylpyrazine-2-carboxylate (130 mg, 63.59%) as a yellow solid. LCMS: m/z (ESI), [M+H]⁺=360.3. ¹H-NMR (400 MHz, DMSO-d₆) δ 2.27 (3H, d), 3.91 (3H, s), 7.09 (1H, dd), 7.34-7.48 (7H, m), 7.55 (2H, d), 8.00 (1H, dd)

Step 3. 3-amino-6-[3-methylimidazo[1,2-a]pyridin-6-yl]-5-phenylpyrazine-2-carboxylic Acid To a solution of methyl 3-amino-6-[3-methylimidazo[1,2-a]pyridin-6-yl]-5-phenylpyrazine-2-carboxylate (130 mg, 0.417 mmol, 1 equiv) in THF (15 mL) and methanol (5 mL) was added LiOH (19.99 mg, 0.835 mmol, 2.00 equiv) at room temperature. The mixture was stirred for 2.5 h at 50° C. under air atmosphere. The mixture was acidified to pH 6 with HCl (aq.). The resulting solid was collected by filtration and dried under vacuum to afford 3-amino-6-[3-methylimidazo[1,2-a]pyridin-6-yl]-5-phenylpyrazine-2-carboxylic acid (100 mg, 80.05%) as a yellow solid. The crude product was used in the next step directly without further purification. LCMS: m/z (ESI), [M+H]⁺=346.2.

Step 4. 3-amino-6-[3-methylimidazo[1,2-a]pyridin-6-yl]-N-[[(2R)-1-methylpyrrolidin-2-yl]methyl]-5-phenylpyrazine-2-carboxamide (Cmpd. 259)

To a stirred mixture of 3-amino-6-[3-methylimidazo[1,2-a]pyridin-6-yl]-5-phenylpyrazine-2-carboxylic acid (100 mg, 0.290 mmol, 1 equiv) and 1-[(2R)-1-methylpyrrolidin-2-yl]methanamine (66.13 mg, 0.579 mmol, 2 equiv) in DMF (5 mL) were added DIEA (112.27 mg, 0.869 mmol, 3 equiv) and T₃P (368.52 mg, 1.158 mmol, 4 equiv) in portions at room temperature under air atmosphere. The resulting mixture was stirred for 2.5h at room temperature under air atmosphere. The resulting mixture was concentrated under reduced pressure. The crude product was purified by Prep-HPLC with the following conditions (Column: XBridge Prep OBD C18 Column 19*250 mm, 5 um; Mobile Phase A: water, Mobile Phase B: ACN; Flow rate: 20 mL/min; Gradient: 38% B to 50% B in 8 min; 254; 220 nm; Rt: 7.65 min) to afford 3-amino-6-[3-methylimidazo[1,2-a]pyridin-6-yl]-N-[[(2R)-1-methylpyrrolidin-2-yl]methyl]-5-phenylpyrazine-2-carboxamide (Cmpd. 259) (33 mg, 25.81%) as a yellow solid. LCMS: m/z (ESI), [M+H]⁺=442.3. ¹H NMR (400 MHz, DMSO-d₆) δ1.54-1.71 (3H, m), 1.79-1.90 (1H, m), 2.16 (1H, q), 2.33 (6H, d), 2.41-2.48 (1H, m), 2.96 (1H, dd), 3.26 (1H, dt), 3.51 (1H, ddd), 7.05 (1H, dd), 7.33-7.46 (5H, m), 7.43-7.51 (2H, m), 7.73 (2H, s), 8.14-8.20 (1H, m), 8.64 (1H, t)

Example 261. Preparation of 3-amino-N-((6-(3-((dimethylamino)methyl)azetidin-1-yl)pyridin-2-yl)methyl)-6-(3-methylimidazo[1,2-a]pyridin-6-yl)-5-(oxazol-2-yl)pyrazine-2-carboxamide (Cmpd. 261)

SCHEME 116

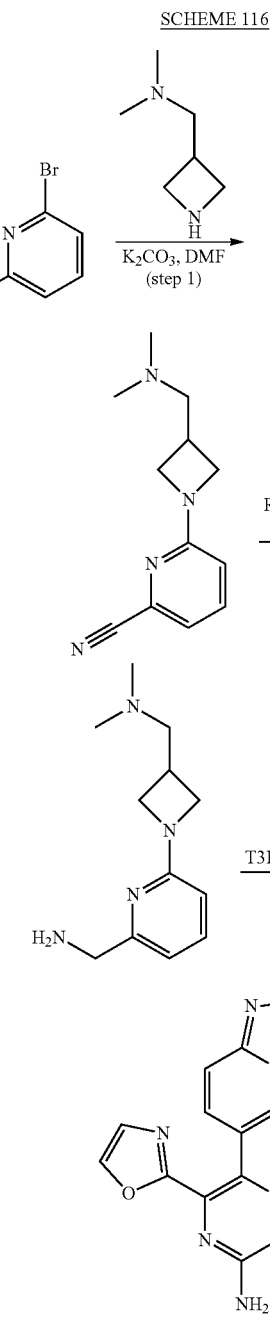

example 261

Step 1. 6-(3-((dimethylamino)methyl)azetidin-1-yl) picolinonitrile

Into a 50-mL round-bottom flask, was placed 6-bromopyridine-2-carbonitrile (423.10 mg, 2.312 mmol, 1.10 equiv), DMF (4 mL, 51.687 mmol, 24.59 equiv), K₂CO3 (871.41 mg, 6.305 mmol, 3 equiv), [(azetidin-3-yl)methyl]

dimethylamine (240 mg, 2.102 mmol, 1 equiv). The resulting solution was stirred for 16 hrs at 50° C. The resulting solution was extracted with 3×10 mL of ethyl acetate and the organic layers was combined and concentrated. The residue was applied onto a silica gel column with dichloromethane/methanol (8:1). This resulted in 190 mg (41.80%) of 6-[3-[(dimethylamino)methyl]azetidin-1-yl]pyridine-2-carbonitrile as a light yellow solid. LCMS: m/z (ESI), [M+H]$^+$=217.1. $^1$H-NMR (400 MHz, DMSO-d$_6$) δ 2.13 (6H, s), 2.47-2.49 (2H, m), 2.84-2.91 (1H, m), 3.62 (2H, t), 4.06 (2H, t), 6.65 (1H, d), 7.16 (1H, d), 7.64 (1H, t).

Step 2. 1-(1-(6-(aminomethyl)pyridin-2-yl)azetidin-3-yl)-N,N-dimethylmethanamine Into a 50-mL round-bottom flask, was placed MeOH (5 mL, 0.094 mmol, 2.03 equiv), Raney Ni (0.75 mg, 0.009 mmol, 0.01 equiv), 6-[3-[(dimethylamino)methyl]azetidin-1-yl]pyridine-2-carbonitrile (190 mg, 0.878 mmol, 1 equiv), NH$_4$OH (1 mL, 25.681 mmol, 29.23 equiv). The resulting solution was stirred for 1 hr at room temperature. This resulted in 40 mg (20.67%) of 1-(6-[3-[(dimethylamino)methyl]azetidin-1-yl]pyridin-2-yl)methanamine as Brown yellow oil. LCMS: m/z (ESI), [M+H]$^+$=220.95. $^1$H-NMR (400 MHz, DMSO-d$_6$) δ 2.13 (6H, s), 2.46 (2H, d), 2.83 (1H, dt), 3.53 (2H, dd), 3.59 (2H, s), 3.98 (2H, t), 6.17 (1H, d), 6.64 (1H, d), 7.43 (1H, t)

Step 3. 3-amino-N-((6-(3-((dimethylamino)methyl) azetidin-1-yl)pyridin-2-yl)methyl)-6-(3-methylimidazo[1,2-a]pyridin-6-yl)-5-(oxazol-2-yl)pyrazine-2-carboxamide (Cmpd. 261)

Into a 25-mL round-bottom flask, was placed 3-amino-6-[3-methylimidazo[1,2-a]pyridin-6-yl]-5-(1,3-oxazol-2-yl)pyrazine-2-carboxylic acid (80 mg, 0.238 mmol, 1 equiv), DMF 0.041 mmol, 0.17 equiv), DIEA (307.44 mg, 2.379 mmol, 10 equiv), T$_3$P (454.12 mg, 1.427 mmol, 6 equiv), 1-(6-[3-[(dimethylamino)methyl]azetidin-1-yl]pyridin-2-yl) methanamine (104.82 mg, 0.476 mmol, 2 equiv). The resulting solution was stirred for 16 hrs at room temperature. The resulting solution was diluted with water (15 mL), extracted with 3×10 mL of dichloromethane and the organic layers were combined and concentrated. The crude product was purified by Prep-HPLC with the following conditions: (Column: Kinetex EVO C18 Column 30*150.5 um; Mobile Phase A: Mobile Phase B: ACN; Flow rate: 60 mL/min; Gradient: 30% B to 40% B in 7 min; 254; 220 nm; Rt: 5.82 min) and the product was obtained. This resulted in 23.6 mg (18.42%) of 3-amino-N-[(6-[3-[(dimethylamino)methyl] azetidin-1-yl]pyridin-2-yl)methyl]-6-[3-methylimidazo[1,2-a]pyridin-6-yl]-5-(1,3-oxazol-2-yl)pyrazine-2-carboxamide (Cmpd. 261) as a yellow solid. LCMS: m/z (ESI), [M+H]$^+$=539.5. $^1$H-NMR (400 MHz, Methanol-d$_4$) δ 2.23 (6H, s), 2.42 (2H, d), 2.53 (3H, d), 2.71-2.80 (1H, m), 3.53 (2H, dd), 4.00 (2H, t), 4.56 (2H, s), 6.27 (1H, d), 6.67 (1H, d), 7.27-7.36 (2H, m), 7.43 (1H, d), 7.46-7.56 (2H, m), 8.02 (1H, d), 8.41 (1H, s)

Example 268. Preparation of (2S)—N-[[3-amino-5-(4-fluorophenyl)-6-[3-methyl-imidazo-[1,2-a]pyridin-6-yl]pyrazin-2-yl]methyl]oxolane-2-carboxamide (Cmpd. 268)

SCHEME 117

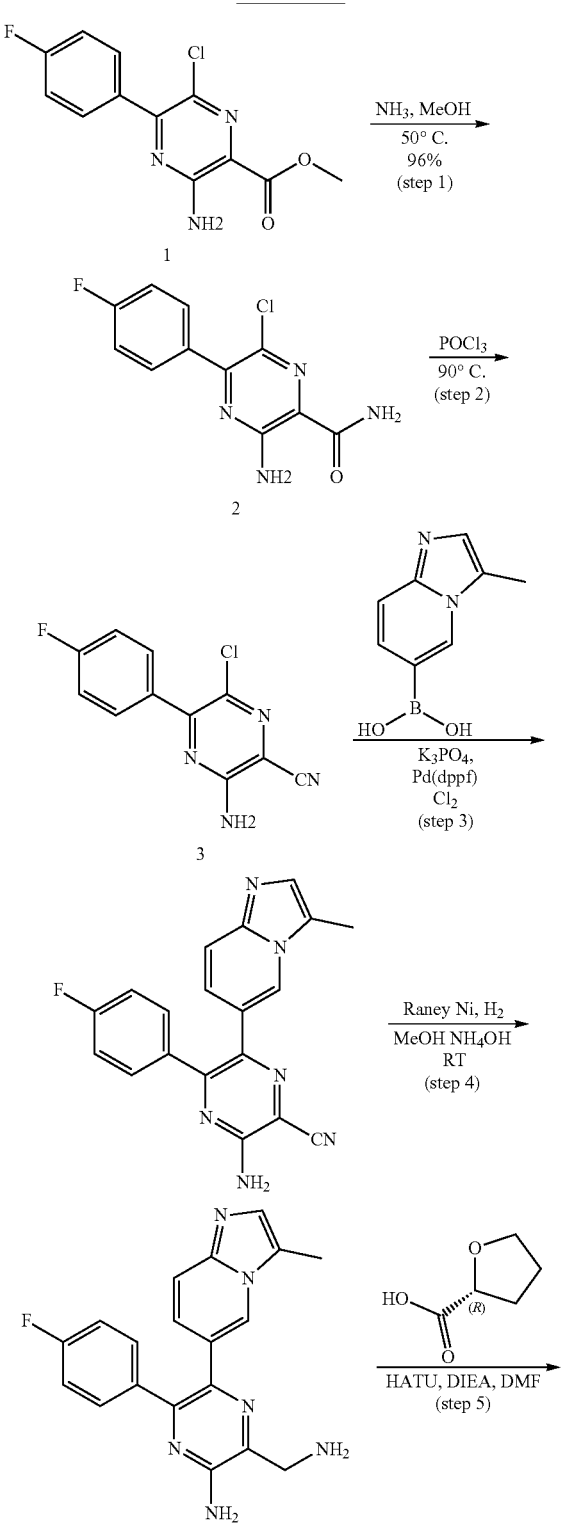

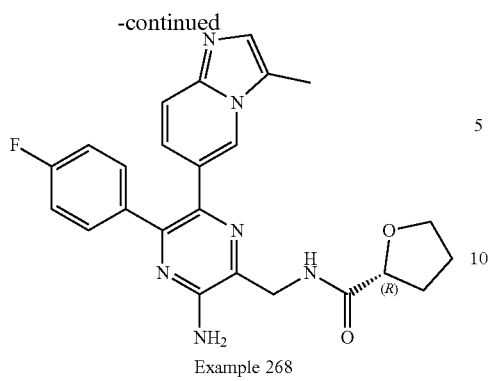

Example 268

Step 1. 3-amino-6-chloro-5-(4-fluorophenyl)pyrazine-2-carboxamide

Into a 50 mL sealed tube were added methyl 3-amino-6-chloro-5-(4-fluorophenyl)pyrazine-2-carboxylate (2.0 g, 7.10 mmol, 1 equiv) and NH3 (g) in MeOH (30 ml, 7.0 mmol/L) at room temperature, heated for 5 h at 50° C., concentrated to afford 3-amino-6-chloro-5-(4-fluorophenyl) pyrazine-2-carboxamide (1.5 g, 79%) as a light yellow solid. LCMS: m/z (ESI), $[M+H]^+=267.0$.

Step 2. 3-amino-6-chloro-5-(4-fluorophenyl)pyrazine-2-carbonitrile

To a stirred solution of $POCl_3$ (20 mL) was added 3-amino-6-chloro-5-(4-fluorophenyl)pyrazine-2-carboxamide (5.0 g, 18.750 mmol, 1 equiv) batchwise at 0° C., stirred for 3 h at 90° C., concentrated. The residue was dissolved into DCM (300 ml), add $NaHCO_3$ (aq.) to PH=8.0. The water layer was extracted with DCM (3×50 ml), the combined organic layer was dried and concentrated to afford 3-amino-6-chloro-5-(4-fluorophenyl)pyrazine-2-carbonitrile (3.5 g, 75%) as a light brown solid. LCMS: m/z (ESI), $[M+H]^+=249.2$.

Step 3. 3-amino-5-(4-fluorophenyl)-6-[3-methylimidazo[1,2-a]pyridin-6-yl]pyrazine-2-carbonitrile To a stirred mixture of 3-amino-6-chloro-5-(4-fluorophenyl)pyrazine-2-carbonitrile (500 mg, 2.01 mmol, 1 equiv), [3-methylimidazo[1,2-a]pyridin-6-yl]boronic acid (530.81 mg, 3.02 mmol, 1.5 equiv) and $Pd(dppf)Cl_2$ (147 mg, 0.20 mmol, 0.1 eq.) in dioxane (15 mL) were added $K_3PO_4$ (854 mg, 4.02 mmol, 2.0 eq.) in $H_2O$ (2.5 mL) in portions at room temperature under nitrogen atmosphere, The resulting mixture was stirred for 2 h at 90° C., concentrated and purified by Prep-TLC (DCM/MeOH=40/1) afford to 3-amino-5-(4-fluorophenyl)-6-[3-methylimidazo[1,2-a]pyridin-6-yl]pyrazine-2-carbonitrile (300 mg, 43%) as a light yellow solid. LCMS: m/z (ESI), $[M+H]^+=345.2$.

Step 4. (2S)—N-[[3-amino-5-(4-fluorophenyl)-6-[3-methylimidazo[1,2-a]pyridin-6-yl]pyrazin-2-yl]methyl]-1-methylpyrrolidine-2-carboxamide To a stirred mixture of 3-amino-5-(4-fluorophenyl)-6-[3-methylimidazo[1,2-a]pyridin-6-yl]pyrazine-2-carbonitrile (500 mg, 1.45 mmol, 1 eq.) and Raney-Ni (62 mg, 0.73 mmol, 0.5 eq.) in ethanol (10 mL) were added $NH_3.H_2O$ (1.0 mL) at room temperature under hydrogen atmosphere, stirred for 2 h at room temperature. The resulting mixture was filtered, the filter cake was washed with MeOH (3×30 mL). The filtrate was concentrated under reduced pressure to afford 3-(aminomethyl)-6-(4-fluorophenyl)-5-[3-methylimidazo[1,2-a]pyridin-6-yl]pyrazin-2-amine (450 mg, 89%) as a light brown solid. $^1$H-NMR (300 MHz, DMSO-$d_6$) δ 2.28 (3H, d), 4.65 (2H, d), 5.47 (1H, t), 6.77 (1H, dd), 6.96 (2H, s), 7.34 (2H, m), 7.63 (1H, dd).

Step 5. (2S)—N-[[3-amino-5-(4-fluorophenyl)-6-[3-methylimidazo[1,2-a]pyridin-6-yl]pyrazin-2-yl]methyl]oxolane-2-carboxamide (Cmpd. 268)

A solution of (2S)-oxolane-2-carboxylic acid (66.66 mg, 0.57 mmol, 2.0 eq.) in DMF (2.0 mL) was treated with HATU (218 mg, 0.57 mmol, 2.0 eq.) for 20 min at room temperature followed by the addition of 3-(aminomethyl)-6-(4-fluorophenyl)-5-[3-methylimidazo[1,2-a]pyridin-6-yl]pyrazin-2-amine (100 mg, 0.29 mmol, 1 eq.), DIEA (111 mg, 0.86 mmol, 3.0 eq.) dropwise at room temperature, stirred for 2 h, quenched by water (20 ml), extracted with DCM (3×20 ml), dried and concentrated then purified by Prep-TLC to afford (2S)—N-[[3-amino-5-(4-fluorophenyl)-6-[3-methylimidazo[1,2-a]pyridin-6-yl]pyrazin-2-yl]m ethyl] oxolane-2-carboxamide (Cmpd. 268) (45.2 mg, 35%) as a white solid. LCMS: m/z (ESI), $[M+H]^+=447.3$. $^1$H-NMR (300 MHz, DMSO-$d_6$) δ 1.80 (2H, q), 1.91 (1H, m), 2.14 (1H, dq), 2.32 (3H, d), 3.78 (1H, q), 3.94 (1H, q), 4.37 (3H, m), 6.69 (2H, s), 6.96 (1H, dd), 7.17 (2H, t), 7.35 (2H, dd), 7.42 (2H, m), 8.06 (1H, d), 8.40 (1H, t).

Example 272. Preparation of 3-amino-5-(3,4-difluorophenyl)-6-[3-methylimidazo[1,2-a]pyridin-6-yl]-N-[[(2R)-1-methylpyrrolidin-2-yl]methyl]pyrazine-2-carboxamide (Cmpd. 272)

SCHEME 118

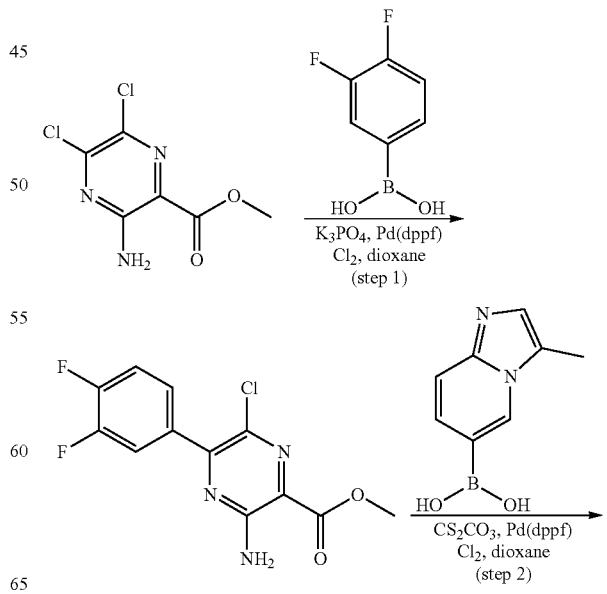

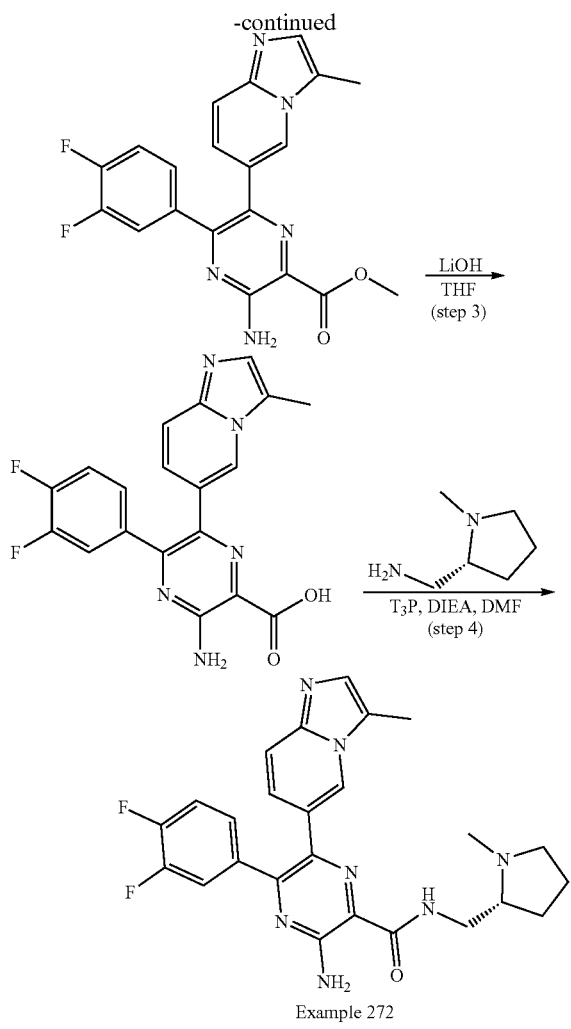

Example 272

Step 1. methyl 3-amino-6-chloro-5-(3,4-difluorophenyl)pyrazine-2-carboxylate To a stirred mixture of methyl 3-amino-5,6-dichloropyrazine-2-carboxylate (2000 mg, 9.008 mmol, 1 equiv) and (3,4-difluorophenyl)boronic acid (1450.87 mg, 9.188 mmol, 1.02 equiv) in dioxane (100 mL) were added $K_3PO_4$ (3824.10 mg, 18.016 mmol, 2 equiv) and Pd(dppf)Cl$_2$ (1318.20 mg, 1.802 mmol, 0.2 equiv) in portions at room temperature under nitrogen atmosphere. The resulting mixture was stirred for 3 h at 70° C. under nitrogen atmosphere. The resulting mixture was concentrated under reduced pressure. The residue was purified by silica gel column chromatography, eluted with PE/EtOAc (5:1) to afford methyl 3-amino-6-chloro-5-(3,4-difluorophenyl)pyrazine-2-carboxylate (1500 mg, 55.57%) as a yellow solid. LCMS: m/z (ESI), [M+H]$^+$=300.2. $^1$H-NMR (400 MHz, DMSO-d$_6$) δ 3.89 (3H, s), 7.54-7.72 (4H, m), 7.78-7.89 (1H, m)

Step 2. 3-amino-5-(3,4-difluorophenyl)-6-[3-methylimidazo[1,2-a]pyridin-6-yl]pyrazine-2-carboxylate To a stirred mixture of methyl 3-amino-6-chloro-5-(3,4-difluorophenyl)pyrazine-2-carboxylate (400 mg, 1.335 mmol, 1 equiv) and [3-methylimidazo[1,2-a]pyridin-6-yl]boronic acid (469.81 mg, 2.670 mmol, 2 equiv) in dioxane (40 mL) were added $CS_2CO_3$ (869.84 mg, 2.670 mmol, 2 equiv) and Pd(dppf)Cl2 (195.34 mg, 0.267 mmol, 0.2 equiv) in portions at room temperature under nitrogen atmosphere. The resulting mixture was stirred for 2 h at 80° C. under nitrogen atmosphere. The resulting mixture was concentrated under reduced pressure. The residue was purified by Prep-TLC (CH$_2$Cl$_2$/MeOH 20:1) to afford methyl 3-amino-5-(3,4-difluorophenyl)-6-[3-methylimidazo[1,2-a]pyridin-6-yl]pyrazine-2-carboxylate (300 mg, 56.84%) as a yellow solid. LCMS: m/z (ESI), [M+H]$^+$=396.3.

Step 3. 3-amino-5-(3,4-difluorophenyl)-6-[3-methylimidazo[1,2-a]pyridin-6-yl]pyrazine-2-carboxylic Acid To a solution of methyl 3-amino-5-(3,4-difluorophenyl)-6-[3-methylimidazo[1,2-a]pyridin-6-yl]pyrazine-2-carboxylate (200 mg, 0.506 mmol, 1 equiv) in THF (20 mL) and methanol (5 mL) was added LiOH (48.46 mg, 2.023 mmol, 4 equiv) at room temperature. The mixture was stirred for 3 h at room temperature under air atmosphere and acidified to pH 6 with HCl (aq.). The resulting solid was collected by filtration and dried under vacuum to afford 3-amino-5-(3,4-difluorophenyl)-6-[3-methylimidazo[1,2-a]pyridin-6-yl]pyrazine-2-carboxylic acid (150 mg, 77.76%) as a yellow solid. The crude product was used in the next step directly without further purification. LCMS: m/z (ESI), [M+H]$^+$=382.2.

Step 4. 3-amino-5-(3,4-difluorophenyl)-6-[3-methylimidazo[1,2-a]pyridin-6-yl]-N-[[(2R)-1-methylpyrrolidin-2-yl]methyl]pyrazine-2-carboxamide (Cmpd. 272)

To a stirred mixture of 3-amino-5-(3,4-difluorophenyl)-6-[3-methylimidazo[1,2-a]pyridin-6-yl]pyrazine-2-carboxylic acid (150 mg, 0.393 mmol, 1 equiv) and 1-[(2R)-1-methylpyrrolidin-2-yl]methanamine (89.83 mg, 0.787 mmol, 2 equiv) in DMF (15 mL) were added DIEA (152.51 mg, 1.180 mmol, 3 equiv) and T$_3$P (500.62 mg, 1.573 mmol, 4 equiv) in portions at room temperature under air atmosphere. The resulting mixture was stirred for 3 h at room temperature under air atmosphere. The resulting mixture was concentrated under reduced pressure. The crude product was purified by Prep-HPLC with the following conditions (Column: XBridge Prep OBD C18 Column 30×150 mm 5 um; Mobile Phase A: 5% ammonia water, Mobile Phase B: ACN; Flow rate: 60 mL/min; Gradient: 36% B to 49% B in 7 min; 254; 220 nm; Rt: 6.83 min) to afford 3-amino-5-(3,4-difluorophenyl)-6-[3-methylimidazo[1,2-a]pyridin-6-yl]-N-[[(2R)-1-methylpyrrolidin-2-yl]methyl]pyrazine-2-carboxamide (Cmpd. 272) (23 mg, 12.25%) as a yellow solid. LCMS: m/z (ESI), [M+H]$^+$=478.3. $^1$H-NMR (400 MHz, DMSO-d$_6$) δ1.53-1.70 (3H, m), 1.78-1.89 (1H, m), 2.15 (1H, q), 2.32 (3H, s), 2.41 (3H, s), 2.41-2.49 (1H, m), 2.95 (1H, dd), 3.25 (1H, dt), 3.50 (1H, ddd,), 6.99 (1H, dd), 7.26 (1H, t), 7.38-7.49 (3H, m), 7.57 (1H, ddd), 7.77 (2H, s), 8.29 (1H, d), 8.66 (1H, t)

Example 273. Preparation of 3-amino-N-[[(3S)-1-(dimethylcarbamoyl)pyrrolidin-3-yl]methyl]-6-[3-methylimidazo[1,2-a]pyridin-6-yl]-5-(1,3-oxazol-2-yl)pyrazine-2-carboxamide (Cmpd. 273)

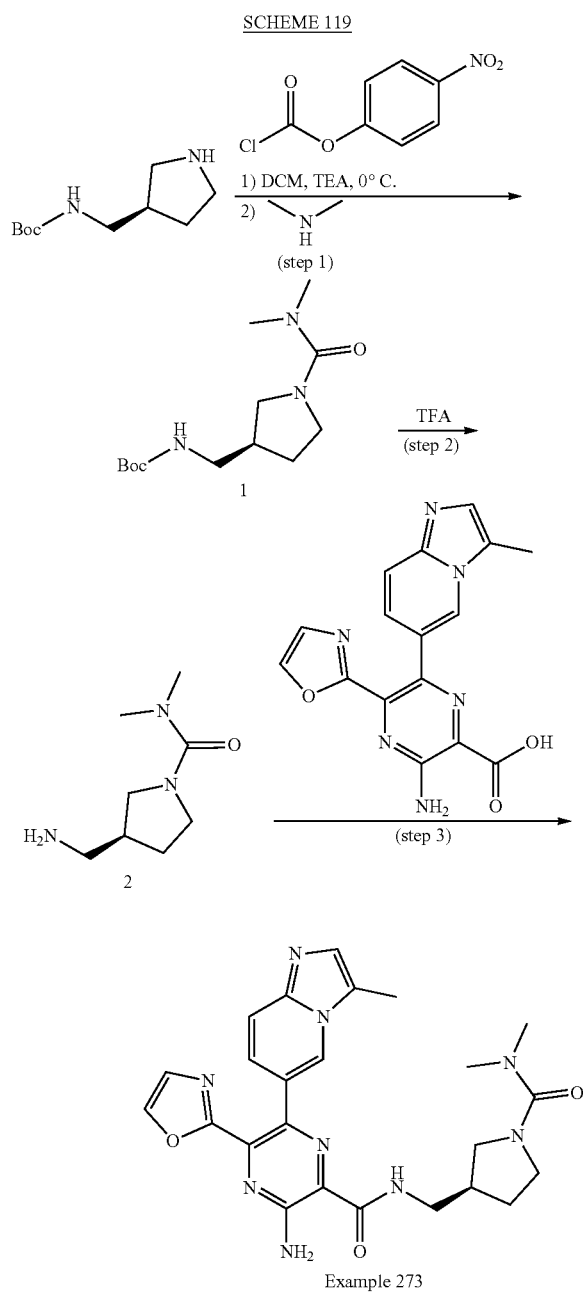

Step 1. tert-butyl N-[[(3S)-1-(dimethylcarbamoyl)pyrrolidin-3-yl]methyl]carbamate A mixture of TEA (854.86 mg, 8.448 mmol, 5 equiv), dimethylamine hydrochloride (206.66 mg, 2.534 mmol, 1.50 equiv), 4-nitrophenyl carbonochloridate (408.67 mg, 2.028 mmol, 1.20 equiv) and tert-butyl N-[[(3R)-pyrrolidin-3-yl]methyl]carbamate hydrochloride (400 mg, 1.690 mmol, 1 equiv) in ACN (20 mL) was stirred for overnight at 70° C. under air atmosphere. The resulting mixture was diluted with water (50 mL) and extracted with EtOAc (3×50 mL). The combined organic layers were washed with brine (3×50 mL), dried over anhydrous $Na_2SO_4$. After filtration, the filtrate was concentrated under reduced pressure. The residue was purified by Prep-TLC (PE/EtOAc 1:1) to afford tert-butyl N-[[(3S)-1-(dimethylcarbamoyl)pyrrolidin-3-yl]methyl]carbamate (370 mg, 80.70%) as a yellow oil. LCMS: m/z (ESI), [M+H]⁺=272.1. ¹H-NMR (300 MHz, Chloroform-d) δ1.47 (9H, s), 1.56-1.70 (1H, m), 1.91-2.04 (1H, m), 2.27-2.43 (1H, m), 2.86 (6H, s), 3.16 (3H, d), 3.46 (3H, q).

Step 2. (3S)-3-(aminomethyl)-N,N-dimethylpyrrolidine-1-carboxamide

A mixture of TFA (2 mL, 26.926 mmol, 42.98 equiv) and tert-butyl N-[[(3S)-1-(dimethylcarbamoyl)pyrrolidin-3-yl]methyl]carbamate (170 mg, 0.626 mmol, 1 equiv) in DCM (5 mL) was stirred for 1 h at room temperature under air atmosphere. Desired product could be detected by LCMS. The resulting mixture was concentrated under reduced pressure to afford (3S)-3-(aminomethyl)-N,N-dimethylpyrrolidine-1-carboxamide (100 mg, 93.21%) as a colorless oil. LCMS: m/z ¹H-NMR (300 MHz, Chloroform-d) δ 1.71 (1H, s), 2.14 (1H, s), 2.59 (1H, s), 2.90 (6H, s), 3.00 (1H, s), 3.18 (1H, s), 3.36 (1H, s), 3.50 (3H, q)

Step 3. 3-amino-N-[[(3S)-1-(dimethylcarbamoyl)pyrrolidin-3-yl]methyl]-6-[3-methylimidazo[1,2-a]pyridin-6-yl]-5-(1,3-oxazol-2-yl)pyrazine-2-carboxamide (Cmpd. 273)

A mixture of DIEA (184.46 mg, 1.427 mmol, 6 equiv), $T_3P$ (227.06 mg, 0.714 mmol, 3 equiv), (3S)-3-(aminomethyl)-N,N-dimethylpyrrolidine-1-carboxamide (81.47 mg, 0.476 mmol, 2 equiv) and 3-amino-6-[3-methylimidazo[1,2-a]pyridin-6-yl]-5-(1,3-oxazol-2-yl)pyrazine-2-carboxylic acid (80 mg, 0.238 mmol, 1 equiv) in DMF (3 mL) was stirred for overnight at room temperature under air atmosphere. The resulting mixture was diluted with water (30 mL) and sat. $NaHCO_3$ (30 mL), extracted with $CH_2Cl_2$ (3×40 mL). The combined organic layers were dried over anhydrous $Na_2SO_4$. After filtration, the filtrate was concentrated under reduced pressure. The residue was purified by Prep-TLC ($CH_2Cl_2$/MeOH 12:1) to afford crude product. The crude product (100 mg) was purified by Prep-HPLC with the following conditions (Column: Kinetex EVO C18 Column 30*150, 5 um; Mobile Phase A: Mobile Phase B: ACN; Flow rate: 60 mL/min; Gradient: 15% B to 35% B in 7 min; 254; 220 nm; Rt: 6.93 min) to afford 3-amino-N-[[(3S)-1-(dimethylcarbamoyl)pyrrolidin-3-yl]methyl]-6-[3-methylimidazo[1,2-a]pyridin-6-yl]-5-(1,3-oxazol-2-yl)pyrazine-2-carboxamide (Cmpd. 273) (20 mg, 17.00%) as a yellow solid. LCMS: m/z (ESI), [M+H]⁺=490.4. ¹H NMR (300 MHz, DMSO-$d_6$) δ 1.60 (1H, d), 1.82-1.92 (1H, m), 2.44 (4H, d), 2.70 (6H, s), 3.11 (1H, d), 3.23-3.35 (4H, m), 3.37 (1H, s), 7.24 (1H, d), 7.38 (2H, d), 7.49 (1H, d), 7.90 (1H, s), 8.28 (1H, d), 8.32-8.39 (1H, m), 8.98 (1H, t)

Example 276. Preparation of 3-amino-6-[3-methyl-imidazo[1,2-a]pyridin-6-yl]-N-[[6-(morpholin-4-yl)pyridin-2-yl]methyl]-5-(1,3-oxazol-2-yl)pyrazine-2-carboxamide (Cmpd. 276)

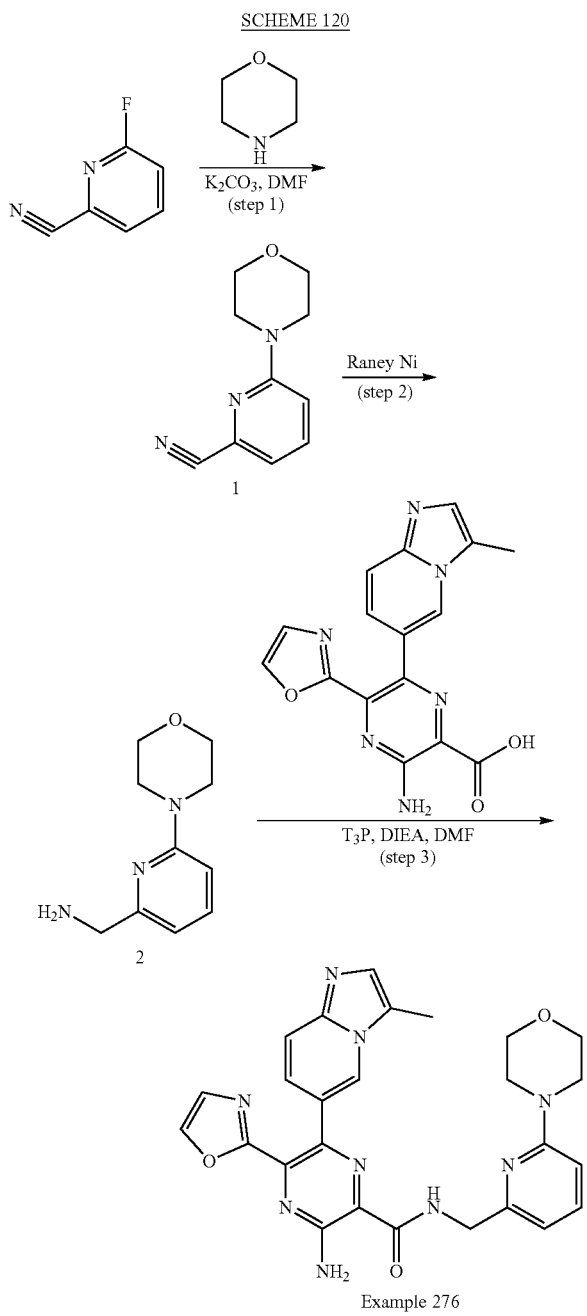

Example 276

Step 1. 6-(morpholin-4-yl)pyridine-2-carbonitrile

Into a 40 mL round-bottom flask were added 6-fluoropyridine-2-carbonitrile (1 g, 8.190 mmol, 1 equiv), morpholine (1.43 g, 0.016 mmol, 2 equiv) and $K_2CO_3$ (2.26 g, 0.016 mmol, 2 equiv) in DMF (15 mL) at room temperature. The resulting mixture was stirred for 6 hs at 80° C. The reaction was quenched with Water at room temperature. The precipitated solids were collected by filtration and washed with water (1×100 mL), dried under vacuum to afford 6-(morpholin-4-yl)pyridine-2-carbonitrile (1.5 g, 96.79%) as a white solid. LCMS: m/z (ESI), $[M+H]^+$=190.3. $^1$H-NMR (300 MHz, DMSO-$d_6$) δ 3.46 (4H, dd), 3.66 (4H, dd), 7.18 (2H, m), 7.70 (1H, dd).

Step 2. 1-[6-(morpholin-4-yl)pyridin-2-yl]methanamine

To a solution of 6-(morpholin-4-yl)pyridine-2-carbonitrile (200 mg, 1.057 mmol, 1 equiv) in MeOH (15 mL) and $NH_3.H_2O$ (1 mL) was added Raney Ni (271.67 mg, 3.171 mmol, 3 equiv) in portions at room temperature. The resulting mixture was stirred for 2 hs at room temperature under hydrogen atmosphere. The resulting mixture was filtered, the filter cake was washed with MeOH (3×10 mL). The filtrate was concentrated under reduced pressure to afford 1-[6-(morpholin-4-yl)pyridin-2-yl]methanamine (150 mg, 73.44%) as a purple oil which was used in the next step directly without further purification. LCMS: m/z (ESI), $[M+H]^+$=194.3.

Step 3. 3-amino-6-[3-methylimidazo[1,2-a]pyridin-6-yl]-N-[[6-(morpholin-4-yl)pyridin-2-yl]methyl]-5-(1,3-oxazol-2-yl)pyrazine-2-carboxamide (Cmpd. 276)

To a solution of 1-[6-(morpholin-4-yl)pyridin-2-yl]methanamine (172.39 mg, 0.892 mmol, 2 equiv) and 3-amino-6-[3-methylimidazo[1,2-a]pyridin-6-yl]-5-(1,3-oxazol-2-yl)pyrazine-2-carboxylic acid (150 mg, 0.446 mmol, 1 equiv) in DMF (15 mL) were added $T_3P$ (283.83 mg, 0.892 mmol, 2 equiv) and DIEA (115.29 mg, 0.892 mmol, 2 equiv) dropwise at room temperature. The resulting mixture was stirred for 30 min at room temperature under air atmosphere. The resulting mixture was concentrated under reduced pressure. The crude product was purified by Prep-HPLC with the following conditions (Column: XBridge Prep OBD C18 Column 19*250 mm, 5 um; Mobile Phase A: Water (10 mMOL/L NH4HCO3), Mobile Phase B: ACN; Flow rate: 20 mL/min; Gradient: 31% B to 50% B in 8 min; 220/254 nm; Rt: 8.15 min) to afford 3-amino-6-[3-methylimidazo[1,2-a]pyridin-6-yl]-N-[[6-(morpholin-4-yl)pyridin-2-yl]methyl]-5-(1,3-oxazol-2-yl)pyrazine-2-carboxamide (Cmpd. 276) (60 mg, 26.30%) as a yellow solid. LCMS: m/z (ESI), $[M+H]^+$=512.4. $^1$H NMR: (300 MHz, DMSO-$d_6$) δ 2.40 (3H, d), 3.35 (4H, s), 3.47 (4H, dd), 4.47 (2H, d), 6.65 (2H, t), 7.31 (3H, m), 7.49 (2H, m), 7.90 (2H, s), 8.26 (1H, d), 8.33 (1H, m), 9.33 (1H, t).

Example 278. Preparation of (R)—N-((3-amino-5-(3-fluorophenyl)-6-(3-methylimidazo[1,2-a]pyridin-6-yl)pyrazin-2-yl)methyl)-1-methylpyrrolidine-2-carboxamide (Cmpd. 278)

SCHEME 121

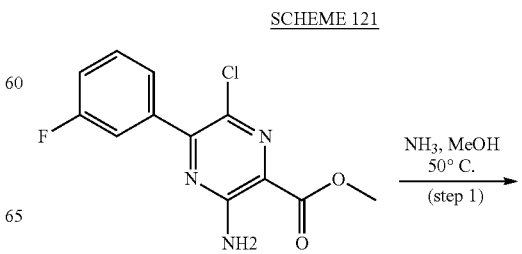

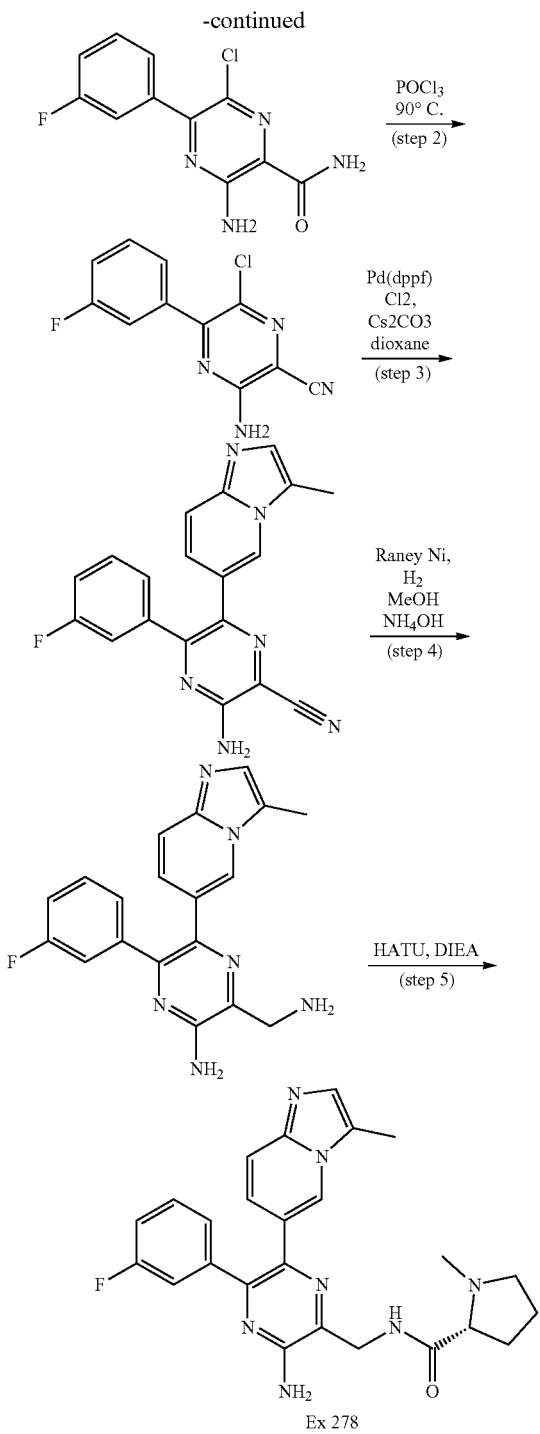

[M+H]⁺=267.0. 1H NMR (400 MHz, Chloroform-d) δ 7.21 (1H, m), 7.42-7.58 (2H, m), 7.62 (1H, m).

Step 2. 3-amino-6-chloro-5-(3-fluorophenyl)pyrazine-2-carbonitrile

To a stirred solution of phosphoryl trichloride (2 mL) was added 3-amino-6-chloro-5-(3-fluorophenyl)pyrazine-2-carboxamide (30 mg) in portions at room temperature. The resulting mixture was stirred for 3h at 90° C. C. The resulting mixture was concentrated under reduced pressure and diluted with DCM (20 mL). The reaction was quenched with sat. NaHCO₃ (aq.) at room temperature. The resulting mixture was extracted with CH₂Cl₂ (2×30 mL). The combined organic layers were dried over anhydrous Na2SO4. After filtration, the filtrate was concentrated under reduced pressure. The residue was purified by Prep-TLC (CH₂Cl₂/EtOAc 5:1) to afford 3-amino-6-chloro-5-(3-fluorophenyl)pyrazine-2-carbonitrile (400 mg) as a yellow solid. LCMS: m/z (ESI), [M+H]⁺=249.0. ¹H-NMR (300 MHz, Chloroform-d) δ 5.32 (2H, d), 7.21 (1H, m), 7.42-7.56 (2H, m), 7.61 (1H, m).

Step 3. 3-amino-5-(3-fluorophenyl)-6-(3-methylimidazo[1,2-a]pyridin-6-yl)pyrazine-2-carbonitrile To a stirred mixture of 3-amino-6-chloro-5-(3-fluorophenyl)pyrazine-2-carbonitrile (350 mg, 1.408 mmol, 1 equiv) and [3-methylimidazo[1,2-a]pyridin-6-yl]boronic acid (371.56 mg, 2.111 mmol, 1.50 equiv) in dioxane (20 mL) and H₂O (2 mL) were added Cs₂CO₃ (1375.87 mg, 4.223 mmol, 3 equiv) and Pd(dppf)Cl₂ (205.99 mg, 0.282 mmol, 0.2 equiv) in portions at room temperature under nitrogen atmosphere. The resulting mixture was stirred for 3 h at 90° C. under nitrogen atmosphere. The resulting mixture was filtered, the filter cake was washed with CH₂Cl₂ (1×10 mL). The filtrate was concentrated under reduced pressure. The residue was purified by Prep-TLC (CH₂Cl₂/MeOH 40:1) to afford 3-amino-5-(3-fluorophenyl)-6-[3-methylimidazo[1,2-a]pyridin-6-yl]pyrazine-2-carbonitrile (300 mg, 61.89%) as a yellow solid. LCMS: m/z (ESI), [M+H]⁺=345.2.

Step 4. 3-(aminomethyl)-6-(3-fluorophenyl)-5-(3-methylimidazo[1,2-a]pyridin-6-yl)pyrazin-2-amine To a stirred solution of 3-amino-5-(3-fluorophenyl)-6-[3-methylimidazo[1,2-a]pyridin-6-yl]pyrazine-2-carbonitrile (20 mg, 0.058 mmol, 1 equiv) and NH₃.H₂O (4.07 mg, 0.116 mmol, 2.00 equiv) in EtOH (2 mL) was added Raney Ni (9.95 mg, 0.116 mmol, 2.00 equiv) in portions at room temperature under nitrogen atmosphere. The resulting mixture was stirred for 2h at room temperature under hydrogen atmosphere. The resulting mixture was filtered, the filter cake was washed with EtOH (1×10 mL). The filtrate was concentrated under reduced pressure to afford 3-(aminomethyl)-6-(3-fluorophenyl)-5-[3-methylimidazo[1,2-a]pyridin-6-yl]pyrazin-2-amine (180 mg, 71.17%) as a Brown yellow solid. LCMS: m/z (ESI), [M+H]⁺=349.3.

Step 5. (R)—N-((3-amino-5-(3-fluorophenyl)-6-(3-methylimidazo[1,2-a]pyridin-6-yl)pyrazin-2-yl)methyl)-1-methylpyrrolidine-2-carboxamide (Cmpd. 278)

To a stirred mixture of (2R)-1-methylpyrrolidine-2-carboxylic acid (36.70 mg, 0.284 mmol, 1.10 equiv) in DMF (10 mL) was added HATU (196.45 mg, 0.517 mmol, 2

Step 1. Preparation of 3-amino-6-chloro-5-(3-fluorophenyl)pyrazine-2-carboxamide To a stirred solution of 30% NH₃ (g) in MeOH (20 mL) was added methyl 3-amino-6-chloro-5-(3-fluorophenyl)pyrazine-2-carboxylate (900 mg) in portions at room temperature. The resulting mixture was stirred for 4 h at 50° C. C. The resulting mixture was concentrated under vacuum to afford 3-amino-6-chloro-5-(3-fluorophenyl)pyrazine-2-carboxamide (600 mg) as a yellow solid. LCMS: m/z (ESI), equiv) and DIEA (133.55 mg, 1.033 mmol, 4 equiv) in portions at room temperature. The resulting mixture was stirred for 10 min at room temperature. To this stirred solution was added 3-(aminomethyl)-6-(3-fluorophenyl)-5-[3-methylimidazo[1,2-a]pyridin-6-yl]pyrazin-2-amine (90 mg, 0.258 mmol, 1 equiv) in portions at room temperature. The resulting mixture was stirred for 3h at room temperature. The resulting mixture was concentrated under reduced pressure. The crude product (mg) was purified by Prep-HPLC with the following conditions (Column: XBridge Prep OBD C18 Column 30×150 mm 5 um; Mobile Phase A (5% NH$_3$ in water: Mobile Phase B: ACN; Flow rate: 60 mL/min; Gradient: 31% B to 43% B in 7 min; 254; 220 nm; Rt: 6.48 min) to afford (R)—N-((3-amino-5-(3-fluorophenyl)-6-(3-methylimidazo[1,2-a]pyridin-6-yl)pyrazin-2-yl)methyl)-1-methylpyrrolidine-2-carboxamide (Cmpd. 278) (26 mg, 21.90%) as a white solid. LCMS: m/z (ESI), [M+H]$^+$=460.3. 1H NMR (400 MHz, DMSO-d$_6$) δ 1.40-1.92 (3H, m), 1.94-2.19 (1H, m), 2.22-2.39 (7H, m), 2.81 (1H, dd), 3.05 (1H, dd), 4.26-4.53 (2H, m), 6.73 (2H, s), 7.02 (1H, dd), 7.09-7.51 (6H, m), 7.91-8.18 (1H, m), 8.46 (1H, t).

Examples 279/280. Preparation of 3-amino-N-((3-methoxytetrahydrofuran-2-yl) methyl)-6-(3-methyl-imidazo[1,2-a]pyridin-6-yl)-5-(oxazol-2-yl)pyrazine-2-carboxamide (Cmpd. 279/280)

SCHEME 122

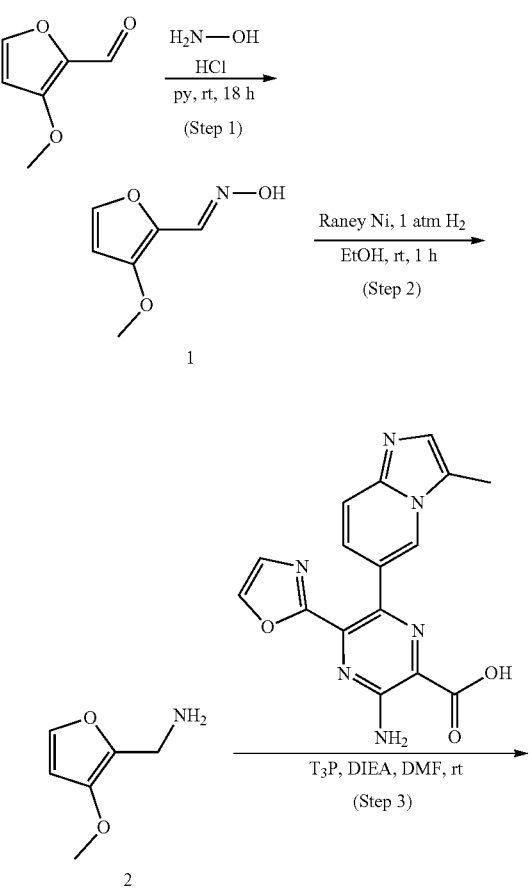

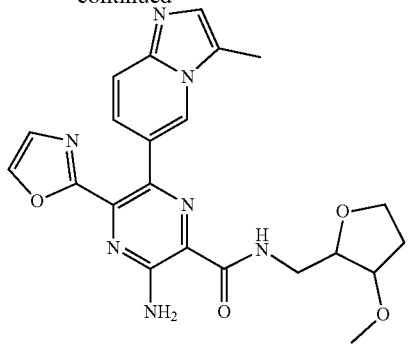

Example 279

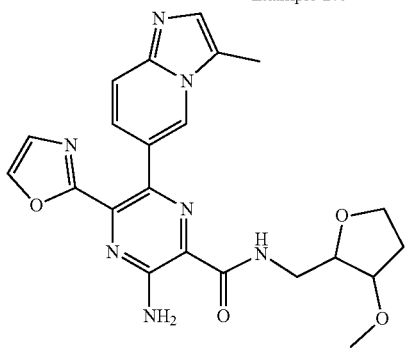

Example 280

Step 1. 3-methoxyfuran-2-carbaldehyde oxime

The mixture of 3-methoxyfuran-2-carbaldehyde (252 mg, 1.998 mmol, 1 equiv) and hydroxylamine hydrochloride (210 mg, 3.022 mmol, 1.51 equiv) in pyridine (4 mL) was stirred at room temperature for 18 h. After concentrated to dryness, the residue was purified by column (PE/EA=2/1) to afford N-[(3-methoxyfuran-2-yl)methyl-idene]hydroxylamine (200 mg, 70.9%) as a white solid. LCMS: m/z (ESI), [M+H]$^+$=142.2.

Step 2. (3-methoxytetrahydrofuran-2-yl)methanamine

The mixture of N-[(3-methoxyfuran-2-yl)methylidene]hydroxylamine (460 mg, 3.26 mmol, 1 equiv) and Raney Ni (300 mg, 3.502 mmol, 1.07 equiv) in ethanol (70 mL) was hydrogenated under 1 atm H$_2$ at room temperature for 1 h. After filtered through celite, the filtrate was concentrated to dryness under vacuum and the residue was used directly for next step. LCMS: m/z (ESI), [M+H]$^+$=132.2.

Step 3. 3-amino-N-((3-methoxytetrahydrofuran-2-yl)methyl)-6-(3-methylimidazo[1,2-a]pyridin-6-yl)-5-(oxazol-2-yl)pyrazine-2-carboxamide To a mixture of 3-amino-6-[3-methylimidazo[1,2-a]pyridin-6-yl]-5-(1,3-oxazol-2-yl)-pyrazine-2-carboxylic acid (313 mg, 0.931 mmol, 1 equiv) and 1-(3-methoxyoxolan-2-yl)methanamine (366 mg, 2.790 mmol, 3.00 equiv) in 5 mL of DMF were added DIEA (1.62 mL, 9.300 mmol, 9.99 equiv) and 50% wt T$_3$P solution in ethyl acetate (1.77 g, 2.793 mmol, 2.99 equiv). The mixture stirred at room temperature for 3 h. The reaction was purified by Prep-HPLC (Column: XBridge Prep OBD C18 Column 30×150 mm 5 um; Mobile Phase A: Water (0.05% NH$_3$H$_2$O), Mobile Phase B: ACN; Flow rate: 60 mL/min; Gradient: 23% B to 33% B in 7 min; 254; 220 nm; Rt: 6.45 min) and chiral separation (Column: CHIRALPAK IG, 20×250 mm, 5 um; Mobile Phase A: Hex:DCM=3:1 (10 mM NH$_3$-MeOH)-HPLC, Mobile Phase B: EtOH-HPLC; Flow rate: 20 mL/min; Gradient: 30 B to 30 B in 50 min; 254/220 nm; RT1: 15.377; RT2: 24.388) to afford 3-amino-N-((3-methoxytetrahydrofuran-2-yl)methyl)-6-(3-methylimidazo[1,2-a]pyridin-6-yl)-5-(oxazol-2-yl)pyrazine-2-carboxamide (Cmpd. 279) (15 mg, 3.5%) and 3-amino-N-((3-methoxytetrahydrofuran-2-yl)methyl)-6-(3-methylimidazo[1,2-a]pyridin-6-yl)-5-(oxazol-2-yl)pyrazine-2-carboxamide (Cmpd. 280) (15 mg, 3.5%) as yellow solid. (Cmpd. 279) LCMS: m/z (ESI), [M+H]$^+$=450.2. $^1$H-NMR (300 MHz, DMSO-d$_6$) δ 1.93-2.00 (2H, m), 2.40 (3H, s), 3.25 (3H, s), 3.41-3.48 (1H, m), 3.54-3.67 (2H, m), 3.75-3.83 (1H, m), 3.91-3.99 (2H, m), 7.20-7.23 (1H, d), 7.34 (1H, s), 7.38 (1H, s), 7.47-7.50 (1H, d), 7.89 (2H, brs), 8.25 (1H, s), 8.32 (1H, s), 8.66-8.70 (1H, t). (Cmpd. 280) LCMS: m/z (ESI), [M+H]$^+$=450.1. $^1$H-NMR (300 MHz, DMSO-d$_6$) δ 1.93-1.99 (2H, m), 2.40 (3H, s), 3.24 (3H, s), 3.41-3.48 (1H, m), 3.54-3.66 (2H, m), 3.75-3.83 (1H, m), 3.91-3.98 (2H, m), 7.20-7.23 (1H, d), 7.34 (1H, s), 7.38 (1H, s), 7.47-7.50 (1H, d), 7.89 (2H, brs), 8.25 (1H, s), 8.32 (1H, s), 8.66-8.70 (1H, t).

Example 281. Preparation of 3-[(3-amino-6-[3-methylimidazo[1,2-a]pyridin-6-yl]-5-(1,3-oxazol-2-yl)pyrazin-2-yl)formamido]-N,N,2,2-tetramethylpropanamide (Cmpd. 281)

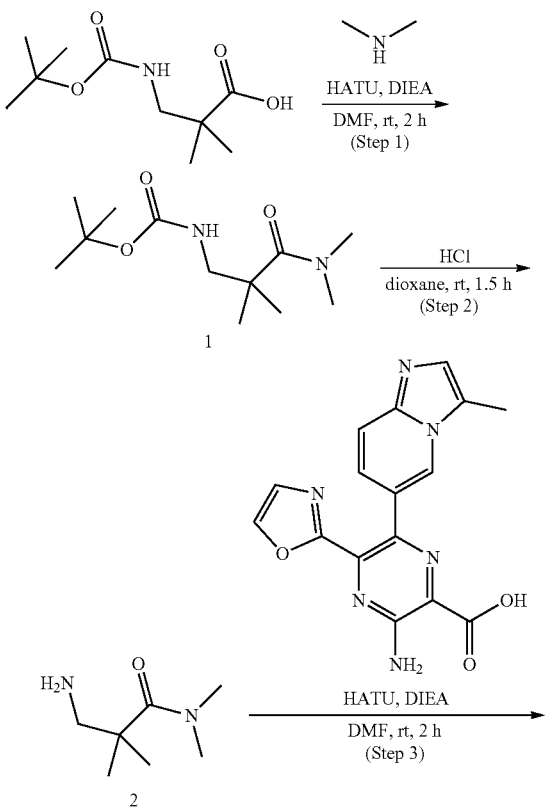

SCHEME 123

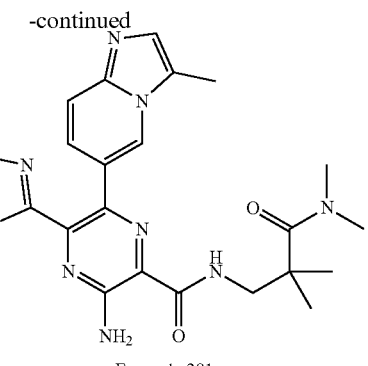

Example 281

Step 1 2-(5-bromo-2-oxo-1,2-dihydropyridin-1-yl)propanenitrile

To a stirred mixture of 3-[[(tert-butoxy)carbonyl]amino]-2,2-dimethylpropanoic acid (250 mg, 1.151 mmol, 1 equiv), HATU (525.02 mg, 1.381 mmol, 1.2 equiv) and DIEA (743.58 mg, 5.753 mmol, 5 equiv) in DMF (5 mL) was added a solution of dimethylamine (1.15 mL, 2.301 mmol, 2 equiv) dropwise at 0° C. followed by stirring for 2 h at 0° C. The resulting mixture was diluted with EtOAc (30 mL). The combined organic layers were washed with water (3×10 mL), dried over anhydrous Na$_2$SO$_4$. After filtration, the filtrate was concentrated under reduced pressure to afford tert-butyl N-[2-(dimethylcarbamoyl)-2,2-dimethylethyl]carbamate (200 mg, 71.1%) as a yellow solid. LCMS: m/z (ESI), [M+H]$^+$=245.4.

Step 2. 3-amino-N,N,2,2-tetramethylpropanamide Into a 6 mL vial were added tert-butyl N-[2-(dimethylcarbamoyl)-2,2-dimethylethyl]carbamate (190 mg, 0.778 mmol, 1 equiv), and a solution of hydrogen chloride in dioxane (4 M, 5 mL) and dioxane (3 mL) at room temperature. Then the mixture was stirred at room temperature for 1.5 h. And the reaction mixture was concentrated to afford 3-amino-N,N,2,2-tetramethylpropanamide (110 mg, 98.0%) as a yellow solid. LCMS: m/z (ESI), [M+H]$^+$=145.4.

Step 3. 3-[(3-amino-6-[3-methylimidazo[1,2-a]pyridin-6-yl]-5-(1,3-oxazol-2-yl)pyrazin-2-yl)formamido]-N,N,2,2-tetramethylpropanamide Into a 6 mL vial were added 3-amino-N,N,2,2-tetramethylpropanamide (110 mg, 0.72 mmol, 2 equiv), and 3-amino-6-[3-methylimidazo[1,2-a]pyridin-6-yl]-5-(1,3-oxazol-2-yl)pyrazine-2-carboxylic acid (120 mg, 0.36 mmol, 1 equiv), HATU (164 mg, 0.432 mmol, 1.2 equiv), DIEA (140 mg, 1.08 mmol, 3 equiv) and DMF (1.5 mL) at room temperature. Then the mixture was stirred at room temperature for 2 h. The resulting mixture was diluted with EtOAc (20 mL). The residue were washed with brine (3×10 mL), dried over anhydrous Na$_2$SO$_4$. After filtration, the filtrate was concentrated under reduced pressure. The crude product was purified by Prep-HPLC with the following conditions (Column: X Bridge Prep OBD C18 Column 30×150 mm 5 um; Mobile Phase A: Water (0.05% NH$_3$H$_2$O), Mobile Phase B: ACN; Flow rate: 60 mL/min; Gradient: 25% B to 40% B in 7 min; 254/220 nm; t$_R$: 5.77 min) to afford 3-[(3-amino-6-[3-methylimidazo[1,2-a]pyridin-6-yl]-5-(1,3-oxazol-2-yl)pyrazin-2-yl)formamido]-N,N,2,2-tetramethylpropanamide (10 mg, 6.0%) as a yellow solid. LCMS: m/z (ESI), [M+H]+= 463.3. ¹H-NMR (400 MHz, DMSO-d₆) δ 1.26 (6H, s), 2.47 (3H, d), 2.95 (6H, s), 3.44 (2H, d), 7.11 (1H, dd), 7.38 (1H, d), 7.41 (1H, d), 7.49 (1H, dd), 7.91 (2H, s), 8.28 (1H, d), 8.35 (1H, dd), 8.79 (1H, t).

Example 284. Preparation of 3-amino-N-[(6-[6-methyl-2,6-diazaspiro[3.3]heptan-2-yl]pyridin-2-yl)methyl]-6-[3-methylimidazo[1,2-a]pyridin-6-yl]-5-(1,3-oxazol-2-yl)pyrazine-2-carboxamide (Cmpd. 284)

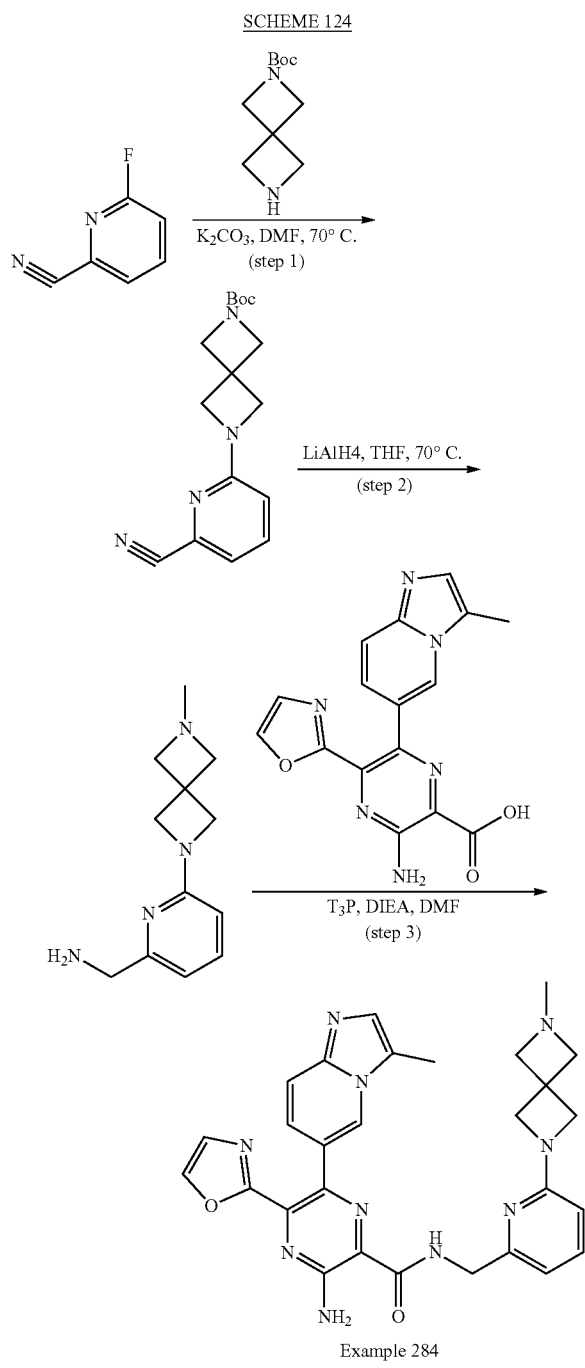

SCHEME 124

Example 284

Step 1. tert-butyl 6-(6-cyanopyridin-2-yl)-2,6-diazaspiro[3.3]heptane-2-carboxylate To a mixture of 6-fluoropyridin-2-carbonitrile (1 g, 8.190 mmol, 1 equiv) and tert-butyl 2,6-diazaspiro[3.3]heptane-2-carboxylate (3.25 g, 16.380 mmol, 2 equiv) in DMF (25 mL) were added K2CO3 (2.26 g, 16.380 mmol, 2 equiv) in portions at room temperature. The resulting mixture was stirred for 3h at 50° C. under air atmosphere. The resulting mixture was concentrated under reduced pressure. The residue was purified by silica gel column chromatography, eluted with PE/EtOAc (2:1) to afford tert-butyl 6-(6-cyanopyridin-2-yl)-2,6-diazaspiro[3.3]heptane-2-carboxylate (1.2 g, 48.78%) as a white solid. LCMS: m/z (ESI), [M+H]+= 301.2. ¹H-NMR: (300 MHz, DMSO-d₆) δ 1.38 (9H, s), 4.03 (4H, s), 4.12 (4H, s), 6.68 (1H, dd), 7.20 (1H, dd), 7.67 (1H, dd).

Step 2. 1-(6-[6-methyl-2,6-diazaspiro[3.3]heptan-2-yl]pyridin-2-yl)methanamine

To a solution of tert-butyl 6-(6-cyanopyridin-2-yl)-2,6-diazaspiro[3.3]heptane-2-carboxylate (300 mg, 0.999 mmol, 1 equiv) in THF (15 mL) was added LiAlH₄ (189.54 mg, 4.994 mmol, 5 equiv) in portions at 0° C. C under air atmosphere. The mixture was stirred for 1 h at room temperature. The resulting mixture was stirred for 3h at 70° C. under air atmosphere. The reaction was quenched with Water/Ice at room temperature and extracted with EtOAc (3×50 mL). The combined organic layers were dried over anhydrous Na₂SO₄. After filtration, the filtrate was concentrated under reduced pressure to afford 1-(6-[6-methyl-2,6-diazaspiro[3.3]heptan-2-yl]pyridin-2-yl)methanamine (100 mg, 45.86%) as a yellow oil. ¹H-NMR: (300 MHz, DMSO-d₆) δ 1.30 (2H, d), 2.18 (3H, s), 3.10 (4H, d), 3.60 (2H, s), 3.94 (4H, s), 6.19 (1H, d), 6.67 (1H, d), 7.45 (1H, t).

Step 3. 3-amino-N-[(6-[6-methyl-2,6-diazaspiro[3.3]heptan-2-yl]pyridin-2-yl)methyl]-6-[3-methylimidazo[1,2-a]pyridin-6-yl]-5-(1,3-oxazol-2-yl)pyrazine-2-carboxamide (Cmpd. 284)

To a solution of 3-amino-6-[3-methylimidazo[1,2-a]pyridin-6-yl]-5-(1,3-oxazol-2-yl)pyrazine-2-carboxylic acid (90 mg, 0.268 mmol, 1 equiv) and 1-(6-[6-methyl-2,6-diazaspiro[3.3]heptan-2-yl]pyridin-2-yl)methanamine (116.84 mg, 0.535 mmol, 2 equiv) in DMF (10 mL) were added T3P (170.30 mg, 0.535 mmol, 2 equiv) and DIEA (69.17 mg, 0.535 mmol, 2 equiv) dropwise at room temperature. The resulting mixture was stirred for 30 min at room temperature under air atmosphere. The resulting mixture was concentrated under reduced pressure. The crude product was purified by Prep-HPLC with the following conditions (Column: XBridge Prep OBD C18 Column 19*250 mm, 5 um; Mobile Phase A: Water (0.05% NH3H2O), Mobile Phase B: ACN; Flow rate: 20 mL/min; Gradient: 29% B to 38% B in 8 min; 254; 220 nm; Rt: 6.95 min) to afford 3-amino-N-[(6-[6-methyl-2,6-diazaspiro[3.3]heptan-2-yl]pyridin-2-yl)methyl]-6-[3-methylimidazo[1,2-a]pyridin-6-yl]-5-(1,3-oxazol-2-yl)pyrazine-2-carboxamide (Cmpd. 284) (30 mg, 20.89%) as a yellow solid. LCMS: m/z (ESI), [M+H]+= 537.4. ¹H NMR: (300 MHz, DMSO-d₆) δ 2.14 (3H, s), 2.40 (3H, d), 3.09 (4H, s), 3.84 (4H, s), 4.43 (2H, d), 6.21 (1H, d), 6.58 (1H, d), 7.26 (1H, dd), 7.34 (1H, d), 7.39 (1H, s), 7.45 (1H, m), 7.52 (1H, dd), 7.89 (2H, s), 8.25 (1H, d), 8.32 (1H, s), 9.34 (1H, s).

Example 285. 3-amino-N-([6-[(3R)-3,4-dimethylpiperazin-1-yl]pyridin-2-yl]methyl)-6-[3-methylimidazo[1,2-a]pyridin-6-yl]-5-(1,3-oxazol-2-yl)pyrazine-2-carboxamide (Cmpd. 285)

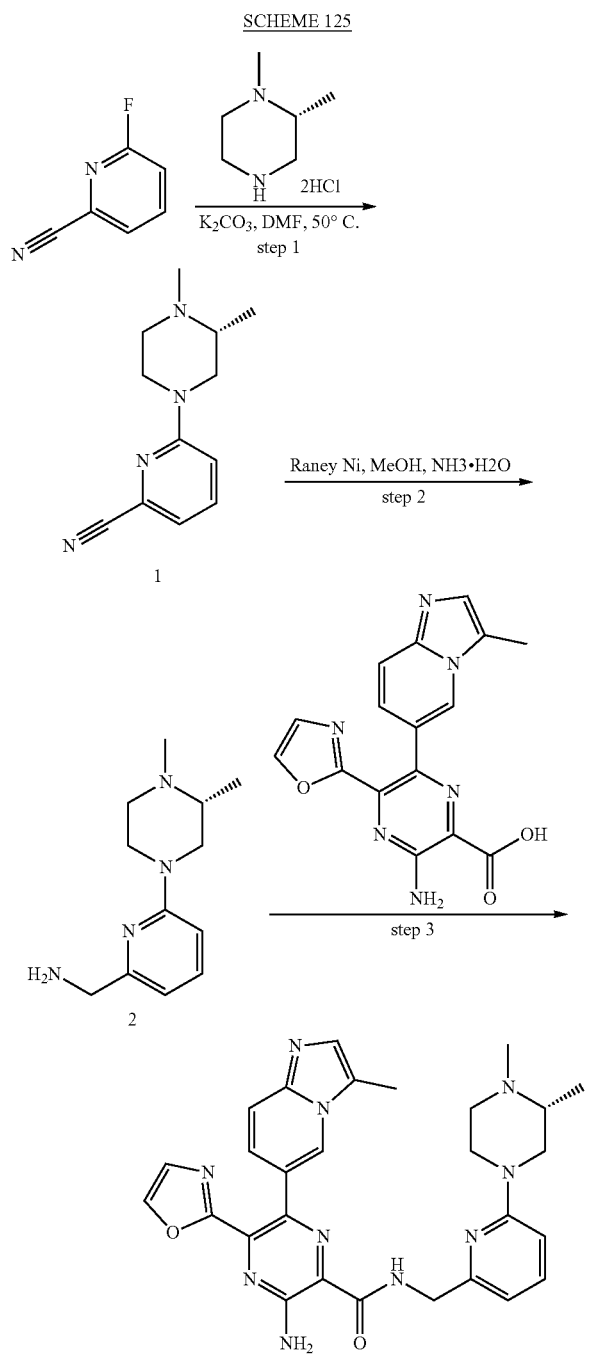

Step 1. 6-[(3R)-3,4-dimethylpiperazin-1-yl]pyridine-2-carbonitrile

Into a 40 mL sealed tube were added (2R)-1,2-dimethylpiperazine (607.9 mg, 5.32 mmol, 1.3 equiv), 6-fluoropyridine-2-carbonitrile (500 mg, 4.095 mmol, 1 equiv), K₂CO3 (1131.89 mg, 8.190 mmol, 2 equiv) and DMF (10 mL) at room temperature. The resulting mixture was stirred for 3 hours at 50° C. The reaction was quenched by the addition of sat. NaCl (aq.) (250 mL) at room temperature. The resulting mixture was extracted with EtOAc (2×125 mL). The combined organic layers were washed with sat. NaCl (aq.) (250 mL), dried over anhydrous Na2SO4. After filtration, the filtrate was concentrated under reduced pressure. The residue was purified by Prep-TLC (CH₂Cl₂/MeOH 30:1) to afford 6-[(3R)-3,4-dimethylpiperazin-1-yl]pyridine-2-carbonitrile (540 mg, 60.97%) as a colorless oil. LCMS: m/z (ESI), [M+H]⁺=217.3

Step 2. 1-[6-[(3R)-3,4-dimethylpiperazin-1-yl]pyridin-2-yl]methanamine

To a stirred mixture of 6-[(3R)-3,4-dimethylpiperazin-1-yl]pyridine-2-carbonitrile (200 mg, 0.925 mmol, 1 equiv) in MeOH (5 mL) and NH₃.H₂O (0.5 mL) were added Raney-Ni (15.84 mg, 0.185 mmol, 0.20 equiv) dropwise/in portions at room temperature under hydrogen atmosphere. The resulting mixture was filtered, the filtrate was concentrated under reduced pressure. The crude product/resulting mixture to afford 1-[6-[(3R)-3,4-dimethylpiperazin-1-yl]pyridin-2-yl]methanamine (162 mg, 79.52%) as a colorless oil and use in the next step directly without further purification. LCMS: m/z (ESI), [M+H]⁺=221.4.

Step 3. 3-amino-N-([6-[(3R)-3,4-dimethylpiperazin-1-yl]pyridin-2-yl]methyl)-6-[3-methylimidazo[1,2-a]pyridin-6-yl]-5-(1,3-oxazol-2-yl)pyrazine-2-carboxamide To a stirred solution/mixture of 3-amino-6-[3-methylimidazo[1,2-a]pyridin-6-yl]-5-(1,3-oxazol-2-yl)pyrazine-2-carboxylic acid (100 mg, 0.297 mmol, 1 equiv) and 1-[6-[(3R)-3,4-dimethylpiperazin-1-yl]pyridin-2-yl]methanamine (98.27 mg, 0.446 mmol, 1.5 equiv) in DMF (5 mL) were added HATU (226.12 mg, 0.595 mmol, 2 equiv) and DIEA (115.29 mg, 0.892 mmol, 3 equiv) dropwise/in portions at room temperature under air atmosphere. The resulting mixture was extracted with CH₂Cl₂ (3×20 mL). The combined organic layers were washed with water (3×10 mL), dried over anhydrous Na2SO4. After filtration, the filtrate was concentrated under reduced pressure. The residue was purified by Prep-TLC (CH₂Cl₂/MeOH 15:1). The crude product (80 mg) was purified by Prep-HPLC with the following conditions (Column: XBridge Prep OBD C18 Column 19*250 mm, 5 um; Mobile Phase A: Mobile Phase B: ACN; Flow rate: 20 mL/min; Gradient: 34% B to 45% B in 8 min; 254; 220 nm; Rt: 7.53 min) to afford 3-amino-N-([6-[(3R)-3,4-dimethylpiperazin-1-yl]pyridin-2-yl]methyl)-6-[3-methylimidazo[1,2-a]pyridin-6-yl]-5-(1,3-oxazol-2-yl)pyrazine-2-carboxamide (Cmpd. 285) (20 mg, 12.49%) as a yellow solid. LCMS: m/z (ESI), [M+H]⁺=539.4. ¹H-NMR (DMSO-d₆, 40 MHz) δ 1.7 (3H, d), 2.7 (2H, s), 2.9 (3H, s), 3.2 (5H, s), 3.6 (1H, s), 4.7-4.9 (2H, m), 5.3 (1H, d), 7.5 (2H, dd), 8.0 (1H, d), 8.2 (2H, d), 8.2-8.4 (2H, m), 8.7 (1H, s), 9.1 (1H, d), 10.1 (1H, t)

Example 287-2. (S)-3-amino-N-((6-(2,4-dimethylpiperazin-1-yl)pyridin-2-yl)methyl)-6-(3-methylimidazo[1,2-a]pyridin-6-yl)-5-(oxazol-2-yl)pyrazine-2-carboxamide (Cmpd. 287-2)

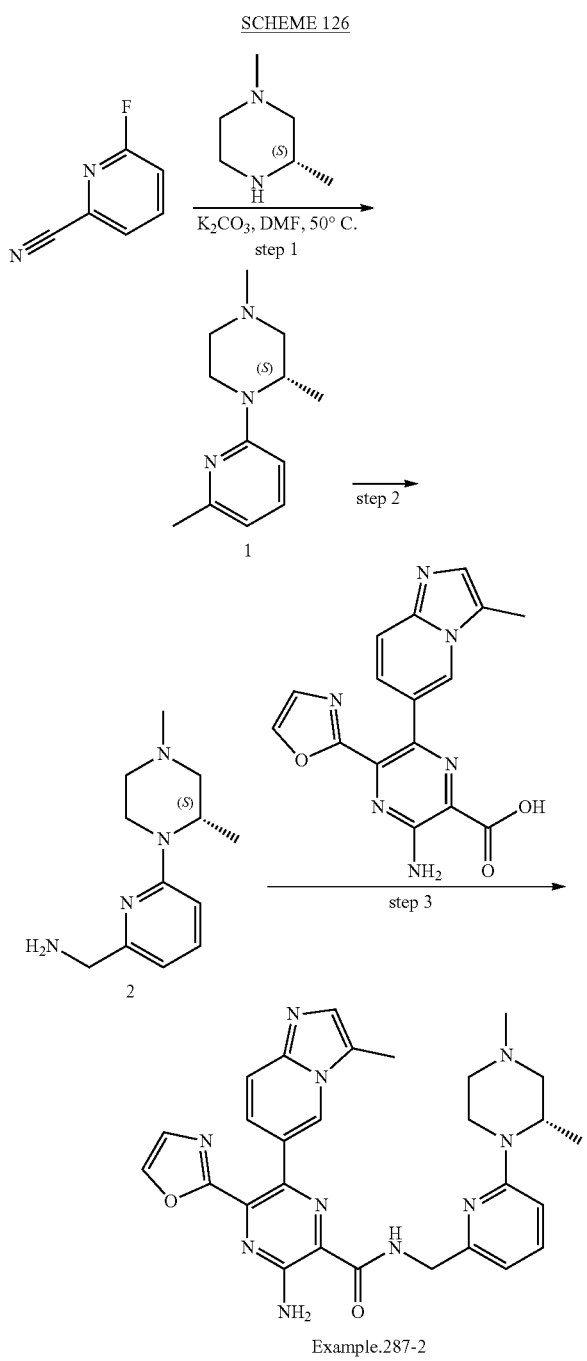

Step 1. 6-[(3S)-3,4-dimethylpiperazin-1-yl]pyridine-2-carbonitrile

Into a 40 mL sealed tube were added (3S)-1,3-dimethylpiperazine (607.89 mg, 5.323 mmol, 1.3 equiv), 6-fluoropyridine-2-carbonitrile (500 mg, 4.095 mmol, 1 equiv), $K_2CO_3$ (1131.89 mg, 8.190 mmol, 2 equiv) and DMF (10 mL) at room temperature. The resulting mixture was stirred for 3 hours at 50° C. The reaction was quenched by the addition of sat. NaCl (aq.) (250 mL) at room temperature. The resulting mixture was extracted with EtOAc (2×125 mL). The combined organic layers were washed with sat. NaCl (aq.) (250 mL), dried over anhydrous $Na_2SO_4$. After filtration, the filtrate was concentrated under reduced pressure. The residue was purified by Prep-TLC ($CH_2Cl_2$/MeOH 30:1) to afford 6-[(2S)-2,4-dimethylpiperazin-1-yl]pyridine-2-carbonitrile (280 mg, 31.61%) as a colorless oil. LCMS: m/z (ESI), $[M+H]^+=217.3$ Step 2. 1-[6-[(2S)-2,4-dimethylpiperazin-1-yl]pyridin-2-yl]methanamine To a stirred solution/mixture of 6-[(2S)-2,4-dimethylpiperazin-1-yl]pyridine-2-carbonitrile (280 mg, 1.295 mmol, 1 equiv) in MeOH (5 mL) and $NH_2NH_2.H_2O$ (0.5 mL) were added Raney-Ni (22.18 mg, 0.259 mmol, 0.2 equiv) dropwise/in portions at room temperature under hydrogen atmosphere. The resulting mixture was filtered, and concentrated under reduced pressure and to afford 1-[6-[(2S)-2,4-dimethylpiperazin-1-yl]pyridin-2-yl]methanamine (200 mg, 70.12%) as a colorless solid. LCMS: m/z (ESI), $[M+H]^+=221.4$.

Step 3. 3-amino-N-([6-[(2S)-2,4-dimethylpiperazin-1-yl]pyridin-2-yl]methyl)-6-[3-methylimidazo[1,2-a]pyridin-6-yl]-5-(1,3-oxazol-2-yl)pyrazine-2-carboxamide (Cmpd. 287-2)

To a stirred solution/mixture of 3-amino-6-[3-methylimidazo[1,2-a]pyridin-6-yl]-5-(1,3-oxazol-2-yl)pyrazine-2-carboxylic acid (100 mg, 0.297 mmol, 1 equiv) and 1-[6-[(2S)-2,4-dimethylpiperazin-1-yl]pyridin-2-yl]methanamine (98.27 mg, 0.446 mmol, 1.50 equiv) in DMF (10 mL) were added HATU (226.12 mg, 0.595 mmol, 2 equiv) and DIEA (115.29 mg, 0.892 mmol, 3 equiv) dropwise/in portions at room temperature under air atmosphere. The resulting mixture was extracted with $CH_2Cl_2$ (3×20 mL). The combined organic layers were washed with water (3×20 mL), dried over anhydrous $Na_2SO_4$. After filtration, the filtrate was concentrated under reduced pressure. The residue was purified by Prep-TLC ($CH_2Cl_2$/MeOH 15:1). The crude product (80 mg) was purified by Prep-HPLC with the following conditions (Column: XBridge Prep OBD C18 Column 19*250 mm, 5 um; Mobile Phase A: Mobile Phase B: ACN; Flow rate: 20 mL/min; Gradient: 36% B to 47% B in 8 min; 254; 220 nm; Rt: 7.65 min) to afford 3-amino-N-([6-[(2S)-2,4-dimethylpiperazin-1-yl]pyridin-2-yl]methyl)-6-[3-methylimidazo[1,2-a]pyridin-6-yl]-5-(1,3-oxazol-2-yl)pyrazine-2-carboxamide (Cmpd. 287-2) (20 mg, 12.49%) as a yellow solid. LCMS: m/z (ESI), $[M+H]^+=539.4$. $^1$H NMR (400 MHz, DMSO-$d_6$) δ 0.9 (3H, d), 1.7 (1H, t), 1.8 (1H, dd), 2.0 (3H, s), 2.3 (1H, d), 2.4 (4H, s), 2.8-2.9 (1H, m), 3.9 (1H, d), 4.3 (1H, s), 4.5 (2H, dd), 6.6 (2H, dd), 7.2 (1H, dd), 7.3 (1H, s), 7.4 (1H, s), 7.4-7.5 (2H, m), 7.9 (1H, s), 8.3 (1H, s), 8.4 (1H, s), 9.3 (1H, t).

Compounds listed in the table below were prepared using methods described in Cmpd. 287-2.

| Example/Cmpd number | Structure | LCMS [M + H]+ | 1H NMR |
|---|---|---|---|
| 173 | 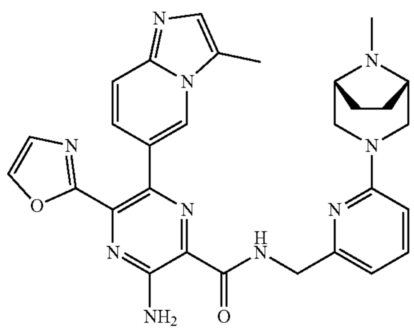 [SMILES: Cc1cnc2ccc(-c3nc(C(=O)NCc4cccc(N5C[C@H]6CC[C@@H](C5)N6C)n4)c(N)nc3-c3ncco3)cn12] | 551.5 | 1H NMR (400 MHz, DMSO-d6) δ 1.57 (4H, s), 1.92-2.33 (7H, m), 2.40-2.51(3H, m) 4.36 (2H, s), 4.48 (2H, d), 6.57 (2H, t), 7.20-7.31 (1H, d), 7.35 (1H, d), 7.39-7.55 (3H, m), 7.94 (2H, s), 8.27 (1H, d), 8.38 (1H, s), 9.33 (1H, d) |
| 174 | 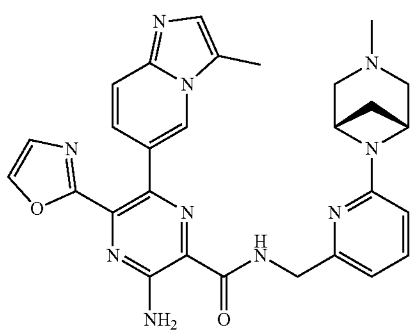 [SMILES: Cc1cnc2ccc(-c3nc(C(=O)NCc4cccc(N5[C@@H]6C[C@H]5CN(C)C6)n4)c(N)nc3-c3ncco3)cn12] | 537.3 | 1H NMR (40 MHz, DMSO-d6) δ 1.57 (1H, d), 1.96 (3H, s), 2.23 (1H, q), 2.44 (5H, d), 2.89 (2H, d), 4.12 (2H, d), 4.47 (2H, d), 6.29 (1H, d), 6.59 (1H, d), 7.24 (1H, dd), 7.32-7.54 (4H, m), 7.93 (2H, s), 8.28 (1H, d), 8.37 (1H, s), 9.38 (1H, t) |
| 176 | 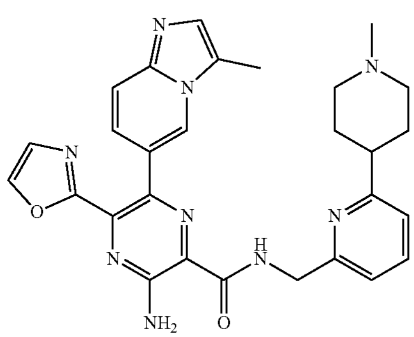 [SMILES: Cc1cnc2ccc(-c3nc(C(=O)NCc4cccc(C5CCN(C)CC5)n4)c(N)nc3-c3ncco3)cn12] | 524.5 | 1H NMR (400 MHz, DMSO-d6) δ 1.75 (6H, td), 2.11 (3H, s), 2.42 (3H, s), 2.68 (3H, d), 4.61 (2H, d), 7.17 (2H, t), 7.28 (1H, dd), 7.38 (2H, dd), 7.51 (1H, d), 7.69 (1H, t), 7.93 (2H, s), 8.25-8.37 (2H, m), 9.46 (1H, t) |
| 282 | 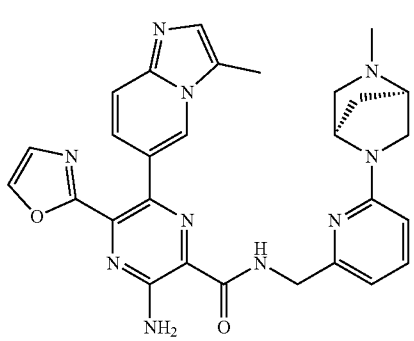 [SMILES: Cc1cnc2ccc(-c3nc(C(=O)NCc4cccc(N5C[C@H]6C[C@@H]5CN6C)n4)c(N)nc3-c3ncco3)cn12] | 537.3 | 1H NMR (400 MHz, DMSO-d6) δ 1.41 (1H, s), 1.47 (1H, d), 2.05 (3H, s), 2.30 (1H, d), 2.36 (1H, d), 2.43 (3H, s), 3.01-3.13 (2H, m), 3.24 (1H, d), 4.39-4.51 (3H, m), 6.32 (1H, d), 6.53 (1H, d), 7.24 (1H, dd), 7.35 (1H, d), 7.38-7.47 (2H, m), 7.47-7.55 (1H, m), 7.94 (2H, s), 8.27 (1H, d), 8.38 (1H, d), 9.41 (1H, t) |

| Example/Cmpd number | Structure | LCMS [M + H]+ | 1H NMR |
|---|---|---|---|
| 283 | 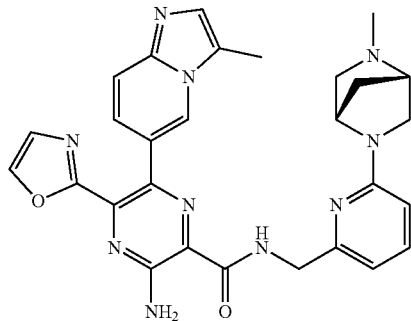 [SMILES: Cc1cnc2ccc(-c3nc(C(=O)NCc4cccc(N5C[C@@H]6C[C@H]5CN6C)n4)c(N)nc3-c3ncco3)cn12] | 537.3 | 1H NMR (400 MHz, DMSO-d6) δ 1.41 (1H, s), 1.47 (1H, d), 2.05 (3H, s), 2.29 (1H, d), 2.36 (1H, d), 2.40-2.46 (3H, m), 3.00-3.13 (2H, m), 3.24 (1H, d), 4.39-4.51 (3H, m), 6.31 (1H, d), 6.53 (1H, d), 7.24 (1H, dd), 7.35 (1H, d), 7.38-7.47 (2H, m), 7.47-7.55 (1H, m), 7.94 (2H, s), 8.27 (1H, d), 8.38 (1H, s), 9.41 (1H, t) |
| 286 | 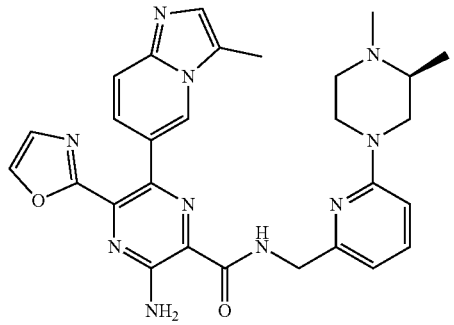 [SMILES: Cc1cnc2ccc(-c3nc(C(=O)NCc4cccc(N5CCN(C)[C@@H](C)C5)n4)c(N)nc3-c3ncco3)cn12] | 539.4 | 1H NMR (DMSO-d6, 40 MHz) δ (3H, d), 1.9 (2H, s), 2.1 (3H, s), 2.4 (5H, s), 2.8 (1H, t), 3.9 (1H, d), 4.0 (1H, d), 4.5 (2H, d), 6.6 (1H, d), 6.7 (1H, d), 7.2 (1H, d), 7.4 (2H, d), 7.5 (2H, t), 7.9 (2H, s), 8.3 (1H, s), 8.4 (1H, s), 9.3 (1H, t) |
| 287-1 | 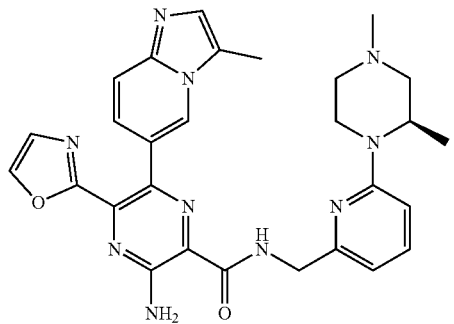 | 539.4 | 1H NMR (400 MHz, DMSO-d6) δ 1.0 (3H, d), 1.7-1.9 (2H, m), 2.0 (3H, s), 2.3-2.4 (4H, m), 2.5 (1H, s), 2.9 (1H, td), 3.9 (1H, d), 4.4 (1H, s), 4.4-4.6 (2H, m), 6.6-6.6 (m, 2H), 6.9 (dd, 1H), 7.4-7.4 (m, 2H), 7.5 (dd, 1H), 8.0 (t, 1H), 8.1 (s, 2H), 9.4 (t, 1H). |

499

Example 290. Preparation of (2S)—N-[[3-amino-5-(4-fluorophenyl)-6-[3-methyl-imidazo-[1,2-a]pyridin-6-yl]pyrazin-2-yl]methyl]oxolane-2-carboxamide Cmpd. 290)

SCHEME 127

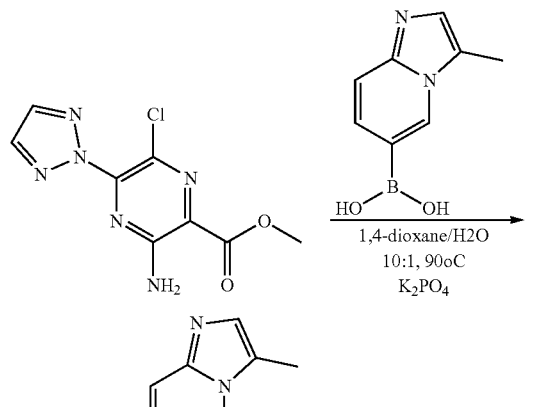

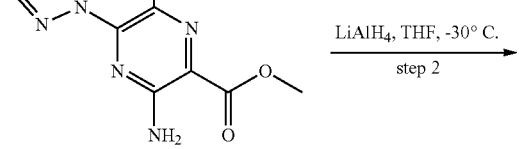

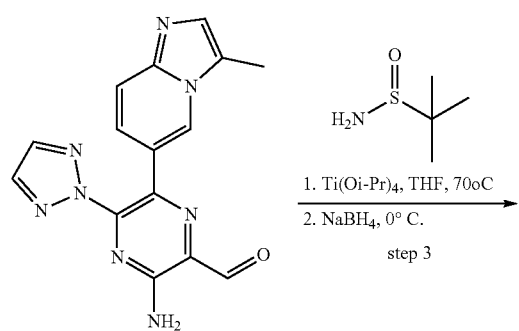

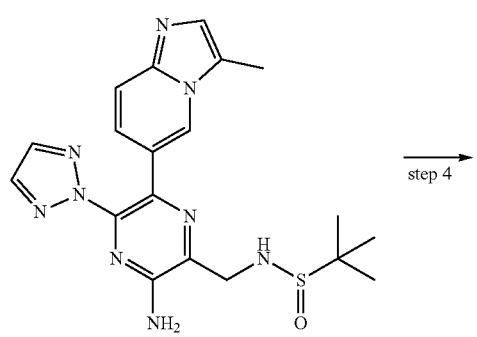

500

-continued

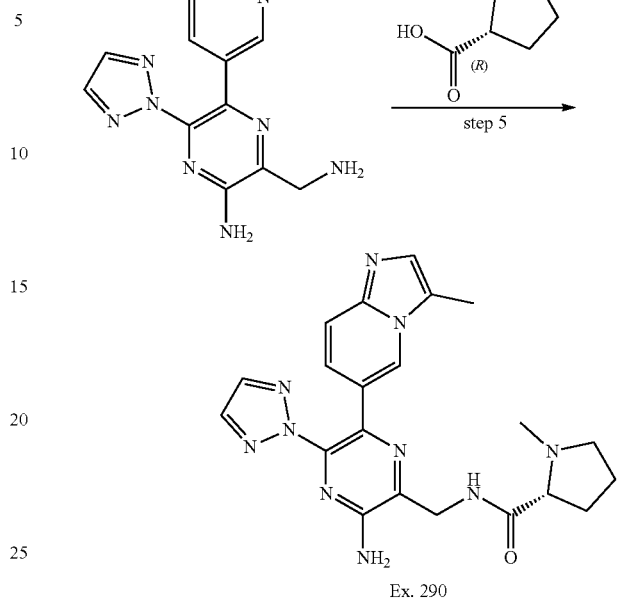

Step 1. methyl 3-methyl-6-[3-methylimidazo[1,2-a]pyridin-6-yl]-5-(2H-1,2,3-triazol-2-yl)pyrazine A solution of methyl 3-amino-6-chloro-5-(2H-1,2,3-triazol-2-yl)pyrazine-2-carboxylate (3.0 g, 11.8 mmol, 1 eq.) in dioxane (50 mL) was treated with [3-methylimidazo[1,2-a]pyridin-6-yl]boronic acid (4.15 g, 23.6 mmol, 2.00 equiv), Pd(dppf)Cl$_2$ (0.86 g, 1.19 mmol, 0.1 equiv) and K$_3$PO$_4$ (7.50 g, 35.3 mmol, 3.0 eq.) in H$_2$O (5.0 mL) under nitrogen atmosphere at room temperature, heated for 2 h at 90° C., cooled to room temperature, concentrated. The residue was purified by silica gel column chromatography, eluted with CH$_2$Cl$_2$/MeOH (20/1) to afford methyl 3-methyl-6-[3-methylimidazo[1,2-a]pyridin-6-yl]-5-(2H-1,2,3-triazol-2-yl)pyrazine-2-carboxylate (1.8 g, 44%) as a light yellow solid. LCMS: m/z (ESI), [M+H]$^+$=351.3.

Step 2. 3-methyl-6-[3-methyl-imidazo[1,2-a]pyridin-6-yl]-5-(2H-1,2,3-triazol-2-yl)pyrazine-2-carbaldehyde A solution of methyl 3-amino-6-[3-methylimidazo[1,2-a]pyridin-6-yl]-5-(2H-1,2,3-triazol-2-yl)pyrazine-2-carboxylate (1.0 g, 2.85 mmol, 1 equiv) in THF (20 mL) was treated with LiAlH4 (162.5 mg, 4.28 mmol, 1.5 eq.) at −70° C., stirred for 2 h, quenched with EA (2.5 ml), purified by Prep-TLC afford to 3-methyl-6-[3-methylimidazo[1,2-a]pyridin-6-yl]-5-(2H-1,2,3-triazol-2-yl)pyrazine-2-carbaldehyde (280 mg, 31%) as alight yellow solid. LCMS: m/z (ESI), [M+H]$^+$=321.1.

Step 3. N-[(3-amino-6-[3-methylimidazo[1,2-a]pyridin-6-yl]-5-(2H-1,2,3-triazol-2-yl)pyrazin-2-yl)methyl]-2-methylpropane-2-sulfinamide A mixture of 3-amino-6-[3-methylimidazo[1,2-a]pyridin-6-yl]-5-(2H-1,2,3-triazol-2-yl)pyrazine-2-carbaldehyde (260 mg, 0.81 mmol, 1 eq.) and 2-methylpropane-2-sulfinamide (195 mg, 1.62 mmol, 2.0 equiv) in THF (2.5 ml) was treated with Ti(Oi-Pr)$_4$ (2.5 mL) at room temperature, heated at 70° C. for 2 h, cooled to room temperature added NaBH$_4$ (123 mg, 3.25 mmol, 4.0 eq.), stirred for 2 h, quenched by water 2.0 ml, filtered. The solid was washed by DCM/MeOH=5/1 (20 ml), combined with organic layer, concentrated, purified by Prep-TLC (DCM/MeOH=50/1) to give N-[(3-amino-6-[3-methylimidazo[1,2-a]pyridin-6-yl]-5-(2H-1,2,3-triazol-2-yl)pyrazin-2-yl) methyl]-2-methylpropane-2-sulfinamide (230 mg, 67%) as a light yellow solid. LCMS: m/z (ESI), [M+H]$^+$=426.3.

Step 4. (2S)—N-[[3-amino-5-(4-fluorophenyl)-6-[3-methylimidazo[1,2-a]pyridin-6-yl]pyrazin-2-yl]methyl]-1-methylpyrrolidine-2-carboxamide A solution of N-[(3-amino-6-[3-methylimidazo[1,2-a]pyridin-6-yl]-5-(2H-1,2,3-triazol-2-yl)pyrazin-2-yl)methyl]-2-methylpropane-2-sulfinamide (160 mg, 0.36 mmol, 1 eq.) in DCM (2.0 mL) was treated with HCl (gas) in 1,4-dioxane (2.0 mL, 4.0 mol/L) at room temperature, stirred for 2 h, concentrated afford to 3-(aminomethyl)-5-[3-methylimidazo[1,2-a]pyridin-6-yl]-6-(2H-1,2,3-triazol-2-yl)pyrazin-2-amine (160 mg, crude). LCMS: m/z (ESI), [M+H]$^+$=322.3.

Step 5. (2S)—N-[[3-amino-5-(4-fluorophenyl)-6-[3-methylimidazo[1,2-a]pyridin-6-yl]pyrazin-2-yl]methyl]oxolane-2-carboxamide (Cmpd. 290)

A solution of (2R)-1-methylpyrrolidine-2-carboxylic acid (112.5 mg, 0.87 mmol, 2.0 eq.) in DMF (3.0 mL) was treated with HATU (331 mg, 0.87 mmol, 2.00 eq.) for 20 min at room temperature followed by the addition of 3-(aminomethyl)-5-[3-methylimidazo[1,2-a]pyridin-6-yl]-6-(2H-1,2,3-triazol-2-yl)pyrazin-2-amine (140 mg, 0.44 mmol, 1 eq.), DIEA (167 mg, 1.31 mmol, 3.0 equiv) dropwise at room temperature, stirred for 2 h, The residue was purified by Prep-TLC (DCM/MeOH=30/1) to afford (2R)—N-[(3-amino-6-[3-methylimidazo[1,2-a]pyridin-6-yl]-5-(2H-1,2,3-triazol-2-yl)pyrazin-2-yl)methyl]-1-methylpyrrolidine-2-carboxamide (65 mg, 35%) as a white solid. LCMS [M+H]= 433.3. $^1$H NMR (400 MHz, DMSO-d$_6$) δ 1.74 (3H, m), 2.11 (1H, m), 2.32 (7H, d), 2.82 (1H, dd), 3.07 (1H, dd), 4.46 (2H, t), 6.87 (1H, dd), 7.15 (2H, s), 7.35 (1H, s), 7.42 (1H, d), 7.55 (1H, d), 8.09 (2H, s), 8.49 (1H, t).

Example 291. Preparation of (2R)—N-[[3-amino-5-(3,5-difluorophenyl)-6-[3-methylimidazo[1,2-a]pyridin-6-yl]pyrazin-2-yl]methyl]-1-methylpyrrolidine-2-carboxamide (Cmpd. 291)

SCHEME 128

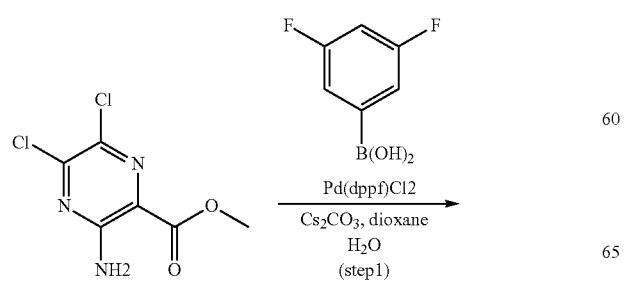

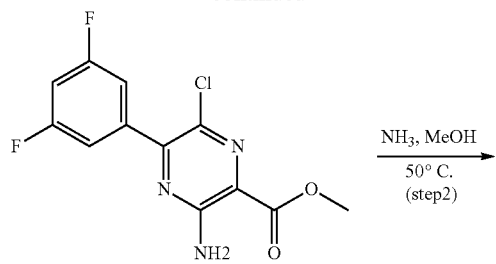

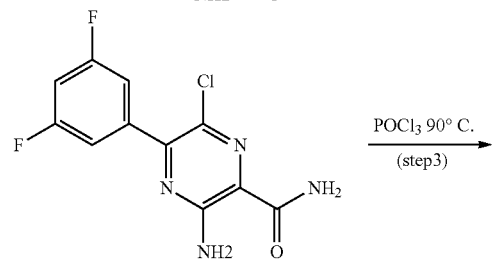

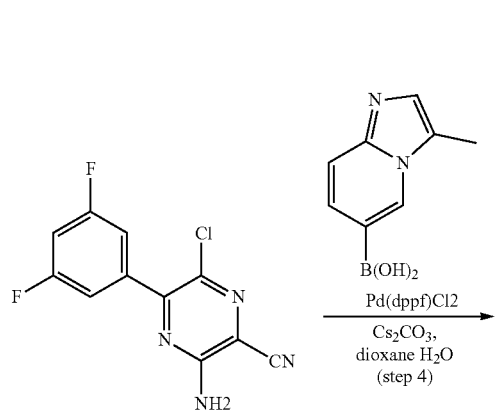

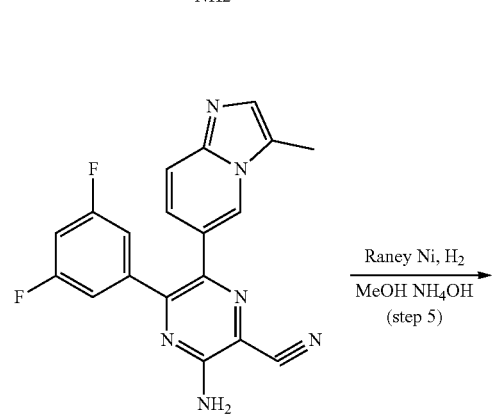

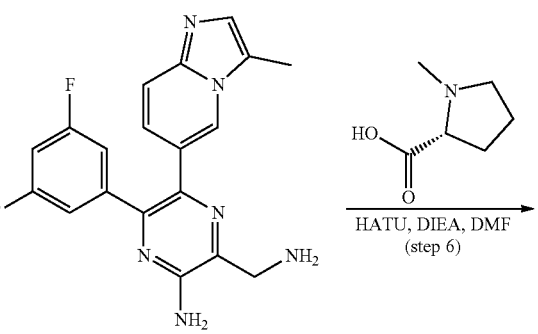

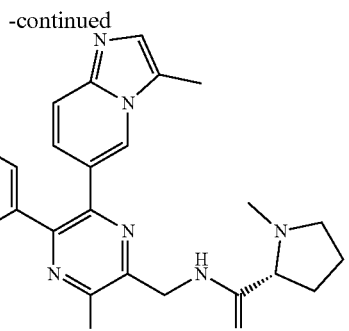

Example 291

Step 1. methyl 3-amino-6-chloro-5-(3,5-difluorophenyl)pyrazine-2-carboxylate To a stirred mixture of methyl 3-amino-5,6-dichloropyrazine-2-carboxylate (4 g, 18.016 mmol, 1 equiv) and (3,5-difluorophenyl)boronic acid (2.90 g, 18.376 mmol, 1.02 equiv) in 1,4-dioxane (100 mL) and H$_2$O (5 mL) were added K$_3$PO$_4$ (7.65 g, 36.031 mmol, 2 equiv) and Pd(dppf)Cl$_2$ (2.64 g, 3.603 mmol, 0.2 equiv) in portions at room temperature under nitrogen atmosphere. The resulting mixture was stirred for 3h at 70° C. under nitrogen atmosphere. The resulting mixture was filtered, the filter cake was washed with CH$_2$Cl$_2$ (1×30 mL). The filtrate was concentrated under reduced pressure. The residue was purified by silica gel column chromatography, eluted with CH$_2$Cl$_2$/EtOAc (4:1) to afford methyl 3-amino-6-chloro-5-(3,5-difluorophenyl)pyrazine-2-carboxylate (4 g, 74.09%) as a yellow solid. LCMS: m/z (ESI), [M+H]$^+$=300.2. $^1$H-NMR: (300 MHz, DMSO-d$_6$) δ 3.89 (3H, s), 7.47 (3H, dd), 7.66 (2H, s).

Step 2. 3-amino-6-chloro-5-(3,5-difluorophenyl)pyrazine-2-carboxamide

To a stirred solution of 30% NH$_3$ in MeOH (100 mL) was added methyl 3-amino-6-chloro-5-(3,5-difluorophenyl)pyrazine-2-carboxylate (4 g, 13.348 mmol, 1 equiv) in portions at room temperature. The resulting mixture was stirred for 4 hs at 50° C. The resulting mixture was concentrated under vacuum to afford 3-amino-6-chloro-5-(3,5-difluorophenyl)pyrazine-2-carboxamide (3.5 g, 92.11%) as a yellow solid. LCMS: m/z (ESI), [M+H]$^+$=285.2. $^1$H-NMR: (300 MHz, DMSO-d$_6$) δ 7.43 (3H, m), 7.75 (3H, s), 8.04 (1H, s).

Step 3. 3-amino-6-chloro-5-(3,5-difluorophenyl)pyrazine-2-carbonitrile

To a stirred solution of phosphoryl trichloride (40 mL) was added 3-amino-6-chloro-5-(3,5-difluorophenyl)pyrazine-2-carboxamide (2 g, 7.026 mmol, 1 equiv) in portions at room temperature. The resulting mixture was stirred for 12h at 90° C. The resulting mixture was concentrated under reduced pressure and diluted with DCM (20 mL). The reaction was quenched with sat. NaHCO$_3$ (aq.) at room temperature. The resulting mixture was extracted with CH$_2$Cl$_2$ (2×30 mL). The combined organic layers were dried over anhydrous Na$_2$SO$_4$. After filtration, the filtrate was concentrated under reduced pressure. The residue was purified by Prep-TLC (PE/EtOAc 1:1) to afford 3-amino-6-chloro-5-(3,5-difluorophenyl)pyrazine-2-carbonitrile (700 mg, 37.36%) as a yellow solid. $^1$H-NMR: (300 MHz, DMSO-d$_6$) δ 7.43 (3H, m), 7.73 (2H, s).

Step 4. 3-amino-5-(3,5-difluorophenyl)-6-[3-methylimidazo[1,2-a]pyridin-6-yl]pyrazine-2-carbonitrile To a stirred mixture of 3-amino-6-chloro-5-(3,5-difluorophenyl)pyrazine-2-carbonitrile (600 mg, 2.250 mmol, 1 equiv) and [3-methylimidazo[1,2-a]pyridin-6-yl]boronic acid (791.99 mg, 4.500 mmol, 2.00 equiv) in 1,4-dioxane (30 mL) and H$_2$O (4 mL) were added Cs$_2$CO$_3$ (1466.34 mg, 4.500 mmol, 2 equiv) and Pd(dppf)Cl2 (329.30 mg, 0.450 mmol, 0.2 equiv) in portions at room temperature under nitrogen atmosphere. The resulting mixture was stirred for 3h at 90° C. under nitrogen atmosphere. The resulting mixture was filtered, the filter cake was washed with CH$_2$Cl$_2$ (1×10 mL). The filtrate was concentrated under reduced pressure. The residue was purified by Prep-TLC (CH$_2$Cl$_2$/MeOH 30:1) to afford 3-amino-5-(3,5-difluorophenyl)-6-[3-methylimidazo[1,2-a]pyridin-6-yl]pyrazine-2-carbonitrile (300 mg, 36.79%) as a yellow solid. LCMS: m/z (ESI), [M+H]$^+$=363.3. $^1$H-NMR: (300 MHz, DMSO-d$_6$) δ 2.37 (3H, m), 6.94 (1H, dd), 7.13 (2H, m), 7.37 (3H, m), 7.67 (2H, s), 8.18 (1H, m).

Step 5. 3-(aminomethyl)-6-(3,5-difluorophenyl)-5-[3-methylimidazo[1,2-a]pyridin-6-yl]pyrazin-2-amine To a stirred solution of 3-amino-5-(3,5-difluorophenyl)-6-[3-methylimidazo[1,2-a]pyridin-6-yl]pyrazine-2-carbonitrile (100 mg, 0.276 mmol, 1 equiv) and NH$_3$·H$_2$O (1 mL) in MeOH (15 mL) was added Raney Ni (47.29 mg, 0.552 mmol, 2 equiv) in portions at room temperature under nitrogen atmosphere. The resulting mixture was stirred for 2h at room temperature under hydrogen atmosphere. The resulting mixture was filtered, the filter cake was washed with MeOH (1×10 mL). The filtrate was concentrated under reduced pressure to afford 3-(aminomethyl)-6-(3,5-difluorophenyl)-5-[3-methylimidazo[1,2-a]pyridin-6-yl]pyrazin-2-amine (90 mg, 89.01%) as a yellow solid. LCMS: m/z (ESI), [M+H]$^+$=367.3.

Step 6. (2R)—N-[[3-amino-5-(3,5-difluorophenyl)-6-[3-methylimidazo[1,2-a]pyridin-6-yl]pyrazin-2-yl]methyl]-1-methylpyrrolidine-2-carboxamide (Cmpd. 291)

To a stirred mixture of (2R)-1-methylpyrrolidine-2-carboxylic acid (56.41 mg, 0.437 mmol, 2.00 equiv) in DMF (10 mL) was added HATU (166.05 mg, 0.437 mmol, 2 equiv) and DIEA (56.44 mg, 0.437 mmol, 2 equiv) in portions at room temperature. The resulting mixture was stirred for 10 min at room temperature. Then to this stirred solution was added 3-(aminomethyl)-6-(3,5-difluorophenyl)-5-[3-methylimidazo[1,2-a]pyridin-6-yl]pyrazin-2-amine (80 mg, 0.218 mmol, 1 equiv) in portions at room temperature. The resulting mixture was stirred for 3h at room temperature. The resulting mixture was concentrated under reduced pressure. The crude product was purified by Prep-HPLC with the following conditions (Column: XBridge Prep C18 OBD Column, 5 um, 19*150 mm; Mobile Phase A: water, Mobile Phase B: ACN; Flow rate: 20 mL/min; Gradient: 35% B to 48% B in 7 min; 254/220 nm; Rt: 6.77 min) to afford (2R)—N-[[3-amino-5-(3,5-difluorophenyl)-6-[3-methylimidazo[1,2-a]pyridin-6-yl]pyrazin-2-yl]methyl]-1-methylpyrrolidine-2-carboxamide (Cmpd.

291) (7 mg, 6.71%) as a yellow solid. LCMS: m/z (ESI), [M+H]⁺=478.4. ¹H NMR: (300 MHz, DMSO-d₆) δ1.72 (3H, s), 2.11 (1H, dd), 2.34 (7H, m), 2.81 (1H, dd), 3.04 (1H, m), 4.40 (2H, m), 6.77 (2H, s), 7.00 (1H, dd), 7.09 (2H, m), 7.25 (1H, tt), 7.40 (2H, m), 8.09 (1H, t), 8.45 (1H, t).

Example 296-1. Preparation of 3-amino-6-[3-methylimidazo[1,2-a]pyridin-6-yl]-5-(1,3-oxazol-2-yl)-N-[(2S)-1-(1H-1,2,3-triazol-1-yl)propan-2-yl]pyrazine-2-carboxamide (Cmpd. 296-1)

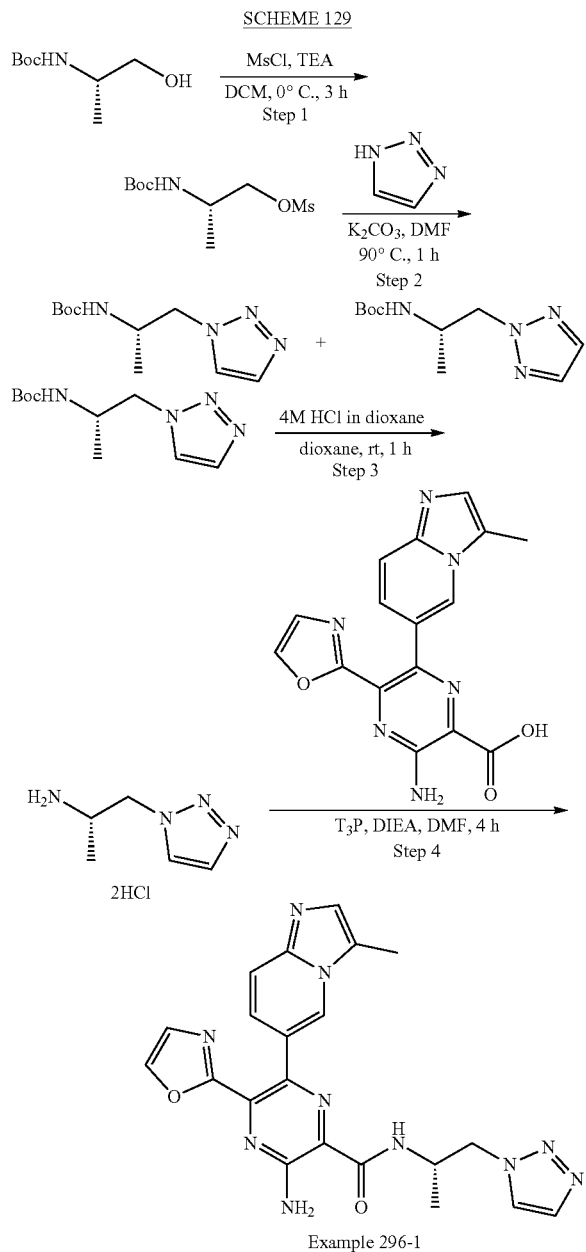

Step 1. (S)-2-((tert-butoxycarbonyl)amino)propyl Methanesulfonate

To a stirred solution of tert-butyl N-[(2S)-1-hydroxypropan-2-yl]carbamate (5.0 g, 28.534 mmol, 1 equiv) and TEA (3753.60 mg, 37.095 mmol, 1.3 equiv) in DCM was added MsCl (4.90 g, 42.801 mmol, 1.5 equiv) dropwise at 0° C. under nitrogen atmosphere. The resulting mixture was extracted with CH₂Cl₂ (2×20 mL). The combined organic layers were washed with water (2×20 mL), dried over anhydrous Na₂SO₄. After filtration, the filtrate was concentrated under reduced pressure. This resulted in (S)-2-((tert-butoxycarbonyl)amino)propyl methanesulfonate (6.5 g, 89.9%) as a white solid. LCMS: m/z (ESI), [M+H]⁺=no MS signal.

Step 2. tert-butyl (S)-(1-(1H-1,2,3-triazol-1-yl)propan-2-yl)carbamate

To a stirred solution of tert-butyl N-[(2S)-1-(methanesulfonyloxy)propan-2-yl]carbamate (3 g, 11.843 mmol, 1 equiv) and 1H-1,2,3-triazole (1.23 g, 17.765 mmol, 1.50 equiv) in DMF (50 mL) was added K₂CO3 (3.27 g, 23.686 mmol, 2.00 equiv) in portions. The resulting mixture was stirred at 90° C. under nitrogen atmosphere. The resulting mixture was diluted with EA (10 mL), washed with water (2×10 mL). The resulting mixture was concentrated under vacuum. The residue was purified by reversed phase HPLC to afford tert-butyl (S)-(1-(2H-1,2,3-triazol-2-yl)propan-2-yl)carbamate (1.2 g, 44.7%) and tert-butyl (S)-(1-(1H-1,2,3-triazol-1-yl)propan-2-yl)carbamate (0.62 g, 23.1%) as white solid. tert-butyl (S)-(1-(2H-1,2,3-triazol-2-yl)propan-2-yl)carbamate H-NMR (300 MHz, Chloroform-d) δ 1.09 (3H, d), 1.43 (9H, s), 4.21 (1H, s), 4.51 (2H, d), 7.63 (2H, s). tert-butyl (S)-(1-(1H-1,2,3-triazol-1-yl)propan-2-yl)carbamate H-NMR (300 MHz, DMSO-d₆) δ 1.02 (4H, d), 1.33 (9H, s), 3.91 (1H, p), 4.34 (2H, qd), 6.92 (1H, d), 7.70 (1H, s), 8.01 (1H, d).

Step 3. (S)-1-(1H-1,2,3-triazol-1-yl)propan-2-amine dihydrochloride

To a stirred solution of tert-butyl (S)-(1-(1H-1,2,3-triazol-1-yl)propan-2-yl)carbamate (280 mg, 1 equiv) in 1, 4-dioxane (5 mL) was added 4 M HCl in 1,4-dioxane (5 mL) dropwise at 25° C. The mixture was stirred at room temperature for 1 h. Concentration to dryness resulted in (S)-1-(1H-1,2,3-triazol-1-yl)propan-2-amine dihydrochloride (266 mg, 90.5%) as a white solid. The crude product was used in the next step directly without further purification. ¹H-NMR (300 MHz, DMSO-d₆) δ 1.13 (3H, d), 3.68 (1H, dt), 4.63 (2H, qd), 7.78 (1H, s), 8.24 (1H, s), 8.44 (2H, s).

Step 4. 3-amino-6-[3-methylimidazo[1,2-a]pyridin-6-yl]-5-(1,3-oxazol-2-yl)-N-[(2S)-1-(1H-1,2,3-triazol-1-yl)propan-2-yl]pyrazine-2-carboxamide To a stirred mixture of (2S)-1-(1H-1,2,3-triazol-1-yl)propan-2-amine (45 mg, 0.357 mmol, 1.50 equiv), 3-amino-6-[3-methylimidazo[1,2-a]pyridin-6-yl]-5-(1,3-oxazol-2-yl) pyrazine-2-carboxylic acid (80 mg, 0.238 mmol, 1 equiv) and DIEA (184.46 mg, 1.427 mmol, 6.00 equiv) in DMF was added T₃P (454.12 mg, 0.714 mmol, 3.00 equiv, 50%) dropwise at 0° C. The reaction mixture was purified by Prep-HPLC with the following conditions (Column: Shiseido CAPCELLCORE C18, 2.1*50 mm, 2.7 um; Mobile-Phase A: Water/0.05% TFA, Mobile Phase B: ACN/0.05% TFA; Flow rate: 1.0 mL/min; Gradient: 5% B to 95% B in 2.0 min, hold 0.7 min; 254 nm) to afford 3-amino-6-[3-methylimidazo[1,2-a]pyridin-6-yl]-5-(1,3-oxazol-2-yl)-N-[(2S)-1-(1H-1,2,3-triazol-1-yl)propan-2-yl]pyrazine-2-carboxamide (Cmpd. 296-1) (75 mg, 70.9%) as a yellow solid.

LCMS: m/z (ESI), [M+H]⁺=445.3. 1H-NMR (300 MHz, DMSO-d6) δ 1.19 (3H, d), 2.45 (3H, d), 4.49-4.71 (3H, m), 7.19 (1H, dd), 7.37 (2H, dd), 7.48 (1H, dd), 7.69 (1H, d), 7.80 (2H, s), 8.10 (1H, d), 8.25 (1H, d), 8.28-8.35 (1H, m), 8.75 (1H, d).

Examples 296-2. Preparation of 3-amino-6-[3-methylimidazo[1,2-a]pyridin-6-yl]-5-(1,3-oxazol-2-yl)-N-[(2R)-1-(2H-1,2,3-triazol-2-yl)propan-2-yl]pyrazine-2-carboxamide (Cmpd. 296-2)

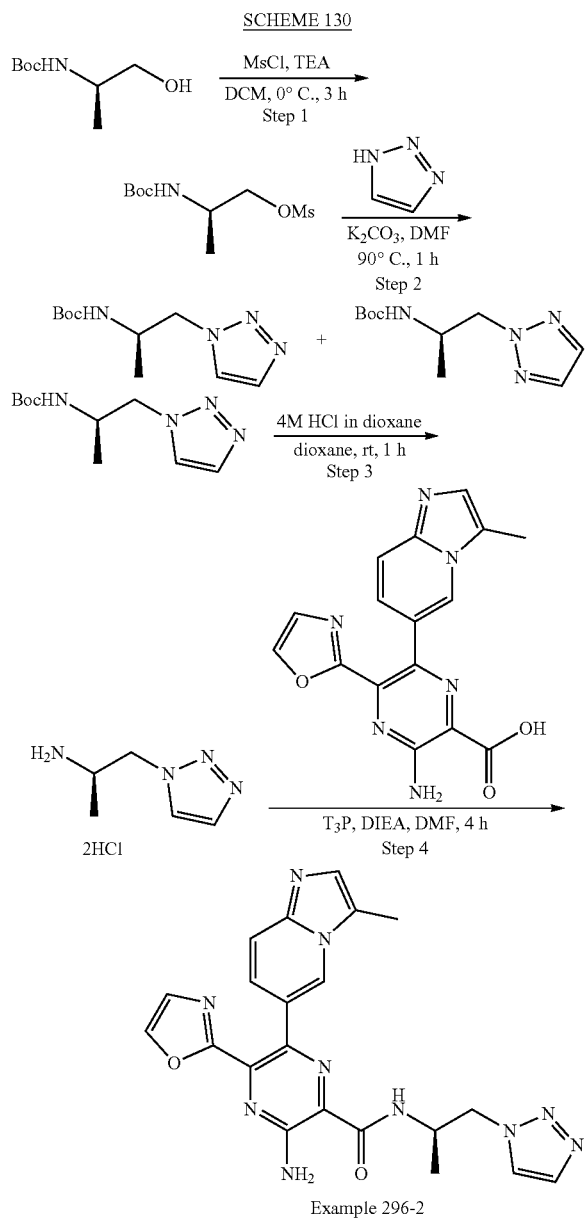

Step 1. (R)-2-((tert-butoxycarbonyl)amino)propyl methanesulfonate

To a stirred solution of tert-butyl N-[(2R)-1-hydroxypropan-2-yl]carbamate (3 g, 17.121 mmol, 1 equiv) and MsCl (2.55 g, 22.257 mmol, 1.3 equiv) in DCM (50 mL) was added TEA (3.46 g, 34.241 mmol, 2 equiv) in portions at 0° C. for 2 h. The reaction mixture was quenched with H₂O with NaHCO₃ (10 mL), extracted with DCM (3×20 mL), the organic layer was dried over Na₂SO₄, This resulted in (R)-2-((tert-butoxycarbonyl)amino)propyl methanesulfonate (6.5 g, 89.9%) as a white solid. LCMS: m/z (ESI), [M+H−tBu+MeCN]⁺=239.1.

Step 2. tert-butyl N-[(2R)-1-(2H-1,2,3-triazol-2-yl) propan-2-yl]carbamate

Into a 10 mL vial were added tert-butyl N-[(2R)-1-(2H-1,2,3-triazol-2-yl)propan-2-yl]carbamate (5 g, 19.739 mmol, 1 equiv), 1H-1,2,3-triazole (2.04 g, 29.608 mmol, 1.50 equiv), K₂CO₃ (5.46 g, 39.477 mmol, 2.00 equiv) and DMF (50 mL) at 0° C. Then the mixture was stirred at 90° C. under nitrogen atmosphere for 1 h. The resulting mixture was diluted with EtOAc (50 mL). The organic layers were washed with brine (3×10 mL), dried over anhydrous Na₂SO₄. After filtration, the filtrate was concentrated under reduced pressure. The residue was purified by reversed phase HPLC with the following conditions: column, Cis silica gel; mobile phase, MeOH in water, 10% to 50% gradient in 10 min; detector, UV 254 nm. to afford: tert-butyl N-[(2R)-1-(1H-1,2,3-triazol-1-yl)propan-2-yl]carbamate (1 g, 22.3%) ¹H-NMR (300 MHz, DMSO-d₆) δ 0.99 (3H, d), 1.31 (9H, s), 3.72-4.00 (1H, m), 4.32 (2H, qd), 6.90 (1H, d), 7.68 (1H, d), 7.99 (1H, d); tert-butyl N-[(2R)-1-(2H-1,2,3-triazol-2-yl)propan-2-yl]carbamate (2.9 g, 64.9%) as a white solid. ¹H-NMR (300 MHz, DMSO-d₆) δ 0.94 (3H, d), 1.31 (9H, s), 3.94 (1H, p), 4.24-4.43 (2H, m), 6.84 (1H, d), 7.74 (2H, s).

Step 3. (R)-1-(1H-1,2,3-triazol-1-yl)propan-2-amine Dihydrochloride

To a stirred solution of tert-butyl (R)-(1-(1H-1,2,3-triazol-1-yl)propan-2-yl)carbamate (280 mg, 1.24 mmol, 1 equiv) in 1,4-dioxane (5 mL) was added 4 M HCl in 1,4-dioxane (5 mL) dropwise at 25° C. The mixture was stirred at room temperature for 1 h. Concentration to dryness resulted in (R)-1-(1H-1,2,3-triazol-1-yl)propan-2-amine dihydrochloride (266 mg, quantitative) as a white solid. The crude product was used in the next step directly without further purification. LCMS: m/z (ESI), [M+H]⁺=127.1.

Step 4. 3-amino-6-[3-methylimidazo[1,2-a]pyridin-6-yl]-5-(1,3-oxazol-2-yl)-N-[(2R)-1-(1H-1,2,3-triazol-1-yl)propan-2-yl]pyrazine-2-carboxamide Into a 10 mL vial were added 3-amino-6-[3-methylimidazo[1,2-a]pyridin-6-yl]-5-(1,3-oxazol-2-yl)pyrazine-2-carboxylic acid (100 mg, 0.297 mmol, 1 equiv), (2R)-1-(1H-1,2,3-triazol-1-yl)propan-2-amine (56.27 mg, 0.446 mmol, 1.5 equiv), T₃P (283.83 mg, 0.892 mmol, 3 equiv), DIEA (192.15 mg, 1.487 mmol, 5 equiv) and DMF (10 mL) at 0° C. Then the mixture was stirred at room temperature under nitrogen atmosphere for 3 h. The resulting mixture was purified by Prep-HPLC with the following conditions (Column: XBridge Prep OBD C18 Column 30×150 mm 5 um; Mobile Phase A: Water (10 MMOL/L NH₄HCO₃), Mobile Phase B: ACN; Flow rate: 60 mL/min; Gradient: 10% B to 50% B in 7 min; 254/220 nm; Rt: 5.48 min) to afford 3-amino-6-[3-methylimidazo[1,2-a]pyridin-6-yl]-5-(1,3-oxazol-2-yl)-N-[(2R)-1-(1H-1,2,3-triazol-1-yl)propan-2-yl]pyrazine-2-carboxamide (Cmpd. 296-2) (20 mg, 15.1%) as a white solid. LCMS: m/z (ESI), [M+H]⁺=445.2. ¹H-NMR (300 MHz, DMSO-d$_6$) δ 1.19 (3H, d), 2.45 (3H, d), 4.49-4.71 (3H, m), 7.20 (1H, dd), 7.37 (2H, dd), 7.48 (1H, dd), 7.69 (1H, d), 7.79 (2H, s), 8.10 (1H, d), 8.25 (1H, d), 8.31 (1H, d), 8.75 (1H, d).

Example 297. Preparation of 3-amino-6-[3-methyl-imidazo[1,2-a]pyridin-6-yl]-5-(1,3-oxazol-2-yl)-N-[(2S)-1-(2H-1,2,3-triazol-2-yl)propan-2-yl]pyrazine-2-carboxamide

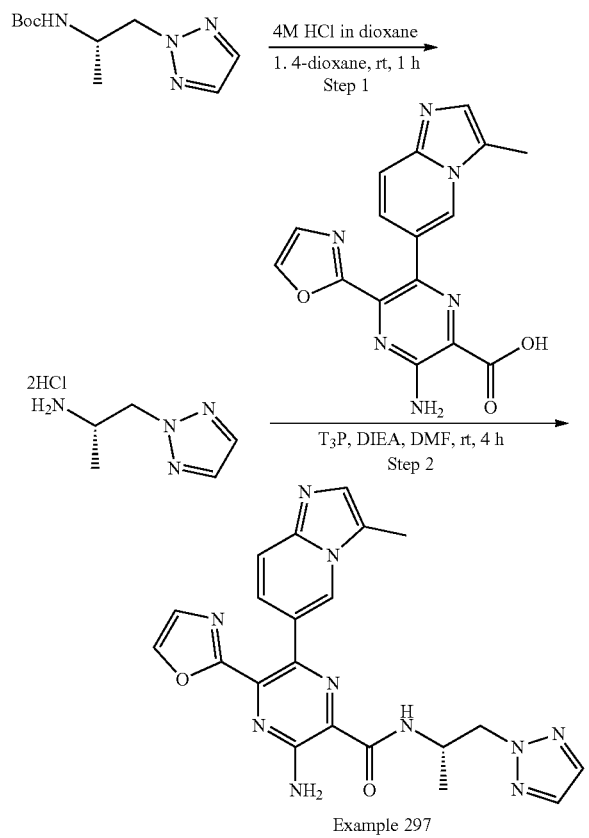

Example 297

Step 1. (2S)-1-(2H-1,2,3-triazol-2-yl)propan-2-amine Dihydrochloride

To a stirred mixture of tert-butyl N-[(2S)-1-(2H-1,2,3-triazol-2-yl)propan-2-yl]carbamate (260 mg, 1.15 mmol, 1 equiv) in 5 mL of 1,4-dioxane was added a solution of HCl in 1,4-dioxane (5 mL) dropwise at room temperature. After stirring for 1 h, the mixture was concentrated to afford (2S)-1-(2H-1, 2,3-triazol-2-yl)propan-2-amine dihydrochloride (230 mg, 90.0%) as a white solid. LCMS: m/z (ESI), [M+H]$^+$=127.2.

Step 2. 3-amino-6-[3-methylimidazo[1,2-a]pyridin-6-yl]-5-(1,3-oxazol-2-yl)-N-[(2S)-1-(2H-1,2,3-triazol-2-yl)propan-2-yl]pyrazine-2-carboxamide To a stirred solution of (2S)-1-(2H-1, 2, 3-triazol-2-yl)propan-2-amine dihydrochloride (71 mg, 0.357 mmol, 1.50 equiv) and 3-amino-6-[3-methylimidazo[1,2-a]pyridin-6-yl]-5-(1, 3-oxazol-2-yl)pyrazine-2-carboxylic acid (80 mg, 0.238 mmol, 1 equiv), DIEA (184 mg, 1.427 mmol, 6.00 equiv) in DMF was added T$_3$P (454 mg, 0.714 mmol, 3.00 equiv, 50% wt) dropwise at 0° C. under air atmosphere. The reaction mixture was purified by Prep-HPLC (Column: Shiseido CAPCELLCORE C18, 2.1*50 mm, 2.7 um; Mobile Phase A: Water/0.05% TFA, Mobile Phase B: ACN/0.05% TFA; Flow rate: 1.0 mL/min; Gradient: 5% B to 95% B in 2.0 min, hold 0.7 min; 254 nm) to afford 3-amino-6-[3-methylimidazo[1, 2-a]pyridin-6-yl]-5-(1, 3-oxazol-2-yl)-N-[(2S)-1-(2H-1,2,3-triazol-2-yl)propan-2-yl]pyrazine-2-carboxamide (Cmpd. 297) (37 mg, 35.0%) as a yellow solid. LCMS: m/z (ESI), [M+H]$^+$=445.3. $^1$H-NMR (300 MHz, DMSO-d$_6$) δ 1.13 (3H, d), 2.43 (3H, d), 4.48-4.74 (3H, m), 7.24 (1H, dd), 7.37 (2H, dd), 7.52 (1H, dd), 7.77 (2H, s), 7.82 (2H, s), 8.25 (1H, d), 8.30 (1H, d), 8.78 (1H, d).

Example 298. Preparation of 3-amino-6-[3-methyl-imidazo[1,2-a]pyridin-6-yl]-5-(1,3-oxazol-2-yl)-N-[(2R)-1-(2H-1,2,3-triazol-2-yl)propan-2-yl]pyrazine-2-carboxamide (Cmpd. 298)

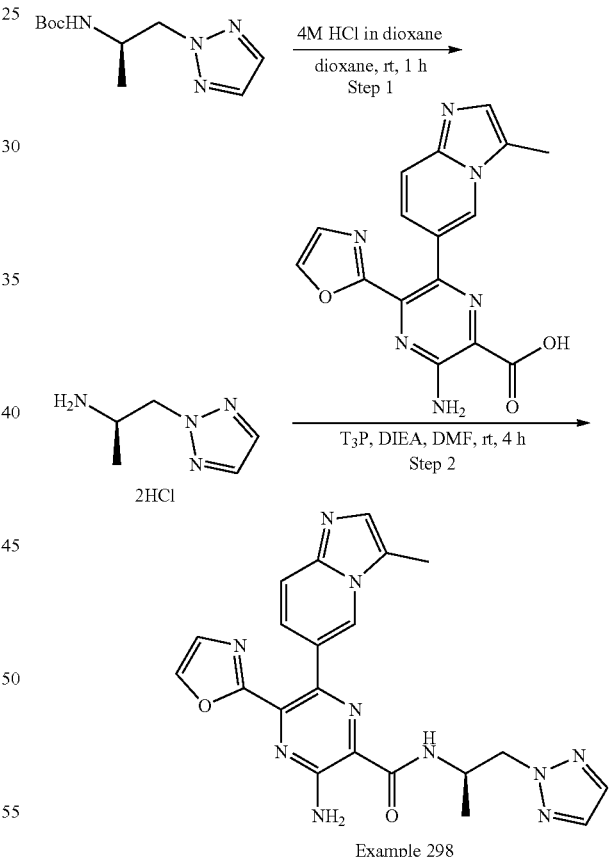

Example 298

Step 1. (2R)-1-(2H-1,2,3-triazol-2-yl)propan-2-amine Dihydrochloride

To a stirred solution of tert-butyl N-[(2R)-1-(2H-1,2,3-triazol-2-yl)propan-2-yl]carbamate (200 mg, 0.88 mmol, 1 eq) was added 4M HCl (gas) in 1,4-dioxane (4 mL) dropwise at room temperature under air atmosphere for 1 h. The solvent was evaporated out. This resulted in (2R)-1-(2H-1, 2,3-triazol-2-yl)propan-2-amine dihydrochloride (180 mg, quantitative) as a white solid. LCMS: m/z (ESI), [M+H]+= 127.2.

Step 2. 3-amino-6-[3-methylimidazo[1,2-a]pyridin-6-yl]-5-(1,3-oxazol-2-yl)-N-[(2R)-1-(1H-1,2,3-triazol-1-yl)propan-2-yl]pyrazine-2-carboxamide Into a 10 mL vial were added 3-amino-6-[3-methylimidazo[1,2-a]pyridin-6-yl]-5-(1,3-oxazol-2-yl)pyrazine-2-carboxylic acid (100 mg, 0.297 mmol, 1 equiv), (2R)-1-(1H-1,2,3-triazol-1-yl)propan-2-amine (56.27 mg, 0.446 mmol, 1.5 equiv), T$_3$P (283.83 mg, 0.892 mmol, 3 equiv), DIEA (192.15 mg, 1.487 mmol, 5 equiv) and DMF (10 mL) at 0° C. Then the mixture was stirred at room temperature under nitrogen atmosphere for 4 h. The resulting mixture was purified by Prep-HPLC with the following conditions (Column: XBridge Prep OBD C18 Column 30×150 mm 5 um; Mobile Phase A: Water (10 MMOL/L NH$_4$HCO$_3$), Mobile Phase B: ACN; Flow rate: 60 mL/min; Gradient: 10% B to 50% B in 7 min; 254/220 nm; Rt: 5.48 min) to afford 3-amino-6-[3-methylimidazo[1,2-a]pyridin-6-yl]-5-(1,3-oxazol-2-yl)-N-[(2R)-1-(1H-1,2,3-triazol-1-yl)propan-2-yl]pyrazine-2-carboxamide (Cmpd. 298) (20 mg, 15.1%) as a white solid. LCMS: m/z (ESI), [M+H]+=445.3. $^1$H-NMR (300 MHz, DMSO-d$_6$) δ 1.13 (3H, d), 2.38-2.44 (3H m,), 4.61 (1H, m), 4.62-4.64 (2H, m), 7.19-7.27 (1H, m), 7.33-7.42 (2H, m), 7.52 (1H, d), 7.77 (4H, s), 8.18-8.34 (2H, m), 8.78 (1H, d).

Example 301. 3-amino-N-([3-[2-(methylamino)ethoxy]pyridin-2-yl]methyl)-6-[3-methylimidazo[1,2-a]pyridin-6-yl]-5-(1,3-oxazol-2-yl)pyrazine-2-carboxamide (Cmpd. 301)

SCHEME 133

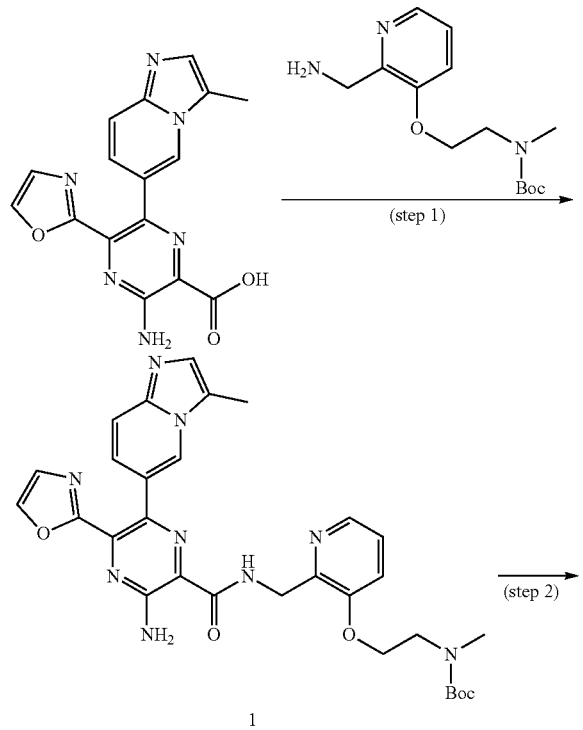

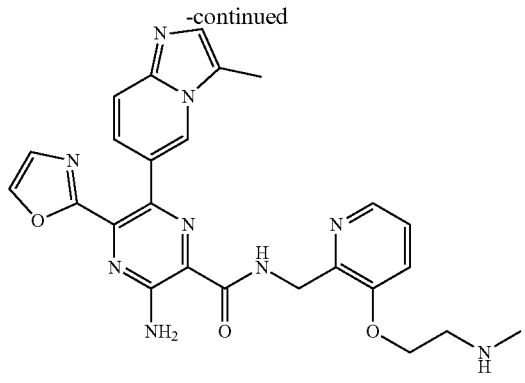

Example 301

Step 1. tert-butyl N-[2-[(2-[[(3-amino-6-[3-methylimidazo[1,2-a]pyridin-6-yl]-5-(1,3-oxazol-2-yl)pyrazin-2-yl)formamido]methyl]pyridin-3-yl)oxy]ethyl]-N-methylcarbamate Into a 6-mL vial, was placed tert-butyl N-(2-[[2-(aminomethyl)pyridin-3-yl]oxy]ethyl)-N-methylcarbamate (209.15 mg, 0.743 mmol, 2.50 equiv), 3-amino-6-[3-methylimidazo[1,2-a]pyridin-6-yl]-5-(1,3-oxazol-2-yl)pyrazine-2-carboxylic acid (100 mg, 0.297 mmol, 1 equiv), DIEA (0.36 mL, 2.805 mmol, 9 equiv), DMF (2.5 mL), T$_3$P (283.83 mg, 0.892 mmol, 3.00 equiv). The resulting solution was stirred for 16 hrs at 0° C. The resulting solution was diluted with 20 mL of H$_2$O. The resulting solution was extracted with 3×15 mL of dichloromethane and the organic layers were combined. The residue was purified by preparative TLC (DCM: MeOH=5: 1). This resulted in 60 mg (33.65%) of tert-butyl N-[2-[(2-[[(3-amino-6-[3-methylimidazo[1,2-a]pyridin-6-yl]-5-(1,3-oxazol-2-yl)pyrazin-2-yl)formamido]methyl]pyridin-3-yl)oxy]ethyl]-N-methylcarbamate as a yellow solid. LCMS: m/z (ESI), [M+H]+=600.3.

Step 2. 3-amino-N-([3-[2-(methylamino)ethoxy]pyridin-2-yl]methyl)-6-[3-methylimidazo[1,2-a]pyridin-6-yl]-5-(1,3-oxazol-2-yl)pyrazine-2-carboxamide Into a 25-mL round-bottom flask, was placed tert-butyl N-[2-[(2-[[(3-amino-6-[3-methylimidazo[1,2-a]pyridin-6-yl]-5-(1,3-oxazol-2-yl)pyrazin-2-yl)formamido]methyl]pyridin-3-yl)oxy]ethyl]-N-methylcarbamate (60 mg, 0.100 mmol, 1 equiv), DCM (3 mL), TFA (1 mL, 13.463 mmol, 134.55 equiv). The resulting solution was stirred for 1 hr at 20° C. The resulting mixture was concentrated under vacuum. The pH value of the solution was adjusted to 8 with saturated sodium bicarbonate (aq.). The resulting mixture was concentrated under vacuum. The residue was purified by preparative TLC (DCM:MeOH=5: 1) to afford a yellow solid. The crude product was purified by preparative HPLC (Column: XBridge Prep C18 OBD Column 19×150 mm 5 um; Mobile Phase A: Mobile Phase B: ACN; Flow rate: 20 mL/min; Gradient: 20% B to 38% B in 8 min; 254/220 nm; Rt: 7.19 min). This resulted in 10.53 mg (19.59%) of 3-amino-N-([3-[2-(methylamino)ethoxy]pyridin-2-yl]methyl)-6-[3-methylimidazo[1,2-a]pyridin-6-yl]-5-(1,3-oxazol-2-yl)pyrazine-2-carboxamide as a yellow solid. LCMS: m/z (ESI), [M+H]+=500.4. $^1$H-NMR (300 MHz, DMSO-d$_6$) δ 2.30 (3H, s), 2.44 (3H, s), 2.85 (2H, d), 4.10 (2H, d), 4.65 (2H, d), 7.20-7.31 (2H, m), 7.37 (1H, d), 7.38-7.46 (2H, m), 7.47-7.54 (1H, m), 8.06-8.08 (2H, s) 8.06 (1H, d), 8.28 (1H, d), 8.37 (1H, s), 9.26 (1H, t)

Example 302. Preparation of 3-amino-N-((6-(4-(dimethylamino)piperidin-1-yl)pyridin-2-yl)methyl)-6-(3-methylimidazo[1,2-a]pyridin-6-1)-5-(oxazol-2-yl)pyrazine-2-carboxamide (Cmpd. 302)

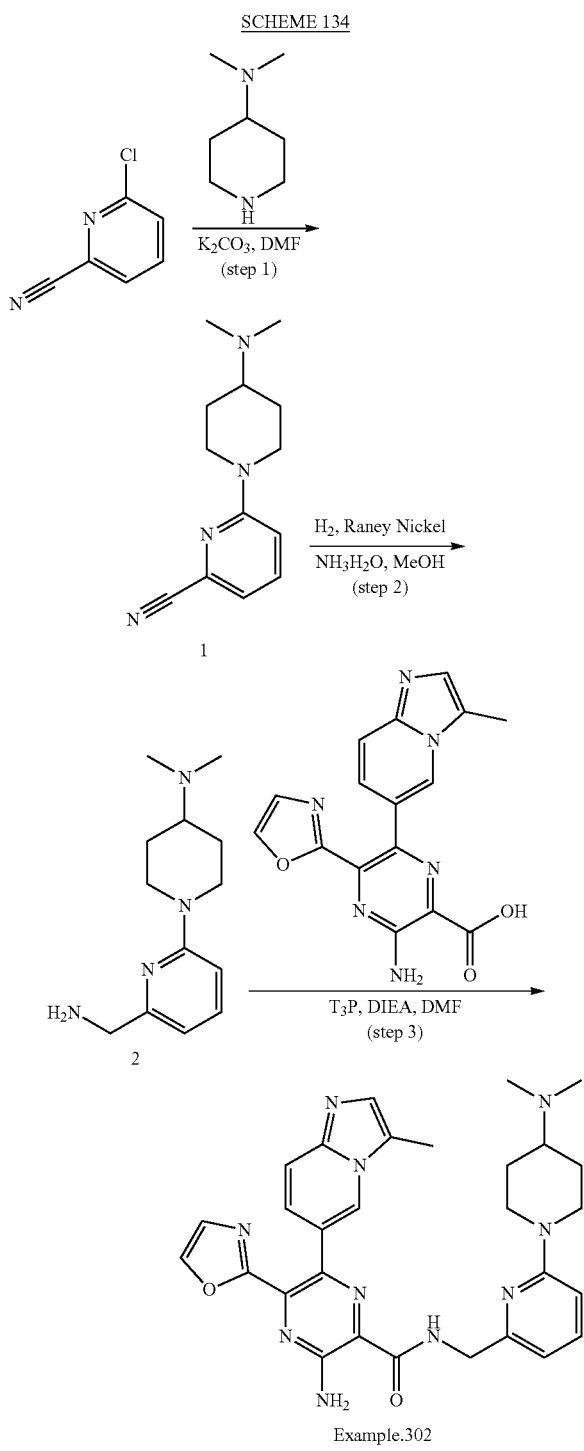

SCHEME 134

Example.302

Step 1.
6-(4-(dimethylamino)piperidin-1-yl)picolinonitrile

Into a 20 mL vial were added 6-chloropyridine-2-carbonitrile (500 mg, 3.609 mmol, 1 equiv) and N,N-dimethylpiperidin-4-amine (508.99 mg, 3.970 mmol, 1.10 equiv), $K_2CO3$ (1496.27 mg, 10.826 mmol, 3.00 equiv) in DMF (10 mL) at room temperature. The resulting mixture was stirred for 15 h at 60° C. under air atmosphere. The resulting mixture was diluted with EtOAc (100 mL). The resulting mixture was washed with 2×100 mL of water, and 2×100 mL of saturated brine. The organic layer was dried over anhydrous $Na_2SO_4$, and the solid was filtered out, the solvent was evaporated out to afford a yellow oil. The crude product was purified by TLC (EA:PE=1:2), to afford 6-[4-(dimethylamino)piperidin-1-yl]pyridine-2-carbonitrile (438 mg, 52.7%) as a yellow oil. LCMS: m/z (ESI), $[M+H]^+$=231.3. $^1$H-NMR (400 MHz, MeOD-$d_4$) δ 1.45 (2H, qd), 1.99 (2H, dt), 2.33 (6H, s), 2.49 (1H, tt), 2.89 (2H, td), 4.46 (2H, dp), 7.02 (1H, d), 7.08 (1H, d), 7.61 (1H, dd)

Step 2. 1-(6-(aminomethyl)pyridin-2-yl)-N,N-dimethylpiperidin-4-amine

Into a 50 mL round-bottom flask were added 6-[4-(dimethylamino)piperidin-1-yl]pyridine-2-carbonitrile (438 mg, 1.902 mmol, 1 equiv) and Raney Ni (162.93 mg, 1.902 mmol, 1.00 equiv), $NH_3.H_2O$ (66.65 mg, 1.902 mmol, 1.00 equiv) at room temperature. The resulting mixture was stirred for 2 h at room temperature under hydrogen atmosphere. The solid was filtered out and the solvent was evaporated out to afford 1-[6-(aminomethyl)pyridin-2-yl]-N,N-dimethylpiperidin-4-amine (406 mg, 91.1%) as a yellow oil. LCMS: m/z (ESI), $[M+H]^+$=235.1. $^1$H-NMR (400 MHz, MeOD-$d_4$) δ 1.39-1.55 (2H, m), 1.97 (2H, d), 2.32 (6H, s), 2.43 (1H, tt), 2.80 (2H, t), 3.74 (2H, s), 4.46 (2H, d), 6.50-6.72 (2H, m), 7.48 (1H, t)

Step 3. 3-amino-N-((6-(4-(dimethylamino)piperidin-1-yl)pyridin-2-yl)methyl)-6-(3-methylimidazo[1,2-a]pyridin-6-yl)-5-(oxazol-2-yl)pyrazine-2-carboxamide (Cmpd. 302)

To a stirred mixture of 1-[6-(aminomethyl)pyridin-2-yl]-N,N-dimethylpiperidin-4-amine (55.75 mg, 0.238 mmol, 1.00 equiv) and 3-amino-6-[3-methylimidazo[1,2-a]pyridin-6-yl]-5-(1,3-oxazol-2-yl)pyrazine-2-carboxylic acid (80 mg, 0.238 mmol, 1 equiv), DIEA (92.23 mg, 0.714 mmol, 3.00 equiv) in DMF were added $T_3P$ (151.37 mg, 0.476 mmol, 2.00 equiv) dropwise at 0° C. under air atmosphere. The resulting mixture was stirred for 12 h at room temperature under air atmosphere. The resulting mixture was diluted with EtOAc (50 mL). The resulting mixture was washed with 1×50 mL of water and 3×50 mL of brine. The organic layer was dried over anhydrous $Na_2SO_4$, filtered and evaporated to afford a crude solid. The residue was purified by Prep-TLC ($CH_2Cl_2$/MeOH 12:1) to afford a yellow solid. The crude product (50 mg) was purified by Prep-HPLC with the following conditions (Column: XBridge Prep OBD C18 Column 30×150 mm 5 um; Mobile Phase A: Water (0.05% $NH_3H_2O$), Mobile Phase B: ACN; Flow rate: 60 mL/min; Gradient: 37% B to 50% B in 7 min; 254; 220 nm; Rt: 5.52 min) to afford 3-amino-N-([6-[4-(dimethylamino)piperidin-1-yl]pyridin-2-yl]methyl)-6-[3-methylimidazo[1,2-a]pyridin-6-yl]-5-(1,3-oxazol-2-yl)pyrazine-2-carboxamide (Cmpd. 302) (20 mg, 15.21%) as a yellow solid. LCMS: m/z (ESI), $[M+H]^+$=553.4. $^1$H-NMR (400 MHz, MeOD-$d_4$) δ

1.21 (2H, tt), 1.52 (2H, d), 2.09-2.15 (7H, m), 2.49 (3H, s), 2.56 (2H, dd), 4.33 (2H, d), 4.57 (2H, s), 6.65 (2H, dd), 7.30 (2H, d), 7.42 (1H, s), 7.47-7.54 (2H, m), 8.00 (1H, s), 8.40 (1H, s)

Example 303. Preparation of 3-amino-N-((6-(3-(methylamino)azetidin-1-yl)pyridin-2-yl)methyl)-6-(3-methylimidazo[1,2-a]pyridin-6-yl)-5-(oxazol-2-yl)pyrazine-2-carboxamide (Cmpd. 303)

SCHEME 135

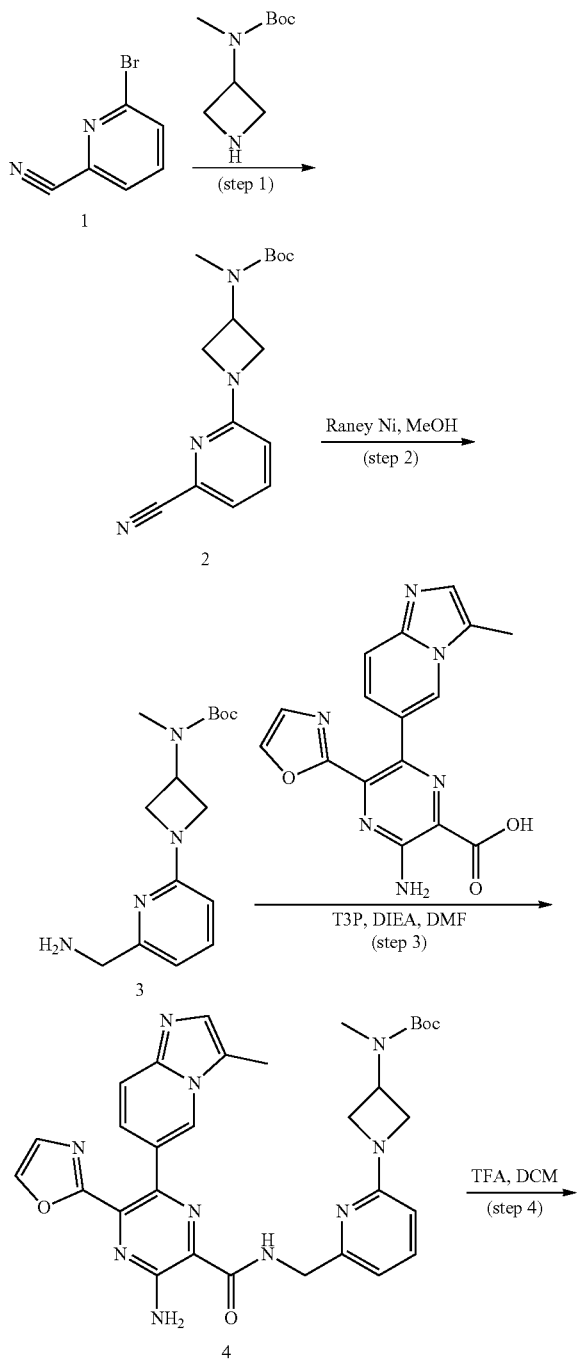

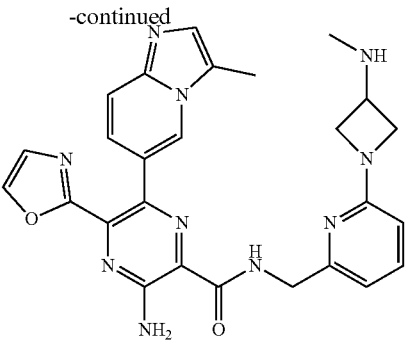

Example 303

Step 1. Preparation of tert-butyl (1-(6-cyanopyridin-2-yl)azetidin-3-yl) (methyl)carbamate A mixture of 6-bromopyridine-2-carbonitrile (500 mg, 2.732 mmol, 1 equiv), tert-butyl N-(azetidin-3-yl)-N-methylcarbamate (559.76 mg, 3.005 mmol, 1.1 equiv) and $K_2CO_3$ (1132.78 mg, 8.196 mmol, 3.0 equiv) in DMF (20 mL) was stirred for 3 h at 60° C. The resulting mixture was diluted with water (40 mL). The resulting mixture was extracted with EtOAc (3×50 mL). The combined organic layers were washed with brine (20 mL), dried over anhydrous $Na_2SO_4$. After filtration, the filtrate was concentrated under reduced pressure. The residue was purified by silica gel column chromatography, eluted with PE/EtOAc (9:1) to afford tert-butyl N-[1-(6-cyanopyridin-2-yl)azetidin-3-yl]-N-methylcarbamate (600 mg, 76.16%) as a light yellow solid. LCMS: m/z (ESI), [M+H]$^+$=289.2. $^1$H-NMR (300 mHz, DMSO-d$_6$) δ 1.38 (9H, s) 2.86-2.88 (3H, m), 4.02-4.05 (2H, m), 4.16-4.19 (2H, m), 4.85 (1H, s), 6.70-6.73 (1H, m), 7.19-7.23 (1H, m), 7.67-7.69 (1H, m)

Step 2. tert-butyl (1-(6-(aminomethyl)pyridin-2-yl) azetidin-3-yl) (methyl)carbamate A mixture of tert-butyl N-[1-(6-cyanopyridin-2-yl)azetidin-3-yl]-N-methylcarbamate (500 mg, 1.734 mmol, 1 equiv). ammonium hydroxide (20.00 mL) and Raney Ni (99.54 mg) in MeOH (20 mL) was stirred for 1 h at room temperature under $H_2$. The resulting mixture was filtered, the filter cake was washed with MeOH (3×10 mL). The filtrate was concentrated under reduced pressure. This gave tert-butyl N-[1-[6-(aminomethyl)pyridin-2-yl]azetidin-3-yl]-N-methylcarbamate (502 mg, 99.02%) as a light yellow oil. LCMS: m/z (ESI), [M+H]$^+$=293.1. $^1$H-NMR (300 mHz, DMSO-d$_6$) δ 1.38 (9H, s), 2.85-2.87 (3H, m), 3.76 (2H, s), 3.92 (2H, s), 4.11 (2H, s), 6.28 (1H, s), 6.69 (1H, s), 7.51 (1H, s), Step 3. tert-butyl (1-(6-((3-amino-6-(3-methylimidazo[1,2-a]pyridin-6-yl)-5-(oxazol-2-yl)pyrazine-2-carboxamido)methyl)pyridin-2-yl)azetidin-3-yl) (methyl)carbamate A solution of 3-amino-6-[3-methylimidazo[1,2-a]pyridin-6-yl]-5-(1,3-oxazol-2-yl)pyrazine-2-carboxylic acid (100 mg, 0.297 mmol, 1 equiv), tert-butyl N-[1-[6-(aminomethyl)pyridin-2-yl]azetidin-3-yl]-N-methylcarbamate (173.88 mg, 0.595 mmol, 2.0 equiv), DIEA (192.15 mg, 1.487 mmol, 5.0 equiv) and $T_3P$ (189.22 mg, 0.595 mmol, 2.0 equiv) in DMF (10 mL) was stirred for 2 h at room temperature. The resulting mixture was diluted with water (20 mL). The resulting mixture was extracted with EtOAc (3×30 mL). The combined organic layers were washed with brine (20 mL), dried over anhydrous Na$_2$SO$_4$. After filtration, the filtrate was concentrated under reduced pressure. The residue was purified by silica gel column chromatography, eluted with CH$_2$Cl$_2$/MeOH (10:1) to afford tert-butyl N-[1-(6-[[(3-amino-6-[3-methylimidazo[1,2-a]pyridin-6-yl]-5-(1,3-oxazol-2-yl)pyrazin-2-yl) formamido]methyl]pyridin-2-yl)azetidin-3-yl]-N-methylcarbamate (80 mg, 44.06%) as a light yellow oil. LCMS: m/z (ESI), [M+H]$^+$=611.3

Step 4. 3-amino-N-((6-(3-(methylamino)azetidin-1-yl)pyridin-2-yl)methyl)-6-(3-methylimidazo[1,2-a]pyridin-6-yl)-5-(oxazol-2-yl)pyrazine-2-carboxamide A solution of tert-butyl N-[1-(6-[[(3-amino-6-[3-methylimidazo[1,2-a]pyridin-6-yl]-5-(1,3-oxazol-2-yl)pyrazin-2-yl) formamido]methyl]pyridin-2-yl)azetidin-3-yl]-N-methylcarbamate (80 mg, 0.131 mmol, 1 equiv) and TFA (2 mL) in DCM (5 mL) was stirred for 2 h at room temperature. The residue was neutralized to pH 7 with saturated NaHCO$_3$ (aq.). The resulting mixture was extracted with EtOAc (3×50 mL). The combined organic layers were washed with water (2×30 mL), dried over anhydrous Na$_2$SO$_4$. After filtration, the filtrate was concentrated under reduced pressure. The crude product was purified by Prep-HPLC with the following conditions (Column: XBridge Shield RP18 OBD Column, 5 um, 19*150 mm; Mobile Phase A: Water (0.05% NH$_3$H$_2$O), Mobile Phase B: ACN; Flow rate: 20 mL/min; Gradient: 32% B to 52% B in 8 min; 254/220 nm; Rt: 7.88 min) to afford 3-amino-N-([6-[3-(methylamino)azetidin-1-yl]pyridin-2-yl]methyl)-6-[3-methylimidazo[1,2-a]pyridin-6-yl]-5-(1,3-oxazol-2-yl)pyrazine-2-carboxamide (Cmpd. 303) (30 mg, 44.85%) as a yellow solid. LCMS: m/z (ESI), [M+H]$^+$=511.3 $^1$H-NMR (300 mHz, DMSO-d$_6$) δ 2.20 (3H, s), 2.49 (3H, s), 3.57-3.59 (1H, m), 3.60-3.63 (2H, m), 4.03-4.07 (2H, m), 4.53 (2H, s), 6.26-6.28 (1H, m), 6.64-6.66 (1H, m), 7.28-7.30 (2H, m), 7.31-7.33 (1H, m), 7.45-7.49 (2H, m), 8.01 (1H, s), 8.37 (1H, s).

Examples 304/305. Preparation of 3-amino-6-(3-methylimidazo[1,2-a]pyridin-6-yl)-5-(pyridin-2-yl)-N-((tetrahydrofuran-3-yl) methyl)pyrazine-2-carboxamide (Cmpd. 304/305)

SCHEME 136

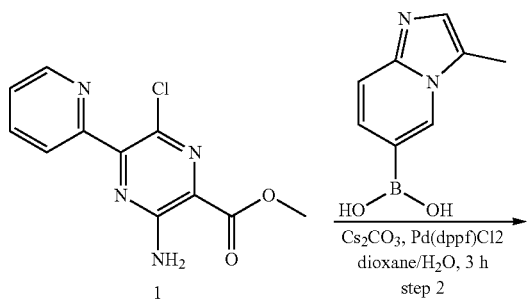

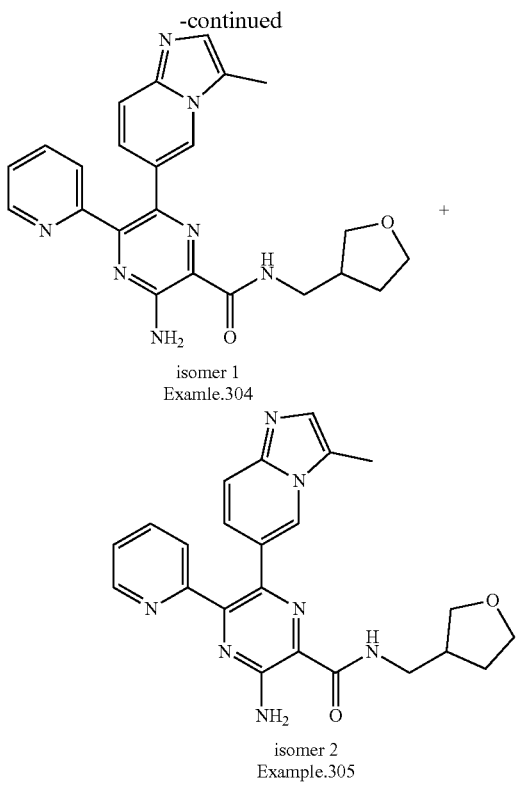

isomer 1
Examle.304 isomer 2
Example.305

Step 1. 3-amino-6-chloro-5-(pyridin-2-yl)pyrazine-2-carboxylate

A solution of 2-(tributylstannyl)pyridine (1658.12 mg, 5.05 mmol, 2.00 equiv), methyl 3-amino-5,6-dichloropyrazine-2-carboxylate (500 mg, 2.525 mmol, 1 equiv), Pd(PPh$_3$)$_2$Cl$_2$ (158.06 mg, 0.226 mmol, 0.1 equiv) and LiCl (190.94 mg, 5.05 mmol, 2 equiv) in 1,4-dioxane (20 mL) was stirred for 16 hours at 90° C. under nitrogen atmosphere. This reaction was purification together with another batch E02189-006. The mixture was through a quick silica gel column chromatography, eluted with CH$_2$Cl$_2$/MeOH (1:1) to afford crude product. The resulting mixture was concentrated under reduced pressure. The residue was purified by Prep-TLC (CH$_2$Cl$_2$/MeOH 30:1) to afford methyl 3-amino-6-chloro-5-(pyridin-2-yl)pyrazine-2-carboxylate (180 mg, 30.20%) as a yellow solid. LCMS: m/z (ESI), [M+H]$^+$= 265.2. $^1$H NMR (300 MHz, DMSO-d$_6$) δ 3.9 (3H, s), 7.5 (1H, ddd), 7.6-7.7 (2H, m), 7.8 (1H, dt), 8.0 (1H, td), 8.7 (1H, ddd)

Step 2. 3-amino-6-[3-methylimidazo[1,2-a]pyridin-6-yl]-5-(pyridin-2-yl)pyrazine-2-carboxylate A solution of methyl 3-amino-6-chloro-5-(pyridin-2-yl)pyrazine-2-carboxylate (120 mg, 0.453 mmol, 1 equiv), [3-methylimidazo[1,2-a]pyridin-6-yl]boronic acid (159.58 mg, 0.907 mmol, 2 equiv), Pd(dppf)Cl$_2$CH$_2$Cl$_2$ (37.03 mg, 0.045 mmol, 0.1 equiv), and Cs$_2$CO$_3$ (295.45 mg, 0.907 mmol, 2 equiv) in 1,4-dioxane (12.5 mL) and H$_2$O (1.5 mL) was stirred for 4 hours under N$_2$. The resulting mixture was concentrated under reduced pressure. The residue was purified by Prep-TLC (CH$_2$Cl$_2$/MeOH 25:1) to afford methyl 3-amino-6-[3-methylimidazo[1,2-a]pyridin-6-yl]-5-(pyridin-2-yl)pyrazine-2-carboxylate (50 mg, 30.60%) as a yellow solid. LCMS: m/z (ESI), [M+H]$^+$=361.3

Step 3. 3-amino-6-[3-methylimidazo[1,2-a]pyridin-6-yl]-5-(pyridin-2-yl)pyrazine-2-carboxylic Acid To a stirred solution of methyl 3-amino-6-[3-methylimidazo[1,2-a]pyridin-6-yl]-5-(pyridin-2-yl)pyrazine-2-carboxylate (1 equiv) in 1,4-dioxane (10 mL) and H$_2$O (1 mL) was added LiOH (3 equiv) in portions at room temperature. The resulting mixture was stirred for 2 hs at room temperature. The mixture was acidified to pH 3 with HCl (aq.). The resulting mixture was concentrated under reduced pressure. The crude product (50 mg) was used in the next step directly without further purification. LCMS: m/z (ESI), [M+H]$^+$= 347.3

Step 4. 3-amino-6-[3-methylimidazo[1,2-a]pyridin-6-yl]-N-[(oxolan-3-yl)methyl]-5-(pyridin-2-yl)pyrazine-2-carboxamide To a stirred solution of 3-amino-6-[3-methylimidazo[1,2-a]pyridin-6-yl]-5-(pyridin-2-yl)pyrazine-2-carboxylic acid (50 mg, 0.144 mmol, 1 equiv), DMF (5 mL) and 1-(oxolan-3-yl)methanamine (73.01 mg, 0.722 mmol, 5 equiv) in DMF (5 mL) was added DIPEA (93.29 mg, 0.722 mmol, 5 equiv) in portions at room temperature. The resulting mixture was stirred for 2 hs at room temperature. The reaction was quenched by the addition of Water (20 mL) at room temperature. The resulting mixture was extracted with CH$_2$Cl$_2$ (2×25 mL). The combined organic layers were washed with water (2×20 mL), dried over anhydrous Na$_2$SO$_4$. After filtration, the filtrate was concentrated under reduced pressure. The residue was purified by Prep-TLC (CH$_2$Cl$_2$/MeOH 15:1) to afford 3-amino-6-[3-methylimidazo[1,2-a]pyridin-6-yl]-N-[(oxolan-3-yl)methyl]-5-(pyridin-2-yl)pyrazine-2-carboxamide (30 mg, 48.39%) as a yellow solid. LCMS: m/z (ESI), [M+H]$^+$=430.3

Step 5. rel-3-amino-6-[3-methylimidazo[1,2-a]pyridin-6-yl]-N-[[(3R)-oxolan-3-yl]methyl]-5-(pyridin-2-yl)pyrazine-2-carboxamide The crude product (30 mg) was purified by Prep-Chiral HPLC with the following conditions (Column: Chiralpak ID-2, 2*25 cm, 5 um; Mobile Phase A: MTBE (10 mM NH$_3$-MEOH)-HPLC, Mobile Phase B: MeOH-HPLC; Flow rate: 20 mL/min; Gradient: 15 B to 15 B in 20 min; 220/254 nm; RT1:12.919; RT2:16.74) to afford 3-amino-6-[3-methylimidazo[1,2-a]pyridin-6-yl]-N-[[oxolan-3-yl]methyl]-5-(pyridin-2-yl)pyrazine-2-carboxamide (Cmpd. 304) (8 mg, 26.67%) and 3-amino-6-[3-methylimidazo[1,2-a]pyridin-6-yl]-N-[[oxolan-3-yl]methyl]-5-(pyridin-2-yl)pyrazine-2-carboxamide (Cmpd. 305) as a yellow solid.

(Cmpd. 304) LCMS: m/z (ESI), [M+H]$^+$=430.3. $^1$H NMR (400 MHz, DMSO-d$_6$) δ 1.7 (1H, dq), 1.9-2.1 (1H, m), 2.3 (3H, s), 2.6 (1H, dt), 3.29-3.37 (2H, m), 3.5 (1H, dd), 3.6-3.7 (2H, m), 3.8 (1H, td), 7.1 (1H, dd), 7.3 (2H, t), 7.4 (1H, dd), 7.8 (2H, d), 7.9 (1H, td), 8.1 (1H, s), 8.4 (1H, d), 9.0 (1H, t).

(Cmpd. 305) LCMS: m/z (ESI), [M+H]$^+$=430.2. $^1$H NMR (400 MHz, DMSO-d$_6$) δ 1.7 (1H, dq), 1.9-2.1 (1H, m), 2.3 (3H, s), 2.6 (1H, dt), 3.37 (2H, m), 3.5-3.8 (4H, td), 7.1 (1H, dd), 7.3 (2H, t), 7.4 (1H, dd), 7.8 (2H, d), 7.9 (1H, td), 8.1 (1H, s), 8.4 (1H, d), 9.0 (1H, t).

Example 307. Binding Affinities to Different Adenosine Receptors

Binding affinity and specificities of the compounds against different subtype of human adenosine receptors (hA1, hA2A, hA2B and hA3) were characterized with cell membrane chromatography binding analysis.

The compounds at different concentrations were incubate with hA1 membrane (from PerkinElmer) and [$^3$H]-8-Cyclopentyl-1,3-dipropylxanthine (DPCPX) for 50 min at 25° C., meanwhile 100 μL 0.5% PEI solution was added into UNFILTER-96 GF/B filter plate for 60 min at 4° C., then UNIFILTER-96 GF/B filter plate was washed twice with 50 ml wash buffer, the membrane mix was transferred into UNIFILTER-96 GF/B filter plate, and the filter plate was washed 4 times before incubated at 55° C. for 10 min. At last, 40 μL ULTIMA GOLD was added into each well, and CPM was read by TopCount.

The compounds at different concentrations were incubate with hA2a membrane (from PerkinElmer) and [$^3$H]-CGS21680 for 90 min at 25° C., meanwhile 100 L 0.5% PEI solution was added into UNFILTER-96 GF/B filter plate for 60 min at 4° C., then UNIFILTER-96 GF/B filter plate was washed twice with 50 ml wash buffer, the membrane mix was transferred into UNIFILTER-96 GF/B filter plate, and the filter plate was washed 4 times before incubated at 55° C. for 10 min. At last, 40 L ULTIMA GOLD was added into each well, and CPM was read by TopCount.

The compounds at different concentrations were incubate with hA2b membrane (from PerkinElmer) and [$^3$H]-DPCPX for 60 min at 27° C., and the binding reactions were stopped by rapid filtration through 0.5% BSA coated UNIFILTER-96 GF/C plates using cell harvester. The filter plates were then washed three times with ice cold wash buffer, and dried at 37° C. for 120 min. At last, 50 μL of scintillation cocktail was added into each well, and CPM was read by TopCount.

The compounds at different concentrations were incubate with hA3 membrane (from PerkinElmer) and [$^{125}$I]-AB-MECA for 60 min at 27° C., the binding reactions were stopped by rapid filtration through 0.5% BSA coated UNIFILTER-96 GF/C plates using cell harvester. The filter plates were then washed three times with ice cold wash buffer, and dried at 37° C. for 120 min. At last, 50 L of scintillation cocktail was added into each well, and CPM was read by TopCount.

Binding affinity and specificities of the exemplary compounds against human A1, A2a, A2b and A3 receptors are shown in Table 3 below. The empty boxes in the tables below indicate data not collected yet.

TABLE 3

Binding Affinities of Exemplary Compounds

| Cmpd. number | Binding Affinity (IC$_{50}$ nM) | | |
|---|---|---|---|
| | hA2a | hA2b | hA1 |
| 3 | 1.9 | 1.4 | 16 |
| 14 | 3.1 | | |
| 16 | 3.9 | | 15 |
| 19 | 10000 | | 10000 |
| 22 | 3.5 | | |
| 23 | 3.5 | 2.9 | |
| 24 | 11 | | |
| 29 | 2.3 | | |
| 34 | 3.7 | | |
| 35 | 3.2 | | |
| 37 | 1.0 | | |
| 40 | 5.2 | | |
| 41 | 3.3 | | |
| 43 | 21 | | 245 |
| 47 | 2.6 | | 696 |
| 48 | 3.1 | | 67 |
| 49 | 5.3 | | 117 |
| 51 | 2.1 | | 78 |
| 61 | 7.9 | | 52 |
| 65 | 13 | 4423 | 30 |
| 88 | 2.4 | | 17 |
| 98 | 9.3 | | 10 |
| 100 | 8.4 | | 685 |
| 101 | 2.4 | | 5.6 |
| 104 | 6.2 | | 49 |
| 115 | 6.9 | | 0.9 |
| 120 | 3.7 | | 156 |
| 121 | 2.9 | | 116 |
| 126 | 1.4 | | 78 |
| 127 | 3.1 | | 68 |
| 133 | 2.7 | | 271 |
| 134 | 5.5 | | 216 |
| 135 | 2.0 | | 161 |
| 136 | 1.7 | | 182 |
| 137 | 3.9 | | 195 |
| 138 | 2.2 | | 17 |
| 139 | 5.2 | | 66 |
| 147 | 5.6 | | 108 |
| 160 | 3.15 | | 333 |
| 218 | 9.1 | | 475 |

Example 308. FLIPR™ and cAMP Inhibition Assay hADORA1/CHO (hA1 expressing) cells (Genscript) were plated at 1×10$^4$ cells/well into 384-well polystyrene plates one day before starting the experiment. On the day of experiment, the supernatant was discard and replaced with 40 μL of dye (FLIPR calcium 5 Assay Kit) per well and the plates were incubated for 60 mins at 37° C. plus 5% CO$_2$. Then testing compounds were added at different concentrations for FLIPR™ inhibition assay. After a 400 s incubation with compound, 10 M adenosine was added into the cells, and the signal was captured by FLIPR.

hA2a/CHO, hA2b/CHO, hA3/CHO and mA2a/CHO (Genscript) were plated at 5×10$^3$ cells/well into 384-well polystyrene plates at the day of experiment. Compounds were pre-incubated with cells for 30 min at 37° C., 5% CO$_2$. Then 10 M adenosine was added to the cells and incubated for 30 min at 37° C., 5% CO$_2$. Detection reagent (CISBIO) was added and the plates were incubated for 60 min at room temperature. The signal was captured by Envision.

FLIPR™ and cAMP inhibition activities of exemplary compounds in different adenosine receptor over-expressing cell lines are shown in Table 4 below.

TABLE 4

FLIPR and cAMP Inhibitory Activity of Exemplary Compounds

| Cmpd. number | cAMP & FLIPR IC$_{50}$ (nM) | | | | |
|---|---|---|---|---|---|
| | hA2a | hA2b | mA2a | hA1 | hA3 |
| 1 | 151 | 10000 | 1061 | | |
| 2 | 0.9 | 92 | 21 | 26 | |

TABLE 4-continued

FLIPR and cAMP Inhibitory Activity of Exemplary Compounds

| Cmpd. number | hA2a | hA2b | mA2a | hA1 | hA3 |
|---|---|---|---|---|---|
| 3 | 4.5 | 53 | 5.8 | 159 | 10000 |
| 4 | 15 | 1216 | 43 | 18 | |
| 5 | 28 | 10000 | 219 | 10000 | |
| 6 | 87 | 10000 | 1061 | 8839 | |
| 7 | 166 | 3862 | 237 | 98 | |
| 8 | 116 | 10000 | 390 | 3405 | |
| 9 | 5.4 | 10000 | 25 | 1003 | 10000 |
| 10 | 17 | 17 | 41 | 58 | 10000 |
| 11 | 89 | 1013 | 87 | 4495 | 10000 |
| 12 | 36 | 9032 | 678 | 414 | 6936 |
| 13 | 6.1 | 4639 | 51 | 72 | 10000 |
| 14 | 98 | 768 | 213 | 10000 | 10000 |
| 15 | 39 | 10000 | 86 | 804 | |
| 16 | 5.3 | 336 | 8.3 | 32 | |
| 17 | 117 | 10000 | 132 | 951 | |
| 18 | 105 | 10000 | 116 | 1154 | |
| 19 | 15 | 51 | 8.8 | 22 | |
| 20 | 41 | 3597 | 170 | 6610 | 10000 |
| 21 | 98 | 638 | 73 | 18 | |
| 22 | 60 | 2549 | 132 | 3384 | 10000 |
| 23 | 25 | 880 | 64 | 281 | 10000 |
| 24 | 199 | 1456 | 641 | 9356 | 10000 |
| 25 | 125 | 10000 | 242 | 3295 | 10000 |
| 26 | 108 | 10000 | 309 | 725 | 10000 |
| 27 | 60 | 10000 | 177 | 1769 | 10000 |
| 28 | 129 | 10000 | 160 | 4905 | 10000 |
| 29 | 6.8 | 103 | 60 | 66 | 10000 |
| 30 | 45 | 603 | 47 | 214 | 10000 |
| 31 | 34 | 164 | 75 | 35 | 10000 |
| 32 | 0.2 | 3.0 | 2.0 | 494 | 10000 |
| 33 | 56 | 10000 | 123 | 3033 | 10000 |
| 34 | 63 | 330 | 192 | 10000 | 10000 |
| 35 | 15 | 203 | 43 | 112 | 10000 |
| 36 | 180 | 2533 | 419 | 3010 | |
| 37 | 9.3 | 95 | 56 | 28 | |
| 38 | 2.4 | 59 | 5.3 | 61 | |
| 39 | 7.8 | 2125 | 3.3 | 32 | |
| 40 | 51 | 1353 | 211 | 10000 | |
| 41 | 1.6 | 38 | 13 | 123 | |
| 42 | 14 | 102 | 16 | 51 | |
| 43 | 49 | 159 | 240 | 10000 | |
| 44 | 131 | 2110 | 786 | 10000 | |
| 45 | 94 | 912 | 566 | 10000 | |
| 46 | 102 | 1615 | 125 | 488 | |
| 47 | 57 | 141 | 3259 | 10000 | |
| 48 | 19 | 84 | 256 | 7161 | |
| 49 | 138 | 309 | 413 | 1711 | |
| 50 | 33 | 249 | 85 | 90 | |
| 51 | 1.2 | 5.5 | 9.6 | 2500 | |
| 52 | 89 | 10000 | 5959 | 2633 | |
| 53 | 60 | 10000 | 529 | | |
| 54 | 117 | 10000 | 2078 | 1595 | |
| 55 | 133 | 4440 | 1590 | 413 | |
| 56 | 28 | 10000 | 623 | 940 | |
| 57 | 41 | 1684 | 278 | 142 | |
| 58 | 19 | 62 | 81 | 18 | |
| 59 | 29 | 10000 | 66 | | |
| 60 | 24 | 10000 | 150 | | |
| 61 | 0.6 | 10000 | 6.0 | | |
| 62 | 1.8 | 10000 | 28 | | |
| 63 | 33 | 10000 | 601 | | |
| 64 | 52 | 10000 | 10000 | | |
| 65 | 19 | 10000 | 50 | | |
| 66 | 107 | 10000 | 730 | | |
| 67 | 6.4 | 67 | 25 | | |
| 68 | 7.5 | 952 | 64 | | |
| 69 | 15 | 213 | 20 | | |
| 70 | 10 | 10000 | 5.2 | | |
| 71 | 64 | 1941 | 1247 | 388 | |
| 72 | 1.3 | 23 | 8.1 | 14 | |
| 73 | 0.4 | 8.1 | 4.2 | 20 | |
| 74 | 44 | 10000 | 1947 | 216 | |
| 75 | 6.1 | 10000 | 157 | 44 | |
| 76 | 4.2 | 76 | 22 | 68 | |
| 77 | 17 | 358 | 26 | | |
| 78 | 44 | 10000 | 934 | 2731 | |
| 79 | 33 | 10000 | 540 | 597 | |
| 80 | 44 | 4174 | 158 | 1405 | |
| 81 | 98 | 10000 | 301 | 4751 | |
| 82 | 19 | 276 | 59 | | |
| 83 | 2.0 | 547 | 116 | 132 | |
| 84 | 18 | 10000 | 238 | 1195 | |
| 85 | 2.5 | 418 | 36 | 299 | |
| 86 | 5.0 | 7834 | 192 | 539 | |
| 87 | 10 | 153 | 22 | 31 | |
| 88 | 61 | 3170 | 272 | 34 | 10000 |
| 89 | 17 | 5621 | 297 | | |
| 90 | 4.0 | 781 | 95 | | |
| 91 | 8.9 | 1419 | 72 | | |
| 92 | 41 | 10000 | 216 | | |
| 93 | 8.0 | 354 | 127 | | |
| 94 | 3.9 | 76 | 34 | 2956 | |
| 95 | 69 | 78 | 667 | 10000 | |
| 96 | 2.5 | 164 | 7.5 | 136 | |
| 97 | 50 | 4885 | 40 | 482 | |
| 98 | 21 | 126 | 64 | 70 | |
| 99 | 5.1 | 200 | 35 | 171 | |
| 100 | 76 | 312 | 4530 | 10000 | |
| 101 | 0.1 | 1.4 | 0.4 | 45 | |
| 102 | 9.9 | 120 | 48 | 78 | |
| 103 | 38 | 2127 | 16 | 272 | |
| 104 | 7.9 | 32 | 52 | 4395 | |
| 105 | 0.1 | 1.8 | 0.8 | 3.5 | |
| 107 | 76 | 3494 | 166 | 341 | |
| 108 | 0.6 | 132 | 3.6 | 55 | |
| 109 | 13 | 240 | 20 | 486 | |
| 110 | 0.7 | 11 | 1.0 | 31 | |
| 111 | 0.5 | 81 | 6.5 | 2812 | |
| 112 | 1.3 | 502 | 18 | 10000 | |
| 113 | 0.4 | 68 | 1.0 | 70 | |
| 114 | 0.7 | 170 | 1.5 | 83 | |
| 115 | 3.2 | 596 | 12 | 81 | |
| 116 | 9.6 | 6022 | 17 | 61 | |
| 117 | 0.7 | 146 | 2.6 | 64 | |
| 118 | 3.1 | 6.8 | 1.7 | 35 | |
| 119 | 1.1 | 31 | 4.7 | 41 | |
| 120 | 14 | 775 | 167 | 10000 | |
| 121 | 15 | 747 | 204 | 10000 | |
| 122 | 34 | 887 | 126 | 10000 | |
| 123 | 56 | 1306 | 153 | 10000 | |
| 124 | 2259 | 10000 | 10000 | 10000 | |
| 125 | 1442 | 10000 | 10000 | 10000 | |
| 126 | 1.6 | 77 | 7.0 | 1229 | |
| 127 | 1.7 | 99 | 14 | 2420 | |
| 128 | 63 | 10000 | 410 | 10000 | |
| 129 | 140 | 10000 | 944 | 10000 | |
| 130 | 295 | 10000 | 2797 | 10000 | |
| 131 | 332 | 10000 | 2698 | 10000 | |
| 132 | 13 | 258 | 65 | 10000 | |
| 133 | 5.9 | 554 | 19 | 10000 | |
| 134 | 4.3 | 314 | 77 | 10000 | |
| 135 | 2.3 | 182 | 23 | 9255 | |
| 136 | 1.8 | 512 | 27 | 10000 | |
| 137 | 1.7 | 464 | 34 | 10000 | |
| 138 | 7.1 | 959 | 70 | 242 | |
| 139 | 8.8 | 932 | 66 | 906 | |
| 142 | 10 | 319 | 73 | 10000 | |
| 143 | 1.7 | 162 | 12 | 180 | |
| 144 | 4.6 | 1415 | 61 | 10000 | |
| 145 | 32 | 789 | 205 | 10000 | |
| 146 | 8.5 | 256 | 101 | 10000 | |
| 147 | 3.8 | 134 | 15 | 2378 | |
| 148 | 0.5 | 99 | 1.1 | 69 | |
| 149 | 1.5 | 85 | 7.8 | 1563 | |
| 150 | 3.4 | 108 | 6.5 | 26 | |
| 151 | 0.8 | 193 | 12 | 10000 | |
| 152 | 5.1 | 369 | 43 | 10000 | |
| 153 | 19 | 592 | 120 | 10000 | |

TABLE 4-continued

FLIPR and cAMP Inhibitory Activity of Exemplary Compounds

| Cmpd. number | cAMP & FLIPR IC$_{50}$ (nM) | | | | |
|---|---|---|---|---|---|
| | hA2a | hA2b | mA2a | hA1 | hA3 |
| 154 | 11 | 1150 | 121 | 10000 | |
| 155 | 0.6 | 188 | 12 | 3655 | |
| 156 | 4.4 | 1203 | 41 | 83 | |
| 157 | 0.3 | 59 | 2.9 | | |
| 158 | 1.27 | 167 | 3.46 | 756 | |
| 159 | 5.31 | 1640 | 13.17 | >10000 | |
| 160 | 0.26 | 163 | 0.89 | 4862 | |
| 161 | 0.95 | 98 | 0.8 | 34 | |
| 162 | 0.71 | 147 | 8.12 | 794 | |
| 163 | 3.28 | 387 | 22 | >10000 | |
| 164 | 0.94 | 479 | 12.68 | >10000 | |
| 165 | 0.24 | 73 | 1.42 | 207 | |
| 166 | 0.24 | 47 | 1.48 | 358 | |
| 167 | 1.2 | | | | |
| 168 | 1.1 | | | | |
| 171 | 1.0 | 228 | 15 | 589 | |
| 172 | 5.1 | | | | |
| 173 | 5.1 | | | 6498 | |
| 174 | 6.9 | | | | |
| 175 | 0.9 | | | | |
| 176 | 11 | | | 599 | |
| 198 | 3.6 | 38 | 31 | >10000 | |
| 199 | 0.7 | 102 | 1.6 | 34 | |
| 200-2 | 12 | 3542 | 169 | >10000 | |
| 201-2 | 29 | >10000 | 519 | >10000 | |
| 202 | 17 | 1128 | 105 | 6924 | |
| 203-1 | 15 | >10000 | 161 | 91 | |
| 204-1 | 49 | >10000 | 249 | 294 | |
| 205 | 2.0 | 67 | 7.5 | 153 | |
| 206 | 5.3 | 707 | 50 | 2486 | |
| 207 | 12 | 774 | 44 | 5948 | |
| 208 | 8.9 | 1227 | 19 | 9537 | |
| 209 | 14 | 1260 | 134 | >10000 | |
| 210 | 11 | 972 | 88 | 14725 | |
| 211 | 3.6 | 160 | 19 | 319 | |
| 212 | 34 | 3432 | 175 | >10000 | |
| 213 | 22 | 2528 | 54 | 505 | |
| 214 | 19 | 1045 | 99 | >10000 | |
| 215 | 12 | 568 | 9.6 | 891 | |
| 216 | 5.1 | 282 | 24 | 799 | |
| 217 | 8.5 | 594 | 8.3 | 4794 | |
| 218 | 1.5 | 359 | 28 | >10000 | |
| 219 | 4.9 | 2297 | 220 | >10000 | |
| 220 | 1.7 | 2095 | 42 | 4665 | |
| 221 | 1.6 | 1026 | 33 | 7535 | |
| 222 | 9.6 | 2774 | 43 | >10000 | |
| 223 | 9.9 | 525 | 132 | >10000 | |
| 224 | 3.2 | 245 | 27 | 7884 | |
| 225 | 32 | 254 | 177 | >10000 | |
| 226 | 3.0 | 177 | 30 | 947 | |
| 227 | 4.4 | 99 | 24 | 781 | |
| 228 | 2.7 | 210 | 23 | 2023 | |
| 229 | 2.4 | 157 | 19 | 1646 | |
| 230 | 15 | | | 6003 | |
| 231 | 6.2 | | | 306 | |
| 232 | 0.5 | | | 1503 | |
| 233 | 38 | | | 1909 | |
| 234 | 5.3 | | | 836 | |
| 235 | 0.8 | | | 5183 | |
| 236 | 17 | | | >10000 | |
| 237 | 5.1 | | | 71 | |
| 238 | 0.5 | | | 401 | |
| 239 | 4.8 | | | 2957 | |
| 240 | 18 | 521 | 65 | 108 | |
| 241 | 4.0 | 205 | 27 | 272 | |
| 242 | 2.9 | 683 | 51 | 294 | |
| 243 | 7.6 | 181 | 30 | 92 | |
| 244 | 16 | 157 | 31 | 260 | |
| 245 | 3.8 | 247 | 39 | 87 | |
| 246 | 17 | 1101 | 67 | 44 | |
| 247 | 36 | 1999 | 345 | 1489 | |
| 248 | 2.9 | 140 | 18 | 121 | |
| 249 | 5.7 | 423 | 50 | >10000 | |
| 250 | 5.0 | 212 | 31 | 36 | |
| 251 | 4.7 | 657 | 34 | 425 | |
| 252 | 2.9 | 821 | 30 | 260 | |
| 253 | 12 | | | 8170 | |
| 254 | 0.7 | | | 99 | |
| 255 | 20 | | | 6855 | |
| 256 | 1.8 | | | 34 | |
| 257 | 1.5 | | | 20 | |
| 258 | 8.1 | | | 2515 | |
| 259 | 3.7 | | | 47 | |
| 260 | 5.9 | | | 30 | |
| 261 | 0.4 | | | 158 | |
| 262 | 12 | | | 11647 | |
| 263 | 0.4 | | | 103 | |
| 264 | 25 | | | 84 | |
| 265 | 7.3 | | | 26 | |
| 266 | 7.6 | | | >10000 | |
| 267 | 0.9 | | | 2.8 | |
| 268 | 0.2 | | | 6.7 | |
| 269 | 37 | | | >10000 | |
| 270 | 7.4 | | | 300 | |
| 271-2 | 23 | | | 865 | |
| 272 | 37 | | | 338 | |
| 273 | 1.5 | | | 1311 | |
| 274 | 0.9 | | | 275 | |
| 275 | 6.1 | | | 39 | |
| 276 | 3.1 | | | 3072 | |
| 277 | 12 | | | 6559 | |
| 278 | 0.4 | | | 12 | |
| 279 | 1.4 | | | | |
| 280 | 0.6 | | | | |
| 281 | 0.3 | | | | |
| 282 | 4.5 | | | | |
| 283 | 3.4 | | | | |
| 284 | 0.7 | | | | |
| 285 | 4.5 | | | | |
| 286 | 3.2 | | | | |
| 287-2 | 4.4 | | | | |
| 288 | 0.6 | | | | |
| 289 | 1.9 | | | | |
| 290 | 5.8 | | | | |
| 291 | 1.1 | | | | |
| 292 | 0.4 | | | | |
| 293 | 0.4 | | | | |
| 294 | 0.2 | | | | |
| 295 | 13 | | | | |
| 296 | 0.9 | | | | |
| 297 | 0.2 | | | | |
| 298 | 47 | | | | |
| 299 | 4.9 | | | | |
| 300 | 0.8 | | | | |
| 301 | 3.0 | | | | |
| 302 | 2.4 | | | | |
| 303 | 0.4 | | | | |
| 304 | 8.2 | | | | |
| 305 | 12 | | | | |
| 306 | 14 | | | | |

What is claimed is:
1. A compound of Formula (I):

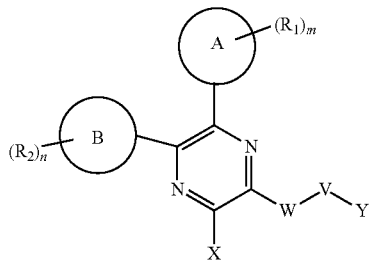

Formula (I)

or a pharmaceutically acceptable salt thereof,
wherein,
X is selected from amino;
ring A is selected from

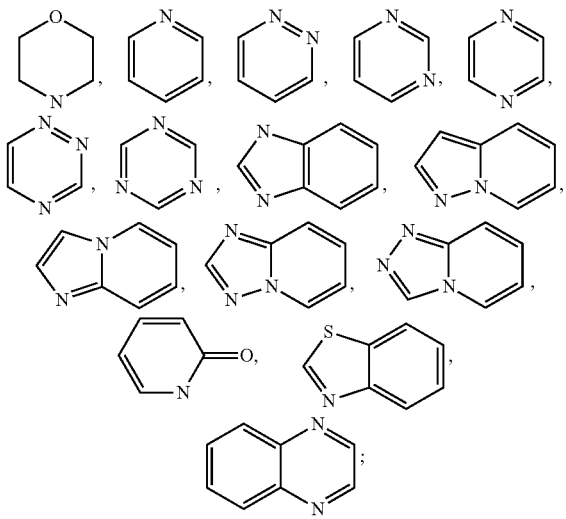

ring B is selected from 5-6 membered saturated or unsaturated carbocyclyl, or 5-6 membered saturated or unsaturated heterocyclyl having 1, 2, or 3 heteroatoms selected from N or O;
W is —$C_{1-12}$ alkylene- or —C(O)—, which can be mono or independently multi-substituted by hydroxyl, $C_{1-12}$ alkyl, $C_{1-12}$ alkoxyl, or $C_{1-12}$ alkyl-OH;
V is —NH—, —NH—$C_{1-12}$ alkylene-, —NH—C(O)—, or N-linked pyrrolidinyl, which can be mono or independently multi-substituted by hydroxyl, $C_{1-12}$ alkyl, $C_{1-12}$ alkoxyl, N—($C_{1-12}$ alkyl)amino, N,N—($C_{1-12}$ alkyl)$_2$amino or $C_{1-12}$ alkyl-OH;
Y is 3-12 membered saturated or unsaturated carbocyclyl, or 3-12 membered saturated or unsaturated heterocyclyl selected from:

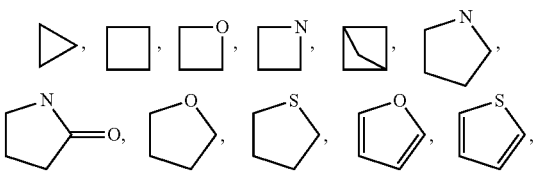

which can be optionally mono- or independently multi-substituted by $R_3$;
optionally, Y is hydroxyl, amino, cyano, carbonyl, carbamoyl, $C_{1-12}$ alkyl, $C_{1-12}$ alkyl-OH, $C_{1-12}$ alkoxyl, sulphonyl, ($C_{1-12}$ alkyl)sulphonyl, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, 3-12 membered saturated or unsaturated carbocyclyl or 3-12 membered saturated or unsaturated heterocyclyl, which can be optionally mono- or independently multi-substituted by $R_3$;
each $R_1$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, a 3-10 membered saturated or unsaturated carbocyclyl, or a 3-10 membered saturated or unsaturated heterocyclyl, wherein each $R_1$ can be optionally further mono- or independently multi-substituted by $R_4$;
each $R_2$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, a 3-10 membered saturated or unsaturated carbocyclyl, or a 3-10 membered saturated or unsaturated heterocyclyl, wherein each $R_2$ can be optionally further mono- or independently multi-substituted by $R_5$;
each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each R₃ can be optionally further mono- or independently multi-substituted by R₆;

wherein each R₄, R₅ or R₆ is independently selected from halogen, hydroxyl, cyano, amino, carbamoyl, sulphonyl, phosphinyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)₂ amino, N—($C_{1-12}$ alkyl)carbamoyl, N,N—($C_{1-12}$ alkyl)₂ carbamoyl, ($C_{1-12}$ alkyl) sulphonyl, ($C_{1-12}$ alkyl)phosphinyl, ($C_{1-12}$ alkyl)₂phosphinyl, $C_{1-12}$ alkanoylamino, $C_{1-12}$ alkylsulphonyl, $C_{1-12}$ alkyl substituted cycloalkyl;

m is 0, 1, 2, 3 or 4;

n is 0, 1, 2, 3, or 4.

2. The compound of claim 1, wherein

X is amino; and/or each R₁ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino, ethylamino, hydroxymethyl, hydroxyethyl, cyclopropyl, oxacyclopentanyl, oxetanyl, or 1,1-dioxothietanyl, which can be optionally further mono- or independently multi-substituted by R₄, wherein each R₄ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl; and/or m is 0, 1 or 2; and/or ring B is selected from:

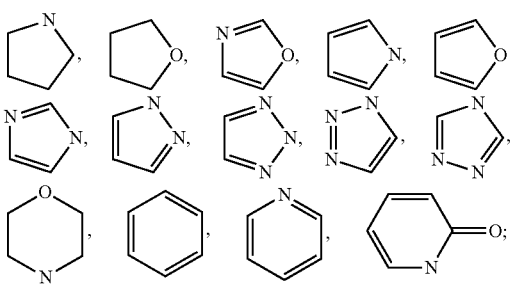

and/or each R₂ is independently selected from halogen, hydroxyl, amino, $C_{1-12}$ alkyl, or $C_{1-12}$ haloalkyl, wherein each R₂ can be optionally further mono- or independently multi-substituted by R₅ selected from halogen, hydroxyl, cyano, $C_{1-12}$ alkyl, $C_{1-12}$ haloalkyl, $C_{1-12}$ alkoxyl, or $C_{1-12}$ haloalkoxyl; optionally, wherein each R₂ is independently selected from cyano, fluoro, chloro, bromo, methyl, ethyl, n-propyl, isopropyl, fluoromethyl, difluoromethyl, trifluoromethyl, fluoroethyl, difluoroethyl, trifluoroethyl, ethoxyl, methoxyl, difluoromethoxy, trifluoromethoxy, methylamino, dimethylamino, ethylamino, isopropanylamino, hydroxymethyl, or hydroxyethyl; and/or n is 0, 1 or 2.

3. The compound of claim 1, wherein W is methylene or —C(O)—.

4. The compound of claim 1, wherein each R₃ is independently selected from hydroxyl, amino, cyano, carbamoyl, sulphonyl, phosphoryl, phosphinyl, fluoro, chloro, bromo, methyl, ethyl, n-propyl, isopropyl, methoxyl, ethoxyl, ethylamino, hydroxyethyl, hydroxymethyl, hydroxyethoxyl, sulphonylmethyl, aminomethyl, cyclopropyl, cyclopropylcarbonyl, cyclobutylamino, cyclopropyl, cyclobutanyl, cyclohexyl, pyranyl, furanyl, phenyl, pyridinyl, pyrazinyl, piperazinyl, morpholinyl, azetidinyl, pyrrolidinyl, piperidinyl, 1,4-oxanyl, bicycle[1.1.1]petanyl, 1,6-diazaspiro[3.3]heptanyl, 2,6-diazaspiro[3.3]heptanyl, 2,6-diazaspiro[3.4]octanyl, 3,6-diazabicyclo[3.1.1]heptanyl, 2,5-diazabicyclo[2.2.1]heptanyl, and 3,8-diazabicyclo[3.2.1]octanyl, which can be optionally further mono- or independently multi-substituted by fluoro, hydroxyl, methoxyl, ethyoxyl, amino, methylamino, dimethylamino, sulphonyl, methylsulphonyl, carbamoyl, N-methylcarbamoyl, N,N-dimethylcarbamoyl, hydroxymethyl, hydroxyethyl, cyclopropyl, cyclopropanecarbonyl.

5. The compound of claim 1, wherein each R₆ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)₂amino, N—($C_{1-12}$ alkyl)carbamoyl, N,N—($C_{1-12}$ alkyl)₂carbamoyl, $C_{1-12}$ alkanoylamino, $C_{1-12}$ alkylsulphonyl or $C_{1-12}$ alkyl substituted cycloalkyl.

6. The compound of claim 1, which having a structure of formula (Ia):

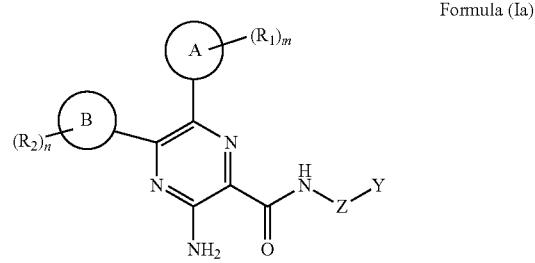

Formula (Ia)

or a pharmaceutically acceptable salt thereof, wherein, ring A is selected from

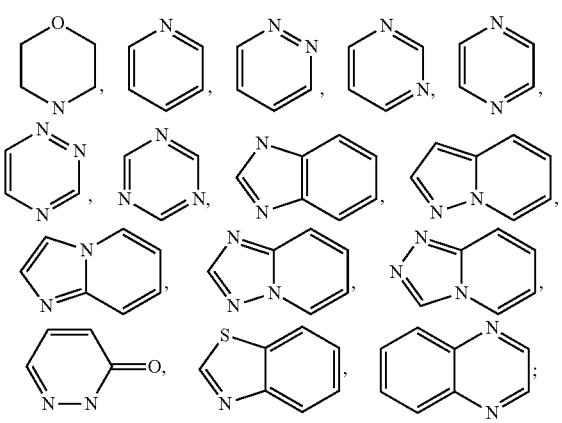

ring B is 5-6 membered saturated or unsaturated carbocyclyl, or 5-6 membered saturated or unsaturated heterocyclyl having 1, 2, or 3 heteroatoms selected from N or 0;

Z is —$C_{1-12}$ alkylene- or a bond;

Y is 3-12 membered saturated or unsaturated carbocyclyl, or 3-12 membered saturated or unsaturated heterocyclyl selected from:

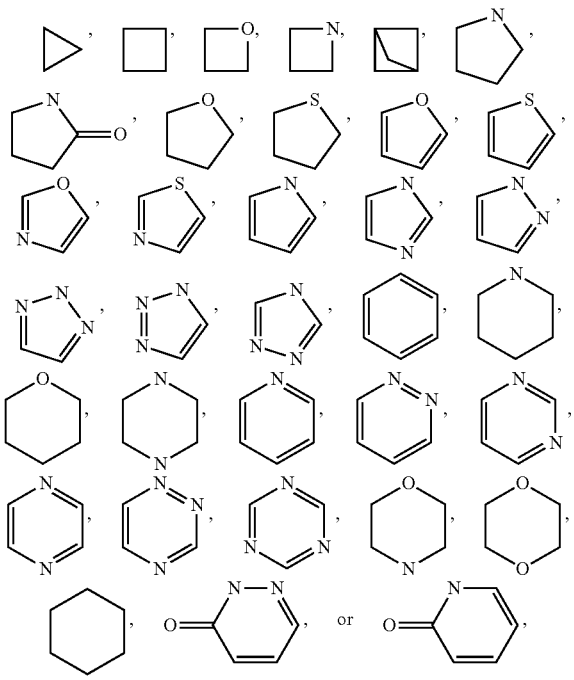

which can be optionally mono- or independently multi-substituted by $R_3$;

optionally, Y is hydroxyl, amino, cyano, carbonyl, carbamoyl, $C_{1-12}$ alkyl, $C_{1-12}$ alkyl-OH, $C_{1-12}$ alkoxyl, sulphonyl, ($C_{1-12}$ alkyl)sulphonyl, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, 3-12 membered saturated or unsaturated carbocyclyl or 3-12 membered saturated or unsaturated heterocyclyl, which can be optionally mono- or independently multi-substituted by $R_3$;

each $R_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino, ethylamino, hydroxymethyl, hydroxyethyl, cyclopropyl, oxacyclopentanyl, oxetanyl, or 1,1-dioxothietanyl, which can be optionally further mono- or independently multi-substituted by $R_4$;

each $R_2$ is independently halogen, hydroxyl, amino, $C_{1-12}$ alkyl, or $C_{1-12}$ haloalkyl, wherein each $R_2$ can be optionally further mono- or independently multi-substituted by $R_5$;

each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_6$;

each $R_4$ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl;

each $R_5$ is independently selected from halogen, hydroxyl, cyano, $C_{1-12}$ alkyl, $C_{1-12}$ haloalkyl, $C_{1-12}$ alkoxyl, or $C_{1-12}$ haloalkoxyl;

each $R_6$ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, $C_{1-12}$ alkylsulphonyl or $C_{1-12}$ alkyl substituted cycloalkyl;

m is 0, 1, 2, 3 or 4; and n is 0, 1, 2, 3 or 4.

7. The compound of claim 6, wherein Z is a bond, Y is cyclobutyl mono-substituted by $C_{1-12}$ alkoxyl.

8. The compound of claim 1, which having a structure of formula (Ia-i):

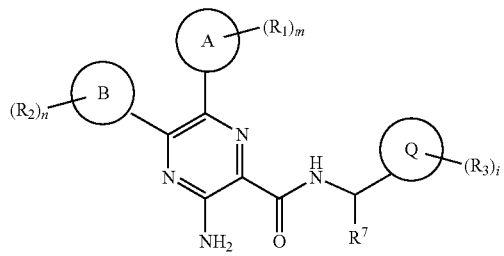

Formula (Ia-i)

or a pharmaceutically acceptable salt thereof,
wherein,
ring A is selected from

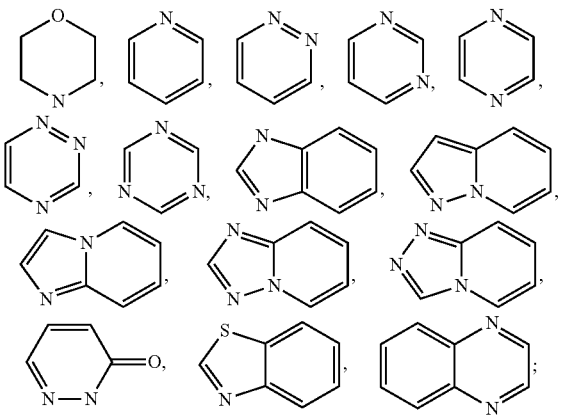

ring B is a phenyl ring or 5-6 membered saturated or unsaturated heterocyclyl having 1, 2, or 3 heteroatoms selected from N or 0;

ring Q is 3-6 membered saturated or unsaturated carbocyclyl, or 3-6 membered saturated or unsaturated heterocyclyl;

R<sub>7</sub> is hydrogen, $C_{1-12}$ alkyl, $C_{1-12}$ alkoxyl, or $C_{1-12}$ alkyl-OH;

each $R_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino, ethylamino, hydroxymethyl, hydroxyethyl, cyclopropyl, oxacyclopentanyl, oxetanyl, or 1,1-dioxothietanyl, which can be optionally further mono- or independently multi-substituted by $R_4$;

each $R_2$ is independently halogen, hydroxyl, amino, $C_{1-12}$ alkyl, or $C_{1-12}$ haloalkyl, wherein each $R_2$ can be optionally further mono- or independently multi-substituted by $R_5$;

each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_6$;

each $R_4$ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl;

each $R_5$ is independently selected from halogen, hydroxyl, cyano, $C_{1-12}$ alkyl, $C_{1-12}$ haloalkyl, $C_{1-12}$ alkoxyl, or $C_{1-12}$ haloalkoxyl;

each $R_6$ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, $C_{1-12}$ alkylsulphonyl or $C_{1-12}$ alkyl substituted cycloalkyl;

m is 0, 1, 2, 3 or 4;

n is 0, 1, 2, 3 or 4; and i is 0, 1, 2, 3 or 4.

9. The compound of claim 1, which having a structure of formula (Ib):

Formula (Ib)

or a pharmaceutically acceptable salt thereof, wherein, ring A is selected from

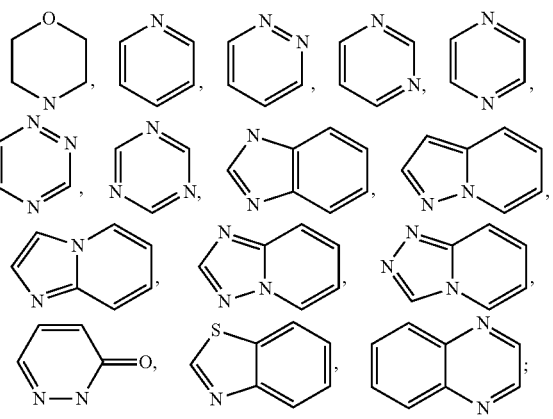

ring B is a phenyl ring, or 5-6 membered saturated or unsaturated heterocyclyl having 1, 2, or 3 heteroatoms selected from N or 0;

ring Q is 3-6 membered saturated or unsaturated carbocyclyl, or 3-6 membered saturated or unsaturated heterocyclyl;

R<sub>7</sub> is hydrogen, $C_{1-12}$ alkyl, $C_{1-12}$ alkoxyl, or $C_{1-12}$ alkyl-OH;

each $R_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino, ethylamino, hydroxymethyl, hydroxyethyl, cyclopropyl, oxacyclopentanyl, oxetanyl, or 1,1-dioxothietanyl, which can be optionally further mono- or independently multi-substituted by $R_4$;

each $R_2$ is independently halogen, hydroxyl, amino, $C_{1-12}$ alkyl, or $C_{1-12}$ haloalkyl, wherein each $R_2$ can be optionally further mono- or independently multi-substituted by $R_5$;

each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_6$;

each $R_4$ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl;

each $R_5$ is independently selected from halogen, hydroxyl, cyano, $C_{1-12}$ alkyl, $C_{1-12}$ haloalkyl, $C_{1-12}$ alkoxyl, or $C_{1-12}$ haloalkoxyl;

each $R_6$ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, $C_{1-12}$ alkylsulphonyl or $C_{1-12}$ alkyl substituted cycloalkyl;

m is 0, 1, 2, 3 or 4;

n is 0, 1, 2, 3 or 4; and i is 0, 1, 2, 3 or 4.

10. The compound of claim 9, wherein each $R_1$ is independently selected from fluoro, chloro, amino, methyl, ethyl, isopropyl, fluoromethyl, difluoromethyl, trifluoromethyl, hydroxyethyl, hydroxypropyl, methoxyethyl, 2-hydroxypropyl, cyclopropyl, or oxetanyl; and/or wherein m is 0, 1 or 2; and/or wherein ring B is selected from:

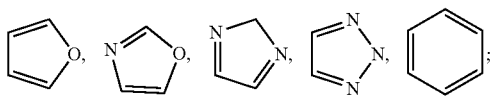

and/or wherein $R_2$ is methyl or fluoro; and/or wherein n is 0 or 1; and/or wherein ring Q is selected from:

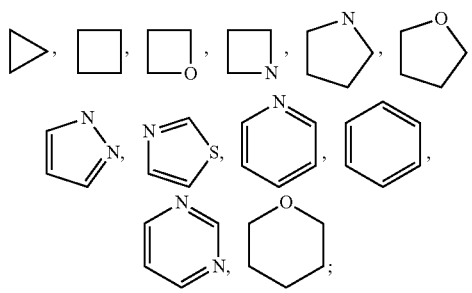

and/or wherein each $R_3$ is independently selected from fluoro, chloro, bromo, cyano, methyl, ethyl, fluoromethyl, difluoromethyl, trifluoromethyl, methoxyl, ethoxyl, difluoromethoxyl, trifluoromethoxyl, trifluoroethoxyl, hydroxymethyl, hydroxyethyl, hydroxyethyloxyl, methoxyethyloxyl, amino, methylamino, dimethylamino, ethylamino, isopropylamino, hydroxyethylamino, methylaminoethyloxyl, dimethylaminoethyloxyl, dimethylphosphinyl-methyl, carbamoyl, carbamoylmethoxyl, azetidinyl, pyrrolidyl, morpholinyl, pyrazinyl, dimethylaminoazetidinyl, 1-methyl-pyrazin-4-yl, 3-methyl-3,8-diaza-bicyclo[3.2.1]octan-8-yl, 3-Methyl-3,6-diaza-bicyclo[3.1.1]heptanyl, 8-methyl-3,8-diaza-bicyclo[3.2.1]octan-3-yl, 6-methyl-2,6-diaza-spiro[3.4]octan-2-yl, or 5-methyl-2,5-diaza-spiro[3.3]-heptan-2-yl; and/or wherein i=0, 1, 2 or 3.

11. The compound of claim 1, which having a structure of formula (Ia-ii):

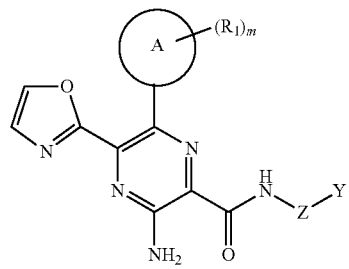

Formula (Ia-ii)

or a pharmaceutically acceptable salt thereof, wherein, ring A is selected from

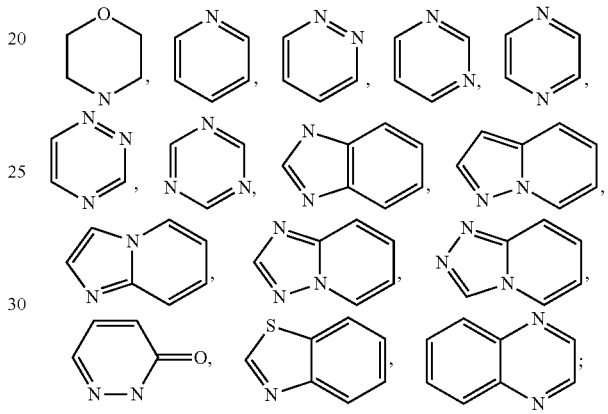

Z is —$C_{1-12}$ alkylene- or a bond;

Y is hydrogen, $C_{1-12}$ alkyl, $C_{1-12}$ alkoxyl, $C_{1-12}$ alkyl-OH, 3-6 membered saturated or unsaturated carbocyclyl, or 3-6 membered saturated or unsaturated heterocyclyl, which can be optionally mono- or independently multi-substituted by $R_3$;

each $R_1$ is independently selected from hydroxyl, fluoro, chloro, bromo, amino, carbamoyl, urea, carbamate, cyano, $C_{1-12}$ alkyl, fluoromethyl, difluoromethyl, trifluoromethyl, fluoroethyl, difluoroethyl, trifluoroethyl, methoxy, ethoxy, trifluoromethoxy, trifluoroethoxy, methylamino, dimethylamino, ethylamino, hydroxymethyl, hydroxyethyl, cyclopropyl, oxacyclopentanyl, oxetanyl, or 1,1-dioxothietanyl, which can be optionally further mono- or independently multi-substituted by $R_4$;

each $R_3$ is independently selected from halogen, hydroxyl, cyano, amino, carbamoyl, urea, carbamate, sulphonyl, phosphate, phosphoryl, phosphinyl, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{3-12}$ cycloalkyl)amino, N—($C_{1-12}$ alkyl)carbamoyl, N,N—($C_{1-12}$ alkyl)$_2$carbamoyl, ($C_{1-12}$ alkyl)sulphonyl, ($C_{1-12}$ alkyl)phosphinyl, ($C_{1-12}$ alkyl)$_2$phosphinyl, ($C_{1-12}$ alkyl)phosphoryl, ($C_{1-12}$ alkyl)$_2$ phosphoryl, $C_{1-12}$ alkanoylamino, N—($C_{1-12}$ alkyl-OH)amino, a 3-10 membered saturated or unsaturated carbocyclyl, or a 3-10 membered saturated or unsaturated heterocyclyl, wherein each $R_3$ can be optionally further mono- or independently multi-substituted by $R_6$;

each R₄ is independently selected from halogen, hydroxyl, cyano, amino, $C_{1-12}$ alkyl, $C_{1-12}$ haloalkyl, $C_{1-12}$ alkoxyl, or $C_{1-12}$ haloalkoxyl;

each R₆ is independently selected from halogen, hydroxyl, cyano, amino, carbamoyl, sulphonyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)₂amino, N—($C_{1-12}$ alkyl)carbamoyl, N,N—($C_{1-12}$ alkyl)₂carbamoyl, $C_{1-12}$ alkanoylamino, $C_{1-12}$ alkylsulphonyl or $C_{1-12}$ alkyl substituted cycloalkyl;

m is 0, 1, 2, 3 or 4; and n is 0, 1, 2, 3 or 4.

12. The compound of claim 11, wherein ring A is azaindolizinyl; and/or
   wherein m is 1, and R₁ is $C_{1-3}$ alkyl.

13. The compound of claim 11, wherein
   Z is a bond, Y is cyclobutyl mono-substituted by methoxyl; or
   Z is ethylene, Y is methoxyl; or
   Z is methylene, Y is phenyl, pyrrolidyl, or tetrahydrofuryl, which can be optionally mono- or independently multi-substituted by R₃.

14. The compound of claim 1, wherein the compound is selected from the group consisting of:
   3-amino-6-(2,6-dimethylpyridin-4-yl)-5-(4-fluorophenyl)-N-((3-fluoropyridin-2-yl)methyl)pyrazine-2-carboxamide;
   3-amino-N-(2,6-difluorobenzyl)-6-(2,6-dimethylpyridin-4-yl)-5-(oxazol-2-yl)pyrazine-2-carboxamide;
   3-amino-N-(2,6-difluorobenzyl)-6-(2,6-dimethylmorpholino)-5-(4-fluorophenyl)pyrazine-2-carboxamide;
   N-((3-amino-6-(2,6-dimethylpyridin-4-yl)-5-(4-fluorophenyl)pyrazin-2-yl)methyl)picolinamide;
   3-amino-N-((6-(dimethylamino)pyridin-2-yl)methyl)-6-(2,6-dimethylpyridin-4-yl)-5-(4-fluorophenyl)pyrazine-2-carboxamide;
   3-amino-N-(2,6-difluorobenzyl)-6-(2-methylpyridin-4-yl)-5-(oxazol-2-yl)pyrazine-2-carboxamide;
   3-amino-N-((6-(dimethylamino)pyridin-2-yl)methyl)-5-(4-fluorophenyl)-6-(2-methylpyridin-4-yl)pyrazine-2-carboxamide;
   3-amino-N-(2,6-difluorobenzyl)-6-(imidazo[1,2-a]pyridin-6-yl)-5-(oxazol-2-yl)pyrazine-2-carboxamide;
   6-([1,2,4]triazolo[4,3-a]pyridin-6-yl)-3-amino-N-(2,6-difluorobenzyl)-5-(oxazol-2-yl)pyrazine-2-carboxamide;
   3-amino-N-(2,6-difluorobenzyl)-6-(1-methyl-6-oxo-1,6-dihydropyridazin-3-yl)-5-(oxazol-2-yl)pyrazine-2-carboxamide;
   3-amino-N-((3-fluoropyridin-2-yl)methyl)-6-(imidazo[1,2-a]pyridin-6-yl)-5-(oxazol-2-yl)pyrazine-2-carboxamide;
   3-amino-6-(imidazo[1,2-a]pyridin-6-yl)-N-((2-methylthiazol-4-yl)methyl)-5-(oxazol-2-yl)pyrazine-2-carboxamide;
   3-amino-6-(imidazo[1,2-a]pyridin-6-yl)-5-(oxazol-2-yl)-N-(thiazol-4-ylmethyl)pyrazine-2-carboxamide;
   3-amino-6-(1H-benzo[d]imidazol-5-yl)-N-((3-fluoropyridin-2-yl)methyl)-5-(oxazol-2-yl)pyrazine-2-carboxamide;
   3-amino-N-((6-aminopyridin-2-yl)methyl)-6-(imidazo[1,2-a]pyridin-6-yl)-5-(oxazol-2-yl)pyrazine-2-carboxamide;
   3-amino-N-((3-fluoropyridin-2-yl)methyl)-6-(3-methyl-3H-benzo[d]imidazol-5-yl)-5-(oxazol-2-yl)pyrazine-2-carboxamide;
   3-amino-6-(2,6-dimethylpyridin-4-yl)-N-(4-fluoro-2-methoxybenzyl)-5-(4-fluorophenyl)pyrazine-2-carboxamide;
   3-amino-6-(2,6-dimethylpyridin-4-yl)-5-(4-fluorophenyl)-N-(2-(trifluoromethyl)benzyl)pyrazine-2-carboxamide
   3-amino-6-(2,6-dimethylpyridin-4-yl)-N-(3-fluoro-2-methoxybenzyl)-5-(4-fluorophenyl)pyrazine-2-carboxamide;
   3-amino-N-(2-(difluoromethyl)benzyl)-6-(2,6-dimethylpyridin-4-yl)-5-(4-fluorophenyl)pyrazine-2-carboxamide;
   3-amino-6-(2,6-dimethylpyridin-4-yl)-N-(2-methoxybenzyl)-5-(1H-pyrazol-1-yl)pyrazine-2-carboxamide;
   3-amino-N-((3-(difluoromethoxy)pyridin-2-yl)methyl)-6-(2,6-dimethylpyridin-4-yl)-5-(4-fluorophenyl)pyrazine-2-carboxamide;
   3-amino-6-(2-amino-6-methylpyridin-4-yl)-N-(2-(difluoromethoxy)phenyl)-5-(3-methyl-1H-pyrazol-1-yl)pyrazine-2-carboxamide;
   3-amino-6-(2,6-dimethylpyridin-4-yl)-N-(2-methoxybenzyl)-5-(5-methylfuran-2-yl)pyrazine-2-carboxamide;
   3-amino-N-(2, 6-difluorobenzyl)-6-(2,6-dimethylpyridin-4-yl)-5-(5-methylfuran-2-yl)pyrazine-2-carboxamide;
   3-amino-6-(2,6-dimethylpyridin-4-yl)-N-(2-methoxybenzyl)-5-(1-methyl-1H-pyrazol-4-yl)pyrazine-2-carboxamide;
   3-amino-N-(2,6-difluorobenzyl)-6-(2,6-dimethylpyridin-4-yl)-5-(1-methyl-1H-pyrazol-4-yl)pyrazine-2-carboxamide;
   3-amino-6-(2,6-dimethylpyridin-4-yl)-5-(4-fluorophenyl)-N-(2-(trifluoromethoxy)benzyl)pyrazine-2-carboxamide;
   3-amino-6-(2,6-dimethylpyridin-4-yl)-5-(4-fluorophenyl)-N-((2-methoxypyridin-3-yl)methyl)pyrazine-2-carboxamide;
   3-amino-6-(2-chloro-6-methylpyridin-4-yl)-5-(4-fluorophenyl)-N-(2-methoxybenzyl)pyrazine-2-carboxamide;
   3-amino-6-(2,6-dimethylpyridin-4-yl)-5-(4-fluorophenyl)-N-((3-methoxypyridin-2-yl)methyl)pyrazine-2-carboxamide;
   3-amino-6-(2,6-dimethylpyridin-4-yl)-N-(2-methoxybenzyl)-5-(5-methyl-1H-pyrazol-1-yl)pyrazine-2-carboxamide;
   3-amino-6-(2,6-dimethylpyridin-4-yl)-N-(2-methoxybenzyl)-5-(3-methyl-1H-pyrazol-1-yl)pyrazine-2-carboxamide;
   3-amino-6-(2,6-dimethylpyridin-4-yl)-N-(2-fluorobenzyl)-5-(4-fluorophenyl)pyrazine-2-carboxamide;
   3-amino-N-(2-chlorobenzyl)-6-(2,6-dimethylpyridin-4-yl)-5-(4-fluorophenyl)pyrazine-2-carboxamide;
   3-amino-N-(2-bromobenzyl)-6-(2,6-dimethylpyridin-4-yl)-5-(4-fluorophenyl)pyrazine-2-carboxamide;
   3-amino-6-(2,6-dimethylpyridin-4-yl)-5-(4-fluorophenyl)-N-(2-methylbenzyl)pyrazine-2-carboxamide;
   3-amino-6-(2-amino-6-methylpyridin-4-yl)-5-(4-fluorophenyl)-N-(2-methoxybenzyl) pyrazine-2-carboxamide;
   3-amino-6-(2,6-dimethylpyridin-4-yl)-N-(2-ethylbenzyl)-5-(4-fluorophenyl)pyrazine-2-carboxamide;
   3-amino-N-(2-(difluoromethoxy)-6-fluorobenzyl)-6-(2,6-dimethylpyridin-4-yl)-5-(4-fluorophenyl)pyrazine-2-carboxamide;
   N-((3-amino-6-(2,6-dimethylpyridin-4-yl)-5-(4-fluorophenyl)pyrazin-2-yl)methyl)-2-methoxybenzamide;

3-amino-6-(2,6-dimethylpyridin-4-yl)-5-(4-fluorophenyl)-N-(2-methoxybenzyl) pyrazine-2-carboxamide;
3-amino-6-(2,6-dimethylpyridin-4-yl)-N-(2-fluoro-6-methoxybenzyl)-5-(4-fluorophenyl) pyrazine-2-carboxamide;
3-amino-N-(2-(difluoromethoxy)benzyl)-6-(2,6-dimethylpyridin-4-yl)-5-(4-fluorophenyl)pyrazine-2-carboxamide;
3-amino-6-(2,6-dimethylpyridin-4-yl)-N-(5-fluoro-2-methoxybenzyl)-5-(4-fluorophenyl)pyrazine-2-carboxamide;
3-amino-6-(2,6-dimethylpyridin-4-yl)-N-(2-methoxybenzyl)-5-phenylpyrazine-2-carboxamide;
3-amino-6-(imidazo[1,2-a]pyridin-6-yl)-N-((5-methylthiazol-4-yl)methyl)-5-(oxazol-2-yl)pyrazine-2-carboxamide;
3-amino-N-((4-aminopyrimidin-2-yl)methyl)-6-(imidazo[1,2-a]pyridin-6-yl)-5-(oxazol-2-yl)pyrazine-2-carboxamide;
3-amino-N-(2-(dimethylphosphoryl)-6-fluorobenzyl)-6-(imidazo[1,2-a]pyridin-6-yl)-5-(oxazol-2-yl)pyrazine-2-carboxamide;
3-amino-6-(imidazo[1,2-a]pyridin-6-yl)-N-((6-(methylamino)pyridin-2-yl)methyl)-5-(oxazol-2-yl)pyrazine-2-carboxamide;
6-([1,2,4]triazolo[1,5-a]pyridin-6-yl)-3-amino-N-((3-fluoropyridin-2-yl)methyl)-5-(oxazol-2-yl)pyrazine-2-carboxamide;
3-amino-N-((3-fluoropyridin-2-yl)methyl)-6-(3-methylimidazo[1,2-a]pyridin-6-yl)-5-(oxazol-2-yl)pyrazine-2-carboxamide;
3-amino-N-((3-fluoropyridin-2-yl)methyl)-6-(imidazo[1,2-a]pyridin-6-yl)-5-(2H-1,2,3-triazol-2-yl)pyrazine-2-carboxamide;
3-amino-N-((6-(3-(dimethylamino)azetidin-1-yl)pyridin-2-yl)methyl)-6-(3-methylimidazo[1,2-a]pyridin-6-yl)-5-(oxazol-2-yl)pyrazine-2-carboxamide;
3-amino-6-(3-methylimidazo[1,2-a]pyridin-6-yl)-N-((6-(4-methylpiperazin-1-yl)pyridin-2-yl)methyl)-5-(oxazol-2-yl)pyrazine-2-carboxamide;
3-amino-5-(4-fluorophenyl)-N-((3-(2-hydroxyethoxy)pyridin-2-yl)methyl)-6-(3-methyl-3H-benzo[d]imidazol-5-yl)pyrazine-2-carboxamide;
3-amino-5-(4-fluorophenyl)-N-((3-(2-methoxyethoxy)pyridin-2-yl)methyl)-6-(3-methyl-3H-benzo[d]imidazol-5-yl)pyrazine-2-carboxamide;
3-amino-5-(4-fluorophenyl)-6-(3-methyl-3H-benzo[d]imidazol-5-yl)-N-((3-(2-(methylamino)ethoxy)pyridin-2-yl)methyl)pyrazine-2-carboxamide;
3-amino-N-((3-(2-(dimethylamino)ethoxy)pyridin-2-yl)methyl)-5-(4-fluorophenyl)-6-(3-methyl-3H-benzo[d]imidazol-5-yl)pyrazine-2-carboxamide;
3-amino-5-(4-fluorophenyl)-N-((3-(2-hydroxyethylamino)pyridin-2-yl)methyl)-6-(3-methyl-3H-benzo[d]imidazol-5-yl)pyrazine-2-carboxamide;
3-amino-N-((4-(dimethylamino)pyridin-3-yl)methyl)-6-(3-methylimidazo[1,2-a]pyridin-6-yl)-5-(oxazol-2-yl)pyrazine-2-carboxamide;
3-amino-N-((3-(2-amino-2-oxoethoxy)pyridin-2-yl)methyl)-5-(4-fluorophenyl)-6-(3-methyl-3H-benzo[d]imidazol-5-yl)pyrazine-2-carboxamide;
3-amino-6-(3-methylimidazo[1,2-a]pyridin-6-yl)-N-((1-methylpyrrolidin-2-yl)methyl)-5-(oxazol-2-yl)pyrazine-2-carboxamide (isomers);
(R)-3-amino-6-(3-methylimidazo[1,2-a]pyridin-6-yl)-5-(oxazol-2-yl)-N-(pyrrolidin-2-ylmethyl)pyrazine-2-carboxamide;
(S)-3-amino-6-(3-methylimidazo[1,2-a]pyridin-6-yl)-5-(oxazol-2-yl)-N-(pyrrolidin-2-ylmethyl)pyrazine-2-carboxamide;
3-amino-6-(3-methylimidazo[1,2-a]pyridin-6-yl)-N-((1-methylpiperidin-2-yl)methyl)-5-(oxazol-2-yl)pyrazine-2-carboxamide (isomers);
(R)-3-amino-6-(3-methylimidazo[1,2-a]pyridin-6-yl)-5-(oxazol-2-yl)-N-((tetrahydrofuran-2-yl)methyl)pyrazine-2-carboxamide;
(S)-3-amino-6-(3-methylimidazo[1,2-a]pyridin-6-yl)-5-(oxazol-2-yl)-N-((tetrahydrofuran-2-yl)methyl)pyrazine-2-carboxamide;
(R)-3-amino-6-(3-ethylpyrazolo[1,5-a]pyridin-5-yl)-N-((1-methylpyrrolidin-2-yl)methyl)-5-(oxazol-2-yl)pyrazine-2-carboxamide;
(S)-3-amino-6-(3-ethylpyrazolo[1,5-a]pyridin-5-yl)-N-((1-methylpyrrolidin-2-yl)methyl)-5-(oxazol-2-yl)pyrazine-2-carboxamide;
(S)-3-amino-6-(3-methyl-3H-benzo[d]imidazol-5-yl)-N-((1-methylpyrrolidin-2-yl)methyl)-5-(2H-1,2,3-triazol-2-yl)pyrazine-2-carboxamide;
(R)-3-amino-6-(3-methyl-3H-benzo[d]imidazol-5-yl)-N-((1-methylpyrrolidin-2-yl)methyl)-5-(2H-1,2,3-triazol-2-yl)pyrazine-2-carboxamide;
3-amino-N-ethyl-6-(3-methylimidazo[1,2-a]pyridin-6-yl)-5-(oxazol-2-yl)pyrazine-2-carboxamide;
3-amino-N-isopropyl-6-(3-methylimidazo[1,2-a]pyridin-6-yl)-5-(oxazol-2-yl)pyrazine-2-carboxamide;
3-amino-6-(3-methylimidazo[1,2-a]pyridin-6-yl)-5-(oxazol-2-yl)-N-(oxetan-2-ylmethyl)pyrazine-2-carboxamide (isomers);
(R)-3-amino-6-(3-methylimidazo[1,2-a]pyridin-6-yl)-5-(oxazol-2-yl)-N-((tetrahydrofuran-3-yl)methyl)pyrazine-2-carboxamide;
(S)-3-amino-6-(3-methylimidazo[1,2-a]pyridin-6-yl)-5-(oxazol-2-yl)-N-((tetrahydrofuran-3-yl)methyl)pyrazine-2-carboxamide;
(R)-3-amino-5-(4-fluorophenyl)-6-(3-methylimidazo[1,2-a]pyridin-6-yl)-N-((1-methylpyrrolidin-2-yl)methyl)pyrazine-2-carboxamide;
(S)-3-amino-5-(4-fluorophenyl)-6-(3-methylimidazo[1,2-a]pyridin-6-yl)-N-((1-methylpyrrolidin-2-yl)methyl)pyrazine-2-carboxamide;
3-amino-N-(2-cyanoethyl)-6-(3-methylimidazo[1,2-a]pyridin-6-yl)-5-(oxazol-2-yl)pyrazine-2-carboxamide;
3-amino-N-(3-(dimethylamino)-3-oxopropyl)-6-(3-methylimidazo[1,2-a]pyridin-6-yl)-5-(oxazol-2-yl)pyrazine-2-carboxamide;
(R)-3-amino-5-(4-fluorophenyl)-6-(3-methylimidazo[1,2-a]pyridin-6-yl)-N-(1-methylpyrrolidin-3-yl)pyrazine-2-carboxamide;
(R)-3-amino-N-(2-hydroxypropyl)-6-(3-methylimidazo[1,2-a]pyridin-6-yl)-5-(oxazol-2-yl)pyrazine-2-carboxamide;
(S)-3-amino-N-(2-hydroxypropyl)-6-(3-methylimidazo[1,2-a]pyridin-6-yl)-5-(oxazol-2-yl)pyrazine-2-carboxamide;
3-amino-N-(2-methoxyethyl)-6-(3-methylimidazo[1,2-a]pyridin-6-yl)-5-(oxazol-2-yl)pyrazine-2-carboxamide;
3-amino-6-(3-methylimidazo[1,2-a]pyridin-6-yl)-5-(oxazol-2-yl)-N-(2-(trifluoromethoxy)ethyl)pyrazine-2-carboxamide;
3-amino-N-(3-methoxypropyl)-6-(3-methylimidazo[1,2-a]pyridin-6-yl)-5-(oxazol-2-yl)pyrazine-2-carboxamide;

3-amino-5-(4-fluorophenyl)-6-(3-methylimidazo[1,2-a]pyridin-6-yl)-N-(2-(methylsulfonyl)ethyl)pyrazine-2-carboxamide;

3-amino-N-(2-(dimethylamino)ethyl)-6-(3-methylimidazo[1,2-a]pyridin-6-yl)-5-(oxazol-2-yl)pyrazine-2-carboxamide;

3-amino-N-((1-(dimethylamino)cyclopropyl)methyl)-5-(4-fluorophenyl)-6-(3-methylimidazo[1,2-a]pyridin-6-yl)pyrazine-2-carboxamide;

3-amino-N-(cyclopropylmethyl)-6-(3-methylimidazo[1,2-a]pyridin-6-yl)-5-(oxazol-2-yl)pyrazine-2-carboxamide;

(S)—N-((3-amino-5-(4-fluorophenyl)-6-(3-methylimidazo[1,2-a]pyridin-6-yl)pyrazin-2-yl)methyl)-1-methylpyrrolidine-2-carboxamide;

(R)—N-((3-amino-5-(4-fluorophenyl)-6-(3-methylimidazo[1,2-a]pyridin-6-yl)pyrazin-2-yl)methyl)-1-methylpyrrolidine-2-carboxamide;

N-(2-(1H-pyrazol-1-yl)ethyl)-3-amino-6-(3-methylimidazo[1,2-a]pyridin-6-yl)-5-(oxazol-2-yl)pyrazine-2-carboxamide;

(R)-3-amino-N-(1-methoxypropan-2-yl)-6-(3-methylimidazo[1,2-a]pyridin-6-yl)-5-(oxazol-2-yl)pyrazine-2-carboxamide;

(S)-3-amino-N-(1-methoxypropan-2-yl)-6-(3-methylimidazo[1,2-a]pyridin-6-yl)-5-(oxazol-2-yl)pyrazine-2-carboxamide;

(S)-3-amino-N-((4,4-difluoro-1-methylpyrrolidin-2-yl)methyl)-6-(3-methylimidazo[1,2-a]pyridin-6-yl)-5-(oxazol-2-yl)pyrazine-2-carboxamide;

(R)-3-amino-N-((4,4-difluoro-1-methylpyrrolidin-2-yl)methyl)-6-(3-methylimidazo[1,2-a]pyridin-6-yl)-5-(oxazol-2-yl)pyrazine-2-carboxamide;

3-amino-6-(3-methylimidazo[1,2-a]pyridin-6-yl)-5-(oxazol-2-yl)-N-(tetrahydro-2H-pyran-3-yl)pyrazine-2-carboxamide (isomers);

3-amino-6-(3-methylimidazo[1,2-a]pyridin-6-yl)-5-(oxazol-2-yl)-N-((tetrahydro-2H-pyran-2-yl)methyl)pyrazine-2-carboxamide (isomers);

3-amino-6-(3-methylimidazo[1,2-a]pyridin-6-yl)-5-(oxazol-2-yl)-N-((tetrahydro-2H-pyran-3-yl)methyl)pyrazine-2-carboxamide(isomers);

(R)-3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide;

(S)-3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide;

3-amino-N-((6-(1-methyl-1,6-diazaspiro[3.3]heptan-6-yl)pyridin-2-yl)methyl)-6-(3-methylimidazo[1,2-a]pyridin-6-yl)-5-(oxazol-2-yl)pyrazine-2-carboxamide;

3-amino-N-((6-((1R,5S)-3-methyl-3,8-diazabicyclo[3.2.1]octan-8-yl)pyridin-2-yl)methyl)-6-(3-methylimidazo[1,2-a]pyridin-6-yl)-5-(oxazol-2-yl)pyrazine-2-carboxamide;

3-amino-N-((6-((1R,5S)-8-methyl-3,8-diazabicyclo[3.2.1]octan-3-yl)pyridin-2-yl)methyl)-6-(3-methylimidazo[1,2-a]pyridin-6-yl)-5-(oxazol-2-yl)pyrazine-2-carboxamide;

3-amino-N-((6-(3-methyl-3,6-diazabicyclo[3.1.1]heptan-6-yl)pyridin-2-yl)methyl)-6-(3-methylimidazo[1,2-a]pyridin-6-yl)-5-(oxazol-2-yl)pyrazine-2-carboxamide;

3-amino-N-((6-(6-methyl-2,6-diazaspiro[3.4]octan-2-yl)pyridin-2-yl)methyl)-6-(3-methylimidazo[1,2-a]pyridin-6-yl)-5-(oxazol-2-yl)pyrazine-2-carboxamide;

3-amino-6-(3-methylimidazo[1,2-a]pyridin-6-yl)-N-((6-(1-methylpiperidin-4-yl)pyridin-2-yl)methyl)-5-(oxazol-2-yl)pyrazine-2-carboxamide;

3-amino-6-(3-methylimidazo[1,2-a]pyridin-6-yl)-N-((1-methylpyrrolidin-2-yl)methyl)-5-(oxazol-2-yl)pyrazine-2-carboxamide;

3-amino-6-(3-methylimidazo[1,2-a]pyridin-6-yl)-5-(oxazol-2-yl)-N-(pyrrolidin-2-ylmethyl)pyrazine-2-carboxamide;

3-amino-6-(3-methylimidazo[1,2-a]pyridin-6-yl)-N-((1-methylpiperidin-2-yl)methyl)-5-(oxazol-2-yl)pyrazine-2-carboxamide;

3-amino-6-(3-methylimidazo[1,2-a]pyridin-6-yl)-5-(oxazol-2-yl)-N-((tetrahydrofuran-2-yl)methyl)pyrazine-2-carboxamide;

3-amino-6-(3-ethylpyrazolo[1,5-a]pyridin-5-yl)-N-((1-methylpyrrolidin-2-yl)methyl)-5-(oxazol-2-yl)pyrazine-2-carboxamide;

3-amino-6-(3-methyl-3H-benzo[d]imidazol-5-yl)-N-((1-methylpyrrolidin-2-yl)methyl)-5-(2H-1,2,3-triazol-2-yl)pyrazine-2-carboxamide;

3-amino-6-(3-methylimidazo[1,2-a]pyridin-6-yl)-5-(oxazol-2-yl)-N-(oxetan-2-ylmethyl)pyrazine-2-carboxamide;

3-amino-6-(3-methylimidazo[1,2-a]pyridin-6-yl)-5-(oxazol-2-yl)-N-((tetrahydrofuran-3-yl)methyl)pyrazine-2-carboxamide;

3-amino-5-(4-fluorophenyl)-6-(3-methylimidazo[1,2-a]pyridin-6-yl)-N-((1-methylpyrrolidin-2-yl)methyl)pyrazine-2-carboxamide;

3-amino-5-(4-fluorophenyl)-6-(3-methylimidazo[1,2-a]pyridin-6-yl)-N-(1-methylpyrrolidin-3-yl)pyrazine-2-carboxamide;

3-amino-N-(2-hydroxypropyl)-6-(3-methylimidazo[1,2-a]pyridin-6-yl)-5-(oxazol-2-yl)pyrazine-2-carboxamide;

N-((3-amino-5-(4-fluorophenyl)-6-(3-methylimidazo[1,2-a]pyridin-6-yl)pyrazin-2-yl)methyl)-1-methylpyrrolidine-2-carboxamide;

3-amino-N-(1-methoxypropan-2-yl)-6-(3-methylimidazo[1,2-a]pyridin-6-yl)-5-(oxazol-2-yl)pyrazine-2-carboxamide;

3-amino-N-((4,4-difluoro-1-methylpyrrolidin-2-yl)methyl)-6-(3-methylimidazo[1,2-a]pyridin-6-yl)-5-(oxazol-2-yl)pyrazine-2-carboxamide;

3-amino-6-(3-methylimidazo[1,2-a]pyridin-6-yl)-5-(oxazol-2-yl)-N-(tetrahydro-2H-pyran-3-yl)pyrazine-2-carboxamide;

3-amino-6-(3-methylimidazo[1,2-a]pyridin-6-yl)-5-(oxazol-2-yl)-N-((tetrahydro-2H-pyran-2-yl)methyl)pyrazine-2-carboxamide;

3-amino-6-(3-methylimidazo[1,2-a]pyridin-6-yl)-5-(oxazol-2-yl)-N-((tetrahydro-2H-pyran-3-yl)methyl)pyrazine-2-carboxamide;

3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide;

3-amino-6-(3-(aminomethyl)imidazo[1,2-a]pyridin-6-yl)-N-((3-fluoropyridin-2-yl)methyl)-5-(oxazol-2-yl)pyrazine-2-carboxamide;

3-amino-5-(4-fluorophenyl)-N-((3-(2-(methylamino)ethoxy)pyridin-2-yl)methyl)-6-(3-methylimidazo[1,2-a]pyridin-6-yl)pyrazine-2-carboxamide 2,2,2-trifluoroacetate;

(R)-3-amino-5-(4-fluorophenyl)-6-(3-methylimidazo[1,2-a]pyridin-6-yl)-N-(1-methylpyrrolidin-3-yl)pyrazine-2-carboxamide;

(S)-3-amino-5-(4-fluorophenyl)-6-(3-methylimidazo[1,2-a]pyridin-6-yl)-N-(1-methylpyrrolidin-3-yl)pyrazine-2-carboxamide;
(S)-3-amino-5-(3-methyl-1H-pyrazol-1-yl)-6-(3-methylimidazo[1,2-a]pyridin-6-yl)-N-((1-methylpyrrolidin-2-yl)methyl)pyrazine-2-carboxamide;
(R)-3-amino-5-(3-methyl-1H-pyrazol-1-yl)-6-(3-methylimidazo[1,2-a]pyridin-6-yl)-N-((1-methylpyrrolidin-2-yl)methyl)pyrazine-2-carboxamide;
3-amino-N-((1-methylpyrrolidin-2-yl)methyl)-5-(oxazol-2-yl)-6-(3-(trifluoromethyl)imidazo[1,2-a]pyridin-6-yl)pyrazine-2-carboxamide(isomers);
(R)-(3-amino-5-(4-fluorophenyl)-6-(3-methylimidazo[1,2-a]pyridin-6-yl)pyrazin-2-yl)(3-(dimethylamino)pyrrolidin-1-yl)methanone;
(S)-(3-amino-5-(4-fluorophenyl)-6-(3-methylimidazo[1,2-a]pyridin-6-yl)pyrazin-2-yl)(3-(dimethylamino)pyrrolidin-1-yl)methanone;
(R)-(3-amino-5-(4-fluorophenyl)-6-(3-methylimidazo[1,2-a]pyridin-6-yl)pyrazin-2-yl)(2-(methoxymethyl)pyrrolidin-1-yl)methanone;
(S)-(3-amino-5-(4-fluorophenyl)-6-(3-methylimidazo[1,2-a]pyridin-6-yl)pyrazin-2-yl)(2-(methoxymethyl)pyrrolidin-1-yl)methanone;
3-amino-N-(2-(1-methyl-1H-imidazol-2-yl)ethyl)-6-(3-methylimidazo[1,2-a]pyridin-6-yl)-5-(oxazol-2-yl)pyrazine-2-carboxamide;
rac-3-amino-6-(3-methylimidazo[1,2-a]pyridin-6-yl)-N-((4-methylmorpholin-2-yl)methyl)-5-(oxazol-2-yl)pyrazine-2-carboxamide;
3-amino-6-(3-methylimidazo[1,2-a]pyridin-6-yl)-5-(oxazol-2-yl)-N-(2-(2-oxopyrrolidin-1-yl)ethyl)pyrazine-2-carboxamide;
(R)-3-amino-6-(3-chloroimidazo[1,2-a]pyridin-6-yl)-N-((1-methylpyrrolidin-2-yl)methyl)-5-(oxazol-2-yl)pyrazine-2-carboxamide;
(S)-3-amino-6-(3-chloroimidazo[1,2-a]pyridin-6-yl)-N-((1-methylpyrrolidin-2-yl)methyl)-5-(oxazol-2-yl)pyrazine-2-carboxamide;
3-amino-N-((1-methyl-5-oxopyrrolidin-3-yl)methyl)-6-(3-methylimidazo[1,2-a]pyridin-6-O-5-(oxazol-2-yl)pyrazine-2-carboxamide (isomers);
rac-N-((1,4-dioxan-2-yl)methyl)-3-amino-6-(3-methylimidazo[1,2-a]pyridin-6-O-5-(oxazol-2-yl)pyrazine-2-carboxamide;
rac-3-amino-N-((1-methyl-5-oxopyrrolidin-2-yl)methyl)-6-(3-methylimidazo[1,2-a]pyridin-6-yl)-5-(oxazol-2-yl)pyrazine-2-carboxamide;
3-amino-6-(3-methylimidazo[1,2-a]pyridin-6-yl)-5-(oxazol-2-yl)-N-(3-oxo-3-(piperidin-1-yl)propyl)pyrazine-2-carboxamide;
3-amino-N-((1-methyl-2-oxopyrrolidin-3-yl)methyl)-6-(3-methylimidazo[1,2-a]pyridin-6-yl)-5-(oxazol-2-yl)pyrazine-2-carboxamide (isomers);
3-amino-6-(3-methylimidazo[1,2-a]pyridin-6-yl)-5-(oxazol-2-yl)-N-(3-oxo-3-(pyrrolidin-1-yl)propyl)pyrazine-2-carboxamide;
3-amino-N-cyclobutyl-6-(3-methylimidazo[1,2-a]pyridin-6-yl)-5-(oxazol-2-yl)pyrazine-2-carboxamide;
(R)-3-amino-N-((1-(cyclopropanecarbonyl)pyrrolidin-3-yl)methyl)-6-(3-methylimidazo[1,2-a]pyridin-6-yl)-5-(oxazol-2-yl)pyrazine-2-carboxamide;
(S)-3-amino-N-((1-(cyclopropanecarbonyl)pyrrolidin-3-yl)methyl)-6-(3-methylimidazo[1,2-a]pyridin-6-yl)-5-(oxazol-2-yl)pyrazine-2-carboxamide;
3-amino-N-(bicyclo[1.1.1]pentan-1-yl)-6-(3-methylimidazo[1,2-a]pyridin-6-yl)-5-(oxazol-2-yl)pyrazine-2-carboxamide;
3-amino-N-((3-fluoropyridin-2-yl)methyl)-6-(3-methylimidazo[1,2-a]pyridin-6-yl)-5-morpholinopyrazine-2-carboxamide;
Cis-3-amino-N-((6-(3-(dimethylamino)cyclobutylamino)pyridin-2-yl)methyl)-6-(3-methylimidazo[1,2-a]pyridin-6-yl)-5-(oxazol-2-yl)pyrazine-2-carboxamide;
Trans-3-amino-N-((6-(3-(dimethylamino)cyclobutylamino)pyridin-2-yl)methyl)-6-(3-methylimidazo[1,2-a]pyridin-6-yl)-5-(oxazol-2-yl)pyrazine-2-carboxamide;
3-amino-N-(3-(methylamino)-3-oxopropyl)-6-(3-methylimidazo[1,2-a]pyridin-6-yl)-5-(oxazol-2-yl)pyrazine-2-carboxamide;
(S)-3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide;
(R)-3-amino-6-(3-methylimidazo[1,2-a]pyridin-6-yl)-N-((tetrahydrofuran-2-yl)methyl)-5-(2H-1,2,3-triazol-2-yl)pyrazine-2-carboxamide;
rac-3-amino-N-(2-methoxypropyl)-6-(3-methylimidazo[1,2-a]pyridin-6-yl)-5-(oxazol-2-yl)pyrazine-2-carboxamide;
3-amino-N-(2-methoxypropyl)-6-(3-methylimidazo[1,2-a]pyridin-6-yl)-5-(oxazol-2-yl)pyrazine-2-carboxamide (isomers);
3-amino-6-(3-methylimidazo[1,2-a]pyridin-6-yl)-5-(oxazol-2-yl)-N-((1,4,4-trimethylpyrrolidin-2-yl)methyl)pyrazine-2-carboxamide (isomers);
(R)-3-amino-5-(3-fluorophenyl)-6-(3-methylimidazo[1,2-a]pyridin-6-yl)-N-((1-methylpyrrolidin-2-yl)methyl)pyrazine-2-carboxamide;
3-amino-N-((6-(3-(dimethylamino)pyrrolidin-1-yl)pyridin-2-yl)methyl)-6-(3-methylimidazo[1,2-a]pyridin-6-yl)-5-(oxazol-2-yl)pyrazine-2-carboxamide (isomers);
rac-3-amino-N-(2-(methyl(tetrahydrofuran-3-yl)amino)ethyl)-6-(3-methylimidazo[1,2-a]pyridin-6-yl)-5-(oxazol-2-yl)pyrazine-2-carboxamide;
(S)-3-amino-N-(4-(dimethylamino)-4-oxobutan-2-yl)-6-(3-methylimidazo[1,2-a]pyridin-6-yl)-5-(oxazol-2-yl)pyrazine-2-carboxamide;
(R)-3-amino-N-(4-(dimethylamino)-4-oxobutan-2-yl)-6-(3-methylimidazo[1,2-a]pyridin-6-yl)-5-(oxazol-2-yl)pyrazine-2-carboxamide;
3-amino-6-(3-methylimidazo[1,2-a]pyridin-6-yl)-5-(oxazol-2-yl)-N-(2-(2-oxopyridin-1(2H)-yl)ethyl)pyrazine-2-carboxamide;
3-amino-N-(2,6-difluorobenzyl)-6-(3-methylimidazo[1,2-a]pyridin-6-yl)-5-morpholinopyrazine-2-carboxamide;
3-amino-6-(3-methylimidazo[1,2-a]pyridin-6-yl)-5-(oxazol-2-yl)-N-((tetrahydro-2H-pyran-4-yl)methyl)pyrazine-2-carboxamide;
3-amino-N-(2-(methyl(pyridin-2-yl)amino)ethyl)-6-(3-methylimidazo[1,2-a]pyridin-6-yl)-5-(oxazol-2-yl)pyrazine-2-carboxamide;
(R)-3-amino-6-(3-methylimidazo[1,2-a]pyridin-6-yl)-N-((tetrahydrofuran-3-yl)methyl)-5-(2H-1,2,3-triazol-2-yl)pyrazine-2-carboxamide;
3-amino-N-(2-methoxyethyl)-6-(3-methylimidazo[1,2-a]pyridin-6-yl)-5-(2H-1,2,3-triazol-2-yl)pyrazine-2-carboxamide;
3-amino-N-(2-(methyl(phenyl)amino)ethyl)-6-(3-methylimidazo[1,2-a]pyridin-6-yl)-5-(oxazol-2-yl)pyrazine-2-carboxamide;

3-amino-N-cyclopropyl-6-(3-methylimidazo[1,2-a]pyridin-6-yl)-5-(oxazol-2-yl)pyrazine-2-carboxamide;
3-amino-5-(4-fluorophenyl)-6-(3-methylimidazo[1,2-a]pyridin-6-yl)-N-((4-methylmorpholin-2-yl)methyl)pyrazine-2-carboxamide (isomers);
3-amino-N-((1,2-dimethylpyrrolidin-2-yl)methyl)-6-(3-methylimidazo[1,2-a]pyridin-6-yl)-5-(oxazol-2-yl)pyrazine-2-carboxamide (isomers);
3-amino-N-(4-methoxycyclohexyl)-6-(3-methylimidazo[1,2-a]pyridin-6-yl)-5-(oxazol-2-yl)pyrazine-2-carboxamide;
3-amino-6-(3-methylimidazo[1,2-a]pyridin-6-yl)-N-((3-methyltetrahydrofuran-3-yl)methyl)-5-(oxazol-2-yl)pyrazine-2-carboxamide (isomers);
3-amino-N-(2-cyclopropyl-2-(dimethylamino)ethyl)-6-(3-methylimidazo[1,2-a]pyridin-6-yl)-5-(oxazol-2-yl)pyrazine-2-carboxamide (isomers);
3-amino-N-((1-methyl-2-oxopiperidin-3-yl)methyl)-6-(3-methylimidazo[1,2-a]pyridin-6-yl)-5-(oxazol-2-yl)pyrazine-2-carboxamide;
(R)-3-amino-6-(3-methylimidazo[1,2-a]pyridin-6-yl)-5-(oxazol-2-yl)-N-(tetrahydrofuran-3-yl)pyrazine-2-carboxamide;
(S)-3-amino-6-(3-methylimidazo[1,2-a]pyridin-6-yl)-5-(oxazol-2-yl)-N-(tetrahydrofuran-3-yl)pyrazine-2-carboxamide;
3-amino-5-(4-fluorophenyl)-N-((1-methyl-2-oxopyrrolidin-3-yl)methyl)-6-(3-methylimidazo[1,2-a]pyridin-6-yl)pyrazine-2-carboxamide;
(R)—N-((3-amino-5-(3,4-difluorophenyl)-6-(3-methylimidazo[1,2-a]pyridin-6-yl)pyrazin-2-yl)methyl)-1-methylpyrrolidine-2-carboxamide;
3-amino-6-(3-methylimidazo[1,2-a]pyridin-6-yl)-5-(oxazol-2-yl)-N-(1-(tetrahydrofuran-2-yl)ethyl)pyrazine-2-carboxamide;
(R)-3-amino-6-(3-methylimidazo[1,2-a]pyridin-6-yl)-N-((1-methylpyrrolidin-2-yl)methyl)-5-phenylpyrazine-2-carboxamide;
3-amino-N-((4,4-dimethyloxetan-2-yl)methyl)-6-(3-methylimidazo[1,2-a]pyridin-6-yl)-5-(oxazol-2-yl)pyrazine-2-carboxamide;
3-amino-N-((6-(3-((dimethylamino)methyl)azetidin-1-yl)pyridin-2-yl)methyl)-6-(3-methylimidazo[1,2-a]pyridin-6-yl)-5-(oxazol-2-yl)pyrazine-2-carboxamide;
(S)—N-((3-amino-5-(4-fluorophenyl)-6-(3-methylimidazo[1,2-a]pyridin-6-yl)pyrazin-2-yl)methyl)tetrahydrofuran-3-carboxamide;
(R)—N-((3-amino-5-(4-fluorophenyl)-6-(3-methylimidazo[1,2-a]pyridin-6-yl)pyrazin-2-yl)methyl)tetrahydrofuran-3-carboxamide;
(S)—N-((3-amino-5-(4-fluorophenyl)-6-(3-methylimidazo[1,2-a]pyridin-6-yl)pyrazin-2-yl)methyl)tetrahydrofuran-2-carboxamide;
(R)—N-((3-amino-5-(4-fluorophenyl)-6-(3-methylimidazo[1,2-a]pyridin-6-yl)pyrazin-2-yl)methyl)tetrahydrofuran-2-carboxamide;
cis-3-amino-N-(3-(dimethylamino)cyclobutyl)-6-(3-methylimidazo[1,2-a]pyridin-6-yl)-5-(oxazol-2-yl)pyrazine-2-carboxamide;
Trans-3-amino-N-(3-(dimethylamino)cyclobutyl)-6-(3-methylimidazo[1,2-a]pyridin-6-yl)-5-(oxazol-2-yl)pyrazine-2-carboxamide;
(R)-3-amino-5-(3,4-difluorophenyl)-6-(3-methylimidazo[1,2-a]pyridin-6-yl)-N-((1-methylpyrrolidin-2-yl)methyl)pyrazine-2-carboxamide;
(S)-3-amino-N-((1-(dimethylcarbamoyl)pyrrolidin-3-yl)methyl)-6-(3-methylimidazo[1,2-a]pyridin-6-yl)-5-(oxazol-2-yl)pyrazine-2-carboxamide;
3-amino-6-(3-methylimidazo[1,2-a]pyridin-6-yl)-N-((6-morpholinopyridin-2-yl)methyl)-5-(oxazol-2-yl)pyrazine-2-carboxamide;
(R)—N-((3-amino-5-(3-fluorophenyl)-6-(3-methylimidazo[1,2-a]pyridin-6-yl)pyrazin-2-yl)methyl)-1-methylpyrrolidine-2-carboxamide;
3-amino-N-((3-methoxytetrahydrofuran-2-yl)methyl)-6-(3-methylimidazo[1,2-a]pyridin-6-yl)-5-(oxazol-2-yl)pyrazine-2-carboxamide;
3-amino-N-(3-(dimethylamino)-2,2-dimethyl-3-oxopropyl)-6-(3-methylimidazo[1,2-a]pyridin-6-yl)-5-(oxazol-2-yl)pyrazine-2-carboxamide;
3-amino-N-((6-((1R,4R)-5-methyl-2,5-diazabicyclo[2.2.1]heptan-2-yl)pyridin-2-yl)methyl)-6-(3-methylimidazo[1,2-a]pyridin-6-yl)-5-(oxazol-2-yl)pyrazine-2-carboxamide;
3-amino-N-((6-((1S,4S)-5-methyl-2,5-diazabicyclo[2.2.1]heptan-2-yl)pyridin-2-yl)methyl)-6-(3-methylimidazo[1,2-a]pyridin-6-yl)-5-(oxazol-2-yl)pyrazine-2-carboxamide;
3-amino-N-((6-(6-methyl-2,6-diazaspiro[3.3]heptan-2-yl)pyridin-2-yl)methyl)-6-(3-methylimidazo[1,2-a]pyridin-6-yl)-5-(oxazol-2-yl)pyrazine-2-carboxamide;
(R)-3-amino-N-((6-(3,4-dimethylpiperazin-1-yl)pyridin-2-yl)methyl)-6-(3-methylimidazo[1,2-a]pyridin-6-yl)-5-(oxazol-2-yl)pyrazine-2-carboxamide;
(S)-3-amino-N-((6-(3,4-dimethylpiperazin-1-yl)pyridin-2-yl)methyl)-6-(3-methylimidazo[1,2-a]pyridin-6-yl)-5-(oxazol-2-yl)pyrazine-2-carboxamide;
(S)-3-amino-N-((6-(2,4-dimethylpiperazin-1-yl)pyridin-2-yl)methyl)-6-(3-methylimidazo[1,2-a]pyridin-6-yl)-5-(oxazol-2-yl)pyrazine-2-carboxamide;
3-amino-N-((3,3-dimethyloxetan-2-yl)methyl)-6-(3-methylimidazo[1,2-a]pyridin-6-yl)-5-(oxazol-2-yl)pyrazine-2-carboxamide;
(R)—N-((3-amino-6-(3-methylimidazo[1,2-a]pyridin-6-yl)-5-(2H-1,2,3-triazol-2-yl)pyrazin-2-yl)methyl)-1-methylpyrrolidine-2-carboxamide;
(R)—N-((3-amino-5-(3,5-difluorophenyl)-6-(3-methylimidazo[1,2-a]pyridin-6-yl)pyrazin-2-yl)methyl)-1-methylpyrrolidine-2-carboxamide;
3-amino-N-(3-methoxycyclohexyl)-6-(3-methylimidazo[1,2-a]pyridin-6-yl)-5-(oxazol-2-yl)pyrazine-2-carboxamide;
(S)—N-(1-(1H-1,2,3-triazol-1-yl)propan-2-yl)-3-amino-6-(3-methylimidazo[1,2-a]pyridin-6-yl)-5-(oxazol-2-yl)pyrazine-2-carboxamide;
(S)—N-(1-(2H-1,2,3-triazol-2-yl)propan-2-yl)-3-amino-6-(3-methylimidazo[1,2-a]pyridin-6-yl)-5-(oxazol-2-yl)pyrazine-2-carboxamide;
(R)—N-(1-(2H-1,2,3-triazol-2-yl)propan-2-yl)-3-amino-6-(3-methylimidazo[1,2-a]pyridin-6-yl)-5-(oxazol-2-yl)pyrazine-2-carboxamide;
3-amino-N-(3-methoxypropyl)-6-(3-methylimidazo[1,2-a]pyridin-6-yl)-5-(2H-1,2,3-triazol-2-yl)pyrazine-2-carboxamide;
3-amino-N-((3-(2-hydroxyethoxy)pyridin-2-yl)methyl)-6-(3-methylimidazo[1,2-a]pyridin-6-yl)-5-(oxazol-2-yl)pyrazine-2-carboxamide;
3-amino-N-((3-(2-(methylamino)ethoxy)pyridin-2-yl)methyl)-6-(3-methylimidazo[1,2-a]pyridin-6-yl)-5-(oxazol-2-yl)pyrazine-2-carboxamide;

3-amino-N-((6-(4-(dimethylamino)piperidin-1-yl)pyridin-2-yl)methyl)-6-(3-methylimidazo[1,2-a]pyridin-6-yl)-5-(oxazol-2-yl)pyrazine-2-carboxamide;

3-amino-N-((6-(3-(methylamino)azetidin-1-yl)pyridin-2-yl)methyl)-6-(3-methylimidazo[1,2-a]pyridin-6-yl)-5-(oxazol-2-yl)pyrazine-2-carboxamide;

3-amino-6-(3-methylimidazo[1,2-a]pyridin-6-yl)-5-(pyridin-2-yl)-N-((tetrahydrofuran-3-yl)methyl)pyrazine-2-carboxamide;

rac-N-(1-(1H-1,2,4-triazol-1-yl)propan-2-yl)-3-amino-6-(3-methylimidazo[1,2-a]pyridin-6-yl)-5-(oxazol-2-yl)pyrazine-2-carboxamide.

15. A pharmaceutical composition comprising one or more compounds of claim 1, and a pharmaceutically acceptable carrier.

16. The compound of claim 3, wherein when W is methylene, V is —NH—C(O)—; or when W is —C(O)—, V is —NH—, —NH—$C_{1-12}$ alkylene-, or N-linked pyrrolidinyl, which can be mono or independently multi-substituted by hydroxyl, $C_{1-12}$ alkyl, $C_{1-12}$ alkoxyl, or $C_{1-12}$ alkyl-OH.

17. The compound of claim 6, wherein Z is ethylene, Y is methoxyl.

18. The compound of claim 7, wherein Y is cyclobutyl mono-substituted by methoxyl.

19. The compound of claim 11, wherein $R_1$ is methyl, ethyl, n-propyl or isopropyl.

20. The compound of claim 19, wherein $R_1$ is methyl.

21. The compound of claim 13, wherein $R_3$ is halogen or $C_{1-12}$ alkyl.

22. The compound of claim 21, wherein $R_3$ is fluoro or methyl.

* * * * *